US009382254B2

(12) United States Patent
De Blieck et al.

(10) Patent No.: US 9,382,254 B2
(45) Date of Patent: Jul. 5, 2016

(54) COMPOUNDS AND PHARMACEUTICAL COMPOSITIONS THEREOF FOR THE TREATMENT OF CYSTIC FIBROSIS

(71) Applicant: Galapagos NV, Mechelen (BE)

(72) Inventors: Ann De Blieck, Mechelen (BE); Tom Roger Lisette De Munck, Mechelen (BE); Caroline Martine Andrée Marie Joannesse, Mechelen (BE); Hans Kelgtermans, Mechelen (BE); Oscar Mammoliti, Mechelen (BE); Christel Jeanne Marie Menet, Mechelen (BE); Giovanni Alessandro Tricarico, Mechelen (BE); Steven Emiel Van der Plas, Mechelen (BE)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 14/271,080

(22) Filed: May 6, 2014

(65) Prior Publication Data
US 2015/0005275 A1 Jan. 1, 2015

(30) Foreign Application Priority Data

May 7, 2013 (GB) .................................. 1308137.7
Aug. 9, 2013 (BS) .............................................. 2523
Oct. 10, 2013 (GB) .................................. 1317932.0

(51) Int. Cl.
C07D 409/12 (2006.01)
C07D 417/12 (2006.01)
C07D 487/04 (2006.01)
C07D 333/36 (2006.01)
C07D 409/14 (2006.01)
C07D 413/12 (2006.01)
C07D 333/38 (2006.01)

(52) U.S. Cl.
CPC ............ *C07D 487/04* (2013.01); *C07D 333/36* (2013.01); *C07D 333/38* (2013.01); *C07D 409/12* (2013.01); *C07D 409/14* (2013.01); *C07D 413/12* (2013.01); *C07D 417/12* (2013.01)

(58) Field of Classification Search
CPC .. C07D 487/04; C07D 333/34; C07D 333/36; C07D 333/38; C07D 409/12; C07D 409/14
See application file for complete search history.

(56) References Cited

U.S. PATENT DOCUMENTS

2006/0293307 A1 12/2006 Mehta et al.
2007/0010537 A1 1/2007 Hamamura et al.
2007/0213325 A1 9/2007 Cee et al.
2010/0331338 A1 12/2010 Burgdorf et al.

FOREIGN PATENT DOCUMENTS

| | | |
|---|---|---|
| BS | 2523 | 11/2013 |
| WO | 9918099 A1 | 4/1999 |
| WO | 2007139795 A1 | 12/2007 |
| WO | 2010013011 A1 | 2/2010 |
| WO | 2010123933 A1 | 10/2010 |
| WO | 2014010737 A1 | 1/2014 |

OTHER PUBLICATIONS

Byrn, Stephen. Solid-State Chemistry of Drugs, 2nd ed., (1999) Chapter 11 Hydrates and Solvates/hydrates, 233-247.*
Morissette, Sherry. Adv. Drug Delivery Rev. (2004), 56, 275-300.*
Rouhi, A. Maureen. Chem. & Eng. News, (2003), 81(8), 32-35.*
Bobadilla, J. et al., "Cystic Fibrosis: A Worldwide Analysis of CFTR Mutations—Correlation with Incidence Data and Application to Screening," Human Mutation 2002, 19(6): 575-606.
Bundgard, H., Editor of Design of Prodrugs, 1985, Elsevier, Amsterdam, pp. 7-9, 21-24.
Conrath, K. et al., "Novel potentiators for treating Cystic Fibrosis," 27th Annual North American Cystic Fibrosis Conference NACFC-2013, Poster #41 (1 page).
Fulcher, M.L. et al., "Well-differentiated human airway epithelial cell cultures," Methods in Molecular Medicine 2005, 107: 183-206.
Galietta, L.J. et al., "Green fluorescent protein-based halide indicators with improved chloride and iodide affinities," FEBS Letters 2001, 499(3): 220-224.
Gennaro, A. R. Editor, "Pharmaceutical Preparations and their Manufacture" Remington's Pharmaceutical Sciences, 18th Edition, 1990, Mack Publishing Company, Easton, PA (Table of Contents only).
Green, T.W. et al., Protecting Groups in Organic Synthesis, 1991, 2nd Edition, John Wiley & Sons, New York (Table of Contents only).
International Search Report and Written Opinion for PCT/EP2014/001202, mailed Jul. 7, 2011 (9 pages).
Kerem, B. et al., "Identification of the Cystic Fibrosis gene: Genetic Analysis," Science, New Series 1989, 245(4922): 1073-1080.

(Continued)

*Primary Examiner* — Golam M M Shameem
*Assistant Examiner* — Laura Daniel
(74) *Attorney, Agent, or Firm* — Quarles & Brady LLP

(57) ABSTRACT

The present invention discloses compounds according to Formula I:

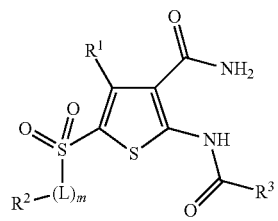

wherein $R^1$, $R^2$, $R^3$, L, and the subscript m are as defined herein. The present invention relates to compounds and their use in the treatment of cystic fibrosis, methods for their production, pharmaceutical compositions, and methods of treatment using the same, for the treatment of cystic fibrosis by administering a compound of the invention.

21 Claims, No Drawings

(56) References Cited

OTHER PUBLICATIONS

Morello, J-P. et al., "Pharmacological chaperones: a new twist on receptor folding," Trends in Pharmacological Sciences 2000, 21(12): 466-469.

Nagai, T. et al., "A variant of yellow fluorescent protein with fast and efficient maturation for cell-biological applications," Nature Biotechnology 2002, 20(1): 87-90.

Pasyl, E.A. et al., "Mutant (ΔF508) Cystic Fibrosis Transmembrane Conductance Regulator Cl⁻ Channel is Functional when Retained in Endoplasmic Reticulum of Mammalian Cells," Journal of Biological Chemistry 1995, 270(21): 12347-12350.

Quinton, P.M. "Cystic fibrosis: a disease in electrolyte transport," FASEB Journal 1990, 4(10): 2709-2717.

Rowe, S.M. et al. "Cystic Fibrosis Transmembrane Regulator Correctors and Potentiators," Cold Spring Harbor Perspectives in Medicine 2013, (3): a009761.

Shastry, B. S., "Neurodegenerative disorders of protein aggregation," Neurochemistry International 2003, 43(1): 1-7.

Zhang, W. et al., "Recent advances and new perspectives in targeting CFTR for therapy of cystic fibrosis and enterotoxin-induced secretory diarrheas," Future Medicinal Chemistry 2012, 4(3): 329-345.

* cited by examiner

COMPOUNDS AND PHARMACEUTICAL COMPOSITIONS THEREOF FOR THE TREATMENT OF CYSTIC FIBROSIS

CROSS-REFERENCE TO RELATED APPLICATIONS

This application claims priority under 35 U.S.C. §119 to United Kingdom Application No. GB1308137.7 filed May 7, 2013; United Kingdom Application No. GB1317932.0 filed Oct. 10, 2013; and Bahaman Application No. 2523 filed Aug. 9, 2013. The contents of each of these applications are incorporated by reference.

FIELD OF THE INVENTION

The present invention relates to compounds that are modulators of cystic fibrosis Transmembrane Conductance regulator (CFTR), and their use in the treatment of cystic fibrosis. The present invention also provides methods for the production of a compound of the invention, pharmaceutical compositions comprising a compound of the invention, methods for the prophylaxis treatment of cystic fibrosis by administering a compound of the invention.

BACKGROUND OF THE INVENTION

ABC transporters are a family of homologous membrane transporter proteins regulating the transport of a wide variety of pharmacological agents (for example drugs, xenobiotics, anions, etc.) that bind and use cellular adenosine triphosphate (ATP) for their specific activities. Some of these transporters were found to defend malignant cancer cells against chemotherapeutic agents, acting as multidrug resistance proteins (like the MDR1-P glycoprotein, or the multidrug resistance protein, MRP 1). So far, 48 ABC transporters grouped into 7 families based on their sequence identity and function have been identified.

ABC transporters provide protection against harmful environmental compounds by regulating a variety of important physiological roles within the body, and therefore represent important potential drug targets for the treatment of diseases associated with transporter defects, outwards cell drug transport, and other diseases in which modulation of ABC transporter activity may be beneficial.

The cAMP/ATP-mediated anion channel, CFTR is one member of the ABC transporter family commonly associated with diseases, which is expressed in a variety of cells types, including absorptive and secretory epithelia cells, where it regulates anion flux across the membrane, as well as the activity of other ion channels and proteins. The activity of CFTR in epithelial cells is essential for the maintenance of electrolyte transport throughout the body, including respiratory and digestive tissue.

The gene encoding CFTR has been identified and sequenced (Kerem, et al., 1989). CFTR comprises about 1480 amino acids that encode a protein made up of a tandem repeat of transmembrane domains, each containing six transmembrane helices and a nucleotide binding domain. The pair of transmembrane domains is linked by a large, polar, regulatory (R)-domain with multiple phosphorylation sites that regulate channel activity and cellular trafficking.

Cystic fibrosis is caused by a defect in this gene which induces mutations in CFTR. Cystic fibrosis is the most common fatal genetic disease in humans, and affects ~0.04% of white individuals (Bobadilla, Macek, Fine, & Farrell, 2002), for example, in the United States, about one in every 2,500 infants is affected, and up to 10 million people carry a single copy of the defective gene without apparent ill effects; moreover subjects bearing a single copy of the gene exhibit increased resistance to cholera and to dehydration resulting from diarrhea. This effect might explain the relatively high frequency of the CF gene within the population.

In contrast, individuals with two copies of the CF associated gene suffer from the debilitating and fatal effects of CF, including chronic lung infections.

In patients afflicted with cystic fibrosis, mutations in endogenous respiratory epithelial CFTR fails to confer chloride and bicarbonate permeability to epithelial cells in lung and other tissues, thus leading to reduced apical anion secretion and disruptions of the ion and fluid transport. This decrease in anion transport causes an enhanced mucus and pathogenic agent accumulation in the lung triggering microbial infections that ultimately cause death in CF patients.

Beyond respiratory disease, CF patients also suffer from gastrointestinal problems and pancreatic insufficiency that result in death if left untreated. Furthermore, female subjects afflicted with cystic fibrosis suffer from decreased fertility, whilst males with are infertile.

A variety of disease causing mutations has been identified through sequence analysis of the CFTR gene of CF chromosomes (Kerem, et al., 1989). ΔF508-CFTR, the most common CF mutation (present in at least 1 allele in ~90% of CF patients) and occurring in approximately 70% of the cases of cystic fibrosis, contains a single amino acid deletion of phenylalanine 508. This deletion prevents the nascent protein from folding correctly, which protein in turn cannot exit the endoplasmic reticulum (ER) and traffic to the plasma membrane, and then is rapidly degraded. As a result, the number of channels present in the membrane is far less than in cells expressing wild-type CFTR. In addition to impaired trafficking, the mutation results in defective channel gating. Indeed, even if ΔF508-CFTR is allowed to reach the cell plasma membrane by low-temperature (27° C.) rescue where it can function as a cAMP-activated chloride channel, its activity is decreased significantly compared with WT-CFTR (Pasyl & Foskett, 1995).

Other mutations with lower incidence have also been identified that alter the channel regulation or the channel conductance. In case of the channel regulation mutants, the mutated protein is properly trafficked and localized to the plasma membrane but either cannot be activated or cannot function as a chloride channel (e.g. missense mutations located within the nucleotide binding domains), examples of these mutations are G551D, G178R, G1349D. Mutations affecting chloride conductance have a CFTR protein that is correctly trafficked to the cell membrane but that generates reduced chloride-flow (e.g. missense mutations located within the membrane-spanning domain), examples of these mutations are R117H, R334W.

In addition to cystic fibrosis, CFTR activity modulation may be beneficial for other diseases not directly caused by mutations in CFTR, such as, for example, chronic obstructive pulmonary disease (COPD), dry eye disease, and Sjogren's Syndrome.

COPD is characterized by a progressive and non reversible airflow limitation, which is due to mucus hypersecretion, bronchiolitis, and emphysema. A potential treatment of mucus hypersecretion and impaired mucociliary clearance that is common in COPD could consist in using activators of mutant or wild-type CFTR. In particular, the anion secretion increase across CFTR may facilitate fluid transport into the airway surface liquid to hydrate the mucus and optimize periciliary fluid viscosity. The resulting enhanced mucociliary clearance would help in reducing the symptoms associated with COPD.

Dry eye disease is characterized by a decrease in tear production and abnormal tear film lipid, protein and mucin profiles. Many factors may cause dry eye disease, some of which include age, arthritis, Lasik eye surgery, chemical/thermal burns, medications, allergies, and diseases, such as cystic fibrosis and Sjogrens's syndrome. Increasing anion secretion via CFTR could enhance fluid transport from the corneal endothelial cells and secretory glands surrounding the eye, and eventually improve corneal hydration, thus helping to alleviate dry eye disease associated symptoms. Sjogrens's syndrome is an autoimmune disease where the immune system harms moisture-producing glands throughout the body, including the eye, mouth, skin, respiratory tissue, liver, vagina, and gut. The ensuing symptoms, include, dry eye, mouth, and vagina, as well as lung disease. Sjogrens's syndrome is also associated with rheumatoid arthritis, systemic lupus, systemic sclerosis, and polymypositis/dermatomyositis. The cause of the disease is believed to lie in defective protein trafficking, for which treatment options are limited. As a consequence, modulation of CFTR activity may help hydrating the various organs afflicted by the disease and help to elevate the associated symptoms.

In addition to CF, the defective protein trafficking induced by the ΔF508-CFTR has been shown to be the underlying basis for a wide range of other diseases, in particular the defective functioning of the endoplasmic reticulum (ER) may either prevent the CFTR protein to exit the cell, and/or the misfolded protein is degraded (Shastry, 2003), (Morello J P, Petaja-Repo, Bichet, & Bouvier, 2000), (Zhang, Fujii, & Naren, 2012).

A number of genetic diseases are associated with a defective ER processing equivalent to the defect observed with CFTR in CF such as glycanosis CDG type 1, hereditary emphysema (α-1-antitrypsin (PiZ variant)), congenital hyperthyroidism, osteogenesis imperfecta (Type I, II, or IV procollagen), hereditary hypofibrinogenemia (fibrinogen), ACT deficiency (α-1-antichymotrypsin), diabetes insipidus (DI), neurophyseal DI (vasopvessin hormoneN2-receptor), neprogenic DI (aquaporin II), Charcot-Marie Tooth syndrome (peripheral myelin protein 22), Perlizaeus-Merzbacher disease, neurodegenerative diseases such as Alzheimer's disease (APP and presenilins), Parkinson's disease, amyotrophic lateral sclerosis, progressive supranuclear plasy, Pick's disease, several polyglutamine neurological disorders such as Huntington's disease, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (prion protein processing defect), Fabry disease (lysosomal a-galactosidase A), Straussler-Scheinker syndrome, chronic obstructive pulmonary disease (COPD), dry eye disease, and Sjogren's Syndrome.

In addition to up-regulation of the activity of CFTR, anion secretion reduction by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Regardless of the cause, excessive chloride transport is seen in all diarrhea, and results in dehydration, acidosis, impaired growth and death. Acute and chronic diarrheas remain a major medical problem worldwide, and are a significant factor in malnutrition, leading to death in children of less than five years old (5,000,000 deaths/year). Furthermore, in patients with chronic inflammatory bowel disease (IBD) and/or acquired immunodeficiency syndrome (AIDS), diarrhea is a dangerous condition.

Accordingly, there is a need for novel compounds able to modulate CFTR. In particular, the present invention discloses compounds that may act as CFTR modulators for the treatment of cystic fibrosis. The present invention also provides methods for the production of these compounds, pharmaceutical compositions comprising these compounds and methods for the treatment of cystic fibrosis by administering the compounds of the invention.

SUMMARY OF THE INVENTION

The present invention is based on the identification of novel compounds, and their ability to act as CFTR modulators and that may be useful for the treatment of cystic fibrosis. The present invention also provides methods for the production of these compounds, pharmaceutical compositions comprising these compounds and methods for the treatment of cystic fibrosis by administering compounds of the invention.

Accordingly, in one aspect of the invention, compounds of the invention are provided having a Formula (I):

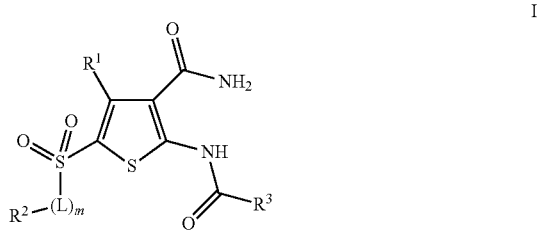

wherein
$R^1$ is H, —$CH_3$, —$CF_3$, or cyclopropyl;
L is —$NR^4$—;
the subscript m is 0, or 1;
$R^2$ is
  $C_{1-4}$ alkyl (optionally substituted with one or more independently selected $R^5$ groups),
  $C_{3-7}$ cycloalkyl,
  4-10 membered monocyclic, bridged-, spiro-, or fused bicyclic heterocycloalkyl comprising one or more heteroatoms independently selected from N, O, and S, and optionally substituted with one or more independently selected $R^a$ groups,
  5-6 membered monocyclic heterocycloalkenyl comprising one or more heteroatoms independently selected from N, O, and S, and optionally substituted with one or more independently selected $R^a$ groups,
  $C_{6-10}$ mono or bicyclic aryl optionally substituted with one or more independently selected $R^b$, or
  5-10 membered monocyclic or fused bicyclic heteroaryl, comprising one or more heteroatoms independently selected from N, O, and S, and optionally substituted with one or more independently selected $R^b$;
$R^3$ is
  $C_{3-7}$ cycloalkyl optionally substituted with one or more independently selected $R^c$ groups,
  4-7 membered monocyclic heterocycloalkyl comprising one or more heteroatoms independently selected from O, and S, and optionally substituted with $R^c$,
  $C_{6-10}$ mono or bicyclic aryl optionally substituted with one or more independently selected $R^d$ groups, phenyl fused to a 5-6 membered heterocycloalkyl comprising one or more heteroatoms independently selected from N, O, and S, and optionally substituted with one or more independently selected $R^d$ groups, phenyl fused to a $C_{5-6}$ cycloalkyl, and optionally substituted with one or more independently selected $R^d$ groups, 5-10 membered mono or fused bicyclic heteroaryl comprising one or more heteroatoms independently selected from N, O, and S, and optionally substituted with one or more independently selected $R^d$ groups, 5-6 membered monocyclic heteroaryl comprising one or more heteroatoms independently selected from N, O, and S, fused to a 5-6 membered heterocycloalkyl comprising one or more heteroatoms independently selected from N, O, and S, and optionally substituted with one or more independently selected $R^d$ groups, 5-6 membered monocyclic heteroaryl comprising one or more heteroatoms independently selected from N, O, and S, fused to a $C_{5-6}$ cycloalkyl, optionally substituted with one or more independently selected $R^d$ groups, $C_{2-6}$ alkenyl, $C_{3-6}$ alkyl, or $C_{1-6}$ alkyl substituted with one or more independently selected $R^e$ groups;

$R^4$ is $C_{1-6}$ alkyl (optionally substituted with one or more independently selected $R^6$ groups), or $C_{3-7}$ cycloalkyl;

each $R^5$ is independently selected from halo,

OH,

—CN, $C_{1-4}$ alkoxy,

—$NR^{8e}R^{8f}$, $C_{3-7}$ cycloalkyl, 6 membered mono or fused bicyclic heteroaryl comprising one or more heteroatoms independently selected from N, O, and S, and phenyl optionally substituted with one or more independently selected halo, $C_{1-4}$ alkyl optionally substituted with one or more independently selected halo, or $C_{1-4}$ alkoxy;

each $R^6$, is independently selected from halo,

OH,

—CN,

—$NR^{8g}R^{8h}$, and $C_{1-4}$ alkoxy;

each $R^a$ is selected from halo,

CN, oxo, $C_{1-4}$ alkyl (optionally substituted with one or more independently selected $R^{7a}$), $C_{1-4}$ alkoxy (optionally substituted with one or more independently selected $R^{7a}$), —C(=O)O—$C_{1-4}$ alkyl, phenyl, 5-10 membered mono, or fused bicyclic heteroaryl comprising one or more heteroatoms independently selected from N, O, or S, and optionally substituted with one or more independently selected $C_{1-4}$ alkyl, and —$NR^{8a}R^{8b}$;

each $R^h$ is selected from halo,

—CN, $C_{1-4}$ alkyl (optionally substituted with one or more independently selected $R^{7b}$), $C_{1-4}$ alkoxy (optionally substituted with one or more independently selected $R^{7b}$), —OC(=O)$C_{1-4}$ alkyl, and —$NR^{8c}R^{8d}$;

each $R^c$ is selected from halo,

OH,

—CN, oxo, $C_{1-4}$ alkyl (optionally substituted with one or more independently selected $R^{7c}$), $C_{1-4}$ alkoxy (optionally substituted with one or more independently selected $R^{7c}$), phenyl (optionally substituted with one or more independently selected halo, $C_{1-4}$ alkyl, $C_{1-4}$ alkoxy, —CN, or —$NR^{9a}R^{9b}$), and 5-6 membered mono, or heteroaryl comprising one or more heteroatoms independently selected from N, O, or S (optionally substituted with one or more independently selected halo, $C_{1-4}$ alkyl, $C_{1-4}$ alkoxy, CN, —$NR^{9c}R^{9d}$);

each $R^d$ is selected from halo,

—CN,

—OH, $C_{1-4}$ alkyl (optionally substituted with one or more independently selected $R^{7d}$), $C_{1-4}$ alkoxy (optionally substituted with one or more independently selected $R^{7d}$), $C_{3-7}$ cycloalkyl, 5-10 membered mono or fused bicyclic heteroaryl comprising one or more heteroatoms independently selected from N, O, or S, and —NH-Phenyl;

each $R^e$ is selected from halo,

OH,

—CN, $C_{1-4}$ alkoxy (optionally substituted with one or more independently selected $R^{7e}$), $C_{3-7}$ cycloalkyl, phenyl (optionally substituted with one or more independently selected halo, $C_{1-4}$ alkyl, $C_{1-4}$ alkoxy, CN, and —$NR^{9e}R^{9f}$), and 5-6 membered mono, or heteroaryl comprising one or more heteroatoms independently selected from N, O, and S (optionally substituted with one or more independently selected halo, $C_{1-4}$ alkyl, $C_{1-4}$ alkoxy, CN, and —$NR^{9g}R^{9h}$);

each $R^{7a}$, $R^{7b}$, $R^{7c}$, $R^{7d}$, and $R^{7e}$ is independently selected from halo,

OH,

—CN,

—$NR^{8i}R^{8j}$, and $C_{1-4}$ alkoxy;

each $R^{8a}$, $R^{8b}$, $R^{8c}$, $R^{8d}$, $R^{8e}$, $R^{8f}$, $R^{8g}$, $R^{8h}$, $R^{8i}$, or $R^{8j}$ is independently selected from H, and $C_{1-4}$ alkyl; and each $R^{9a}$, $R^{9b}$, $R^{9c}$, $R^{9d}$, $R^{9e}$, $R^{9f}$, $R^{9g}$, or $R^{9h}$ is independently selected from H, and $C_{1-4}$ alkyl.

In another aspect of the invention, compounds of the invention are provided having a Formula (I):

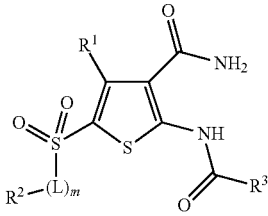

wherein
R$^1$ is H, —CH$_3$, —CF$_3$, or cyclopropyl;
L is —NR$^4$—;
the subscript m is 0, or 1;
R$^2$ is
  C$_{1-4}$ alkyl (optionally substituted with one or more independently selected R$^5$ groups),
  C$_{3-7}$ cycloalkyl,
  4-10 membered monocyclic, bridged-, spiro-, or fused bicyclic heterocycloalkyl comprising one or more heteroatoms independently selected from N, O, and S, and optionally substituted with one or more independently selected R$^a$ groups,
  5-6 membered monocyclic heterocycloalkenyl comprising one or more heteroatoms independently selected from N, O, and S, and optionally substituted with one or more independently selected R$^a$ groups,
  C$_{6-10}$ mono or bicyclic aryl optionally substituted with one or more independently selected R$^b$, or
  5-10 membered monocyclic or fused bicyclic heteroaryl, comprising one or more heteroatoms independently selected from N, O, and S, and optionally substituted with one or more independently selected R$^b$;
R$^3$ is
  C$_{3-7}$ cycloalkyl optionally substituted with one or more independently selected R$^c$ groups,
  4-7 membered monocyclic heterocycloalkyl comprising one or more heteroatoms independently selected from O, and S, and optionally substituted with R$^c$,
  C$_{6-10}$ mono or bicyclic aryl optionally substituted with one or more independently selected R$^d$ groups,
  5-10 membered mono or fused bicyclic heteroaryl comprising one or more heteroatoms independently selected from N, O, and S, and optionally substituted with one or more independently selected R$^d$ groups,
  C$_{3-6}$ alkyl, or
  C$_{1-6}$ alkyl substituted with one or more independently selected R$^e$ groups;
R$^4$ is
  C$_{1-6}$ alkyl (optionally substituted with one or more independently selected R$^6$ groups), or
  C$_{3-7}$ cycloalkyl;
each R$^5$ is independently selected from
  halo,
  OH,
  —CN,
  C$_{1-4}$ alkoxy,
  —NR$^{8e}$R$^{8f}$,
  C$_{3-7}$ cycloalkyl,
  6 membered mono or fused bicyclic heteroaryl comprising one or more heteroatoms independently selected from N, O, and S, and
  phenyl optionally substituted with one or more independently selected
    halo,
    C$_{1-4}$ alkyl optionally substituted with one or more independently selected halo, or
    C$_{1-4}$ alkoxy;
each R$^6$, is independently selected from
  halo,
  OH,
  —CN,
  —NR$^{8g}$R$^{8h}$, and
  C$_{1-4}$ alkoxy;
each R$^a$ is selected from
  halo,
  CN,
  oxo,
  C$_{1-4}$ alkyl (optionally substituted with one or more independently selected R$^{7a}$),
  C$_{1-4}$ alkoxy (optionally substituted with one or more independently selected R$^{7a}$),
  —C(=O)O—C$_{1-4}$ alkyl,
  phenyl,
  5-10 membered mono, or fused bicyclic heteroaryl comprising one or more heteroatoms independently selected from N, O, or S, and optionally substituted with one or more independently selected C$_{1-4}$ alkyl, and
  —NR$^{8a}$R$^{8b}$;
each R$^b$ is selected from
  halo,
  —CN,
  C$_{1-4}$ alkyl (optionally substituted with one or more independently selected R$^{7b}$),
  C$_{1-4}$ alkoxy (optionally substituted with one or more independently selected R$^{7b}$), and
  —NR$^{8c}$R$^{8d}$;
each R$^c$ is selected from
  halo,
  OH,
  —CN,
  oxo,
  C$_{1-4}$ alkyl (optionally substituted with one or more independently selected R$^{7c}$),
  C$_{1-4}$ alkoxy (optionally substituted with one or more independently selected R$^{7c}$),
  phenyl (optionally substituted with one or more independently selected halo, C$_{1-4}$ alkyl, C$_{1-4}$ alkoxy, —CN, or —NR$^{9a}$R$^{9b}$), and
  5-6 membered mono, or heteroaryl comprising one or more heteroatoms independently selected from N, O, or S (optionally substituted with one or more independently selected halo, C$_{1-4}$ alkyl, C$_{1-4}$ alkoxy, CN, —NR$^{9c}$R$^{9d}$);
each R$^d$ is selected from
  halo,
  —CN,
  —OH,
  C$_{1-4}$ alkyl (optionally substituted with one or more independently selected R$^{7d}$),
  C$_{1-4}$ alkoxy (optionally substituted with one or more independently selected R$^{7d}$),
  C$_{3-7}$ cycloalkyl,
  5-10 membered mono or fused bicyclic heteroaryl comprising one or more heteroatoms independently selected from N, O, or S, and
  —NH-Phenyl;
each R$^e$ is selected from
  halo,
  OH, —CN,
C$_{1-4}$ alkoxy (optionally substituted with one or more independently selected R$^{7e}$),
phenyl (optionally substituted with one or more independently selected halo, C$_{1-4}$ alkyl, C$_{1-4}$ alkoxy, CN, and —NR$^{9e}$R$^{9f}$), and
5-6 membered mono, or heteroaryl comprising one or more heteroatoms independently selected from N, O, and S (optionally substituted with one or more independently selected halo, C$_{1-4}$ alkyl, C$_{1-4}$ alkoxy, CN, and —NR$^{9g}$R$^{9h}$);

each R$^{7a}$, R$^{7b}$, R$^{7c}$, R$^{7d}$, and R$^{7e}$ is independently selected from
halo,
OH,
—CN,
—NR$^{8i}$R$^{8j}$, and
C$_{1-4}$ alkoxy;
each R$^{8a}$, R$^{8b}$, R$^{8c}$, R$^{8d}$, R$^{8e}$, R$^{8f}$, R$^{8g}$, R$^{8h}$, R$^{8i}$, or R$^{8j}$ is independently selected from H, and C$_{1-4}$ alkyl; and
each R$^{9a}$, R$^{9b}$, R$^{9c}$, R$^{9d}$, R$^{9e}$, R$^{9f}$, R$^{9g}$, or R$^{9h}$ is independently selected from H, and C$_{1-4}$ alkyl.

In a particular aspect, the compounds of the invention are provided for use in the treatment of cystic fibrosis. In a particular aspect, the compounds of the invention are provided for use in the treatment of cystic fibrosis caused by class I, II, III, IV, and/or VI mutations.

In a further aspect, the present invention provides pharmaceutical compositions comprising a compound of the invention, and a pharmaceutical carrier, excipient or diluent. In a particular aspect, the pharmaceutical composition may additionally comprise further therapeutically active ingredients suitable for use in combination with the compounds of the invention. In a more particular aspect, the further therapeutically active ingredient is an agent for the treatment of cystic fibrosis.

Moreover, the compounds of the invention, useful in the pharmaceutical compositions and treatment methods disclosed herein, are pharmaceutically acceptable as prepared and used.

In a further aspect of the invention, this invention provides a method of treating a mammal, in particular humans, afflicted with a condition selected from among those listed herein, and particularly cystic fibrosis, which method comprises administering an effective amount of the pharmaceutical composition or compounds of the invention as described herein.

The present invention also provides pharmaceutical compositions comprising a compound of the invention, and a suitable pharmaceutical carrier, excipient or diluent for use in medicine. In a particular aspect, the pharmaceutical composition is for use in the treatment of cystic fibrosis.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

It will be appreciated that compounds of the invention may be metabolized to yield biologically active metabolites.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Alkyl' means straight or branched aliphatic hydrocarbon with the number of carbon atoms specified. Particular alkyl groups have 1 to 8 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Alkoxy' refers to the group —OR$^{26}$ where R$^{26}$ is alkyl with the number of carbon atoms specified. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Alkylene' refers to divalent alkene radical groups having the number of carbon atoms specified, in particular having 1 to 6 carbon atoms and more particularly 1 to 4 carbon atoms which can be straight-chained or branched. This term is exemplified by groups such as methylene (—CH$_2$—), ethylene (—CH$_2$—CH$_2$—), or —CH(CH$_3$)— and the like.

'Alkenyl' refers to monovalent olefinically (unsaturated) hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$) and the like.

'Amino' refers to the radical —NH$_2$.

'Aryl' refers to a monovalent aromatic hydrocarbon group derived by the removal of one hydrogen atom from a single carbon atom of a parent aromatic ring system. In particular aryl refers to an aromatic ring structure, monocyclic or polycyclic, with the number of ring atoms specified. Specifically, the term includes groups that include from 6 to 10 ring members. Where the aryl group is a monocyclic ring system it preferentially contains 6 carbon atoms. Particularly aryl groups include phenyl, naphthyl, indenyl, and tetrahydronaphthyl.

'Cycloalkyl' refers to a non-aromatic hydrocarbyl ring structure, monocyclic or polycyclic, with the number of ring atoms specified. A cycloalkyl may have from 3 to 10 carbon atoms, and in particular from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 4, and particularly from 1 to 3 heteroatoms, more typically 1 or 2 heteroatoms, for example a single heteroatom.

'Heteroaryl' means an aromatic ring structure, monocyclic or polycyclic, that includes one or more heteroatoms independently selected from O, N and S and the number of ring atoms specified. In particular, the aromatic ring structure may have from 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g. adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

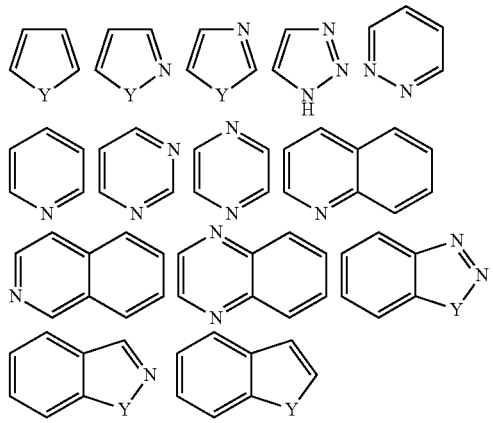

wherein each Y is selected from >C(=O), NH, O and S.

As used herein, the term 'heterocycloalkyl' means a stable non-aromatic ring structure, mono-cyclic or polycyclic, that includes one or more heteroatoms independently selected from O, N and S and the number of ring atoms specified. The non-aromatic ring structure may have from 4 to 10 ring members, and in particular from 4 to 7 ring members. A fused heterocyclic ring system may include carbocyclic rings and need only to include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran, tetrahydropyran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

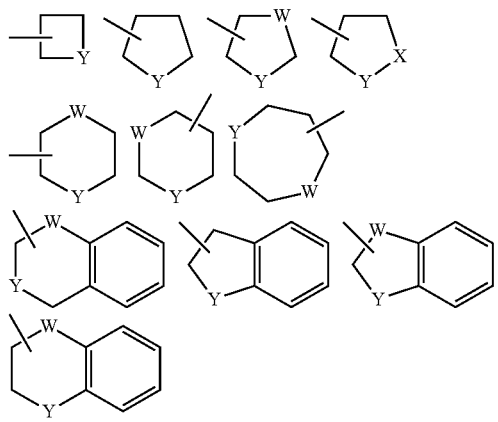

wherein each W is selected from CH$_2$, NH, O and S; and each Y is selected from NH, O, C(=O), SO$_2$, and S.

As used herein, the term 'heterocycloalkenyl' means a 'heterocycloalkyl', wherein one bond of the ring is reduced, thus the ring comprises a double bond. Particular examples of heterocycloalkenyl groups are shown in the following illustrative examples:

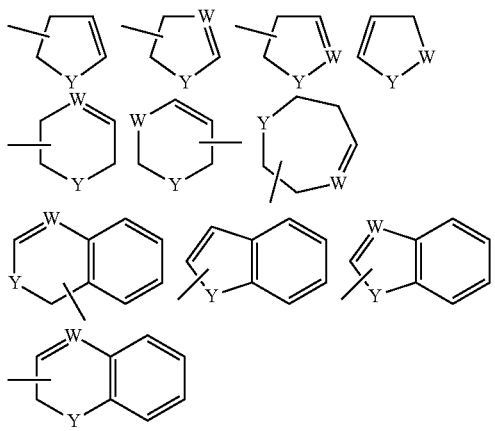

wherein each W is selected from CH$_2$, NH, O and S; and each Y is selected from NH, O, C(=O), SO$_2$, and S.

'Hydroxyl' refers to the radical —OH.

'Oxo' refers to the radical =O.

'Substituted' refers to a group in which one or more hydrogen atoms are each independently replaced with the same or different substituent(s).

'Sulfo' or 'sulfonic acid' refers to a radical such as —SO$_3$H.

'Thiol' refers to the group —SH.

As used herein, term 'substituted with one or more' refers to one to four substituents. In one embodiment it refers to one to three substituents. In further embodiments it refers to one or two substituents. In a yet further embodiment it refers to one substituent.

'Thioalkoxy' refers to the group —SR$^{26}$ where R$^{26}$ has the number of carbon atoms specified and particularly C$_1$-C$_8$ alkyl. Particular thioalkoxy groups are thiomethoxy, thioethoxy, n-thiopropoxy, isothiopropoxy, n-thiobutoxy, tert-thiobutoxy, sec-thiobutoxy, n-thiopentoxy, n-thiohexoxy, and 1,2-dimethylthiobutoxy. Particular thioalkoxy groups are lower thioalkoxy, i.e. with between 1 and 6 carbon atoms. Further particular alkoxy groups have between 1 and 4 carbon atoms.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalene sulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

'Compound(s) of the invention', and equivalent expressions, are meant to embrace compounds of the Formula (e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

As used herein, "Class I mutations" refers to mutations interfering with protein synthesis. They result in the introduction of a premature signal of termination of translation (stop codon) in the mRNA. The truncated proteins are unstable, rapidly degraded, so, the net effect is that there is no protein at the apical membrane. In particular, Class I mutation refers to p.Gly542X (G542X), W1282X, c.489+1G>T (621+1G>T), or c.579+1G>T (711+1G>T) mutation. More particularly, Class I mutation refers to G542X; or W1282X mutations.

As used herein, "Class II mutations" refers to mutations affecting the protein maturation. These lead to the production of a protein that cannot be correctly folded and trafficked to its site of function on the apical membrane. In particular, Class II mutation refers to p.Phe508del (F508del), p.Ile507del, or p.Asn1303Lys (N1303K) mutations. More particularly, Class II mutation refers to F508del or N1303K mutations.

As used herein, "Class III mutations" refers to mutations altering the channel regulation. The mutated protein is properly trafficked and localized to the plasma membrane but cannot be activated or function as a chloride channel (missenses located within the NBD). In particular, Class III mutation refers to p.Gly551Asp (G551D), G551S, R553G; G1349D; 51251N, G178R, S549N mutations. More particularly, Class III mutation refers to G551D, R553G, G1349D, 51251N, G178R, or S549N mutations.

As used herein, "Class IV mutations" refers to mutations affecting chloride conductance. The CFTR protein is correctly trafficked to the cell membrane but generates reduced Cl— flow or "gating defect" (most are missenses located within the membrane-spanning domain). In particular, Class IV mutation refers to p.Arg117His (R117H), R347P, or p.Arg334Trp (R334W) mutations.

As used herein, "Class V mutations" refers to mutations reducing the level of normally functioning CFTR at the apical membrane or "conductance defect" (partially aberrant splicing mutation or inefficient trafficking missenses). In particular, Class V mutation refers to c.1210-12T[5] (5T allele), c.3140-26A>G (3272-26A>G), c.3850-2477C>T (3849+10 kbC>T) mutations.

As used herein, "Class VI mutations" refers to mutations decreasing stability of CFTR present or affecting the regulation of other channels, resulting in inherent lability of the CFTR protein. In effect, although functional, the CFTR protein is unstable at cell surface and is rapidly removed and degraded by cell machinery. In particular, Class V mutation refers to Rescued F508del, 120del23, N287Y, 4326dellTC, or 4279insA mutations. More particularly, Class VI mutation refers to Rescued F508del mutations.

When ranges are referred to herein, for example but without limitation, $C_{1-8}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (Bundgard, H, 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_{1-8}$ alkyl, $C_{2-8}$ alkenyl, $C_{6-10}$ optionally substituted aryl, and ($C_{6-10}$ aryl)-($C_{1-4}$ alkyl) esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2H$ or D), carbon-13 ($^{13}C$), nitroGen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radio-isotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e. as (+) or (−)-isomers respectively). A chiral compound can exist as either individual enantiomer or as a mixture thereof A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

The Invention

The present invention is based on the identification of novel compounds, that they may be useful for the treatment of cystic fibrosis.

The present invention also provides methods for the production of these compounds, pharmaceutical compositions comprising these compounds and methods for the treatment of cystic fibrosis by administering the compounds of the invention.

Accordingly, in one aspect of the invention, compounds of the invention are provided having a Formula (I):

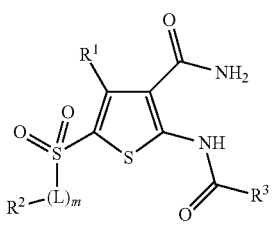

I wherein
$R^1$ is H, —$CH_3$, —$CF_3$, or cyclopropyl;
L is —$NR^4$—;
the subscript m is 0, or 1;
$R^2$ is
  $C_{1-4}$ alkyl (optionally substituted with one or more independently selected $R^5$ groups),
  $C_{3-7}$ cycloalkyl,
  4-10 membered monocyclic, bridged-, spiro-, or fused bicyclic heterocycloalkyl comprising one or more heteroatoms independently selected from N, O, and S, and optionally substituted with one or more independently selected $R^a$ groups,
  5-6 membered monocyclic heterocycloalkenyl comprising one or more heteroatoms independently selected from N, O, and S, and optionally substituted with one or more independently selected $R^a$ groups,
  $C_{6-10}$ mono or bicyclic aryl optionally substituted with one or more independently selected $R^b$, or
  5-10 membered monocyclic or fused bicyclic heteroaryl, comprising one or more heteroatoms independently selected from N, O, and S, and optionally substituted with one or more independently selected $R^b$;
$R^3$ is
  $C_{3-7}$ cycloalkyl optionally substituted with one or more independently selected $R^c$ groups,
  4-7 membered monocyclic heterocycloalkyl comprising one or more heteroatoms independently selected from O, and S, and optionally substituted with $R^c$,
  $C_{6-10}$ mono or bicyclic aryl optionally substituted with one or more independently selected $R^d$ groups,
  phenyl fused to a 5-6 membered heterocycloalkyl comprising one or more heteroatoms independently selected from N, O, and S, and optionally substituted with one or more independently selected $R^d$ groups,
  phenyl fused to a $C_{5-6}$ cycloalkyl comprising one or more heteroatoms independently selected from N, O, and S, and optionally substituted with one or more independently selected $R^d$ groups,
  5-10 membered mono or fused bicyclic heteroaryl comprising one or more heteroatoms independently selected from N, O, and S, and optionally substituted with one or more independently selected $R^d$ groups,
  5-6 membered monocyclic heteroaryl comprising one or more heteroatoms independently selected from N, O, and S, fused to a 5-6 membered heterocycloalkyl comprising one or more heteroatoms independently selected from N, O, and S, and optionally substituted with one or more independently selected $R^d$ groups,
  5-6 membered monocyclic heteroaryl comprising one or more heteroatoms independently selected from N, O, and S, fused to a $C_{5-6}$ cycloalkyl comprising one or more heteroatoms independently selected from N, O, and S, and optionally substituted with one or more independently selected $R^d$ groups,
  $C_{2-6}$ alkenyl,
  $C_{3-6}$ alkyl, or
  $C_{1-6}$ alkyl substituted with one or more independently selected $R^e$ groups;
$R^4$ is
  $C_{1-6}$ alkyl (optionally substituted with one or more independently selected $R^6$ groups), or
  $C_{3-7}$ cycloalkyl,
each $R^5$ is independently selected from
  halo,
  OH,
  —CN,
  $C_{1-4}$ alkoxy,
  —$NR^{8e}R^{8f}$,
  $C_{3-7}$ cycloalkyl,
  6 membered mono or fused bicyclic heteroaryl comprising one or more heteroatoms independently selected from N, O, and S, and phenyl optionally substituted with one or more independently selected
  halo,
  $C_{1-4}$ alkyl optionally substituted with one or more independently selected halo, or
  $C_{1-4}$ alkoxy;
each $R^6$, is independently selected from
  halo,
  OH,
  —CN,
  —NR$^{8g}$R$^{8h}$, and
  $C_{1-4}$ alkoxy;
each $R^a$ is selected from
  halo,
  CN,
  oxo,
  $C_{1-4}$ alkyl (optionally substituted with one or more independently selected $R^{7a}$),
  $C_{1-4}$ alkoxy (optionally substituted with one or more independently selected $R^{7a}$),
  —C(=O)O—$C_{1-4}$ alkyl,
  phenyl,
  5-10 membered mono, or fused bicyclic heteroaryl comprising one or more heteroatoms independently selected from N, O, or S, and optionally substituted with one or more independently selected $C_{1-4}$ alkyl, and
  —NR$^{8a}$R$^{8b}$;
each $R^b$ is selected from
  halo,
  —CN,
  $C_{1-4}$ alkyl (optionally substituted with one or more independently selected $R^{7b}$),
  $C_{1-4}$ alkoxy (optionally substituted with one or more independently selected $R^{7b}$),
  —OC(=O)$C_{1-4}$ alkyl, and
  —NR$^{8c}$R$^{8d}$;
each $R^c$ is selected from
  halo,
  OH,
  —CN,
  oxo,
  $C_{1-4}$ alkyl (optionally substituted with one or more independently selected $R^{7c}$),
  $C_{1-4}$ alkoxy (optionally substituted with one or more independently selected $R^{7c}$),
  phenyl (optionally substituted with one or more independently selected halo, $C_{1-4}$ alkyl, $C_{1-4}$ alkoxy, —CN, or —NR$^{9a}$R$^{9b}$), and
  5-6 membered mono, or heteroaryl comprising one or more heteroatoms independently selected from N, O, or S (optionally substituted with one or more independently selected halo, $C_{1-4}$ alkyl, $C_{1-4}$ alkoxy, CN, —NR$^{9c}$R$^{9d}$);
each $R^d$ is selected from
  halo,
  —CN,
  —OH,
  $C_{1-4}$ alkyl (optionally substituted with one or more independently selected $R^{7d}$),
  $C_{1-4}$ alkoxy (optionally substituted with one or more independently selected $R^{7d}$),
  $C_{3-7}$ cycloalkyl,
  5-10 membered mono or fused bicyclic heteroaryl comprising one or more heteroatoms independently selected from N, O, or S, and
  —NH-Phenyl;
each $R^e$ is selected from
  halo,
  OH,
  —CN,
  $C_{1-4}$ alkoxy (optionally substituted with one or more independently selected $R^{7e}$),
  $C_{3-7}$ cycloalkyl,
  phenyl (optionally substituted with one or more independently selected halo, $C_{1-4}$ alkyl, $C_{1-4}$ alkoxy, CN, and —NR$^{9e}$R$^{9f}$), and
  5-6 membered mono, or heteroaryl comprising one or more heteroatoms independently selected from N, O, and S (optionally substituted with one or more independently selected halo, $C_{1-4}$ alkyl, $C_{1-4}$ alkoxy, CN, and —NR$^{9g}$R$^{9h}$);
each $R^{7a}$, $R^{7b}$, $R^{7c}$, $R^{7d}$, and $R^{7e}$ is independently selected from
  halo,
  OH,
  —CN,
  —NR$^{8i}$R$^{8j}$, and
  $C_{1-4}$ alkoxy;
each $R^{8a}$, $R^{8b}$, $R^{8c}$, $R^{8d}$, $R^{8e}$, $R^{8f}$, $R^{8g}$, $R^{8h}$, $R^{8i}$, or $R^{8j}$ is independently selected from H, and $C_{1-4}$ alkyl; and
each $R^{9a}$, $R^{9b}$, $R^{9c}$, $R^{9d}$, $R^{9e}$, $R^{9f}$, $R^{9g}$, or $R^{9b}$ is independently selected from H, and $C_{1-4}$ alkyl.

In another aspect of the invention, compounds of the invention are provided having a Formula (I):

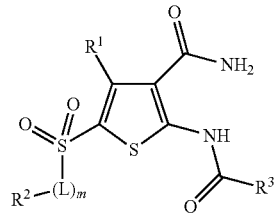

wherein
$R^1$ is H, —CH$_3$, —CF$_3$, or cyclopropyl;
L is —NR$^4$—;
the subscript m is 0, or 1;
$R^2$ is
  $C_{1-4}$ alkyl (optionally substituted with one or more independently selected $R^5$ groups),
  $C_{3-7}$ cycloalkyl,
  4-10 membered monocyclic, bridged-, spiro-, or fused bicyclic heterocycloalkyl comprising one or more heteroatoms independently selected from N, O, and S, and optionally substituted with one or more independently selected $R^a$ groups,
  5-6 membered monocyclic heterocycloalkenyl comprising one or more heteroatoms independently selected from N, O, and S, and optionally substituted with one or more independently selected $R^a$ groups,
  $C_{6-10}$ mono or bicyclic aryl optionally substituted with one or more independently selected $R^b$, or
  5-10 membered monocyclic or fused bicyclic heteroaryl, comprising one or more heteroatoms independently selected from N, O, and S, and optionally substituted with one or more independently selected $R^b$;
$R^3$ is
  $C_{3-7}$ cycloalkyl optionally substituted with one or more independently selected $R^c$ groups,
  4-7 membered monocyclic heterocycloalkyl comprising one or more heteroatoms independently selected from O, and S, and optionally substituted with $R^c$, $C_{6-10}$ mono or bicyclic aryl optionally substituted with one or more independently selected $R^d$ groups, 5-10 membered mono or fused bicyclic heteroaryl comprising one or more heteroatoms independently selected from N, O, and S, and optionally substituted with one or more independently selected $R^d$ groups, $C_{3-6}$ alkyl, or $C_{1-6}$ alkyl substituted with one or more independently selected $R^e$ groups;

$R^4$ is $C_{1-6}$ alkyl (optionally substituted with one or more independently selected $R^6$ groups), or $C_{3-7}$ cycloalkyl;

each $R^5$ is independently selected from halo,

OH,

—CN, $C_{1-4}$ alkoxy,

—$NR^{8e}R^{8f}$, $C_{3-7}$ cycloalkyl, 6 membered mono or fused bicyclic heteroaryl comprising one or more heteroatoms independently selected from N, O, and S, and phenyl optionally substituted with one or more independently selected halo, $C_{1-4}$ alkyl optionally substituted with one or more independently selected halo, or $C_{1-4}$ alkoxy;

each $R^6$, is independently selected from halo,

OH,

—CN,

—$NR^{8g}R^{8h}$, and $C_{1-4}$ alkoxy;

each $R^a$ is selected from halo,

CN, oxo, $C_{1-4}$ alkyl (optionally substituted with one or more independently selected $R^{7a}$), $C_{1-4}$ alkoxy (optionally substituted with one or more independently selected $R^{7a}$), —C(=O)O—$C_{1-4}$ alkyl, phenyl, 5-10 membered mono, or fused bicyclic heteroaryl comprising one or more heteroatoms independently selected from N, O, or S, and optionally substituted with one or more independently selected $C_{1-4}$ alkyl, and —$NR^{8a}R^{8b}$;

each $R^b$ is selected from halo,

—CN, $C_{1-4}$ alkyl (optionally substituted with one or more independently selected $R^{7b}$), $C_{1-4}$ alkoxy (optionally substituted with one or more independently selected $R^{7b}$), and —$NR^{8c}R^{8d}$;

each $R^c$ is selected from halo,

OH,

—CN, oxo, $C_{1-4}$ alkyl (optionally substituted with one or more independently selected $R^{7c}$), $C_{1-4}$ alkoxy (optionally substituted with one or more independently selected $R^{7c}$), phenyl (optionally substituted with one or more independently selected halo, $C_{1-4}$ alkyl, $C_{1-4}$ alkoxy, —CN, or —$NR^{9a}R^{9b}$), and 5-6 membered mono, or heteroaryl comprising one or more heteroatoms independently selected from N, O, or S (optionally substituted with one or more independently selected halo, $C_{1-4}$ alkyl, $C_{1-4}$ alkoxy, CN, —$NR^{9c}R^{9d}$);

each $R^d$ is selected from halo,

—CN,

—OH, $C_{1-4}$ alkyl (optionally substituted with one or more independently selected $R^{7d}$), $C_{1-4}$ alkoxy (optionally substituted with one or more independently selected $R^{7d}$), $C_{3-7}$ cycloalkyl, 5-10 membered mono or fused bicyclic heteroaryl comprising one or more heteroatoms independently selected from N, O, or S, and —NH-Phenyl;

each $R^e$ is selected from halo,

OH,

—CN, $C_{1-4}$ alkoxy (optionally substituted with one or more independently selected $R^{7e}$), phenyl (optionally substituted with one or more independently selected halo, $C_{1-4}$ alkyl, $C_{1-4}$ alkoxy, CN, and —$NR^{9e}R^{9f}$), and 5-6 membered mono, or heteroaryl comprising one or more heteroatoms independently selected from N, O, and S (optionally substituted with one or more independently selected halo, $C_{1-4}$ alkyl, $C_{1-4}$ alkoxy, CN, and —$NR^{9g}R^{9h}$);

each $R^{7a}$, $R^{7b}$, $R^{7c}$, $R^{7d}$, and $R^{7e}$ is independently selected from halo,

OH,

—CN,

—$NR^{8i}R^{8j}$, and $C_{1-4}$ alkoxy;

each $R^{8a}$, $R^{8b}$, $R^{8c}$, $R^{8d}$, $R^{8e}$, $R^{8f}$, $R^{8g}$, $R^{8h}$, $R^{8i}$ or $R^{8j}$ is independently selected from H, and $C_{1-4}$ alkyl; and each $R^{9a}$, $R^{9b}$, $R^{9c}$, $R^{9d}$, $R^{9e}$, $R^{9f}$, $R^{9g}$, or $R^{9h}$ is independently selected from H, and $C_{1-4}$ alkyl.

In one embodiment, a compound of the invention is according to Formula I, wherein the subscript m is 1.

In one embodiment, a compound of the invention is according to Formula I, wherein the compound is according to Formula II:

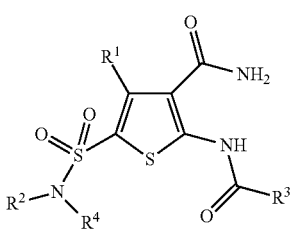

wherein $R^1$, $R^2$, $R^3$, and $R^4$ are as described above.

In one embodiment, a compound of the invention is according to Formula I or II, wherein $R^4$ is $C_{1-6}$ alkyl. In a particular embodiment, $R^4$ is —$CH_3$, —$CH_2$—$CH_3$, —$CH(CH_3)_2$, or —C(CH$_3$)$_3$. In a more particular embodiment, R$^4$ is —CH$_3$, —CH$_2$—CH$_3$, or —CH(CH$_3$)$_2$. In a most particular embodiment, R$^4$ is —CH$_3$, or —CH$_2$—CH$_3$.

In one embodiment, a compound of the invention is according to Formula I or II, wherein R$^4$ is C$_{1-6}$ alkyl substituted with one or more independently selected R$^6$ groups, and wherein R$^6$ is as described above. In another embodiment, R$^4$ is —CH$_3$, —CH$_2$—CH$_3$, —CH(CH$_3$)$_2$, or —C(CH$_3$)$_3$, each of which is substituted with one or more independently selected R$^6$ groups. In a particular embodiment, R$^4$ is C$_{1-6}$ alkyl substituted with one, two or three independently selected R$^6$ groups. In another particular embodiment, R$^4$ is —CH$_3$, —CH$_2$—CH$_3$, —CH(CH$_3$)$_2$, or —C(CH$_3$)$_3$, each of which is substituted with one, two or three independently selected R$^6$ groups. In a more particular embodiment, R$^4$ is C$_{1-6}$ alkyl substituted with one R$^6$ groups. In another more particular embodiment, R$^4$ is —CH$_3$, —CH$_2$—CH$_3$, —CH(CH$_3$)$_2$, or —C(CH$_3$)$_3$, each of which is substituted with one R$^6$ groups. In a particular embodiment, each R$^6$ is selected from F, Cl, OH, CN, —OCH$_3$, and —OCH$_2$CH$_3$. In another particular embodiment, R$^6$ is —NR$^{8g}$R$^{8h}$, wherein each R$^{8g}$ and R$^{8h}$ are as described above. In a more particular embodiment, R$^6$ is —NR$^{8g}$R$^{8h}$, wherein each R$^{8g}$ and R$^{8h}$ is selected from H, —CH$_3$, and —CH$_2$—CH$_3$. In a most particular embodiment, R$^4$ is selected from —CH$_2$—CN, —CH$_2$—CH$_2$—CN, —CH$_2$—CHF$_2$, —CH$_2$—CF$_3$, and —CH$_2$—CH$_2$—OCH$_3$.

In one embodiment, a compound of the invention is according to Formula I or III, wherein
R$^4$ is C$_{3-7}$ cycloalkyl. In a particular embodiment, R$^4$ is cyclopropyl, cyclobutyl, cyclopentyl, or cyclohexyl. In a more particular embodiment, R$^4$ is cyclopropyl.

In one embodiment, a compound of the invention is according to Formula III:

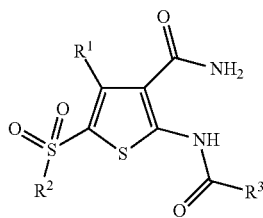

III wherein R$^1$, R$^2$, and R$^3$ are as described above.

In one embodiment, a compound of the invention is according to any one of Formula I-III, wherein R$^2$ is C$_{1-4}$ alkyl. In a particular embodiment, R$^2$ is —CH$_3$, —CH$_2$—CH$_3$, —CH(CH$_3$)$_2$, or —C(CH$_3$)$_3$.

In one embodiment, a compound of the invention is according to any one of Formula I-III, wherein R$^2$ is C$_{1-4}$ alkyl substituted with one or more independently selected R$^5$ groups, wherein R$^5$ is as described above. In another embodiment, R$^2$ is —CH$_3$, —CH$_2$—CH$_3$, —CH(CH$_3$)$_2$, or —C(CH$_3$)$_3$, each of which is substituted with one or more independently selected R$^5$ groups, wherein R$^5$ is as described above. In yet another embodiment, R$^2$ is C$_{1-4}$ alkyl substituted with one, two or three independently selected R$^5$ groups, wherein R$^5$ is as described above. In another embodiment, R$^2$ is —CH$_3$, —CH$_2$—CH$_3$, —CH(CH$_3$)$_2$, or —C(CH$_3$)$_3$, each of which is substituted with one, two or three independently selected R$^5$ groups, wherein R$^5$ is as described above. In a further embodiment, R$^2$ is C$_{1-4}$ alkyl substituted with one R$^5$ groups, wherein R$^5$ is as described above. In yet a further embodiment, R$^2$ is —CH$_3$, —CH$_2$—CH$_3$, —CH(CH$_3$)$_2$, or —C(CH$_3$)$_3$, each of which is substituted with one R$^5$ group, wherein R$^5$ is as described above.

In one embodiment, a compound of the invention is according to any one of Formula I-III, wherein R$^2$ is C$_{1-4}$ alkyl substituted with one or more independently selected R$^5$ groups, wherein R$^5$ is as described above. In another embodiment, R$^2$ is —CH$_3$, —CH$_2$—CH$_3$, —CH(CH$_3$)$_2$, or —C(CH$_3$)$_3$, each of which is substituted with one or more independently selected R$^5$ groups, wherein R$^5$ is as described above. In a particular embodiment, R$^5$ is halo, OH, —CN, or C$_{1-4}$ alkoxy. In a more particular embodiment, R$^5$ is F, Cl, OH, CN, or —OCH$_3$. In a most particular embodiment, R$^2$ is —CF$_3$, —CH$_2$—OH, —CH$_2$—CN, —CH$_2$—CHF$_2$, —CH$_2$—CF$_3$, —CH$_2$—CH$_2$—OH, or —CH$_2$—CH$_2$—OCH$_3$.

In one embodiment, a compound of the invention is according to any one of Formula I-III, wherein R$^2$ is C$_{1-4}$ alkyl substituted with one or more independently selected R$^5$ groups, wherein R$^5$ is as described above. In another embodiment, R$^2$ is —CH$_3$, —CH$_2$—CH$_3$, —CH(CH$_3$)$_2$, or —C(CH$_3$)$_3$, each of which is substituted with one or more independently selected R$^5$ groups, wherein R$^5$ is as described above. In a particular embodiment, R$^5$ is —NR$^{8e}$R$^{8f}$, wherein R$^{8e}$ and R$^{8f}$ are as described above. In a more particular embodiment, R$^5$ is —NR$^{8e}$R$^{8f}$, wherein each R$^{8e}$ and R$^{8f}$ is independently selected from H, —CH$_3$, and —CH$_2$—CH$_3$.

In one embodiment, a compound of the invention is according to any one of Formula I-III, wherein R$^2$ is C$_{1-4}$ alkyl substituted with one or more independently selected R$^5$ groups, wherein R$^5$ is as described above. In another embodiment, R$^2$ is —CH$_3$, —CH$_2$—CH$_3$, —CH(CH$_3$)$_2$, or —C(CH$_3$)$_3$, each of which is substituted with one or more independently selected R$^5$ groups, wherein R$^5$ is as described above. In a particular embodiment, R$^5$ is C$_{3-7}$ cycloalkyl. In another particular embodiment, R$^5$ is cyclopropyl, cyclobutyl, cyclopentyl or cyclohexyl. In a more particular embodiment, R$^5$ is cyclopropyl.

In one embodiment, a compound of the invention is according to any one of Formula I-III, wherein R$^2$ is C$_{1-4}$ alkyl substituted with one or more independently selected R$^5$ groups, wherein R$^5$ is as described above. In another embodiment, R$^2$ is —CH$_3$, —CH$_2$—CH$_3$, —CH(CH$_3$)$_2$, or —C(CH$_3$)$_3$, each of which is substituted with one or more independently selected R$^5$ groups, wherein R$^5$ is as described above. In a particular embodiment, R$^5$ is 6 membered mono or fused bicyclic heteroaryl comprising one or more heteroatoms independently selected from N, O, and S. In another particular embodiment, R$^5$ is pyridyl, pyrimidyl, or pyrazinyl. In a more particular embodiment, R$^5$ is pyridinyl.

In one embodiment, a compound of the invention is according to any one of Formula I-III, wherein R$^2$ is C$_{1-4}$ alkyl substituted with one or more independently selected R$^5$ groups, wherein R$^5$ is as described above. In another embodiment, R$^2$ is —CH$_3$, —CH$_2$—CH$_3$, —CH(CH$_3$)$_2$, or —C(CH$_3$)$_3$, each of which is substituted with one or more independently selected R$^5$ groups, wherein R$^5$ is as described above. In a particular embodiment, R$^5$ is phenyl. In another particular embodiment, R$^5$ is phenyl substituted with one or more independently selected F, Cl, —CH$_3$, —CH$_2$—CH$_3$, —CH(CH$_3$)$_2$, —CF$_3$, —CH$_2$—CF$_3$, —OCH$_3$, or —OCH$_2$CH$_3$. In a more particular embodiment, R$^5$ is phenyl substituted with one or two independently selected F, Cl, —CH$_3$, —CH$_2$—CH$_3$, —CH(CH$_3$)$_2$, —CF$_3$, —CH$_2$—CF$_3$, —OCH$_3$, or —OCH$_2$CH$_3$.

In one embodiment, a compound of the invention is according to any one of Formula I-III, wherein R$^2$ is C$_{3-7}$ cycloalkyl. In a particular embodiment, R$^2$ is cyclopropyl, cyclobutyl, cyclopentyl, or cyclohexyl. In a more particular embodiment, $R^2$ is cyclopentyl, or cyclohexyl.

In one embodiment, a compound of the invention is according to any one of Formula I-III, wherein $R^2$ is 4-10 membered monocyclic, bridged-, spiro-, or fused bicyclic heterocycloalkyl comprising one or more heteroatoms independently selected from N, O, and S. In a particular embodiment, $R^2$ is azetidinyl, pyrrolidinyl, tetrahydropyranyl, piperidinyl, morpholinyl 2-oxa-5-aza-bicyclo[2.2.1]heptanyl, [1,4]oxazepanyl, 2,3-dihydro-1H-isoindolyl, or 1,2,3,4-tetrahydro-isoquinolinyl.

In one embodiment, a compound of the invention is according to any one of Formula I-III, wherein $R^2$ is 4-10 membered monocyclic, bridged-, spiro-, or fused bicyclic heterocycloalkyl comprising one or more heteroatoms independently selected from N, O, and S, substituted with one or more independently selected $R^a$ groups, wherein $R^a$ is as defined above. In a particular embodiment, $R^2$ is azetidinyl, pyrrolidinyl, tetrahydropyranyl, piperidinyl, morpholinyl 2-oxa-5-aza-bicyclo[2.2.1]heptanyl, [1,4]oxazepanyl, 2,3-dihydro-1H-isoindolyl, or 1,2,3,4-tetrahydro-isoquinolinyl, each of which is substituted with one or more independently selected $R^a$ groups, wherein $R^a$ is as defined above. In another embodiment, $R^2$ is 4-10 membered monocyclic, bridged-, spiro-, or fused bicyclic heterocycloalkyl comprising one or more heteroatoms independently selected from N, O, and S, substituted with one, two or three independently selected $R^a$ groups, wherein $R^a$ is as defined above. In a particular embodiment, $R^2$ is azetidinyl, pyrrolidinyl, tetrahydropyranyl, piperidinyl, morpholinyl 2-oxa-5-aza-bicyclo[2.2.1]heptanyl, [1,4]oxazepanyl, 2,3-dihydro-1H-isoindolyl, or 1,2,3,4-tetrahydro-isoquinolinyl, each of which is substituted with one, two or three independently selected $R^a$ groups, wherein $R^a$ is as defined above. In another embodiment, $R^2$ is 4-10 membered monocyclic, bridged-, spiro-, or fused bicyclic heterocycloalkyl comprising one or more heteroatoms independently selected from N, O, and S, substituted with one $R^a$ group, wherein $R^a$ is as defined above. In a particular embodiment, $R^2$ is azetidinyl, pyrrolidinyl, tetrahydropyranyl, piperidinyl, morpholinyl 2-oxa-5-aza-bicyclo[2.2.1]heptanyl, [1,4]oxazepanyl, 2,3-dihydro-1H-isoindolyl, or 1,2,3,4-tetrahydro-isoquinolinyl, each of which is substituted with one $R^a$ group, wherein $R^a$ is as defined above.

In one embodiment, a compound of the invention is according to any one of Formula I-III, wherein $R^2$ is 4-10 membered monocyclic, bridged-, spiro-, or fused bicyclic heterocycloalkyl comprising one or more heteroatoms independently selected from N, O, and S, substituted with one or more independently selected $R^a$ groups, wherein $R^a$ is halo, —CN, oxo, —C(=O)O—$C_{1-4}$ alkyl, or phenyl. In a particular embodiment, $R^2$ is azetidinyl, pyrrolidinyl, tetrahydropyranyl, piperidinyl, morpholinyl 2-oxa-5-aza-bicyclo[2.2.1]heptanyl, [1,4]oxazepanyl, 2,3-dihydro-1H-isoindolyl, or 1,2,3,4-tetrahydro-isoquinolinyl, each of which is substituted with one or more independently selected $R^a$ groups, wherein $R^a$ is halo, —CN, oxo, —C(=O)O—$C_{1-4}$ alkyl, or phenyl. In a particular embodiment, $R^a$ is F, Cl, —CN, oxo, —C(=O)OCH$_3$, —C(=O)OCH$_2$CH$_3$, —C(=O)OC(CH$_3$)$_3$, or phenyl. In a more particular embodiment, $R^a$ is F, Cl, —CN, oxo, —C(=O)OC(CH$_3$)$_3$, or phenyl.

In one embodiment, a compound of the invention is according to any one of Formula I-III, wherein $R^2$ is 4-10 membered monocyclic, bridged-, spiro-, or fused bicyclic heterocycloalkyl comprising one or more heteroatoms independently selected from N, O, and S, substituted with one or more independently selected $R^a$ groups, wherein $R^a$ is $C_{1-4}$ alkyl optionally substituted with one or more independently selected $R^{7a}$, and each $R^{7a}$ is as defined above. In another embodiment, $R^2$ is azetidinyl, pyrrolidinyl, tetrahydropyranyl, piperidinyl, morpholinyl 2-oxa-5-aza-bicyclo[2.2.1]heptanyl, [1,4]oxazepanyl, 2,3-dihydro-1H-isoindolyl, or 1,2,3,4-tetrahydro-isoquinolinyl, each of which is substituted with one or more independently selected $R^a$ groups, wherein $R^a$ is $C_{1-4}$ alkyl optionally substituted with one or more independently selected $R^{7a}$, and each $R^{7a}$ is as defined above. In a particular embodiment, $R^a$ is —CH$_3$, —CH$_2$—CH$_3$, or —CH(CH$_3$)$_2$. In another particular embodiment, $R^a$ is —CH$_3$, —CH$_2$—CH$_3$, or —CH(CH$_3$)$_2$, each of which is substituted with one or more independently selected $R^{7a}$, and each $R^{7a}$ is as defined above. In a more particular embodiment, $R^a$ is $C_{1-4}$ alkyl, substituted with one or more independently selected $R^{7a}$, and each $R^{7a}$ is F, Cl, OH, —CN, —OCH$_3$, —OCH$_2$CH$_3$, —NH(CH$_3$) or —N(CH$_3$)$_2$. In another more particular embodiment, $R^a$ is —CH$_3$, —CH$_2$—CH$_3$, or —CH(CH$_3$)$_2$, each of which is substituted with one or more independently selected $R^{7a}$, and each $R^{7a}$ is F, Cl, OH, —CN, —OCH$_3$, —OCH$_2$CH$_3$, —NH(CH$_3$) or —N(CH$_3$)$_2$. In a most particular embodiment, $R^a$ is —CH$_3$, —CH$_2$—CH$_3$, —C(OH)(CH$_3$)$_2$, —CF$_3$, —CH$_2$—CHF$_2$, —CH$_2$CH$_2$OCH$_3$, or —CH$_2$CH$_2$N(CH$_3$)$_2$.

In one embodiment, a compound of the invention is according to any one of Formula I-III, wherein $R^2$ is 4-10 membered monocyclic, bridged-, spiro-, or fused bicyclic heterocycloalkyl comprising one or more heteroatoms independently selected from N, O, and S, substituted with one or more independently selected $R^a$ groups, wherein $R^a$ is $C_{1-4}$ alkoxy optionally substituted with one or more independently selected $R^{7a}$, and each $R^{7a}$ is as defined above. In another embodiment, $R^2$ is azetidinyl, pyrrolidinyl, tetrahydropyranyl, piperidinyl, morpholinyl 2-oxa-5-aza-bicyclo[2.2.1]heptanyl, [1,4]oxazepanyl, 2,3-dihydro-1H-isoindolyl, or 1,2,3,4-tetrahydro-isoquinolinyl, each of which is substituted with one or more independently selected $R^a$ groups, wherein $R^a$ is $C_{1-4}$ alkoxy optionally substituted with one or more independently selected $R^{7a}$, and each $R^{7a}$ is as defined above. In a particular embodiment, $R^a$ is —OCH$_3$, —OCH$_2$—CH$_3$, or —OCH(CH$_3$)$_2$. In another particular embodiment, $R^a$ is —OCH$_3$, —OCH$_2$—CH$_3$, or —OCH(CH$_3$)$_2$, each of which is substituted with one or more independently selected $R^{7a}$, and each $R^{7a}$ is as defined above. In a more particular embodiment, $R^a$ is $C_{1-4}$ alkoxy, substituted with one or more independently selected $R^{7a}$, and each $R^{7a}$ is F, Cl, OH, —CN, —OCH$_3$, —OCH$_2$CH$_3$, —NH(CH$_3$) or —N(CH$_3$)$_2$. In another more particular embodiment, $R^a$ is —OCH$_3$, —OCH$_2$—CH$_3$, or —OCH(CH$_3$)$_2$, each of which is substituted with one or more independently selected $R^{7a}$, and each $R^{7a}$ is F, Cl, OH, —CN, —OCH$_3$, —OCH$_2$CH$_3$, —NH(CH$_3$) or —N(CH$_3$)$_2$. In a most particular embodiment, $R^a$ is —OCH$_3$, —OCH$_2$—CH$_3$, O—CF$_3$, —OCH$_2$—CHF$_2$, —OCH$_2$CH$_2$OCH$_3$, or —OCH$_2$CH$_2$N(CH$_3$)$_2$.

In one embodiment, a compound of the invention is according to any one of Formula I-III, wherein $R^2$ is 4-10 membered monocyclic, bridged-, spiro-, or fused bicyclic heterocycloalkyl comprising one or more heteroatoms independently selected from N, O, and S, substituted with one or more independently selected $R^a$ groups, wherein $R^a$ is 5-10 membered mono, or fused bicyclic heteroaryl comprising one or more heteroatoms independently selected from N, O, or S, and optionally substituted with one or more independently selected $C_{1-4}$ alkyl. In a particular embodiment, $R^2$ is azetidinyl, pyrrolidinyl, tetrahydropyranyl, piperidinyl, morpholinyl 2-oxa-5-aza-bicyclo[2.2.1]heptanyl, [1,4]oxazepanyl, 2,3-dihydro-1H-isoindolyl, or 1,2,3,4-tetrahydro-isoquinolinyl, each of which is substituted with one or more independently selected $R^a$ groups, wherein $R^a$ is 5-10 membered mono, or fused bicyclic heteroaryl comprising one or more heteroatoms independently selected from N, O, or S, and optionally substituted with one or more independently selected $C_{1-4}$ alkyl. In a particular embodiment, $R^a$ is 5-10 membered mono, or fused bicyclic heteroaryl comprising one or more heteroatoms independently selected from N, O, or S, and optionally substituted with one or more independently selected —CH$_3$, —CH$_2$—CH$_3$, or —CH(CH$_3$)$_2$. In another particular embodiment, $R^a$ is imidazolyl, pyrazolyl, furanyl, thiophenyl, thiazolyl, oxazolyl, pyridyl, pyridazyl, pyrimidyl, or pyrazinyl, each of which is optionally substituted with one or more independently selected $C_{1-4}$ alkyl. In a more particular embodiment, $R^a$ is imidazolyl, pyrazolyl, furanyl, thiophenyl, thiazolyl, oxazolyl, pyridyl, pyridazyl, pyrimidyl, or pyrazinyl, each of which is optionally substituted with one or more independently selected —CH$_3$, —CH$_2$—CH$_3$, or —CH(CH$_3$)$_2$.

In one embodiment, a compound of the invention is according to any one of Formula I-III, wherein $R^2$ is 4-10 membered monocyclic, bridged-, spiro-, or fused bicyclic heterocycloalkyl comprising one or more heteroatoms independently selected from N, O, and S, substituted with one or more independently selected $R^a$ groups, wherein $R^a$ is —NR$^{8a}$R$^{8b}$, and $R^{8a}$ and $R^{8b}$ as described above. In a particular embodiment, $R^2$ is azetidinyl, pyrrolidinyl, tetrahydropyranyl, piperidinyl, morpholinyl 2-oxa-5-aza-bicyclo[2.2.1]heptanyl, [1,4]oxazepanyl, 2,3-dihydro-1H-isoindolyl, or 1,2,3,4-tetrahydro-isoquinolinyl, each of which is substituted with one or more independently selected $R^a$ groups, wherein $R^a$ is —NR$^{8a}$R$^{8b}$, and $R^{8a}$ and $R^{8b}$ as described above. In a particular embodiment, $R^a$ is —N(CH$_3$)$_2$, or —NH(CH$_3$).

In one embodiment, a compound of the invention is according to any one of Formula I-III, wherein $R^2$ is 5-6 membered monocyclic heterocycloalkenyl comprising one or more heteroatoms independently selected from N, O, and S. In a particular embodiment, $R^2$ is tetrahydropyridinyl.

In one embodiment, a compound of the invention is according to any one of Formula I-III, wherein $R^2$ is 5-6 membered monocyclic heterocycloalkenyl comprising one or more heteroatoms independently selected from N, O, and S, substituted with one or more independently selected $R^a$ groups, wherein $R^a$ is as defined above. In a particular embodiment, $R^2$ is tetrahydropyridinyl substituted with one or more independently selected $R^a$ groups, wherein $R^a$ is as defined above. In another embodiment, $R^2$ is 5-6 membered monocyclic heterocycloalkenyl comprising one or more heteroatoms independently selected from N, O, and S, substituted with one, two or three independently selected $R^a$ groups, wherein $R^a$ is as defined above. In a particular embodiment, $R^2$ is tetrahydropyridinyl substituted with one, two or three independently selected $R^a$ groups, wherein $R^a$ is as defined above.

In one embodiment, a compound of the invention is according to any one of Formula I-III, wherein $R^2$ is 5-6 membered monocyclic heterocycloalkenyl comprising one or more heteroatoms independently selected from N, O, and S, substituted with one or more independently selected $R^a$ groups, wherein $R^a$ is halo, —CN, oxo, —C(=O)O—C$_{1-4}$ alkyl, or phenyl. In a particular embodiment, $R^2$ is tetrahydropyridinyl substituted with one or more independently selected $R^a$ groups, wherein $R^a$ is halo, —CN, oxo, —C(=O)O—C$_{1-4}$ alkyl, or phenyl. In a particular embodiment, $R^a$ is F, Cl, —CN, oxo, —C(=O)OCH$_3$, —C(=O)OCH$_2$CH$_3$, —C(=O)OC(CH$_3$)$_3$, or phenyl. In a more particular embodiment, $R^a$ is F, Cl, —CN, oxo, —C(=O)OC(CH$_3$)$_3$, or phenyl.

In one embodiment, a compound of the invention is according to any one of Formula I-III, wherein $R^2$ is 5-6 membered monocyclic heterocycloalkenyl comprising one or more heteroatoms independently selected from N, O, and S, substituted with one or more independently selected $R^a$ groups, wherein $R^a$ is $C_{1-4}$ alkyl optionally substituted with one or more independently selected $R^{7a}$, and each $R^{7a}$ is as defined above. In another embodiment, $R^2$ is tetrahydropyridinyl, substituted with one or more independently selected $R^a$ groups, wherein $R^a$ is $C_{1-4}$ alkyl optionally substituted with one or more independently selected $R^{7a}$, and each $R^{7a}$ is as defined above. In a particular embodiment, $R^a$ is —CH$_3$, —CH$_2$—CH$_3$, or —CH(CH$_3$)$_2$. In another particular embodiment, $R^a$ is —CH$_3$, —CH$_2$—CH$_3$, or —CH(CH$_3$)$_2$, each of which is substituted with one or more independently selected $R^{7a}$, and each $R^{7a}$ is as defined above. In another particular embodiment, $R^a$ is $C_{1-4}$ alkyl optionally substituted with one or more independently selected $R^{7a}$, and each $R^{7a}$ is F, Cl, OH, —CN, —OCH$_3$, —OCH$_2$CH$_3$, —NH(CH$_3$) or —N(CH$_3$)$_2$. In a more particular embodiment, $R^a$ is —CH$_3$, —CH$_2$—CH$_3$, or —CH(CH$_3$)$_2$, each of which is substituted with one or more independently selected $R^{7a}$, and each $R^{7a}$ is F, Cl, OH, —CN, —OCH$_3$, —OCH$_2$CH$_3$, —NH(CH$_3$) or —N(CH$_3$)$_2$. In a most particular embodiment, $R^a$ is —CH$_3$, —CH$_2$—CH$_3$, —C(OH)(CH$_3$)$_2$, —CF$_3$, —CH$_2$—CHF$_2$, —CH$_2$CH$_2$OCH$_3$, or —CH$_2$CH$_2$N(CH$_3$)$_2$.

In one embodiment, a compound of the invention is according to any one of Formula I-III, wherein $R^2$ is 5-6 membered monocyclic heterocycloalkenyl comprising one or more heteroatoms independently selected from N, O, and S, substituted with one or more independently selected $R^a$ groups, wherein $R^a$ is $C_{1-4}$ alkoxy optionally substituted with one or more independently selected $R^{7a}$, and each $R^{7a}$ is as defined above. In another embodiment, $R^2$ is tetrahydropyridinyl, substituted with one or more independently selected $R^a$ groups, wherein $R^a$ is $C_{1-4}$ alkoxy optionally substituted with one or more independently selected $R^{7a}$, and each $R^{7a}$ is as defined above. In a particular embodiment, $R^a$ is —OCH$_3$, —OCH$_2$—CH$_3$, or —OCH(CH$_3$)$_2$. In another particular embodiment, $R^a$ is —OCH$_3$, —OCH$_2$—CH$_3$, or —OCH(CH$_3$)$_2$, each of which is substituted with one or more independently selected $R^{7a}$, and each $R^{7a}$ is as defined above. In another particular embodiment, $R^a$ is $C_{1-4}$ alkoxy optionally substituted with one or more independently selected $R^{7a}$, and each $R^{7a}$ is F, Cl, OH, —CN, —OCH$_3$, —OCH$_2$CH$_3$, —NH(CH$_3$) or —N(CH$_3$)$_2$. In a more particular embodiment, $R^a$ is —OCH$_3$, —OCH$_2$—CH$_3$, or —OCH(CH$_3$)$_2$, each of which is substituted with one or more independently selected $R^{7a}$, and each $R^{7a}$ is F, Cl, OH, —CN, —OCH$_3$, —OCH$_2$CH$_3$, —NH(CH$_3$) or —N(CH$_3$)$_2$. In a most particular embodiment, $R^a$ is —OCH$_3$, —OCH$_2$—CH$_3$, O—CF$_3$, —OCH$_2$—CHF$_2$, —OCH$_2$CH$_2$OCH$_3$, or —OCH$_2$CH$_2$N(CH$_3$)$_2$.

In one embodiment, a compound of the invention is according to any one of Formula I-III, wherein $R^2$ is $C_{6-10}$ mono or bicyclic aryl. In a particular embodiment, $R^2$ is phenyl.

In one embodiment, a compound of the invention is according to any one of Formula I-III, wherein $R^2$ is $C_{6-10}$ mono or bicyclic aryl optionally substituted with one or more independently selected $R^b$, wherein $R^b$ is as defined above. In another embodiment, $R^2$ is phenyl substituted with one or more independently selected $R^b$ groups, wherein $R^b$ is as defined above. In a particular embodiment, $R^2$ is $C_{6-10}$ mono or bicyclic aryl, substituted with one, two or three independently selected $R^b$ groups, wherein $R^b$ is as defined above. In another particular embodiment, $R^2$ is phenyl substituted with one, two or three independently selected $R^b$ groups, wherein $R^b$ is as defined above. In a more particular embodiment, $R^2$ is $C_{6-10}$ mono or bicyclic aryl, substituted with one $R^b$ group, wherein $R^b$ is as defined above. In another particular embodiment, $R^2$ is phenyl substituted with one $R^b$ group, wherein $R^b$ is as defined above.

In one embodiment, a compound of the invention is according to any one of Formula I-III, wherein $R^2$ is $C_{6-10}$ mono or bicyclic aryl optionally substituted with one or more independently selected $R^b$, wherein $R^b$ is halo, or —CN. In another embodiment, $R^2$ is phenyl substituted with one or more independently selected $R^b$ groups, wherein $R^b$ is halo, or —CN. In a particular embodiment, $R^b$ is F, Cl, or —CN.

In one embodiment, a compound of the invention is according to any one of Formula I-III, wherein $R^2$ is $C_{6-10}$ mono or bicyclic aryl optionally substituted with one or more independently selected $R^b$, wherein $R^b$ is $C_{1-4}$ alkyl optionally substituted with one or more independently selected $R^{7b}$, and each $R^{7b}$ is as defined above. In another embodiment, $R^2$ is phenyl substituted with one or more independently selected $R^b$ groups, wherein $R^b$ is $C_{1-4}$ alkyl optionally substituted with one or more independently selected $R^{7b}$, and each $R^{7b}$ is as defined above. In a particular embodiment, $R^b$ is —CH$_3$, —CH$_2$—CH$_3$, or —CH(CH$_3$)$_2$. In another particular embodiment, $R^b$ is —CH$_3$, —CH$_2$—CH$_3$, or —CH(CH$_3$)$_2$, each of which is substituted with one or more independently selected $R^{7b}$, and each $R^{7b}$ is as defined above. In a more particular embodiment, $R^b$ is $C_{1-4}$ alkyl, substituted with one or more independently selected $R^{7b}$, and each $R^{7b}$ is F, Cl, OH, —CN, —OCH$_3$, —OCH$_2$CH$_3$, —NH(CH$_3$) or —N(CH$_3$)$_2$. In another more particular embodiment, $R^b$ is —CH$_3$, —CH$_2$—CH$_3$, or —CH(CH$_3$)$_2$, each of which is optionally substituted with one or more independently selected $R^{7b}$, and each $R^{7b}$ is F, Cl, OH, —CN, —OCH$_3$, —OCH$_2$CH$_3$, —NH(CH$_3$) or —N(CH$_3$)$_2$. In a most particular embodiment, $R^b$ is —CH$_3$, —CH$_2$—CH$_3$, —C(OH)(CH$_3$)$_2$, —CF$_3$, —CH$_2$—CHF$_2$, —CH$_2$CH$_2$OCH$_3$, or —CH$_2$CH$_2$N(CH$_3$)$_2$.

In one embodiment, a compound of the invention is according to any one of Formula I-III, wherein $R^2$ is $C_{6-10}$ mono or bicyclic aryl optionally substituted with one or more independently selected $R^b$, wherein $R^b$ is $C_{1-4}$ alkoxy optionally substituted with one or more independently selected $R^{7b}$, and each $R^{7b}$ is as defined above. In another embodiment, $R^2$ is phenyl substituted with one or more independently selected $R^b$ groups, wherein $R^b$ is $C_{1-4}$ alkoxy optionally substituted with one or more independently selected $R^{7b}$, and each $R^{7b}$ is as defined above. In a particular embodiment, $R^b$ is —OCH$_3$, —OCH$_2$—CH$_3$, or —OCH(CH$_3$)$_2$. In another particular embodiment, $R^b$ is —OCH$_3$, —OCH$_2$—CH$_3$, or —OCH(CH$_3$)$_2$, each of which is substituted with one or more independently selected $R^{7b}$, and each $R^{7b}$ is as defined above. In a more particular embodiment, $R^b$ is $C_{1-4}$ alkoxy, substituted with one or more independently selected $R^{7b}$, and each $R^{7b}$ is F, Cl, OH, —CN, —OCH$_3$, —OCH$_2$CH$_3$, —NH(CH$_3$) or —N(CH$_3$)$_2$. In another more particular embodiment, $R^b$ is —OCH$_3$, —OCH$_2$—CH$_3$, or —OCH(CH$_3$)$_2$, each of which is optionally substituted with one or more independently selected $R^{7b}$, and each $R^{7b}$ is F, Cl, OH, —CN, —OCH$_3$, —OCH$_2$CH$_3$, —NH(CH$_3$) or —N(CH$_3$)$_2$. In a most particular embodiment, $R^b$ is —OCH$_3$, —OCH$_2$—CH$_3$, O—CF$_3$, —OCH$_2$—CHF$_2$, —OCH$_2$CH$_2$OCH$_3$, or —OCH$_2$CH$_2$N(CH$_3$)$_2$.

In one embodiment, a compound of the invention is according to any one of Formula I-III, wherein $R^2$ is $C_{6-10}$ mono or bicyclic aryl optionally substituted with one or more independently selected $R^b$, wherein $R^b$ is —NR$^{8c}$R$^{8d}$, and R$^{8e}$ and R$^{8d}$ as described above. In a particular embodiment, $R^2$ is phenyl substituted with one or more independently selected $R^b$ groups, wherein $R^b$ is —NR$^{8c}$R$^{8d}$, and R$^{8c}$ and R$^{8d}$ as described above. In a particular embodiment, $R^b$ is —N(CH$_3$)$_2$, or —NH(CH$_3$).

In one embodiment, a compound of the invention is according to any one of Formula I-III, wherein $R^2$ is 5-10 membered monocyclic or fused bicyclic heteroaryl, comprising one or more heteroatoms independently selected from N, O, and S. In a particular embodiment, $R^2$ is imidazolyl, furanyl, thiophenyl, pyrazolyl, thiazolyl, oxazolyl, pyridinyl, pyridazinyl, pyrimidinyl, or pyrazinyl.

In one embodiment, a compound of the invention is according to any one of Formula I-III, wherein $R^2$ is 5-10 membered monocyclic or fused bicyclic heteroaryl, comprising one or more heteroatoms independently selected from N, O, and S, and optionally substituted with one or more independently selected $R^b$, wherein $R^b$ is as defined above. In another embodiment, $R^2$ is imidazolyl, furanyl, thiophenyl, pyrazolyl, thiazolyl, oxazolyl, pyridinyl, pyridazinyl, pyrimidinyl, or pyrazinyl, each of which is substituted with one or more independently selected $R^b$ groups, wherein $R^b$ is as defined above. In a particular embodiment, $R^2$ is 5-10 membered monocyclic or fused bicyclic heteroaryl, comprising one or more heteroatoms independently selected from N, O, and S, substituted with one, two or three independently selected $R^b$ groups, wherein $R^b$ is as defined above. In another particular embodiment, $R^2$ is imidazolyl, furanyl, thiophenyl, pyrazolyl, thiazolyl, oxazolyl, pyridinyl, pyridazinyl, pyrimidinyl, or pyrazinyl, each of which is substituted with one, two or three independently selected $R^b$ groups, wherein $R^b$ is as defined above. In a more particular embodiment, $R^2$ is 5-10 membered monocyclic or fused bicyclic heteroaryl, comprising one or more heteroatoms independently selected from N, O, and S, substituted with one $R^b$ group, wherein $R^b$ is as defined above. In another embodiment, $R^2$ is imidazolyl, furanyl, thiophenyl, pyrazolyl, thiazolyl, oxazolyl, pyridinyl, pyridazinyl, pyrimidinyl, or pyrazinyl, each of which is substituted with one $R^b$ group, wherein $R^b$ is as defined above.

In one embodiment, a compound of the invention is according to any one of Formula I-III, wherein $R^2$ is 5-10 membered monocyclic or fused bicyclic heteroaryl, comprising one or more heteroatoms independently selected from N, O, and S, optionally substituted with one or more independently selected $R^b$, wherein $R^b$ is halo, or —CN. In another embodiment, $R^2$ is imidazolyl, furanyl, thiophenyl, pyrazolyl, thiazolyl, oxazolyl, pyridinyl, pyridazinyl, pyrimidinyl, or pyrazinyl, each of which is substituted with one or more independently selected $R^b$ groups, wherein $R^b$ is halo, or —CN. In a particular embodiment, $R^b$ is F, Cl, or —CN.

In one embodiment, a compound of the invention is according to any one of Formula I-III, wherein $R^2$ is 5-10 membered monocyclic or fused bicyclic heteroaryl, comprising one or more heteroatoms independently selected from N, O, and S, optionally substituted with one or more independently selected $R^b$, wherein $R^b$ is $C_{1-4}$ alkyl optionally substituted with one or more independently selected $R^{7b}$, and each $R^{7b}$ is as defined above. In another embodiment, $R^2$ is imidazolyl, furanyl, thiophenyl, pyrazolyl, thiazolyl, oxazolyl, pyridinyl, pyridazinyl, pyrimidinyl, or pyrazinyl, each of which is substituted with one or more independently selected $R^b$ groups, wherein $R^b$ is $C_{1-4}$ alkyl optionally substituted with one or more independently selected $R^{7b}$, and each $R^{7b}$ is as defined above. In a particular embodiment, $R^b$ is —CH$_3$, —CH$_2$—CH$_3$, or —CH(CH$_3$)$_2$. In another particular embodiment, $R^b$ is —CH$_3$, —CH$_2$—CH$_3$, or —CH(CH$_3$)$_2$, each of which is substituted with one or more independently selected $R^{7b}$, and each $R^{7b}$ is as defined above. In a more particular embodiment, $R^b$ is $C_{1-4}$ alkyl, substituted with one or more independently selected $R^{7b}$, and each $R^{7b}$ is F, Cl, OH, —CN, —OCH$_3$, —OCH$_2$CH$_3$, NH(CH$_3$) or —N(CH$_3$)$_2$. In another more particular embodiment, $R^b$ is —CH$_3$, —CH$_2$—CH$_3$, or —CH(CH$_3$)$_2$, each of which is optionally substituted with one or more independently selected $R^{7b}$, and each $R^{7b}$ is F, Cl, OH, —CN, —OCH$_3$, —OCH$_2$CH$_3$, —NH(CH$_3$) or —N(CH$_3$)$_2$. In a most particular embodiment, $R^b$ is —CH$_3$, —CH$_2$—CH$_3$, —C(OH)(CH$_3$)$_2$, —CF$_3$, —CH$_2$—CHF$_2$, —CH$_2$CH$_2$OCH$_3$, or —CH$_2$CH$_2$N(CH$_3$)$_2$.

In another most particular embodiment, $R^2$ is imidazolyl, furanyl, thiophenyl, pyrazolyl, thiazolyl, oxazolyl, pyridinyl, pyridazinyl, pyrimidinyl, or pyrazinyl, each of which is substituted with one or more independently selected $R^b$ groups, wherein $R^b$ is —CH$_3$, —CH$_2$—CH$_3$, or —CH(CH$_3$)$_2$, each of which is optionally substituted with one or more independently selected $R^{7b}$, and each $R^{7b}$ is F, Cl, OH, —CN, —OCH$_3$, —OCH$_2$CH$_3$, —NH(CH$_3$) or —N(CH$_3$)$_2$.

In one embodiment, a compound of the invention is according to any one of Formula I-III, wherein $R^2$ is 5-10 membered monocyclic or fused bicyclic heteroaryl, comprising one or more heteroatoms independently selected from N, O, and S, optionally substituted with one or more independently selected $R^b$, wherein $R^b$ is $C_{1-4}$ alkoxy optionally substituted with one or more independently selected $R^{7b}$, and each $R^{7b}$ is as defined above. In another embodiment, $R^2$ is imidazolyl, furanyl, thiophenyl, pyrazolyl, thiazolyl, oxazolyl, pyridinyl, pyridazinyl, pyrimidinyl, or pyrazinyl, each of which is substituted with one or more independently selected $R^b$ groups, wherein $R^b$ is $C_{1-4}$ alkoxy optionally substituted with one or more independently selected $R^{7b}$, and each $R^{7b}$ is as defined above. In a particular embodiment, $R^b$ is —OCH$_3$, —OCH$_2$—CH$_3$, or —OCH(CH$_3$)$_2$. In another particular embodiment, $R^b$ is —OCH$_3$, —OCH$_2$—CH$_3$, or —OCH(CH$_3$)$_2$, each of which is substituted with one or more independently selected $R^{7b}$, and each $R^{7b}$ is as defined above. In a more particular embodiment, $R^b$ is $C_{1-4}$ alkoxy, substituted with one or more independently selected $R^{7b}$, and each $R^{7b}$ is F, Cl, OH, —CN, —OCH$_3$, —OCH$_2$CH$_3$, —NH(CH$_3$) or —N(CH$_3$)$_2$. In another more particular embodiment, $R^b$ is —OCH$_3$, —OCH$_2$—CH$_3$, or —OCH(CH$_3$)$_2$, each of which is optionally substituted with one or more independently selected $R^{7b}$, and each $R^{7b}$ is F, Cl, OH, —CN, —OCH$_3$, —OCH$_2$CH$_3$, —NH(CH$_3$) or —N(CH$_3$)$_2$. In a most particular embodiment, $R^b$ is —OCH$_3$, —OCH$_2$—CH$_3$, O—CF$_3$, —OCH$_2$—CHF$_2$, —OCH$_2$CH$_2$OCH$_3$, or —OCH$_2$CH$_2$N(CH$_3$)$_2$.

In one embodiment, a compound of the invention is according to any one of Formula I-III, wherein $R^2$ is 5-10 membered monocyclic or fused bicyclic heteroaryl, comprising one or more heteroatoms independently selected from N, O, and S, optionally substituted with one or more independently selected $R^b$, wherein $R^b$ is —NR$^{8c}$R$^{8d}$, and R$^{8c}$ and R$^{8d}$ as described above. In a particular embodiment, $R^2$ is imidazolyl, furanyl, thiophenyl, pyrazolyl, thiazolyl, oxazolyl, pyridinyl, pyridazinyl, pyrimidinyl, or pyrazinyl, each of which is substituted with one or more independently selected $R^b$ groups, wherein $R^b$ is —NR$^{8c}$R$^{8d}$, and R$^{8c}$ and R$^{8d}$ as described above. In another particular embodiment, $R^b$ is —N(CH$_3$)$_2$, or —NH(CH$_3$).

In one embodiment, a compound of the invention is according to Formula IV:

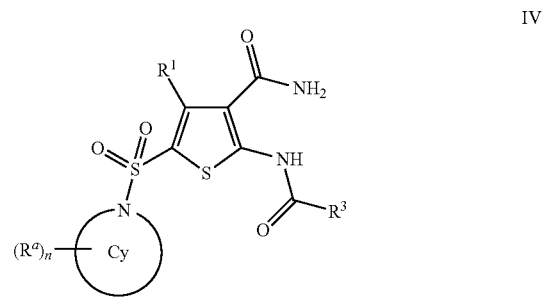

wherein Cy is 4-10 membered monocyclic heterocycloalkyl comprising one or more heteroatoms independently selected from N, O, and S, $R^a$ is as previously defined, and the subscript n is 0, 1 or 2.

In one embodiment, a compound of the invention is according to Formula IV, wherein Cy is azetidinyl, pyrrolidinyl, tetrahydropyranyl, piperidinyl, morpholinyl 2-oxa-5-aza-bicyclo[2.2.1]heptanyl, [1,4]oxazepanyl, 2,3-dihydro-1H-isoindolyl, or 1,2,3,4-tetrahydro-isoquinolinyl. In a particular embodiment, Cy is piperidinyl.

In one embodiment, a compound of the invention is according to Formula IV, wherein the subscript n is 1, or 2, and $R^a$ is halo, CN, —C(=O)O—C$_{1-4}$ alkyl, or phenyl. In a particular embodiment, $R^a$ is F, Cl, CN, —C(=O)OCH$_3$, or phenyl. In a more particular embodiment, $R^a$ is F, Cl, or phenyl.

In one embodiment, a compound of the invention is according to Formula IV, wherein the subscript n is 1, or 2, and $R^a$ is $C_{1-4}$ alkyl, optionally substituted with one or more independently selected $R^{7a}$, wherein $R^{7a}$ is as described above. In another embodiment, $R^a$ is —CH$_3$, —CH$_2$—CH$_3$, or —CH(CH$_3$)$_2$, each of which is optionally substituted with one or more independently selected $R^{7a}$. In a particular embodiment, and $R^a$ is $C_{1-4}$ alkyl, optionally substituted with one or more independently selected $R^{7a}$, wherein $R^{7a}$ is halo, OH, CN, or $C_{1-4}$ alkoxy. In another particular embodiment, $R^a$ is —CH$_3$, —CH$_2$—CH$_3$, or —CH(CH$_3$)$_2$, each of which is optionally substituted with one or more independently selected halo, OH, CN, or $C_{1-4}$ alkoxy. In a more particular embodiment, and $R^a$ is $C_{1-4}$ alkyl, optionally substituted with one or more independently selected $R^{7a}$, wherein $R^{7a}$ is F, Cl, OH, CN, or —OCH$_3$. In another particular embodiment, $R^a$ is —CH$_3$, —CH$_2$—CH$_3$, or —CH(CH$_3$)$_2$, each of which is optionally substituted with one or more independently selected F, Cl, OH, CN, or —OCH$_3$. In a most particular embodiment, $R^a$ is —CH$_3$, —CH$_2$—CH$_3$, or —CH(CH$_3$)$_2$, —CF$_3$, or —C(OH)(CH$_3$)$_2$.

In one embodiment, a compound of the invention is according to Formula IV, wherein the subscript n is 1, or 2, and $R^a$ is $C_{1-4}$ alkoxy, optionally substituted with one or more independently selected $R^{7a}$, wherein $R^{7a}$ is as described above. In another embodiment, $R^a$ is —OCH$_3$, —OCH$_2$—CH$_3$, or —OCH(CH$_3$)$_2$, each of which is optionally substituted with one or more independently selected $R^{7a}$. In a particular embodiment, $R^a$ is $C_{1-4}$ alkoxy, optionally substituted with one or more independently selected $R^{7a}$, wherein $R^{7a}$ is halo, OH, CN, or $C_{1-4}$ alkoxy. In another particular embodiment, $R^a$ is —OCH$_3$, —OCH$_2$—CH$_3$, or —OCH(CH$_3$)$_2$, each of which is optionally substituted with one or more independently selected selected $R^{7a}$, wherein $R^{7a}$ is halo, OH, CN, or $C_{1-4}$ alkoxy. In a more particular embodiment, and $R^a$ is $C_{1-4}$ alkoxy, optionally substituted with one or more independently selected $R^{7a}$, wherein $R^{7a}$ is F, Cl, OH, CN, or —$OCH_3$. In another particular embodiment, $R^a$ is —$OCH_3$, —$OCH_2$—$CH_3$, or —$OCH(CH_3)_2$, each of which is optionally substituted with one or more independently selected F, Cl, OH, CN, or —$OCH_3$. In a most particular embodiment, $R^a$ is —$OCH_3$, —$OCH_2$—$CH_3$, or —$OCH(CH_3)_2$, or —$OCF_3$.

In one embodiment, a compound of the invention is according to Formula IV, wherein the subscript n is 1, or 2, and $R^a$ is $C_{1-4}$ alkyl, optionally substituted with one or more independently selected $R^{7a}$, wherein $R^{7a}$ is as described above. In another embodiment, $R^a$ is —$CH_3$, —$CH_2$—$CH_3$, or —$CH(CH_3)_2$, each of which is optionally substituted with one or more independently selected $R^{7a}$. In a particular embodiment, and $R^a$ is $C_{1-4}$ alkyl, optionally substituted with one or more independently selected $R^{7a}$, wherein $R^{7a}$ is —$NR^{8i}R^{8j}$, and wherein $R^{8i}$ and $R^{8j}$ are independently selected from H, —$CH_3$, and —$CH_2$—$CH_3$. In another particular embodiment, $R^a$ is —$CH_3$, —$CH_2$—$CH_3$, or —$CH(CH_3)_2$, each of which is optionally substituted with one or more independently selected $R^{7a}$, wherein $R^{7a}$ is —$NR^{8i}R^{8j}$, and wherein $R^{8i}$ and $R^{8j}$ are independently selected from H, —$CH_3$, and —$CH_2$—$CH_3$. In a more particular embodiment, and $R^a$ is $C_{1-4}$ alkyl, optionally substituted with one or more independently selected $R^{7a}$, wherein $R^{7a}$ is —$NHCH_3$, —$N(CH_3)_2$, —$NH(CH_2$—$CH_3)$, —$N(CH_2$—$CH_3)CH_3$, or —$N(CH_2$—$CH_3)_2$. In another particular embodiment, $R^a$ is —$CH_3$, —$CH_2$—$CH_3$, or —$CH(CH_3)_2$, each of which is optionally substituted with one or more independently selected —$NHCH_3$, —$N(CH_3)_2$, —$NH(CH_2$—$CH_3)$, —$N(CH_2$—$CH_3)CH_3$, or —$N(CH_2$—$CH_3)_2$.

In one embodiment, a compound of the invention is according to Formula IV, wherein the subscript n is 1, or 2, and $R^a$ is $C_{1-4}$ alkoxy, optionally substituted with one or more independently selected $R^{7a}$, wherein $R^{7a}$ is as described above. In another embodiment, $R^a$ is —$OCH_3$, —$OCH_2$—$CH_3$, or —$OCH(CH_3)_2$, each of which is optionally substituted with one or more independently selected $R^{7a}$. In a particular embodiment, and $R^a$ is $C_{1-4}$ alkoxy, optionally substituted with one or more independently selected $R^{7a}$, wherein $R^{7a}$ is —$NR^{8i}R^{8j}$, and wherein $R^{8i}$ and $R^{8j}$ are independently selected from H, —$CH_3$, and —$CH_2$—$CH_3$. In another particular embodiment, $R^a$ is —$OCH_3$, —$OCH_2$—$CH_3$, or —$OCH(CH_3)_2$, each of which is optionally substituted with one or more independently selected $R^{7a}$, wherein $R^{7a}$ is —$NR^{8i}R^{8j}$, and wherein $R^{8i}$ and $R^{8j}$ are independently selected from H, —$CH_3$, and —$CH_2$—$CH_3$. In a more particular embodiment, and $R^a$ is $C_{1-4}$ alkoxy, optionally substituted with one or more independently selected $R^{7a}$, wherein $R^{7a}$ is —$NHCH_3$, —$N(CH_3)_2$, —$NH(CH_2$—$CH_3)$, —$N(CH_2$—$CH_3)CH_3$, or —$N(CH_2$—$CH_3)_2$. In another particular embodiment, $R^a$ is —$OCH_3$, —$OCH_2$—$CH_3$, or —$OCH(CH_3)_2$, each of which is optionally substituted with one or more independently selected —$NHCH_3$, —$N(CH_3)_2$, —$NH(CH_2$—$CH_3)$, —$N(CH_2$—$CH_3)CH_3$, or —$N(CH_2$—$CH_3)_2$.

In one embodiment, a compound of the invention is according to Formula IV, wherein the subscript n is 1, or 2, and $R^a$ is —$NR^{8a}R^{8b}$, wherein $R^{8a}$ and $R^{8b}$ are as described above. In a particular embodiment, $R^a$ is —$NR^{8a}R^{8b}$, wherein each $R^{8a}$ and $R^{8b}$ are independently selected from H, —$CH_3$, or —$CH_2$—$CH_3$. In a more particular embodiment, $R^a$ is —$NHCH_3$, —$N(CH_3)_2$, —$NH(CH_2$—$CH_3)$, —$N(CH_2$—$CH_3)CH_3$, —$N(CH_2$—$CH_3)_2$.

In one embodiment, a compound of the invention is according to Formula IV, wherein the subscript n is 0.

In one embodiment, a compound of the invention is according to any one of Formula I-IV, wherein $R^3$ is $C_{3-7}$ cycloalkyl. In a particular embodiment, $R^3$ is cyclopropyl, cyclobutyl, cyclopentyl, or cyclohexyl.

In one embodiment, a compound of the invention is according to any one of Formula I-IV, wherein $R^3$ is $C_{3-7}$ cycloalkyl substituted with one or more independently selected $R^c$ groups, and $R^c$ is as described above. In another embodiment, $R^3$ is cyclopropyl, cyclobutyl, cyclopentyl, or cyclohexyl, each of which is substituted with one or more independently selected $R^c$ groups. In a particular embodiment, $R^3$ is $C_{3-7}$ cycloalkyl substituted with one or two independently selected $R^c$ groups. In another particular embodiment, $R^3$ is cyclopropyl, cyclobutyl, cyclopentyl, or cyclohexyl, each of which is substituted with one or two independently selected $R^c$ groups. In a more particular embodiment, $R^3$ is $C_{3-7}$ cycloalkyl substituted with one $R^c$ group. In another particular embodiment, $R^3$ is cyclopropyl, cyclobutyl, cyclopentyl, or cyclohexyl, each of which is substituted with one $R^c$ group.

In one embodiment, a compound of the invention is according to any one of Formula I-IV, wherein $R^3$ is $C_{3-7}$ cycloalkyl substituted with one or more independently selected $R^c$ groups, and $R^c$ is as described above. In a particular embodiment, $R^3$ is cyclopropyl, cyclobutyl, cyclopentyl, or cyclohexyl, each of which is substituted with one or more independently selected $R^c$ groups. In a particular embodiment, $R^c$ is selected from halo, CN, oxo, and OH. In a more particular embodiment, $R^c$ is selected from F, Cl, CN, oxo, and OH.

In one embodiment, a compound of the invention is according to any one of Formula I-IV, wherein $R^3$ is $C_{3-7}$ cycloalkyl substituted with one or more independently selected $R^c$ groups, and $R^c$ is as described above. In a particular embodiment, $R^3$ is cyclopropyl, cyclobutyl, cyclopentyl, or cyclohexyl, each of which is substituted with one or more independently selected $R^c$ groups. In a particular embodiment, $R^c$ is $C_{1-4}$ alkyl, optionally substituted with one or more independently selected $R^{7c}$, wherein $R^{7c}$ is as defined above. In a more particular embodiment, $R^c$ is —$CH_3$, —$CH_2CH_3$, or —$CH(CH_3)_2$. In another more particular embodiment, $R^c$ is —$CH_3$, —$CH_2CH_3$, or —$CH(CH_3)_2$, each of which is optionally substituted with one or more independently selected $R^{7c}$. In yet another more particular embodiment, $R^c$ is $C_{1-4}$ alkyl, optionally substituted with one or more independently selected $R^{7c}$, wherein $R^{7c}$ is F, Cl, OH, CN, —$OCH_3$, —$OCH_2CH_3$, —$NHCH_3$, —$N(CH_3)_2$, —$NH(CH_2$—$CH_3)$, —$N(CH_2$—$CH_3)CH_3$, or —$N(CH_2$—$CH_3)_2$. In a further more particular embodiment, $R^c$ is —$CH_3$, —$CH_2CH_3$, or —$CH(CH_3)_2$, each of which is optionally substituted with one or more independently selected $R^{7c}$, wherein $R^{7c}$ is F, Cl, OH, CN, —$OCH_3$, —$OCH_2CH_3$, —$NHCH_3$, —$N(CH_3)_2$, —$NH(CH_2$—$CH_3)$, —$N(CH_2$—$CH_3)CH_3$, or —$N(CH_2$—$CH_3)_2$. In a most particular embodiment, $R^c$ is —$CH_3$, —$CH_2$—$CH_3$, —$C(OH)(CH_3)_2$, —$CF_3$, —$CH_2$—$CHF_2$, —$CH_2CH_2OCH_3$, or —$CH_2CH_2N(CH_3)_2$.

In one embodiment, a compound of the invention is according to any one of Formula I-IV, wherein $R^3$ is $C_{3-7}$ cycloalkyl substituted with one or more independently selected $R^c$ groups, and $R^c$ is as described above. In another embodiment, $R^3$ is cyclopropyl, cyclobutyl, cyclopentyl, or cyclohexyl, each of which is substituted with one or more independently selected $R^c$ groups. In a particular embodiment, $R^c$ is $C_{1-4}$ alkoxy, optionally substituted with one or more independently selected $R^{7c}$, wherein $R^{7c}$ is as defined above. In a particular embodiment, $R^c$ is —$OCH_3$, —$OCH_2CH_3$, or —$OCH(CH_3)_2$. In a particular embodiment, $R^c$ is —$OCH_3$, —$OCH_2CH_3$, or —$OCH(CH_3)_2$, each of which is optionally substituted with one or more independently selected $R^{7c}$. In another particular embodiment, $R^c$ is $C_{1-4}$ alkoxy, optionally substituted with one or more independently selected $R^{7c}$, wherein $R^{7c}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In a more particular embodiment, $R^c$ is —OCH$_3$, —OCH$_2$CH$_3$, or —OCH(CH$_3$)$_2$, each of which is optionally substituted with one or more independently selected $R^{7c}$, wherein $R^{7c}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In a most particular embodiment, $R^c$ is —OCH$_3$, —OCH$_2$—CH$_3$, O—CF$_3$, —OCH$_2$—CHF$_2$, —OCH$_2$CH$_2$OCH$_3$, or —OCH$_2$CH$_2$N(CH$_3$)$_2$.

In one embodiment, a compound of the invention is according to any one of Formula I-IV, wherein $R^3$ is $C_{3-7}$ cycloalkyl substituted with one or more independently selected $R^c$ groups, and $R^c$ is as described above. In a particular embodiment, $R^3$ is cyclopropyl, cyclobutyl, cyclopentyl, or cyclohexyl, each of which is substituted with one or more independently selected $R^c$ groups. In a particular embodiment, $R^c$ is phenyl. In another particular embodiment, $R^c$ is phenyl optionally substituted with one or more independently selected halo, $C_{1-4}$ alkyl, $C_{1-4}$ alkoxy, —CN, or —NR$^{9a}$R$^{9b}$, wherein R$^{9a}$ and R$^{9b}$ are as described above In another more particular embodiment, $R^c$ is phenyl substituted with one or more independently selected F, Cl, —CH$_3$, —CH$_2$CH$_3$, —CH(CH$_3$)$_2$, —OCH$_3$, —OCH$_2$CH$_3$, —OCH(CH$_3$)$_2$, CN, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$.

In one embodiment, a compound of the invention is according to any one of Formula I-IV, wherein $R^3$ is $C_{3-7}$ cycloalkyl substituted with one or more independently selected $R^c$ groups, and $R^c$ is as described above. In a particular embodiment, $R^3$ is cyclopropyl, cyclobutyl, cyclopentyl, or cyclohexyl, each of which is substituted with one or more independently selected $R^c$ groups. In a particular embodiment, $R^c$ is 5-6 membered mono, or heteroaryl comprising one or more heteroatoms independently selected from N, O, or S. In another particular embodiment, $R^c$ is 5-6 membered mono, or heteroaryl comprising one or more heteroatoms independently selected from N, O, or S, substituted with one or more independently selected halo, $C_{1-4}$ alkyl, $C_{1-4}$ alkoxy, CN, or —NR$^{9c}$R$^{9d}$, wherein R$^{9c}$ and R$^{9d}$ is as described above. In a more particular embodiment, $R^c$ is furanyl, thiophenyl, pyrazolyl, imidazolyl, thiazolyl, oxazolyl, pyridinyl, pyridazinyl, pyrimidyl, or pyrazinyl. In another more particular embodiment, $R^c$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected halo, $C_{1-4}$ alkyl, $C_{1-4}$ alkoxy, CN, or —NR$^{9c}$R$^{9d}$, wherein R$^{9c}$ and R$^{9d}$ is as described above. In a most particular embodiment, $R^c$ is 5-6 membered mono, or heteroaryl comprising one or more heteroatoms independently selected from N, O, or S, substituted with one or more independently selected F, Cl, —CH$_3$, —CH$_2$CH$_3$, —CH(CH$_3$)$_2$, —OCH$_3$, —OCH$_2$CH$_3$, —OCH(CH$_3$)$_2$, CN, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In another most particular embodiment, $R^c$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected F, Cl, —CH$_3$, —CH$_2$CH$_3$, —CH(CH$_3$)$_2$, —OCH$_3$, —OCH$_2$CH$_3$, —OCH(CH$_3$)$_2$, CN, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$.

In one embodiment, a compound of the invention is according to any one of Formula I-IV, wherein $R^3$ is 4-7 membered monocyclic heterocycloalkyl comprising one or more heteroatoms independently selected from O, and S. In a particular embodiment, $R^3$ is pyrrolidinyl, tetrahydrofuranyl, tetrahydropyranyl, piperidinyl, piperazinyl, morpholinyl, or thiomorpholinyl.

In one embodiment, a compound of the invention is according to any one of Formula I-IV, wherein $R^3$ is 4-7 membered monocyclic heterocycloalkyl comprising one or more heteroatoms independently selected from O, and S, substituted with one or more independently selected $R^c$ groups, and $R^c$ is as described above. In another embodiment, $R^3$ is pyrrolidinyl, tetrahydrofuranyl, tetrahydropyranyl, piperidinyl, piperazinyl, morpholinyl, or thiomorpholinyl, each of which is substituted with one or more independently selected $R^c$ groups. In a particular embodiment, $R^3$ is 4-7 membered monocyclic heterocycloalkyl comprising one or more heteroatoms independently selected from O, and S, substituted with one or two independently selected $R^c$ groups. In another particular embodiment, $R^3$ is pyrrolidinyl, tetrahydrofuranyl, tetrahydropyranyl, piperidinyl, piperazinyl, morpholinyl, or thiomorpholinyl, each of which is substituted with one or two independently selected $R^c$ groups. In a more particular embodiment, $R^3$ is 4-7 membered monocyclic heterocycloalkyl comprising one or more heteroatoms independently selected from O, and S, substituted with one $R^c$ group. In another particular embodiment, $R^3$ is pyrrolidinyl, tetrahydrofuranyl, tetrahydropyranyl, piperidinyl, piperazinyl, morpholinyl, or thiomorpholinyl, each of which is substituted with one $R^c$ group.

In one embodiment, a compound of the invention is according to any one of Formula I-IV, wherein $R^3$ is 4-7 membered monocyclic heterocycloalkyl comprising one or more heteroatoms independently selected from O, and S, substituted with one or more independently selected $R^c$ groups, and $R^c$ is as described above. In a particular embodiment, $R^3$ is pyrrolidinyl, tetrahydrofuranyl, tetrahydropyranyl, piperidinyl, piperazinyl, morpholinyl, or thiomorpholinyl, each of which is substituted with one or more independently selected $R^c$ groups. In a particular embodiment, $R^c$ is selected from halo, CN, oxo, and OH. In a more particular embodiment, $R^c$ is selected from F, Cl, CN, oxo, and OH.

In one embodiment, a compound of the invention is according to any one of Formula I-IV, wherein $R^3$ is 4-7 membered monocyclic heterocycloalkyl comprising one or more heteroatoms independently selected from O, and S, substituted with one or more independently selected $R^c$ groups, and $R^c$ is as described above. In a particular embodiment, $R^3$ is pyrrolidinyl, tetrahydrofuranyl, tetrahydropyranyl, piperidinyl, piperazinyl, morpholinyl, or thiomorpholinyl, each of which is substituted with one or more independently selected $R^c$ groups. In a particular embodiment, $R^c$ is $C_{1-4}$ alkyl, optionally substituted with one or more independently selected $R^{7c}$, wherein $R^{7c}$ is as defined above. In a more particular embodiment, $R^c$ is —CH$_3$, —CH$_2$CH$_3$, or —CH(CH$_3$)$_2$, each of which is optionally substituted with one or more independently selected $R^{7c}$. In another more particular embodiment, $R^c$ is $C_{1-4}$ alkyl, optionally substituted with one or more independently selected $R^{7c}$, wherein $R^{7c}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In yet another more particular embodiment, $R^c$ is —CH$_3$, —CH$_2$CH$_3$, or —CH(CH$_3$)$_2$, each of which is optionally substituted with one or more independently selected $R^{7c}$, wherein $R^{7c}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$.

In one embodiment, a compound of the invention is according to any one of Formula I-IV, wherein $R^3$ is 4-7 membered monocyclic heterocycloalkyl comprising one or more heteroatoms independently selected from O, and S, substituted with one or more independently selected $R^c$ groups, and $R^c$ is as described above. In a particular embodiment, $R^3$ is pyrrolidinyl, tetrahydrofuranyl, tetrahydropyranyl, piperidinyl, piperazinyl, morpholinyl, or thiomorpholinyl, each of which is substituted with one or more independently selected $R^c$ groups. In a particular embodiment, $R^c$ is $C_{1-4}$ alkoxy, optionally substituted with one or more independently selected $R^{7c}$, wherein $R^{7c}$ is as defined above. In a more particular embodiment, $R^c$ is —OCH$_3$, —OCH$_2$CH$_3$, or —OCH(CH$_3$)$_2$, each of which is optionally substituted with one or more independently selected $R^{7c}$. In another more particular embodiment, $R^c$ is $C_{1-4}$ alkoxy, optionally substituted with one or more independently selected $R^{7c}$, wherein $R^{7c}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In yet another more particular embodiment, $R^c$ is —OCH$_3$, —OCH$_2$CH$_3$, or —OCH(CH$_3$)$_2$, each of which is optionally substituted with one or more independently selected $R^{7c}$, wherein $R^{7c}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$.

In one embodiment, a compound of the invention is according to any one of Formula I-IV, wherein $R^3$ is 4-7 membered monocyclic heterocycloalkyl comprising one or more heteroatoms independently selected from O, and S, substituted with one or more independently selected $R^c$ groups, and $R^c$ is as described above. In a particular embodiment, $R^3$ is pyrrolidinyl, tetrahydrofuranyl, tetrahydropyranyl, piperidinyl, piperazinyl, morpholinyl, or thiomorpholinyl, each of which is substituted with one or more independently selected $R^c$ groups. In a particular embodiment, $R^c$ is phenyl. In another particular embodiment, $R^c$ is phenyl optionally substituted with one or more independently selected halo, $C_{1-4}$ alkyl, $C_{1-4}$ alkoxy, —CN, or —NR$^{9a}$R$^{9b}$, wherein R$^{9a}$ and R$^{9b}$ are as described above In another more particular embodiment, $R^c$ is phenyl substituted with one or more independently selected F, Cl, —CH$_3$, —CH$_2$CH$_3$, —CH(CH$_3$)$_2$, —OCH$_3$, —OCH$_2$CH$_3$, —OCH(CH$_3$)$_2$, CN, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$.

In one embodiment, a compound of the invention is according to any one of Formula I-IV, wherein $R^3$ is 4-7 membered monocyclic heterocycloalkyl comprising one or more heteroatoms independently selected from O, and S, substituted with one or more independently selected $R^c$ groups, and $R^c$ is as described above. In a particular embodiment, $R^3$ is pyrrolidinyl, tetrahydrofuranyl, tetrahydropyranyl, piperidinyl, piperazinyl, morpholinyl, or thiomorpholinyl, each of which is substituted with one or more independently selected $R^c$ groups. In a particular embodiment, $R^c$ is 5-6 membered monocyclic heteroaryl comprising one or more heteroatoms independently selected from N, O, or S. In another particular embodiment, $R^c$ is 5-6 membered monocyclic heteroaryl comprising one or more heteroatoms independently selected from N, O, or S, substituted with one or more independently selected halo, $C_{1-4}$ alkyl, $C_{1-4}$ alkoxy, CN, or —NR$^{9c}$R$^{9d}$, wherein R$^{9c}$ and R$^{9d}$ is as described above. In a more particular embodiment, $R^c$ is furanyl, thiophenyl, pyrazolyl, imidazolyl, thiazolyl, oxazolyl, pyridinyl, pyridazinyl, pyrimidyl, or pyrazinyl. In another more particular embodiment, $R^c$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected halo, $C_{1-4}$ alkyl, $C_{1-4}$ alkoxy, CN, or —NR$^{9c}$R$^{9d}$, wherein R$^{9c}$ and R$^{9d}$ is as described above. In a most particular embodiment, $R^c$ is 5-6 membered monocyclic heteroaryl comprising one or more heteroatoms independently selected from N, O, or S, substituted with one or more independently selected F, Cl, —CH$_3$, —CH$_2$CH$_3$, —CH(CH$_3$)$_2$, —OCH$_3$, —OCH$_2$CH$_3$, —OCH(CH$_3$)$_2$, CN, —N(CH$_3$)$_2$, —NH(CH$_2$—CH$_3$), —N(CH$_2$—CH$_3$)CH$_3$, or —N(CH$_2$—CH$_3$)$_2$. In another most particular embodiment, $R^c$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected F, Cl, —CH$_3$, —CH$_2$CH$_3$, —CH(CH$_3$)$_2$, —OCH$_3$, —OCH$_2$CH$_3$, —OCH(CH$_3$)$_2$, —CN, —N(CH$_3$)$_2$, —NH(CH$_2$—CH$_3$), —N(CH$_2$—CH$_3$)CH$_3$, or —N(CH$_2$—CH$_3$)$_2$.

In one embodiment, a compound of the invention is according to any one of Formula I-IV, wherein $R^3$ is $C_{6-10}$ mono or bicyclic aryl. In a particular embodiment, $R^3$ is phenyl.

In one embodiment, a compound of the invention is according to any one of Formula I-IV, wherein $R^3$ is $C_{6-10}$ mono or bicyclic aryl optionally substituted with one or more independently selected $R^d$ groups, and $R^d$ is as described above. In another embodiment, $R^3$ is phenyl is substituted with one or more independently selected $R^d$ groups. In a particular embodiment, $R^3$ is $C_{6-10}$ mono or bicyclic aryl, substituted with one or two independently selected $R^d$ groups. In another particular embodiment, $R^3$ is phenyl substituted with one or two independently selected $R^d$ groups. In a more particular embodiment, $R^3$ is $C_{6-10}$ mono or bicyclic aryl, substituted with one $R^d$ group. In another particular embodiment, $R^3$ is phenyl substituted with one $R^d$ group.

In one embodiment, a compound of the invention is according to any one of Formula I-IV, wherein $R^3$ is $C_{6-10}$ mono or bicyclic aryl, substituted with one or more independently selected $R^d$ groups, and $R^d$ is as described above. In a particular embodiment, $R^3$ is phenyl substituted with one or more independently selected $R^d$ groups. In a particular embodiment, $R^d$ is selected from halo, CN, and OH. In a more particular embodiment, $R^d$ is selected from F, Cl, CN, and OH.

In one embodiment, a compound of the invention is according to any one of Formula I-IV, wherein $R^3$ is $C_{6-10}$ mono or bicyclic aryl, substituted with one or more independently selected $R^d$ groups, and $R^d$ is as described above. In a particular embodiment, $R^3$ is phenyl substituted with one or more independently selected $R^d$ groups. In a particular embodiment, $R^d$ is $C_{1-4}$ alkyl, optionally substituted with one or more independently selected $R^{7d}$, wherein $R^{7d}$ is as defined above. In a more particular embodiment, $R^d$ is —CH$_3$, —CH$_2$CH$_3$, or —CH(CH$_3$)$_2$, each of which is optionally substituted with one or more independently selected $R^{7d}$. In another more particular embodiment, $R^d$ is $C_{1-4}$ alkyl, optionally substituted with one or more independently selected $R^{7d}$, wherein $R^{7d}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In yet another more particular embodiment, $R^d$ is —CH$_3$, —CH$_2$CH$_3$, or —CH(CH$_3$)$_2$, each of which is optionally substituted with one or more independently selected $R^{7d}$, wherein $R^{7c}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$.

In one embodiment, a compound of the invention is according to any one of Formula I-IV, wherein $R^3$ is $C_{6-10}$ mono or bicyclic aryl, substituted with one or more independently selected $R^d$ groups, and $R^d$ is as described above. In a particular embodiment, $R^3$ is phenyl substituted with one or more independently selected $R^d$ groups. In a particular embodiment, $R^d$ is $C_{1-4}$ alkoxy, optionally substituted with one or more independently selected $R^{7d}$, wherein $R^{7d}$ is as defined above. In a more particular embodiment, $R^d$ is —OCH$_3$, —OCH$_2$CH$_3$, or —OCH(CH$_3$)$_2$, each of which is optionally substituted with one or more independently selected $R^{7d}$. In another more particular embodiment, $R^d$ is $C_{1-4}$ alkoxy, optionally substituted with one or more independently selected $R^{7d}$, wherein $R^{7d}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In yet another more particular embodiment, $R^d$ is —OCH$_3$, —OCH$_2$CH$_3$, or —OCH(CH$_3$)$_2$, each of which is optionally substituted with one or more independently selected $R^{7d}$, wherein $R^{7d}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$.

In one embodiment, a compound of the invention is according to any one of Formula I-IV, wherein $R^3$ is $C_{6-10}$ mono or bicyclic aryl, substituted with one or more independently selected $R^d$ groups, and $R^c$ is as described above. In a particular embodiment, $R^3$ is phenyl substituted with one or more independently selected $R^d$ groups. In a particular embodiment, $R^d$ is $C_{3-7}$ cycloalkyl. In a more particular embodiment, $R^d$ is cyclopropyl, cyclobutyl, cylopentyl, or cyclohexyl. In a most particular embodiment, $R^d$ is cyclopropyl.

In one embodiment, a compound of the invention is according to any one of Formula I-IV, wherein $R^3$ is $C_{6-10}$ mono or bicyclic aryl, substituted with one or more independently selected $R^d$ groups, and $R^c$ is as described above. In a particular embodiment, $R^3$ is phenyl substituted with one or more independently selected $R^d$ groups. In a particular embodiment, $R^d$ is 5-10 membered mono or fused bicyclic heteroaryl comprising one or more heteroatoms independently selected from N, O, or S. In a more particular embodiment, $R^d$ is furanyl, thiophenyl, pyrazolyl, imidazolyl, thiazolyl, oxazolyl, pyridinyl, pyridazinyl, pyrimidyl, or pyrazinyl.

In one embodiment, a compound of the invention is according to any one of Formula I-IV, wherein $R^3$ is $C_{6-10}$ mono or bicyclic aryl, substituted with one or more independently selected $R^d$ groups, and $R^c$ is as described above. In a particular embodiment, $R^3$ is phenyl substituted with one or more independently selected $R^d$ groups. In a particular embodiment, $R^d$ is —NH-Phenyl.

In one embodiment, a compound of the invention is according to any one of Formula I-IV, wherein $R^3$ is phenyl fused to a 5-6 membered heterocycloalkyl comprising one or more heteroatoms independently selected from N, O, and S, and optionally substituted with one or more independently selected $R^d$ groups. In a particular embodiment, $R^3$ is dihydroisoindole, benzodioxole, dihydrobenzooxazole, or dihydrobenzodioxine, each of which is optionally substituted with one or more independently selected $R^d$ groups. In a particular embodiment, $R^d$ is selected from halo, CN, and OH. In a more particular embodiment, $R^d$ is selected from F, Cl, CN, and OH.

In one embodiment, a compound of the invention is according to any one of Formula I-IV, wherein $R^3$ is phenyl fused to a $C_{5-6}$ cycloalkyl, optionally substituted with one or more independently selected $R^d$ groups. In a particular embodiment, $R^3$ is indan, or 1,2,3,4-tetrahydronaphthalen, each of which is optionally substituted with one or more independently selected $R^d$ groups. In a particular embodiment, $R^d$ is selected from halo, CN, and OH. In a more particular embodiment, $R^d$ is selected from F, Cl, CN, and OH.

In one embodiment, a compound of the invention is according to any one of Formula I-IV, wherein $R^3$ is 5-10 membered mono or fused bicyclic heteroaryl comprising one or more heteroatoms independently selected from N, O, and S. In a particular embodiment, $R^3$ is furanyl, thiophenyl, pyrazolyl, imidazolyl, thiazolyl, oxazolyl, pyridinyl, pyridazinyl, pyrimidyl, or pyrazinyl. In a more particular embodiment, $R^3$ is pyrazolyl, thiazolyl, or thiophenyl.

In one embodiment, a compound of the invention is according to any one of Formula I-IV, wherein $R^3$ is 5-10 membered mono or fused bicyclic heteroaryl comprising one or more heteroatoms independently selected from N, O, and S, optionally substituted with one or more independently selected $R^d$ groups, and $R^d$ is as described above. In another embodiment, $R^3$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected $R^d$ groups. In a particular embodiment, $R^3$ is 5-10 membered mono or fused bicyclic heteroaryl comprising one or more heteroatoms independently selected from N, O, and S, substituted with one or two independently selected $R^d$ groups. In another particular embodiment, $R^3$ is furanyl, thiophenyl, pyrazolyl, imidazolyl, thiazolyl, oxazolyl, pyridinyl, pyridazinyl, pyrimidyl, or pyrazinyl, each of which is substituted with one or two independently selected $R^d$ groups. In a more particular embodiment, $R^3$ is 5-10 membered mono or fused bicyclic heteroaryl comprising one or more heteroatoms independently selected from N, O, and S, substituted with one $R^d$ group. In another particular embodiment, $R^3$ is furanyl, thiophenyl, pyrazolyl, imidazolyl, thiazolyl, oxazolyl, pyridinyl, pyridazinyl, pyrimidyl, or pyrazinyl, each of which is substituted with one $R^d$ group.

In one embodiment, a compound of the invention is according to any one of Formula I-IV, wherein $R^3$ is 5-10 membered mono or fused bicyclic heteroaryl comprising one or more heteroatoms independently selected from N, O, and S, substituted with one or more independently selected $R^d$ groups, and $R^d$ is as described above. In a particular embodiment, $R^3$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected $R^d$ groups. In a particular embodiment, $R^d$ is selected from halo, CN, and OH. In a more particular embodiment, $R^d$ is selected from F, Cl, CN, and OH.

In one embodiment, a compound of the invention is according to any one of Formula I-IV, wherein $R^3$ is 5-10 membered mono or fused bicyclic heteroaryl comprising one or more heteroatoms independently selected from N, O, and S, substituted with one or more independently selected $R^d$ groups, and $R^d$ is as described above. In a particular embodiment, $R^3$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected $R^d$ groups. In a particular embodiment, $R^d$ is $C_{1-4}$ alkyl, optionally substituted with one or more independently selected $R^{7d}$, wherein $R^{7d}$ is as defined above. In a more particular embodiment, $R^d$ is —CH$_3$, —CH$_2$CH$_3$, or —CH(CH$_3$)$_2$, each of which is optionally substituted with one or more independently selected $R^{7d}$. In another more particular embodiment, $R^d$ is $C_{1-4}$ alkyl, optionally substituted with one or more independently selected $R^{7d}$, wherein $R^{7d}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In yet another more particular embodiment, $R^d$ is —CH$_3$, —CH$_2$CH$_3$, or —CH(CH$_3$)$_2$, each of which is optionally substituted with one or more independently selected $R^{7d}$, wherein $R^{7c}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$.

In one embodiment, a compound of the invention is according to any one of Formula I-IV, wherein $R^3$ is 5-10 membered mono or fused bicyclic heteroaryl comprising one or more heteroatoms independently selected from N, O, and S, substituted with one or more independently selected $R^d$ groups, and $R^d$ is as described above. In a particular embodiment, $R^3$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected $R^d$ groups. In a particular embodiment, $R^d$ is $C_{1-4}$ alkoxy, optionally substituted with one or more independently selected $R^{7d}$, wherein $R^{7d}$ is as defined above. In a more particular embodiment, $R^d$ is —OCH$_3$, —OCH$_2$CH$_3$, or —OCH(CH$_3$)$_2$, each of which is optionally substituted with one or more independently selected $R^{7d}$. In another more particular embodiment, $R^d$ is $C_{1-4}$ alkoxy, optionally substituted with one or more independently selected $R^{7d}$, wherein $R^{7d}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$. In yet another more particular embodiment, $R^d$ is —OCH$_3$, —OCH$_2$CH$_3$, —OCH(CH$_3$)$_2$, each of which is optionally substituted with one or more independently selected $R^{7d}$, wherein $R^{7d}$ is F, Cl, OH, CN, —OCH$_3$, —OCH$_2$CH$_3$, —NHCH$_3$, —N(CH$_3$)$_2$, —NH(CH$_2$—CH$_3$), —N(CH$_2$—CH$_3$)CH$_3$, or —N(CH$_2$—CH$_3$)$_2$.

In one embodiment, a compound of the invention is according to any one of Formula I-IV, wherein $R^3$ is 5-10 membered mono or fused bicyclic heteroaryl comprising one or more heteroatoms independently selected from N, O, and S, substituted with one or more independently selected $R^d$ groups, and $R^d$ is as described above. In a particular embodiment, $R^3$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected $R^d$ groups. In a particular embodiment, $R^d$ is $C_{3-7}$ cycloalkyl. In a more particular embodiment, $R^d$ is cyclopropyl, cyclobutyl, cylopentyl, or cyclohexyl. In a most particular embodiment, $R^d$ is cyclopropyl.

In one embodiment, a compound of the invention is according to any one of Formula I-IV, wherein $R^3$ is 5-10 membered mono or fused bicyclic heteroaryl comprising one or more heteroatoms independently selected from N, O, and S, substituted with one or more independently selected $R^d$ groups, and $R^d$ is as described above. In a particular embodiment, $R^3$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected $R^d$ groups. In a particular embodiment, $R^d$ is 5-10 membered mono or fused bicyclic heteroaryl comprising one or more heteroatoms independently selected from N, O, or S. In a more particular embodiment, $R^d$ is furanyl, thiophenyl, pyrazolyl, imidazolyl, thiazolyl, oxazolyl, pyridinyl, pyridazinyl, pyrimidyl, or pyrazinyl.

In one embodiment, a compound of the invention is according to any one of Formula I-IV, wherein $R^3$ is 5-10 membered mono or fused bicyclic heteroaryl comprising one or more heteroatoms independently selected from N, O, and S, substituted with one or more independently selected $R^d$ groups, and $R^d$ is as described above. In a particular embodiment, $R^3$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected $R^d$ groups. In a particular embodiment, $R^d$ is —NH-Phenyl.

In one embodiment, a compound of the invention is according to any one of Formula I-IV, wherein $R^3$ is 5-6 membered monocyclic heteroaryl comprising one or more heteroatoms independently selected from N, O, and S, fused to a 5-6 membered heterocycloalkyl comprising one or more heteroatoms independently selected from N, O, and S, and optionally substituted with one or more independently selected $R^d$ groups. In a particular embodiment, $R^d$ is selected from halo, CN, and OH. In a more particular embodiment, $R^d$ is selected from F, Cl, CN, and OH.

In one embodiment, a compound of the invention is according to any one of Formula I-IV, wherein $R^3$ is 5-6 membered monocyclic heteroaryl comprising one or more heteroatoms independently selected from N, O, and S, fused to a $C_{5-6}$ cycloalkyl, optionally substituted with one or more independently selected $R^d$ groups. In a particular embodiment, $R^d$ is selected from halo, CN, and OH. In a more particular embodiment, $R^d$ is selected from F, Cl, CN, and OH.

In one embodiment, a compound of the invention is according to any one of Formula I-IV, wherein $R^3$ is $C_{2-6}$ alkenyl. In a particular embodiment, $R^3$ is —CH═CH$_2$, —CH═CH—CH$_3$, —CH═CH—CH$_2$CH$_3$, —CH$_2$—CH═CH—CH$_3$, —CH$_2$—CH$_2$—CH═CH$_2$, —C(CH$_3$)═CH$_2$, —CH═CH(CH$_3$), or —C(CH$_3$)═CH(CH$_3$).

In one embodiment, a compound of the invention is according to any one of Formula I-IV, wherein $R^3$ is $C_{3-6}$ alkyl. In a particular embodiment, $R^3$ is —CH(CH$_3$)$_2$, —C(CH$_3$)$_3$, or —CH$_2$CH(CH$_3$)$_2$. In a more particular embodiment, $R^3$ is —C(CH$_3$)$_3$, or —CH$_2$CH(CH$_3$)$_2$. In another particular embodiment, $R^3$ is —C(CH$_3$)$_2$—CH$_3$, or —CH(CH$_3$)—CH$_2$(CH$_3$). In a most particular embodiment, $R^3$ is —C(CH$_3$)$_3$.

In one embodiment, a compound of the invention is according to any one of Formula I-IV, wherein $R^3$ is $C_{1-6}$ alkyl substituted with one or more independently selected $R^e$ groups. In a particular embodiment, $R^3$ is $C_{1-6}$ alkyl substituted with one, two or three independently selected $R^e$ groups. In a more particular embodiment, $R^3$ is $C_{1-6}$ alkyl substituted with one $R^e$ group.

In one embodiment, a compound of the invention is according to any one of Formula I-IV, wherein $R^3$ is $C_{1-6}$ alkyl substituted with one or more independently selected $R^e$ groups. In a particular embodiment, $R^3$ is —CH$_3$, —CH$_2$CH$_3$, —CH(CH$_3$)$_2$, —C(CH$_3$)$_3$, or —CH$_2$CH(CH$_3$)$_2$, each of which is substituted with one or more independently selected $R^e$ groups. In another particular embodiment, $R^3$ is $C_{1-6}$ alkyl substituted with one or more independently selected F, Cl, OH, or CN. In a most particular embodiment, $R^3$ is —CF$_3$, —CH$_2$CF$_3$, —CH(OH)CF$_3$, —CH$_2$—OH, —CH$_2$—CH$_2$—OH, —C(CH$_3$)$_2$—CH$_2$—OH, —CH$_2$—CN, or —CH$_2$—CH$_2$—CN.

In one embodiment, a compound of the invention is according to any one of Formula I-IV, wherein $R^3$ is $C_{1-6}$ alkyl substituted with one or more independently selected $R^e$ groups, wherein $R^e$ is $C_{1-4}$ alkoxy optionally substituted with one or more independently selected $R^{7e}$. In a particular embodiment, $R^3$ is —CH$_3$, —CH$_2$CH$_3$, —CH(CH$_3$)$_2$, —C(CH$_3$)$_3$, or —CH$_2$CH(CH$_3$)$_2$, each of which is substituted with one or more independently selected $R^e$ groups, wherein $R^e$ is $C_{1-4}$ alkoxy optionally substituted with one or more independently selected $R^{7e}$. In a more particular embodiment, $R^e$—OCH$_3$, —OCH$_2$CH$_3$, —OCH(CH$_3$)$_2$, each of which is optionally substituted with one or more independently selected $R^{7e}$. In another more particular embodiment, $R^e$ is $C_{1-4}$ alkoxy optionally substituted with one or more independently selected $R^{7e}$, wherein $R^{7e}$ is selected from F, Cl, OH, —CN, —OCH$_3$, —OCH$_2$CH$_3$, —NH(CH$_3$) or —N(CH$_3$)$_2$. In a further more particular embodiment, $R^e$ is —OCH$_3$, —OCH$_2$—CH$_3$, or —OCH(CH$_3$)$_2$, each of which is substituted with one or more independently selected $R^{7e}$, and each $R^{7e}$ is F, Cl, OH, —CN, —OCH$_3$, —OCH$_2$CH$_3$, —NH(CH$_3$)

or —N(CH$_3$)$_2$. In a most particular embodiment, R$^e$ is —OCH$_3$, —OCH$_2$—CH$_3$, O—CF$_3$, —OCH$_2$—CHF$_2$, —OCH$_2$CH$_2$OCH$_3$, or —OCH$_2$CH$_2$N(CH$_3$)$_2$.

In one embodiment, a compound of the invention is according to Formula I, wherein R$^3$ is C$_{1-6}$ alkyl substituted with one or more independently selected R$^e$ groups. In a particular embodiment, R$^1$ is —CH$_3$, —CH$_2$—CH$_3$, —CH(CH$_3$)$_2$, —C(CH$_3$)$_3$, —C(CH$_3$)$_2$—CH$_3$, or —C(CH$_3$)H—C(CH$_3$)$_2$H, each of which is substituted with one or more independently selected R$^e$ groups, and R$^e$ is C$_{3-7}$ cycloalkyl. In another particular embodiment, R$^3$ is C$_{1-6}$ alkyl substituted with one or more independently selected R$^e$ groups selected from cyclopropyl, cyclobutyl, cyclopentyl, and cyclohexyl. In a particular embodiment, R$^3$ is —CH$_3$, —CH$_2$—CH$_3$, —CH(CH$_3$)$_2$, —C(CH$_3$)$_3$, —C(CH$_3$)$_2$—CH$_3$, or —C(CH$_3$)H—C(CH$_3$)$_2$H, each of which is substituted with one or more independently selected R$^e$ groups selected from cyclopropyl, cyclobutyl, cyclopentyl, and cyclohexyl. In a most particular embodiment, R$^3$ is —CH$_2$-cyclopropyl, —CH(CH$_3$)-cyclopropyl.

In one embodiment, a compound of the invention is according to Formula I, wherein R$^3$ is

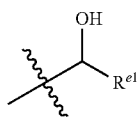

wherein R$^{e1}$ is C$_{1-5}$ alkyl optionally substituted with one or more independently selected halo, CN, C$_{1-4}$ alkoxy, or C$_{3-7}$ cycloalkyl. In a particular embodiment, R$^{e1}$ is —CH$_3$, —CH$_2$CH$_3$, —CH(CH$_3$)$_2$, —C(CH$_3$)$_3$, —CH$_2$CH(CH$_3$)$_2$, or —CH$_2$C(CH$_3$)$_3$, each of which is optionally substituted with one or more independently selected halo, CN, C$_{1-4}$ alkoxy, or C$_{3-7}$ cycloalkyl. In a particular embodiment, R$^{e1}$ is C$_{1-5}$ alkyl optionally substituted with one or more independently selected F, Cl, OH, CN, —OCH$_3$, —OCH$_2$CH$_3$, cyclopropyl, cyclobutyl, or cyclopentyl. In another particular embodiment, R$^3$ is —CH$_3$, —CH$_2$CH$_3$, —CH(CH$_3$)$_2$, —C(CH$_3$)$_3$, —CH$_2$CH(CH$_3$)$_2$, or —CH$_2$C(CH$_3$)$_3$, each of which is optionally substituted with one or more independently selected F, Cl, OH, CN, —OCH$_3$, —OCH$_2$CH$_3$, cyclopropyl, cyclobutyl, or cyclopentyl. In a most particular embodiment, R$^{e1}$ is —CH$_3$, —CH$_2$CH$_3$, —CH(CH$_3$)$_2$, —C(CH$_3$)$_3$, —CH$_2$CH(CH$_3$)$_2$, or —CH$_2$C(CH$_3$)$_3$. In another most particular embodiment, R$^{e1}$ is —CF$_3$, —CH$_2$CF$_3$, or —CH$_2$CN.

In one embodiment, a compound of the invention is according to Formula I, wherein R$^3$ is

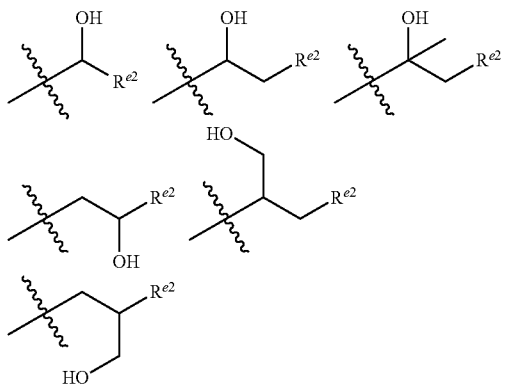

wherein R$^{e2}$ is C$_{3-7}$ cycloalkyl. In a particular embodiment, R$^{e2}$ is cyclopropyl, cyclobutyl, or cyclopentyl. In a more particular embodiment, R$^{e2}$ is cyclopropyl.

In one embodiment, a compound of the invention is according to any one of Formula I-IV, wherein R$^3$ is C$_{1-6}$ alkyl substituted with one or more independently selected R$^e$ groups, wherein R$^e$ is phenyl optionally substituted with one or more independently selected halo, C$_{1-4}$ alkyl, C$_{1-4}$ alkoxy, CN, or —NR$^{9e}$R$^{9f}$. In a particular embodiment, R$^3$ is —CH$_3$, —CH$_2$CH$_3$, —CH(CH$_3$)$_2$, —C(CH$_3$)$_3$, or —CH$_2$CH(CH$_3$)$_2$, each of which is substituted with one or more independently selected R$^e$ groups, wherein R$^e$ is phenyl optionally substituted with one or more independently selected halo, C$_{1-4}$ alkyl, C$_{1-4}$ alkoxy, CN, and —NR$^{9e}$R$^{9f}$. In a more particular embodiment, R$^e$ phenyl optionally substituted with one or more independently selected F, Cl, —CH$_3$, —CH$_2$CH$_3$, —CH(CH$_3$)$_2$, —OCH$_3$, —OCH$_2$CH$_3$, —OCH(CH$_3$)$_2$, or CN. In a more particular embodiment, R$^e$ phenyl optionally substituted with one or more independently selected —NR$^{9e}$R$^{9f}$ wherein each R$^{9e}$ and R$^{9f}$ are independently selected from H, —CH$_3$, and —CH$_2$CH$_3$.

In one embodiment, a compound of the invention is according to any one of Formula I-IV, wherein R$^3$ is C$_{1-6}$ alkyl substituted with one or more independently selected R$^e$ groups, wherein R$^e$ is 5-6 membered mono, or heteroaryl comprising one or more heteroatoms independently selected from N, O, and S, optionally substituted with one or more independently selected halo, C$_{1-4}$ alkyl, C$_{1-4}$ alkoxy, CN, and —NR$^{9g}$R$^{9h}$. In a particular embodiment, R$^3$ is —CH$_3$, —CH$_2$CH$_3$, —CH(CH$_3$)$_2$, —C(CH$_3$)$_3$, or —CH$_2$CH(CH$_3$)$_2$, each of which is substituted with one or more independently selected R$^e$ groups, wherein R$^e$ is thienyl, furanyl, pyrazolyl, imidazolyl, oxazolyl, thiazolyl, pyridyl, pyrimidyl, pyrazinyl, or pyridazinyl, each of which is optionally substituted with one or more independently selected halo, C$_{1-4}$ alkyl, C$_{1-4}$ alkoxy, CN, or —NR$^{9g}$R$^{9h}$. In a more particular embodiment, R$^e$ or 5-6 membered mono, or heteroaryl comprising one or more heteroatoms independently selected from N, O, and S, optionally substituted with one or more independently selected F, Cl, —CH$_3$, —CH$_2$CH$_3$, —CH(CH$_3$)$_2$, —OCH$_3$, —OCH$_2$CH$_3$, —OCH(CH$_3$)$_2$, CN, or —NR$^{9g}$R$^{9h}$ wherein each R$^{9e}$ and R$^{9f}$ are independently selected from H, —CH$_3$, and —CH$_2$CH$_3$.

In one embodiment, a compound of the invention is according to any one of Formula I-IV, wherein R$^1$ is H.

In one embodiment, a compound of the invention is according to any one of Formula I-IV, wherein R$^1$ is —CH$_3$.

In one embodiment, a compound of the invention is according to any one of Formula I-IV, wherein R$^1$ is —CF$_3$.

In one embodiment, a compound of the invention is according to any one of Formula I-IV, wherein R$^1$ is cyclopropyl.

In one embodiment, the compound of the invention is selected from:
N-(3-carbamoyl-5-(piperidin-1-ylsulfonyl)thiophen-2-yl)-5-methylthiophene-2-carboxamide,
N-(3-carbamoyl-5-(piperidin-1-ylsulfonyl)thiophen-2-yl)-4-fluorobenzo[b]thiophene-2-carboxamide,
N-(3-carbamoyl-5-(N-ethyl-N-methylsulfamoyl)thiophen-2-yl)-5-methylthiophene-2-carboxamide,
N-(3-carbamoyl-5-(N,N-diethylsulfamoyl)thiophen-2-yl)-5-methylthiophene-2-carboxamide,
N-(3-carbamoyl-5-(4-methylpiperazin-1-ylsulfonyl)thiophen-2-yl)-5-methylthiophene-2-carboxamide,
N-(5-(N-benzyl-N-methylsulfamoyl)-3-carbamoylthiophen-2-yl)-5-methylthiophene-2-carboxamide,
N-(3-carbamoyl-5-(N-methyl-N-phenylsulfamoyl)thiophen-2-yl)-5-methylthiophene-2-carboxamide, N-(3-carbamoyl-5-(isoindolin-2-ylsulfonyl)thiophen-2-yl)-5-methylthiophene-2-carboxamide,
N-(3-carbamoyl-5-(piperidin-1-ylsulfonyl)thiophen-2-yl)-4,5,6,7-tetrahydrobenzo[b]thiophene-2-carboxamide,
N-(3-carbamoyl-5-(piperidin-1-ylsulfonyl)thiophen-2-yl)benzo[b]thiophene-2-carboxamide,
2-(3-cyanobenzamido)-5-(piperidin-1-ylsulfonyl)thiophene-3-carboxamide,
N-(3-carbamoyl-5-(piperidin-1-ylsulfonyl)thiophen-2-yl)benzo[d]thiazole-6-carboxamide,
2-(cyclopentanecarboxamido)-5-(piperidin-1-ylsulfonyl)thiophene-3-carboxamide,
2-(3-fluorobenzamido)-5-(piperidin-1-ylsulfonyl)thiophene-3-carboxamide,
N-(3-carbamoyl-5-(N,N-dimethylsulfamoyl)thiophen-2-yl)-5-methylthiophene-2-carboxamide,
N-(3-carbamoyl-5-(phenylsulfonyl)thiophen-2-yl)-5-methylthiophene-2-carboxamide,
2-(2-chlorobenzamido)-5-(piperidin-1-ylsulfonyl)thiophene-3-carboxamide,
2-(3-methoxybenzamido)-5-(piperidin-1-ylsulfonyl)thiophene-3-carboxamide,
2-(2-fluorobenzamido)-5-(piperidin-1-ylsulfonyl)thiophene-3-carboxamide,
2-(4-chlorobenzamido)-5-(piperidin-1-ylsulfonyl)thiophene-3-carboxamide,
2-(4-methoxybenzamido)-5-(piperidin-1-ylsulfonyl)thiophene-3-carboxamide,
2-(4-cyanobenzamido)-5-(piperidin-1-ylsulfonyl)thiophene-3-carboxamide,
5-tert-butyl-N-(3-carbamoyl-5-(piperidin-1-ylsulfonyl)thiophen-2-yl)thiophene-2-carboxamide,
2-(2-methoxybenzamido)-5-(piperidin-1-ylsulfonyl)thiophene-3-carboxamide,
2-(2-cyanobenzamido)-5-(piperidin-1-ylsulfonyl)thiophene-3-carboxamide,
2-(4-fluorobenzamido)-5-(piperidin-1-ylsulfonyl)thiophene-3-carboxamide,
2-(4-tert-butylbenzamido)-5-(piperidin-1-ylsulfonyl)thiophene-3-carboxamide,
2-butyramido-5-(piperidin-1-ylsulfonyl)thiophene-3-carboxamide,
5-(piperidin-1-ylsulfonyl)-2-pivalamidothiophene-3-carboxamide,
N-(3-carbamoyl-5-(piperidin-1-ylsulfonyl)thiophen-2-yl)-1-methyl-1H-pyrazole-3-carboxamide,
2-(1-methylcyclopropanecarboxamido)-5-(piperidin-1-ylsulfonyl)thiophene-3-carboxamide,
2-(2-(4-fluorophenyl)acetamido)-5-(piperidin-1-ylsulfonyl)thiophene-3-carboxamide,
N-(3-carbamoyl-5-(piperidin-1-ylsulfonyl)thiophen-2-yl)-5-methyl-1,3,4-oxadiazole-2-carboxamide,
N-(3-carbamoyl-5-(piperidin-1-ylsulfonyl)thiophen-2-yl)pyrazine-2-carboxamide,
N-(3-carbamoyl-5-(piperidin-1-ylsulfonyl)thiophen-2-yl)-1H-imidazole-4-carboxamide,
N-(3-carbamoyl-5-(piperidin-1-ylsulfonyl)thiophen-2-yl)-1H-pyrazole-3-carboxamide,
2-(4,4-difluorocyclohexanecarboxamido)-5-(piperidin-1-ylsulfonyl)thiophene-3-carboxamide,
5-(piperidin-1-ylsulfonyl)-2-(1-(trifluoromethyl)cyclopropanecarboxamido)thiophene-3-carboxamide,
N-(3-carbamoyl-5-(piperidin-1-ylsulfonyl)thiophen-2-yl)-5-fluorothiophene-2-carboxamide,
2-(3-phenylpropanamido)-5-(piperidin-1-ylsulfonyl)thiophene-3-carboxamide,
N-(3-carbamoyl-5-(piperidin-1-ylsulfonyl)thiophen-2-yl)pyrazolo[1,5-a]pyrimidine-3-carboxamide,
2-(cyclopropanecarboxamido)-5-(piperidin-1-ylsulfonyl)thiophene-3-carboxamide,
1-tert-butyl-N-(3-carbamoyl-5-(piperidin-1-ylsulfonyl)thiophen-2-yl)-1H-pyrazole-4-carboxamide,
2-(3,3-difluorocyclobutanecarboxamido)-5-(piperidin-1-ylsulfonyl)thiophene-3-carboxamide,
2-(1-methylcyclopropanecarboxamido)-5-(morpholinosulfonyl)thiophene-3-carboxamide,
2-(2-fluorobenzamido)-5-(morpholinosulfonyl)thiophene-3-carboxamide,
5-(morpholinosulfonyl)-2-pivalamidothiophene-3-carboxamide,
2-(2-methoxybenzamido)-5-(morpholinosulfonyl)thiophene-3-carboxamide,
2-(4-tert-butylbenzamido)-5-(morpholinosulfonyl)thiophene-3-carboxamide,
N-(3-carbamoyl-5-(morpholinosulfonyl)thiophen-2-yl)benzo[b]thiophene-2-carboxamide,
5-tert-butyl-N-(3-carbamoyl-5-(morpholinosulfonyl)thiophen-2-yl)thiophene-2-carboxamide,
2-(2-cyclopropylbenzamido)-5-(piperidin-1-ylsulfonyl)thiophene-3-carboxamide,
2-(3-(1H-pyrazol-1-yl)benzamido)-5-(piperidin-1-ylsulfonyl)thiophene-3-carboxamide,
2-(3-(1H-pyrazol-3-yl)benzamido)-5-(piperidin-1-ylsulfonyl)thiophene-3-carboxamide,
N-(3-carbamoyl-5-(pyrrolidin-1-ylsulfonyl)thiophen-2-yl)benzo[b]thiophene-2-carboxamide,
N-(3-carbamoyl-5-(pyrrolidin-1-ylsulfonyl)thiophen-2-yl)-1H-pyrazole-3-carboxamide,
2-(1-phenylcyclopropanecarboxamido)-5-(piperidin-1-ylsulfonyl)thiophene-3-carboxamide,
2-(1-cyanocyclopropanecarboxamido)-5-(piperidin-1-ylsulfonyl)thiophene-3-carboxamide,
N-(3-carbamoyl-5-(piperidin-1-ylsulfonyl)thiophen-2-yl)thiazole-4-carboxamide,
N-(3-carbamoyl-5-(piperidin-1-ylsulfonyl)thiophen-2-yl)pyrazolo[1,5-a]pyridine-3-carboxamide,
2-(1-(4-chlorophenyl)cyclopropanecarboxamido)-5-(piperidin-1-ylsulfonyl)thiophene-3-carboxamide,
N-(3-carbamoyl-5-(piperidin-1-ylsulfonyl)thiophen-2-yl)thiazole-5-carboxamide,
N-(3-carbamoyl-5-(morpholinosulfonyl)thiophen-2-yl)-1H-pyrazole-3-carboxamide,
N-(3-carbamoyl-5-(piperidin-1-ylsulfonyl)thiophen-2-yl)-5-(pyridin-3-yl)thiophene-2-carboxamide,
2-(4-tert-butylbenzamido)-5-(4,4-difluoropiperidin-1-ylsulfonyl)thiophene-3-carboxamide,
5-(4,4-difluoropiperidin-1-ylsulfonyl)-2-(2-fluorobenzamido)thiophene-3-carboxamide,
5-(4,4-difluoropiperidin-1-ylsulfonyl)-2-pivalamidothiophene-3-carboxamide,
5-tert-butyl-N-(3-carbamoyl-5-(morpholinosulfonyl)thiophen-2-yl)-1H-pyrazole-3-carboxamide,
N-(3-carbamoyl-5-(morpholinosulfonyl)thiophen-2-yl)-5-ethyl-1H-pyrazole-3-carboxamide,
2-(2-methoxy-4-(phenylamino)benzamido)-5-(morpholinosulfonyl)thiophene-3-carboxamide,
5-(N-benzyl-N-methylsulfamoyl)-2-(1-(2,2-difluorobenzo[d][1,3]dioxol-5-yl)cyclopropanecarboxamido)thiophene-3-carboxamide,
5-(N-benzyl-N-methylsulfamoyl)-2-(2-fluorobenzamido)thiophene-3-carboxamide,
N-(5-(N-benzyl-N-methylsulfamoyl)-3-carbamoylthiophen-2-yl)-1H-pyrazole-3-carboxamide, 5-(N,N-dimethylsulfamoyl)-2-(2-fluorobenzamido)thiophene-3-carboxamide,
N-(3-carbamoyl-5-(N,N-dimethylsulfamoyl)thiophen-2-yl)-1H-pyrazole-3-carboxamide,
N-(3-carbamoyl-5-(morpholinosulfonyl)thiophen-2-yl)thiazole-4-carboxamide,
N-(3-carbamoyl-5-(morpholinosulfonyl)thiophen-2-yl)-3-fluoropicolinamide,
5-(morpholinosulfonyl)-2-(2-(trifluoromethyl)benzamido)thiophene-3-carboxamide,
N-(3-carbamoyl-5-(morpholinosulfonyl)thiophen-2-yl)pyridazine-3-carboxamide,
N-(3-carbamoyl-5-(morpholinosulfonyl)thiophen-2-yl)pyridazine-4-carboxamide,
N-(3-carbamoyl-5-(morpholinosulfonyl)thiophen-2-yl)pyrimidine-2-carboxamide,
N-(5-(benzylsulfonyl)-3-carbamoylthiophen-2-yl)-5-methylthiophene-2-carboxamide,
N-(3-carbamoyl-5-(phenylsulfonyl)thiophen-2-yl)-1H-pyrazole-3-carboxamide,
N-(3-carbamoyl-5-(tetrahydro-2H-pyran-4-ylsulfonyl)thiophen-2-yl)-5-methylthiophene-2-carboxamide,
2-(2-fluorobenzamido)-4-methyl-5-(morpholinosulfonyl)thiophene-3-carboxamide,
N-(3-carbamoyl-4-methyl-5-(phenylsulfonyl)thiophen-2-yl)-5-methylthiophene-2-carboxamide,
2-(2-fluorobenzamido)-4-methyl-5-(phenylsulfonyl)thiophene-3-carboxamide,
5-(N-benzyl-N-methylsulfamoyl)-2-pivalamidothiophene-3-carboxamide,
N-(3-carbamoyl-5-(pyridin-2-ylsulfonyl)thiophen-2-yl)-5-methylthiophene-2-carboxamide,
N-(3-carbamoyl-4-methyl-5-(morpholinosulfonyl)thiophen-2-yl)-1H-pyrazole-3-carboxamide,
N-(3-carbamoyl-5-(morpholinosulfonyl)thiophen-2-yl)picolinamide,
4-methyl-5-(morpholinosulfonyl)-2-pivalamidothiophene-3-carboxamide,
N-(3-carbamoyl-5-(morpholinosulfonyl)thiophen-2-yl)thiazole-2-carboxamide,
N-(3-carbamoyl-5-(morpholinosulfonyl)thiophen-2-yl)oxazole-4-carboxamide,
N-(3-carbamoyl-5-(phenylsulfonyl)thiophen-2-yl)-5-ethyl-1H-pyrazole-3-carboxamide,
5-tert-butyl-N-(3-carbamoyl-5-(phenylsulfonyl)thiophen-2-yl)-1H-pyrazole-3-carboxamide,
N-(3-carbamoyl-5-(morpholinosulfonyl)thiophen-2-yl)-1H-pyrrole-2-carboxamide,
N-(3-carbamoyl-5-(morpholinosulfonyl)thiophen-2-yl)oxazole-2-carboxamide,
N-(3-carbamoyl-5-(morpholinosulfonyl)thiophen-2-yl)furan-2-carboxamide,
2-(2-fluorobenzamido)-5-(phenylsulfonyl)thiophene-3-carboxamide,
N-(3-carbamoyl-4-methyl-5-(phenylsulfonyl)thiophen-2-yl)-1H-pyrazole-3-carboxamide,
N-(3-carbamoyl-5-(morpholinosulfonyl)thiophen-2-yl)-5-(trifluoromethyl)-1H-pyrazole-3-carboxamide,
N-(3-carbamoyl-4-methyl-5-(phenylsulfonyl)thiophen-2-yl)-5-ethyl-1H-pyrazole-3-carboxamide,
4-methyl-5-(phenylsulfonyl)-2-(2-(trifluoromethyl)benzamido)thiophene-3-carboxamide,
4-methyl-5-(morpholinosulfonyl)-2-(2-(trifluoromethyl)benzamido)thiophene-3-carboxamide,
2-(2-fluorobenzamido)-5-(N-(4-fluorobenzyl)-N-methylsulfamoyl)thiophene-3-carboxamide,
5-(N-tert-butyl-N-methylsulfamoyl)-2-(2-fluorobenzamido)thiophene-3-carboxamide,
5-(N-(2,2-difluoroethyl)-N-methylsulfamoyl)-2-(2-fluorobenzamido)thiophene-3-carboxamide,
N-(3-carbamoyl-5-(4-fluorophenylsulfonyl)thiophen-2-yl)-1H-pyrazole-3-carboxamide,
N-(3-carbamoyl-5-(4-fluorophenylsulfonyl)thiophen-2-yl)-5-ethyl-1H-pyrazole-3-carboxamide,
2-(2-fluorobenzamido)-5-(4-fluorophenylsulfonyl)thiophene-3-carboxamide,
5-(4-fluorophenylsulfonyl)-2-pivalamidothiophene-3-carboxamide,
N-(3-carbamoyl-5-(3-fluorophenylsulfonyl)thiophen-2-yl)-1H-pyrazole-3-carboxamide,
N-(3-carbamoyl-5-(3-fluorophenylsulfonyl)thiophen-2-yl)-5-ethyl-1H-pyrazole-3-carboxamide,
2-(2-fluorobenzamido)-5-(3-fluorophenylsulfonyl)thiophene-3-carboxamide,
N-(3-carbamoyl-5-(2-fluorophenylsulfonyl)thiophen-2-yl)-5-ethyl-1H-pyrazole-3-carboxamide,
2-(2-fluorobenzamido)-5-(2-fluorophenylsulfonyl)thiophene-3-carboxamide,
N-(3-carbamoyl-5-(3,4-difluorophenylsulfonyl)thiophen-2-yl)-1H-pyrazole-3-carboxamide,
N-(3-carbamoyl-5-(3,4-difluorophenylsulfonyl)thiophen-2-yl)-5-ethyl-1H-pyrazole-3-carboxamide,
5-(3,4-difluorophenylsulfonyl)-2-pivalamidothiophene-3-carboxamide,
5-(2-ethylphenylsulfonyl)-2-(2-fluorobenzamido)thiophene-3-carboxamide,
5-(3-fluorophenylsulfonyl)-2-pivalamidothiophene-3-carboxamide,
2-(2-fluorobenzamido)-5-(4-methoxypiperidin-1-ylsulfonyl)thiophene-3-carboxamide,
2-(2-fluorobenzamido)-5-(N-methyl-N-(4-methylbenzyl)sulfamoyl)thiophene-3-carboxamide,
5-(N-(cyanomethyl)-N-methylsulfamoyl)-2-(2-fluorobenzamido)thiophene-3-carboxamide,
5-(3,3-difluoroazetidin-1-ylsulfonyl)-2-(2-fluorobenzamido)thiophene-3-carboxamide,
2-(2-fluorobenzamido)-5-(methylsulfonyl)thiophene-3-carboxamide,
5-(ethylsulfonyl)-2-(2-fluorobenzamido)thiophene-3-carboxamide,
5-(cyclohexylsulfonyl)-2-(2-fluorobenzamido)thiophene-3-carboxamide,
2-(2-fluorobenzamido)-5-(4-methoxybenzylsulfonyl)thiophene-3-carboxamide,
2-(1-hydroxycyclopropanecarboxamido)-5-(morpholinosulfonyl)thiophene-3-carboxamide,
N-(3-carbamoyl-5-(morpholinosulfonyl)thiophen-2-yl)-2-methylthiazole-4-carboxamide,
2-(4-chloro-2-fluorobenzamido)-5-(morpholinosulfonyl)thiophene-3-carboxamide,
2-(3-cyclopropylbenzamido)-5-(morpholinosulfonyl)thiophene-3-carboxamide,
2-(2-methoxy-4-methylbenzamido)-5-(morpholinosulfonyl)thiophene-3-carboxamide,
2-(2-methylbenzamido)-5-(morpholinosulfonyl)thiophene-3-carboxamide,
2-(3-hydroxybenzamido)-5-(morpholinosulfonyl)thiophene-3-carboxamide,
2-(2,4-difluorobenzamido)-5-(morpholinosulfonyl)thiophene-3-carboxamide,
5-(4,4-difluoropiperidin-1-ylsulfonyl)-2-(1-hydroxycyclopropanecarboxamido)thiophene-3-carboxamide, N-(3-carbamoyl-5-(4,4-difluoropiperidin-1-ylsulfonyl)thiophen-2-yl)-1H-pyrazole-3-carboxamide,
N-(3-carbamoyl-5-(4,4-difluoropiperidin-1-ylsulfonyl)thiophen-2-yl)-5-ethyl-1H-pyrazole-3-carboxamide,
5-tert-butyl-N-(3-carbamoyl-5-(4,4-difluoropiperidin-1-ylsulfonyl)thiophen-2-yl)-1H-pyrazole-3-carboxamide,
2-(2-Hydroxy-benzoylamino)-5-(morpholine-4-sulfonyl)-thiophene-3-carboxylic acid amide,
5-((1S,4S)-2-oxa-5-azabicyclo[2.2.1]heptan-5-ylsulfonyl)-2-(2-fluorobenzamido)thiophene-3-carboxamide,
N-(3-carbamoyl-5-(N-(4-fluorobenzyl)-N-methylsulfamoyl)thiophen-2-yl)-1H-pyrazole-3-carboxamide,
N-(5-(1,4-oxazepan-4-ylsulfonyl)-3-carbamoylthiophen-2-yl)-1H-pyrazole-3-carboxamide,
2-(2-fluorobenzamido)-5-(N-(4-methoxybenzyl)-N-methylsulfamoyl)thiophene-3-carboxamide,
tert-butyl 2-(4-carbamoyl-5-(2-fluorobenzamido)thiophen-2-ylsulfonyl)-2,8-diazaspiro[4.5]decane-8-carboxylate,
2-(2-fluorobenzamido)-5-(4-(2-hydroxypropan-2-yl)piperidin-1-ylsulfonyl)thiophene-3-carboxamide,
5-(3,4-dihydroisoquinolin-2(1H)-ylsulfonyl)-2-(2-fluorobenzamido)thiophene-3-carboxamide,
2-(2-fluorobenzamido)-5-(isoindolin-2-ylsulfonyl)thiophene-3-carboxamide,
5-(N-cyclopropyl-N-methylsulfamoyl)-2-(2-fluorobenzamido)thiophene-3-carboxamide,
2-(2-fluorobenzamido)-5-(N-isopropyl-N-methylsulfamoyl)thiophene-3-carboxamide,
5-(N,N-diisopropylsulfamoyl)-2-(2-fluorobenzamido)thiophene-3-carboxamide,
2-(2-fluorobenzamido)-5-(N-methyl-N-(1-methylpiperidin-4-yl)sulfamoyl)thiophene-3-carboxamide,
5-(N-cyclopropyl-N-(3-fluorobenzyl)sulfamoyl)-2-(2-fluorobenzamido)thiophene-3-carboxamide,
2-(2-fluorobenzamido)-5-(N-(2-methoxyethyl)-N-(2,2,2-trifluoroethyl)sulfamoyl)thiophene-3-carboxamide,
2-(2-fluorobenzamido)-5-(4-(trifluoromethyl)-5,6-dihydropyridin-1(2H)-ylsulfonyl)thiophene-3-carboxamide,
2-(2-fluorobenzamido)-5-(4-phenylpiperidin-1-ylsulfonyl)thiophene-3-carboxamide,
N-(3-carbamoyl-5-(N-(3-fluoro-4-methoxybenzyl)-N-methylsulfamoyl)thiophen-2-yl)-1H-pyrazole-3-carboxamide,
2-(2-fluorobenzamido)-5-(N-methyl-N-(tetrahydro-2H-pyran-4-yl)sulfamoyl)thiophene-3-carboxamide,
5-(4-cyanopiperidin-1-ylsulfonyl)-2-(2-fluorobenzamido)thiophene-3-carboxamide,
2-(2-fluorobenzamido)-5-(isopropylsulfonyl)thiophene-3-carboxamide,
5-(tert-butylsulfonyl)-2-(2-fluorobenzamido)thiophene-3-carboxamide,
2-(2-fluorobenzamido)-5-(tetrahydro-2H-pyran-4-ylsulfonyl)thiophene-3-carboxamide,
N-(3-carbamoyl-5-(morpholinosulfonyl)thiophen-2-yl)-5-methyl-1H-pyrazole-3-carboxamide,
3-tert-butyl-N-(3-carbamoyl-5-(morpholinosulfonyl)thiophen-2-yl)-1-methyl-1H-pyrazole-5-carboxamide,
2-(4-fluoro-2-methoxybenzamido)-5-(morpholinosulfonyl)thiophene-3-carboxamide,
2-(4-fluoro-2-methylbenzamido)-5-(morpholinosulfonyl)thiophene-3-carboxamide,
N-(3-carbamoyl-5-(N-methyl-N-(4-methylbenzyl)sulfamoyl)thiophen-2-yl)-1H-pyrazole-3-carboxamide,
N-(3-carbamoyl-5-(N-(4-methoxybenzyl)-N-methylsulfamoyl)thiophen-2-yl)-1H-pyrazole-3-carboxamide,
N-(3-carbamoyl-5-(N-(2,4-difluorobenzyl)-N-methylsulfamoyl)thiophen-2-yl)-1H-pyrazole-3-carboxamide,
N-(3-carbamoyl-5-(N-(4-fluorophenyl)-N-methylsulfamoyl)thiophen-2-yl)-1H-pyrazole-3-carboxamide,
5-(4-(dimethylamino)piperidin-1-ylsulfonyl)-2-(2-fluorobenzamido)thiophene-3-carboxamide,
N-(3-carbamoyl-5-(N-methyl-N-(4-(trifluoromethyl)benzyl)sulfamoyl)thiophen-2-yl)-1H-pyrazole-3-carboxamide,
5-(3-cyanoazetidin-1-ylsulfonyl)-2-(2-fluorobenzamido)thiophene-3-carboxamide,
5-(3-fluoroazetidin-1-ylsulfonyl)-2-(2-fluorobenzamido)thiophene-3-carboxamide,
2-(2-fluorobenzamido)-5-(pyridin-2-ylsulfonyl)thiophene-3-carboxamide,
2-(2-fluorobenzamido)-5-(2-isopropylphenylsulfonyl)thiophene-3-carboxamide,
2-(2-fluorobenzamido)-5-(o-tolylsulfonyl)thiophene-3-carboxamide,
2-(2-fluorobenzamido)-5-(2-methoxyphenylsulfonyl)thiophene-3-carboxamide,
5-(2,5-dimethoxyphenylsulfonyl)-2-(2-fluorobenzamido)thiophene-3-carboxamide,
5-(3,3-dimethylazetidin-1-ylsulfonyl)-2-(2-fluorobenzamido)thiophene-3-carboxamide,
2-(2-fluorobenzamido)-5-(N-methyl-N-neopentylsulfamoyl)thiophene-3-carboxamide,
2-(2-fluorobenzamido)-5-(N-methyl-N-(3,3,3-trifluoropropyl)sulfamoyl)thiophene-3-carboxamide,
2-(2-fluorobenzamido)-5-(N-(3-methoxypropyl)-N-methylsulfamoyl)thiophene-3-carboxamide,
5-(3-(dimethylamino)azetidin-1-ylsulfonyl)-2-(2-fluorobenzamido)thiophene-3-carboxamide,
5-(2-oxa-6-azaspiro[3.3]heptan-6-ylsulfonyl)-2-(2-fluorobenzamido)thiophene-3-carboxamide,
N-(3-carbamoyl-5-(4,4-difluoropiperidin-1-ylsulfonyl)thiophen-2-yl)-5-(trifluoromethyl)-1H-pyrazole-3-carboxamide,
5-(4,4-difluoropiperidin-1-ylsulfonyl)-2-(2-hydroxybenzamido)thiophene-3-carboxamide,
N-(3-carbamoyl-5-(N-cyclopropyl-N-(4-fluorobenzyl)sulfamoyl)thiophen-2-yl)-1H-pyrazole-3-carboxamide,
N-(3-carbamoyl-5-(N-methyl-N-neopentylsulfamoyl)thiophen-2-yl)-1H-pyrazole-3-carboxamide,
N-(3-carbamoyl-5-(N-(cyclopropylmethyl)-N-methylsulfamoyl)thiophen-2-yl)-1H-pyrazole-3-carboxamide,
N-(3-carbamoyl-5-(N-methyl-N-(3,3,3-trifluoropropyl)sulfamoyl)thiophen-2-yl)-1H-pyrazole-3-carboxamide,
N-(3-carbamoyl-5-(N-methyl-N-(2,2,2-trifluoro-1-phenylethyl)sulfamoyl)thiophen-2-yl)-1H-pyrazole-3-carboxamide,
5-(4-fluoro-2-(hydroxymethyl)phenylsulfonyl)-2-(2-fluorobenzamido)thiophene-3-carboxamide,
2-(2-hydroxybenzamido)-5-(isopropylsulfonyl)thiophene-3-carboxamide,
2-(4-fluoro-2-hydroxybenzamido)-5-(morpholinosulfonyl)thiophene-3-carboxamide,
2-(1-hydroxycyclobutanecarboxamido)-5-(morpholinosulfonyl)thiophene-3-carboxamide,
N-(3-carbamoyl-5-(morpholinosulfonyl)thiophen-2-yl)-4-hydroxytetrahydro-2H-pyran-4-carboxamide,
2-(2-hydroxy-3,5-diisopropylbenzamido)-5-(morpholinosulfonyl)thiophene-3-carboxamide,
N-(3-carbamoyl-5-(4,4-difluoropiperidin-1-ylsulfonyl)thiophen-2-yl)-4-hydroxytetrahydro-2H-pyran-4-carboxamide,
2-(2-hydroxy-2-methylpropanamido)-5-(morpholinosulfonyl)thiophene-3-carboxamide, N-(3-carbamoyl-5-(N-(3-methoxypropyl)-N-methylsulfamoyl)thiophen-2-yl)-1H-pyrazole-3-carboxamide,
N-(3-carbamoyl-5-(3-fluoroazetidin-1-ylsulfonyl)thiophen-2-yl)-1H-pyrazole-3-carboxamide,
N-(3-carbamoyl-5-(3,3-dimethylazetidin-1-ylsulfonyl)thiophen-2-yl)-1H-pyrazole-3-carboxamide,
N-(3-carbamoyl-5-(N-methyl-N-(pyridin-4-ylmethyl)sulfamoyl)thiophen-2-yl)-1H-pyrazole-3-carboxamide,
N-(5-(azetidin-1-ylsulfonyl)-3-carbamoylthiophen-2-yl)-1H-pyrazole-3-carboxamide,
N-(3-carbamoyl-5-(N-cyclopropyl-N-methylsulfamoyl)thiophen-2-yl)-1H-pyrazole-3-carboxamide,
N-(3-carbamoyl-5-(N-isopropyl-N-methylsulfamoyl)thiophen-2-yl)-1H-pyrazole-3-carboxamide,
2-(2-hydroxybenzamido)-5-(methylsulfonyl)thiophene-3-carboxamide,
2-(2,4-difluoro-6-hydroxybenzamido)-5-(morpholinosulfonyl)thiophene-3-carboxamide,
5-(4,4-difluoropiperidin-1-ylsulfonyl)-2-(1-hydroxycyclobutanecarboxamido)thiophene-3-carboxamide,
2-(2,4-difluoro-6-hydroxybenzamido)-5-(4,4-difluoropiperidin-1-ylsulfonyl)thiophene-3-carboxamide,
5-(4,4-difluoropiperidin-1-ylsulfonyl)-2-(2-hydroxy-3,5-diisopropylbenzamido)thiophene-3-carboxamide,
2-(2-hydroxy-3-methylbenzamido)-5-(morpholinosulfonyl)thiophene-3-carboxamide,
5-(4,4-difluoropiperidin-1-ylsulfonyl)-2-(3-hydroxy-2,2-dimethylpropanamido)thiophene-3-carboxamide,
5-(N-(cyclopropylmethyl)-N-methylsulfamoyl)-2-(2-fluorobenzamido)thiophene-3-carboxamide,
2-(2-hydroxy-2-methylpropanamido)-5-(methylsulfonyl)thiophene-3-carboxamide,
2-(2-hydroxy-2-methylpropanamido)-5-(isopropylsulfonyl)thiophene-3-carboxamide,
5-(4-fluorophenylsulfonyl)-2-(2-hydroxy-2-methylpropanamido)thiophene-3-carboxamide,
5-(4-fluoro-2-methylphenylsulfonyl)-2-(1-hydroxycyclopropanecarboxamido)thiophene-3-carboxamide,
5-(4-fluorophenylsulfonyl)-2-(2-hydroxybenzamido)thiophene-3-carboxamide,
5-(4-fluorophenylsulfonyl)-2-(1-hydroxycyclopropanecarboxamido)thiophene-3-carboxamide,
5-(4-chlorophenylsulfonyl)-2-(1-hydroxycyclopropanecarboxamido)thiophene-3-carboxamide,
5-(4-fluorophenylsulfonyl)-2-(1-hydroxycyclobutanecarboxamido)thiophene-3-carboxamide,
5-(3-fluorophenylsulfonyl)-2-(1-hydroxycyclopropanecarboxamido)thiophene-3-carboxamide,
2-(1-hydroxycyclopropanecarboxamido)-5-(2-isopropylphenylsulfonyl)thiophene-3-carboxamide,
5-(4-fluorophenylsulfonyl)-2-(3-methoxypropanamido)thiophene-3-carboxamide,
N-(3-carbamoyl-5-(4-fluorophenylsulfonyl)thiophen-2-yl)-2-fluoronicotinamide,
5-(N-(4-fluorobenzyl)-N-methylsulfamoyl)-2-(1-hydroxycyclopropanecarboxamido)thiophene-3-carboxamide,
5-(N-cyclopropyl-N-methylsulfamoyl)-2-(1-hydroxycyclopropanecarboxamido)thiophene-3-carboxamide,
5-(N,N-diisopropylsulfamoyl)-2-(1-hydroxycyclopropanecarboxamido)thiophene-3-carboxamide,
5-(3,5-dimethylmorpholinosulfonyl)-2-(1-hydroxycyclopropanecarboxamido)thiophene-3-carboxamide,
2-(1-hydroxycyclopropanecarboxamido)-5-(N-(4-methoxybenzyl)-N-methylsulfamoyl)thiophene-3-carboxamide,
5-(N-(4-fluorophenyl)-N-methylsulfamoyl)-2-(1-hydroxycyclopropanecarboxamido)thiophene-3-carboxamide,
5-(N-(4-fluorophenyl)-N-isopropylsulfamoyl)-2-(1-hydroxycyclopropanecarboxamido)thiophene-3-carboxamide,
5-(2,6-dimethylmorpholinosulfonyl)-2-(1-hydroxycyclopropanecarboxamido)thiophene-3-carboxamide,
2-(1-hydroxycyclopropanecarboxamido)-5-(4-methoxypiperidin-1-ylsulfonyl)thiophene-3-carboxamide,
2-(1-hydroxycyclopropanecarboxamido)-5-(2-methylmorpholinosulfonyl)thiophene-3-carboxamide,
5-(3,3-dimethylmorpholinosulfonyl)-2-(1-hydroxycyclopropanecarboxamido)thiophene-3-carboxamide,
5-(2H-benzo[b][1,4]oxazin-4(3H)-ylsulfonyl)-2-(1-hydroxycyclopropanecarboxamido)thiophene-3-carboxamide,
2-(1-hydroxycyclopropanecarboxamido)-5-(3-methoxyazetidin-1-ylsulfonyl)thiophene-3-carboxamide,
5-(N-cyclopropyl-N-(2-methoxyethyl)sulfamoyl)-2-(1-hydroxycyclopropanecarboxamido)thiophene-3-carboxamide,
2-(1-hydroxycyclopropanecarboxamido)-5-(4-methoxyphenylsulfonyl)thiophene-3-carboxamide,
5-(2,5-dimethoxyphenylsulfonyl)-2-(1-hydroxycyclopropanecarboxamido)thiophene-3-carboxamide,
5-(2,6-dichlorophenylsulfonyl)-2-(1-hydroxycyclopropanecarboxamido)thiophene-3-carboxamide,
5-(4-fluorophenylsulfonyl)-2-(2-hydroxypropanamido)thiophene-3-carboxamide,
N-(3-carbamoyl-5-(4-fluorophenylsulfonyl)thiophen-2-yl)pyridazine-3-carboxamide,
N-(3-carbamoyl-5-(4-fluorophenylsulfonyl)thiophen-2-yl)pyridazine-4-carboxamide,
5-(2,6-dimethylphenylsulfonyl)-2-(1-hydroxycyclopropanecarboxamido)thiophene-3-carboxamide,
5-(4-fluorophenylsulfonyl)-2-(3,3,3-trifluoro-2-hydroxypropanamido)thiophene-3-carboxamide,
5-(4-fluorophenylsulfonyl)-2-(3-hydroxy-2,2-dimethylpropanamido)thiophene-3-carboxamide,
5-(4-fluorophenylsulfonyl)-2-(1-(hydroxymethyl)cyclopropanecarboxamido)thiophene-3-carboxamide,
N-(3-carbamoyl-5-(4-fluorophenylsulfonyl)thiophen-2-yl)-4-hydroxytetrahydro-2H-pyran-4-carboxamide,
5-(2-chloro-4-fluorophenylsulfonyl)-2-(1-hydroxycyclopropanecarboxamido)thiophene-3-carboxamide,
5-(2,4-difluorophenylsulfonyl)-2-(1-hydroxycyclopropanecarboxamido)thiophene-3-carboxamide,
2-(1-hydroxycyclopropanecarboxamido)-5-(2-(trifluoromethyl)phenylsulfonyl)thiophene-3-carboxamide,
5-(2,6-dimethylmorpholinosulfonyl)-2-(2-(trifluoromethyl)benzamido)thiophene-3-carboxamide,
5-(3,5-dimethylmorpholinosulfonyl)-2-(2-(trifluoromethyl)benzamido)thiophene-3-carboxamide,
5-(3,3-dimethylmorpholinosulfonyl)-2-(2-(trifluoromethyl)benzamido)thiophene-3-carboxamide,
5-(N-cyclopropyl-N-(2-methoxyethyl)sulfamoyl)-2-(2-(trifluoromethyl)benzamido)thiophene-3-carboxamide,
5-(N-cyclopropyl-N-methylsulfamoyl)-2-(2-(trifluoromethyl)benzamido)thiophene-3-carboxamide,
2-(2-(trifluoromethyl)benzamido)-5-(2,5,5-trimethylmorpholinosulfonyl)thiophene-3-carboxamide,
5-(2-bromo-4-fluorophenylsulfonyl)-2-(1-hydroxycyclopropanecarboxamido)thiophene-3-carboxamide,
2-(2-hydroxy-2-methylpropanamido)-5-(3-isopropoxyphenylsulfonyl)thiophene-3-carboxamide,
N-(3-carbamoyl-5-(4-fluorophenylsulfonyl)thiophen-2-yl)-5-fluoropicolinamide,
5-(4-fluorophenylsulfonyl)-2-(pyridin-2-ylamino)thiophene-3-carboxamide, 5-(4-fluorophenylsulfonyl)-2-(2-methoxy-2-methylpropanamido)thiophene-3-carboxamide,
2-(2-hydroxy-2-methylpropanamido)-5-(3-(trifluoromethoxy)phenylsulfonyl)thiophene-3-carboxamide,
2-(2-hydroxy-2-methylpropanamido)-5-(4-(trifluoromethoxy)phenylsulfonyl)thiophene-3-carboxamide,
2-(2-hydroxy-2-methylpropanamido)-5-(2-(trifluoromethoxy)phenylsulfonyl)thiophene-3-carboxamide,
5-(4-fluorophenylsulfonyl)-2-(2-hydroxycyclopentanecarboxamido)thiophene-3-carboxamide,
5-(4-fluorophenylsulfonyl)-2-(3-hydroxy-2-methylpropanamido)thiophene-3-carboxamide,
5-(4-fluorophenylsulfonyl)-2-(3-methylbut-2-enamido)thiophene-3-carboxamide,
5-(4-fluorophenylsulfonyl)-2-(3,3,3-trifluoro-2-hydroxy-2-(trifluoromethyl)propanamido)thiophene-3-carboxamide,
5-(4-fluorophenylsulfonyl)-2-(2-(2-methoxyethoxy)propanamido)thiophene-3-carboxamide,
N-(3-carbamoyl-5-(4-fluorophenylsulfonyl)thiophen-2-yl)-1,4-dioxane-2-carboxamide,
2-(2-hydroxy-2-methylpropanamido)-5-(3-methylpyridin-2-ylsulfonyl)thiophene-3-carboxamide,
2-(2-hydroxy-2-methylpropanamido)-5-(4-isopropoxyphenylsulfonyl)thiophene-3-carboxamide,
5-(4-fluorophenylsulfonyl)-2-(2-hydroxycyclohexanecarboxamido)thiophene-3-carboxamide,
5-(4-fluoro-2-isopropoxyphenylsulfonyl)-2-(2-hydroxy-2-methylpropanamido)thiophene-3-carboxamide,
5-(4-fluoro-2-(2-methoxyethoxy)phenylsulfonyl)-2-(2-hydroxy-2-methylpropanamido)thiophene-3-carboxamide,
5-(2-(difluoromethoxy)-4-fluorophenylsulfonyl)-2-(2-hydroxy-2-methylpropanamido)thiophene-3-carboxamide,
5-(2-(difluoromethoxy)-4-methoxyphenylsulfonyl)-2-(2-hydroxy-2-methylpropanamido)thiophene-3-carboxamide,
2-(2-hydroxy-2-methylpropanamido)-5-(1-methyl-1H-imidazol-2-ylsulfonyl)thiophene-3-carboxamide,
5-(2-chloro-4-fluorophenylsulfonyl)-2-(2-hydroxy-2-methylpropanamido)thiophene-3-carboxamide,
N-(5-(4-bromophenylsulfonyl)-3-carbamoylthiophen-2-yl)-1H-pyrazole-3-carboxamide,
2-(2,3-dihydroxypropanamido)-5-(4-fluorophenylsulfonyl)thiophene-3-carboxamide,
2-(2-hydroxy-2-methylpropanamido)-5-(2-(trifluoromethyl)phenylsulfonyl)thiophene-3-carboxamide,
5-(2-chlorophenylsulfonyl)-2-(2-hydroxy-2-methylpropanamido)thiophene-3-carboxamide,
(S)-5-(4-fluorophenylsulfonyl)-2-(2-hydroxypropanamido)thiophene-3-carboxamide,
5-(3-(dimethylamino)phenylsulfonyl)-2-(2-hydroxy-2-methylpropanamido)thiophene-3-carboxamide,
2-(2-hydroxy-2-methylpropanamido)-5-(2-isopropylphenylsulfonyl)thiophene-3-carboxamide,
1-(3-carbamoyl-5-(2-isopropylphenylsulfonyl)thiophen-2-ylamino)-2-methyl-1-oxopropan-2-yl acetate,
5-(5-fluoro-2-methoxyphenylsulfonyl)-2-(2-hydroxy-2-methylpropanamido)thiophene-3-carboxamide,
5-(5-fluoro-2-hydroxyphenylsulfonyl)-2-(2-hydroxy-2-methylpropanamido)thiophene-3-carboxamide,
2-(2-Hydroxy-2-methyl-propionylamino)-5-(6-methyl-pyridine-3-sulfonyl)-thiophene-3-carboxylic acid amide,
5-(2,6-Dichloro-benzenesulfonyl)-2-(2-hydroxy-2-methyl-propionylamino)-thiophene-3-carboxylic acid amide,
2-(2-Hydroxy-2-methyl-propionylamino)-5-(2-methyl-pyridine-4-sulfonyl)-thiophene-3-carboxylic acid amide,
5-(4-fluoro-2-(methoxymethyl)phenylsulfonyl)-2-(2-hydroxy-2-methylpropanamido)thiophene-3-carboxamide,
2-(2-hydroxy-2-methylpropanamido)-5-(2-methoxyphenylsulfonyl)thiophene-3-carboxamide,
2-(2-hydroxy-2-methylpropanamido)-5-(2-(2,2,2-trifluoroethyl)phenylsulfonyl)thiophene-3-carboxamide,
5-(5-chloro-2-fluorophenylsulfonyl)-2-(2-hydroxy-2-methylpropanamido)thiophene-3-carboxamide,
5-(N-(4-fluorophenyl)-N-methylsulfamoyl)-2-(2-hydroxy-2-methylpropanamido)thiophene-3-carboxamide,
5-(N-(4-fluorobenzyl)-N-methylsulfamoyl)-2-(2-hydroxy-2-methylpropanamido)thiophene-3-carboxamide,
5-(N-cyclopropyl-N-(2-methoxyethyl)sulfamoyl)-2-(2-hydroxy-2-methylpropanamido)thiophene-3-carboxamide,
5-(2H-benzo[b][1,4]oxazin-4(3H)-ylsulfonyl)-2-(2-hydroxy-2-methylpropanamido)thiophene-3-carboxamide,
5-(4,4-difluoropiperidin-1-ylsulfonyl)-2-(2-hydroxy-2-methylpropanamido)thiophene-3-carboxamide,
5-(3,3-Dimethyl-azetidine-1-sulfonyl)-2-(2-hydroxy-2-methyl-propionylamino)-thiophene-3-carboxylic acid amide,
5-(2,2-difluorobenzo[d][1,3]dioxol-5-ylsulfonyl)-2-(2-hydroxy-2-methylpropanamido)thiophene-3-carboxamide,
2-(2-hydroxypropanamido)-5-(2-(trifluoromethoxy)phenylsulfonyl)thiophene-3-carboxamide,
5-(2-Ethyl-benzenesulfonyl)-2-(2-hydroxy-propionylamino)-thiophene-3-carboxylic acid amide,
5-(2,6-Difluoro-benzenesulfonyl)-2-(2-hydroxy-propionylamino)-thiophene-3-carboxylic acid amide,
5-(2,6-Dichloro-benzenesulfonyl)-2-(S)-2-hydroxy-propionylamino)-thiophene-3-carboxylic acid amide,
5-(2-Fluoro-4-isopropoxy-benzenesulfonyl)-2-(2-hydroxy-2-methyl-propionylamino)-thiophene-3-carboxylic acid amide,
2-(2-Hydroxy-2-methyl-propionylamino)-5-(toluene-4-sulfonyl)-thiophene-3-carboxylic acid amide,
5-(3-Chloro-pyridine-2-sulfonyl)-2-(2-hydroxy-2-methyl-propionylamino)-thiophene-3-carboxylic acid amide,
2-(2-Hydroxy-propionylamino)-5-(4-trifluoromethoxy-benzenesulfonyl)-thiophene-3-carboxylic acid amide,
2-(2-Hydroxy-acetylamino)-5-(2-trifluoromethoxy-benzenesulfonyl)-thiophene-3-carboxylic acid amide,
2-[(1-Hydroxymethyl-cyclopropanecarbonyl)-amino]-5-(2-trifluoromethoxy-benzenesulfonyl)-thiophene-3-carboxylic acid amide,
5-(2-Chloro-benzenesulfonyl)-2-(2-hydroxy-propionylamino)-thiophene-3-carboxylic acid amide,
5-(2-Chloro-4-isopropoxy-benzenesulfonyl)-2-(2-hydroxy-2-methyl-propionylamino)-thiophene-3-carboxylic acid amide,
5-(2-Bromo-5-fluoro-benzenesulfonyl)-2-(2-hydroxy-2-methyl-propionylamino)-thiophene-3-carboxylic acid amide,
2-(2-Hydroxy-2-methyl-propionylamino)-5-(4-isopropoxy-2-trifluoromethyl-benzenesulfonyl)-thiophene-3-carboxylic acid amide,
5-[4-fluoro-2-(trifluoromethyl)phenyl]sulfonyl-2-(2-hydroxypropanoylamino)thiophene-3-carboxamide,
2-(2-hydroxypropanoylamino)-5-[(2-methyl-3-pyridyl)sulfonyl]thiophene-3-carboxamide,
5-(4-fluorophenyl)sulfonyl-2-[[(2R)-2-hydroxypropanoyl]amino]thiophene-3-carboxamide,
5-[2-chloro-4-(trifluoromethoxy)phenyl]sulfonyl-2-(2-hydroxypropanoylamino)thiophene-3-carboxamide,
5-(2-chloro-4-fluoro-phenyl)sulfonyl-2-(2-hydroxypropanoylamino)thiophene-3-carboxamide,
5-[(2,2-difluoro-1,3-benzodioxol-4-yl)sulfonyl]-2-[(2-hydroxy-2-methyl-propanoyl)amino]thiophene-3-carboxamide,
2-[[(2S)-2-hydroxypropanoyl]amino]-5-[4-(trifluoromethoxy)phenyl]sulfonyl-thiophene-3-carboxamide, 2-[[(2R)-2-hydroxypropanoyl]amino]-5-[4-(trifluoromethoxy)phenyl]sulfonyl-thiophene-3-carboxamide,
5-(2-chloro-5-fluoro-phenyl)sulfonyl-2-(2-hydroxypropanoylamino)thiophene-3-carboxamide,
5-[5-fluoro-2-(2,2,2-trifluoroethyl)phenyl]sulfonyl-2-(2-hydroxypropanoylamino)thiophene-3-carboxamide,
5-[5-fluoro-2-(trifluoromethyl)phenyl]sulfonyl-2-(2-hydroxypropanoylamino)thiophene-3-carboxamide,
5-(2-Chloro-4,5-difluoro-benzenesulfonyl)-2-(2-hydroxy-2-methyl-propionylamino)-thiophene-3-carboxylic acid amide,
5-(2-chloro-5-fluoro-phenyl)sulfonyl-2-[(2-hydroxy-2-methyl-propanoyl)amino]thiophene-3-carboxamide,
5-[5-fluoro-2-(2,2,2-trifluoroethyl)phenyl]sulfonyl-2-[(2-hydroxy-2-methyl-propanoyl)amino]thiophene-3-carboxamide,
5-(2-Chloro-5-fluoro-benzenesulfonyl)-2-(2-hydroxyacetylamino)-thiophene-3-carboxylic acid amide,
5-[5-Fluoro-2-(2,2,2-trifluoro-ethyl)-benzenesulfonyl]-2-(2-hydroxy-acetylamino)-thiophene-3-carboxylic acid amide,
5-(4-fluorophenyl)sulfonyl-2-[(2-hydroxy-3-methyl-butanoyl)amino]thiophene-3-carboxamide,
5-(4-fluorophenyl)sulfonyl-2-[(2-hydroxy-3,3-dimethyl-butanoyl)amino]thiophene-3-carboxamide,
5-(4-fluorophenyl)sulfonyl-2-[(2-hydroxy-4-methyl-pentanoyl)amino]thiophene-3-carboxamide,
2-[(2-hydroxy-2-methyl-propanoyl)amino]-5-[4-(trifluoromethyl)phenyl]sulfonyl-thiophene-3-carboxamide,
2-[(2-hydroxy-3-methyl-butanoyl)amino]-5-[4-(trifluoromethoxy)phenyl]sulfonyl-thiophene-3-carboxamide,
2-[(2-hydroxy-4-methyl-pentanoyl)amino]-5-[4-(trifluoromethyl)phenyl]sulfonyl-thiophene-3-carboxamide,
5-(4-chlorophenyl)sulfonyl-2-[[(2S)-2-hydroxypropanoyl]amino]thiophene-3-carboxamide, Enantiomer 1,
5-[4-fluoro-2-(trifluoromethyl)phenyl]sulfonyl-2-[[(2S)-2-hydroxypropanoyl]amino]thiophene-3-carboxamide, Enantiomer 1,
2-[(2-hydroxy-3,3-dimethyl-butanoyl)amino]-5-[4-(trifluoromethoxy)phenyl]sulfonyl-thiophene-3-carboxamide,
2-[(3-hydroxy-2-methyl-propanoyl)amino]-5-[4-(trifluoromethoxy)phenyl]sulfonyl-thiophene-3-carboxamide,
5-[5-fluoro-2-(trifluoromethoxy)phenyl]sulfonyl-2-[(3-hydroxy-2-methyl-propanoyl)amino]thiophene-3-carboxamide,
5-(4-fluorophenyl)sulfonyl-2-[[(2S)-2-hydroxy-3-methyl-butanoyl]amino]thiophene-3-carboxamide, Enantiomer 1,
5-(2-chloro-4-fluoro-phenyl)sulfonyl-2-[[(2S)-2-hydroxypropanoyl]amino]thiophene-3-carboxamide, Enantiomer 1, and
5-(2,6-dichloro-4-fluoro-phenyl)sulfonyl-2-[[(2S)-2-hydroxypropanoyl]amino]thiophene-3-carboxamide, Enantiomer 1.

In one embodiment, the compound of the invention is selected from:
5-(2,6-dichloro-4-fluoro-phenyl)sulfonyl-2-[[(2S)-2-hydroxypropanoyl]amino]thiophene-3-carboxamide,
5-[4-fluoro-2-(trifluoromethyl)phenyl]sulfonyl-2-[[(2S)-2-hydroxy-3-methyl-butanoyl]amino]thiophene-3-carboxamide,
2-[[1-(hydroxymethyl)cyclopropanecarbonyl]amino]-5-[4-(trifluoromethoxy)phenyl]sulfonyl-thiophene-3-carboxamide,
5-(4-chlorophenyl)sulfonyl-2-[(2-hydroxy-2-methyl-propanoyl)amino]thiophene-3-carboxamide,
5-[4-fluoro-2-(trifluoromethyl)phenyl]sulfonyl-2-[(3-hydroxy-2-methyl-propanoyl)amino]thiophene-3-carboxamide,
5-(2-chloro-4-fluoro-phenyl)sulfonyl-2-[(3-hydroxy-2-methyl-propanoyl)amino]thiophene-3-carboxamide,
5-(2-chloro-4-fluoro-phenyl)sulfonyl-2-[[(2S)-2-hydroxy-3-methyl-butanoyl]amino]thiophene-3-carboxamide,
5-(4-chlorophenyl)sulfonyl-2-[(3-hydroxy-2-methyl-propanoyl)amino]thiophene-3-carboxamide,
2-[(2-hydroxy-2-methyl-propanoyl)amino]-5-[[5-(trifluoromethyl)-2-pyridyl]sulfonyl]thiophene-3-carboxamide,
2-[[1-(hydroxymethyl)cyclobutanecarbonyl]amino]-5-[4-(trifluoromethoxy)phenyl]sulfonyl-thiophene-3-carboxamide,
2-[[(2S)-2-hydroxy-3,3-dimethyl-butanoyl]amino]-5-[4-(trifluoromethyl)phenyl]sulfonyl-thiophene-3-carboxamide,
2-[[(2S)-2-hydroxy-3-methyl-butanoyl]amino]-5-[4-(trifluoromethyl)phenyl]sulfonyl-thiophene-3-carboxamide,
5-(4-chlorophenyl)sulfonyl-2-[[(2S)-2-hydroxy-3-methyl-butanoyl]amino]thiophene-3-carboxamide,
5-[2-fluoro-4-(trifluoromethyl)phenyl]sulfonyl-2-(2-hydroxypropanoylamino)thiophene-3-carboxamide,
2-[(3-hydroxy-2-methyl-propanoyl)amino]-5-[4-(trifluoromethyl)phenyl]sulfonyl-thiophene-3-carboxamide,
2-[(3-hydroxy-2-methyl-propanoyl)amino]-5-[5-methoxy-2-(trifluoromethoxy)phenyl]sulfonyl-thiophene-3-carboxamide,
2-[(2-hydroxy-2-methyl-propanoyl)amino]-5-[4-(2-methoxyethoxy)phenyl]sulfonyl-thiophene-3-carboxamide,
5-[5-cyano-2-(trifluoromethoxy)phenyl]sulfonyl-2-[(2-hydroxy-2-methyl-propanoyl)amino]thiophene-3-carboxamide,
2-[(2-hydroxy-2-methyl-propanoyl)amino]-5-[5-methoxy-2-(trifluoromethoxy)phenyl]sulfonyl-thiophene-3-carboxamide,
2-[(2-hydroxy-2-methyl-propanoyl)amino]-5-[[5-(trifluoromethoxy)-2-pyridyl]sulfonyl]thiophene-3-carboxamide,
5-[2-fluoro-4-(trifluoromethoxy)phenyl]sulfonyl-2-[(2-hydroxy-2-methyl-propanoyl)amino]thiophene-3-carboxamide,
5-[2-fluoro-4-(trifluoromethoxy)phenyl]sulfonyl-2-[(2-hydroxy-2-methyl-propanoyl)amino]thiophene-3-carboxamide,
5-[3-fluoro-4-(trifluoromethoxy)phenyl]sulfonyl-2-[(2-hydroxy-2-methyl-propanoyl)amino]thiophene-3-carboxamide,
5-[2,3-difluoro-4-(trifluoromethoxy)phenyl]sulfonyl-2-[(2-hydroxy-2-methyl-propanoyl)amino]thiophene-3-carboxamide,
2-[[(2S)-3-hydroxy-2-methyl-propanoyl]amino]-5-[4-(trifluoromethoxy)phenyl]sulfonyl-thiophene-3-carboxamide,
5-[4-(difluoromethoxy)phenyl]sulfonyl-2-[(2-hydroxy-2-methyl-propanoyl)amino]thiophene-3-carboxamide,
5-(4-cyanophenyl)sulfonyl-2-[(2-hydroxy-2-methyl-propanoyl)amino]thiophene-3-carboxamide,
2-[[(2R)-3-hydroxy-2-methyl-propanoyl]amino]-5-[4-(trifluoromethoxy)phenyl]sulfonyl-thiophene-3-carboxamide,
5-[(5-fluoro-4-methyl-2-pyridyl)sulfonyl]-2-[(2-hydroxy-2-methyl-propanoyl)amino]thiophene-3-carboxamide,
2-[(2-hydroxy-2-methyl-propanoyl)amino]-5-[(5-methyl-2-pyridyl)sulfonyl]thiophene-3-carboxamide,
5-[(6-chloro-3-pyridyl)sulfonyl]-2-[(2-hydroxy-2-methyl-propanoyl)amino]thiophene-3-carboxamide, 5-[5-chloro-2-(trifluoromethoxy)phenyl]sulfonyl-2-[(3-hydroxy-2-methyl-propanoyl)amino]thiophene-3-carboxamide,
5-[4-chloro-2-(trifluoromethoxy)phenyl]sulfonyl-2-[(3-hydroxy-2-methyl-propanoyl)amino]thiophene-3-carboxamide,
5-[4-chloro-2-(trifluoromethoxy)phenyl]sulfonyl-2-[(2-hydroxy-2-methyl-propanoyl)amino]thiophene-3-carboxamide,
2-[(2-hydroxy-2-methyl-propanoyl)amino]-5-[[6-(trifluoromethyl)-3-pyridyl]sulfonyl]thiophene-3-carboxamide,
5-[[5-chloro-2-(trifluoromethyl)-4-pyridyl]sulfonyl]-2-[(2-hydroxy-2-methyl-propanoyl)amino]thiophene-3-carboxamide,
5-[5-chloro-2-(trifluoromethoxy)phenyl]sulfonyl-2-[(2-hydroxy-2-methyl-propanoyl)amino]thiophene-3-carboxamide,
2-[(3-hydroxy-2-methyl-propanoyl)amino]-5-[[5-(trifluoromethoxy)-2-pyridyl]sulfonyl]thiophene-3-carboxamide,
5-[4-cyano-2-(trifluoromethoxy)phenyl]sulfonyl-2-[(2-hydroxy-2-methyl-propanoyl)amino]thiophene-3-carboxamide,
2-[(2-hydroxy-2-methyl-propanoyl)amino]-5-[2-(trifluoromethyl)pyrimidin-5-yl]sulfonyl-thiophene-3-carboxamide,
5-[[5-(difluoromethyl)-2-pyridyl]sulfonyl]-2-[(2-hydroxy-2-methyl-propanoyl)amino]thiophene-3-carboxamide,
2-(2-hydroxypropanoylamino)-5-[[5-(trifluoromethyl)-2-pyridyl]sulfonyl]thiophene-3-carboxamide,
2-[(2-hydroxy-2-methyl-propanoyl)amino]-5-[5-(trifluoromethyl)pyrazin-2-yl]sulfonyl-thiophene-3-carboxamide,
2-(2-hydroxypropanoylamino)-5-[4-(trifluoromethyl)phenyl]sulfonyl-thiophene-3-carboxamide,
5-(3-cyano-5-methyl-phenyl)sulfonyl-2-[(2-hydroxy-2-methyl-propanoyl)amino]thiophene-3-carboxamide,
2-[(2-hydroxy-2-methyl-propanoyl)amino]-5-(4-methoxyphenyl)sulfonyl-thiophene-3-carboxamide,
5-[5-chloro-2-(difluoromethoxy)phenyl]sulfonyl-2-[(2-hydroxy-2-methyl-propanoyl)amino]thiophene-3-carboxamide,
5-[2-(difluoromethoxy)-4-fluoro-5-methoxy-phenyl]sulfonyl-2-[(2-hydroxy-2-methyl-propanoyl)amino]thiophene-3-carboxamide,
5-[4-(difluoromethoxy)phenyl]sulfonyl-2-(2-hydroxypropanoylamino)thiophene-3-carboxamide,
5-[2-(difluoromethoxy)-4,5-difluoro-phenyl]sulfonyl-2-[(2-hydroxy-2-methyl-propanoyl)amino]thiophene-3-carboxamide,
5-[2-(difluoromethoxy)-4,6-difluoro-phenyl]sulfonyl-2-[(2-hydroxy-2-methyl-propanoyl)amino]thiophene-3-carboxamide,
5-(4-cyano-2-fluoro-phenyl)sulfonyl-2-[(2-hydroxy-2-methyl-propanoyl)amino]thiophene-3-carboxamide,
5-[4-cyano-2-(trifluoromethyl)phenyl]sulfonyl-2-[(2-hydroxy-2-methyl-propanoyl)amino]thiophene-3-carboxamide,
2-[(2-hydroxy-2-methyl-propanoyl)amino]-5-[3-(trifluoromethyl)phenyl]sulfonyl-thiophene-3-carboxamide,
5-(3-cyanophenyl)sulfonyl-2-[(2-hydroxy-2-methyl-propanoyl)amino]thiophene-3-carboxamide,
5-[[3-fluoro-5-(trifluoromethyl)-2-pyridyl]sulfonyl]-2-[(2-hydroxy-2-methyl-propanoyl)amino]thiophene-3-carboxamide,
2-[(2-hydroxy-2-methyl-propanoyl)amino]-5-[[3-(trifluoromethyl)-2-pyridyl]sulfonyl]thiophene-3-carboxamide,
5-[[3,6-bis(trifluoromethyl)-2-pyridyl]sulfonyl]-2-[(2-hydroxy-2-methyl-propanoyl)amino]thiophene-3-carboxamide,
2-[(2-hydroxy-2-methyl-propanoyl)amino]-5-[[6-methyl-3-(trifluoromethyl)-2-pyridyl]sulfonyl]thiophene-3-carboxamide,
5-(6-chloro-5-methoxy-pyrimidin-4-yl)sulfonyl-2-[(2-hydroxy-2-methyl-propanoyl)amino]thiophene-3-carboxamide,
2-[(2-hydroxy-2-methyl-propanoyl)amino]-5-[5-methoxy-2-(trifluoromethyl)pyrimidin-4-yl]sulfonyl-thiophene-3-carboxamide,
2-[(2-hydroxy-2-methyl-propanoyl)amino]-5-(3-methoxy-5-methyl-phenyl)sulfonyl-thiophene-3-carboxamide,
2-[(2-hydroxy-2-methyl-propanoyl)amino]-5-[3-(trifluoromethyl)pyrazin-2-yl]sulfonyl-thiophene-3-carboxamide,
5-[[5-(difluoromethoxy)-2-methoxy-4-pyridyl]sulfonyl]-2-[(2-hydroxy-2-methyl-propanoyl)amino]thiophene-3-carboxamide,
5-[5-cyano-2-(difluoromethoxy)-3-methoxy-phenyl]sulfonyl-2-[(2-hydroxy-2-methyl-propanoyl)amino]thiophene-3-carboxamide,
2-[(2-hydroxy-2-methyl-propanoyl)amino]-5-[[6-methoxy-3-(trifluoromethyl)-2-pyridyl]sulfonyl]thiophene-3-carboxamide,
2-[(2-hydroxy-2-methyl-propanoyl)amino]-5-(3-isopropyl-1-methyl-pyrazol-4-yl)sulfonyl-thiophene-3-carboxamide,
5-[3-fluoro-4-(trifluoromethyl)phenyl]sulfonyl-2-[(2-hydroxy-2-methyl-propanoyl)amino]thiophene-3-carboxamide,
5-[[6-chloro-5-(trifluoromethyl)-2-pyridyl]sulfonyl]-2-[(2-hydroxy-2-methyl-propanoyl)amino]thiophene-3-carboxamide,
5-[[6-chloro-3-(trifluoromethyl)-2-pyridyl]sulfonyl]-2-[(2-hydroxy-2-methyl-propanoyl)amino]thiophene-3-carboxamide,
2-[(2-hydroxy-2-methyl-propanoyl)amino]-5-[[2-(trifluoromethyl)-3-thienyl]sulfonyl]thiophene-3-carboxamide,
5-[[6-tert-butyl-3-(trifluoromethyl)-2-pyridyl]sulfonyl]-2-[(2-hydroxy-2-methyl-propanoyl)amino]thiophene-3-carboxamide,
2-[(2-hydroxy-2-methyl-propanoyl)amino]-5-[[6-(trifluoromethyl)-2-pyridyl]sulfonyl]thiophene-3-carboxamide,
5-[3-(cyanomethyl)-5-(trifluoromethoxy)phenyl]sulfonyl-2-[(2-hydroxy-2-methyl-propanoyl)amino]thiophene-3-carboxamide,
5-[3-chloro-5-(trifluoromethyl)phenyl]sulfonyl-2-[(2-hydroxy-2-methyl-propanoyl)amino]thiophene-3-carboxamide,
2-[(2-hydroxy-2-methyl-propanoyl)amino]-5-[3-methyl-5-(trifluoromethyl)phenyl]sulfonyl-thiophene-3-carboxamide,
2-[(2-hydroxy-2-methyl-propanoyl)amino]-5-[6-(trifluoromethyl)pyridazin-3-yl]sulfonyl-thiophene-3-carboxamide,
5-[(2-chloro-5-cyano-4-pyridyl)sulfonyl]-2-[(2-hydroxy-2-methyl-propanoyl)amino]thiophene-3-carboxamide,
5-[(5-tert-butyl-2-pyridyl)sulfonyl]-2-[(2-hydroxy-2-methyl-propanoyl)amino]thiophene-3-carboxamide,
2-[(2-hydroxy-2-methyl-propanoyl)amino]-5-[(1-methyl-2,4-dihydro-3,1-benzoxazin-6-yl)sulfonyl]thiophene-3-carboxamide,
5-[2-fluoro-4-(trifluoromethoxy)phenyl]sulfonyl-2-[[1-(hydroxymethyl)cyclopropanecarbonyl]amino]thiophene-3-carboxamide, 2-[(2-hydroxy-2-methyl-propanoyl)amino]-5-[[2-(trifluoromethyl)-3-pyridyl]sulfonyl]thiophene-3-carboxamide,
2-[(2-hydroxy-2-methyl-propanoyl)amino]-4-methyl-5-[4-(trifluoromethoxy)phenyl]sulfonyl-thiophene-3-carboxamide,
2-[(2-hydroxy-2-methyl-propanoyl)amino]-5-[[6-(hydroxymethyl)-3-(trifluoromethyl)-2-pyridyl]sulfonyl]thiophene-3-carboxamide,
5-[2-fluoro-4-(trifluoromethyl)phenyl]sulfonyl-2-[(2-hydroxy-2-methyl-propanoyl)amino]-4-methyl-thiophene-3-carboxamide,
5-[[5-chloro-2-(trifluoromethyl)-3-pyridyl]sulfonyl]-2-[(2-hydroxy-2-methyl-propanoyl)amino]thiophene-3-carboxamide,
5-[[5-bromo-6-(trifluoromethyl)-3-pyridyl]sulfonyl]-2-[(2-hydroxy-2-methyl-propanoyl)amino]thiophene-3-carboxamide,
N-[3-carbamoyl-5-[4-(trifluoromethoxy)phenyl]sulfonyl-2-thienyl]tetrahydrofuran-2-carboxamide,
N-[3-carbamoyl-5-[4-(trifluoromethoxy)phenyl]sulfonyl-2-thienyl]tetrahydrofuran-3-carboxamide,
5-[2-fluoro-4-(trifluoromethoxy)phenyl]sulfonyl-2-[[(2S)-2-hydroxypropanoyl]amino]thiophene-3-carboxamide,
5-[2-fluoro-4-(trifluoromethyl)phenyl]sulfonyl-2-[[(2S)-2-hydroxypropanoyl]amino]thiophene-3-carboxamide, and
2-[(3-hydroxy-2,2-dimethyl-propanoyl)amino]-5-[4-(trifluoromethoxy)phenyl]sulfonyl-thiophene-3-carboxamide.

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula (e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (Bundgard, H, 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Particularly useful are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Clauses

1) A compound according to Formula I:

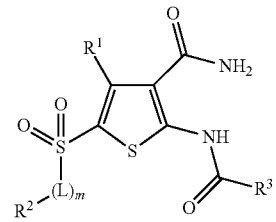

I wherein
$R^1$ is H, —$CH_3$, —$CF_3$, or cyclopropyl;
L is —$NR^4$—;
the subscript m is 0, or 1;
$R^2$ is
$C_{1-4}$ alkyl (optionally substituted with one or more independently selected $R^5$ groups), $C_{3-7}$ cycloalkyl,
4-10 membered monocyclic, bridged-, spiro-, or fused bicyclic heterocycloalkyl comprising one or more heteroatoms independently selected from N, O, and S, and optionally substituted with one or more independently selected $R^a$ groups, or
5-6 membered monocyclic heterocycloalkenyl comprising one or more heteroatoms independently selected from N, O, and S, and optionally substituted with one or more independently selected $R^a$ groups,
$C_{6-10}$ mono or bicyclic aryl optionally substituted with one or more independently selected $R^b$, or
5-10 membered monocyclic or fused bicyclic heteroaryl, comprising one or more heteroatoms independently selected from N, O, and S, and optionally substituted with one or more independently selected $R^b$;
$R^3$ is
$C_{3-7}$ cycloalkyl optionally substituted with one or more independently selected $R^c$ groups,
4-7 membered monocyclic heterocycloalkyl comprising one or more heteroatoms independently selected from O, and S, and optionally substituted with $R^c$, $C_{6-10}$ mono or bicyclic aryl optionally substituted with one or more independently selected $R^d$ groups, phenyl fused to a 5-6 membered heterocycloalkyl comprising one or more heteroatoms independently selected from N, O, and S, and optionally substituted with one or more independently selected $R^d$ groups, phenyl fused to a $C_{5-6}$ cycloalkyl, optionally substituted with one or more independently selected $R^d$ groups, 5-10 membered mono or fused bicyclic heteroaryl comprising one or more heteroatoms independently selected from N, O, and S, and optionally substituted with one or more independently selected $R^d$ groups, 5-6 membered monocyclic heteroaryl comprising one or more heteroatoms independently selected from N, O, and S, fused to a 5-6 membered heterocycloalkyl comprising one or more heteroatoms independently selected from N, O, and S, and optionally substituted with one or more independently selected $R^d$ groups, 5-6 membered monocyclic heteroaryl comprising one or more heteroatoms independently selected from N, O, and S, fused to a $C_{5-6}$ cycloalkyl comprising one or more heteroatoms independently selected from N, O, and S, and optionally substituted with one or more independently selected $R^d$ groups, $C_{2-6}$ alkenyl, $C_{3-6}$ alkyl, or $C_{1-6}$ alkyl substituted with one or more independently selected $R^e$ groups;

$R^4$ is $C_{1-6}$ alkyl (optionally substituted with one or more independently selected $R^6$ groups), $C_{3-7}$ cycloalkyl, Each $R^5$ is independently selected from halo,

OH,

—CN, $C_{1-4}$ alkoxy,

—NR$^{8e}$R$^{8f}$, $C_{3-7}$ cycloalkyl, 6 membered mono or fused bicyclic heteroaryl comprising one or more heteroatoms independently selected from N, O, and S, and phenyl optionally substituted with one or more independently selected halo, $C_{1-4}$ alkyl optionally substituted with one or more independently selected halo, or $C_{1-4}$ alkoxy;

Each $R^6$, is independently selected from halo,

OH,

—CN,

—NR$^{8g}$R$^{8h}$, and $C_{1-4}$ alkoxy;

each $R^a$ is selected from halo,

CN, oxo, $C_{1-4}$ alkyl (optionally substituted with one or more independently selected $R^{7a}$), $C_{1-4}$ alkoxy (optionally substituted with one or more independently selected $R^{7a}$), —C(=O)O—$C_{1-4}$ alkyl, phenyl, 5-10 membered mono, or fused bicyclic heteroaryl comprising one or more heteroatoms independently selected from N, O, or S, and optionally substituted with one or more independently selected $C_{1-4}$ alkyl, and —NR$^{8a}$R$^{8b}$;

each $R^b$ is selected from halo,

—CN, $C_{1-4}$ alkyl (optionally substituted with one or more independently selected $R^{7b}$), $C_{1-4}$ alkoxy (optionally substituted with one or more independently selected $R^{7b}$), —OC(=O)$C_{1-4}$ alkyl, and —NR$^{8c}$R$^{8d}$;

each $R^c$ is selected from halo,

OH,

—CN, oxo, $C_{1-4}$ alkyl (optionally substituted with one or more independently selected $R^{7c}$), $C_{1-4}$ alkoxy (optionally substituted with one or more independently selected $R^{7c}$), phenyl (optionally substituted with one or more independently selected halo, $C_{1-4}$ alkyl, $C_{1-4}$ alkoxy, —CN, or —NR$^{9a}$R$^{9b}$), and 5-6 membered monocyclic heteroaryl comprising one or more heteroatoms independently selected from N, O, or S (optionally substituted with one or more independently selected halo, $C_{1-4}$ alkyl, $C_{1-4}$ alkoxy, CN, —NR$^{9c}$R$^{9d}$);

each $R^d$ is selected from halo,

—CN,

—OH, $C_{1-4}$ alkyl (optionally substituted with one or more independently selected $R^{7d}$), $C_{1-4}$ alkoxy (optionally substituted with one or more independently selected $R^{7d}$), $C_{3-7}$ cycloalkyl, 5-10 membered mono or fused bicyclic heteroaryl comprising one or more heteroatoms independently selected from N, O, or S, and —NH-Phenyl;

each $R^e$ is selected from halo,

OH,

—CN, $C_{1-4}$ alkoxy (optionally substituted with one or more independently selected $R^{7e}$), $C_{3-7}$ cycloalkyl, phenyl (optionally substituted with one or more independently selected halo, $C_{1-4}$ alkyl, $C_{1-4}$ alkoxy, CN, and —NR$^{9e}$R$^{9f}$), and 5-6 membered mono, or heteroaryl comprising one or more heteroatoms independently selected from N, O, and S (optionally substituted with one or more independently selected halo, $C_{1-4}$ alkyl, $C_{1-4}$ alkoxy, CN, and —NR$^{9g}$R$^{9h}$);

Each $R^{7a}$, $R^{7b}$, $R^{7c}$, $R^{7d}$, and $R^{7e}$ is independently selected from halo,

OH,

—CN,

—NR$^{8i}$R$^{8j}$, and $C_{1-4}$ alkoxy;

Each $R^{8a}$, $R^{8b}$, $R^{8c}$, $R^{8d}$, $R^{8e}$, $R^{8f}$, $R^{8g}$, $R^{8h}$, $R^{8i}$, or $R^{8j}$ is independently selected from H, and $C_{1-4}$ alkyl;

Each $R^{9a}$, $R^{9b}$, $R^{9c}$, $R^{9d}$, $R^{9e}$, $R^{9f}$, $R^{9g}$, or $R^{9h}$ is independently selected from H, and $C_{1-4}$ alkyl; or a pharmaceutically acceptable salt, or a solvate, or a pharmaceutically acceptable salt of a solvate thereof.

2) A compound according to clause 1,

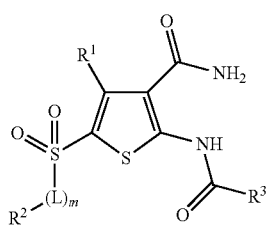

I wherein
$R^1$ is H, —$CH_3$, —$CF_3$, or cyclopropyl;
L is —$NR^4$—;
the subscript m is 0, or 1;
$R^2$ is
$C_{1-4}$ alkyl (optionally substituted with one or more independently selected $R^5$ groups),
$C_{3-7}$ cycloalkyl,
4-10 membered monocyclic, bridged-, spiro-, or fused bicyclic heterocycloalkyl comprising one or more heteroatoms independently selected from N, O, and S, and optionally substituted with one or more independently selected $R^a$ groups, or
5-6 membered monocyclic heterocycloalkenyl comprising one or more heteroatoms independently selected from N, O, and S, and optionally substituted with one or more independently selected $R^a$ groups,
$C_{6-10}$ mono or bicyclic aryl optionally substituted with one or more independently selected $R^b$, or
5-10 membered monocyclic or fused bicyclic heteroaryl, comprising one or more heteroatoms independently selected from N, O, and S, and optionally substituted with one or more independently selected $R^b$;
$R^3$ is
$C_{3-7}$ cycloalkyl optionally substituted with one or more independently selected $R^c$ groups,
4-7 membered monocyclic heterocycloalkyl comprising one or more heteroatoms independently selected from O, and S, and optionally substituted with $R^c$,
$C_{6-10}$ mono or bicyclic aryl optionally substituted with one or more independently selected $R^d$ groups,
5-10 membered mono or fused bicyclic heteroaryl comprising one or more heteroatoms independently selected from N, O, and S, and optionally substituted with one or more independently selected $R^d$ groups,
$C_{3-6}$ alkyl, or
$C_{1-6}$ alkyl substituted with one or more independently selected $R^c$ groups;
$R^4$ is
$C_{1-6}$ alkyl (optionally substituted with one or more independently selected $R^6$ groups),
$C_{3-7}$ cycloalkyl;
Each $R^5$ is independently selected from
halo,
OH,
—CN,
$C_{1-4}$ alkoxy,
—$NR^{8e}R^{8f}$,
$C_{3-7}$ cycloalkyl,
6 membered mono or fused bicyclic heteroaryl comprising one or more heteroatoms independently selected from N, O, and S, and
phenyl optionally substituted with one or more independently selected
halo,
$C_{1-4}$ alkyl optionally substituted with one or more independently selected halo, or
$C_{1-4}$ alkoxy;
Each $R^6$, is independently selected from
halo,
OH,
—CN,
—$NR^{8g}R^{8h}$, and
$C_{1-4}$ alkoxy;
each $R^a$ is selected from
halo,
CN,
oxo,
$C_{1-4}$ alkyl (optionally substituted with one or more independently selected $R^{7a}$),
$C_{1-4}$ alkoxy (optionally substituted with one or more independently selected $R^{7a}$),
—C(=O)O—$C_{1-4}$ alkyl,
phenyl,
5-10 membered mono, or fused bicyclic heteroaryl comprising one or more heteroatoms independently selected from N, O, or S, and optionally substituted with one or more independently selected $C_{1-4}$ alkyl, and
—$NR^{8a}R^{8b}$;
each $R^b$ is selected from
halo,
—CN,
$C_{1-4}$ alkyl (optionally substituted with one or more independently selected $R^{7b}$),
$C_{1-4}$ alkoxy (optionally substituted with one or more independently selected $R^{7b}$), and
—$NR^{8c}R^{8d}$;
each $R^c$ is selected from
halo,
OH,
—CN,
oxo,
$C_{1-4}$ alkyl (optionally substituted with one or more independently selected $R^{7c}$),
$C_{1-4}$ alkoxy (optionally substituted with one or more independently selected $R^{7c}$),
phenyl (optionally substituted with one or more independently selected halo, $C_{1-4}$ alkyl, $C_{1-4}$ alkoxy, —CN, or —$NR^{9a}R^{9b}$), and
5-6 membered monocyclic heteroaryl comprising one or more heteroatoms independently selected from N, O, or S (optionally substituted with one or more independently selected halo, $C_{1-4}$ alkyl, $C_{1-4}$ alkoxy, CN, —$NR^{9c}R^{9d}$);
each $R^d$ is selected from
halo,
—CN,
—OH,
$C_{1-4}$ alkyl (optionally substituted with one or more independently selected $R^{7d}$),
$C_{1-4}$ alkoxy (optionally substituted with one or more independently selected $R^{7d}$),
$C_{3-7}$ cycloalkyl,
5-10 membered mono or fused bicyclic heteroaryl comprising one or more heteroatoms independently selected from N, O, or S, and —NH-Phenyl;
each $R^e$ is selected from
halo,
OH,
—CN,
$C_{1-4}$ alkoxy (optionally substituted with one or more independently selected $R^{7e}$),
phenyl (optionally substituted with one or more independently selected halo, $C_{1-4}$ alkyl, $C_{1-4}$ alkoxy, CN, and —$NR^{9e}R^{9f}$), and
5-6 membered mono, or heteroaryl comprising one or more heteroatoms independently selected from N, O, and S (optionally substituted with one or more independently selected halo, $C_{1-4}$ alkyl, $C_{1-4}$ alkoxy, CN, and —$NR^{9g}R^{9h}$);
Each $R^{7a}$, $R^{7b}$, $R^{7c}$, $R^{7d}$, and $R^{7e}$ is independently selected from
halo,
OH,
—CN,
—$NR^{8i}R^{8j}$, and
$C_{1-4}$ alkoxy;
Each $R^{8a}$, $R^{8b}$, $R^{8c}$, $R^{8d}$, $R^{8e}$, $R^{8f}$, $R^{8g}$, $R^{8h}$, $R^{8i}$, or $R^{8j}$ is independently selected from H, and $C_{1-4}$ alkyl;
Each $R^{9a}$, $R^{9b}$, $R^{9c}$, $R^{9d}$, $R^{9e}$, $R^{9f}$, $R^{9g}$, or $R^{9h}$ is independently selected from H, and $C_{1-4}$ alkyl; or a pharmaceutically acceptable salt, or a solvate, or a pharmaceutically acceptable salt of a solvate thereof 3) A compound or pharmaceutically acceptable salt thereof, according to clause 1 or 2, wherein the subscript m is 1.

4) A compound or pharmaceutically acceptable salt thereof, according to clause 1 or 2, wherein the compound is according to Formula II:

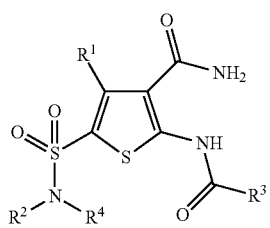

II wherein $R^1$, $R^2$, $R^3$, and $R^4$ are as described in clause 1.

5) A compound or pharmaceutically acceptable salt thereof, according to clause 4, wherein $R^4$ is $C_{1-6}$ alkyl.

6) A compound or pharmaceutically acceptable salt thereof, according to clause 5, wherein $R^4$ is —$CH_3$, —$CH_2$—$CH_3$, or —$CH(CH_3)_2$.

7) A compound or pharmaceutically acceptable salt thereof, according to clause 4, wherein $R^4$ is $C_{1-6}$ alkyl substituted with one, two or three independently selected $R^6$ groups, and $R^6$ is described in clause 1.

8) A compound or pharmaceutically acceptable salt thereof, according to clause 7, wherein $R^6$ is selected from F, Cl, OH, CN, —$OCH_3$, and —$OCH_2CH_3$.

9) A compound or pharmaceutically acceptable salt thereof, according to clause 7, wherein $R^6$ is $NR^{8g}R^{8h}$, and wherein each $R^{8g}$ and $R^{8h}$ are as described in clause 1.

10) A compound or pharmaceutically acceptable salt thereof, according to clause 7, wherein $R^6$ is —$NR^{8g}R^{8h}$, and wherein each $R^{8g}$ and $R^{8h}$ are selected from H, —$CH_3$, and —$CH_2$—$CH_3$.

11) A compound or pharmaceutically acceptable salt thereof, according to clause 4, wherein $R^4$ is selected from —$CH_2$—CN, —$CH_2$—$CH_2$—CN, —$CH_2$—$CHF_2$, —$CH_2$—$CF_3$, or —$CH_2$—$CH_2$—$OCH_3$.

12) A compound or pharmaceutically acceptable salt thereof, according to clause 4, wherein $R^4$ is $C_{3-7}$ cycloalkyl.

13) A compound or pharmaceutically acceptable salt thereof, according to clause 12, wherein $R^4$ is cyclopropyl.

14) A compound or pharmaceutically acceptable salt thereof, according to clause 1 or 2, wherein the compound is according to Formula III:

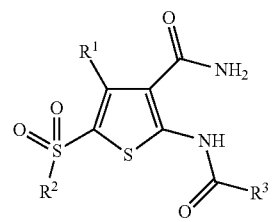

III wherein $R^1$, $R^2$, and $R^3$ are as described in clause 1.

15) A compound or pharmaceutically acceptable salt thereof, according to any one of clauses 1-14, wherein $R^2$ is $C_{1-4}$ alkyl.

16) A compound or pharmaceutically acceptable salt thereof, according to any one of clauses 1-14, wherein $R^2$ is —$CH_3$, —$CH_2$—$CH_3$, —$CH(CH_3)_2$, or —$C(CH_3)_3$.

17) A compound or pharmaceutically acceptable salt thereof, according to any one of clauses 1-14, wherein $R^2$ is $C_{1-4}$ alkyl substituted with one or more independently selected $R^5$ groups.

18) A compound or pharmaceutically acceptable salt thereof, according to clause 17, wherein $R^5$ is halo, OH, CN, $C_{1-4}$ alkoxy or phenyl.

19) A compound or pharmaceutically acceptable salt thereof, according to clause 17 or 18, wherein $R^5$ is F, Cl, OH, CN, or —$OCH_3$.

20) A compound or pharmaceutically acceptable salt thereof, according to clause 17, wherein $R^5$ is —$NR^{8e}R^{8f}$, and wherein each $R^{8e}$ and $R^{8f}$ are as described in clause 1.

21) A compound or pharmaceutically acceptable salt thereof, according to clause 7, wherein $R^6$ is —$NR^{8e}R^{8f}$, and wherein each $R^{8e}$ and $R^{8f}$ are selected from H, —$CH_3$, and —$CH_2$—$CH_3$.

22) A compound or pharmaceutically acceptable salt thereof, according to clause 17, wherein $R^5$ is phenyl substituted with one or more independently selected halo, $C_{1-4}$ alkyl (which alkyl is optionally substituted with one or more independently selected halo), or $C_{1-4}$ alkoxy.

23) A compound or pharmaceutically acceptable salt thereof, according to clause 22, wherein $R^5$ is phenyl substituted with one or more independently selected F, Cl, —$CH_3$, —$CH_2CH_3$, —$OCH_3$, or —$CF_3$.

24) A compound or pharmaceutically acceptable salt thereof, according to any one of clauses 1-14, wherein $R^2$ is $C_{3-7}$ cycloalkyl.

25) A compound or pharmaceutically acceptable salt thereof, according to clause 24, wherein $R^2$ is cyclopentyl, or cyclohexyl.

26) A compound or pharmaceutically acceptable salt thereof, according to any one of clauses 1-14, wherein $R^2$ is 4-10 membered monocyclic, bridged-, spiro-, or fused bicyclic heterocycloalkyl comprising one or more heteroatoms independently selected from N, O, and S.

27) A compound or pharmaceutically acceptable salt thereof, according to any one of clauses 1-14, wherein $R^2$ is azetidinyl, pyrrolidinyl, tetrahydropyranyl, piperidinyl, morpholinyl 2-oxa-5-aza-bicyclo[2.2.1]heptanyl, [1,4]oxazepanyl, 2,3-dihydro-1H-isoindolyl, or 1,2,3,4-tetrahydro-isoquinolinyl.

28) A compound or pharmaceutically acceptable salt thereof, according to any one of clauses 1-14, wherein $R^2$ is 4-10 membered monocyclic, bridged-, spiro-, or fused bicyclic heterocycloalkyl comprising one or more heteroatoms independently selected from N, O, and S, substituted with one or more independently selected $R^a$ groups.

29) A compound or pharmaceutically acceptable salt thereof, according to any one of clauses 1-14, wherein $R^2$ is azetidinyl, pyrrolidinyl, tetrahydropyranyl, piperidinyl, morpholinyl, piperidinyl, 2-oxa-5-aza-bicyclo[2.2.1]heptanyl, [1,4]oxazepanyl, or 2,8-Diaza-spiro[4.5]decane, each of which is substituted with one or more independently selected $R^a$ groups.

30) A compound or pharmaceutically acceptable salt thereof, according to clause 28 or 29, wherein $R^a$ is F, Cl, CN, oxo, —C(=O)OtBu or phenyl.

31) A compound or pharmaceutically acceptable salt thereof, according to clause 28 or 29, wherein $R^a$ is $C_{1-4}$ alkyl or $C_{1-4}$ alkoxy, each of which is optionally substituted with one or more independently selected $R^{7a}$, and $R^{7a}$ is as described in clause 1.

32) A compound or pharmaceutically acceptable salt thereof, according to clause 31, wherein $R^a$ is —$CH_3$, —$CH_2$—$CH_3$, —$CH(CH_3)_2$, —$OCH_3$, or —$OCH_2$—$CH_3$, each of which is optionally substituted with one or more independently selected $R^{7a}$, and $R^{7a}$ is as described in clause 1.

33) A compound or pharmaceutically acceptable salt thereof, according to clause 31, or 32, wherein $R^{7a}$ is F, Cl, OH, CN, or —$OCH_3$.

34) A compound or pharmaceutically acceptable salt thereof, according to clause 31, or 32, wherein $R^{7a}$ is —$NR^{8i}R^{8j}$, wherein $R^{8i}$ and $R^{8j}$ are independently selected from H, —$CH_3$, and —$CH_2$—$CH_3$.

35) A compound or pharmaceutically acceptable salt thereof, according to any one of clauses 1-14, wherein $R^2$ is 5-6 membered monocyclic heterocycloalkenyl comprising one or more heteroatoms independently selected from N, O, and S, substituted with one or more independently selected $R^a$ groups.

36) A compound or pharmaceutically acceptable salt thereof, according to any one of clauses 1-14, wherein $R^2$ is tetrahydropyridinyl, substituted with one or more independently selected $R^a$ groups.

37) A compound or pharmaceutically acceptable salt thereof, according to clause 35 or 36, wherein $R^a$ is F, Cl, CN, oxo, —C(=O)OtBu or phenyl.

38) A compound or pharmaceutically acceptable salt thereof, according to clause 35 or 36, wherein $R^a$ is $C_{1-4}$ alkyl or $C_{1-4}$ alkoxy, each of which is optionally substituted with one or more independently selected $R^{7a}$, and $R^{7a}$ is as described in clause 1.

39) A compound or pharmaceutically acceptable salt thereof, according to clause 38, wherein $R^a$ is —$CH_3$, —$CH_2$—$CH_3$, —$CH(CH_3)_2$, —$OCH_3$, or —$OCH_2$—$CH_3$, each of which is optionally substituted with one or more independently selected $R^{7a}$, and $R^{7a}$ is as described in clause 1.

40) A compound or pharmaceutically acceptable salt thereof, according to clause 38, or 39, wherein $R^{7a}$ is F, Cl, OH, CN, or —$OCH_3$.

41) A compound or pharmaceutically acceptable salt thereof, according to clause 38, or 39, wherein $R^{7a}$ is —$NR^{8i}R^{8j}$, wherein $R^{8i}$ and $R^{8j}$ are independently selected from H, —$CH_3$, and —$CH_2$—$CH_3$.

42) A compound or pharmaceutically acceptable salt thereof, according to any one of clauses 1-14, wherein $R^2$ is $C_{6-10}$ mono or bicyclic aryl.

43) A compound or pharmaceutically acceptable salt thereof, according to any one of clauses 1-14, wherein $R^2$ is $C_{6-10}$ mono or bicyclic aryl substituted with one or more independently selected $R^b$.

44) A compound or pharmaceutically acceptable salt thereof, according to clause 43, wherein $R^b$ is F, Cl, or CN.

45) A compound or pharmaceutically acceptable salt thereof, according to clause 43, wherein $R^b$ is $C_{1-4}$ alkyl or $C_{1-4}$ alkoxy, each of which is optionally substituted with one or more independently selected $R^{7b}$, and $R^{7b}$ is as described in clause 1.

46) A compound or pharmaceutically acceptable salt thereof, according to clause 45, wherein $R^a$ is —$CH_3$, —$CH_2$—$CH_3$, —$CH(CH_3)_2$, —$OCH_3$, or —$OCH_2$—$CH_3$, each of which is optionally substituted with one or more independently selected $R^{7b}$, and $R^{7b}$ is as described in clause 1.

47) A compound or pharmaceutically acceptable salt thereof, according to clause 45, or 46, wherein $R^{7b}$ is F, Cl, OH, CN, or —$OCH_3$.

48) A compound or pharmaceutically acceptable salt thereof, according to clause 45, or 46, wherein $R^{7b}$ is —$NR^{8c}R^{8d}$, wherein $R^{8c}$ and $R^{8d}$ are independently selected from H, —$CH_3$, and —$CH_2$—$CH_3$.

49) A compound or pharmaceutically acceptable salt thereof, according to any one of clauses 42-48, wherein $R^2$ is phenyl.

50) A compound or pharmaceutically acceptable salt thereof, according to any one of clauses 1-14, wherein $R^2$ is 5-10 membered monocyclic or fused bicyclic heteroaryl, comprising one or more heteroatoms independently selected from N, O, and S.

51) A compound or pharmaceutically acceptable salt thereof, according to any one of clauses 1-14, wherein $R^2$ is 5-10 membered monocyclic or fused bicyclic heteroaryl, comprising one or more heteroatoms independently selected from N, O, and S substituted with one or more independently selected $R^b$.

52) A compound or pharmaceutically acceptable salt thereof, according to clause 51, wherein $R^b$ is F, Cl, or CN.

53) A compound or pharmaceutically acceptable salt thereof, according to clause 51, wherein $R^b$ is $C_{1-4}$ alkyl or $C_{1-4}$ alkoxy, each of which is optionally substituted with one or more independently selected $R^{7b}$, and $R^{7b}$ is as described in clause 1.

54) A compound or pharmaceutically acceptable salt thereof, according to clause 53, wherein $R^b$ is —$CH_3$, —$CH_2$—$CH_3$, —$CH(CH_3)_2$, —$OCH_3$, or —$OCH_2$—$CH_3$, each of which is optionally substituted with one or more independently selected $R^{7b}$, and $R^{7b}$ is as described in clause 1.

55) A compound or pharmaceutically acceptable salt thereof, according to clause 53, or 54, wherein $R^{7b}$ is F, Cl, OH, CN, or —$OCH_3$.

56) A compound or pharmaceutically acceptable salt thereof, according to clause 53, or 54, wherein $R^{7b}$ is —$NR^{8c}R^{8d}$, wherein $R^{8c}$ and $R^{8d}$ are independently selected from H, —$CH_3$, and —$CH_2$—$CH_3$.

57) A compound or pharmaceutically acceptable salt thereof, according to any one of clauses 50-56, wherein $R^2$ is furanyl, thiophenyl, pyrazolyl, imidazolyl, thiazolyl, oxazolyl, pyridinyl, pyrimidyl, or pyrazinyl.

58) A compound or pharmaceutically acceptable salt thereof, according to clause 1 or 2, wherein the compound is according to Formula IV:

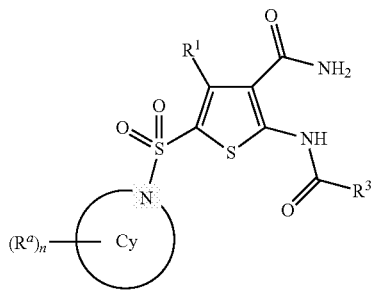

wherein Cy is 4-10 membered monocyclic heterocycloalkyl comprising one or more heteroatoms independently selected from N, O, and S, $R^a$ is as described in clause 1, and the subscript n is 0, 1 or 2.

59) A compound or pharmaceutically acceptable salt thereof, according to clause 58, wherein Cy is azetidinyl, pyrrolidinyl, tetrahydropyranyl, piperidinyl, morpholinyl 2-oxa-5-aza-bicyclo[2.2.1]heptanyl, [1,4]oxazepanyl, 2,3-dihydro-1H-isoindolyl, or 1,2,3,4-tetrahydro-isoquinolinyl.

60) A compound or pharmaceutically acceptable salt thereof, according to clause 58 or 59, wherein the subscript n is 1 or 2.

61) A compound or pharmaceutically acceptable salt thereof, according to clause 58 or 59, wherein $R^a$ is F, Cl, CN, oxo, —C(=O)OtBu or phenyl.

62) A compound or pharmaceutically acceptable salt thereof, according to clause 58 or 59, wherein $R^a$ is $C_{1-4}$ alkyl or $C_{1-4}$ alkoxy, each of which is optionally substituted with one or more independently selected $R^{7a}$, and $R^{7a}$ is as described in clause 1.

63) A compound or pharmaceutically acceptable salt thereof, according to clause 62, wherein $R^a$ is —CH$_3$, —CH$_2$—CH$_3$, —CH(CH$_3$)$_2$, —OCH$_3$, or —OCH$_2$—CH$_3$, each of which is optionally substituted with one or more independently selected $R^{7a}$, and $R^{7a}$ is as described in clause 1.

64) A compound or pharmaceutically acceptable salt thereof, according to clause 62, or 63, wherein $R^{7a}$ is F, Cl, OH, CN, or —OCH$_3$.

65) A compound or pharmaceutically acceptable salt thereof, according to clause 62, or 63, wherein $R^{7a}$ is —NR$^{8i}$R$^{8j}$, wherein R$^{8i}$ and R$^{8j}$ are independently selected from H, —CH$_3$, and —CH$_2$—CH$_3$.

66) A compound or pharmaceutically acceptable salt thereof, according to clause 58 or 59, wherein the subscript n is 0.

67) A compound or pharmaceutically acceptable salt thereof, according to any one of clauses 1 to 66, wherein $R^3$ is $C_{3-7}$ cycloalkyl.

68) A compound or pharmaceutically acceptable salt thereof, according to any one of clauses 1 to 66, wherein $R^3$ is $C_{3-7}$ cycloalkyl substituted with one or more independently selected $R^c$ groups.

69) A compound or pharmaceutically acceptable salt thereof, according to clause 67 or 68, wherein $R^3$ is cyclopropyl, cyclobutyl, cyclopentyl, or cyclohexyl.

70) A compound or pharmaceutically acceptable salt thereof, according to clause 68, wherein $R^c$ is F, Cl, OH, oxo, or CN.

71) A compound or pharmaceutically acceptable salt thereof, according to clause 68, wherein $R^c$ is $C_{1-4}$ alkyl or $C_{1-4}$ alkoxy, each of which is optionally substituted with one or more independently selected $R^{7c}$, and $R^{7c}$ is as described in clause 1.

72) A compound or pharmaceutically acceptable salt thereof, according to clause 68, wherein $R^c$ is —CH$_3$, —CH$_2$—CH$_3$, —CH(CH$_3$)$_2$, —OCH$_3$, or —OCH$_2$—CH$_3$, each of which is optionally substituted with one or more independently selected $R^{7c}$, and $R^{7c}$ is as described in clause 1.

73) A compound or pharmaceutically acceptable salt thereof, according to clause 71, or 72, wherein $R^{7c}$ is F, Cl, OH, CN, or —OCH$_3$.

74) A compound or pharmaceutically acceptable salt thereof, according to clause 67, wherein $R^c$ is phenyl.

75) A compound or pharmaceutically acceptable salt thereof, according to clause 67, wherein $R^c$ is phenyl substituted with one or more independently selected F, Cl, —CH$_3$, —CH$_2$—CH$_3$, —CH(CH$_3$)$_2$, —OCH$_3$, —OCH$_2$—CH$_3$, or —CN.

76) A compound or pharmaceutically acceptable salt thereof, according to clause 67, wherein $R^c$ is phenyl substituted with one or more independently selected —NR$^{9a}$R$^{9b}$, wherein R$^{9a}$ and R$^{9b}$ are independently selected from H, —CH$_3$, and —CH$_2$—CH$_3$.

77) A compound or pharmaceutically acceptable salt thereof, according to clause 67, wherein $R^c$ is 5-6 membered mono, or heteroaryl comprising one or more heteroatoms independently selected from N, O, or S.

78) A compound or pharmaceutically acceptable salt thereof, according to clause 67, wherein $R^c$ is 5-6 membered mono, or heteroaryl comprising one or more heteroatoms independently selected from N, O, or S, substituted with one or more independently selected F, Cl, —CH$_3$, —CH$_2$—CH$_3$, —CH(CH$_3$)$_2$, —OCH$_3$, —OCH$_2$—CH$_3$, or —CN.

79) A compound or pharmaceutically acceptable salt thereof, according to clause 67, wherein $R^c$ is 5-6 membered mono, or heteroaryl comprising one or more heteroatoms independently selected from N, O, or S, substituted with one or more independently selected —NR$^{9a}$R$^{9b}$, wherein R$^{9a}$ and R$^{9b}$ are independently selected from H, —CH$_3$, and —CH$_2$—CH$_3$.

80) A compound or pharmaceutically acceptable salt thereof, according to clause 77, 78, or 79, wherein $R^c$ is 5-6 membered mono, or heteroaryl comprising one or more heteroatoms independently selected from N, O, or S, and the heteroaryl is pyrrazolyl, imidazolyl, thiazolyl, oxazolyl, pyridinyl, pyrimidyl, or pyrazinyl.

81) A compound or pharmaceutically acceptable salt thereof, according to any one of clauses 1 to 66, wherein $R^3$ is 4-7 membered monocyclic heterocycloalkyl comprising one or more heteroatoms independently selected from O, and S.

82) A compound or pharmaceutically acceptable salt thereof, according to any one of clauses 1 to 66, wherein $R^3$ is 4-7 membered monocyclic heterocycloalkyl comprising one or more heteroatoms independently selected from O, and S, substituted with one or more independently selected $R^c$ groups.

83) A compound or pharmaceutically acceptable salt thereof, according to clause 81 or 82, wherein $R^3$ is pyrrolidinyl, tetrahydrofuranyl, tetrahydropyranyl, piperidinyl, piperazinyl, morpholinyl, or thiomorpholinyl.

84) A compound or pharmaceutically acceptable salt thereof, according to clause 82, wherein $R^c$ is F, Cl, CN, oxo, or OH.

85) A compound or pharmaceutically acceptable salt thereof, according to clause 82, wherein $R^c$ is $C_{1-4}$ alkyl or $C_{1-4}$ 86) A compound or pharmaceutically acceptable salt thereof, according to clause 82, wherein $R^c$ is —$CH_3$, —$CH_2$—$CH_3$, —$CH(CH_3)_2$, —$OCH_3$, or —$OCH_2$—$CH_3$, each of which is optionally substituted with one or more independently selected $R^{7c}$, and $R^{7c}$ is as described in clause 1.
87) A compound or pharmaceutically acceptable salt thereof, according to clause 85, or 86, wherein $R^{7c}$ is F, Cl, OH, CN, or —$OCH_3$.
88) A compound or pharmaceutically acceptable salt thereof, according to clause 83, wherein $R^c$ is phenyl.
89) A compound or pharmaceutically acceptable salt thereof, according to clause 83, wherein $R^c$ is phenyl substituted with one or more independently selected F, Cl, —$CH_3$, —$CH_2$—$CH_3$, —$CH(CH_3)_2$, —$OCH_3$, —$OCH_2$—$CH_3$, or —CN.
90) A compound or pharmaceutically acceptable salt thereof, according to clause 83, wherein $R^c$ is phenyl substituted with one or more independently selected —$NR^{9a}R^{9b}$, wherein $R^{9a}$ and $R^{9b}$ are independently selected from H, —$CH_3$, and —$CH_2$—$CH_3$.
91) A compound or pharmaceutically acceptable salt thereof, according to clause 83, wherein $R^c$ is 5-6 membered mono, or heteroaryl comprising one or more heteroatoms independently selected from N, O, or S.
92) A compound or pharmaceutically acceptable salt thereof, according to clause 83, wherein $R^c$ is 5-6 membered mono, or heteroaryl comprising one or more heteroatoms independently selected from N, O, or S, substituted with one or more independently selected F, Cl, —$CH_3$, —$CH_2$—$CH_3$, —$CH(CH_3)_2$, —$OCH_3$, —$OCH_2$—$CH_3$, or —CN.
93) A compound or pharmaceutically acceptable salt thereof, according to clause 83, wherein $R^c$ is 5-6 membered mono, or heteroaryl comprising one or more heteroatoms independently selected from N, O, or S, substituted with one or more independently selected —$NR^{9a}R^{9b}$, wherein $R^{9a}$ and $R^{9b}$ are independently selected from H, —$CH_3$, and —$CH_2$—$CH_3$.
94) A compound or pharmaceutically acceptable salt thereof, according to clause 91, 92, or 93, wherein $R^c$ is 5-6 membered mono, or heteroaryl comprising one or more heteroatoms independently selected from N, O, or S, and the heteroaryl is pyrrazolyl, imidazolyl, thiazolyl, oxazolyl, pyridinyl, pyrimidyl, or pyrazinyl.
95) A compound or pharmaceutically acceptable salt thereof, according to any one of clauses 1 to 66, wherein $R^3$ is $C_{6-10}$ mono or bicyclic aryl.
96) A compound or pharmaceutically acceptable salt thereof, according to any one of clauses 1 to 66, wherein $R^3$ is $C_{6-10}$ mono or bicyclic aryl, substituted with one or more independently selected $R^d$ groups.
97) A compound or pharmaceutically acceptable salt thereof, according to clause 95 or 96, wherein $R^3$ is phenyl.
98) A compound or pharmaceutically acceptable salt thereof, according to clause 96, wherein $R^d$ is F, Cl, OH, or CN.
99) A compound or pharmaceutically acceptable salt thereof, according to clause 96, wherein $R^d$ is $C_{1-4}$ alkyl or $C_{1-4}$ alkoxy, each of which is optionally substituted with one or more independently selected $R^{7d}$, and $R^{7d}$ is as described in clause 1.
100) A compound or pharmaceutically acceptable salt thereof, according to clause 87, wherein $R^d$ is —$CH_3$, —$CH_2$—$CH_3$, —$CH(CH_3)_2$, —$OCH_3$, or —$OCH_2$—$CH_3$, each of which is optionally substituted with one or more independently selected $R^{7d}$, and $R^{7d}$ is as described in clause 1.
101) A compound or pharmaceutically acceptable salt thereof, according to clause 99, or 100, wherein $R^{7d}$ is F, Cl, OH, CN, or —$OCH_3$.
102) A compound or pharmaceutically acceptable salt thereof, according to clause 96, wherein $R^d$ is cyclopropyl, cyclobutyl, cyclopentyl, or cyclohexyl.
103) A compound or pharmaceutically acceptable salt thereof, according to clause 96, wherein $R^d$ is 5-6 membered mono, or heteroaryl comprising one or more heteroatoms independently selected from N, O, or S.
104) A compound or pharmaceutically acceptable salt thereof, according to clause 103, wherein $R^d$ is pyrrazolyl, imidazolyl, thiazolyl, oxazolyl, pyridinyl, pyrimidyl, or pyrazinyl.
105) A compound or pharmaceutically acceptable salt thereof, according to clause 96, wherein $R^d$ is —NH-Phenyl.
106) A compound or pharmaceutically acceptable salt thereof, according to any one of clauses 1 to 65, wherein $R^3$ is phenyl fused to a 5-6 membered heterocycloalkyl comprising one or more heteroatoms independently selected from N, O, and S, and optionally substituted with one or more independently selected $R^d$ groups.
107) A compound or pharmaceutically acceptable salt thereof, according to any one of clauses 1 to 65, wherein $R^3$ is dihydroisoindole, benzodioxole, dihydrobenzooxazole, or dihydrobenzodioxine, each of which is optionally substituted with one or more independently selected $R^d$ groups.
108) A compound or pharmaceutically acceptable salt thereof, according to clause 106 or 107, wherein $R^d$ is selected from F, Cl, CN, and OH.
109) A compound or pharmaceutically acceptable salt thereof, according to any one of clauses 1 to 66, wherein $R^3$ is 5-10 membered mono or fused bicyclic heteroaryl comprising one or more heteroatoms independently selected from N, O, and S.
110) A compound or pharmaceutically acceptable salt thereof, according to any one of clauses 1 to 66, wherein $R^3$ is 5-10 membered mono or fused bicyclic heteroaryl comprising one or more heteroatoms independently selected from N, O, and S, substituted with one or more independently selected $R^d$ groups.
111) A compound or pharmaceutically acceptable salt thereof, according to clause 109 or 110, wherein $R^3$ is furanyl, thiophenyl, pyrazolyl, imidazolyl, thiazolyl, oxazolyl, pyridinyl, pyridazinyl, pyrimidyl, or pyrazinyl.
112) A compound or pharmaceutically acceptable salt thereof, according to clause 110, wherein $R^d$ is F, Cl, OH, or CN.
113) A compound or pharmaceutically acceptable salt thereof, according to clause 110, wherein $R^d$ is $C_{1-4}$ alkyl or $C_{1-4}$ alkoxy, each of which is optionally substituted with one or more independently selected $R^{7d}$, and $R^{7d}$ is as described in clause 1.
114) A compound or pharmaceutically acceptable salt thereof, according to clause 113, wherein $R^d$ is —$CH_3$, —$CH_2$—$CH_3$, —$CH(CH_3)_2$, —$OCH_3$, or —$OCH_2$—$CH_3$, each of which is optionally substituted with one or more independently selected $R^{7d}$, and $R^{7d}$ is as described in clause 1.
115) A compound or pharmaceutically acceptable salt thereof, according to clause 113, or 110, wherein $R^{7d}$ is F, Cl, OH, CN, or —$OCH_3$.

116) A compound or pharmaceutically acceptable salt thereof, according to clause 110, wherein $R^d$ is cyclopropyl, cyclobutyl, cyclopentyl, or cyclohexyl.

117) A compound or pharmaceutically acceptable salt thereof, according to clause 110, wherein $R^d$ is 5-6 membered mono, or heteroaryl comprising one or more heteroatoms independently selected from N, O, or S.

118) A compound or pharmaceutically acceptable salt thereof, according to clause 117, wherein $R^d$ is is pyrrazolyl, imidazolyl, thiazolyl, oxazolyl, pyridinyl, pyrimidyl, or pyrazinyl.

119) A compound or pharmaceutically acceptable salt thereof, according to clause 110, wherein $R^d$ is —NH-Phenyl.

120) A compound or pharmaceutically acceptable salt thereof, according to any one of clauses 1 to 66, wherein $R^3$ is 5-6 membered monocyclic heteroaryl comprising one or more heteroatoms independently selected from N, O, and S, fused to a 5-6 membered heterocycloalkyl comprising one or more heteroatoms independently selected from N, O, and S, and optionally substituted with one or more independently selected $R^d$ groups.

121) A compound or pharmaceutically acceptable salt thereof, according to any one of clauses 1 to 66, wherein $R^3$ is 5-6 membered monocyclic heteroaryl comprising one or more heteroatoms independently selected from N, O, and S, fused to a $C_{5-6}$ cycloalkyl, optionally substituted with one or more independently selected $R^d$ groups.

122) A compound or pharmaceutically acceptable salt thereof, according to clause 120 or 121, wherein $R^d$ is selected from F, Cl, CN, and OH.

123) A compound or pharmaceutically acceptable salt thereof, according to any one of clauses 1 to 66, wherein $R^3$ is $C_{2-6}$ alkenyl.

124) A compound or pharmaceutically acceptable salt thereof, according to any one of clauses 1 to 66, wherein $R^3$ is —CH=CH$_2$, —CH=CH—CH$_3$, —CH=CH—CH$_2$CH$_3$, —CH$_2$—CH=CH—CH$_3$, —CH$_2$—CH$_2$—CH=CH$_2$, —C(CH$_3$)=CH$_2$, —CH=CH(CH$_3$), or —C(CH$_3$)=CH(CH$_3$).

125) A compound or pharmaceutically acceptable salt thereof, according to any one of clauses 1 to 66, wherein $R^3$ is $C_{3-6}$ alkyl.

126) A compound or pharmaceutically acceptable salt thereof, according to any one of clauses 1 to 66, wherein $R^3$ is $C_{1-6}$ alkyl substituted with one or more independently selected $R^e$ groups.

127) A compound or pharmaceutically acceptable salt thereof, according to any one of clauses 1 to 66, wherein $R^3$ is —CH(CH$_3$)$_2$, —C(CH$_3$)$_3$, —CH$_2$CH(CH$_3$)$_2$, —C(CH$_3$)$_2$—CH$_3$, or —CH(CH$_3$)—CH$_2$(CH$_3$).

128) A compound or pharmaceutically acceptable salt thereof, according to clause 126, wherein $R^e$ is F, Cl, OH, or CN.

129) A compound or pharmaceutically acceptable salt thereof, according to clause 126, wherein $R^e$ is $C_{1-4}$ alkoxy, each of which is optionally substituted with one or more independently selected $R^{7e}$, and $R^{7e}$ is as described in clause 1.

130) A compound or pharmaceutically acceptable salt thereof, according to clause 134, wherein $R^e$ is —OCH$_3$, —OCH$_2$—CH$_3$, or —OCH(CH$_3$)$_2$, each of which is optionally substituted with one or more independently selected $R^{7e}$, and $R^{7e}$ is as described in clause 1.

131) A compound or pharmaceutically acceptable salt thereof, according to clause 134, or 121, wherein $R^{7e}$ is F, Cl, OH, —CN, —OCH$_3$, —OCH$_2$CH$_3$, —NH(CH$_3$) or —N(CH$_3$)$_2$ 132) A compound or pharmaceutically acceptable salt thereof, according to clause 126, wherein $R^e$ is phenyl.

133) A compound or pharmaceutically acceptable salt thereof, according to clause 126, wherein $R^e$ is phenyl substituted with one or more independently selected F, Cl, —CH$_3$, —CH$_2$CH$_3$, —CH(CH$_3$)$_2$, —OCH$_3$, —OCH$_2$CH$_3$, —OCH(CH$_3$)$_2$, or CN.

134) A compound or pharmaceutically acceptable salt thereof, according to clause 126, wherein $R^e$ is phenyl substituted with one or more independently selected —NR$^{9e}$R$^{9f}$, wherein R$^{9a}$ and R$^{9b}$ are as described in clause 1.

135) A compound or pharmaceutically acceptable salt thereof, according to clause 126, wherein $R^e$ is phenyl substituted with one or more independently selected —NR$^{9e}$R$^{9f}$, wherein R$^{9a}$ and R$^{9b}$ are independently selected from H, —CH$_3$, and —CH$_2$—CH$_3$.

136) A compound or pharmaceutically acceptable salt thereof, according to clause 126, wherein $R^e$ is 5-6 membered mono, or heteroaryl comprising one or more heteroatoms independently selected from N, O, and S.

137) A compound or pharmaceutically acceptable salt thereof, according to clause 126, wherein $R^e$ is 5-6 membered mono, or heteroaryl comprising one or more heteroatoms independently selected from N, O, and S, substituted with one or more independently selected F, Cl, —CH$_3$, —CH$_2$—CH$_3$, —CH(CH$_3$)$_2$, —C(CH$_3$)$_3$, —OCH$_3$, —OCH$_2$—CH$_3$, —OCH(CH$_3$)$_2$, or CN.

138) A compound or pharmaceutically acceptable salt thereof, according to clause 126, wherein $R^e$ is 5-6 membered mono, or heteroaryl comprising one or more heteroatoms independently selected from N, O, and S substituted with one or more independently selected —NR$^{9e}$R$^{9f}$ wherein R$^{9a}$ and R$^{9b}$ are as described in clause 1.

139) A compound or pharmaceutically acceptable salt thereof, according to clause 126, wherein $R^e$ is 5-6 membered mono, or heteroaryl comprising one or more heteroatoms independently selected from N, O, and S, substituted with one or more independently selected —NR$^{9e}$R$^{9f}$, wherein R$^{9a}$ and R$^{9b}$ are independently selected from H, —CH$_3$, and —CH$_2$—CH$_3$.

140) A compound or pharmaceutically acceptable salt thereof, according to any one of clauses 136-139, wherein $R^e$ is 5-6 membered mono, or heteroaryl comprising one or more heteroatoms independently selected from N, O, and S, and the heteroaryl is furanyl, thiophenyl, pyrazolyl, imidazolyl, thiazolyl, oxazolyl, pyridinyl, pyrimidinyl, or pyrazinyl.

141) A compound or pharmaceutically acceptable salt thereof, according to any one of clauses 1 to 66, wherein $R^3$ is

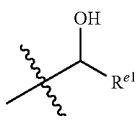

wherein $R^{e1}$ is $C_{1-5}$ alkyl optionally substituted with one or more independently selected halo, CN, $C_{1-4}$ alkoxy, or $C_{3-7}$ cycloalkyl.

142) A compound or pharmaceutically acceptable salt thereof, according to clause 141, wherein $R^{e1}$ is $C_{1-5}$ alkyl optionally substituted with one or more independently selected halo, CN, $C_{1-4}$ alkoxy, or $C_{3-7}$ cycloalkyl.

143) A compound or pharmaceutically acceptable salt thereof, according to clause 141, wherein $R^{e1}$ is —CH$_3$, —CH$_2$CH$_3$, —CH(CH$_3$)$_2$, —C(CH$_3$)$_3$, —CH$_2$CH(CH$_3$)$_2$, or —CH$_2$C(CH$_3$)$_3$. In another most particular embodiment, $R^{e1}$ is —CF$_3$, —CH$_2$CF$_3$, or —CH$_2$CN.

144) A compound or pharmaceutically acceptable salt thereof, according to any one of clauses 1 to 66, wherein $R^3$ is

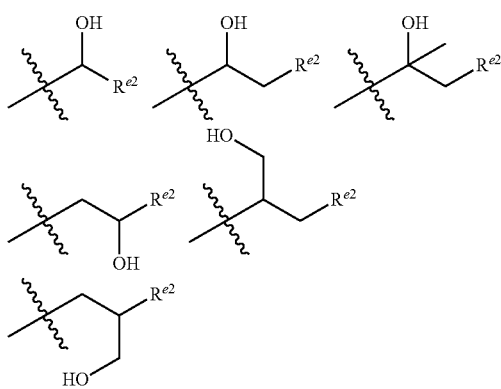

wherein $R^{4b}$ is $C_{3-7}$ cycloalkyl.

145) A compound or pharmaceutically acceptable salt thereof, according to clause 144, wherein $R^{e2}$ is cyclopropyl.

146) A compound or pharmaceutically acceptable salt thereof, according to any one of clauses 1-145, wherein $R^1$ is H.

147) A compound or pharmaceutically acceptable salt thereof, according to any one of clauses 1-145, wherein $R^1$ is —CH$_3$.

148) A pharmaceutical composition comprising a pharmaceutically acceptable carrier and a pharmaceutically effective amount of a compound according to any one of clauses 1-147.

149) A pharmaceutical composition according to clause 134 comprising a further therapeutic agent.

150) A compound or pharmaceutically acceptable salt thereof, according to any one of clauses 1-147, or a pharmaceutical composition according to clause 148 or 149, for use in medicine.

151) A compound or pharmaceutically acceptable salt thereof, according to any one of clauses 1-147, or a pharmaceutical composition according to clause 148 or 149, for use in the treatment of cystic fibrosis.

152) A method for the treatment of cystic fibrosis, comprising administering an amount of the compound according to any one of clauses 1-147, or the pharmaceutical composition according to clause 148 or 149, sufficient to effect said treatment.

153) The use according to clause 151, or the method according to clause 152, wherein the cystic fibrosis is caused by a Class I, II, III, IV and/or VI mutation.

154) The use or method according to clause 153, wherein the Class I mutation is G452X; and/or W1282X.

155) The use or method according to clause 153, wherein the Class II mutation is F508del and/or N1303K.

156) The use or method according to clause 153, wherein the Class III mutation is G551D, R553G, G1349D, S1251N, G178R, and/or S549N.

157) The use or method according to clause 153, wherein the Class IV mutation is R117H, and/or R334W.

158) The use or method according to clause 153, wherein the Class VI mutation is Rescued F508del.

159) The method according to clause 152, wherein the compound according to any one of clauses 1-147, or the pharmaceutical composition according to clause 148 or 149, is administered in combination with a further therapeutic agent.

160) The pharmaceutical composition according to clause 149, or the method according to claim 159, wherein the further therapeutic agent is an agent for the treatment of cystic fibrosis.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, a compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17$^{th}$ edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2—Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3—Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4—Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5—Injection

A compound of the invention according to Formula I may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of A compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the treatment of cystic fibrosis. In a more particular embodiment, the cystic fibrosis is caused by a Class I, II, III, IV and/or VI mutation.

In another embodiment, the present invention provides compounds of the invention, or pharmaceutical compositions comprising a compound of the invention for use in the manufacture of a medicament for use in the treatment of cystic fibrosis. In a more particular embodiment, the cystic fibrosis is caused by a Class I, II, III, IV and/or VI mutation.

In one embodiment, the present invention provides pharmaceutical compositions comprising a compound of the invention, and another therapeutic agent. In a particular embodiment, the other therapeutic agent is a cystic fibrosis treatment agent. In a more particular embodiment, the cystic fibrosis is caused by a Class I, II, III, IV and/or VI mutation.

In additional method of treatment aspects, this invention provides methods of treatment of a mammal afflicted with cystic fibrosis, which methods comprise the administration of an effective amount of a compound of the invention or one or more of the pharmaceutical compositions herein described to a patient in need thereof. In a more particular embodiment, the cystic fibrosis is caused by a Class I, II, III, IV and/or VI mutation.

A compound of the invention can be administered as the sole active agent or it can be administered in combination with other therapeutic agents, including other compounds that demonstrate the same or a similar therapeutic activity and that are determined to safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment of cystic fibrosis, particular agents include but are not limited to antibiotics (for example aminoglycosides, colistin, aztreonam, ciprofloxacin azithromycin), expectorants (for example hypertonic saline, acetylcysteine, dornase alfa, denufosol), CFTR correctors (for example VX-809, VX-661, VX-983), pancreatic enzyme supplements (for example pancreatin, pancrelipase).

By co-administration is included any means of delivering two or more therapeutic agents to the patient as part of the same treatment regime, as will be apparent to the skilled person. Whilst the two or more agents may be administered simultaneously in a single formulation this is not essential. The agents may be administered in different formulations and at different times.

Chemical Synthetic Procedures

General

The compounds of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Greene, T W; Wuts, P G M; 1991).

The following methods are presented with details as to the preparation of a compound of the invention as defined hereinabove and the comparative examples. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 µm). Thin layer chromatography was carried out using pre-coated silica gel F-254 plates (thickness 0.25 mm) $^1$H NMR spectra were recorded on a Bruker DPX 400 NMR spectrometer (400 MHz or a Bruker Advance 300 NMR spectrometer (300 MHz). Chemical shifts (δ) for $^1$H NMR spectra are reported in parts per million (ppm) relative to tetramethylsilane (δ 0.00) or the appropriate residual solvent peak, i.e. $CHCl_3$ (δ 7.27), as internal reference. Multiplicities are given as singlet (s), doublet (d), triplet (t), quartet (q), quintuplet (quin), multiplet (m) and broad (br). Electrospray MS spectra were obtained on a Waters platform LC/MS spectrometer or with Waters Acquity H-Class UPLC coupled to a Waters Mass detector 3100 spectrometer. Columns used: Waters Acquity UPLC BEH C18 1.7 µm, 2.1 mm ID×50 mm L, Waters Acquity UPLC BEH C18 1.7 µm, 2.1 mm ID×30 mm L, or Waters Xterra MS 5 µm C18, 100×4.6 mm. The methods are using either $MeCN/H_2O$ gradients ($H_2O$ contains either 0.1% TFA or 0.1% $NH_3$) or $MeOH/H_2O$ gradients ($H_2O$ contains 0.05% TFA). Microwave heating was performed with a Biotage Initiator.

Racemic mixtures were separated on a Agilent HP1100 system with UV detection. Column used: Chiralpak 1A (10× 250 mm, 5 µm). Solvents used: iPrOH and tBME. Alternatively, separation was done using a SFC2 system. Column used: Lux Cellulose-4. Solvents used: $CO_2$ and MeOH. Enantiomeric purity was determined on a Agilent HP1100 system with UV detection. Column used: Chiralpak IA (4.6×250 mm, 5 µm). Solvents used: iPrOH and tBME.

List of abbreviations used in the experimental section:

| Abbreviation | Definition |
|---|---|
| DCM | Dichloromethane |
| DIEA | N,N-diisopropylethylamine |
| MeCN | Acetonitrile |
| DMF | N,N-dimethylformamide |
| Cat. | Catalytic amount |
| TFA | Trifluoroacetic acid |
| THF | Tetrahydrofuran |
| NMR | Nuclear Magnetic Resonance |
| DMSO | Dimethylsulfoxide |
| LC-MS | Liquid Chromatography- Mass Spectrometry |
| EtOAc | Ethyl acetate |
| APCI | Atmospheric pressure chemical ionization |
| Rt | Retention time |
| s | Singlet |
| br s | Broad singlet |
| m | Multiplet |
| min | Minute |
| mL | Milliliter |
| µL | Microliter |
| g | Gram |
| mg | Milligram |
| $PdCl_2$dppf | [1,1'-Bis(diphenylphosphino)ferrocene] dichloropalladium(II) |
| TEA | Triethylamine |
| mmol | Millimoles |
| HATU | O-(Benzotriazol-1-yl)-N,N,N',N'-tetramethyluronium hexafluorophosphate |
| HPLC | High pressure liquid chromatography |
| NMP | N-Methylpyrrolidone |
| NCS | N-Chlorosuccinimide |
| NBS | N-Bromosuccinimide |
| AcCl | Acetyl Chloride |
| mCPBA | meta-chloroperoxybenzoic acid |
| ppm | parts per million |
| $NaHCO_3$ | Sodium bicarbonate |
| $H_2O_2$ | Hydrogen peroxide |
| $MgSO_4$ | Magnesium sulfate |
| $Na_2SO_4$ | Sodium sulfate |
| NaOtBu | Sodium tert-butoxide |
| DiPPF | 1,1'-Bis(diisopropylphosphino)ferrocene |
| $Pd(OAc)_2$ | Palladium (ii) acetate |
| $Cs_2CO_3$ | Cesium carbonate |
| HCl | Hydrogen chloride |
| $ClSO_3H$ | Chorosulfonic acid |
| Cpd | Compound |
| Mtd | Method |

| Abbreviation | Definition |
|---|---|
| Int | Intermediate |
| MW | Molecular weight |
| Mes | Molecular weight measured |
| NA | Not active |
| DBU | 1,8-Diazabicyclo[5.4.0]-undec-7-ene |
| EtOH | Ethanol |
| h | Hours |
| MeI | Methyl iodide |
| MeOH | Methanol |
| $K_2CO_3$ | Potassium carbonate |
| KOH | Potassium hydroxide |
| MTBE | Methyl tertiary butyl ether |
| NaOEt | Sodium ethoxide |
| NaOH | Sodium hydroxide |
| NaOMe | Sodium methoxide |
| $NH_4Cl$ | Ammonium chloride |
| NXS | N-halosuccinimide |
| $Pd_2(dba)_3$ | Tris(dibenzylideneacetone)-dipalladium(0) |

Synthetic Preparation of the Compound of the Invention

Example 1

General Synthetic Methods

The compounds of the invention and the comparative examples can be produced according to the following schemes.

Scheme 1: Sulfones via $S_NAr$

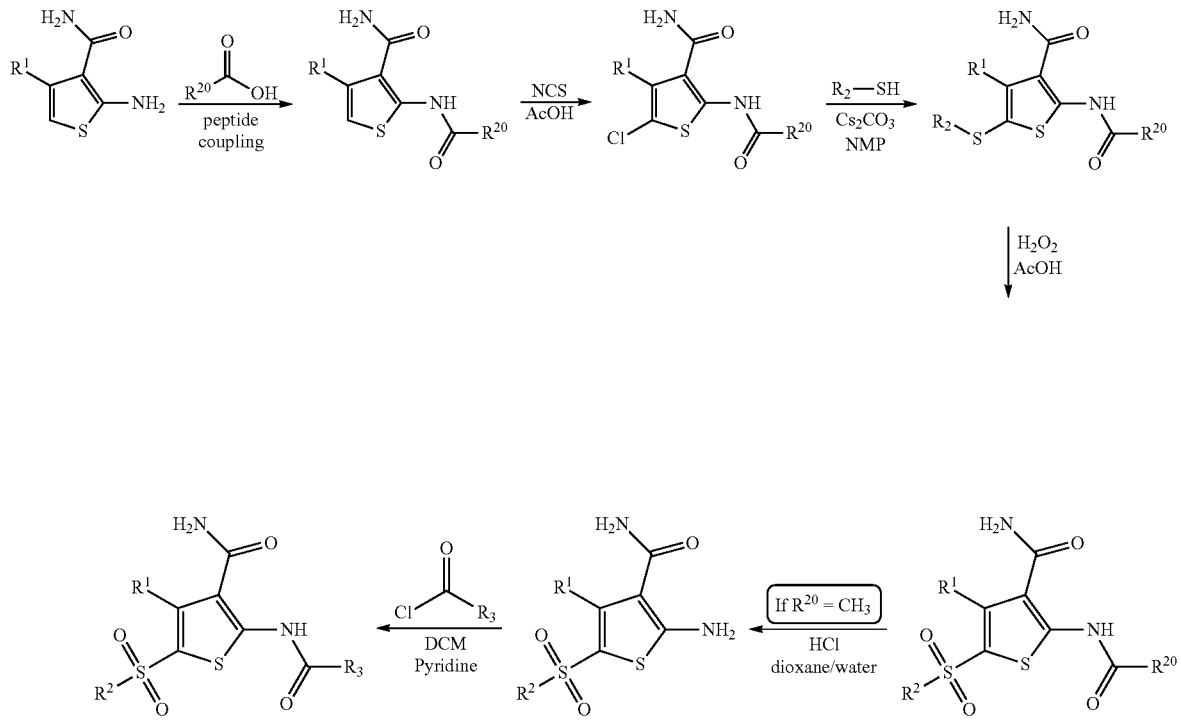

Scheme 2: Sulfones via Buchwald

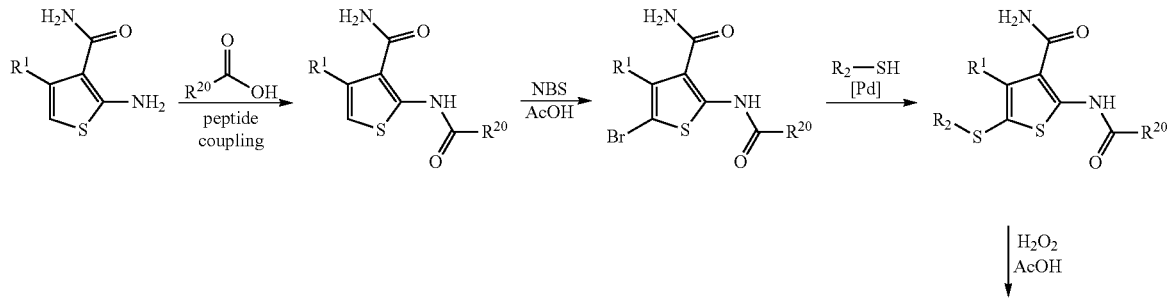

83 84
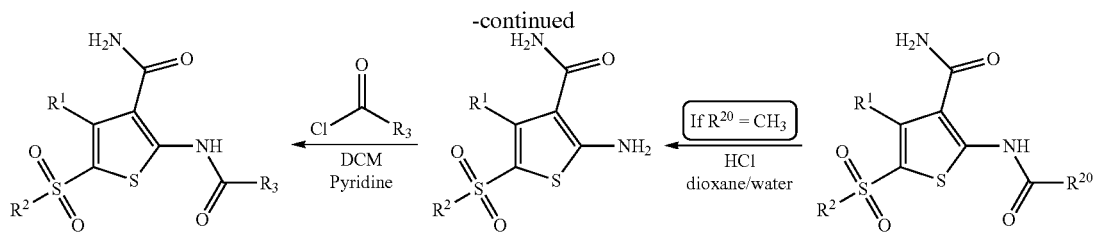
Scheme 3: Sulfonamides
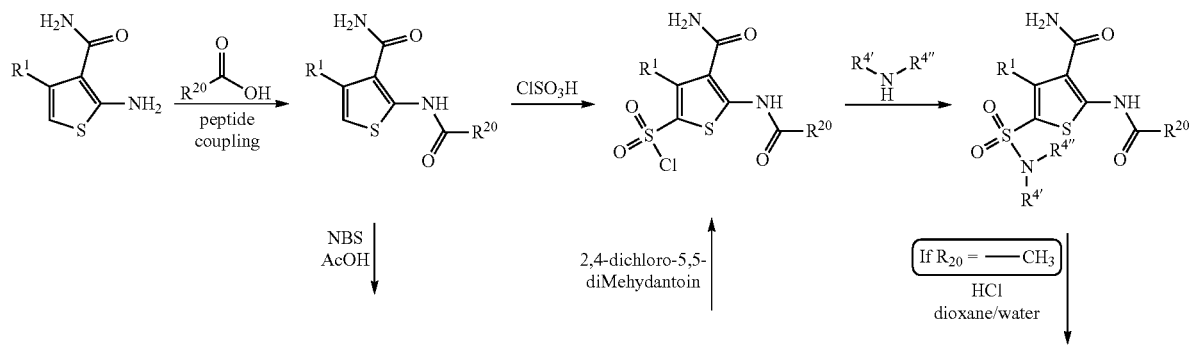
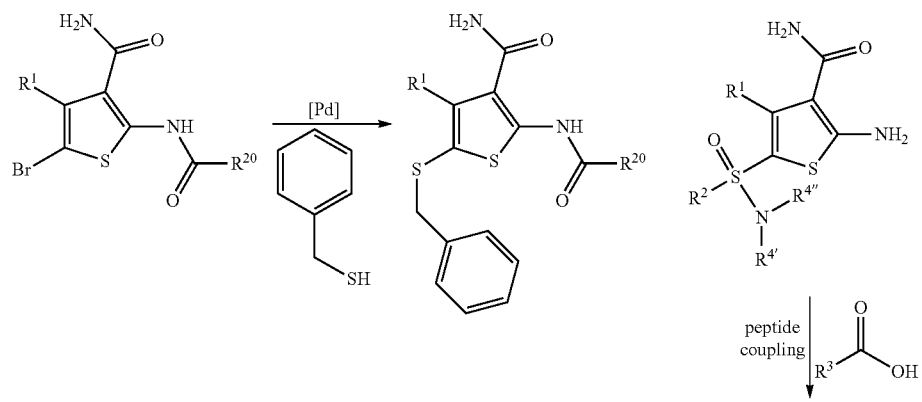
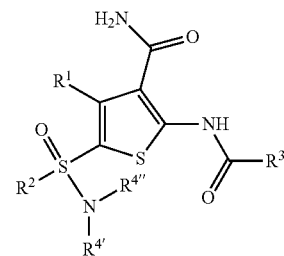

Scheme 4: Synthesis of thiols
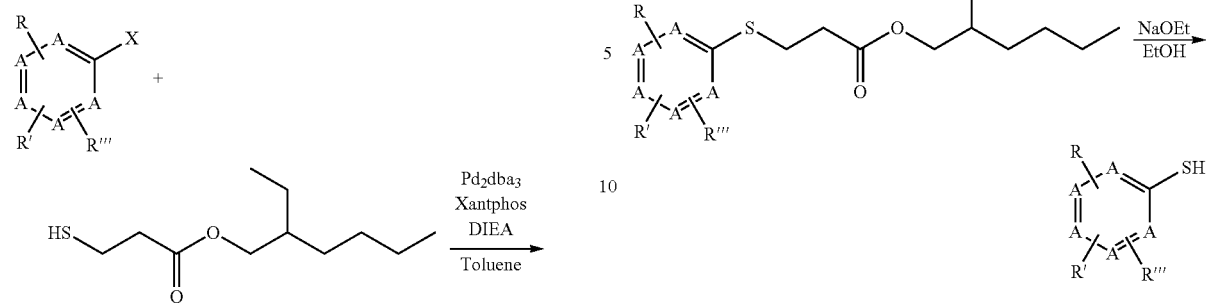
Scheme 5: Synthesis of sulfones starting from a general thio-intermediate
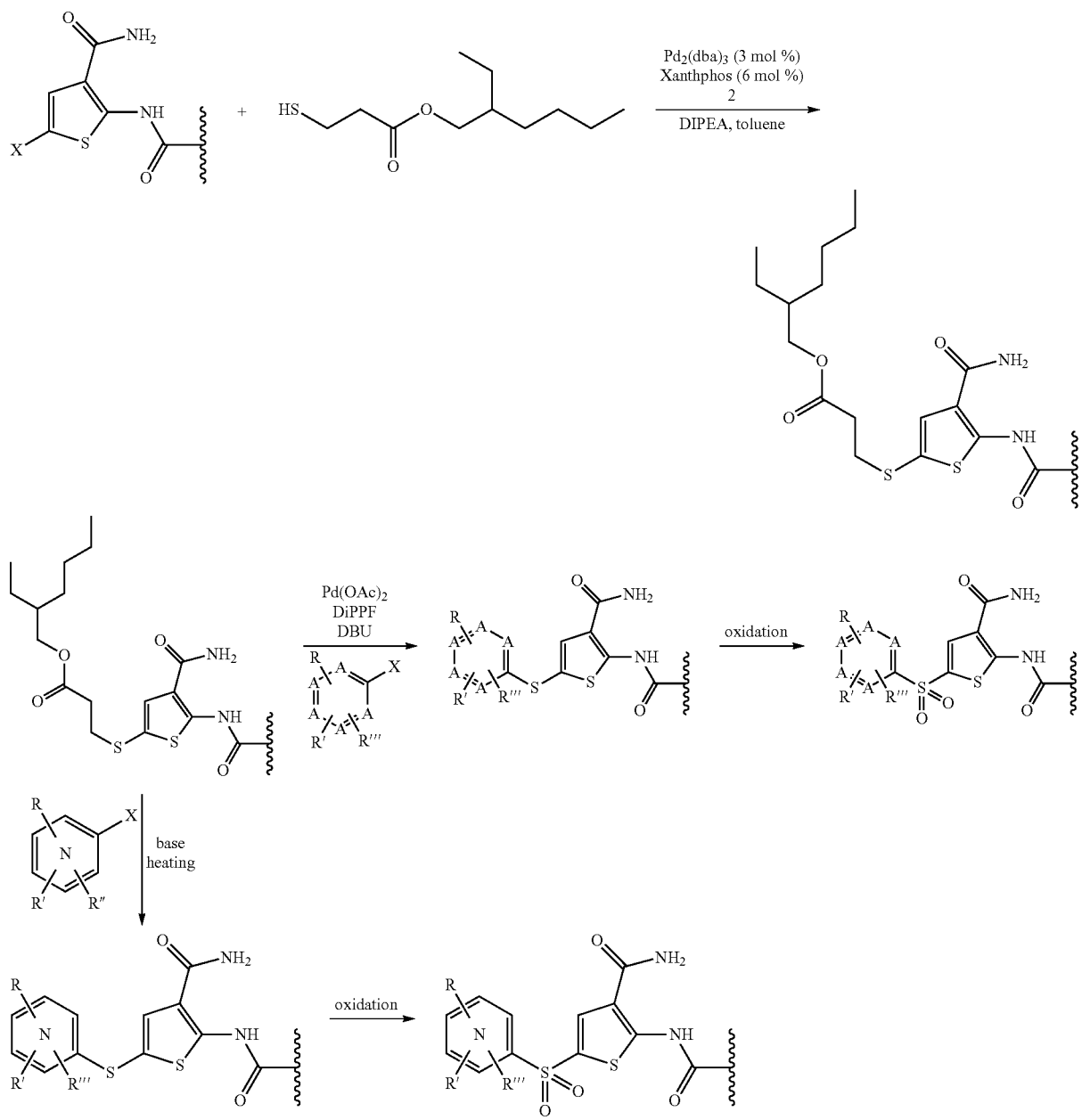

Example 2

Synthesis of Intermediates

Intermediate 1: 2-acetylamino-thiophene-3-carboxylic acid amide

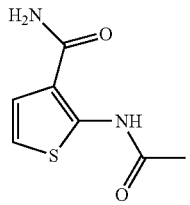

A solution of 2-Amino-thiophene-3-carboxylic acid amide (20.3 g, 143 mmol) in dry pyridine (150 mL) is cooled to 0° C. Acetylchloride (11 mL, 156 mmol) is added dropwise to the solution. The resulting mixture was stirred at room temperature overnight. The mixture is then diluted with water and the resulting suspension is filtered. The cake is dried overnight in a vacuum-oven at 50° C. to yield the desired product.

Intermediate 2: 2-Acetylamino-5-chloro-thiophene3-carboxylic acid amide

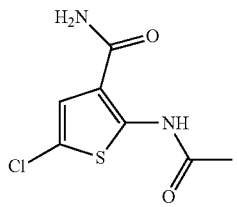

2-acetylamino-thiophene-3-carboxylic acid amide (2.38 g, 12.9 mmol) is dissolved in AcOH (25 mL). NCS (1.9 g, 14.3 mmol) is added and the resulting suspension is stirred at room temperature. After overnight stirring, another 150 mg (1.13 mmol) of NCS is added to the mixture and stirring is continued at 35° C. for 3 h. The mixture is evaporated, and the resulting residue is suspended in water, sonicated, and filtered to give the desired product.

Intermediate 3: 2-Acetylamino-5-bromo-thiophene-3-carboxylic acid amide

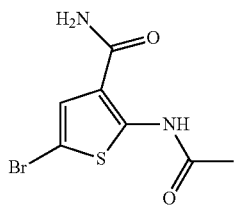

2-acetylamino-thiophene-3-carboxylic acid amide (2.76 g, 15 mmol) is dissolved in AcOH (25 mL), NBS (2.8 g, 15.7) is then added and the resulting suspension is stirred overnight at room temperature. The mixture is concentrated, the resulting residue is dissolved in DCM and washed with aqueous NaHCO$_3$. The organic phase is dried over MgSO$_4$, filtered and the filtrate is concentrated under vacuo. The residue is triturated in di-isopropylether to afford the desired product.

Intermediate 4: 5-acetylamino-4-carbamoyl-thiophene-2-sulfonylchloride

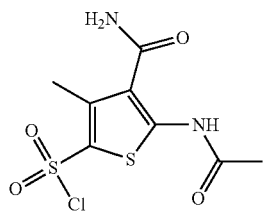 [SMILES: CC(=O)Nc1sc(S(=O)(=O)Cl)c(C)c1C(N)=O]

Neat ClSO$_3$H (29 mL, 440 mmol) is cooled to 0° C., and 2-acetylamino-thiophene-3-carboxylic acid amide (8.1 g, 44 mmol) is added in portions over a period of 15 min. The mixture is then stirred at 50° C. for 3 h, cooled to room temperature, and then poured slowly to ice cold water. The resulting suspension is washed twice with EtOAc, the combined organic fractions are dried over MgSO$_4$, filtered and evaporated to give the desired product, which is used as such.

Intermediate 5: 2-acetylamino-4-methyl-thiophene-3-carboxylic acid amide

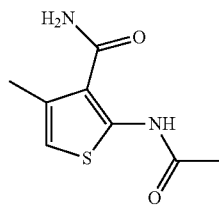

A solution of 2-amino-4-methyl-thiophene-3-carboxylic acid amide (5 g, 32 mmol) in DCM (100 mL) is cooled to 0° C. Dry pyridine (3.6 mL, 45 mmol) is added, followed by acetylchloride (11 mL, 156 mmol) which is added dropwise to the solution. The resulting mixture is stirred at room temperature overnight, then diluted with DCM and washed with aqueous NaHCO$_3$. The organic phase is dried over MgSO$_4$, filtered and concentrated. The obtained residue is triturated in di-isopropylether, filtered, and the cake is dried to afford the desired product.

Intermediate 6: 2-Acetylamino-5-chloro-4-methyl-thiophene-3-carboxylic acid amide

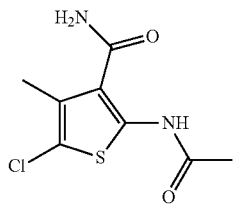

2-acetylamino-4-methylthiophene-3-carboxylic acid amide (2 g, 10.1 mmol) is dissolved in MeOH (40 mL). NCS (1.47 g, 11.1 mmol) is added and the resulting suspension is stirred at 60° C. for 1 h. The mixture is then concentrated under vacuo, the obtained residue is dissolved in DCM and washed with aqueous NaHCO₃. The organic phase is then dried over MgSO₄, filtered and concentrated under vacuo to yield the desired compound which is used as such.

Intermediate 7: 5-Acetylamino-4-carbamoyl-3-methyl-thiophene-2-sulfonyl chloride

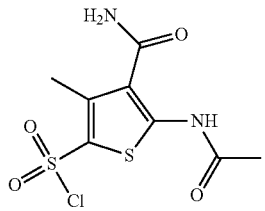 [SMILES: CC(=O)Nc1sc(S(=O)(=O)Cl)c(C)c1C(N)=O]

Neat ClSO₃H (6.7 mL, 100 mmol) is cooled to 0° C. 2-acetylamino-4-methyl-thiophene-3-carboxylic acid amide (1.98 g, 10 mmol) is added in portions over a period of 15 min, and the mixture is stirred at 40° C. for 3 h. The mixture is cooled down to room temperature and poured slowly onto ice cold water. The resulting suspension is washed twice with EtOAc, the combined organic fractions are dried over MgSO₄, filtered and evaporated to yield the desired product which is used as such.

Intermediate 10: [2-[(3-carbamoyl-2-thienyl)amino]-1,1-dimethyl-2-oxo-ethyl]acetate

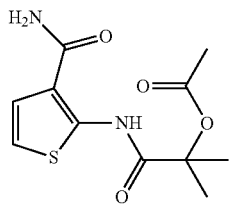

Intermediate 8 (42 g, 295 mmol) is dissolved in pyridine (38 mL) and DCM (250 mL). This mixture is cooled at 0° C.

A solution of 2-acetoxyisobutyryl chloride (48.4 mL, 340 mmol) is dissolved in DCM (250 mL) and added dropwise to the mixture. After complete addition, the mixture is stirred at room temperature. Next, the mixture is evaporated and the obtained slurry is added slowly to water. A precipitate is formed which is filtered off and dried in a vacuum oven at 50° C. This precipitate is used as such.

Intermediate 11: [2-[(5-bromo-3-carbamoyl-2-thienyl)amino]-1,1-dimethyl-2-oxo-ethyl]acetate

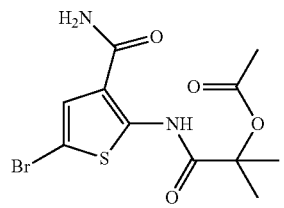 [SMILES: CC(=O)OC(C)(C)C(=O)Nc1sc(Cl)cc1C(N)=O]

Intermediate 10 (46.5 g, 172 mmol) is dissolved in AcOH (700 mL). To the resulting suspension, NBS (32.2 g, 181 mmol) is added. The mixture is stirred at room temperature, after which it is evaporated to give a slurry. This slurry is taken up in water to give a suspension that is filtered. Resulting precipitate is dried in the vacuum oven and used as such.

Intermediate 12: [2-[(3-carbamoyl-5-chloro-2-thienyl)amino]-1,1-dimethyl-2-oxo-ethyl]acetate

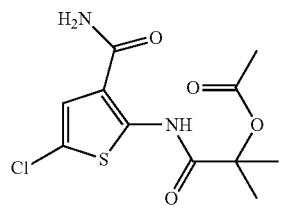

Intermediate 10 (78.5 g, 291 mmol) is dissolved in AcOH (850 mL). To the resulting suspension, NCS (42.9 g, 320 mmol) is added. The mixture is stirred at room temperature, after which it is evaporated to give a slurry. This slurry is taken up in water to give a suspension that is filtered. Resulting precipitate is dried in the vacuum oven and used as such.

Intermediate 13: 3-[5-(2-Acetoxy-2-methyl-propionylamino)-4-carbamoyl-thiophen-2-ylsulfanyl]-propionic acid 2-ethyl-hexyl ester

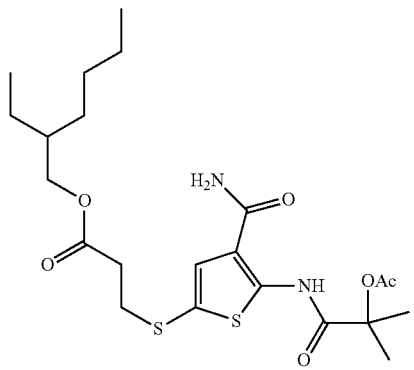 [SMILES: CCCCC(CC)COC(=O)CCSc1cc(C(N)=O)c(NC(=O)C(C)(C)OC(C)=O)s1]

Intermediate 11 (1.4 g, 4 mmol) is dissolved in toluene (16 mL) and DIEA (1.4 mL, 8 mmol). Next, Pd$_2$dba$_3$ (110 mg, 0.12 mmol), Xantphos (139 mg, 0.24 mmol) and 3-Mercaptopropionic acid 2-ethylhexylester (1.14 mL, 5 mmol) are added, and the resulting solution is flushed with N$_2$. Reaction mixture is stirred at 110° C. overnight. After evaporation, the crude is purified using column chromatography. The resulting product is obtained as an oil, which crystallised overnight. Obtained product is used as such.

TABLE I

Illustrative intermediates towards the compounds of the invention

| Int | Structure | Starting Material | MW | Mes |
|-----|-----------|-------------------|-----|-----|
| 1 | 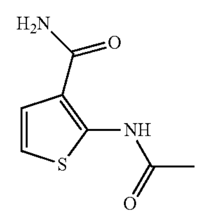 | Int 8 | 184 | 168 |
| 2 | 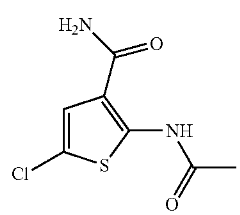 | Int 1 | 219 | 202 |
| 3 | 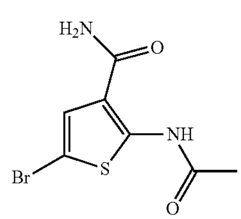 | Int 1 | 263 | 247 |
| 4 | 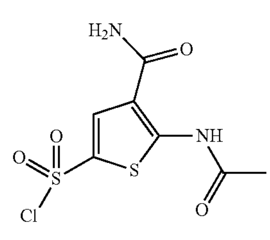 [SMILES: CC(=O)Nc1sc(S(=O)(=O)Cl)cc1C(N)=O] | Int 1 | 283 | 280 |

TABLE I-continued

Illustrative intermediates towards the compounds of the invention

| Int | Structure | Starting Material | MW | Mes |
|-----|-----------|-------------------|-----|-----|
| 5 | (structure) | Int 9 | 198 | 182 |
| 6 | (structure) | Int 5 | 233 | 216 |
| 7 | (structure) | Int 5 | 297 | 293 |
| 8 | (structure) | Commercially available | 142 | 126 |
| 9 | (structure) | Commercially available | 156 | 140 |
| 10 | (structure) | Int 8 | 270 | 254 |
| 11 | (structure) | Int 8 | 349 | 349-351 |

TABLE I-continued

Illustrative intermediates towards the compounds of the invention

| Int | Structure | Starting Material | MW | Mes |
|---|---|---|---|---|
| 12 | 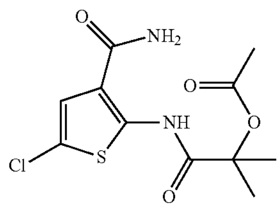 [SMILES: CC(=O)OC(C)(C)C(=O)Nc1sc(Cl)cc1C(N)=O] | Int 8 | 305 | 305-307 |
| 13 | 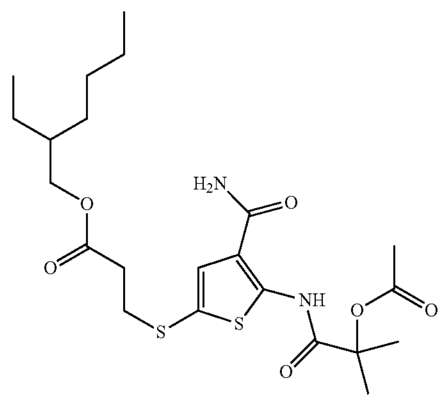 [SMILES: CCCCC(CC)COC(=O)CCSc1cc(C(N)=O)c(NC(=O)C(C)(C)OC(C)=O)s1] | Int 11 | 486 | 487 |

Example 3

General Synthetic Methods for Preparation of the Compounds of Invention

Method A: Halogenation of the Thiophene Ring

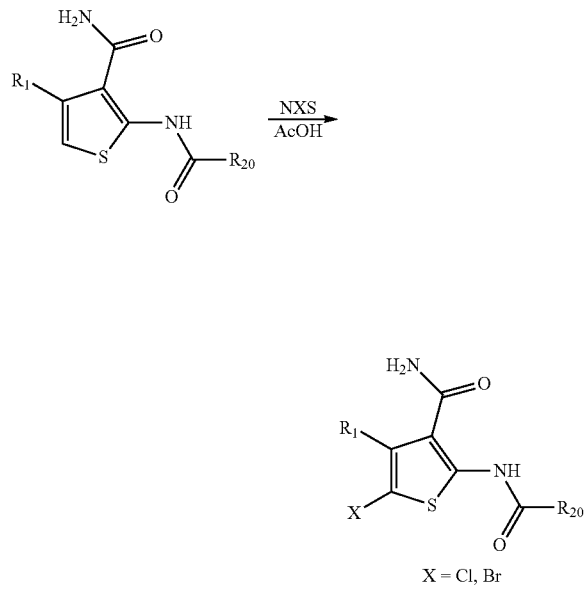

X = Cl, Br

The thiophene (1 eq) is mixed with AcOH. After the addition of NXS (1.05 eq), the resulting reaction mixture is stirred at room temperature overnight. The suspension is then diluted with water and filtered. The cake is dried and used as such in subsequent reactions.

Method B₁: Buchwald

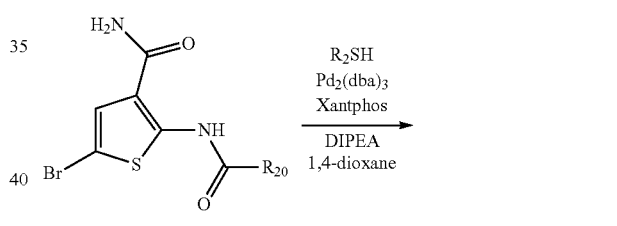

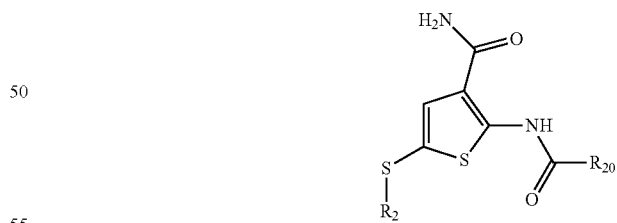

The thiophene-bromide (1 eq), R'SH (1.05 eq) and DIPEA (2 eq) are dissolved in degassed 1,4-dioxane. A separate solution of Pd$_2$(dba)$_3$ (0.02 eq) and Xantphos (0.08 eq) in degassed 1,4-dioxane is sonicated for 5 min and then added the reaction mixture. The resulting mixture is stirred at 100° C. After 1.5 h, the reaction is cooled down to room temperature, diluted with DCM, and washed with an aqueous NaHCO$_3$. The organic phases are combined and dried over Na$_2$SO$_4$, filtered and concentrated under vacuo to give the desired product that is used in the next step without purification.

Method B₂: Buchwald

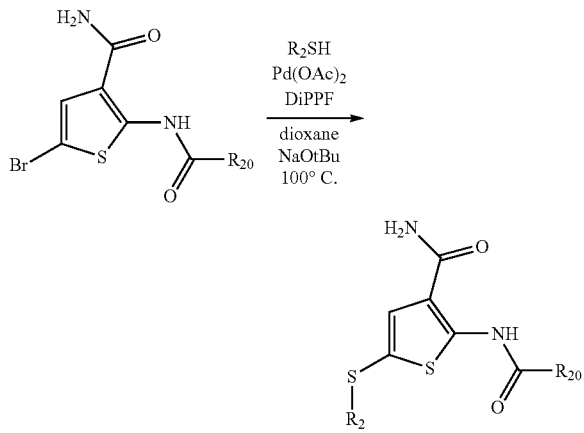

A mixture of thiophene-bromide (1 eq), R₂SH (1 eq), Pd(OAc)₂ (0.05 eq), DiPPF (0.06 eq) and NaOtBu (1.2 eq) in dioxane is heated to 100° C. in a closed vial. After overnight heating, the mixture is diluted with EtOAc and filtered over a silica plug. Evaporation gives the desired product that is used without further purification. Instead of dioxane, solvents like toluene can be used. The base NaOtBu can be replaced with DBU.

Method B₃: Buchwald

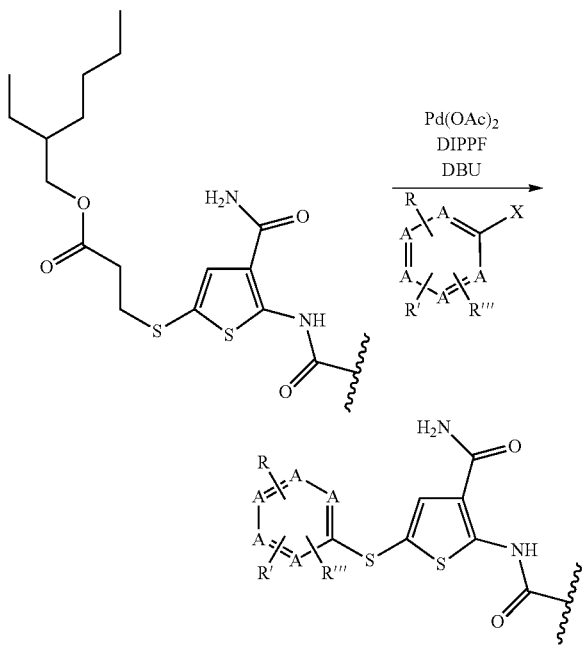

A mixture of thiophene (1 eq), Aryl-halide (1 eq), Pd(OAc)₂ (0.05 eq), DiPPF (0.06 eq) and DBU (2 eq) in dioxane is heated to 95° C. in a closed vial under N₂ atmosphere. After overnight heating, the mixture is diluted with EtOAc and filtered over a silica plug. Evaporation gives a crude mixture that is used as such or is purified by chromatography.

Method C: S$_N$Ar

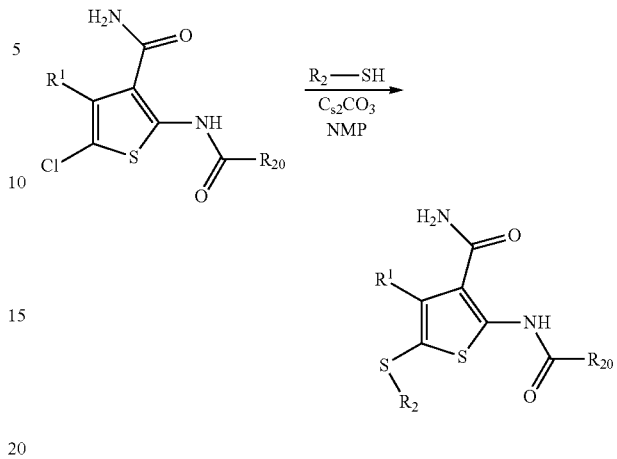

The thiophene-chloride (1.0 eq) is dissolved in dry NMP. To the resulting solution, Cs₂CO₃ (2.0 eq) and the desired thiol (1.1 eq) are added. The mixture is heated under N₂ at 110° C. for 3 h, and then cooled down to room temperature. The solution is diluted with EtOAc to give an organic phase that is washed with water. The organic phase is then dried over Na₂SO₄, filtered, and concentrated under vacuo to give the desired product that is used as such without further purification.

Method C₂: S$_N$Ar

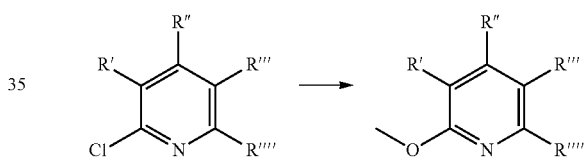

The chloro-pyridine (1 eq) is dissolved in MTBE and this solution is cooled in an ice bath. Next, NaOMe (1 eq, 25% solution in MeOH) is added and the mixture is stirred at room temperature. When the reaction is incomplete, NaOMe (1 eq, 25% solution in MeOH) is added. Evaporation of the solvent gives a crude mixture that can be used as such or that can be purified via chromatography to give the desired product.

Method D₁: Oxidation of the Thio-Ether to the Sulfone with Hydrogen Peroxide

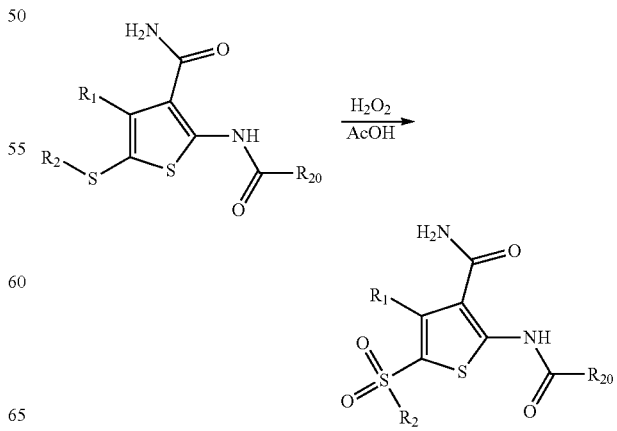

A suspension of the thioether (1 eq) in AcOH is treated dropwise with $H_2O_2$ (3 eq). Resulting mixture is stirred at 65° C. overnight. The mixture is then evaporated to dryness, and the obtained residue is filtered over a plug of silica using EtOAc as an eluent. The filtrate is then concentrated under vacuo, and the residue is either triturated with MeOH or purified by preparative chromatography, to afford the desired product.

If $R^{20}$ contains an acetyl protected alcohol, this ester may be hydrolysed during the oxidation with $H_2O_2$. In this case, purification by preparative chromatography affords the final compound.

Method $D_2$: Oxidation of the Thio-Ether to the Sulfone with mCPBA

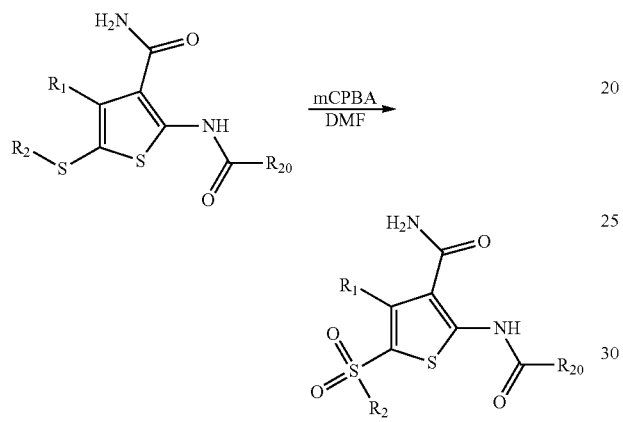

A mixture of the thioether (1 eq) and mCPBA (2.5 eq) in DMF is stirred at room temperature for 1.25 h, then the mixture is diluted with DCM and washed with aqueous $NaHCO_3$. The organic phase is evaporated to give a residue that is purified by preparative chromatography to yield the desired product. DMF can be replaced by DCM as a solvent. The crude can also be used as such without purification.

Method $E_1$: Chloro-Sulfonylation of the Thiophene Ring

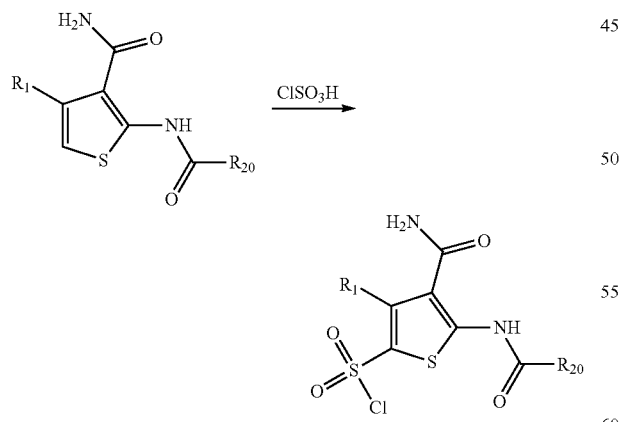

Chloro-sulfonic acid (10 eq) is cooled to 0° C. The thiophene (1 eq) is added portionwise to the cooled reaction mixture. The resulting mixture is stirred at 15 min at 0° C. The ice bath is then removed and the mixture is heated to 50° C. for 3 h. The mixture is then cooled to room temperature which is used as such the next step.

Alternatively, the desired product can be isolated by diluting carefully the mixture with ice-water, to yield a suspension. The solid is diluted by adding EtOAc, the organic fraction is dried over $MgSO_4$, filtered and evaporated to yield the desired product that is used as such.

Method $E_2$: Chloro-Sulfonylation of the Thiophene Ring

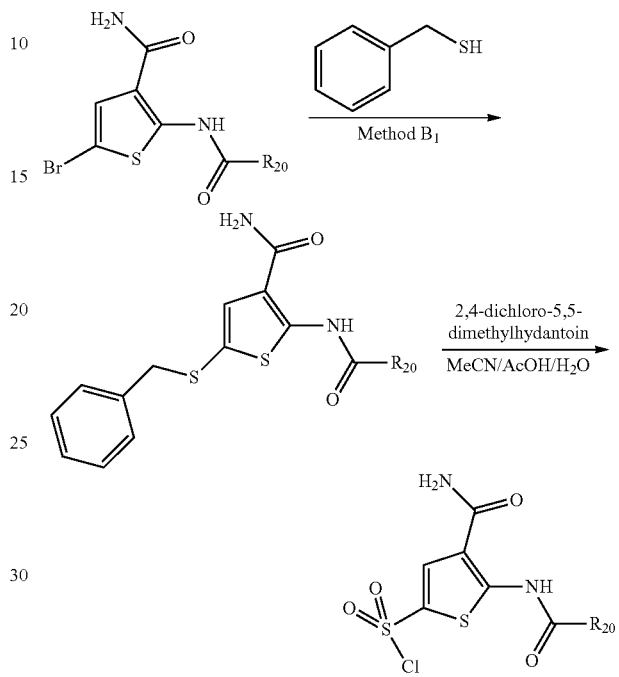

Step $E_1$-1:
Starting from the bromo-thiophene, the desired product is prepared according to method $B_1$.

Step $E_1$-2:
To an ice-cold suspension of the thiophene (1 eq) in MeCN/AcOH/$H_2O$ is added portion wise 2,4-5,5-dichloro-dimethylhydantoin. The suspension is stirred for 1 h at 0° C., and the resulting mixture is then diluted with EtOAc and washed with water. The organic phase is dried over $MgSO_4$, filtered and evaporated. The obtained residue is re-suspended in petroleum ether, the solid is separated by filtration, and subsequently used as such.

Method $E_3$: Chloro-Sulfonylation of the Thiophene Ring

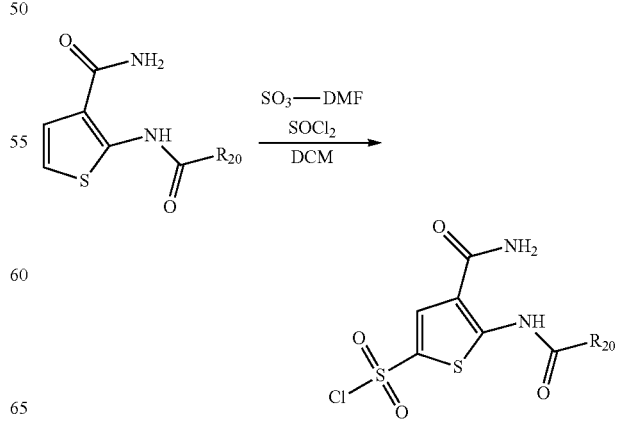

A mixture of the thiophene (1 eq) and SO$_3$-DMF (1.05 eq) in DCM is stirred at 50° C. in a sealed tube. After 45 min, a solution of thionyl chloride (2.5 eq) in DCM is added dropwise to the mixture. When the addition is complete, the mixture is stirred at 50° C. After 2 h, extra thionyl chloride (1 eq) is added. After another 2 h, the mixture is evaporated. This residue is then used as such.

Method F$_1$: Sulfonamide Formation

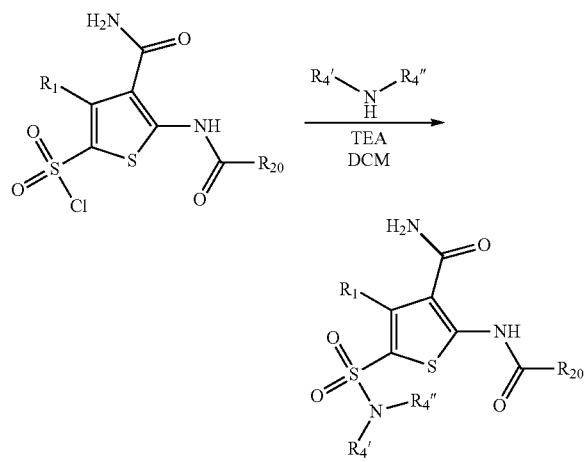

A mixture of thiophenylsulfonylchloride (1 eq), amine (1.1 eq) and TEA (1.3 eq) is heated at 50° C. for 18 h. After evaporation to dryness, the obtained residues are purified by either trituration in water or preparative chromatography.

Method F$_2$: Sulfonamide Formation

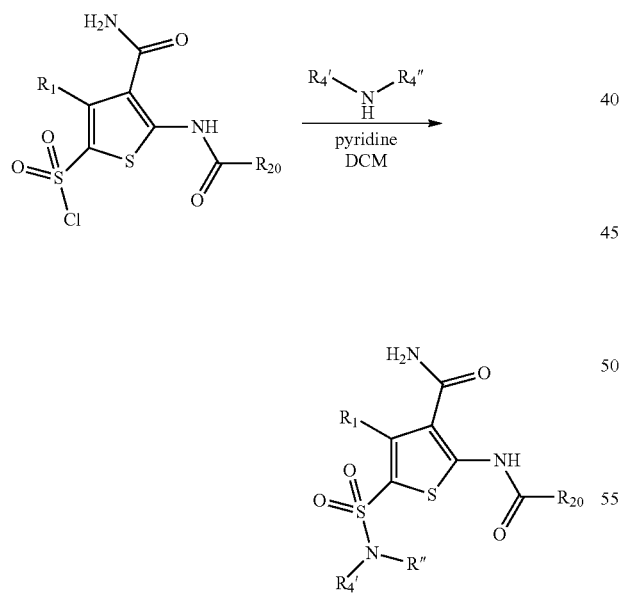

A mixture of the sulfonylchloride (1 eq), amine (3 eq) and pyridine (3 eq) is stirred at room temperature for 1 h. The mixture is then diluted with DCM and washed with aqueous NaHCO$_3$. After separation, the organic layer is dried over MgSO$_4$, filtered and evaporated to give the desired product. The product is either used as such either purified by preparative chromatography.

Method G: Deprotection of the Acetyl Group

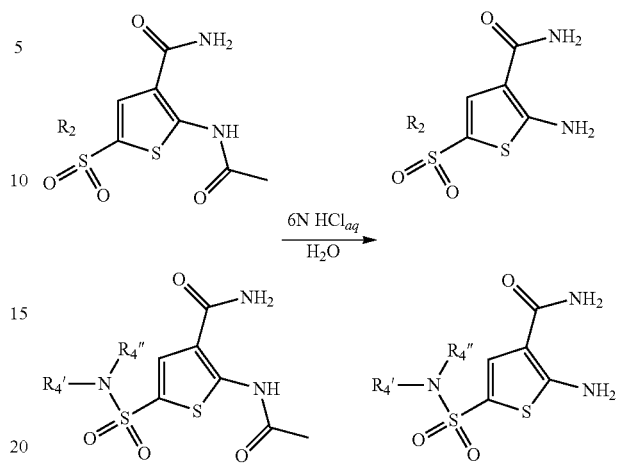

A solution of the acetyl protected amine (1 eq) in a 1:1 mixture of aqueous 6 N HCl and 1,4-dioxane is heated at 85° C. After completion, the mixture is evaporated. The obtained residue is suspended in MeOH and filtered. The precipitate is again triturated with a mixture of di-isopropylether and MeOH to obtain the desired product. The desired product can also be isolated by chromatography. Instead of 6 N HCl, a 2N HCl solution can also be used.

Method H$_1$: Amide Formation, Mukaiyama

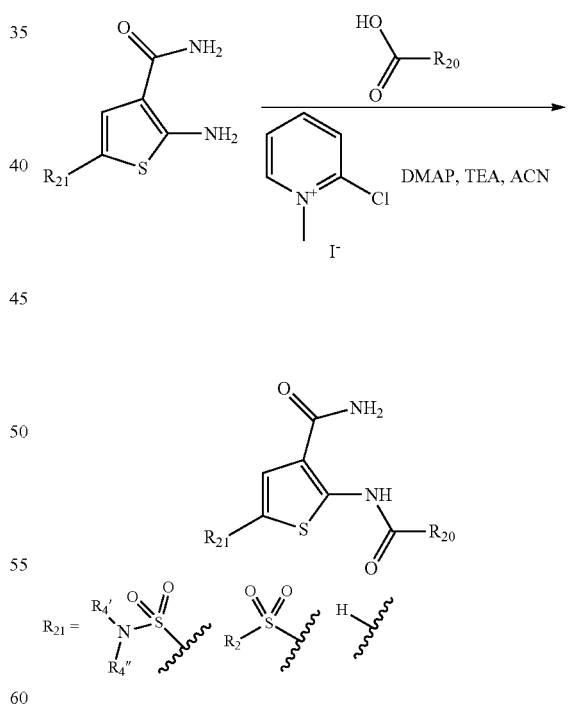

A microwave tube is charged with the amino-thiophene (1 eq), carboxylic acid (1.3 eq), DMAP (0.2 eq), TEA (4 eq) and 2-Chloro-1-methylpyridinium iodide (1.3 eq). After adding MeCN, the tube is flushed with N$_2$, sealed and heated at 60° C. for 18 h. Evaporation gives a crude residue that is purified preparative chromatography.

Method H₂: Amide Formation, Acid-Chloride

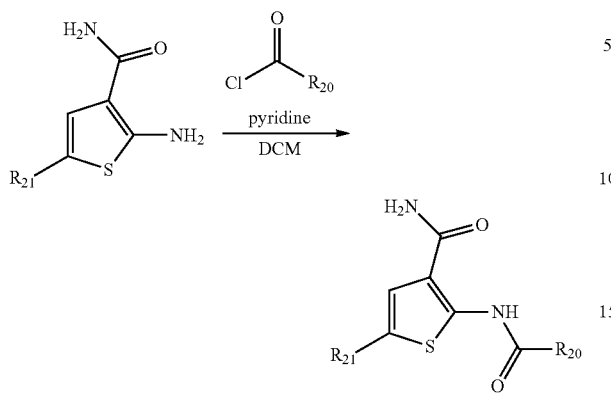

The amino-thiophene (1 eq) is mixed with DCM and pyridine (1.5 eq). This mixture is cooled in an ice bath. The acid chloride (1.15 eq) as obtained by Method H₁ or from a commercial source, is dissolved in DCM and added to this mixture. When the addition is complete, the ice bath is removed and the resulting mixture is stirred at room temperature overnight. The mixture is then evaporated, and the residue is either triturated in water or subjected to preparative chromatography to yield the desired product.

Method H₃: Amide Formation, In Situ Acid-Chloride Activation

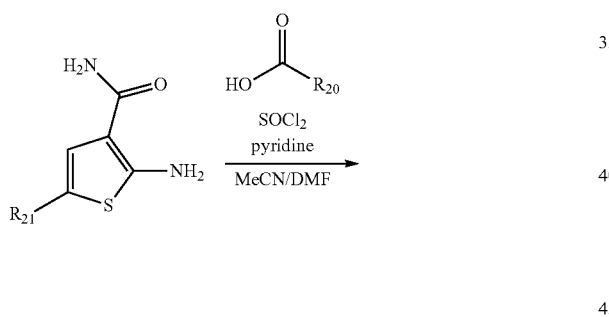

The acid (2 eq) is weighed into a MW vial. A mixture of MeCN and DMF (9/1) is added. In a separate vial, SOCl₂ (2.1 eq) is mixed with MeCN. This solution is then added to the vial containing the acid. The obtained mixture is heated to 50° C. overnight. The amino-thiophene (1 eq) and pyridine (2 eq) are then added to the mixture, stirring is continued at 50° C. for 4 h, and finally the mixture is quenched with water. Evaporation gives a crude mixture that is purified by preparative chromatography to yield the desired product.

Method H₄: HATU Coupling

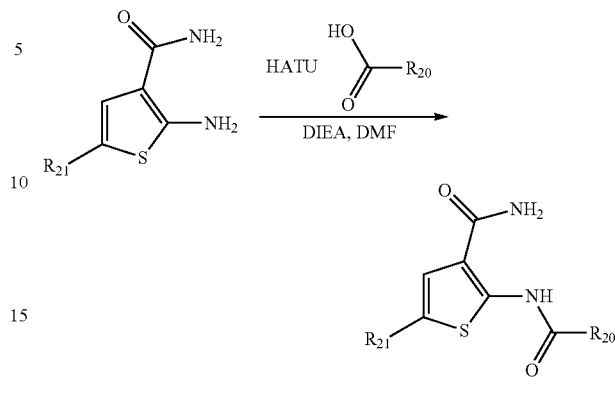

The amino-thiophene (1 eq) is mixed with HATU (3 eq), DIEA (3 eq) and the carboxylic acid (3 eq) in DMF. Obtained mixture is stirred at 30° C. overnight. An extra equivalent of HATU, DIEA and acid are added and the mixture is stirred at 80° C. overnight. The mixture is then diluted with DCM and washed with aqueous NaHCO₃. Organic phase is evaporated and obtained residue is purified by preparative chromatography to yield the desired product.

Note: Ring closure may be observed using method H₁, H₂, H₃ or H₄. In this case, the cyclized product can be opened again by following Method L.

Method H₅: Lactide Opening

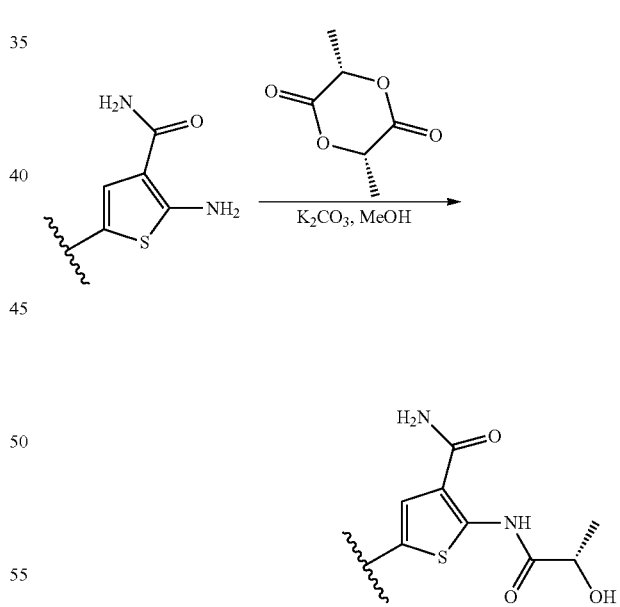

The amino-thiophene (1 eq) is mixed with L-(−)-lactide (1.1 eq) and K₂CO₃ (1.1 eq) in MeOH. Obtained mixture is stirred at 60° C. for 1 h. The resulting mixture is concentrated, taken up in EtOAc/water and acidified with aqueous 2 M HCl until pH~4. The organic layer is separated and the aqueous further extracted with EtOAc (3×). The combined organic is dried, filtered and concentrated in vacuo. Purification by silica chromatography, preparative chromatography or by precipitation gives the desired compound.

Method I: Acetyl Protection of Hydroxy-Acids

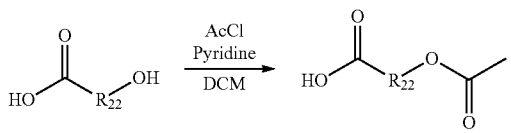

The alcohol (1 eq) is mixed with pyridine (1.2 eq) and DCM and the resulting solution is cooled at 0° C. After the dropwise addition of AcCl (1.05 eq), the mixture is stirred at room temperature. After 3 h, the mixture is washed with aqueous $NH_4Cl$. The organic phase is dried over $MgSO_4$, filtered and evaporated to give a residue that is used as such.

Illustrative Example

1-Acetoxy-cyclopropanecarboxylic acid

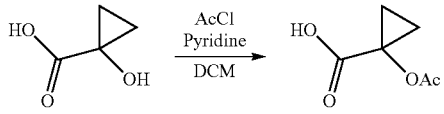 [SMILES: O=C(O)C1(O)CC1 ; CC(=O)OC1(C(=O)O)CC1]

A solution of 1-hydroxy-cyclopropanecarboxylic acid (1.02 g, 10 mmol) is mixed with pyridine (1 mL, 12 mmol) and DCM (50 mL). Mixture is cooled to 0° C. Next, AcCl (0.75 mL, 10.5 mmol) is added dropwise to the mixture. The resulting mixture is stirred at room temperature. After 3 h, the mixture is washed with aqueous $NH_4Cl$. The organic phase is dried over $MgSO_4$, filtered and evaporated to give a residue that is used as such.

Method J: Acetyl Deprotection Using $K_2CO_3$

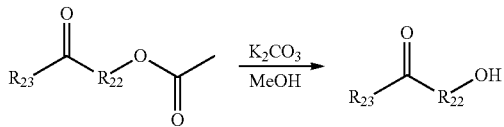

The acetyl ester (1 eq) is dissolved in MeOH and treated with $K_2CO_3$ (2 eq) and is stirred at room temperature overnight Monitoring of the reaction by UPLC shows the presence of unconsumed starting material. Therefore, extra 2 eq of $K_2CO_3$ is added and the obtained mixture is heated at 60° C. After 5 h, the conversion is complete. Evaporation gives a residue that is purified by preparative chromatography.

Method $J_2$: Acetyl Deprotection Using LiOH

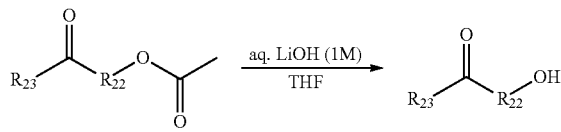

A solution of the acetyl ester (1 eq) in THF is treated with LiOH (1.5 eq, 1M in $H_2O$) and is stirred at 55° C. overnight. After completion of the reaction, the mixture is added to water and extracted with EtOAc. The combined organic fractions are dried over $Na_2SO_4$, filtered and concentrated in vacuo, yielding a crude residue that is used as such or purified by chromatography.

Method $J_3$: Acetyl Deprotection Using aq. HCl

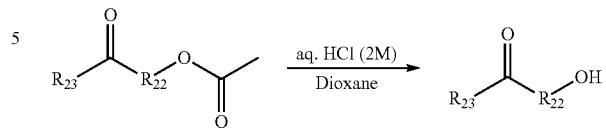

A solution of the acetyl ester (1 eq) in dioxane is treated with an aqueous HCl solution (2 M, 8 eq) and is stirred at 45° C. overnight. After completion of the reaction, the mixture is added to water and extracted with EtOAc. The combined organic fractions are dried over $Na_2SO_4$, filtered and concentrated in vacuo, yielding a crude residue that is purified by preparative chromatography to yield the desired product.

If the reaction is incomplete, the reaction can be performed at higher temperature like 75° C.

Method $J_4$: Ketal Deprotection

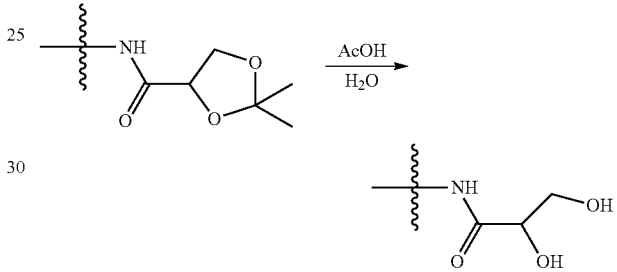

A solution of the dioxolane (1 eq) in $AcOH:H_2O$ (1:1) is stirred at 90° C. in a sealed tube. After 2 h, the reaction mixture is diluted with EtOAc and the pH is adjusted to 7~8 using aqueous $NaHCO_3$. The organic phase is collected, washed with brine, dried over $Na_2SO_4$, filtered and concentrated in vacuo, yielding a crude that is used as such or purified by preparative chromatography to yield the desired product.

Method K: Acid Chloride Formation

The acid (1.15 eq) is dissolved in DCM and treated with $SOCl_2$ (3 eq) and a few drops of DMF. The mixture is stirred at 45° C. in a sealed tube. After 90 min, the mixture is evaporated, and the crude is used as such.

Method L: Ring Opening

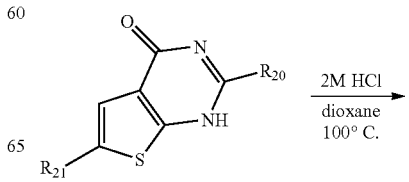

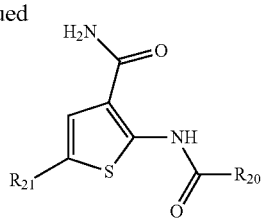

The cyclized product (1 eq) is dissolved in 1:1 solution of 1,4-dioxane and 2 M aqueous HCl. The obtained mixture is stirred at 100° C. overnight, then the mixture is diluted with DCM and washed with aqueous NaHCO$_3$. The organic phase is subsequently evaporated to give a residue that is purified by preparative chromatography to yield the desired product.

Method M$_1$: Synthesis of Thiols

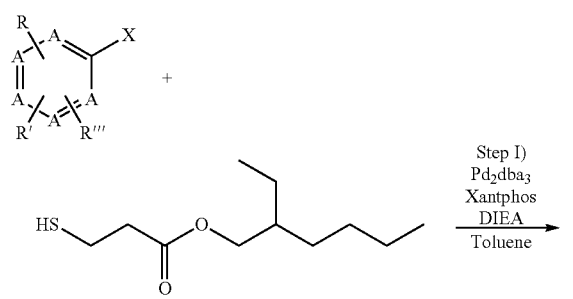

Step i)

A solution of the aryl-halide (1 eq) and DIEA (2 eq) in toluene is put under N$_2$ atmosphere. Next, Pd$_2$(dba)$_3$ (0.03 eq), Xantphos (0.06 eq) and the thiol (1.25 eq) are added and the resulting mixture is heated at reflux overnight. Subsequently, the mixture is filtered over a plug of silica (EtOAc as eluent) and the combined organic fractions are concentrated in vacuo. The obtained crude oil is used as such or purified using chromatography.

This method can also be applied to introduce a thio-ether on a thiophene:

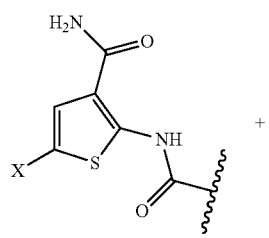

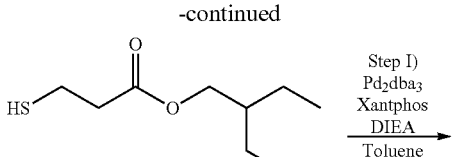

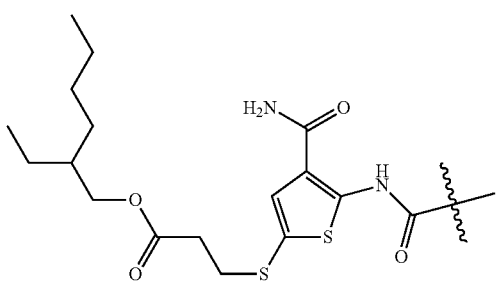

Step ii)

A solution of the aryl-sulfide (1 eq) in EtOH is treated with NaOEt (2 eq, 21 w % in EtOH) and stirred at room temperature. After 2 hours, the reaction is added to water, alkalized with NaOH (5M) and washed with DCM. The alkaline aqueous phase is collected, acidified using HCl (12M) and extracted using DCM. The combined organic fractions are dried over Na$_2$SO$_4$, filtered and concentrated in vacuo, yielding the desired thiophenol which is used as such.

Method M$_2$: One Pot Deprotection and SnAr of Thiols

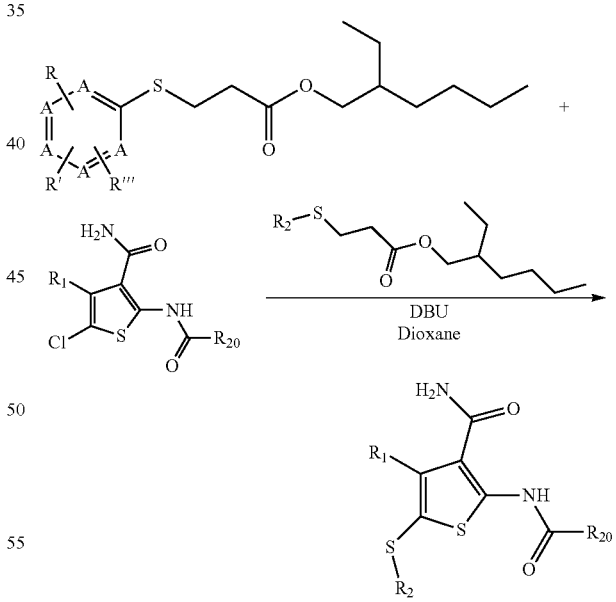

A solution of the thiophene (1 eq), the aryl sulfide (1 eq, as prepared in method M1, Step 1)) and DBU (2 eq) in dioxane is heated in a closed vial at 110° C. Heating can be performed in the microwave or thermally. After completion of the reaction, the mixture is added to water, acidified using HCl (2M) and extracted with EtOAc. The organic fraction is dried over Na$_2$SO$_4$, filtered and concentrated in vacuo, yielding the desired product which is used as such.

Method M₃: Synthesis of Thiols Using Na₂S

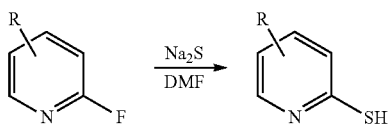

A solution of the fluoro-pyridine (1 eq) in DMF is treated with Na₂S (1.1 eq). The mixture is heated in a closed vial at 120° C. overnight. After completion of the reaction, the solution is added to water, neutralized with NH₄Cl and extracted with EtOAc. The combined organic fractions are dried over Na₂SO₄, filtered and concentrated in vacuo. The obtained thiophenol is used as such without additional purification.

Method M₄: One Pot Deprotection and Reversed SnAr

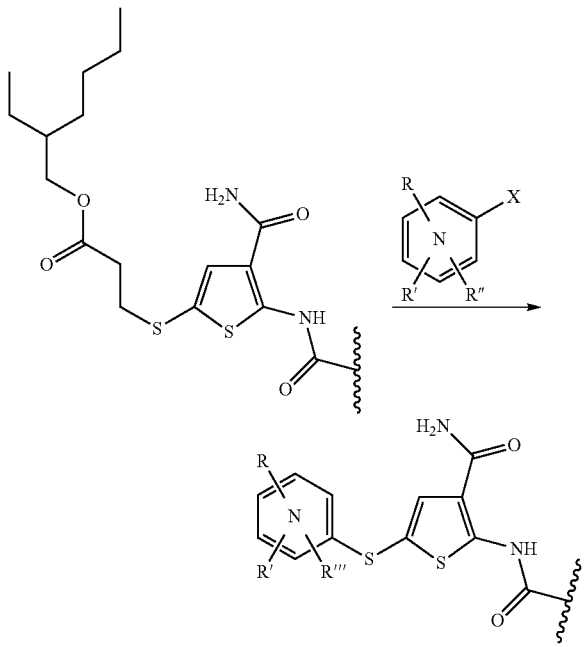

The starting thiophene can be prepared by method M1 (step i). A solution of the thiophene (1 eq), the aryl halide (1 eq)) and DBU (2 eq) in dioxane is heated in a closed vial at 120° C. in the microwave. Thermal heating is also possible. After completion of the reaction, the mixture is added to water and extracted with EtOAc. The organic fraction evaporated and the obtained crude is used as such or purified by chromatography to yield the desired product.

Method O₁: Reduction of Sulfonyl Chloride

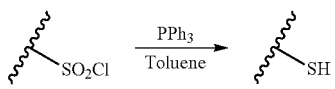

To a solution of the sulfonyl chloride (1 eq) in toluene, PPh₃ (3 eq) is added portion wise under nitrogen. After stirring the reaction for three hours at room temperature, water is added and the resulting mixture is stirred for another hour. After completion, the organic layer is separated and extracted with aq. NaOH (5M). The alkaline aqueous phase is washed with toluene, acidified with HCl (12M) and extracted with DCM. The organic fraction is dried over Na₂SO₄, filtered and concentrated in vacuo, yielding the desired thiophenol which is used as such.

Method O₂: Reduction of N-oxide

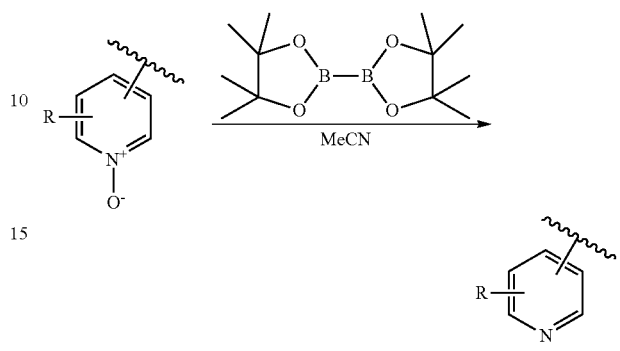

A solution of the N-oxide (1 eq, obtained when oxidising a pyridine containing thioether to the respective sulfoxide) in MeCN is treated with bis(pinacolato)diboron (1.5 eq) and is stirred at room temperature. After completion of the reaction, ethylenediamine (20 eq) is added and stirred for another hour. Next, the mixture is added to water, extracted with EtOAc and the combined organic fractions are dried over Na₂SO₄, filtered and concentrated in vacuo. The obtained product is used without additional purification.

Method O₃: Ester Reduction with LiBH₄

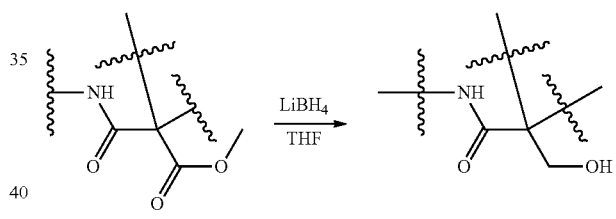

The ester (1 eq) is weighed in a flask together with LiBH₄ (3 eq). The flask is placed in an ice bath followed by the addition of dry THF. When the solvent is added, the mixture is stirred at room temperature. After 4 h, another 3 eq of LiBH₄ are added and the reaction mixture is stirred at room temperature overnight. Next, the reaction is quenched with 2 M HCl. The org solvent is evaporated and obtained mixture is extracted with DCM. The organic phase is concentrated under vacuo, and the residue is purified by preparative chromatography.

Method O₄: Ketone Reduction with NaBH₄

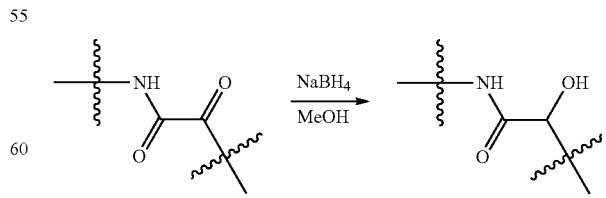

The ketone (1 eq) is dissolved in MeOH and the resulting solution is cooled at 0° C. NaBH₄ (2 eq) is added and the mixture is stirred at room temperature overnight. The reaction is quenched with water and extracted with EtOAc. The organic phase is evaporated and the obtained residue is purified by preparative chromatography to give desired compound.

Method P: Sulfinate Reaction

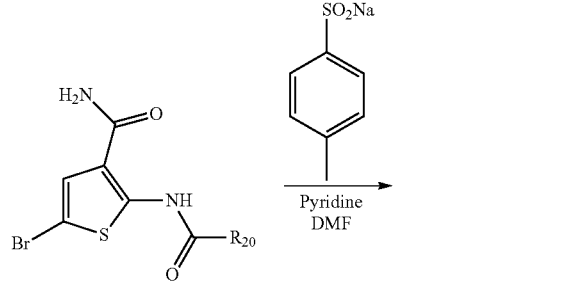

A solution of the thiophene (1 eq) in DMF is treated with pyridine (1.2 eq) and the sulfinate (1.1 eq). The mixture is evacuated, recharged with N₂ and heated at 110° C. After 2 hours, the solution is added to water, neutralized with NH₄Cl and extracted with EtOAc. The combined organic fractions are dried over Na₂SO₄, filtered and concentrated in vacuo yielding a crude residue that is purified by preparative chromatography.

Method Q: CF₂H Alkylation

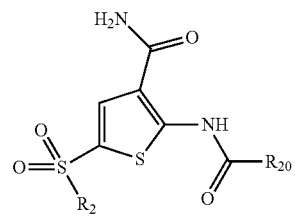

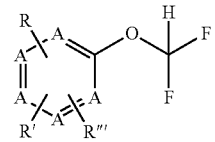

A solution of the alcohol (1 eq) is mixed with KOH (20 eq) in a mixture of MeCN and water. This mixture is cooled in an ice cold brine bath and then the bromodifluoromethyldiethyl phosphonate is added. After the addition, the mixture is stirred at room temperature. The mixture is extracted with EtOAc and the combined org fractions are washed with a NaOH solution. The organic fraction is dried and evaporated to give a precipitate that is used as such.

Method R: Hydrolysis to Pyridone

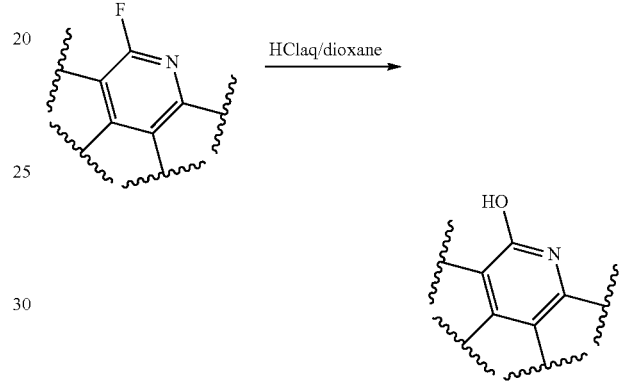

The 2-fluoropyridine is dissolved in a mixture of 4 M HCl and dioxane. The mixture is 80° C. When the reaction is finished, the mixture is brought to pH=7 with NaHCO₃ and extracted with EtOAc. Organic phase is dried over Na₂SO₄, filtered and evaporated to give a crude that is purified by chromatography.

Example 4

Illustrative Examples for the Preparation of the Compounds of Invention

Compound 102: 1H-pyrazole-3-carboxylic acid (5-benzenesulfonyl-3-carbamoyl-4-methyl-thiophen-2-yl)-amide

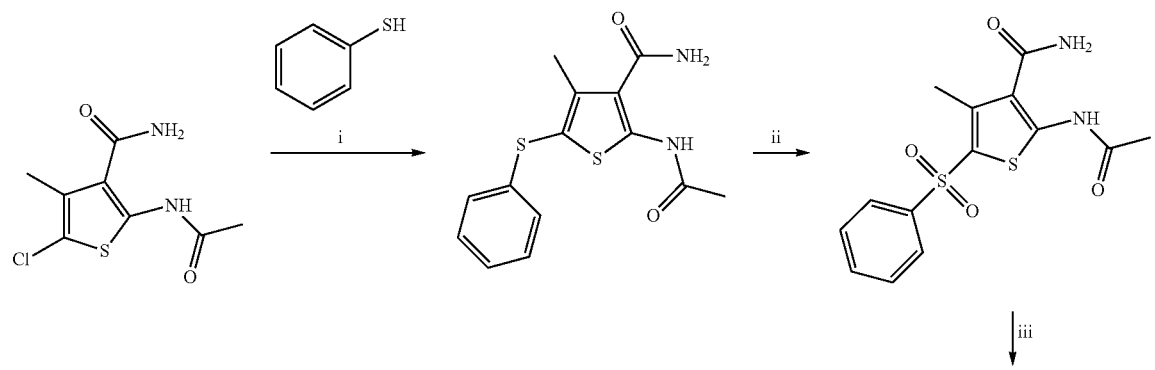

113 114

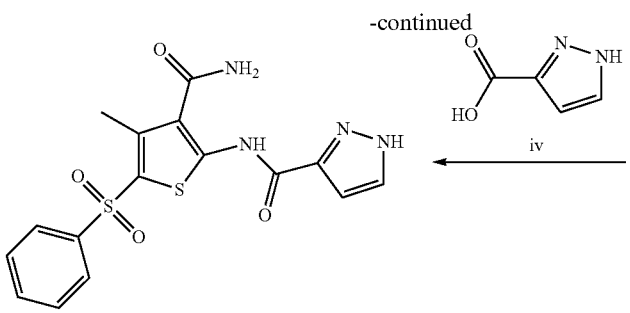
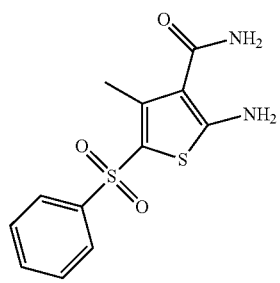

Step (i): 2-Acetylamino-4-methyl-5-phenylsulfanyl-thiophene-3-carboxylic acid amide

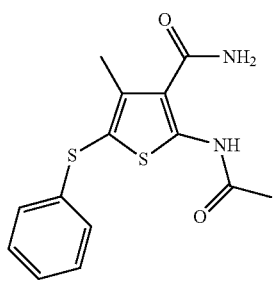 [SMILES: CC(=O)Nc1sc(Sc2ccccc2)c(C)c1C(N)=O]

Intermediate 6 (2-Acetylamino-5-chloro-4-methyl-thiophene-3-carboxylic acid amide) (1.16 g, 5 mmol) is mixed with benzenethiol (535 µL, 5.25 mmol) and Cs$_2$CO$_3$ (3.25 g, 10 mmol) in DMF (15 mL). The resulting mixture is stirred at 120° C. for 30 min, then diluted with water, affording a suspension which is left to stir at room temperature overnight. The solid is separated by filtration, the cake is dried, and the resulting solid is used as such.

Step (ii): 2-Acetylamino-5-benzenesulfonyl-4-methyl-thiophene-3-carboxylic acid amide

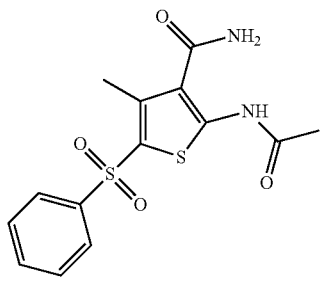 [SMILES: CC(=O)Nc1sc(S(=O)(=O)c2ccccc2)c(C)c1C(N)=O]

2-Acetylamino-4-methyl-5-phenylsulfanyl-thiophene-3-carboxylic acid amide (1.29 g, 4.2 mmol) is mixed with H$_2$O$_2$ (35% w/w, 1.25 mL, 12.6 mmol) in AcOH (20 mL). The resulting mixture is stirred at 65° C. After 2 h, the mixture is evaporated. The obtained residue is suspended in water, filtered, and the resulting cake is dried to give the desired product which is used as such.

Step 2-Amino-5-benzenesulfonyl-4-methyl-thiophene-3-carboxylic acid

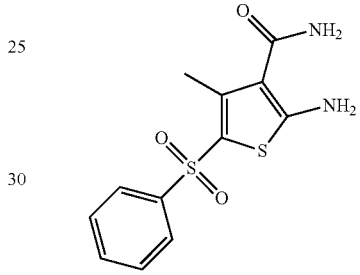

2-Acetylamino-5-benzenesulfonyl-4-methyl-thiophene-3-carboxylic acid amide (980 mg 2.9 mmol) is dissolved in a mixture of 6 M aqueous HCl and 1,4-dioxane (1:1, 10 mL). This mixture is then heated at 80° C. for 6 h, and concentrated by evaporation to yield a residue that is as such.

Step (iv): 1H-pyrazole-3-carboxylic acid (5-benzenesulfonyl-3-carbamoyl-4-methyl-thiophen-2-yl)-amid) (Compound 102)

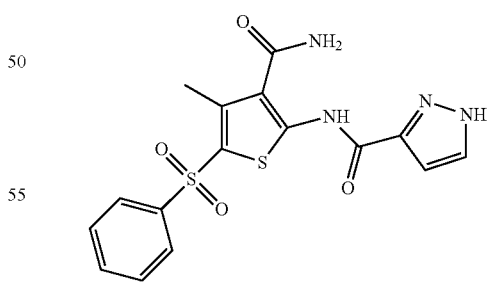

2-Amino-5-benzenesulfonyl-4-methyl-thiophene-3-carboxylic acid (85 mg, 0.22 mmol) is mixed with 1H-pyrazole-3-carboxylic acid (37 mg, 0.33 mmol), 2-Chloro-1-methyl-pyridinium iodide (69 mg, 0.33 mmol), TEA (95 µL, 0.66 mmol) and DMAP (8 mg, 0.066 mmol) in MeCN (3 mL). The mixture is stirred overnight at 65° C., then diluted with DCM and washed with aqueous NaHCO$_3$. The organic phase is evaporated, and the obtained residue is purified by preparative chromatography to give compound 102.

Compound 66: 5-(4,4-difluoropiperidin-1-ylsulfonyl)-2-(2-fluorobenzamido)thiophene-3-carboxamide

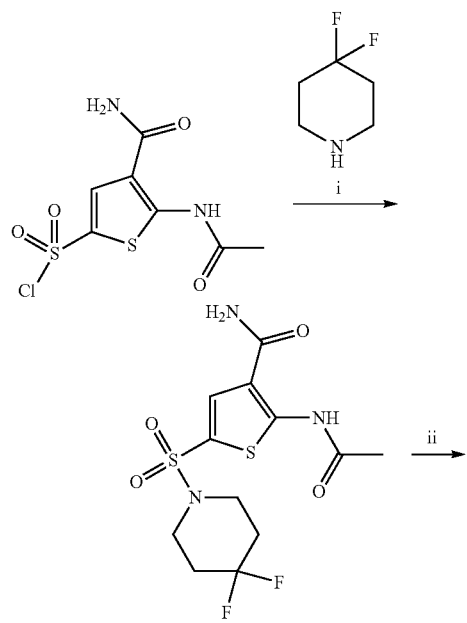

Step (i): 2-Amino-5-(4,4-difluoro-piperidine-1-sulfonyl)-thiophene-3-carboxylic acid amide

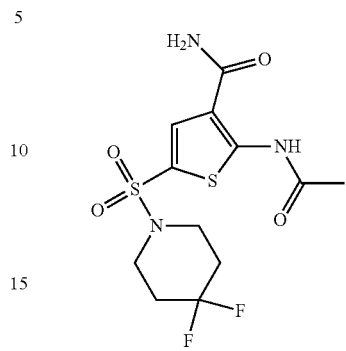

4,4-Difluoropiperidine (540 mg, 4.50 mmol) is mixed with pyridine (0.53 mL, 6.6 mmol) and 15 mL DCM. To this mixture, 0.5 mL of DIEA is added to obtain a clear solution, which is then added dropwise to an ice cold mixture of intermediate 4 (5-acetylamino-4-carbamoyl-thiophene-2-sulfonylchloride, 750 mg, 2.65 mmol) in DCM (5 mL). When the addition is complete, the mixture is stirred at 0° C. for 1 h. The reaction is then stirred at room temperature for another 20 min, after which the mixture is diluted with DCM and washed with aqueous $NaHCO_3$. The organic phase was dried over $MgSO_4$, filtered and evaporated to give the desired product that is used as such.

Step (ii): 2-Amino-5-(4,4-difluoro-piperidine-1-sulfonyl)-thiophene-3-carboxylic acid amide

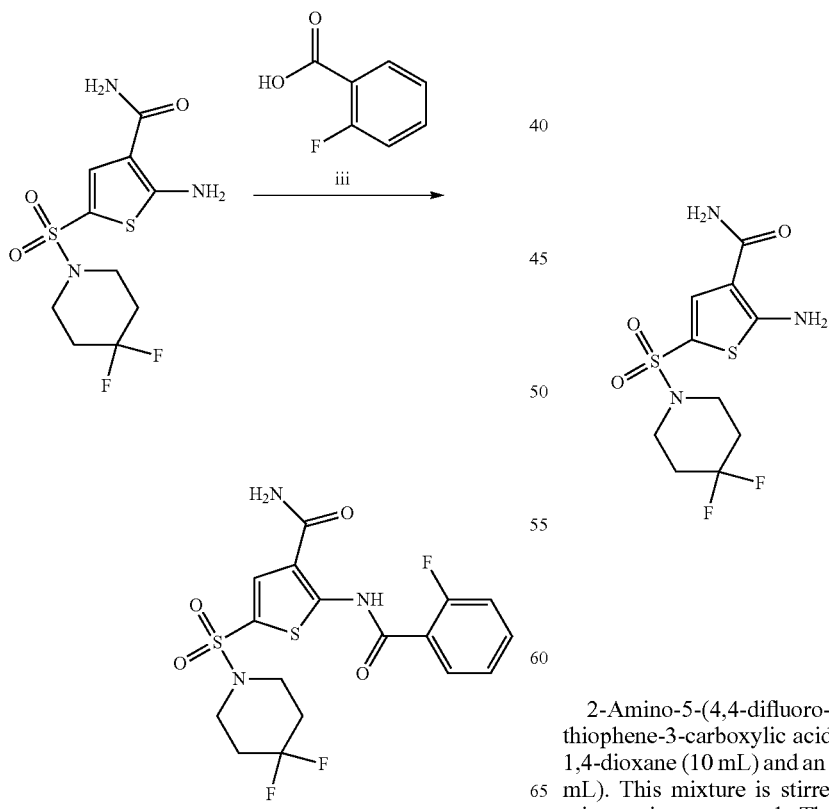

2-Amino-5-(4,4-difluoro-piperidine-1-sulfonyl)-thiophene-3-carboxylic acid amide (950 mg) is dissolved in 1,4-dioxane (10 mL) and an aqueous solution of 6 M HCl (10 mL). This mixture is stirred at 100° C. After 75 min, the mixture is evaporated. The obtained residue mixed with EtOH and evaporated. Again, a residue is obtained that is then triturated with a mixture of di-isopropyl ether and MeOH to give the desired product that is used as such.

Step 5-(4,4-difluoropiperidin-1-ylsulfonyl)-2-(2-fluorobenzamido)thiophene-3-carboxamide (Compound 66)

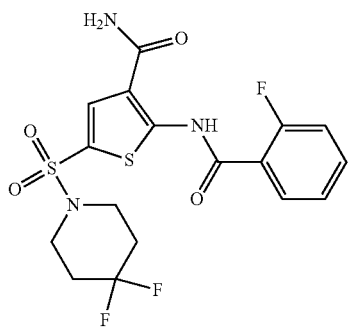 [SMILES: NC(=O)c1cc(S(=O)(=O)N2CCC(F)(F)CC2)sc1NC(=O)c1ccccc1F]

A solution of 2-Amino-5-(4,4-difluoro-piperidine-1-sulfonyl)-thiophene-3-carboxylic acid amide (53 mg, 0.18 mmol), TEA (125 µL, 0.90 mmol), DMAP (7 mg, 0.054 mmol), 2-Chloro-1-methylpyridinium iodide (60 mg, 0.23 mmol) and 2-fluorobenzoic acid (33 mg, 0.23 mmol) in DCM is stirred at 80° C. overnight. The mixture is then diluted with DCM and washed with aqueous $NaHCO_3$. The organic phase is isolated evaporated, and the residue is purified by preparative chromatography to yield the desired product.

Compound 143: 2-(2-Hydroxy-benzoylamino)-5-(morpholine-4-sulfonyl)-thiophene-3-carboxylic acid amide

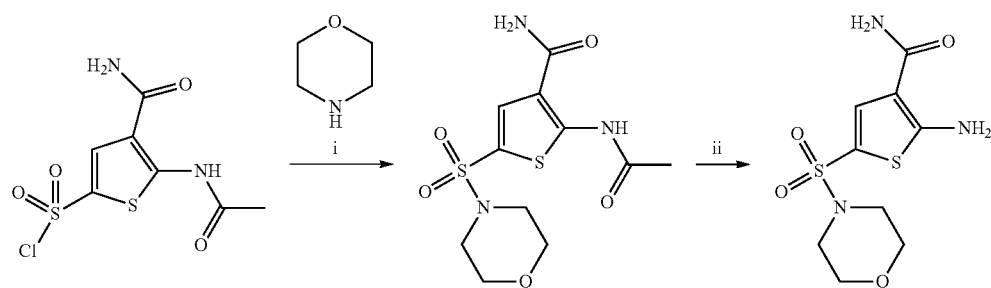

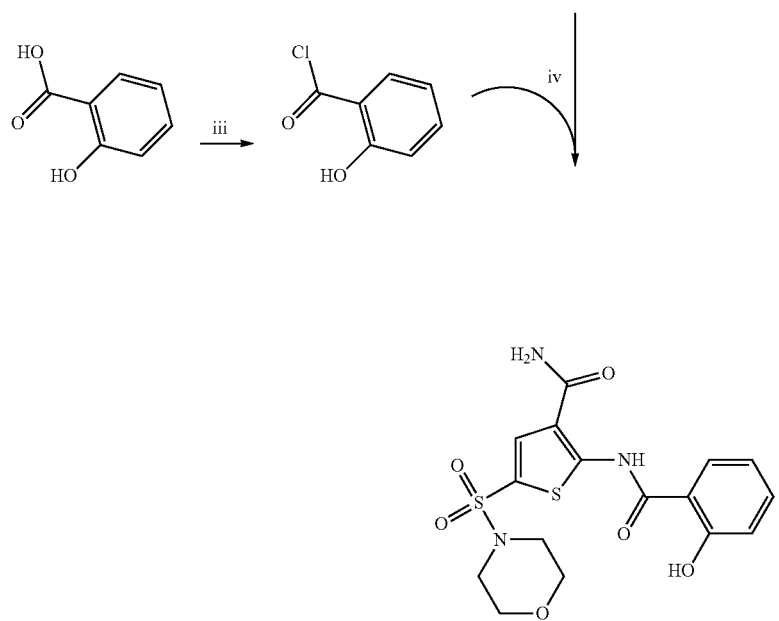

Step (i): 2-Acetyl amino-5-(morpholine-4-sulfonyl)-thiophene-3-carboxylic acid amide

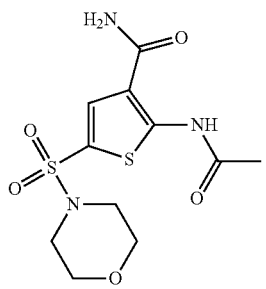 [SMILES: CC(=O)Nc1sc(S(=O)(=O)N2CCOCC2)cc1C(N)=O]

Intermediate 4 (5-acetylamino-4-carbamoyl-thiophene-2-sulfonylchloride, 2.5 mg, 8.84 mmol) is mixed with morpholine (2.32 mL, 26.6 mmol), pyridine (2.14 mL, 26.6 mmol) and DCM (25 mL). The resulting mixture is stiffed for 1 h, then diluted with DCM and washed with aqueous NaHCO$_3$. After isolation, the organic phase is evaporated to give an oily residue that is used as such.

Step (ii): 2-Amino-5-(morpholine-4-sulfonyl)-thiophene-3-carboxylic acid amide

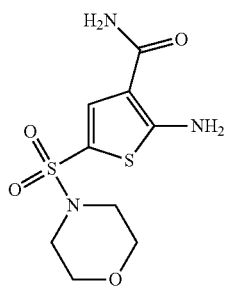 [SMILES: NC(=O)c1cc(S(=O)(=O)N2CCOCC2)sc1N]

2-Acetyl amino-5-(morpholine-4-sulfonyl)-thiophene-3-carboxylic acid amide (2.8 g, 6 mmol) is dissolved in 1,4-dioxane (22 mL) and an aqueous solution of 6 M HCl (22 mL). This mixture is stirred at 100° C., for 75 min, after which the mixture is evaporated to yield a residue that is mixed with EtOH. The resulting solution is evaporated again, and a residue is obtained that is then triturated with a mixture of di-isopropyl ether and MeOH to give the desired product that is used as such.

Step 2-Hydroxy-Benzoyl Chloride

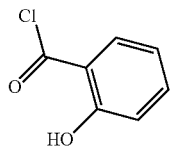

2-Hydroxy benzoic acid (1 g, 7.2 mmol) is dissolved in DCM (14 mL). To this mixture, thionyl chloride (1.57 mL, 22 mmol) and a catalytic amount of dry DMF are added. The resulting mixture is heated to 60° C. overnight, after which the resulting mixture is evaporated to give the desired product that is used as such.

Step (iv): 2-(2-Hydroxy-benzoyl amino)-5-(morpholine-4-sulfonyl)-thiophene-3-carboxylic acid amide (Compound 143)

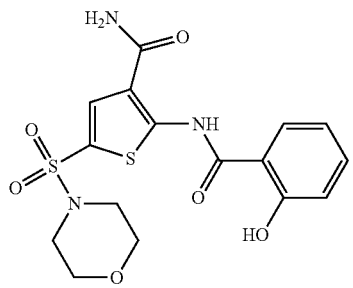 [SMILES: NC(=O)c1cc(S(=O)(=O)N2CCOCC2)sc1NC(=O)c1ccccc1O]

2-Amino-5-(morpholine-4-sulfonyl)-thiophene-3-carboxylic acid amide (150 mg, 0.51 mmol) is mixed with pyridine (63 µL, 0.77 mmol) and DMAP (15 mg, 0.12 mmol) in MeCN (1 mL). 2-Hydroxy-benzoyl chloride (103 mg, 0.65 mmol) is dissolved in 2 mL of MeCN and added to the reaction mixture. The resulting solution is stirred at 60° C. for 2 h, then diluted with DCM and finally washed with aqueous NaHCO$_3$. The organic phase is evaporated to yield a residue which is purified by preparative chromatography to afford the desired product.

Compound 145: 1H-Pyrazole-3-carboxylic acid {3-carbamoyl-5-[(4-fluoro-benzyl)-methyl-sulfamoyl]-thiophen-2-yl}-amide

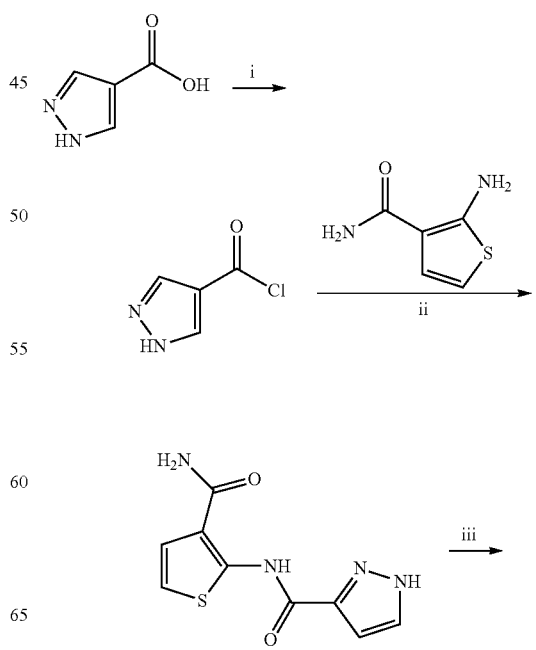

-continued

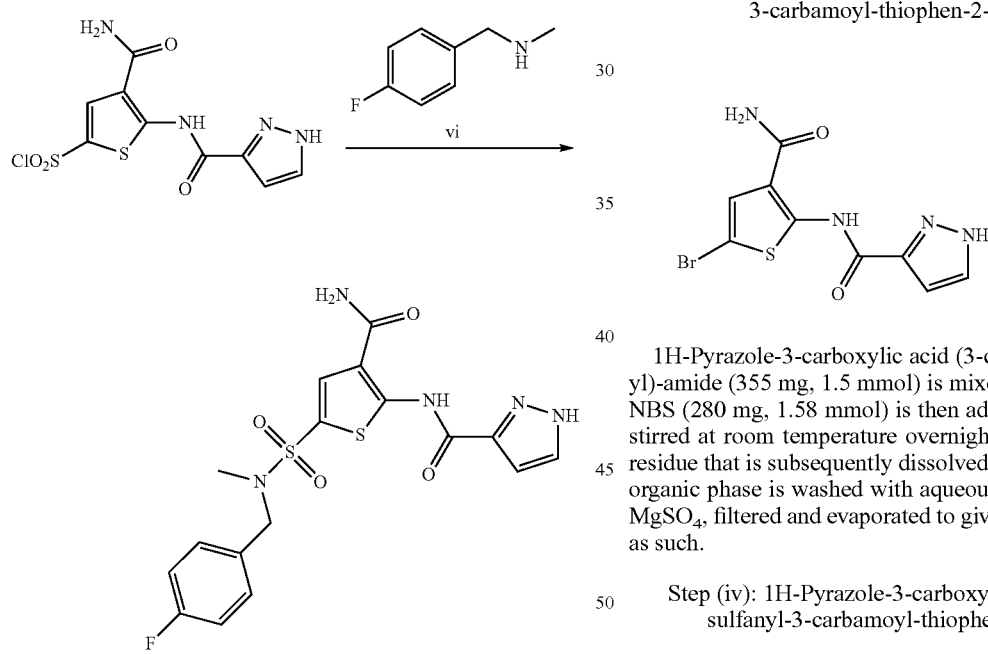

Step (i): 1H-Pyrazole-3-carbonyl chloride

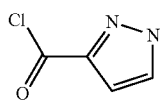

1H-Pyrazole-3-carboxylic acid (560 mg, 5 mmol) is dissolved in DCM (20 mL). To this mixture, thionyl chloride (1.80 mL, 25 mmol) and dry DMF (few drops) are added. Resulting mixture is heated at 60° C. overnight. Mixture is evaporated to give a residue that is used as such.

Step (ii): 1H-Pyrazole-3-carboxylic acid(3-carbamoyl-thiophen-2-yl)-amide

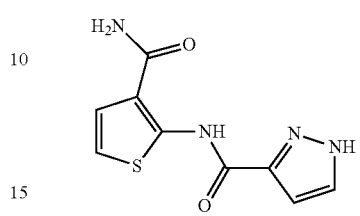

A solution of 1H-Pyrazole-3-carbonyl chloride (5 mmol) in MeCN (5 mL) is added drop wise to a solution of 2-aminothiophene-3-carboxylic acid amide (570 mg, 4 mmol), pyridine (0.5 mL, 6 mmol) and DMAP (25 mg, 0.20 mmol) in MeCN (5 mL). The resulting solution is than stirred at 60° C. over 2 days. Next, the mixture is quenched with aqueous NaHCO₃. Evaporation of the MeCN gives a suspension that is filtered, the cake is dried, and used as such.

Step (iii): 1H-Pyrazole-3-carboxylic acid (5-bromo-3-carbamoyl-thiophen-2-yl)-amide

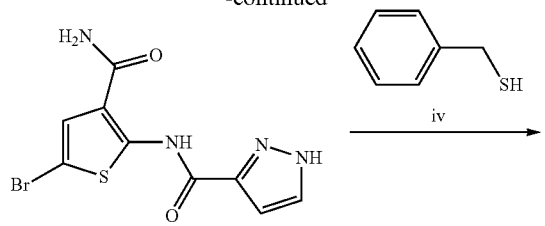

1H-Pyrazole-3-carboxylic acid (3-carbamoyl-thiophen-2-yl)-amide (355 mg, 1.5 mmol) is mixed with AcOH (5 mL). NBS (280 mg, 1.58 mmol) is then added and the mixture is stirred at room temperature overnight. Evaporation gives a residue that is subsequently dissolved in DCM, the resulting organic phase is washed with aqueous NaHCO₃, dried over MgSO₄, filtered and evaporated to give a residue that is used as such.

Step (iv): 1H-Pyrazole-3-carboxylic acid (5-benzylsulfanyl-3-carbamoyl-thiophen-2-yl)-amide

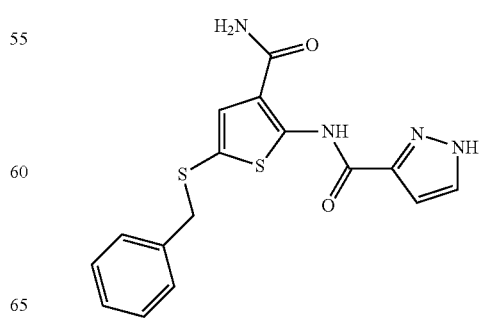

A mixture of Pd$_2$(dba)$_3$ (20 mg, 0.022 mmol) and Xantphos (51 mg, 0.087 mmol) in 1,4-dioxane (5 mL) is degassed, put under N$_2$ and sonicated. This mixture is then added to a degassed mixture of 1H-Pyrazole-3-carboxylic acid (5-bromo-3-carbamoyl-thiophen-2-yl)-amide (345 mg, 1.09 mmol), phenyl-methanethiol (135 μL, 1.15 mmol) and DIEA (380 μL, 2.18 mmol) in 1,4-dioxane (5 mL). Resulting mixture is stirred at 100° C. under N$_2$. After 75 min, the reaction is diluted with DCM and washed with aqueous NaHCO$_3$. The organic is then dried over MgSO$_4$, filtered and evaporated to an oily residue. This residue is triturated in di-isopropylether, separated by filtration, the cake is dried, and the resulting solid is used as such.

Step (v): 4-Carbamoyl-5-[1H-Pyrazole-3-carbonyl) amino]-thiophene-2-sulfonylchloride

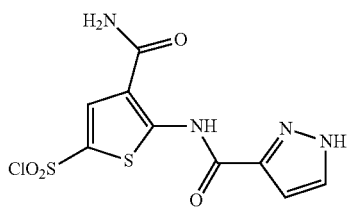 [SMILES: NC(=O)c1cc(S(=O)(=O)Cl)sc1NC(=O)c1cc[nH]n1]

An ice-cold mixture of 1H-Pyrazole-3-carboxylic acid (5-benzylsulfanyl-3-carbamoyl-thiophen-2-yl)-amide (315 mg, 0.8 mmol) in a mixture of MeCN/AcOH/H$_2$O (7 mL/0.37 mL/0.18 mL) is treated portionwise with 2,4-dichloro-5,5-dimethylhydantoin. When the addition is complete, the resulting suspension is stirred at 0° C. for 90 min. The mixture is then diluted with EtOAc and washed with water. The organic phase is dried over MgSO$_4$, filtered and evaporated to give a residue that is triturated with petroleum ether to afford a precipitate that is separated by filtration, dried and used as such.

Step (vi): 1H-Pyrazole-3-carboxylic acid {3-carbamoyl-5-[(4-fluoro-benzyl)-methyl-sulfamoyl]-thiophen-2-yl}-amide (compound 145)

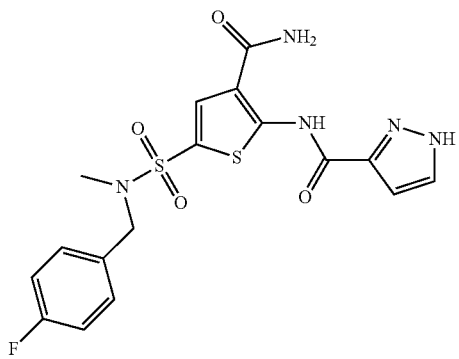 [SMILES: CN(Cc1ccc(F)cc1)S(=O)(=O)c1cc(C(N)=O)c(NC(=O)c2cc[nH]n2)s1]

A suspension of 4-carbamoyl-5-[1H-Pyrazole-3-carbonyl)-amino]-thiophene-2-sulfonylchloride (100 mg, 0.2 mmol) in DCM (3 mL) is treated with pyridine (50 μL, 0.6 mmol) and (4-fluoro-benzyl)-methyl-amine (35 μL, 0.26 mmol). After overnight stirring at room temperature, the mixture is diluted with DCM and washed with aqueous NaHCO$_3$.

The organic phase is dried over MgSO$_4$, filtered and evaporated to give a residue that is purified by preparative chromatography to afford the desired product.

Compound 173: 1H-Pyrazole-3-carboxylic acid {3-carbamoyl-5-[(4-fluoro-phenyl)-methyl-sulfamoyl]-thiophen-2-yl}-amide

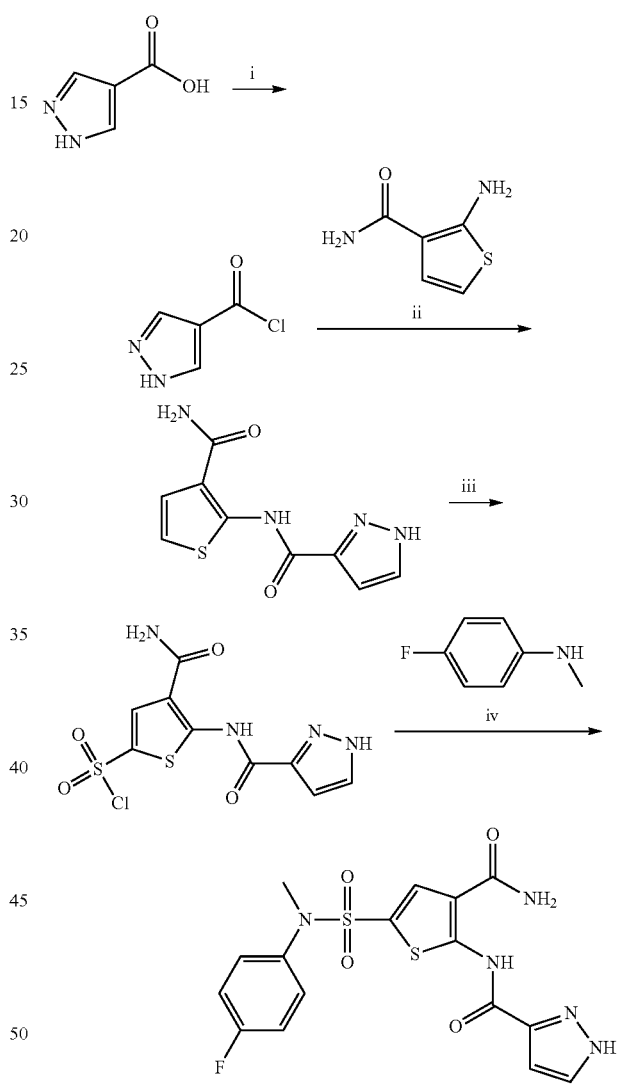

Step (i): 1H-Pyrazole-3-carbonyl chloride

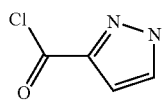

1H-Pyrazole-3-carboxylic acid (560 mg, 5 mmol) is dissolved in DCM (20 mL). To this mixture, thionyl chloride (1.80 mL, 25 mmol) and dry DMF (few drops) are added. The resulting mixture is heated to 60° C. overnight, and then concentrated under vacuo to give a residue that is used as such.

Step (ii): 1H-Pyrazole-3-carboxylic acid (3-carbamoyl-thiophen-2-yl)-amide

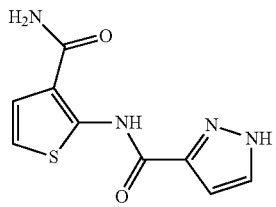 [SMILES: NC(=O)c1ccsc1NC(=O)c1cc[nH]n1]

A solution of 1H-Pyrazole-3-carbonyl chloride (5 mmol) in MeCN (5 mL) is added dropwise to a solution of 2-aminothiophene-3-carboxylic acid amide (570 mg, 4 mmol), pyridine (0.5 mL, 6 mmol) and DMAP (25 mg, 0.20 mmol) in MeCN (5 mL). The resulting solution is than stirred at 60° C. over 2 days. The mixture is then quenched with aqueous NaHCO₃, concentrated under vacuo to afford a suspension that is filtered. The cake is dried and the solid is used as such.

Step 4-Carbamoyl-5-[1H-Pyrazole-3-carbonyl)amino]-thiophene-2-sulfonylchloride

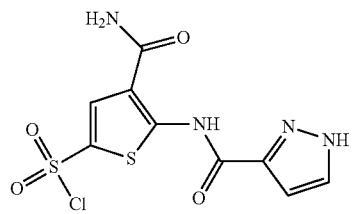 [SMILES: NC(=O)c1cc(S(=O)(=O)Cl)sc1NC(=O)c1cc[nH]n1]

A solution of 1H-pyrazole-3-carboxylic acid (3-carbamoyl-thiophen-2-yl)-amide (515 mg, 2.18 mmol) is mixed with ice cold ClSO₃H (1.49 mL, 22.4 mmol). When the addition is complete, the mixture is stirred at 40° C. for 2 h, the mixture is carefully diluted with EtOAc and ice is added. Extraction with EtOAc gives an organic phase that is dried over Na₂SO₄, filtered and evaporated to give a residue that is used as such.

Step (iv): 1H-Pyrazole-3-carboxylic acid {3-carbamoyl-5-[(4-fluoro-phenyl)-methyl-sulfamoyl]-thiophen-2-yl}-amide (Compound 173)

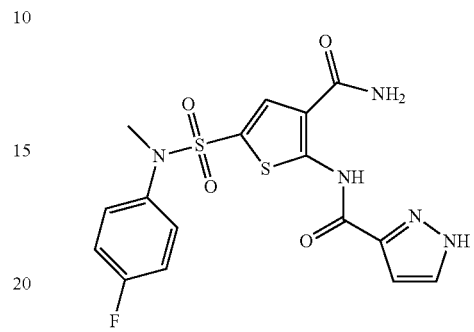

A mixture of 4-carbamoyl-5-[1H-Pyrazole-3-carbonyl)amino]-thiophene-2-sulfonylchloride (100 mg, 0.299 mmol), TEA (54 µL, 0.389 mmol) and (4-fluoro-phenyl)-methylamine (41 mg, 0.329 mmol) in dry DCM (6 mL) is heated at 50° C. overnight. Next, the mixture is evaporated and the obtained residue is purified by preparative chromatography to afford the desired product.

Compound 331: 2-[[(2S)-2-hydroxypropanoyl]amino]-5-[4-(trifluoromethoxy)phenyl]sulfonyl-thiophene-3-carboxamide Compound 331 can prepared as described below or, alternatively, in accordance with the synthesis identified for Compound 331 in Table II.

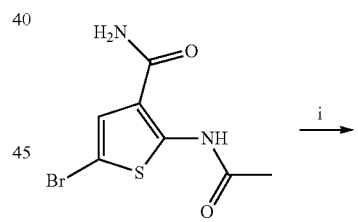

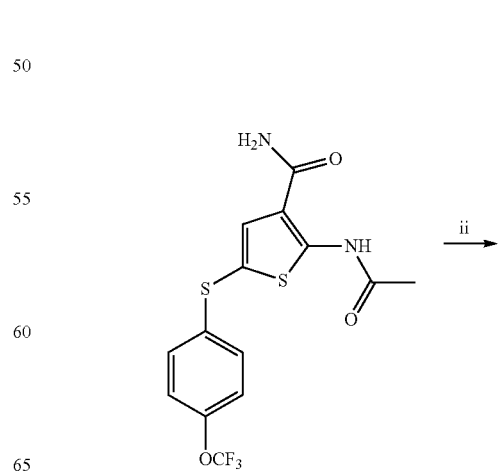

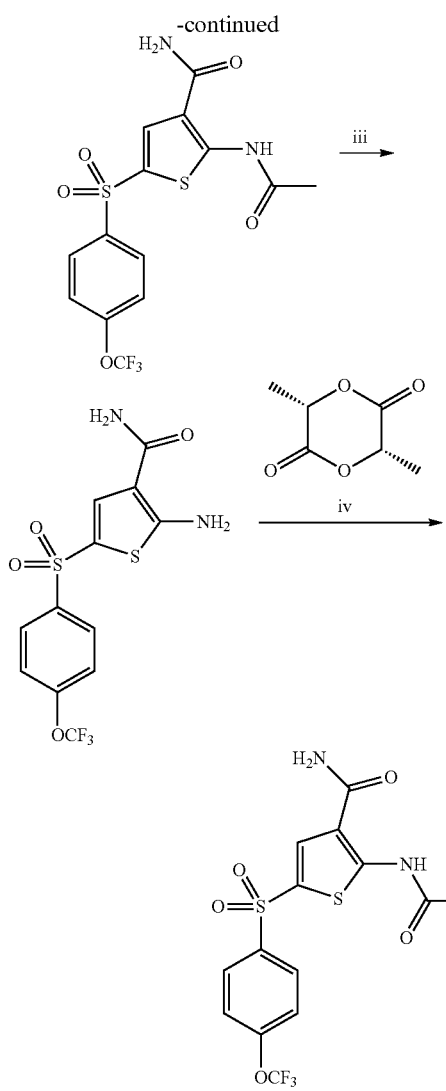

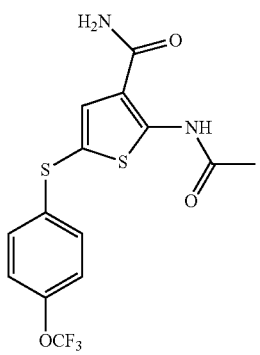 [SMILES: CC(=O)Nc1sc(Sc2ccc(OC(F)(F)F)cc2)cc1C(N)=O]

Step (i): 2-Acetylamino-5-(4-trifluoromethoxy-phenylsulfanyl)-thiophene-3-carboxylic acid amide A suspension of intermediate 3 (10.5 g, 40 mmol) in toluene (400 mL) is degassed under N₂ atmosphere. Pd(OAc)₂ (440 mg, 2 mmol), DiPPF (1.0 g, 2.4 mmol) and 4-trifluoromethoxy-benzenethiol (9.32 g, 48 mmol) are added followed by DBU (6 mL, 40 mmol) and the reaction mixture is heated at 105° C. for 3 h. The resulting mixture is concentrated in vacuo until a thick slurry is obtained, which is filtered over a plug of silica (EtOAc). The filtrate is concentrated and purification by silica chromatography (EtOAc/petroleum ether; 25:75 to 50:50) to afford the desired compound.

Step (ii): 2-Acetylamino-5-(4-trifluoromethoxy-benzenesulfonyl)-thiophene-3-carboxylic acid amide

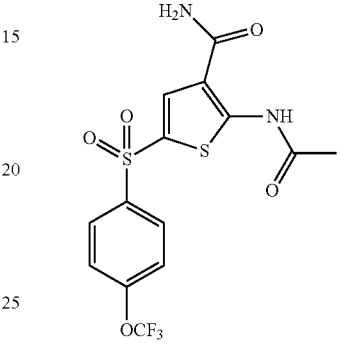

To a solution of the thioether (10 g, 26.6 mmol) in DCM (300 mL) is added mCPBA (13.8 g, 55.8 mmol) portionwised and the mixture is stirred at room temperature for 3 h. The resulting mixture is added to water, extracted with DCM and the combined organic washed with aqueous saturated NaHCO₃, dried over Na₂SO₄, filtered and concentrated in vacuo to give the desired compound that is used as such.

Step 2-Amino-5-(4-trifluoromethoxy-benzenesulfonyl)-thiophene-3-carboxylic acid amide

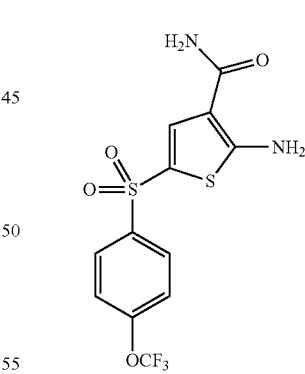

The 2-acetylamino-5-(4-trifluoromethoxy-benzenesulfonyl)-thiophene-3-carboxylic acid amide (10 g, crude) is dissolved in 1,4-dioxane (300 mL) and an aqueous solution of 2 M HCl (100 mL). This mixture is stirred at 105° C. overnight, after which the dioxane is concentrated in vacuo and the remaining aqueous basified with an aqueous solution of 5 M NaOH to pH-8-9. The resulting precipitate is collected by filtration, washed thoroughly with water and dried to afford the desired compound.

Step (iv): 2-((S)-2-Hydroxy-propionylamino)-5-(4-trifluoromethoxy-benzenesulfonyl)-thiophene-3-carboxylic acid amide

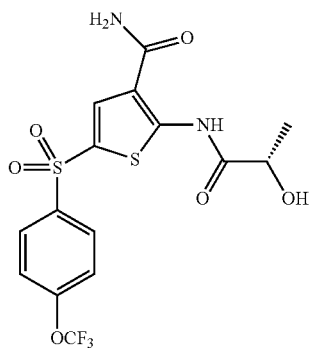 [SMILES: C[C@H](O)C(=O)Nc1sc(S(=O)(=O)c2ccc(OC(F)(F)F)cc2)cc1C(N)=O]

A mixture of 2-amino-5-(4-trifluoromethoxy-benzenesulfonyl)-thiophene-3-carboxylic acid amide (6 g, 16.38 mmol), L-(−)-lactide (2.6 g, 18.02 mmol) and $K_2CO_3$ (2.49 g, 18.02 mmol) in MeOH (165 mL) is heated at 60° C. for 1 h. The resulting mixture is concentrated, taken up in EtOAc/water and acidified with aqueous 2 M HCl until pH~4. The organic layer is separated and the aqueous further extracted with EtOAc (3×). The combined organic is dried over $Na_2SO_4$, filtered and concentrated in vacuo. Purification by silica chromatography (EtOAc/petroleum ether; 1:1) followed by precipitation in DCM afford the desired compound.

Compound 344: 2-[(2-hydroxy-2-methyl-propanoyl)amino]-5-[4-(trifluoromethyl)phenyl]sulfonyl-thiophene-3-carboxamide

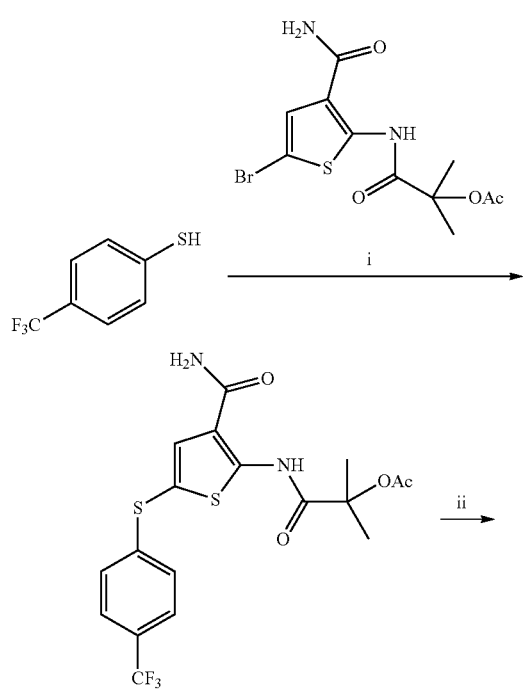

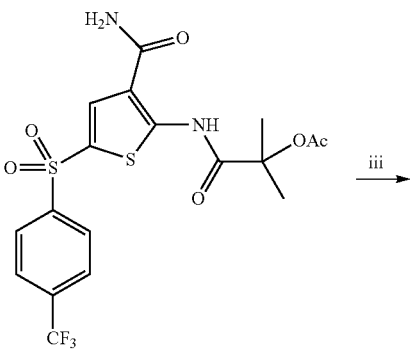

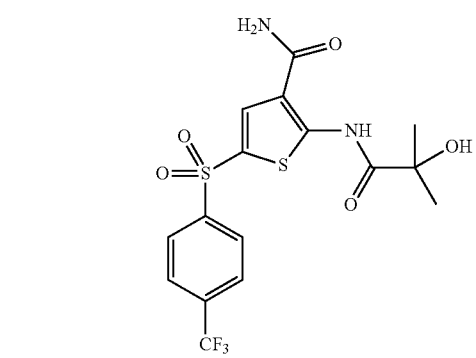

Step (i): Acetic acid 1-[3-carbamoyl-5-(4-trifluoromethyl-phenylsulfanyl)-thiophen-2-ylcarbamoyl]-1-methyl-ethyl ester

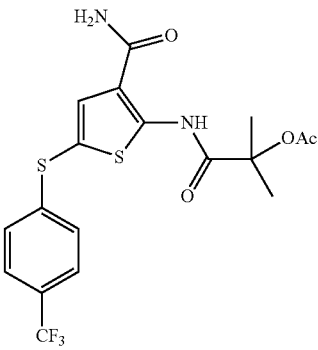 [SMILES: CC(=O)OC(C)(C)C(=O)Nc1sc(Sc2ccc(C(F)(F)F)cc2)cc1C(N)=O]

A mixture of compound the thiol (1.5 g, 7.4 mmol) and Intermediate 11 (2 g, 5.7 mmol) is mixed with $Pd(OAc)_2$ (64 mg, 0.28 mmol), DiPPF (142 mg, 0.34 mmol) and NaOtBu (657 mg, 6.84 mmol) in dioxane (8 mL) is heated at 130° C. in a closed vial after flushing with argon over the night. Reaction mixture is filtrated over plug of silica (EtOAc) and evaporated in vacuo to afford the crude product. The crude is purified by dissolving it in EtOAc and precipitating it out using cyclohexylhexane.

Step (ii): Acetic acid 1-[3-carbamoyl-5-(4-trifluoromethyl-benzenesulfonyl)-thiophen-2-ylcarbamoyl]-1-methyl-ethyl ester

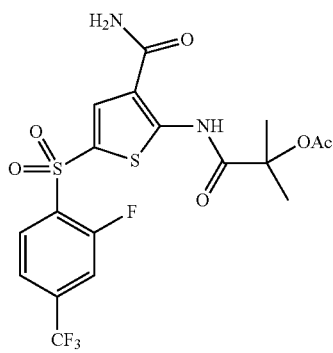 [SMILES: CC(=O)OC(C)(C)C(=O)Nc1sc(S(=O)(=O)c2ccc(C(F)(F)F)cc2F)cc1C(N)=O]

A mixture of the thioether (8.7 g, 19.5 mmol) and mCPBA (7.4 g, 43 mmol) in dry DCM (500 mL) is heated overnight at 40° C. The resulting mixture is diluted with DCM and washed with aqueous saturated NaHCO$_3$. The aqueous is extracted with DCM (2×), the combined organic is washed with brine, dried over Na$_2$SO$_4$, filtered and concentrated in vacuo to give the desired compound that is used as such.

Step (2-Hydroxy-2-methyl-propionylamino)-5-(4-trifluoromethyl-benzenesulfonyl)-thiophene-3-carboxylic acid amide

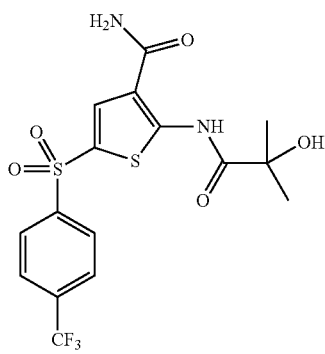 [SMILES: CC(C)(O)C(=O)Nc1sc(S(=O)(=O)c2ccc(C(F)(F)F)cc2)cc1C(N)=O]

The ester (9.3 g, 19.4 mmol) is dissolved in 1,4-dioxane (350 mL) and an aqueous solution of 6 M HCl (250 mL). This mixture is stirred at 60° C. overnight, after which the mixture is neutralized by adding a 40% NaOH solution. The product is extracted with EtOAc, dried and evaporated to give the crude. Purification by silica chromatography (DCM:MeOH:NH$_4$OH 90:5:5) affords the desired compound.

Compound 376: 5-(2-fluoro-4-trifluoromethyl-benzenesulfonyl)-2-(2-hydroxy-2-methyl-propionylamino)-thiophene-3-carboxylic acid amide

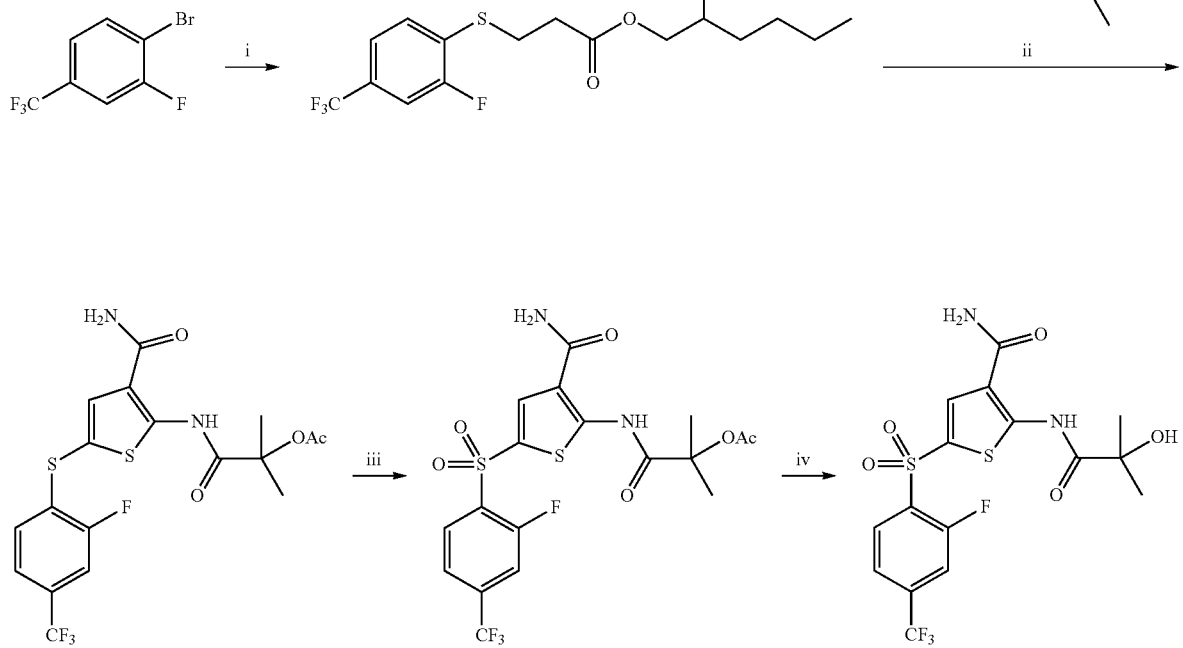

Step (i): 3-(2-Fluoro-4-trifluoromethyl-phenylsulfanyl)-propionic acid 2-ethyl-hexyl ester

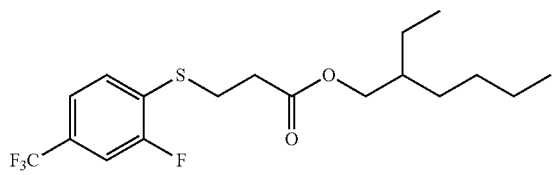 [SMILES: CCCCC(CC)COC(=O)CCSc1ccc(C(F)(F)F)cc1F]

A solution of 1-bromo-2-fluoro-4-trifluoromethyl-benzene (5.0 g, 20.6 mmol) and DIEA (7.2 mL, 41.1 mmol) in toluene (100 mL) is degased under N₂ atmosphere. To this mixture, Pd₂ dba₃ (753 mg, 0.82 mmol), Xantphos (952 mg, 1.65 mmol) and 3-mercapto-propionic acid 2-ethyl-hexyl ester (5.9 mL, 25.7 mmol) are added and the reaction is heated at reflux overnight. The resulting mixture is filtered over a plug of silica (EtOAc) and the organic is concentrated in vacuo. Purification by silica chromatography (EtOAc/petroleum ether; 3:97) affords the desired product.

Step (ii): Acetic acid 1-[3-carbamoyl-5-(2-fluoro-4-trifluoromethyl-phenylsulfanyl)-thiophen-2-ylcarbamoyl]-1-methyl-ethyl ester

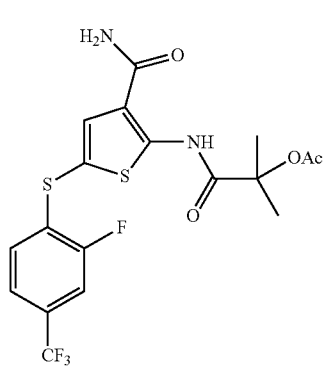 [SMILES: CC(=O)OC(C)(C)C(=O)Nc1sc(Sc2ccc(C(F)(F)F)cc2F)cc1C(N)=O]

A solution of the intermediate 12 (6.4 g, 20.8 mmol), 3-(2-fluoro-4-trifluoromethyl-phenylsulfanyl)-propionic acid 2-ethyl-hexyl ester (8.0 g, 20.8 mmol) and DBU (6.4 mL, 41.6 mmol) in dioxane (40 mL) is divided in 4 closed vials and heated at 120° C. overnight. The resulting mixture is added to water, acidified and extracted with EtOAc. The combined organic is dried over Na₂SO₄, filtered and concentrated in vacuo. Precipitation (EtOAc/cyclohexane) affords the desired compound.

Step (iii): Acetic acid 1-[3-carbamoyl-5-(2-fluoro-4-trifluoromethyl-benzenesulfonyl)-thiophen-2-ylcarbamoyl]-1-methyl-ethyl ester

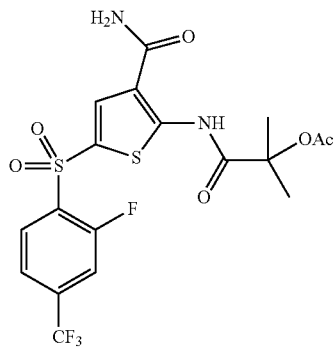 [SMILES: CC(=O)OC(C)(C)C(=O)Nc1sc(S(=O)(=O)c2ccc(C(F)(F)F)cc2F)cc1C(N)=O]

A mixture of the thioether (6.6 g, 14.2 mmol) and mCPBA (10.3 g, 41.8 mmol) in dry DCM (150 mL) is heated overnight at 40° C. The resulting mixture is diluted with DCM and washed with aqueous saturated NaHCO₃. The aqueous is extracted with DCM (2×), the combined organic is washed with brine, dried over Na₂SO₄, filtered and concentrated in vacuo to give the desired compound that is used as such.

Step (iv): 5-(2-Fluoro-4-trifluoromethyl-benzenesulfonyl)-2-(2-hydroxy-2-methyl-propionylamino)-thiophene-3-carboxylic acid amide

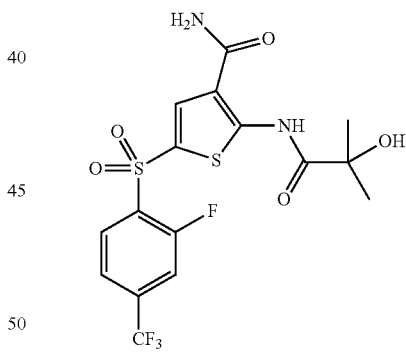

The acetic acid 1-[3-carbamoyl-5-(2-fluoro-4-trifluoromethyl-benzenesulfonyl)-thiophen-2-ylcarbamoyl]-1-methyl-ethyl ester (1.24 g, 2.5 mmol) is dissolved in 1,4-dioxane (35 mL) and an aqueous solution of 6 M HCl (25 mL). This mixture is stirred at 60° C. overnight, after which the mixture is evaporated. Purification by silica chromatography (EtOAc/hexane; 1:1) affords the desired compound.

Compound 375: 5-(2-Fluoro-4-trifluoromethoxy-benzenesulfonyl)-2-(2-hydroxy-2-methyl-propionylamino)-thiophene-3-carboxylic acid amide Compound 375 can be prepared using the same method as disclosed above for Compound 376 starting instead from 4-bromo-3-fluoro-trifluoromethoxybenzene.

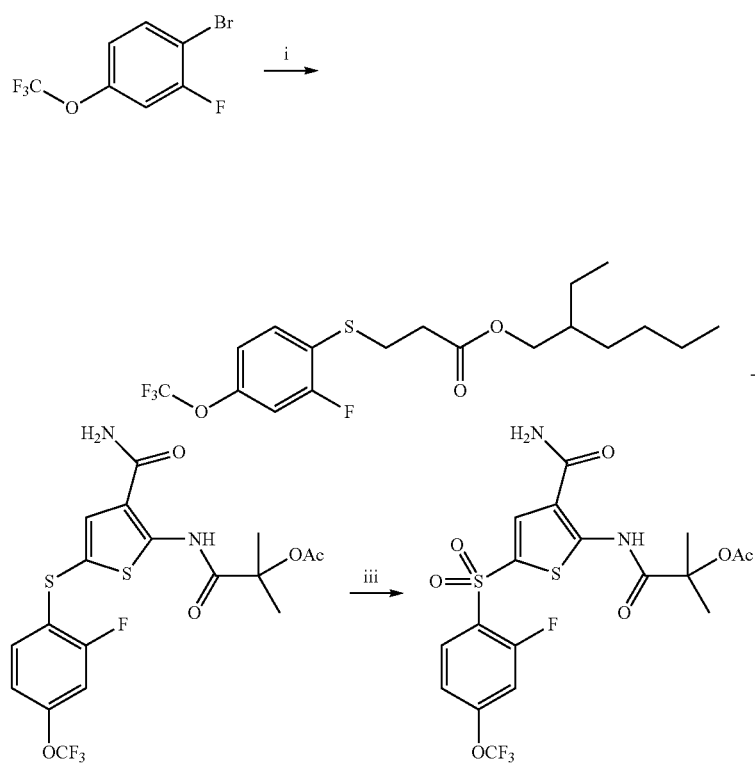
Step (i): 3-(2-Fluoro-4-trifluoromethoxy-phenylsulfanyl)-propionic acid 2-ethyl-hexyl ester
Step (iii) Acetic acid 1-[3-carbamoyl-5-(2-fluoro-4-trifluoromethoxy-benzenesulfonyl)-thiophen-2-yl-carbamoyl]-1-methyl-ethyl ester
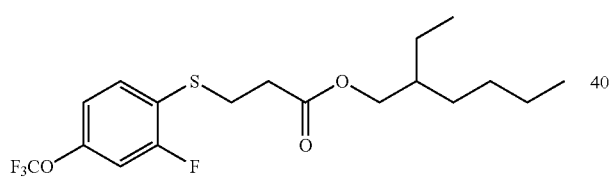
Step (ii): Acetic acid 1-[3-carbamoyl-5-(2-fluoro-4-trifluoromethoxy-phenylsulfanyl)-thiophen-2-ylcarbamoyl]-1-methyl-ethyl ester
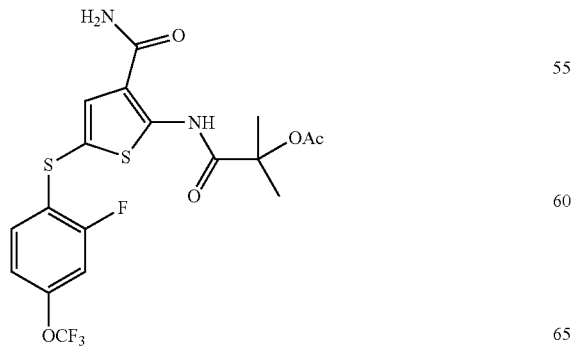
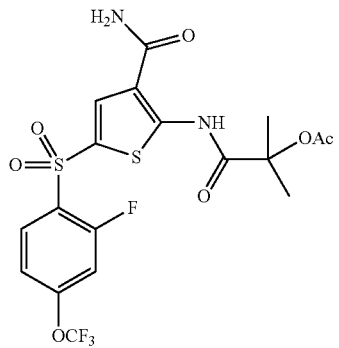 [SMILES: CC(=O)OC(C)(C)C(=O)Nc1sc(S(=O)(=O)c2ccc(OC(F)(F)F)cc2F)cc1C(N)=O]

Step (iv): 5-(2-Fluoro-4-trifluoromethoxy-benzene-sulfonyl)-2-(2-hydroxy-2-methyl-propionylamino)-thiophene-3-carboxylic acid amide

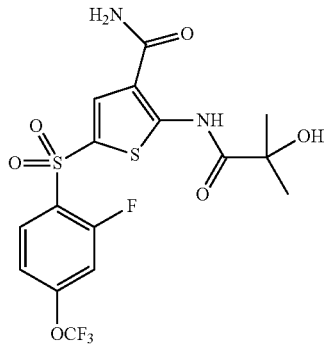 [SMILES: CC(C)(O)C(=O)Nc1sc(S(=O)(=O)c2ccc(OC(F)(F)F)cc2F)cc1C(N)=O]

The compounds of the invention and the comparative examples that have been prepared according to the synthetic methods described herein are listed in Table II below. The NMR spectral data of the compounds of the invention and some of the comparative examples is given in Table III. The "Mtd" entries in Table II refer to the synthetic methods previously described in Example 3 that can be used to prepare the compound to which the entry corresponds. For example, Compound I can be prepared as follows:

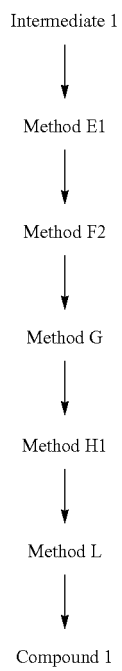

TABLE II

| Cpd # | Structure | Name | Mtd | Int | MW | Mes |
|---|---|---|---|---|---|---|
| 1 | 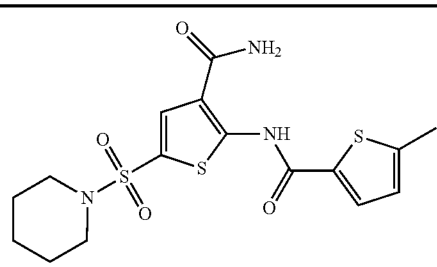 | N-(3-carbamoyl-5-(piperidin-1-ylsulfonyl)thiophen-2-yl)-5-methylthiophene-2-carboxamide | E1, F2, G, H1, L | 1 | 414 | 414 |
| 2 | 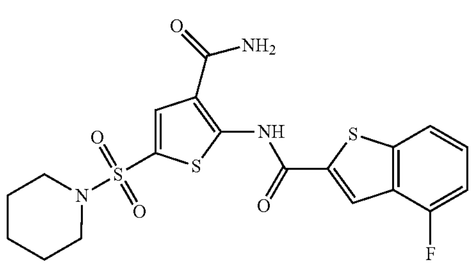 [SMILES: NC(=O)c1cc(S(=O)(=O)N2CCCCC2)sc1NC(=O)c1cc2c(F)cccc2s1] | N-(3-carbamoyl-5-(piperidin-1-ylsulfonyl)thiophen-2-yl)-4-fluorobenzo[b]thiophene-2-carboxamide | E1, F2, G, H1, L | 1 | 468 | 468 |
| 3 | 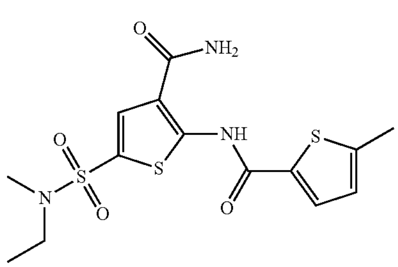 | N-(3-carbamoyl-5-(N-ethyl-N-methylsulfamoyl)thiophen-2-yl)-5-methylthiophene-2-carboxamide | E1, F2, G, H1 | 1 | 388 | 388 |

TABLE II-continued

List of final compounds

| Cpd # | Structure | Name | Mtd | Int | MW | Mes |
|---|---|---|---|---|---|---|
| 4 | 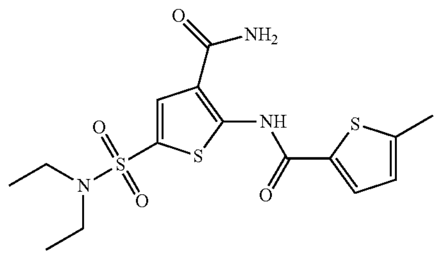 [SMILES: CCN(CC)S(=O)(=O)c1cc(C(N)=O)c(NC(=O)c2ccc(C)s2)s1] | N-(3-carbamoyl-5-(N,N-diethylsulfamoyl)thiophen-2-yl)-5-methylthiophene-2-carboxamide | E1, F2, G, H3 | 1 | 402 | 402 |
| 5 | 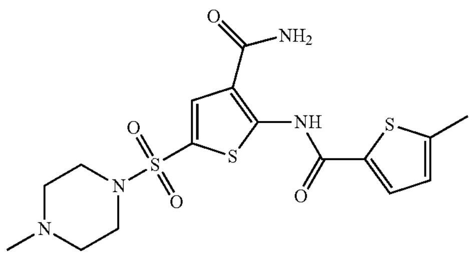 | N-(3-carbamoyl-5-(4-methylpiperazin-1-ylsulfonyl)thiophen-2-yl)-5-methylthiophene-2-carboxamide | E1, F2, G, H3, L | 1 | 429 | 429 |
| 6 | 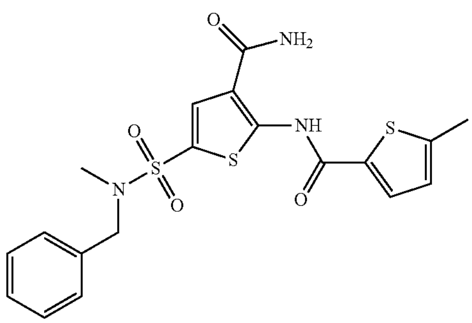 [SMILES: Cc1ccc(C(=O)Nc2sc(S(=O)(=O)N(C)Cc3ccccc3)cc2C(N)=O)s1] | N-(5-(N-benzyl-N-methylsulfamoyl)-3-carbamoylthiophen-2-yl)-5-methylthiophene-2-carboxamide | E1, F2, G, H3, L | 1 | 450 | 450 |
| 7 | 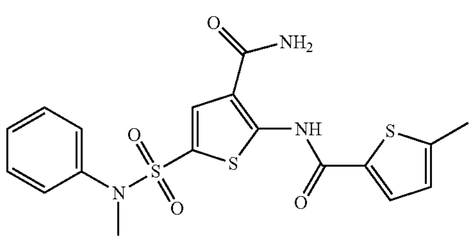 [SMILES: Cc1ccc(C(=O)Nc2sc(S(=O)(=O)N(C)c3ccccc3)cc2C(N)=O)s1] | N-(3-carbamoyl-5-(N-methyl-N-phenylsulfamoyl)thiophen-2-yl)-5-methylthiophen-2-carboxamide | E1, F2, G, H3, L | 1 | 436 | 436 |
| 8 | 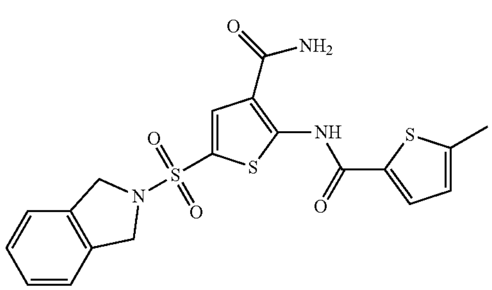 [SMILES: Cc1ccc(C(=O)Nc2sc(S(=O)(=O)N3Cc4ccccc4C3)cc2C(N)=O)s1] | N-(3-carbamoyl-5-(isoindolin-2-ylsulfonyl)thiophen-2-yl)-5-methylthiphen-2-carboxamide | E1, F2, G, H3, L | 1 | 448 | 448 |

TABLE II-continued

List of final compounds

| Cpd # | Structure | Name | Mtd | Int | MW | Mes |
|---|---|---|---|---|---|---|
| 9 | 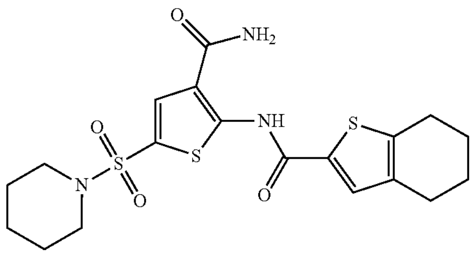 [SMILES: NC(=O)c1cc(S(=O)(=O)N2CCCCC2)sc1NC(=O)c1cc2c(s1)CCCC2] | N-(3-carbamoyl-5-(piperidin-1-ylsulfonyl)thiophen-2-yl)-4,5,6,7-tetrahydrobenzo[b]thiophene-2-carboxamide | E1, F2, G, H1 | 1 | 454 | 454 |
| 10 | 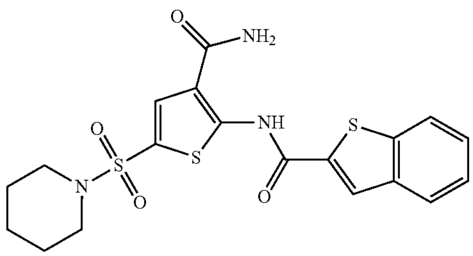 [SMILES: NC(=O)c1cc(S(=O)(=O)N2CCCCC2)sc1NC(=O)c1cc2ccccc2s1] | N-(3-carbamoyl-5-(piperidin-1-ylsulfonyl)thiophen-2-yl)benzo[b]thiophene-2-carboxamide | E1, F2, G, H1 | 1 | 450 | 450 |
| 11 | 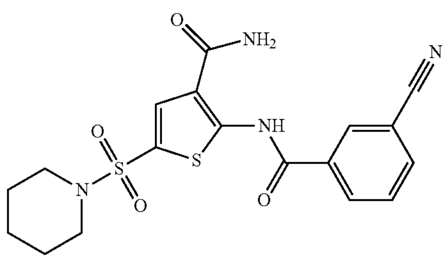 [SMILES: N#Cc1cccc(C(=O)Nc2sc(S(=O)(=O)N3CCCCC3)cc2C(N)=O)c1] | 2-(3-cyanobenzamido)-5-(piperidin-1-ylsulfonyl)thiophene-3-carboxamide | E1, F2, G, H1 | 1 | 418 | 419 |
| 12 | 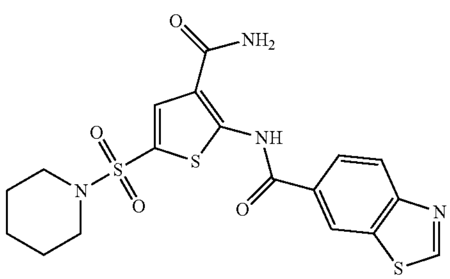 [SMILES: NC(=O)c1cc(S(=O)(=O)N2CCCCC2)sc1NC(=O)c1ccc2ncsc2c1] | N-(3-carbamoyl-5-(piperidin-1-ylsulfonyl)thiophen-2-yl)benzo[d]thiazole-6-carboxamide | E1, F2, G, H1, L | 1 | 451 | 451 |
| 13 | 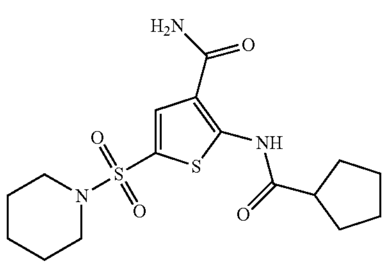 [SMILES: NC(=O)c1cc(S(=O)(=O)N2CCCCC2)sc1NC(=O)C1CCCC1] | 2-(cyclopentanecarboxamido)-5-(piperidin-1-ylsulfonyl)thiophene-3-carboxamide | E1, F2, G, H1 | 4 | 386 | 386 |
| 14 | 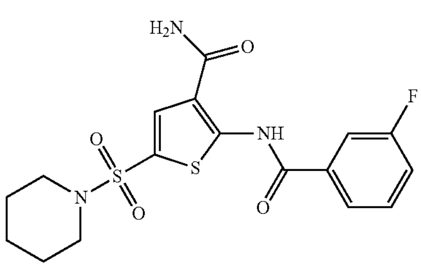 [SMILES: NC(=O)c1cc(S(=O)(=O)N2CCCCC2)sc1NC(=O)c1cccc(F)c1] | 2-(3-fluorobenzamido)-5-(piperidin-1-ylsulfonyl)thiophene-3-carboxamide | E1, F2, G, H1 | 4 | 411 | 412 |

TABLE II-continued

List of final compounds

| Cpd # | Structure | Name | Mtd | Int | MW | Mes |
|---|---|---|---|---|---|---|
| 15 | 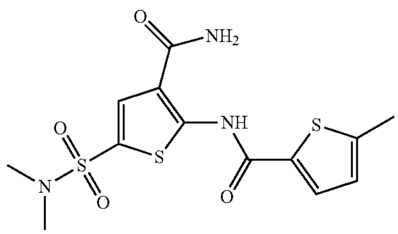 | N-(3-carbamoyl-5-(N,N-dimethylsulfamoyl)thiophen-2-yl)-5-methylthiophene-2-carboxamide | E1, F2, G, H3 | 1 | 373 | 374 |
| 16 | 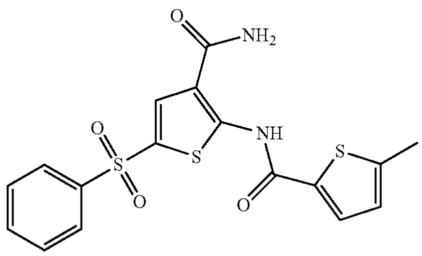 [SMILES: Cc1ccc(C(=O)Nc2sc(S(=O)(=O)c3ccccc3)cc2C(N)=O)s1] | N-(3-carbamoyl-5-(phenylsulfonyl)thiophen-2-yl)-5-methylthiophene-2-carboxamide | A, C, D2 | 2 | 407 | 407 |
| 17 | 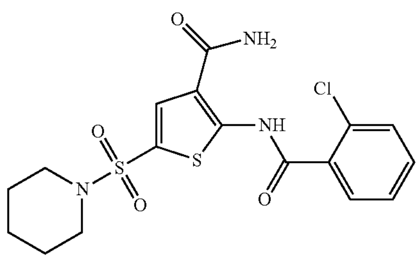 | 2-(2-chlorobenzamido)-5-(piperidin-1-ylsulfonyl)thiophene-3-carboxamide | E1, F2, G, H1 | 1 | 428 | 428 |
| 18 | 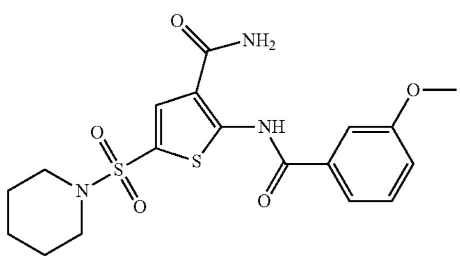 [SMILES: COc1cccc(C(=O)Nc2sc(S(=O)(=O)N3CCCCC3)cc2C(N)=O)c1] | 2-(3-methoxybenzamido)-5-(piperidin-1-ylsulfonyl)thiophene-3-carboxamide | E1, F2, G, H1, L | 1 | 424 | 424 |
| 19 | 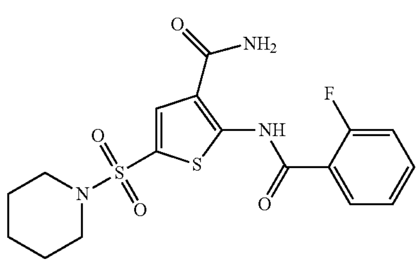 [SMILES: NC(=O)c1cc(S(=O)(=O)N2CCCCC2)sc1NC(=O)c1ccccc1F] | 2-(2-fluorobenzamido)-5-(piperidin-1-ylsulfonyl)thiophene-3-carboxamide | E1, F2, G, H1, L | 1 | 411 | 412 |
| 20 | 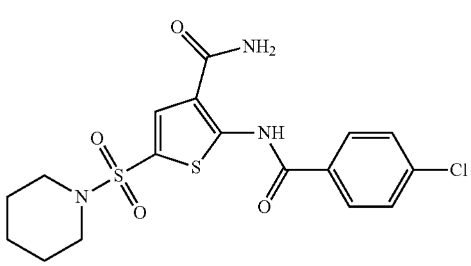 [SMILES: NC(=O)c1cc(S(=O)(=O)N2CCCCC2)sc1NC(=O)c1ccc(Cl)cc1] | 2-(4-chlorobenzamido)-5-(piperidin-1-ylsulfonyl)thiophene-3-carboxamide | E1, F2, G, H1, L | 1 | 428 | 428 |

TABLE II-continued

List of final compounds

| Cpd # | Structure | Name | Mtd | Int | MW | Mes |
|---|---|---|---|---|---|---|
| 21 | 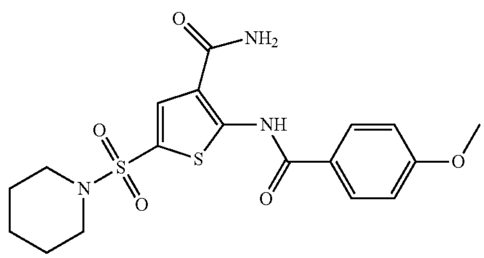 [SMILES: COc1ccc(C(=O)Nc2sc(S(=O)(=O)N3CCCCC3)cc2C(N)=O)cc1] | 2-(4-methoxybenzamido)-5-(piperidin-1-ylsulfonyl)thiophene-3-carboxamide | E1, F2, G, H1, L | 1 | 424 | 424 |
| 22 | 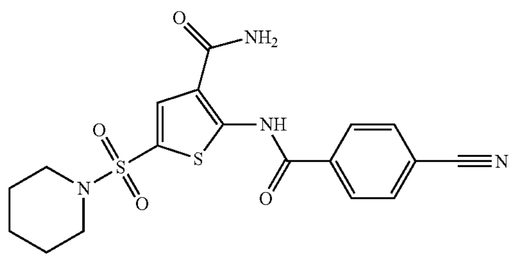 [SMILES: N#Cc1ccc(C(=O)Nc2sc(S(=O)(=O)N3CCCCC3)cc2C(N)=O)cc1] | 2-(4-cyanobenzamido)-5-(piperidin-1-ylsulfonyl)thiophene-3-carboxamide | E1, F2, G, H1, L | 1 | 418 | 419 |
| 23 | 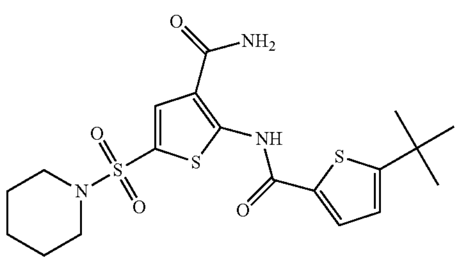 [SMILES: CC(C)(C)c1ccc(C(=O)Nc2sc(S(=O)(=O)N3CCCCC3)cc2C(N)=O)s1] | 5-tert-butyl-N-(3-carbamoyl-5-(piperidin-1-ylsulfonyl)thiophen-2-yl)thiophene-2-carboxamide | E1, F2, G, H1, L | 1 | 456 | 456 |
| 24 | 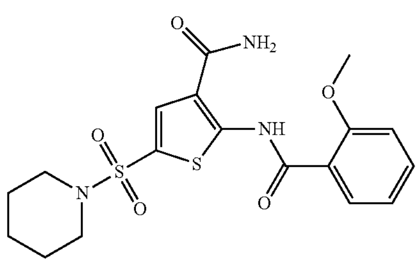 [SMILES: COc1ccccc1C(=O)Nc1sc(S(=O)(=O)N2CCCCC2)cc1C(N)=O] | 2-(2-methoxybenzamido)-5-(piperidin-1-ylsulfonyl)thiophene-3-carboxamide | E1, F2, G, H1 | 1 | 424 | 424 |
| 25 | 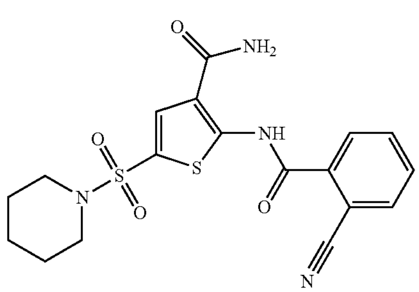 [SMILES: N#Cc1ccccc1C(=O)Nc1sc(S(=O)(=O)N2CCCCC2)cc1C(N)=O] | 2-(2-cyanobenzamido)-5-(piperidin-1-ylsulfonyl)thiophene-3-carboxamide | E1, F2, G, H1 | 1 | 418 | 419 |

TABLE II-continued

List of final compounds

| Cpd # | Structure | Name | Mtd | Int | MW | Mes |
|---|---|---|---|---|---|---|
| 26 | 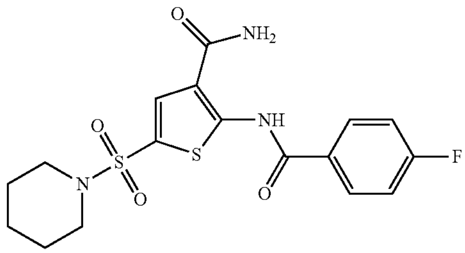 [SMILES: NC(=O)c1cc(S(=O)(=O)N2CCCCC2)sc1NC(=O)c1ccc(F)cc1] | 2-(4-fluorobenzamido)-5-(piperidin-1-ylsulfonyl)thiophene-3-carboxamide | E1, F2, G, H1 | 1 | 411 | 412 |
| 27 | 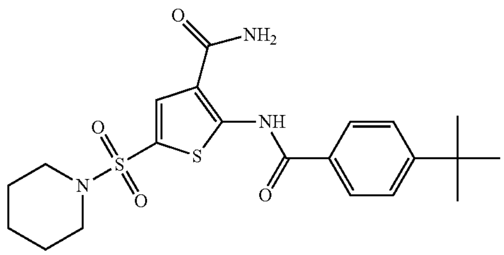 [SMILES: CC(C)(C)c1ccc(C(=O)Nc2sc(S(=O)(=O)N3CCCCC3)cc2C(N)=O)cc1] | 2-(4-tert-butylbenzamido)-5-(piperidin-1-ylsulfonyl)thiophene-3-carboxamide | E1, F2, G, H1, L | 1 | 450 | 450 |
| 28 | 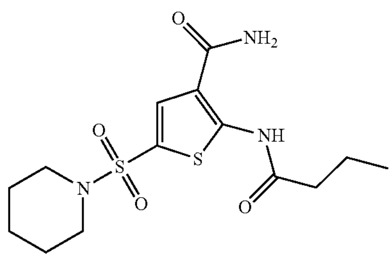 [SMILES: CCCC(=O)Nc1sc(S(=O)(=O)N2CCCCC2)cc1C(N)=O] | 2-butyramido-5-(piperidin-1-ylsulfonyl)thiophene-3-carboxamide | E1, F2, G, H1 | 4 | 359 | 360 |
| 29 | 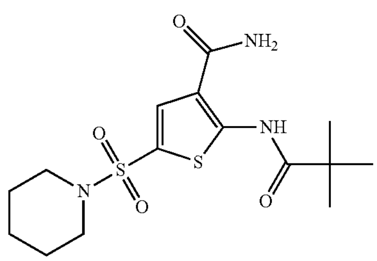 [SMILES: CC(C)(C)C(=O)Nc1sc(S(=O)(=O)N2CCCCC2)cc1C(N)=O] | 5-(piperidin-1-ylsulfonyl)-2-pivalamidothiophene-3-carboxamide | E1, F2, G, H1 | 4 | 373 | 374 |
| 30 | 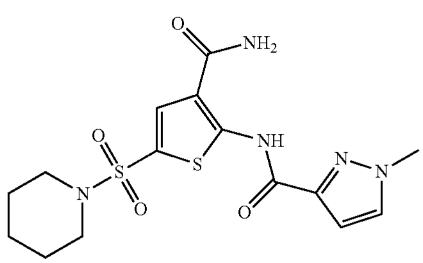 [SMILES: Cn1ccc(C(=O)Nc2sc(S(=O)(=O)N3CCCCC3)cc2C(N)=O)n1] | N-(3-carbamoyl-5-(piperidin-1-ylsulfonyl)thiophen-2-yl)-1-methyl-1H-pyrazole-3-carboxamide | E1, F2, G, H1 | 4 | 397 | 398 |
| 31 | 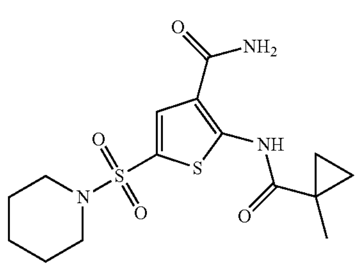 [SMILES: CC1(C(=O)Nc2sc(S(=O)(=O)N3CCCCC3)cc2C(N)=O)CC1] | 2-(1-methylcyclopropanecarboxamido)-5-(piperidin-1-ylsulfonyl)thiophene-3-carboxamide | E1, F2, G, H1 | 4 | 371 | 372 |

TABLE II-continued

List of final compounds

| Cpd # | Structure | Name | Mtd | Int | MW | Mes |
|---|---|---|---|---|---|---|
| 32 | 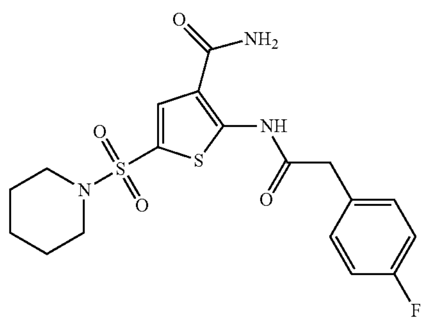 [SMILES: NC(=O)c1cc(S(=O)(=O)N2CCCCC2)sc1NC(=O)Cc1ccc(F)cc1] | 2-(2-(4-fluorophenyl)acetamido)-5-(piperidin-1-ylsulfonyl)thiophene-3-carboxamide | E1, F2, G, H1 | 4 | 426 | 426 |
| 33 | 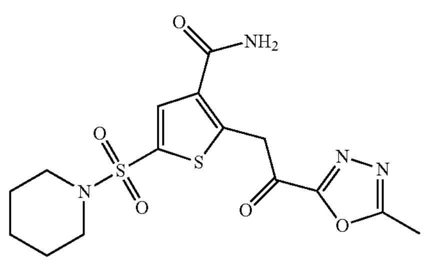 [SMILES: Cc1nnc(C(=O)Cc2sc(S(=O)(=O)N3CCCCC3)cc2C(N)=O)o1] | N-(3-carbamoyl-5-(piperidin-1-ylsulfonyl)thiophen-2-yl)-5-methyl-1,3,4-oxadiazole-2-carboxamide | E1, F2, G, H1 | 4 | 399 | 400 |
| 34 | 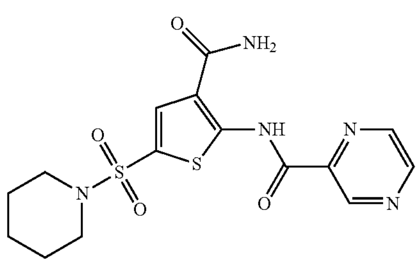 [SMILES: NC(=O)c1cc(S(=O)(=O)N2CCCCC2)sc1NC(=O)c1cnccn1] | N-(3-carbamoyl-5-(piperidin-1-ylsulfonyl)thiophen-2-yl)pyrazine-2-carboxamide | E1, F2, G, H1 | 4 | 395 | 396 |
| 35 | 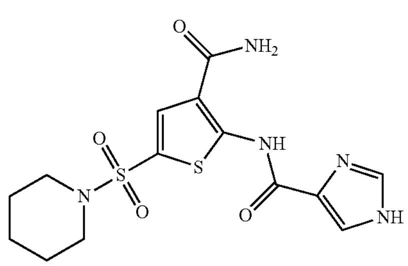 [SMILES: NC(=O)c1cc(S(=O)(=O)N2CCCCC2)sc1NC(=O)c1c[nH]cn1] | N-(3-carbamoyl-5-(piperidin-1-ylsulfonyl)thiophen-2-yl)-1H-imidazole-4-carboxamide | E1, F2, G, H1 | 4 | 383 | 168 |
| 36 | 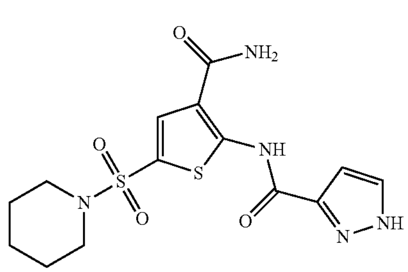 [SMILES: NC(=O)c1cc(S(=O)(=O)N2CCCCC2)sc1NC(=O)c1cc[nH]n1] | N-(3-carbamoyl-5-(piperidin-1-ylsulfonyl)thiophen-2-yl)-1H-pyrazole-3-carboxamide | E1, F2, G, H1 | 4 | 383 | 384 |

TABLE II-continued

List of final compounds

| Cpd # | Structure | Name | Mtd | Int | MW | Mes |
|---|---|---|---|---|---|---|
| 37 | 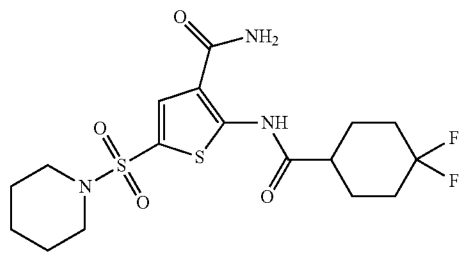 [SMILES: NC(=O)c1cc(S(=O)(=O)N2CCCCC2)sc1NC(=O)C1CCC(F)(F)CC1] | 2-(4,4-difluorocyclohexanecarboxamide)-5-(piperidin-1-ylsulfonyl)thiophene-3-carboxamide | E1, F2, G, H1 | 4 | 436 | 436 |
| 38 | 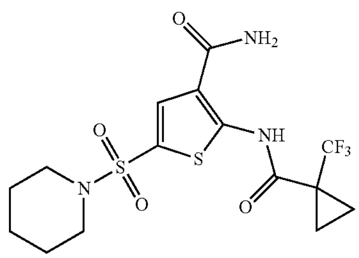 [SMILES: NC(=O)c1cc(S(=O)(=O)N2CCCCC2)sc1NC(=O)C1(C(F)(F)F)CC1] | 5-(piperidin-1-ylsulfonyl)-2-(1-(trifluoromethyl)cyclopropanecarboxamido)thiophene-3-carboxamide | E1, F2, G, H1 | 4 | 425 | 426 |
| 39 | 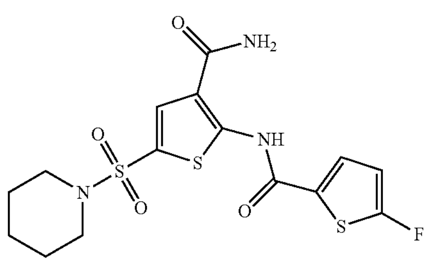 [SMILES: NC(=O)c1cc(S(=O)(=O)N2CCCCC2)sc1NC(=O)c1ccc(F)s1] | N-(3-carbamoyl-5-(piperidin-1-ylsulfonyl)thiophen-2-yl)-5-fluorothiophene-2-carboxamide | E1, F2, G, H1 | 4 | 418 | 418 |
| 40 | 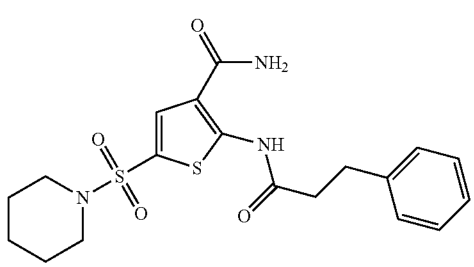 [SMILES: NC(=O)c1cc(S(=O)(=O)N2CCCCC2)sc1NC(=O)CCc1ccccc1] | 2-(3-phenylpropanamido)-5-(piperidin-1-ylsulfonyl)thiophene-3-carboxamide | E1, F2, G, H1 | 4 | 422 | 422 |
| 41 | 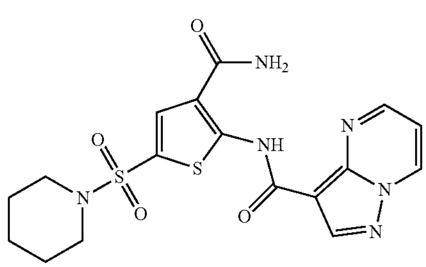 [SMILES: NC(=O)c1cc(S(=O)(=O)N2CCCCC2)sc1NC(=O)c1cnn2cccnc12] | N-(3-carbamoyl-5-(piperidin-1-ylsulfonyl)thiophen-2-yl)pyrazolo[1,5-a]pyrimidine-3-carboxamide | E1, F2, G, H1 | 4 | 435 | 435 |
| 42 | 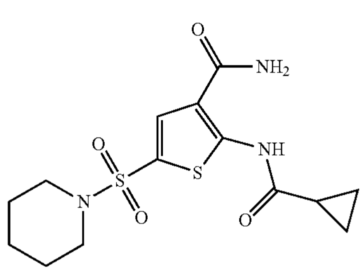 [SMILES: NC(=O)c1cc(S(=O)(=O)N2CCCCC2)sc1NC(=O)C1CC1] | 2-(cyclopropanecarboxamido)-5-(piperidin-1-ylsulfonyl)thiophene-3-carboxamide | E1, F2, G, H1 | 4 | 357 | 358 |

TABLE II-continued

List of final compounds

| Cpd # | Structure | Name | Mtd | Int | MW | Mes |
|---|---|---|---|---|---|---|
| 43 | 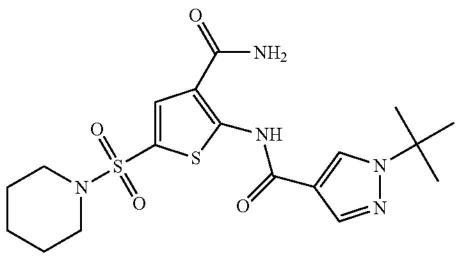 [SMILES: CC(C)(C)n1cc(C(=O)Nc2sc(S(=O)(=O)N3CCCCC3)cc2C(N)=O)cn1] | 1-tert-butyl-N-(3-carbamoyl-5-(piperidin-1-ylsulfonyl)thiophen-2-yl)-1H-pyrazole-4-carboxamide | E1, F2, G, H1 | 4 | 440 | 440 |
| 44 | 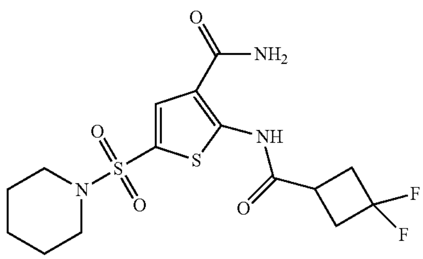 [SMILES: NC(=O)c1cc(S(=O)(=O)N2CCCCC2)sc1NC(=O)C1CC(F)(F)C1] | 2-(3,3-difluorocyclobutanecarboxamido)-5-(piperidin-1-ylsulfonyl)thiophene-3-carboxamide | E1, F2, G, H1 | 4 | 407 | 408 |
| 45 | 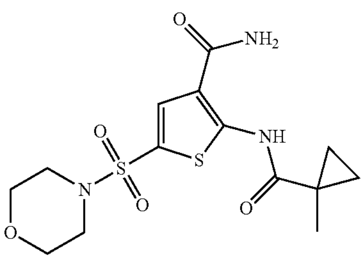 [SMILES: CC1(C(=O)Nc2sc(S(=O)(=O)N3CCOCC3)cc2C(N)=O)CC1] | 2-(1-methylcyclopropanecarboxamido)-5-(morpholinosulfonyl)thiophene-3-carboxamide | F2, G, H1 | 4 | 373 | 374 |
| 46 | 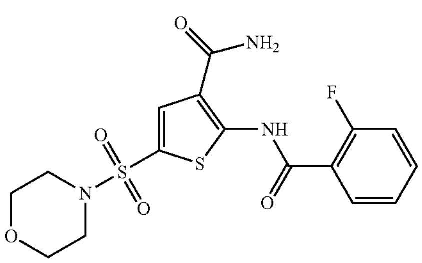 [SMILES: NC(=O)c1cc(S(=O)(=O)N2CCOCC2)sc1NC(=O)c1ccccc1F] | 2-(2-fluorobenzamido)-5-(morpholinosulfonyl)thiophene-3-carboxamide | F2, G, H1 | 4 | 413 | 414 |
| 47 | 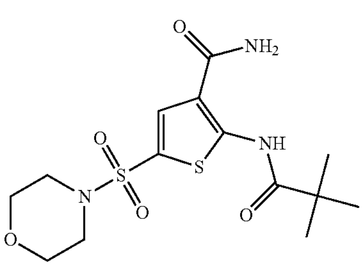 [SMILES: CC(C)(C)C(=O)Nc1sc(S(=O)(=O)N2CCOCC2)cc1C(N)=O] | 5-(morpholinosulfonyl)-2-pivalamidothiophene-3-carboxamide | F2, G, H1 | 4 | 375 | 358 |

TABLE II-continued

List of final compounds

| Cpd # | Structure | Name | Mtd | Int | MW | Mes |
|---|---|---|---|---|---|---|
| 48 | 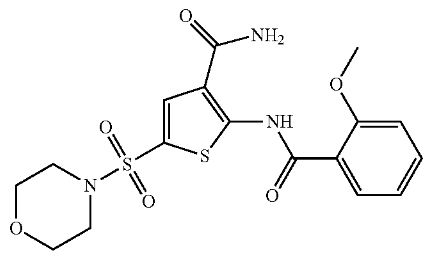 [SMILES: COc1ccccc1C(=O)Nc1sc(S(=O)(=O)N2CCOCC2)cc1C(N)=O] | 2-(2-methoxybenzomido)-5-(morpholinosulfonyl)thiophene-3-carboxamide | F2, G, H1 | 4 | 425 | 426 |
| 49 | 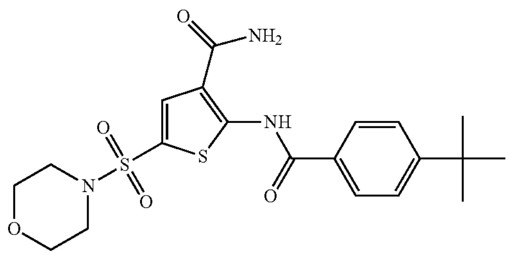 [SMILES: CC(C)(C)c1ccc(C(=O)Nc2sc(S(=O)(=O)N3CCOCC3)cc2C(N)=O)cc1] | 2-(4-tert-butylbenzamido)-5-(morpholinosulfonyl)thiophene-3-carboxamide | F2, G, H1 | 4 | 452 | 452 |
| 50 | 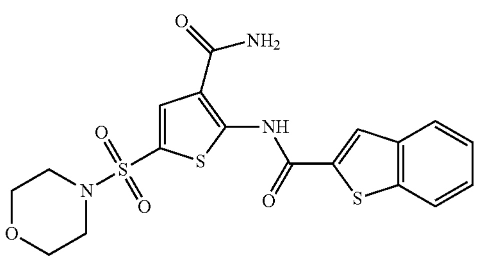 [SMILES: NC(=O)c1cc(S(=O)(=O)N2CCOCC2)sc1NC(=O)c1cc2ccccc2s1] | N-(3-carbamoyl-5-(morpholinosulfonyl)thiophen-2-yl)benzo[b]thiophene-2-carboxamide | F2, G, H1 | 4 | 452 | 452 |
| 51 | 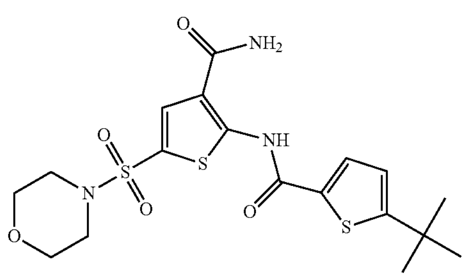 [SMILES: CC(C)(C)c1ccc(C(=O)Nc2sc(S(=O)(=O)N3CCOCC3)cc2C(N)=O)s1] | 5-tert-butyl-N-(3-carbamoyl-5-(morpholinosulfonyl)thiophen-2-yl)thiophene-2-carboxamide | F2, G, H1 | 4 | 458 | 458 |
| 52 | 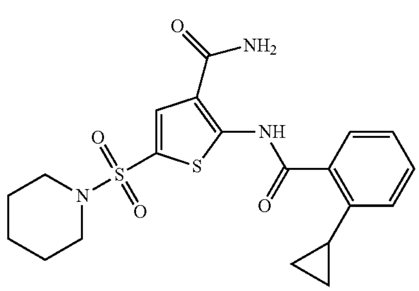 [SMILES: NC(=O)c1cc(S(=O)(=O)N2CCCCC2)sc1NC(=O)c1ccccc1C1CC1] | 2-(2-cyclopropylbenzamido)-5-(piperidin-1-ylsulfonyl)thiophene-3-carboxamide | F2, G, H1 | 4 | 434 | 434 |

TABLE II-continued

List of final compounds

| Cpd # | Structure | Name | Mtd | Int | MW | Mes |
|---|---|---|---|---|---|---|
| 53 | 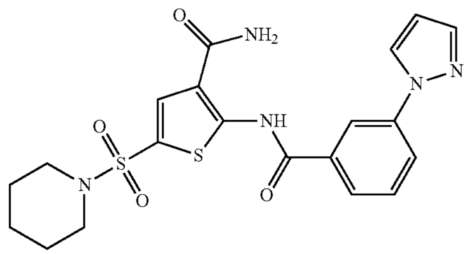 [SMILES: NC(=O)c1cc(S(=O)(=O)N2CCCCC2)sc1NC(=O)c1cccc(-n2cccn2)c1] | 2-(3-(1H-pyrazol-1-yl) benzamido)-5-(piperidin-1-ylsulfonyl)thiophene-3-carboxamide | F2, G, H1 | 4 | 460 | 460 |
| 54 | 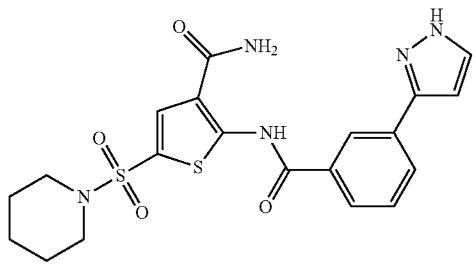 [SMILES: NC(=O)c1cc(S(=O)(=O)N2CCCCC2)sc1NC(=O)c1cccc(-c2cc[nH]n2)c1] | 2-(3-(1H-pyrazol-3-yl) benzamido)-5-(piperidin-1-ylsulfonyl)thiophene-3-carboxamide | F2, G, H1 | 4 | 460 | 460 |
| 55 | 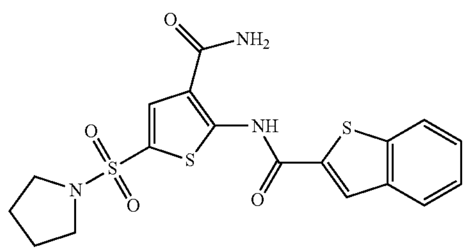 [SMILES: NC(=O)c1cc(S(=O)(=O)N2CCCC2)sc1NC(=O)c1cc2ccccc2s1] | N-(3-carbamoyl-5-(pyrrolidini-1-ylsulfonyl) thiophen-2-yl)benzo[b] thiophene-2-carboxamide | E1, F2, G, H1 | 1 | 436 | 436 |
| 56 | 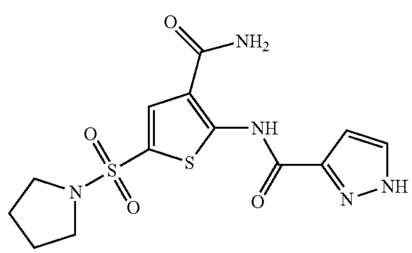 [SMILES: NC(=O)c1cc(S(=O)(=O)N2CCCC2)sc1NC(=O)c1cc[nH]n1] | N-(3-carbamoyl-5-(pyrrolidin-1-ylsulfonyl) thiophen-2-yl)-1H-pyrazole-3-carboxamide | E1, F2, G, H1 | 1 | 369 | 370 |
| 57 | 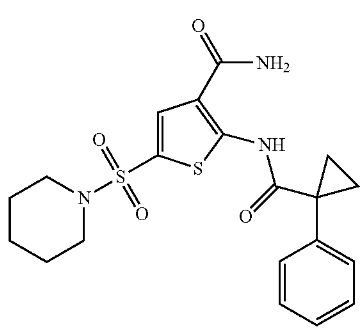 [SMILES: NC(=O)c1cc(S(=O)(=O)N2CCCCC2)sc1NC(=O)C1(c2ccccc2)CC1] | 2-(1-phenylcyclopropanecarboxamido)-5-(piperidin-1-ylsulfonyl) thiophene-3-carboxamide | E1, F2, G, H1 | 4 | 434 | 434 |

TABLE II-continued

List of final compounds

| Cpd # | Structure | Name | Mtd | Int | MW | Mes |
|---|---|---|---|---|---|---|
| 58 | 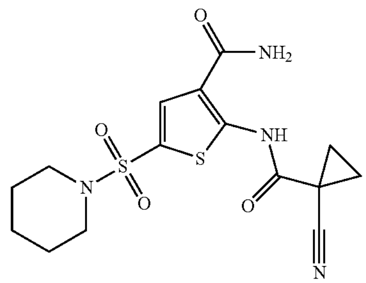 [SMILES: N#CC1(C(=O)Nc2sc(S(=O)(=O)N3CCCCC3)cc2C(N)=O)CC1] | 2-(1-cyanocyclopropanecarboxamido)-5-(piperidin-1-ylsulfonyl)thiophene-3-carboxamide | E1, F2, G, H1 | 4 | 382 | 383 |
| 59 | 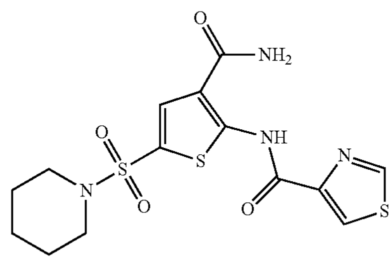 [SMILES: NC(=O)c1cc(S(=O)(=O)N2CCCCC2)sc1NC(=O)c1cscn1] | N-(3-carbamoyl-5-(piperidin-1-ylsulfonyl)thiophen-2-yl)thiazole-4-carboxamide | E1, F2, G, H1 | 4 | 401 | 401 |
| 60 | 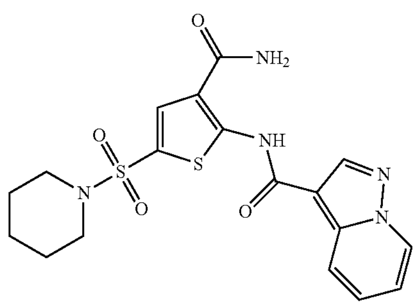 [SMILES: NC(=O)c1cc(S(=O)(=O)N2CCCCC2)sc1NC(=O)c1cnn2ccccc12] | N-(3-carbamoyl-5-(piperidin-1-ylsulfonyl)thiophen-2-yl)pyrazolo[1,5-a]pyridine-3-carboxamide | E1, F2, G, H1 | 4 | 434 | 434 |
| 61 | 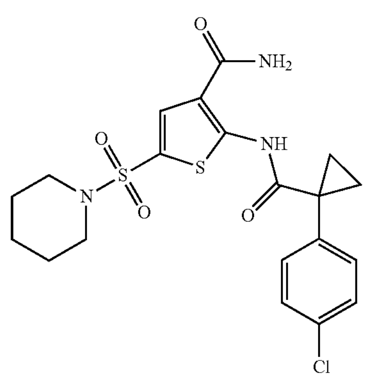 [SMILES: NC(=O)c1cc(S(=O)(=O)N2CCCCC2)sc1NC(=O)C1(c2ccc(Cl)cc2)CC1] | 2-(1-(4-chlorophenyl)cyclopropanecarboxamido)-5-(piperidin-1-ylsulfonyl)thiophene-3-carboxamide | E1, F2, G, H1 | 4 | 468 | 468 |
| 62 | 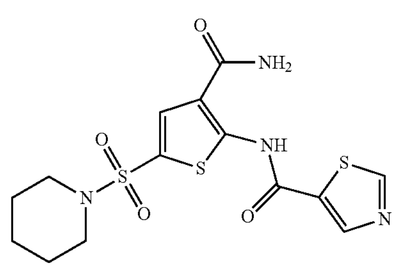 [SMILES: NC(=O)c1cc(S(=O)(=O)N2CCCCC2)sc1NC(=O)c1cncs1] | N-(3-carbamoyl-5-(piperidin-1-ylsulfonyl)thiophen-2-yl)thiazole-5-carboxamide | E1, F2, G, H1 | 4 | 401 | 401 |

TABLE II-continued

List of final compounds

| Cpd # | Structure | Name | Mtd | Int | MW | Mes |
|---|---|---|---|---|---|---|
| 63 | 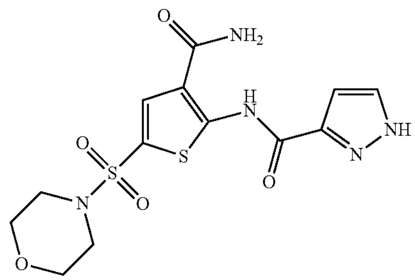 [SMILES: NC(=O)c1cc(S(=O)(=O)N2CCOCC2)sc1NC(=O)c1cc[nH]n1] | N-(3-carbamoyl-5-(morpholinosulfonyl)thiophen-2-yl)-1H-pyrazole-3-carboxamide | F2, G, H1 | 4 | 385 | 386 |
| 64 | 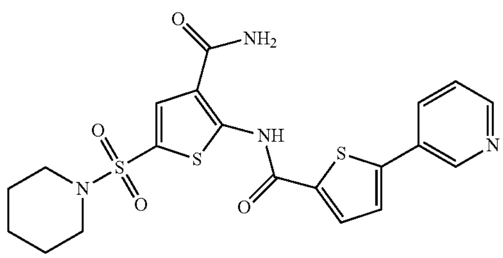 [SMILES: NC(=O)c1cc(S(=O)(=O)N2CCCCC2)sc1NC(=O)c1ccc(-c2cccnc2)s1] | N-(3-carbamoyl-5-(piperidin-1-ylsulfonyl)thiophen-2-yl)-5-(pyridin-3-yl)thiphene-2-carboxamide | F2, G, H1 | 4 | 477 | 477 |
| 65 | 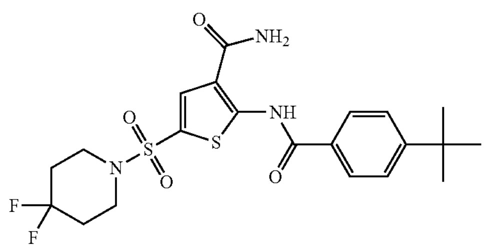 [SMILES: CC(C)(C)c1ccc(C(=O)Nc2sc(S(=O)(=O)N3CCC(F)(F)CC3)cc2C(N)=O)cc1] | 2-(4-tert-butylbenzamido)-5-(4,4-difluoropiperidin-1-ylsulfonyl)thiophene-3-carboxamide | F2, G, H1 | 4 | 486 | 486 |
| 66 | 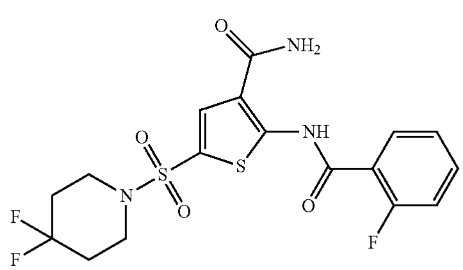 [SMILES: NC(=O)c1cc(S(=O)(=O)N2CCC(F)(F)CC2)sc1NC(=O)c1ccccc1F] | 5-(4,4-difluoropiperidin-1-ylsulfonyl)-2-(2-fluorobenzamido)thiophene-3-carboxamide | F2, G, H1 | 4 | 447 | 448 |
| 67 | 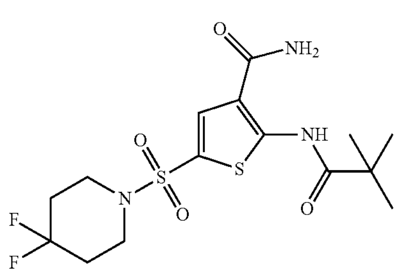 [SMILES: CC(C)(C)C(=O)Nc1sc(S(=O)(=O)N2CCC(F)(F)CC2)cc1C(N)=O] | 5-(4,4-difluoropiperidin-1-ylsulfonyl)-2-pivalamidothiophene-3-carboxamide | F2, G, H1 | 4 | 409 | 410 |

TABLE II-continued

List of final compounds

| Cpd # | Structure | Name | Mtd | Int | MW | Mes |
|---|---|---|---|---|---|---|
| 68 | 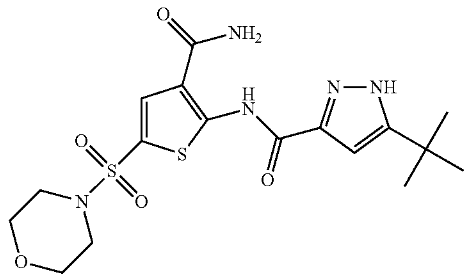 [SMILES: CC(C)(C)c1cc(C(=O)Nc2sc(S(=O)(=O)N3CCOCC3)cc2C(N)=O)n[nH]1] | 5-tert-butyl-N-(3-carbamoyl-5-(morpholinosulfonyl)thiophen-2-yl)-1H-pyrazole-3-carboxamide | F2, G, H1 | 4 | 442 | 442 |
| 69 | 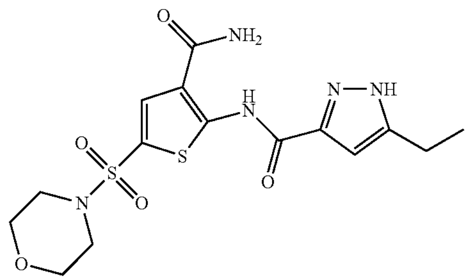 [SMILES: CCc1cc(C(=O)Nc2sc(S(=O)(=O)N3CCOCC3)cc2C(N)=O)n[nH]1] | N-(3-carbamoyl-5-(morpholinosulfonyl)thiophen-2-yl)-5-ethyl-1H-pyrazole-3-carboxamide | F2, G, H1 | 4 | 413 | 414 |
| 70 | 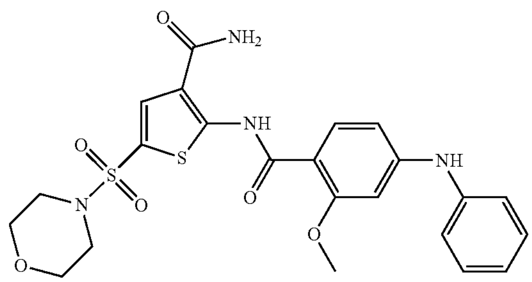 [SMILES: COc1cc(Nc2ccccc2)ccc1C(=O)Nc1sc(S(=O)(=O)N2CCOCC2)cc1C(N)=O] | 2-(2-methoxy-4-(phenylamino)benzamido)-5-(morpholinosulfonyl)thiophene-3-carboxamide | F2, G, H1 | 4 | 517 | 517 |
| 71 | 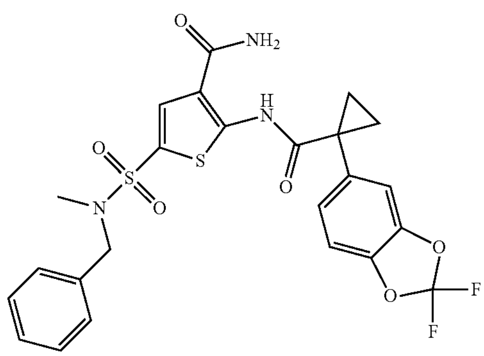 [SMILES: CN(Cc1ccccc1)S(=O)(=O)c1cc(C(N)=O)c(NC(=O)C2(c3ccc4c(c3)OC(F)(F)O4)CC2)s1] | 5-(N-benzyl-N-methylsulfamoyl)-2-(1-(2,2-difluorobenzo[d][1,3]dioxol-5-yl)cyclopropanecarboxamido)thiophene-3-carboxamide | F2, G, H1 | 4 | 550 | 550 |
| 72 | 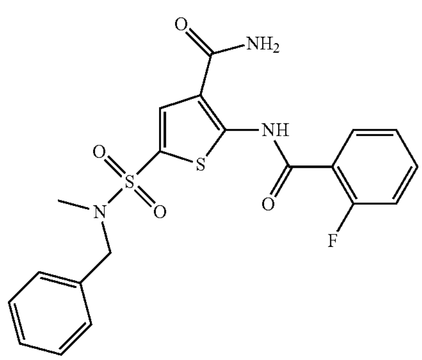 [SMILES: CN(Cc1ccccc1)S(=O)(=O)c1cc(C(N)=O)c(NC(=O)c2ccccc2F)s1] | 5-(N-benzyl-N-methylsulfamoyl)-2-(2-fluorobenzamido)thiophene-3-carboxamide | F2, G, H1 | 4 | 448 | 448 |

TABLE II-continued

List of final compounds

| Cpd # | Structure | Name | Mtd | Int | MW | Mes |
|---|---|---|---|---|---|---|
| 73 | 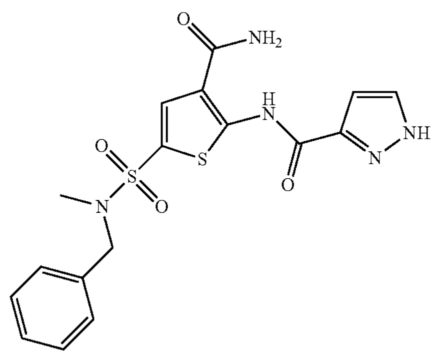 [SMILES: CN(Cc1ccccc1)S(=O)(=O)c1cc(C(N)=O)c(NC(=O)c2cc[nH]n2)s1] | N-(5-(N-benzyl-N-methylsulfamoyl)-3-carbamoylthiophen-2-yl)-1H-pyrazole-3-carboxamide | F2, G, H1 | 4 | 419 | 420 |
| 74 | 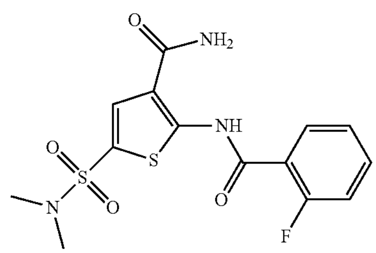 [SMILES: CN(C)S(=O)(=O)c1cc(C(N)=O)c(NC(=O)c2ccccc2F)s1] | 5-(N,N-dimethylsulfamoyl)-2-(2-fluorobenzamido)thiophene-3-carboxamide | F2, G, H1 | 4 | 371 | 372 |
| 75 | 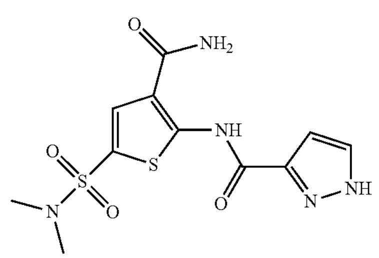 [SMILES: CN(C)S(=O)(=O)c1cc(C(N)=O)c(NC(=O)c2cc[nH]n2)s1] | N-(3-carbamoyl-5-(N,N-dimethylsulfamoyl)thiophen-2-yl)-1H-pyrazole-3-carboxamide | F2, G, H1 | 4 | 343 | 344 |
| 76 | 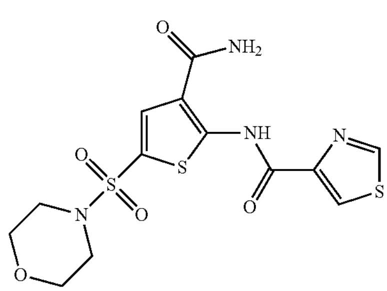 [SMILES: NC(=O)c1cc(S(=O)(=O)N2CCOCC2)sc1NC(=O)c1cscn1] | N-(3-carbamoyl-5-(morpholinosulfonyl)thiophen-2-yl)thiazole-4-carboxamide | F2, G, H1 | 4 | 402 | 403 |
| 77 | 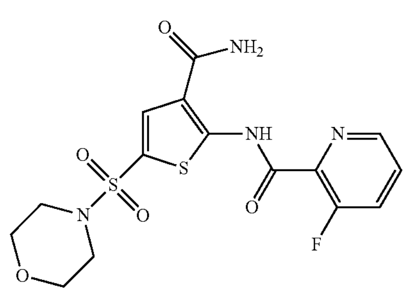 [SMILES: NC(=O)c1cc(S(=O)(=O)N2CCOCC2)sc1NC(=O)c1ncccc1F] | N-(3-carbamoyl-5-(morpholinosulfonyl)thiophen-2-yl)-3-fluoropicolinamide | F2, G, H1 | 4 | 414 | 415 |

TABLE II-continued

List of final compounds

| Cpd # | Structure | Name | Mtd | Int | MW | Mes |
|---|---|---|---|---|---|---|
| 78 | 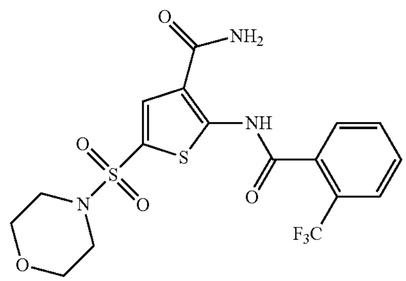 [SMILES: NC(=O)c1cc(S(=O)(=O)N2CCOCC2)sc1NC(=O)c1ccccc1C(F)(F)F] | 5-(morpholinosulfonyl)-2-(2-(trifluoromethyl)benzamido)thiophene-3-carboxamide | F2, G, H1 | 4 | 463 | 464 |
| 79 | 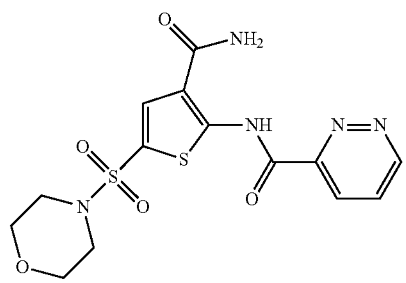 [SMILES: NC(=O)c1cc(S(=O)(=O)N2CCOCC2)sc1NC(=O)c1cccnn1] | N-(3-carbamoyl-5-(morpholinosulfonyl)thiophen-2-yl)pyridazine-3-carboxamide | F2, G, H1 | 4 | 397 | 398 |
| 80 | 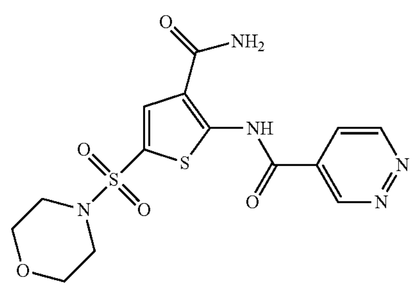 [SMILES: NC(=O)c1cc(S(=O)(=O)N2CCOCC2)sc1NC(=O)c1ccnnc1] | N-(3-carbamoyl-5-(morpholinosulfonyl)thiophen-2-yl)pyridazine-4-carboxamide | F2, G, H1 | 4 | 397 | 398 |
| 81 | 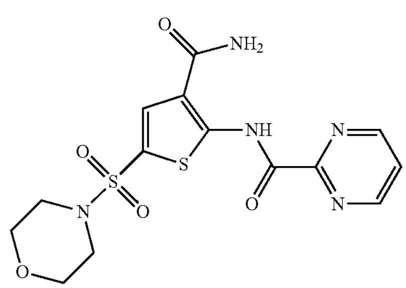 | N-(3-carbamoyl-5-(morpholinosulfonyl)thiophen-2-yl)pyrimidine-2-carboxamide | F2, G, H1 | 4 | 397 | 398 |
| 82 | 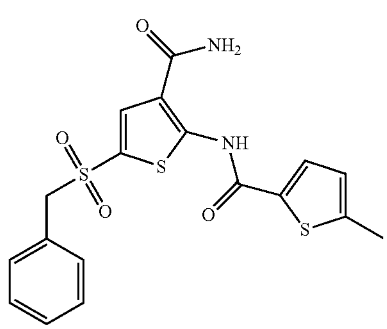 [SMILES: Cc1ccc(C(=O)Nc2sc(S(=O)(=O)Cc3ccccc3)cc2C(N)=O)s1] | N-(5-(benzylsulfonyl)-3-carbamoylthiophen-2-yl)-5-methylthiophene-2-carboxamide | E2, D2, G, H1 | 3 | 421 | 422 |

TABLE II-continued

List of final compounds

| Cpd # | Structure | Name | Mtd | Int | MW | Mes |
|---|---|---|---|---|---|---|
| 83 | 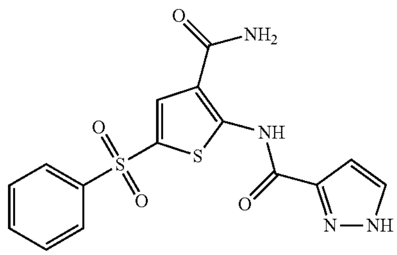 [SMILES: NC(=O)c1cc(S(=O)(=O)c2ccccc2)sc1NC(=O)c1cc[nH]n1] | N-(3-carbamoyl-5-(phenylsulfonyl)thiophen-2-yl)-1H-pyrazole-3-carboxamide | C, D1, G, H1 | 2 | 376 | 377 |
| 84 | 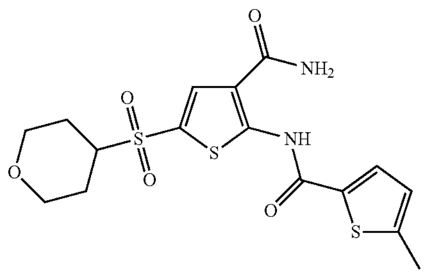 [SMILES: Cc1ccc(C(=O)Nc2sc(S(=O)(=O)C3CCOCC3)cc2C(N)=O)s1] | N-(3-carbamoyl-5-(tetrahydro-2H-pyran-4-ylsulfonyl)thiophen-2-yl)-5-methylthiophene-2-carboxamide | C, D1, G, H1 | 2 | 415 | 416 |
| 85 | 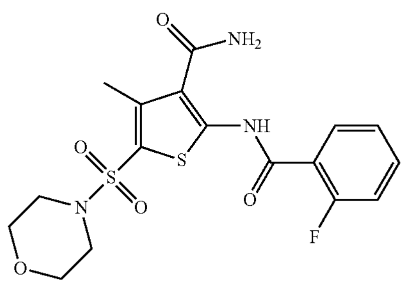 [SMILES: Cc1c(S(=O)(=O)N2CCOCC2)sc(NC(=O)c2ccccc2F)c1C(N)=O] | 2-(2-fluorobenzamido)-4-methyl-5-(morpholinosulfonyl)thiophene-3-carboxamide | F2, G, H1 | 7 | 427 | 428 |
| 86 | 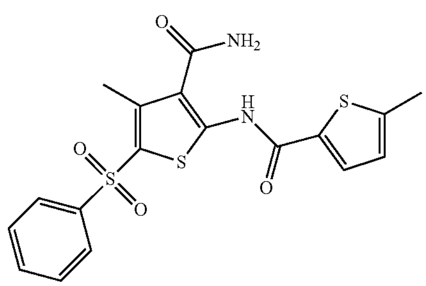 [SMILES: Cc1ccc(C(=O)Nc2sc(S(=O)(=O)c3ccccc3)c(C)c2C(N)=O)s1] | N-(3-carbamoyl-4-methyl-5-(phenylsulfonyl)thiophen-2-yl)-5-methylthiophene-2-carboxamide | C, D1, G, H1 | 6 | 421 | 422 |
| 87 | 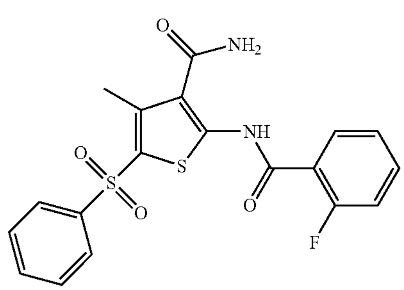 [SMILES: Cc1c(S(=O)(=O)c2ccccc2)sc(NC(=O)c2ccccc2F)c1C(N)=O] | 2-(2-fluorobenzamido)-4-methyl-5-(phenylsulfonyl)thiophene-3-carboxamide | C, D1, G, H1 | 6 | 418 | 419 |

TABLE II-continued

List of final compounds

| Cpd # | Structure | Name | Mtd | Int | MW | Mes |
|---|---|---|---|---|---|---|
| 88 | 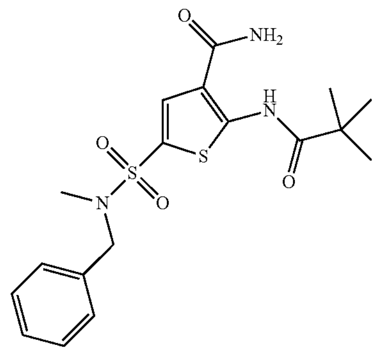 [SMILES: CN(Cc1ccccc1)S(=O)(=O)c1cc(C(N)=O)c(NC(=O)C(C)(C)C)s1] | 5-(N-benzyl-N-methylsulfamoyl)-2-pivalamidothiophene-3-carboxamide | F2, G, H1 | 4 | 410 | 411 |
| 89 | 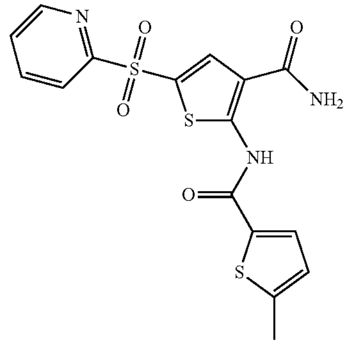 [SMILES: Cc1ccc(C(=O)Nc2sc(S(=O)(=O)c3ccccn3)cc2C(N)=O)s1] | N-(3-carbamoyl-5-(pyridin-2-ylsulfonyl)thiophen-2-yl)-5-methylthiophene-2-carboxamide | C, D1, G, H1 | 2 | 407 | 408 |
| 90 | 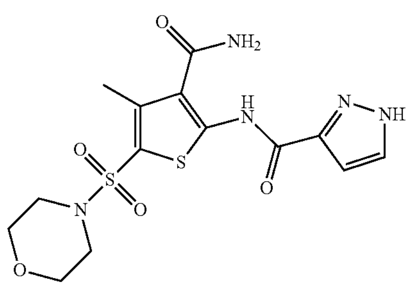 [SMILES: Cc1c(S(=O)(=O)N2CCOCC2)sc(NC(=O)c2cc[nH]n2)c1C(N)=O] | N-(3-carbamoyl-4-methyl-5-(morpholinosulfonyl)thiophen-2-yl)-1H-pyrazole-3-carboxamide | F2, G, H1 | 7 | 399 | 400 |
| 91 | 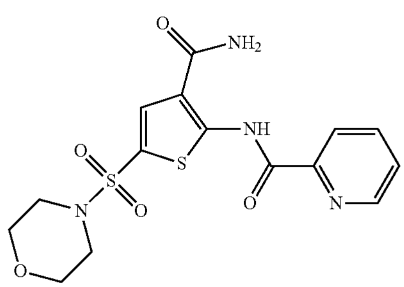 [SMILES: NC(=O)c1cc(S(=O)(=O)N2CCOCC2)sc1NC(=O)c1ccccn1] | N-(3-carbamoyl-5-(morpholinosulfonyl)thiophen-2-yl)picolinamide | F2, G, H1 | 4 | 396 | 397 |
| 92 | 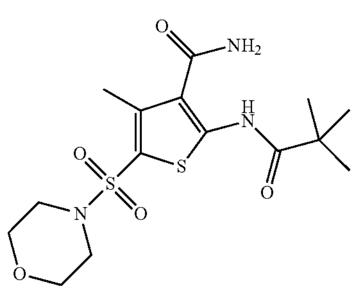 [SMILES: Cc1c(S(=O)(=O)N2CCOCC2)sc(NC(=O)C(C)(C)C)c1C(N)=O] | 4-methyl-5-(morpholinosulfonyl)-2-pivalamidothiophene-3-carboxamide | F2, G, H1 | 7 | 389 | 390 |

TABLE II-continued

List of final compounds

| Cpd # | Structure | Name | Mtd | Int | MW | Mes |
|---|---|---|---|---|---|---|
| 93 | 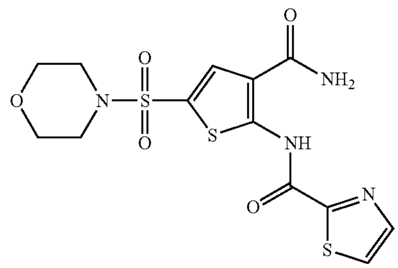 [SMILES: NC(=O)c1cc(S(=O)(=O)N2CCOCC2)sc1NC(=O)c1nccs1] | N-(3-carbamoyl-5-(morpholinosulfonyl)thiophen-2-yl)thiazole-2-carboxamide | F2, G, H1 | 4 | 402 | 403 |
| 94 | 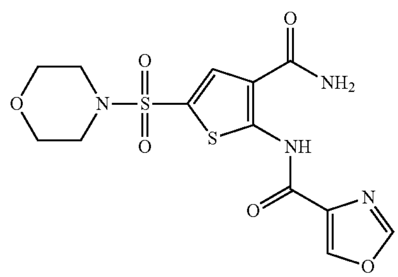 [SMILES: NC(=O)c1cc(S(=O)(=O)N2CCOCC2)sc1NC(=O)c1cocn1] | N-(3-carbamoyl-5-(morpholinosulfonyl)thiophen-2-yl)oxazole-4-carboxamide | F2, G, H1 | 4 | 386 | 387 |
| 95 | 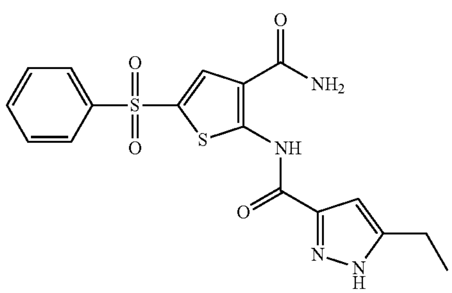 [SMILES: CCc1cc(C(=O)Nc2sc(S(=O)(=O)c3ccccc3)cc2C(N)=O)n[nH]1] | N-(3-carbamoyl-5-(phenylsulfonyl)thiophen-2-yl)-5-ethyl-1H-pyrazole-3-carboxamide | C, D1, G, H1 | 2 | 404 | 405 |
| 96 | 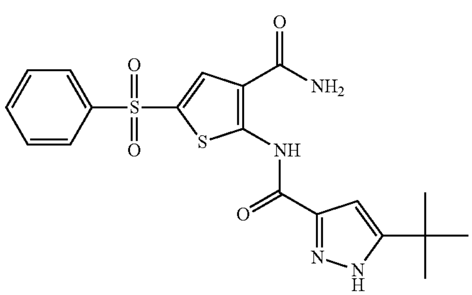 [SMILES: CC(C)(C)c1cc(C(=O)Nc2sc(S(=O)(=O)c3ccccc3)cc2C(N)=O)n[nH]1] | 5-tert-butyl-N-(3-carbamoyl-5-(phenylsulfonyl)thiophen-2-yl)-1H-pyrazole-3-carboxamide | C, D1, G, H1 | 2 | 433 | 434 |
| 97 | 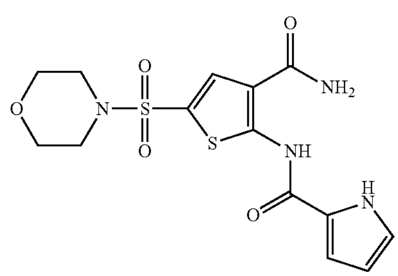 [SMILES: NC(=O)c1cc(S(=O)(=O)N2CCOCC2)sc1NC(=O)c1ccc[nH]1] | N-(3-carbamoyl-5-(morpholinosulfonyl)thiophen-2-yl)-1H-pyrrole-2-carboxamide | F2, G, H1 | 4 | 384 | 385 |

TABLE II-continued

List of final compounds

| Cpd # | Structure | Name | Mtd | Int | MW | Mes |
|---|---|---|---|---|---|---|
| 98 | 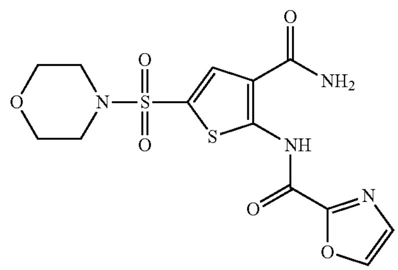 | N-(3-carbamoyl-5-(morpholinosulfonyl)thiophen-2-yl)oxazole-2-carboxamide | F2, G, H1 | 4 | 386 | 387 |
| 99 | 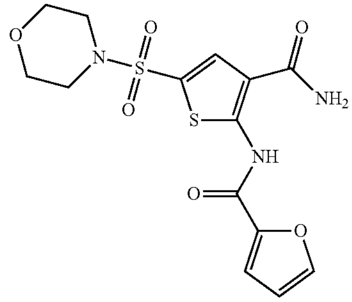 [SMILES: NC(=O)c1cc(S(=O)(=O)N2CCOCC2)sc1NC(=O)c1ccco1] | N-(3-carbamoyl-5-(morpholinosulfonyl)thiophen-2-yl)furan-2-carboxamide | F2, G, H1 | 4 | 385 | 386 |
| 100 | 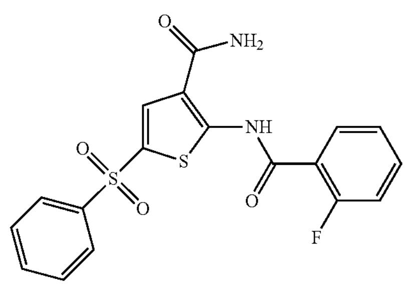 [SMILES: NC(=O)c1cc(S(=O)(=O)c2ccccc2)sc1NC(=O)c1ccccc1F] | 2-(2-fluorobenzamido)-5-(phenylsulfonyl)thiophene-3-carboxamide | A, C, D1, H2 | 8 | 404 | 405 |
| 101 | 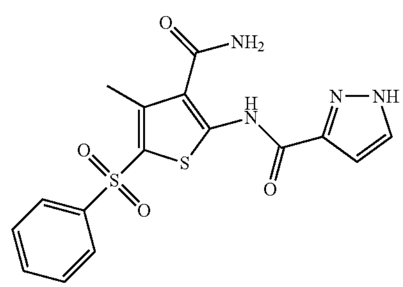 [SMILES: Cc1c(S(=O)(=O)c2ccccc2)sc(NC(=O)c2cc[nH]n2)c1C(N)=O] | N-(3-carbamoyl-4-methyl-5-(phenylsulfonyl)thiophen-2-yl)-1H-pyrazole-3-carboxamide | C, D1, G, H1 | 6 | 390 | 391 |
| 102 | 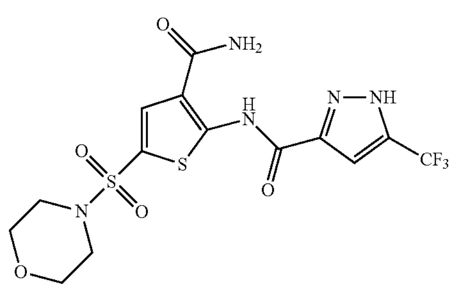 [SMILES: NC(=O)c1cc(S(=O)(=O)N2CCOCC2)sc1NC(=O)c1cc(C(F)(F)F)[nH]n1] | N-(3-carbamoyl-5-(morpholinosulfonyl)thiophen-2-yl)-5-(trifluoromethyl)-1H-pyrazole-3-carboxamide | F2, G, H1 | 4 | 453 | 454 |

TABLE II-continued

List of final compounds

| Cpd # | Structure | Name | Mtd | Int | MW | Mes |
|---|---|---|---|---|---|---|
| 103 | 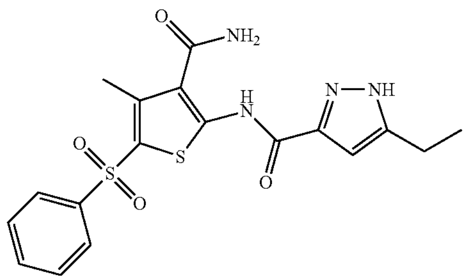 [SMILES: CCc1cc(C(=O)Nc2sc(S(=O)(=O)c3ccccc3)c(C)c2C(N)=O)n[nH]1] | N-(3-carbamoyl-4-methyl-5-(phenylsulfonyl)thiophen-2-yl)-5-ethyl-1H-pyrazole-3-carboxamide | C, D1, G, H1 | 6 | 418 | 419 |
| 104 | 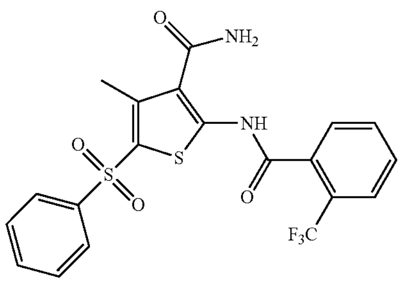 [SMILES: Cc1c(S(=O)(=O)c2ccccc2)sc(NC(=O)c2ccccc2C(F)(F)F)c1C(N)=O] | 4-methyl-5-(phenylsulfonyl)-2-(2-(trifluoromethyl)benzamido)thiophene-3-carboxamide | C, D1, G, H1 | 6 | 468 | 469 |
| 105 | 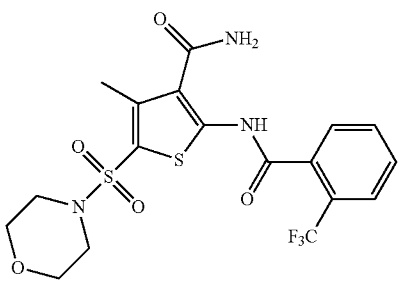 | 4-methyl-5-(morpholinosulfonyl)-2-(2-(trifluoromethyl)benzamido)thiophene-3-carboxamide | F2, G, H1 | 7 | 477 | 478 |
| 106 | 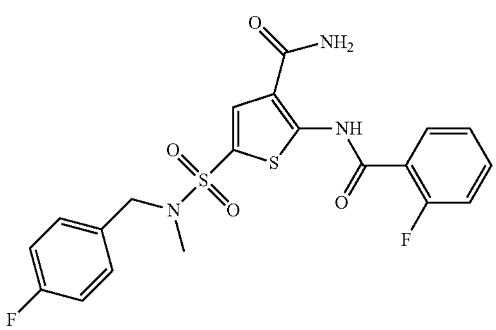 [SMILES: CN(Cc1ccc(F)cc1)S(=O)(=O)c1cc(C(N)=O)c(NC(=O)c2ccccc2F)s1] | 2-(2-fluorobenzamido)-5-(N-(4-fluorobenzyl)-N-methylsulfamoyl)thiophene-3-carboxamide | H2, E3, F2 | 8 | 466 | 466 |
| 107 | 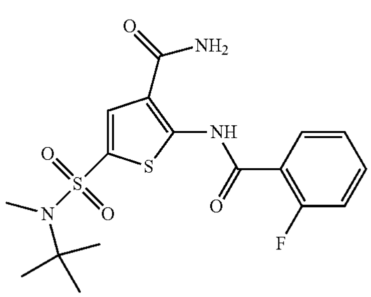 [SMILES: CN(C(C)(C)C)S(=O)(=O)c1cc(C(N)=O)c(NC(=O)c2ccccc2F)s1] | 5-(N-tert-butyl-N-methylsulfamoyl)-2-(2-fluorobenzamido)thiophene-3-carboxamide | H2, E3, F2 | 8 | 413 | 414 |

TABLE II-continued

List of final compounds

| Cpd # | Structure | Name | Mtd | Int | MW | Mes |
|---|---|---|---|---|---|---|
| 108 | 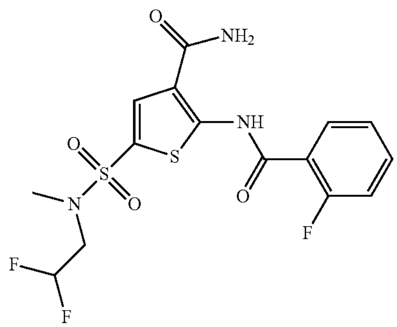 [SMILES: CN(CC(F)F)S(=O)(=O)c1cc(C(N)=O)c(NC(=O)c2ccccc2F)s1] | 5-(N-(2,2-difluoroethyl)-N-methylsulfamoyl)-2-(2-fluorobenzamido)thiophene-3-carboxamide | H2, E3, F2 | 8 | 421 | 422 |
| 109 | 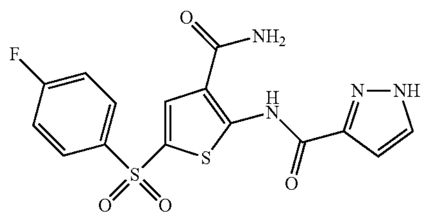 [SMILES: NC(=O)c1cc(S(=O)(=O)c2ccc(F)cc2)sc1NC(=O)c1cc[nH]n1] | N-(3-carbamoyl-5-(4-fluorophenylsulfonyl)thiophen-2-yl)-1H-pyrazole-3-carboxamide | A, C, D1, G, H1 | 1 | 394 | 395 |
| 110 | 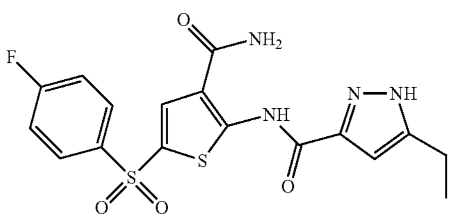 [SMILES: CCc1cc(C(=O)Nc2sc(S(=O)(=O)c3ccc(F)cc3)cc2C(N)=O)n[nH]1] | N-(3-carbamoyl-5-(4-fluorophenylsulfonyl)thiophen-2-yl)-5-ethyl-1H-pyrazole-3-carboxamide | A, C, D1, G, H1 | 1 | 422 | 423 |
| 111 | 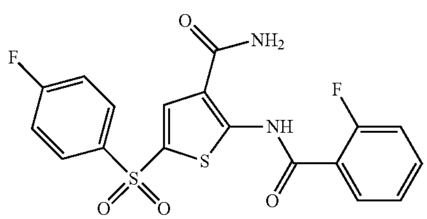 [SMILES: NC(=O)c1cc(S(=O)(=O)c2ccc(F)cc2)sc1NC(=O)c1ccccc1F] | 2-(2-fluorobenzamido)-5-(4-fluorophenylsulfonyl)thiophene-3-carboxamide | A, C, D1, G, H1 | 1 | 422 | 423 |
| 112 | 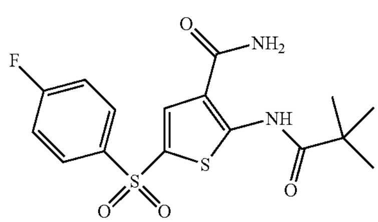 [SMILES: CC(C)(C)C(=O)Nc1sc(S(=O)(=O)c2ccc(F)cc2)cc1C(N)=O] | 5-(4-fluorophenylsulfonyl)-2-pivalamidothiophene-3-carboxamide | A, C, D1, G, H1 | 1 | 384 | 385 |
| 113 | 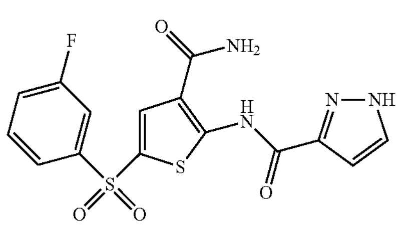 [SMILES: NC(=O)c1cc(S(=O)(=O)c2cccc(F)c2)sc1NC(=O)c1cc[nH]n1] | N-(3-carbamoyl-5-(3-fluorophenylsulfonyl)thiophen-2-yl)-1H-pyrazole-3-carboxamide | A, C, D1, G, H1 | 1 | 394 | 395 |

TABLE II-continued

List of final compounds

| Cpd # | Structure | Name | Mtd | Int | MW | Mes |
|---|---|---|---|---|---|---|
| 114 | 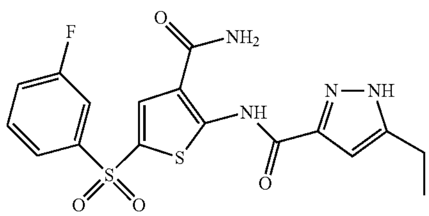 [SMILES: CCc1cc(C(=O)Nc2sc(S(=O)(=O)c3cccc(F)c3)cc2C(N)=O)n[nH]1] | N-(3-carbamoyl-5-(3-fluorophenylsulfonyl)thiophen-2-yl)-5-ethyl-1H-pyrazole-3-carboxamide | A, C, D1, G, H1 | 1 | 422 | 423 |
| 115 | 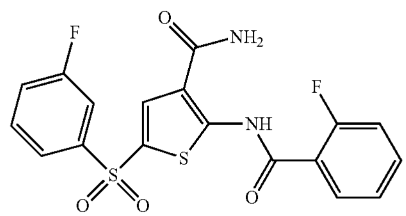 [SMILES: NC(=O)c1cc(S(=O)(=O)c2cccc(F)c2)sc1NC(=O)c1ccccc1F] | 2-(2-fluorobenzamido)-5-(3-fluorophenylsulfonyl)thiophene-3-carboxamide | A, C, D1, G, H1 | 1 | 422 | 423 |
| 116 | 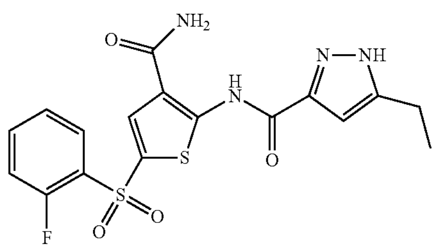 [SMILES: CCc1cc(C(=O)Nc2sc(S(=O)(=O)c3ccccc3F)cc2C(N)=O)n[nH]1] | N-(3-carbamoyl-5-(2-fluorophenylsulfonyl)thiophen-2-yl)-5-ethyl-1H-pyrazole-3-carboxamide | A, C, D1, G, H1 | 1 | 422 | 423 |
| 117 | 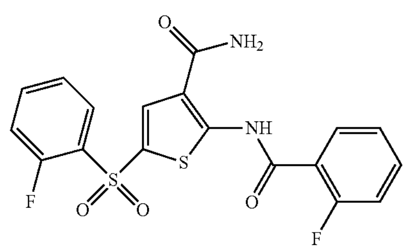 [SMILES: NC(=O)c1cc(S(=O)(=O)c2ccccc2F)sc1NC(=O)c1ccccc1F] | 2-(2-fluorobenzamido)-5-(2-fluorophenylsulfonyl)thiophene-3-carboxamide | A, C, D1, G, H1 | 1 | 422 | 423 |
| 118 | 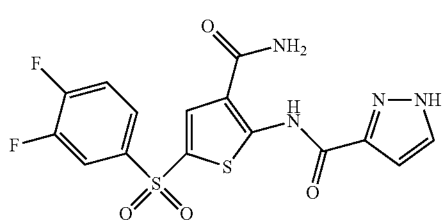 [SMILES: NC(=O)c1cc(S(=O)(=O)c2ccc(F)c(F)c2)sc1NC(=O)c1cc[nH]n1] | N-(3-carbamoyl-5-(3,4-difluorophenylsulfonyl)thiophen-2-yl)-1H-pyrazole-3-carboxamide | A, C, D1, G, H1 | 1 | 412 | 413 |
| 119 | 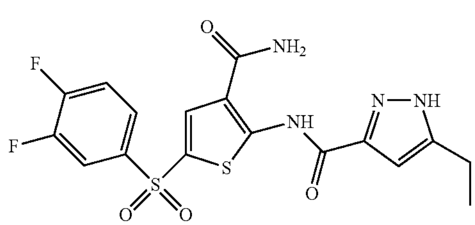 [SMILES: CCc1cc(C(=O)Nc2sc(S(=O)(=O)c3ccc(F)c(F)c3)cc2C(N)=O)n[nH]1] | N-(3-carbamoyl-5-(3,4-difluorophenylsulfonyl)thiophen-2-yl)-5-ethyl-1H-pyrazole-3-carboxamide | A, C, D1, G, H1 | 1 | 440 | 441 |

TABLE II-continued

List of final compounds

| Cpd # | Structure | Name | Mtd | Int | MW | Mes |
|---|---|---|---|---|---|---|
| 120 | 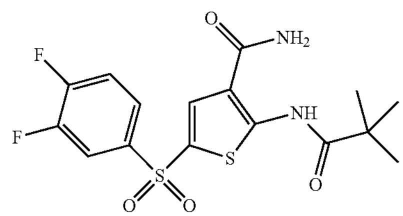 [SMILES: CC(C)(C)C(=O)Nc1sc(S(=O)(=O)c2ccc(F)c(F)c2)cc1C(N)=O] | 5-(3,4-difluorophenylsulfonyl)-2-pivalamidothiophene-3-carboxamide | A, C, D1, G, H1 | 1 | 402 | 403 |
| 121 | 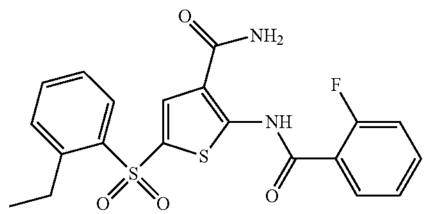 [SMILES: CCc1ccccc1S(=O)(=O)c1cc(C(N)=O)c(NC(=O)c2ccccc2F)s1] | 5-(2-ethylphenylsulfonyl)-2-(2-fluorobenzamido)thiophene-3-carboxamide | A, C, D1, G, H1 | 1 | 432 | 433 |
| 122 | 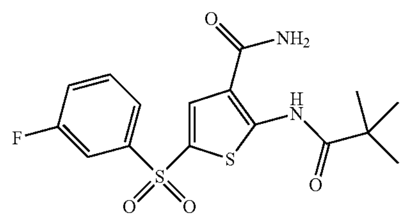 [SMILES: CC(C)(C)C(=O)Nc1sc(S(=O)(=O)c2cccc(F)c2)cc1C(N)=O] | 5-(3-fluorophenylsulfonyl)-2-pivalamidothiophene-3-carboxamide | A, C, D1, G, H1 | 1 | 384 | 385 |
| 123 | 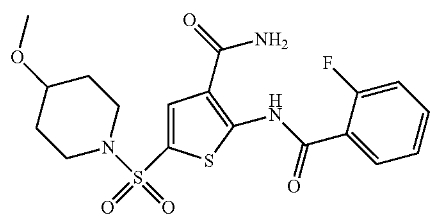 [SMILES: COC1CCN(S(=O)(=O)c2cc(C(N)=O)c(NC(=O)c3ccccc3F)s2)CC1] | 2-(2-fluorobenzamido)-5-(4-methoxypiperidin-1-ylsulfonyl)thiophene-3-carboxamide | H3, E1, F1 | 8 | 442 | 442 |
| 124 | 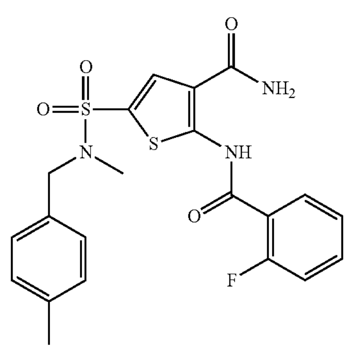 [SMILES: Cc1ccc(CN(C)S(=O)(=O)c2cc(C(N)=O)c(NC(=O)c3ccccc3F)s2)cc1] | 2-(2-fluorobenzamido)-5-(N-methyl-N-(4-methylbenzyl)sulfamoyl)thiophene-3-carboxamide | H3, E1, F2 | 8 | 462 | 462 |
| 125 | 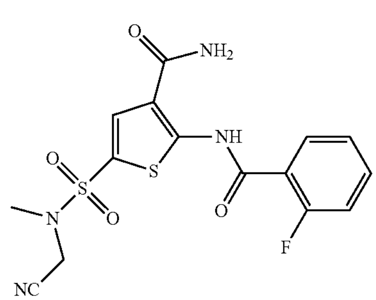 [SMILES: CN(CC#N)S(=O)(=O)c1cc(C(N)=O)c(NC(=O)c2ccccc2F)s1] | 5-(N-(cyanomethyl)-N-methylsulfamoyl)-2-(2-fluorobenzamido)thiophene-3-carboxamide | H2, E3, F2 | 8 | 396 | 397 |

TABLE II-continued

List of final compounds

| Cpd # | Structure | Name | Mtd | Int | MW | Mes |
|---|---|---|---|---|---|---|
| 126 | 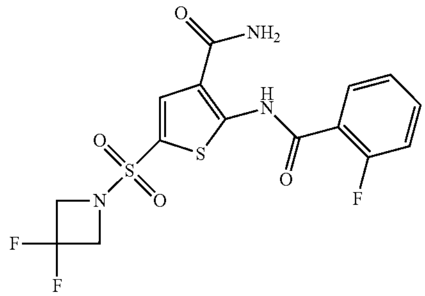 [SMILES: NC(=O)c1cc(S(=O)(=O)N2CC(F)(F)C2)sc1NC(=O)c1ccccc1F] | 5-(3,3-difluoroazetidin-1-ylsulfonyl)-2-(2-fluorobenzamido)thiophene-3-carboxamide | H2, E3, F2 | 8 | 419 | 420 |
| 127 | 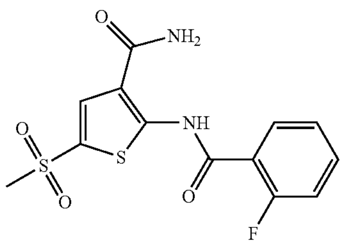 [SMILES: CS(=O)(=O)c1cc(C(N)=O)c(NC(=O)c2ccccc2F)s1] | 2-(2-fluorobenzamido)-5-(methylsulfonyl)thiophene-3-carboxamide | A, B1, D1, H2 | 8 | 342 | 343 |
| 128 | 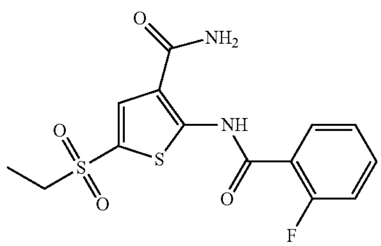 [SMILES: CCS(=O)(=O)c1cc(C(N)=O)c(NC(=O)c2ccccc2F)s1] | 5-(ethylsulfonyl)-2-(2-fluorobenzamido)thiophene-3-carboxamide | A, B1, D1, H2 | 8 | 356 | 357 |
| 129 | 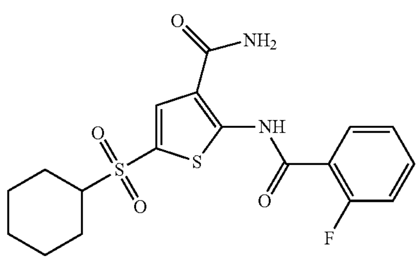 [SMILES: NC(=O)c1cc(S(=O)(=O)C2CCCCC2)sc1NC(=O)c1ccccc1F] | 5-(cyclohexylsulfonyl)-2-(2-fluorobenzamido)thiophene-3-carboxamide | A, B1, D1, H2 | 8 | 410 | 411 |
| 130 | 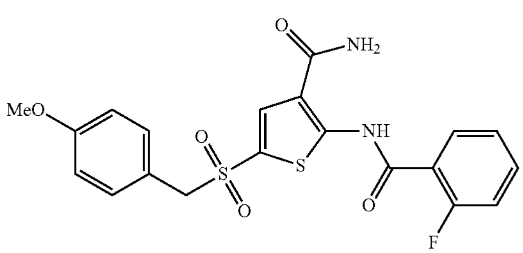 [SMILES: COc1ccc(CS(=O)(=O)c2cc(C(N)=O)c(NC(=O)c3ccccc3F)s2)cc1] | 2-(2-fluorobenzamido)-5-(4-methoxybenzylsulfonyl)thiophene-3-carboxamide | A, B1, D1, H2 | 8 | 448 | 449 |
| 131 | 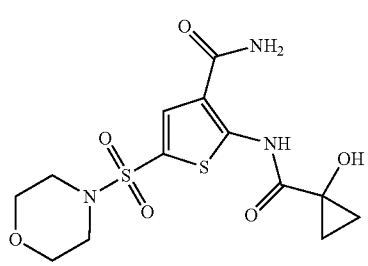 [SMILES: NC(=O)c1cc(S(=O)(=O)N2CCOCC2)sc1NC(=O)C1(O)CC1] | 2-(1-hydroxycyclopropanecarboxamido)-5-(morpholinosulfonyl)thiophene-3-carboxamide | A, E1, F1, H2, K | 8 | 375 | 376 |

TABLE II-continued

List of final compounds

| Cpd # | Structure | Name | Mtd | Int | MW | Mes |
|---|---|---|---|---|---|---|
| 132 | 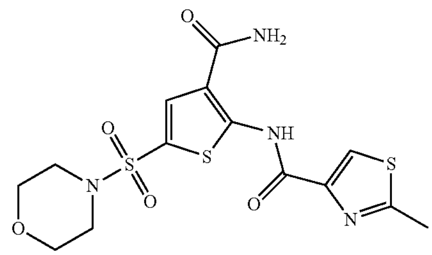 [SMILES: Cc1nc(C(=O)Nc2sc(S(=O)(=O)N3CCOCC3)cc2C(N)=O)cs1] | N-(3-carbamoyl-5-(morpholinosulfonyl)thiophen-2-yl)-2-methylthiazole-4-carboxamide | F2, G, H1 | 4 | 417 | 417 |
| 133 | 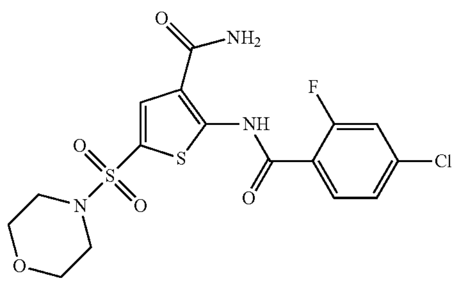 [SMILES: NC(=O)c1cc(S(=O)(=O)N2CCOCC2)sc1NC(=O)c1ccc(Cl)cc1F] | 2-(4-chloro-2-fluorobenzamido)-5-(morpholinosulfonyl)thiophene-3-carboxamide | F2, G, H1 | 4 | 448 | 448 |
| 134 | 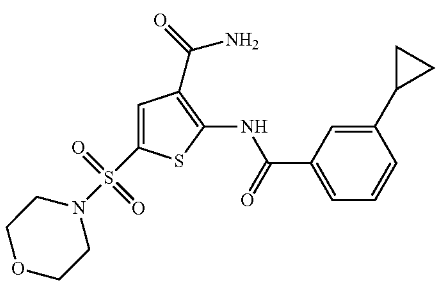 [SMILES: NC(=O)c1cc(S(=O)(=O)N2CCOCC2)sc1NC(=O)c1cccc(C2CC2)c1] | 2-(3-cyclopropylbenzamido)-5-(morpholinosulfonyl)thiophene-3-carboxamide | F2, G, H1 | 4 | 436 | 436 |
| 135 | 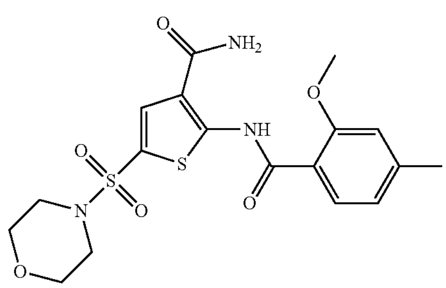 [SMILES: COc1cc(C)ccc1C(=O)Nc1sc(S(=O)(=O)N2CCOCC2)cc1C(N)=O] | 2-(2-methoxy-4-methylbenzamido)-5-(morpholinosulfonyl)thiophene-3-carboxamide | F2, G, H1 | 4 | 440 | 440 |
| 136 | 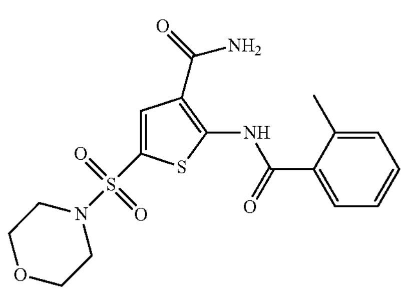 [SMILES: Cc1ccccc1C(=O)Nc1sc(S(=O)(=O)N2CCOCC2)cc1C(N)=O] | 2-(2-methylbenzamido)-5-(morpholinosulfonyl)thiophene-3-carboxamide | F2, G, H1 | 4 | 409 | 410 |

TABLE II-continued

List of final compounds

| Cpd # | Structure | Name | Mtd | Int | MW | Mes |
|---|---|---|---|---|---|---|
| 137 | 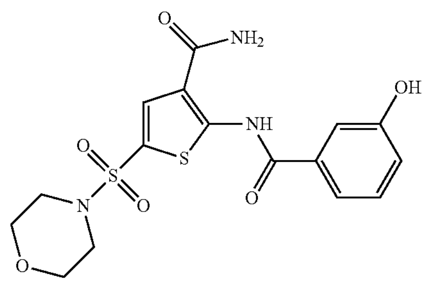 [SMILES: NC(=O)c1cc(S(=O)(=O)N2CCOCC2)sc1NC(=O)c1cccc(O)c1] | 2-(3-hydroxybenzamido)-5-(morpholinosulfonyl)thiphene-3-carboxamide | F2, G, H1 | 4 | 411 | 412 |
| 138 | 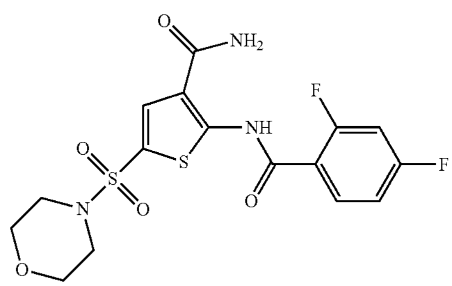 [SMILES: NC(=O)c1cc(S(=O)(=O)N2CCOCC2)sc1NC(=O)c1ccc(F)cc1F] | 2-(2,4-difluorobenzamido)-5-(morpholinosulfonyl)thiophene-3-carboxamide | F2, G, H1 | 4 | 431 | 432 |
| 139 | 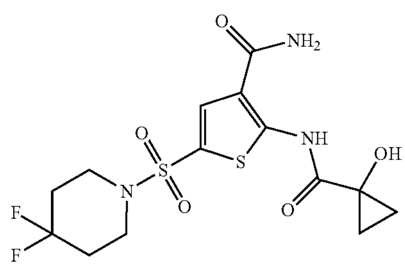 [SMILES: NC(=O)c1cc(S(=O)(=O)N2CCC(F)(F)CC2)sc1NC(=O)C1(O)CC1] | 5-(4,4-difluoropiperidin-1-ylsulfonyl)-2-(1-hydroxycyclopropanecarboxamido)thiophene-3-carboxamide | A, C, D1, H2, K | 8 | 409 | 410 |
| 140 | 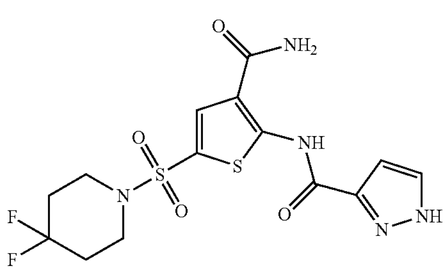 [SMILES: NC(=O)c1cc(S(=O)(=O)N2CCC(F)(F)CC2)sc1NC(=O)c1cc[nH]n1] | N-(3-carbamoyl-5-(4,4-difluoropiperidin-1-ylsulfonyl)thiophen-2-yl)-1H-pyrazole-3-carboxamide | A, B1, D1, H2, J | 8 | 419 | 420 |
| 141 | 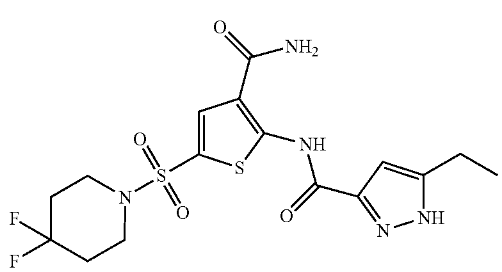 [SMILES: CCc1cc(C(=O)Nc2sc(S(=O)(=O)N3CCC(F)(F)CC3)cc2C(N)=O)n[nH]1] | N-(3-carbamoyl-5-(4,4-difluoropiperidin-1-ylsulfonyl)thiophen-2-yl)-5-ethyl-1H-pyrazole-3-carboxamide | F2, G, H3 | 4 | 447 | 448 |

TABLE II-continued

List of final compounds

| Cpd # | Structure | Name | Mtd | Int | MW | Mes |
|---|---|---|---|---|---|---|
| 142 | 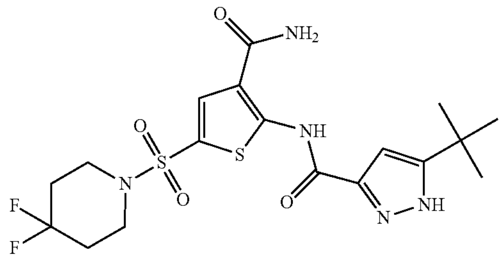 [SMILES: CC(C)(C)c1cc(C(=O)Nc2sc(S(=O)(=O)N3CCC(F)(F)CC3)cc2C(N)=O)n[nH]1] | 5-tert-butyl-N-(3-carbamoyl-5-(4,4-difluoropiperidin-1-ylsulfonyl)thiophen-2-yl)-1H-pyrazole-3-carboxamide | F2, G, H3 | 4 | 476 | 476 |
| 143 | 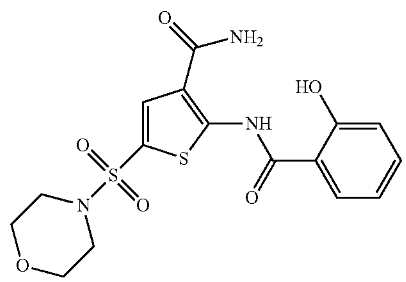 [SMILES: NC(=O)c1cc(S(=O)(=O)N2CCOCC2)sc1NC(=O)c1ccccc1O] | 2-(2-Hydroxy-benzoyl amino)-5-(morpholine-4-sulfonyl)-thiophene-3-carboxylic acid amide | F2, G, H3 | 4 | 411 | 412 |
| 144 | 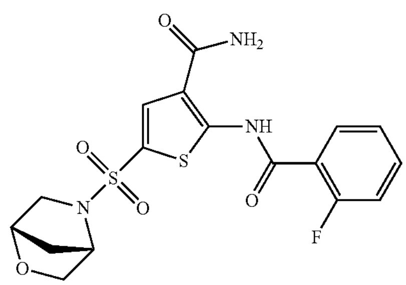 [SMILES: NC(=O)c1cc(S(=O)(=O)N2C[C@@H]3C[C@H]2CO3)sc1NC(=O)c1ccccc1F] | 5-(((1S,4S)-2-oxa-5-azabicyclo[2.2.1]heptan-5-ylsulfonyl)-2-(2-fluorobenzamido)thiophene-3-carboxamide | A, E2, F2, H2 | 8 | 425 | 426 |
| 145 | 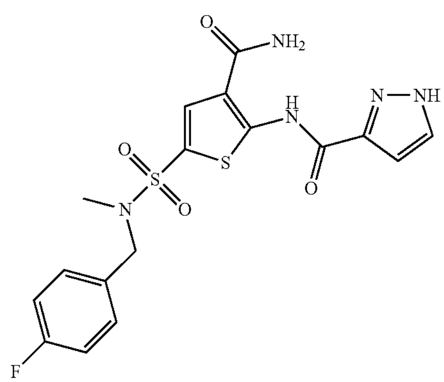 [SMILES: CN(Cc1ccc(F)cc1)S(=O)(=O)c1cc(C(N)=O)c(NC(=O)c2cc[nH]n2)s1] | N-(3-carbamoyl-5-(N-(4-fluorobenzyl)-N-methylsulfamoyl)thiophen-2-yl)-1H-pyrazole-3-carboxamide | A, E2, F2, H2 | 8 | 437 | 438 |
| 146 | 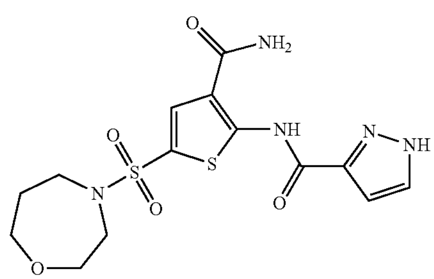 [SMILES: NC(=O)c1cc(S(=O)(=O)N2CCCOCC2)sc1NC(=O)c1cc[nH]n1] | N-(5-(1,4-oxazepan-4-ylsulfonyl)-3-carbamoylthiophen-2-yl)-1H-pyrazole-3-carboxamide | A, E2, F2, H2 | 8 | 399 | 400 |

TABLE II-continued

List of final compounds

| Cpd # | Structure | Name | Mtd | Int | MW | Mes |
|---|---|---|---|---|---|---|
| 147 | 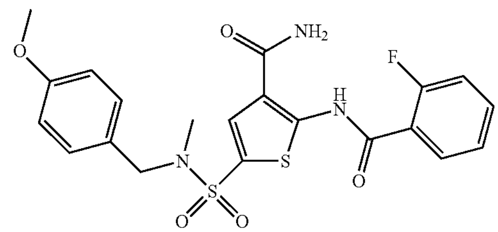 [SMILES: COc1ccc(CN(C)S(=O)(=O)c2cc(C(N)=O)c(NC(=O)c3ccccc3F)s2)cc1] | 2-(2-fluorobenzamido)-5-(N-(4-methoxybenzyl)-N-methylsulfamoyl)thiophene-3-carboxamide | H3, E1 F2 | 8 | 478 | 479 |
| 148 | 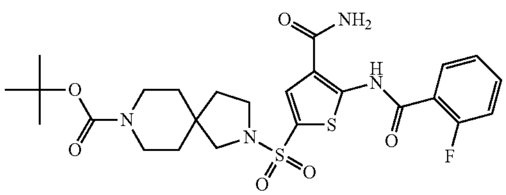 [SMILES: CC(C)(C)OC(=O)N1CCC2(CC1)CCN(S(=O)(=O)c1cc(C(N)=O)c(NC(=O)c3ccccc3F)s1)C2] | tert-butyl 2-(4-carbamoyl-5-(2-fluorobenzamido)thiophen-2-ylsulfonyl)-2,8-diazaspiro[4.5]decane-8-carboxylate | H3, E1, F2 | 8 | 567 | 568 |
| 149 | 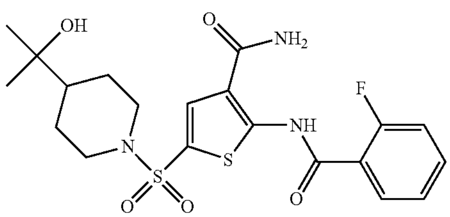 [SMILES: CC(C)(O)C1CCN(S(=O)(=O)c2cc(C(N)=O)c(NC(=O)c3ccccc3F)s2)CC1] | 2-(2-fluorobenzamido)-5-(4-(2-hydroxypropan-2-yl)piperidin-1-ylsulfonyl)thiophene-3-carboxamide | H3, E1, F2 | 8 | 470 | 470 |
| 150 | 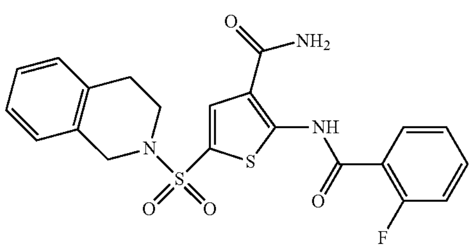 [SMILES: NC(=O)c1cc(S(=O)(=O)N2CCc3ccccc3C2)sc1NC(=O)c1ccccc1F] | 5-(3,4-dihydroisoquinolin-2(1H-ylsulfonyl)-2-(2-fluorobenzamido)thiophene-3-carboxamide | H3, E1, F2 | 8 | 460 | 460 |
| 151 | 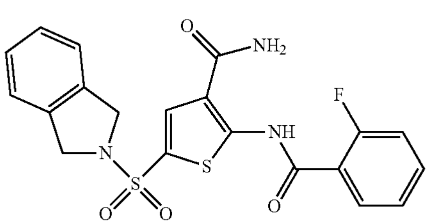 [SMILES: NC(=O)c1cc(S(=O)(=O)N2Cc3ccccc3C2)sc1NC(=O)c1ccccc1F] | 2-(2-fluorobenzamido)-5-(isoindolin-2-ylsulfonyl)thiophene-3-carboxamide | H3, E1, F2 | 8 | 445 | 446 |
| 152 | 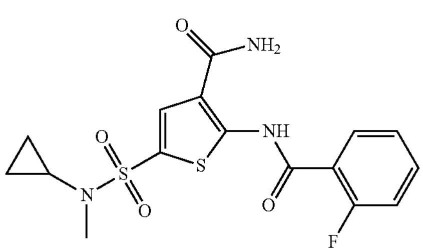 [SMILES: CN(C1CC1)S(=O)(=O)c1cc(C(N)=O)c(NC(=O)c2ccccc2F)s1] | 5-(N-cyclopropyl-N-methylsulfamoyl)-2-(2-fluorobenzamido)thiophene-3-carboxamide | A, E2, F2, H2 | 8 | 397 | 398 |

TABLE II-continued

List of final compounds

| Cpd # | Name | Mtd | Int | MW | Mes |
|---|---|---|---|---|---|
| 153 | 2-(2-fluorobenzamido)-5-(N-isopropyl-N-methylsulfamoyl)thiophene-3-carboxamide | A, E2, F2, H2 | 8 | 399 | 400 |
| 154 | 5-(N,N-diisopropylsulfamoyl)-2-(2-fluorobenzamido)thiophene-3-carboxamide | A, E2, F2, H2 | 8 | 428 | 428 |
| 155 | 2-(2-fluorobenzamido)-5-(N-methyl-N-(1-methylpiperidin-4-yl)sulfamoyl)thiophene-3-carboxamide | A, E2, F2, H2 | 8 | 455 | 455 |
| 156 | 5-(N-cyclopropyl-N-(3-fluorobenzyl)sulfamoyl)-2-(2-fluorobenzamido)thiophene-3-carboxamide | A, E2, F2, H2 | 8 | 492 | 492 |
| 157 | 2-(2-fluorobenzamido)-5-(N-(2-methoxyethyl)-N-(2,2,2-trifluoroethy)sulfamoyl)thiophene-3-carboxamide | A, E2, F2, H2 | 8 | 483 | 484 |

TABLE II-continued

List of final compounds

| Cpd # | Structure | Name | Mtd | Int | MW | Mes |
|---|---|---|---|---|---|---|
| 158 | 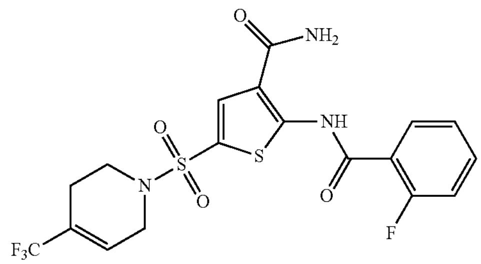 [SMILES: NC(=O)c1cc(S(=O)(=O)N2CC=C(C(F)(F)F)CC2)sc1NC(=O)c1ccccc1F] | 2-(2-fluorobenzamido)-5-(4-(trifluoromethyl)-5,6-dihydropyridin-1(2H)-ylsulfonyl)thiophene-3-carboxamide | A, E2, F2, H2 | 8 | 477 | 478 |
| 159 | 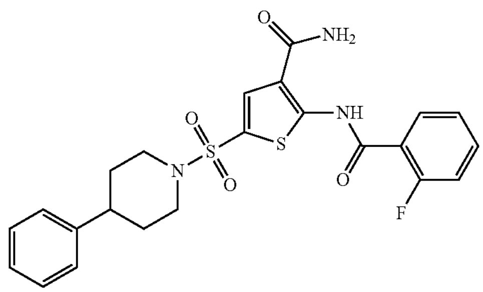 [SMILES: NC(=O)c1cc(S(=O)(=O)N2CCC(c3ccccc3)CC2)sc1NC(=O)c1ccccc1F] | 2-(2-fluorobenzamido)-5-(4-phenylpiperidin-1-ylsulfonyl)thiophene-3-carboxamide | A, E2, F2, H2 | 8 | 488 | 488 |
| 160 | 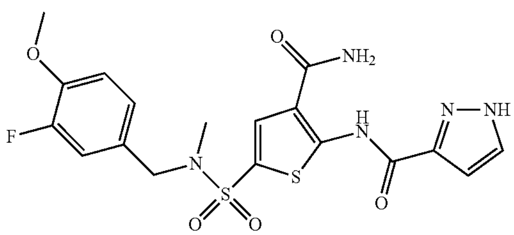 [SMILES: COc1ccc(CN(C)S(=O)(=O)c2cc(C(N)=O)c(NC(=O)c3cc[nH]n3)s2)cc1F] | N-(3-carbamoyl-5-(N-(3-fluoro-4-methoxybenzyl)-N-methylsulfamoyl)thiophen-2-yl)-1H-pyrazole-3-carboxamide | H3, E1, F1 | 8 | 468 | 468 |
| 161 | 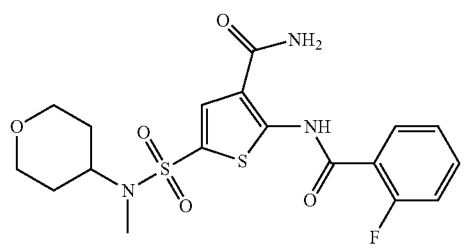 [SMILES: CN(C1CCOCC1)S(=O)(=O)c1cc(C(N)=O)c(NC(=O)c2ccccc2F)s1] | 2-(2-fluorobenzamido)-5-(N-methyl-N-(tetrahydro-2H-pyran-4-yl)sulfamoyl)thiophene-3-carboxamide | A, E2, F2, H2 | 8 | 442 | 442 |
| 162 | 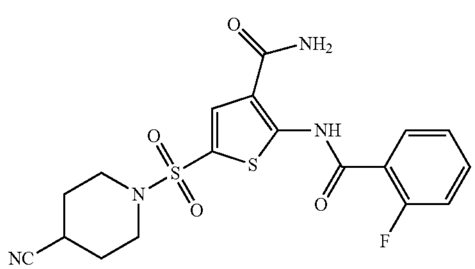 [SMILES: N#CC1CCN(S(=O)(=O)c2cc(C(N)=O)c(NC(=O)c3ccccc3F)s2)CC1] | 5-(4-cyanopiperidin-1-ylsulfonyl)-2-(2-fluorobenzamido)thiophene-3-carboxamide | A, E2, F2, H2 | 8 | 436 | 437 |
| 163 | 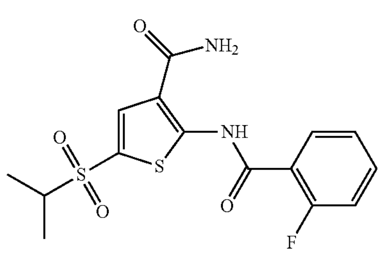 [SMILES: CC(C)S(=O)(=O)c1cc(C(N)=O)c(NC(=O)c2ccccc2F)s1] | 2-(2-fluorobenzamido)-5-(isopropylsulfonyl)thiophene-3-carboxamide | A, B1, D1, H2 | 8 | 370 | 371 |

TABLE II-continued

List of final compounds

| Cpd # | Structure | Name | Mtd | Int | MW | Mes |
|---|---|---|---|---|---|---|
| 164 | 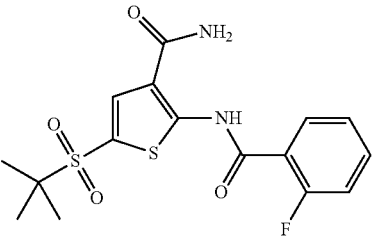 [SMILES: CC(C)(C)S(=O)(=O)c1cc(C(N)=O)c(NC(=O)c2ccccc2F)s1] | 5-(tert-butylsulfonyl)-2-(2-fluorobenzamido)thiophene-3-carboxamide | A, B1, D1, H2 | 8 | 384 | 385 |
| 165 | 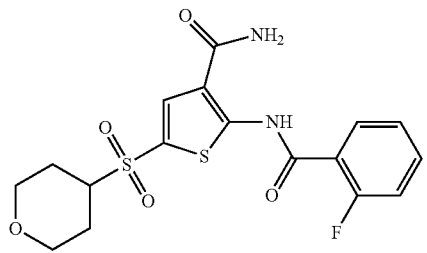 [SMILES: NC(=O)c1cc(S(=O)(=O)C2CCOCC2)sc1NC(=O)c1ccccc1F] | 2-(2-fluorobenzamido)-5-(tetrahydro-2H-pyran-4-ylsulfonyl)thiophene-3-carboxamide | A, B1, D1, H2 | 8 | 412 | 413 |
| 166 | 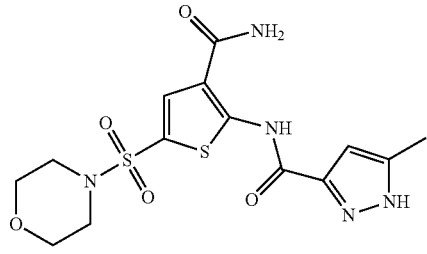 [SMILES: Cc1cc(C(=O)Nc2sc(S(=O)(=O)N3CCOCC3)cc2C(N)=O)n[nH]1] | N-(3-carbamoyl-5-(morpholinosulfonyl)thiophen-2-yl)-5-methyl-1H-pyrazole-3-carboxamide | F2, G, H3 | 4 | 399 | 400 |
| 167 | 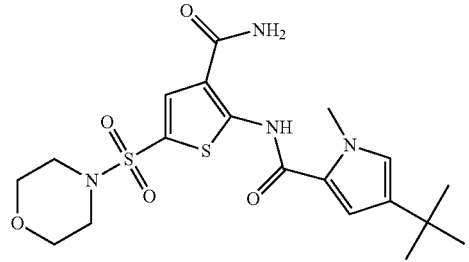 [SMILES: Cn1cc(C(C)(C)C)cc1C(=O)Nc1sc(S(=O)(=O)N2CCOCC2)cc1C(N)=O] | 3-tert-butyl-N-(3-carbamoyl-5-(morpholinosulfonyl)thiophen-2-yl)-1-methyl-1H-pyrazole-5-carboxamide | F2, G, H1 | 4 | 456 | 456 |
| 168 | 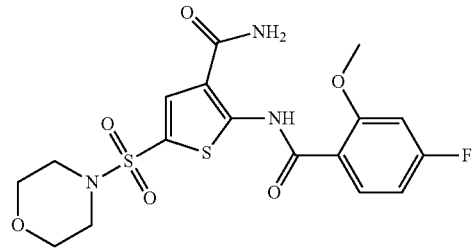 [SMILES: COc1cc(F)ccc1C(=O)Nc1sc(S(=O)(=O)N2CCOCC2)cc1C(N)=O] | 2-(4-fluoro-2-methoxybenzamido)-5-(morpholinosulfonyl)thiophene-3-carboxamide | F2, G, H1 | 4 | 443 | 444 |
| 169 | 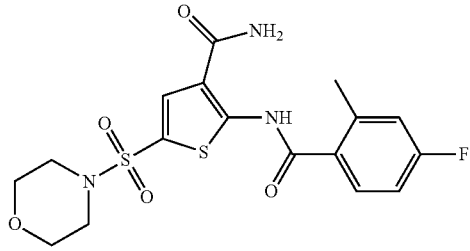 [SMILES: Cc1cc(F)ccc1C(=O)Nc1sc(S(=O)(=O)N2CCOCC2)cc1C(N)=O] | 2-(4-fluoro-2-methylbenzamido)-5-(morpholinosulfonyl)thiophene-3-carboxamide | F2, G, H1 | 4 | 427 | 428 |

TABLE II-continued

List of final compounds

| Cpd # | Structure | Name | Mtd | Int | MW | Mes |
|---|---|---|---|---|---|---|
| 170 | 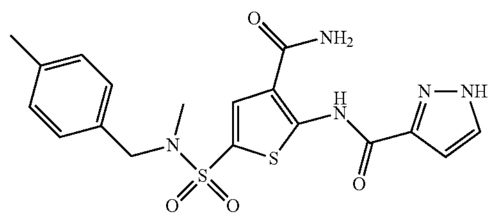 [SMILES: Cc1ccc(CN(C)S(=O)(=O)c2cc(C(N)=O)c(NC(=O)c3cc[nH]n3)s2)cc1] | N-(3-carbamoyl-5-(N-methyl-N-(4-methylbenzyl)sulfamoyl)thiophen-2-yl)-1H-pyrazole-3-carboxamide | H3, E1, F1 | 8 | 434 | 434 |
| 171 | 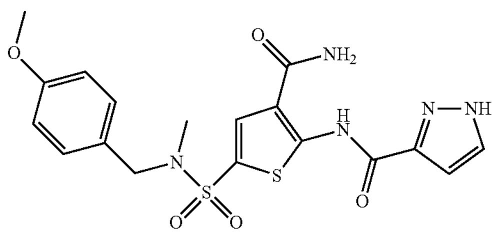 [SMILES: COc1ccc(CN(C)S(=O)(=O)c2cc(C(N)=O)c(NC(=O)c3cc[nH]n3)s2)cc1] | N-(3-carbamoyl-5-(N-(4-methoxybenzyl)-N-methylsulfamoyl)thiophen-2-yl)-1H-pyrazole-3-carboxamide | H3, E1, F1 | 8 | 450 | 126 |
| 172 | 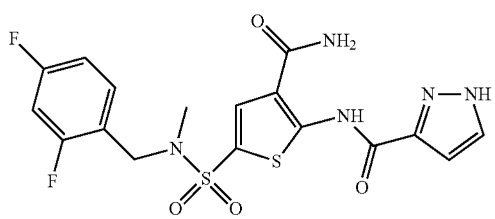 [SMILES: CN(Cc1ccc(F)cc1F)S(=O)(=O)c1cc(C(N)=O)c(NC(=O)c2cc[nH]n2)s1] | N-(3-carbamoyl-5-(N-(2,4-difluorobenzyl)-N-methylsulfamoyl)thiophen-2-yl)-1H-pyrazole-3-carboxamide | H3, E1, F1 | 8 | 455 | 456 |
| 173 | 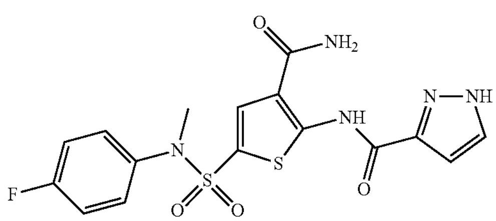 [SMILES: CN(c1ccc(F)cc1)S(=O)(=O)c1cc(C(N)=O)c(NC(=O)c2cc[nH]n2)s1] | N-(3-carbamoyl-5-(N-(4-fluorophenyl)-N-methylsulfamoyl)thiophen-2-yl)-1H-pyrazole-3-carboxamide | H3, E1, F1 | 8 | 423 | 424 |
| 174 | 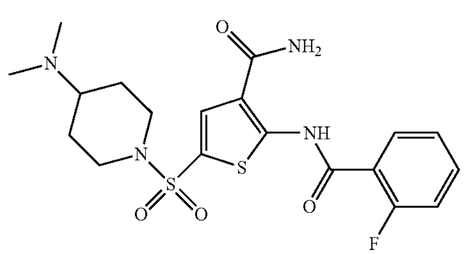 [SMILES: CN(C)C1CCN(S(=O)(=O)c2cc(C(N)=O)c(NC(=O)c3ccccc3F)s2)CC1] | 5-(4-(dimethylamino)piperidin-1-ylsulfonyl)-2-(2-fluorobenzamido)thiophene-3-carboxamide | H3, E1, F2 | 8 | 455 | 455 |
| 175 | 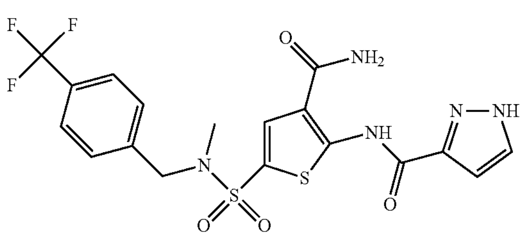 [SMILES: CN(Cc1ccc(C(F)(F)F)cc1)S(=O)(=O)c1cc(C(N)=O)c(NC(=O)c2cc[nH]n2)s1] | N-(3-carbamoyl-5-(N-methyl-N-(4-(trifluoromethyl)benzyl)sulfamoyl)thiophen-2-yl)-1H-pyrazole-3-carboxamide | H3, E1, F1 | 8 | 487 | 488 |

TABLE II-continued

List of final compounds

| Cpd # | Structure | Name | Mtd | Int | MW | Mes |
|---|---|---|---|---|---|---|
| 176 | 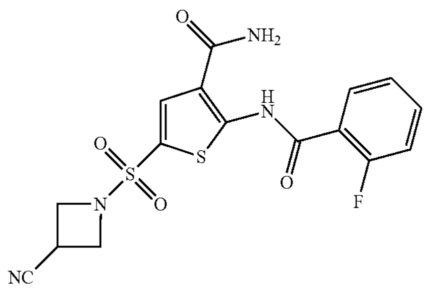 [SMILES: N#CC1CN(S(=O)(=O)c2cc(C(N)=O)c(NC(=O)c3ccccc3F)s2)C1] | 5-(3-cyanoazetidin-1-ylsulfonyl)-2-(2-fluorobenzamido)thiophene-3-carboxamide | A, E2, F2, H2 | 8 | 408 | 409 |
| 177 | 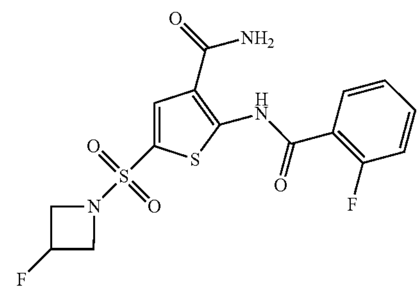 [SMILES: NC(=O)c1cc(S(=O)(=O)N2CC(F)C2)sc1NC(=O)c1ccccc1F] | 5-(3-fluoroazetidin-1-ylsulfonyl)-2-(2-fluorobenzamido)thiophene-3-carboxamide | A, E2, F2, H2 | 8 | 401 | 402 |
| 178 | 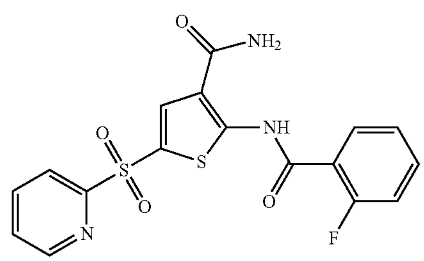 [SMILES: NC(=O)c1cc(S(=O)(=O)c2ccccn2)sc1NC(=O)c1ccccc1F] | 2-(2-fluorobenzamido)-5-(pyridin-2-ylsulfonyl)thiophene-3-carboxamide | A, B1, D1, H2 | 8 | 405 | 406 |
| 179 | 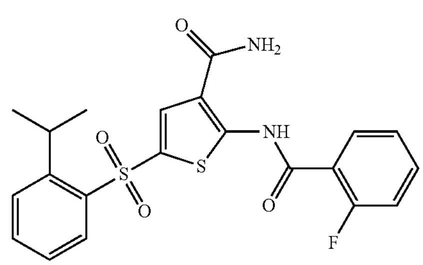 [SMILES: CC(C)c1ccccc1S(=O)(=O)c1cc(C(N)=O)c(NC(=O)c2ccccc2F)s1] | 2-(2-fluorobenzamido)-5-(2-isopropylphenylsulfonyl)thiophene-3-carboxamide | A, B1, D1, H2 | 8 | 447 | 447 |
| 180 | 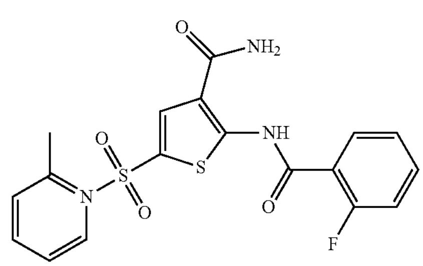 | 2-(2-fluorobenzamido)-5-(o-tolylsulfonyl)thiophene-3-carboxamide | A, B1, D1, H2 | 8 | 418 | 419 |

TABLE II-continued

List of final compounds

| Cpd # | Structure | Name | Mtd | Int | MW | Mes |
|---|---|---|---|---|---|---|
| 181 | 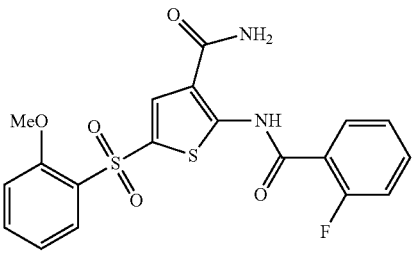 [SMILES: COc1ccccc1S(=O)(=O)c1cc(C(N)=O)c(NC(=O)c2ccccc2F)s1] | 2-(2-fluorobenzamido)-5-(2-methoxyphenylsulfonyl)thiophene-3-carboxamide | A, B1, D1, H2 | 8 | 434 | 435 |
| 182 | 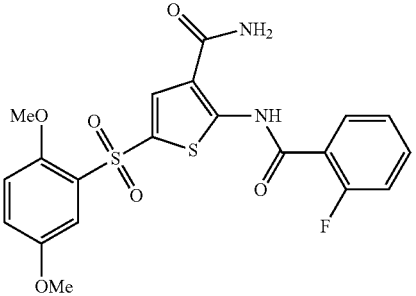 [SMILES: COc1ccc(OC)c(S(=O)(=O)c2cc(C(N)=O)c(NC(=O)c3ccccc3F)s2)c1] | 5-(2,5-dimethoxyphenylsulfonyl)-2-(2-fluorobenzamido)thiophene-3-carboxamide | A, B1, D1, H2 | 8 | 464 | 465 |
| 183 | 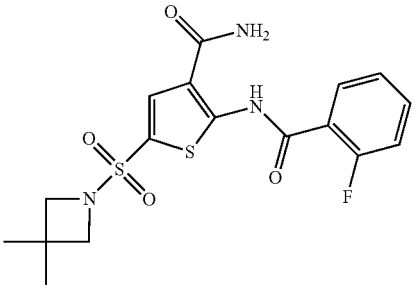 [SMILES: CC1(C)CN(S(=O)(=O)c2cc(C(N)=O)c(NC(=O)c3ccccc3F)s2)C1] | 5-(3,3-dimethylazetidin-1-ylsulfonyl)-2-(2-fluorobenzamido)thiophene-3-carboxamide | A, E1, F1, H2 | 8 | 411 | 412 |
| 184 | 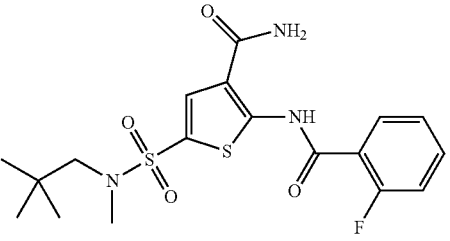 [SMILES: CN(CC(C)(C)C)S(=O)(=O)c1cc(C(N)=O)c(NC(=O)c2ccccc2F)s1] | 2-(2-fluorobenzamido)-5-(N-methyl-N-neopentylsulfamoyl)thiophene-3-carboxamide | A, E1, F1, H2 | 8 | 428 | 428 |
| 185 | 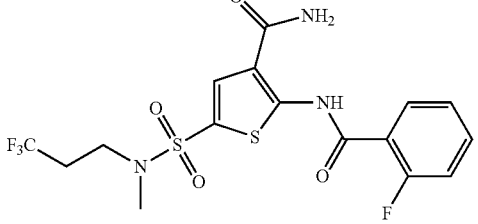 | 2-(2-fluorobenzamido)-5-(N-methyl-N-(3,3,3-trifluoropropyl)sulfamoyl)thiophene-3-carboxamide | A, E1, F1, H2 | 8 | 453 | 454 |

TABLE II-continued

List of final compounds

| Cpd # | Structure | Name | Mtd | Int | MW | Mes |
|---|---|---|---|---|---|---|
| 186 | 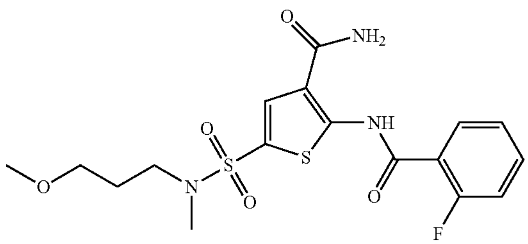 [SMILES: COCCCN(C)S(=O)(=O)c1cc(C(N)=O)c(NC(=O)c2ccccc2F)s1] | 2-(2-fluorobenzamido)-5-(N-(3-methoxypropyl)-N-methylsulfamoyl)thiophene-3-carboxamide | A, E1, F1, H2 | 8 | 429 | 430 |
| 187 | 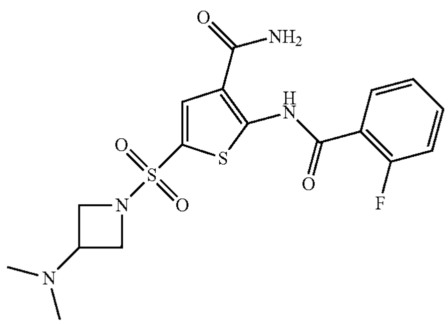 [SMILES: CN(C)C1CN(S(=O)(=O)c2cc(C(N)=O)c(NC(=O)c3ccccc3F)s2)C1] | 5-(3-(dimethylamino)azetidin-1-ylsulfonyl)-2-(2-fluorobenzamido)thiophene-3-carboxamide | A, E1, F1, H2 | 8 | 426 | 427 |
| 188 | 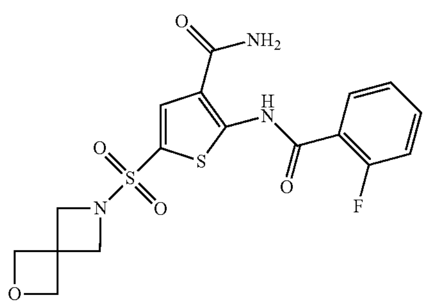 [SMILES: NC(=O)c1cc(S(=O)(=O)N2CC3(COC3)C2)sc1NC(=O)c1ccccc1F] | 5-(2-oxa-6-azaspiro[3.3]heptan-6-ylsulfonyl)-2-(2-fluorobenzamido)thiophene-3-carboxamide | A, E1, F1, H2 | 8 | 425 | 426 |
| 189 | 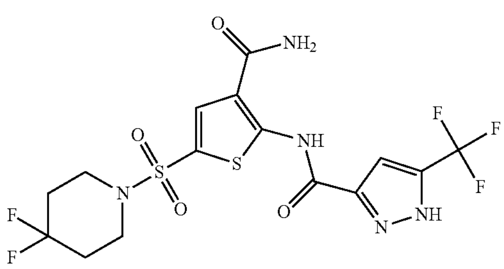 [SMILES: NC(=O)c1cc(S(=O)(=O)N2CCC(F)(F)CC2)sc1NC(=O)c1cc(C(F)(F)F)[nH]n1] | N-(3-carbmoyl-5-(4,4-difluoropiperidin-1-ylsulfonyl)thiophen-2-yl)-5-(trifluoromethyl)-1H-pyrazole-3-carboxamide | F2, G, H1 | 4 | 487 | 488 |
| 190 | 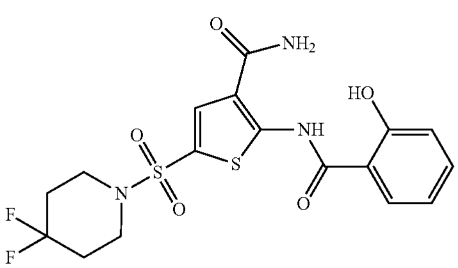 [SMILES: NC(=O)c1cc(S(=O)(=O)N2CCC(F)(F)CC2)sc1NC(=O)c1ccccc1O] | 5-(4,4-difluoropiperidin-1-ylsulfonyl)-2-(2-hydroxybenzamido)thiophene-3-carboxamide | F2, G, H1 | 4 | 445 | 446 |

TABLE II-continued

List of final compounds

| Cpd # | Structure | Name | Mtd Int | MW | Mes |
|---|---|---|---|---|---|
| 191 | 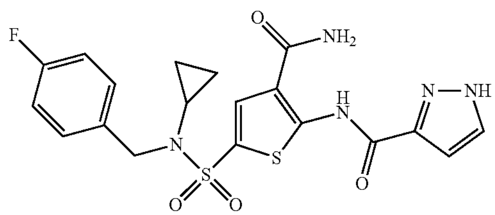 [SMILES: NC(=O)c1cc(S(=O)(=O)N(Cc2ccc(F)cc2)C2CC2)sc1NC(=O)c1cc[nH]n1] | N-(3-carbamoyl-5-(N-cyclopropyl-N-(4-fluorobenzyl)sulfamoyl)thiophen-2-yl)-1H-pyrazole-3-carboxamide | H3, E1, 8 F1 | 464 | 464 |
| 192 | 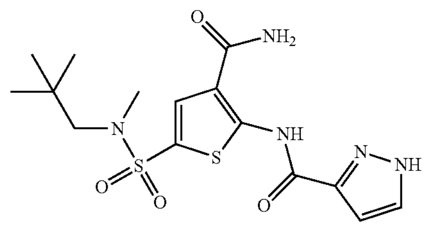 [SMILES: CN(CC(C)(C)C)S(=O)(=O)c1cc(C(N)=O)c(NC(=O)c2cc[nH]n2)s1] | N-(3-carbamoyl-5-(N-methyl-N-neopentylsulfamoyl)thiophen-2-yl)-1H-pyrazole-3-carboxamide | H3, E1, 8 F1 | 399 | 400 |
| 193 | 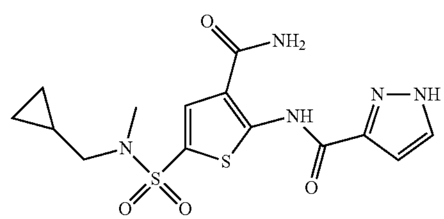 [SMILES: CN(CC1CC1)S(=O)(=O)c1cc(C(N)=O)c(NC(=O)c2cc[nH]n2)s1] | N-(3-carbamoyl-5-(N-(cyclopropylmethyl)-N-methylsulfamoyl)thiophen-2-yl)-1H-pyrazole-3-carboxamide | H3, E1, 8 F1 | 383 | 384 |
| 194 | 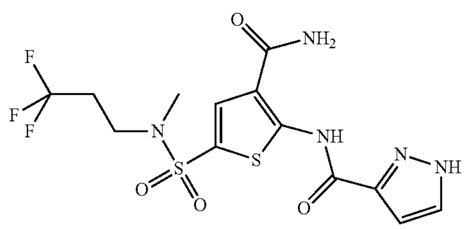 [SMILES: CN(CCC(F)(F)F)S(=O)(=O)c1cc(C(N)=O)c(NC(=O)c2cc[nH]n2)s1] | N-(3-carbamoyl-5-(N-methyl-N-(3,3,3-trifluoropropyl)sulfamoyl)thiophen-2-yl)-1H-pyrazole-3-carboxamide | H3, E1, 8 F1 | 425 | 426 |
| 195 | 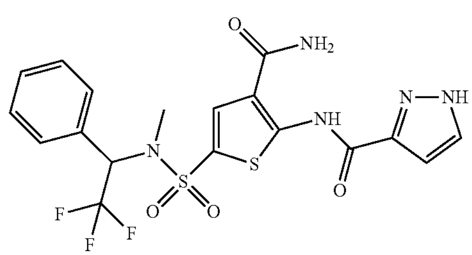 [SMILES: CN(C(c1ccccc1)C(F)(F)F)S(=O)(=O)c1cc(C(N)=O)c(NC(=O)c2cc[nH]n2)s1] | N-(3-carbamoyl-5-(N-methyl-N-(2,2,2-trifluoro-phenylethyl)sulfamoyl)thiophen-2-yl)-1H-pyrazole-3-carboxamide | H3, E1, 8 F1 | 487 | 488 |
| 196 | 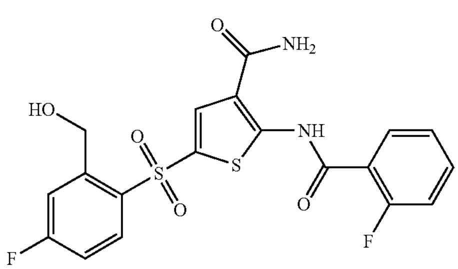 [SMILES: NC(=O)c1cc(S(=O)(=O)c2ccc(F)cc2CO)sc1NC(=O)c1ccccc1F] | 5-(4-fluoro-2-(hydroxymethyl)phenylsulfonyl)-2-(2-fluorobenzamido)thiophene-3-carboxamide | A, C, 8 D1, H2 | 452 | 453 |

TABLE II-continued

List of final compounds

| Cpd # | Structure | Name | Mtd | Int | MW | Mes |
|---|---|---|---|---|---|---|
| 197 | 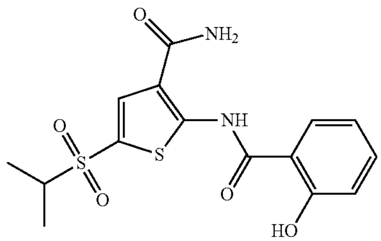 [SMILES: CC(C)S(=O)(=O)c1cc(C(N)=O)c(NC(=O)c2ccccc2O)s1] | 2-(2-hydroxybenzaido)-5-(isopropylsulfonyl)thiophene-3-carboxamide | A, B1, D1, H2 | 8 | 368 | 369 |
| 198 | 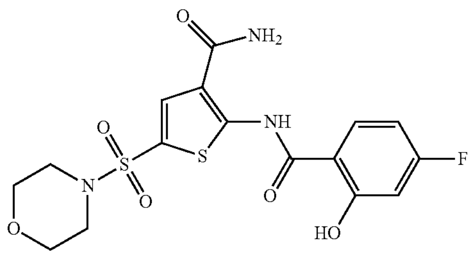 [SMILES: NC(=O)c1cc(S(=O)(=O)N2CCOCC2)sc1NC(=O)c1ccc(F)cc1O] | 2-(4-fluoro-2-hydroxybenzamido)-5-(morpholinosulfonyl)thiophene-3-carboxamide | F2, G, H3 | 4 | 429 | 430 |
| 199 | 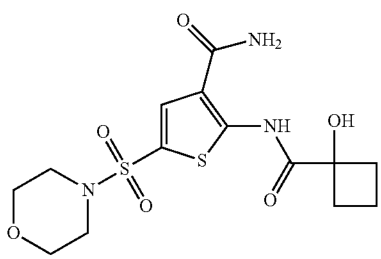 [SMILES: NC(=O)c1cc(S(=O)(=O)N2CCOCC2)sc1NC(=O)C1(O)CCC1] | 2-(1-hydroxycyclobutanecarboxamido)-5-(morpholinosulfonyl)thiophene-3-carboxamide | F2, G, H3 | 4 | 389 | 390 |
| 200 | 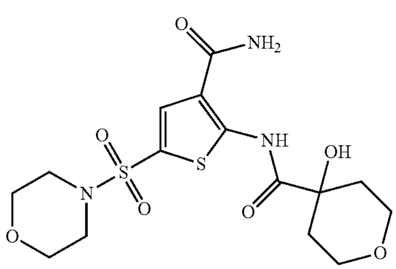 [SMILES: NC(=O)c1cc(S(=O)(=O)N2CCOCC2)sc1NC(=O)C1(O)CCOCC1] | N-(3-carbamoyl-5-(morpholinosulfonyl)thiophen-2-yl)-4-hydroxytetrahydro-2H-pyran-4-carboxamide | A, B1, D1, H2, J | 8 | 419 | 420 |
| 201 | 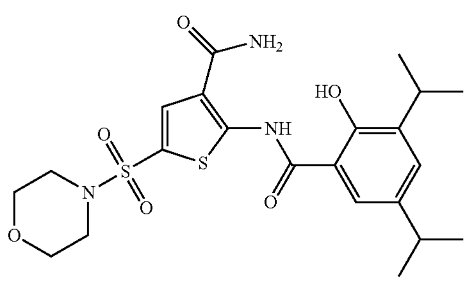 [SMILES: CC(C)c1cc(C(=O)Nc2sc(S(=O)(=O)N3CCOCC3)cc2C(N)=O)c(O)c(C(C)C)c1] | 2-(2-hydroxy-3,5-diisopropylbenzamido)-5-(morpholinosulfonyl)thiophene-3-carboxamide | F2, G, H3 | 4 | 496 | 496 |
| 202 | 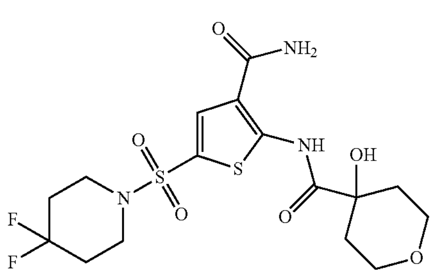 [SMILES: NC(=O)c1cc(S(=O)(=O)N2CCC(F)(F)CC2)sc1NC(=O)C1(O)CCOCC1] | N-(3-carbamoyl-5-(4,4-difluoropiperidin-1-ylsulfonyl)thiophen-2-yl)-4-hydroxytetrahydro-2H-pyran-4-carboxamide | F2, G, H3 | 4 | 453 | 454 |

TABLE II-continued

List of final compounds

| Cpd # | Structure | Name | Mtd | Int | MW | Mes |
|---|---|---|---|---|---|---|
| 203 | 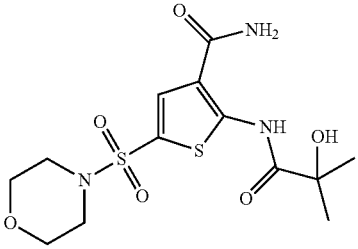 [SMILES: CC(C)(O)C(=O)Nc1sc(S(=O)(=O)N2CCOCC2)cc1C(N)=O] | 2-(2-hydroxy-2-methylpropanamido)-5-(morpholinosulfonyl)thiophene-3-carboxamide | F2, G, H3 | 4 | 377 | 378 |
| 204 | 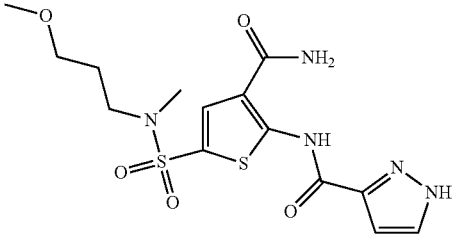 [SMILES: COCCCN(C)S(=O)(=O)c1cc(C(N)=O)c(NC(=O)c2cc[nH]n2)s1] | N-(3-carbamoyl-5-(N-(3-methoxypropyl)-N-methylsulfamoyl)thiophen-2-yl)-1H-pyrazole-3-carboxamide | H3, E1, F1 | 8 | 401 | 402 |
| 205 | 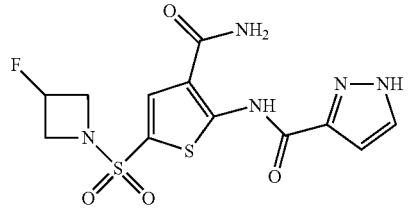 [SMILES: NC(=O)c1cc(S(=O)(=O)N2CC(F)C2)sc1NC(=O)c1cc[nH]n1] | N-(3-carbamoyl-5-(3-fluoroazetidin-1-ylsulfonyl)thiophen-2-yl)-1H-pyrazole-3-carboxamide | H3, E1, F1 | 8 | 373 | 374 |
| 206 | 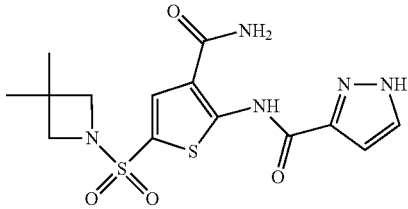 [SMILES: CC1(C)CN(S(=O)(=O)c2cc(C(N)=O)c(NC(=O)c3cc[nH]n3)s2)C1] | N-(3-carbamoyl-5-(3,3-dimethylazetidin-1-ylsulfonyl)thiophen-2-yl)-1H-pyrazole-3-carboxamide | H3, E1, F1 | 8 | 383 | 384 |
| 207 | 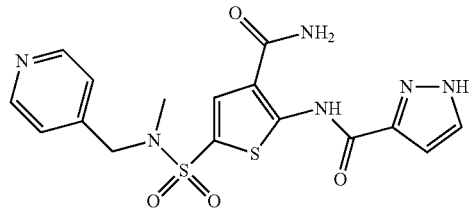 [SMILES: CN(Cc1ccncc1)S(=O)(=O)c1cc(C(N)=O)c(NC(=O)c2cc[nH]n2)s1] | N-(3-carbamoyl-5-(N-methyl-N-(pyridin-4-ylmethyl)sulfamoyl)thiophen-2-yl)-1H-pyrazole-3-carboxamide | H3, E1, F1 | 8 | 420 | 421 |
| 208 | 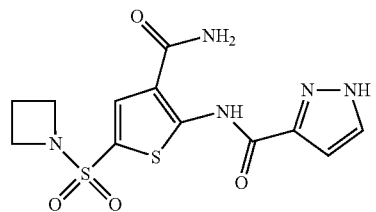 [SMILES: NC(=O)c1cc(S(=O)(=O)N2CCC2)sc1NC(=O)c1cc[nH]n1] | N-(5-(azetidin-1-ylsulfonyl)-3-carbamoylthiophen-2-yl)-1H-pyrazole-3-carboxamide | H3, E1, F1 | 8 | 355 | 356 |

TABLE II-continued

List of final compounds

| Cpd # | Structure | Name | Mtd | Int | MW | Mes |
|---|---|---|---|---|---|---|
| 209 | 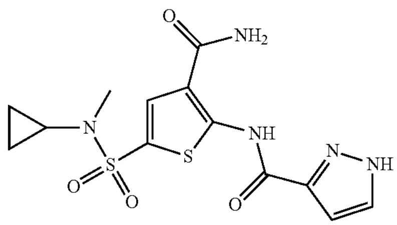 [SMILES: CN(C1CC1)S(=O)(=O)c1cc(C(N)=O)c(NC(=O)c2cc[nH]n2)s1] | N-(3-carbamoyl-5-(N-cyclopropyl-N-methylsulfamoyl)thiophen-2-yl)-1H-pyrazole-3-carboxamide | H3, E1, F1 | 8 | 369 | 370 |
| 210 | 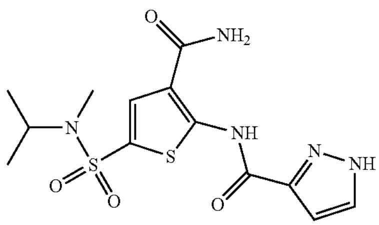 [SMILES: CC(C)N(C)S(=O)(=O)c1cc(C(N)=O)c(NC(=O)c2cc[nH]n2)s1] | N-(3-carbamoyl-5-(N-isopropyl-N-methylsulfamoyl)thiophen-2-yl)-1H-pyrazole-3-carboxamide | H3, E1, F1 | 8 | 371 | 372 |
| 211 | 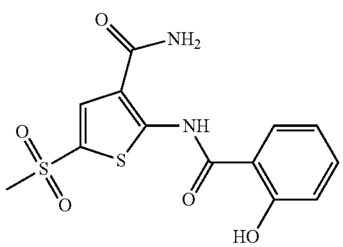 [SMILES: CS(=O)(=O)c1cc(C(N)=O)c(NC(=O)c2ccccc2O)s1] | 2-(2-hydroxybenzamido)-5-(methylsulfonyl)thiophene-3-carboxamide | A, B1, D1, H2 | 8 | 340 | 341 |
| 212 | 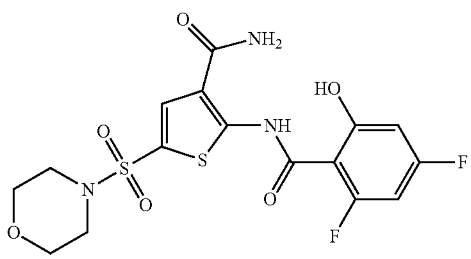 [SMILES: NC(=O)c1cc(S(=O)(=O)N2CCOCC2)sc1NC(=O)c1c(O)cc(F)cc1F] | 2-(2,4-difluoro-6-hydroxybenzamido)-5-(morpholinosulfonyl)thiophene-3-carboxamide | F2, G, H3 | 4 | 447 | 448 |
| 213 | 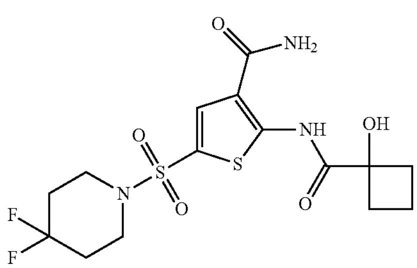 [SMILES: NC(=O)c1cc(S(=O)(=O)N2CCC(F)(F)CC2)sc1NC(=O)C1(O)CCC1] | 5-(4,4-difluoropiperidin-1-ylsulfonyl)-2-(1-hydroxycyclobutanecarboxamido)thiophene-3-carboxamide | F2, G, H3 | 4 | 423 | 424 |
| 214 | 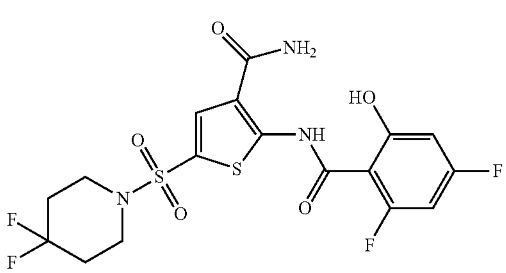 [SMILES: NC(=O)c1cc(S(=O)(=O)N2CCC(F)(F)CC2)sc1NC(=O)c1c(O)cc(F)cc1F] | 2-(2,4-difluoro-6-hydroxybenzamido)-5-(4,4-difluoropiperidin-1-ylsulfonyl)thiophene-3-carboxamide | F2, G, H3 | 4 | 481 | 482 |

TABLE II-continued

List of final compounds

| Cpd # | Structure | Name | Mtd | Int | MW | Mes |
|---|---|---|---|---|---|---|
| 215 | 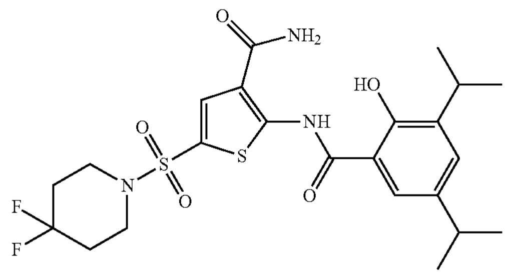 [SMILES: CC(C)c1cc(C(=O)Nc2sc(S(=O)(=O)N3CCC(F)(F)CC3)cc2C(N)=O)c(O)c(C(C)C)c1] | 5-(4,4-difluoropiperidin-1-ylsulfonyl)-2-(2-hydroxy-3,5-diisopropylbenzamido)thiophene-3-carboxamide | A, E1, F1, H2, K | 8 | 530 | 530 |
| 216 | 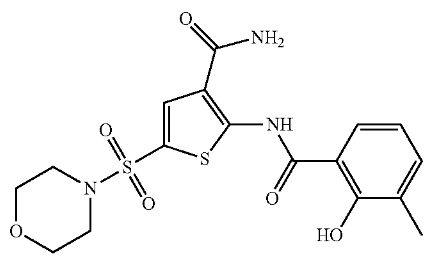 [SMILES: Cc1cccc(C(=O)Nc2sc(S(=O)(=O)N3CCOCC3)cc2C(N)=O)c1O] | 2-(2-hydroxy-3-methylbenzamido)-5-(morpholinosulfonyl)thiophene-3-carboxamide | A, B1, D1, H2, J | 8 | 425 | 426 |
| 217 | 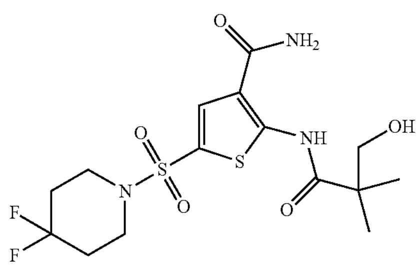 [SMILES: CC(C)(CO)C(=O)Nc1sc(S(=O)(=O)N2CCC(F)(F)CC2)cc1C(N)=O] | 5-(4,4-difluoropiperidin-1-ylsulfonyl)-2-(3-hydroxy-2,2-dimethylpropanamido)thiophene-3-carboxamide | A, B1, D1, H2, J | 8 | 425 | 426 |
| 218 | 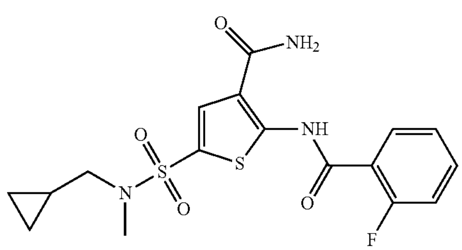 [SMILES: CN(CC1CC1)S(=O)(=O)c1cc(C(N)=O)c(NC(=O)c2ccccc2F)s1] | 5-(N-(cyclopropylmethyl)-N-methylsulfamoyl)-2-(2-fluorobenzamido)thiophene-3-carboxamide | A, E1, F1, H2 | 8 | 411 | 412 |
| 219 | 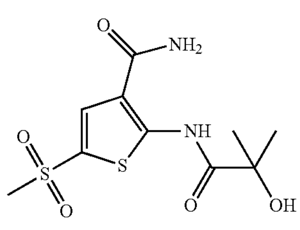 [SMILES: CC(C)(O)C(=O)Nc1sc(S(C)(=O)=O)cc1C(N)=O] | 2-(2-hydroxy-2-methylpropanamido)-5-(methylsulfonyl)thiophene-3-carboxamide | A, B1, D1, H2 | 8 | 306 | 307 |
| 220 | 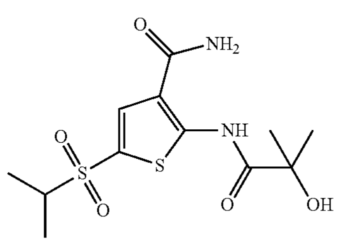 [SMILES: CC(C)S(=O)(=O)c1cc(C(N)=O)c(NC(=O)C(C)(C)O)s1] | 2-(2-hydroxy-2-methylpropanamido)-5-(isopropylsulfonyl)thiophene-3-carboxamide | A, B1, D1, H2 | 8 | 334 | 335 |

TABLE II-continued

List of final compounds

| Cpd # | Structure | Name | Mtd | Int | MW | Mes |
|---|---|---|---|---|---|---|
| 221 | 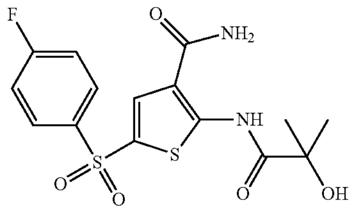 [SMILES: CC(C)(O)C(=O)Nc1sc(S(=O)(=O)c2ccc(F)cc2)cc1C(N)=O] | 5-(4-fluorophenylsulfonyl)-2-(2-hydroxy-2-methylpropanamido)thiophene-3-carboxamide | A, C, D1, G, H1, J | 1 | 386 | 387 |
| 222 | 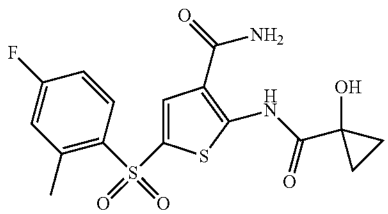 [SMILES: Cc1cc(F)ccc1S(=O)(=O)c1cc(C(N)=O)c(NC(=O)C2(O)CC2)s1] | 5-(4-fluoro-2-methylphenylsulfonyl)-2-(1-hydroxycyclopropanecarboxamido)thiophene-3-carboxamide | A, C, D1, H2, I, J, K | 8 | 398 | 399 |
| 223 | 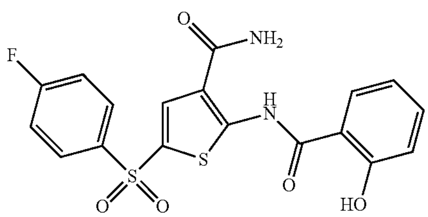 [SMILES: NC(=O)c1cc(S(=O)(=O)c2ccc(F)cc2)sc1NC(=O)c1ccccc1O] | 5-(4-fluorophenylsulfonyl)-2-(2-hydroxybenzamido)thiophene-3-carboxamide | A, C, D1, G, H1, J | 1 | 420 | 421 |
| 224 | 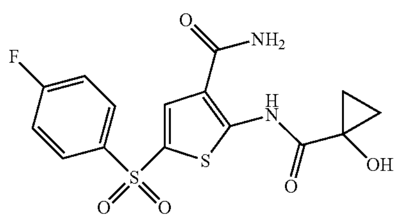 [SMILES: NC(=O)c1cc(S(=O)(=O)c2ccc(F)cc2)sc1NC(=O)C1(O)CC1] | 5-(4-fluorophenylsulfonyl)-2-(1-hydroxycyclopropanecarboxamido)thiophene-3-carboxamide | A, C, D1, G, H1, J | 1 | 384 | 385 |
| 225 | 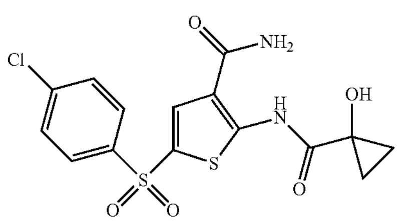 [SMILES: NC(=O)c1cc(S(=O)(=O)c2ccc(Cl)cc2)sc1NC(=O)C1(O)CC1] | 5-(4-chlorophenylsulfonyl)-2-(1-hydroxycyclopropanecarboxamido)thiophene-3-carboxamide | A, B2, D1, H2, I, J, K | 8 | 401 | 401 |
| 226 | 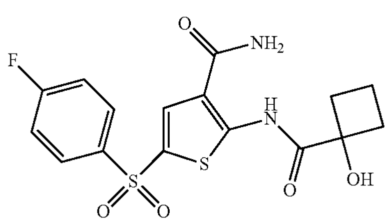 [SMILES: NC(=O)c1cc(S(=O)(=O)c2ccc(F)cc2)sc1NC(=O)C1(O)CCC1] | 5-(4-fluorophenylsulfonyl)-2-(1-hydroxycyclobutanecarboxamido)thiophene-3-carboxamide | A, C, D1, G, H1, J | 1 | 398 | 399 |
| 227 | 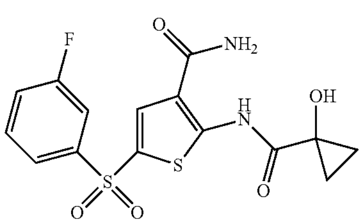 [SMILES: NC(=O)c1cc(S(=O)(=O)c2cccc(F)c2)sc1NC(=O)C1(O)CC1] | 5-(3-fluorophenylsulfonyl)-2-(1-hydroxycyclopropanecarboxamido)thiophene-3-carboxamide | A, C, D1, H2, I, J, K | 8 | 384 | 385 |

TABLE II-continued

List of final compounds

| Cpd # | Structure | Name | Mtd | Int | MW | Mes |
|---|---|---|---|---|---|---|
| 228 | 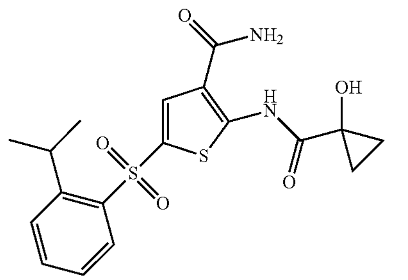 [SMILES: CC(C)c1ccccc1S(=O)(=O)c1cc(C(N)=O)c(NC(=O)C2(O)CC2)s1] | 2-(1-hydroxycyclopropanecarboxamido)-5-(2-isopropylphenylsulfonyl) thiophene-3-carboxamide | A, C, D1, H2, I, J, K | 8 | 408 | 409 |
| 229 | 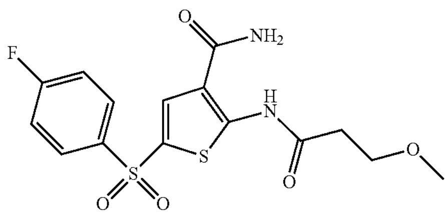 [SMILES: COCCC(=O)Nc1sc(S(=O)(=O)c2ccc(F)cc2)cc1C(N)=O] | 5-(4-fluorophenylsulfonyl)-2-(3-methoxypropanamido) thiophene-3-carboxamide | A, C, D1, G, H1 | 1 | 386 | 387 |
| 230 | 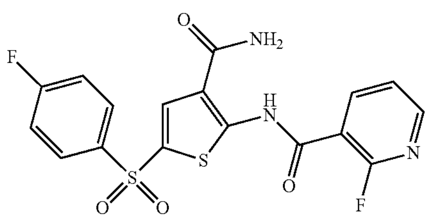 [SMILES: NC(=O)c1cc(S(=O)(=O)c2ccc(F)cc2)sc1NC(=O)c1cccnc1F] | N-(3-carbamoyl-5-(4-fluorophenylsulfonyl) thiophen-2-yl)-2-fluoronicotinamide | A, C, D1, G, H1 | 1 | 423 | 424 |
| 231 | 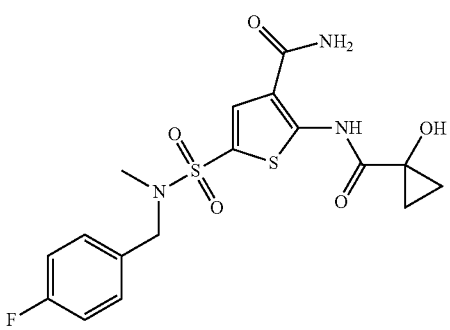 [SMILES: CN(Cc1ccc(F)cc1)S(=O)(=O)c1cc(C(N)=O)c(NC(=O)C2(O)CC2)s1] | 5-(N-(4-fluorobenzyl)-N-methylsulfamoyl)-2-(1-hydroxycyclopropanecarboxamido) thiophene-3-carboxamide | I, H2, A, B1, E2, F2, J | 8 | 427 | 428 |
| 232 | 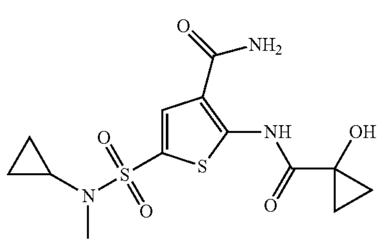 [SMILES: CN(C1CC1)S(=O)(=O)c1cc(C(N)=O)c(NC(=O)C2(O)CC2)s1] | 5-(N-cyclopropyl-N-methylsulfamoyl)-2-(1-hydroxycyclopropanecarboxamido) thiophene-3-carboxamide | I, H2, A, B1, E2, F2, J | 8 | 359 | 360 |
| 233 | 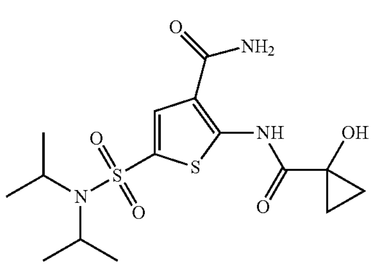 [SMILES: CC(C)N(C(C)C)S(=O)(=O)c1cc(C(N)=O)c(NC(=O)C2(O)CC2)s1] | 5-(N,N-diisopropylsulfamoyl)-2-(1-hydroxycyclopropanecarboxamido) thiophene-3-carboxamide | I, H2, A, B1, E2, F2, J | 8 | 389 | 390 |

TABLE II-continued

List of final compounds

| Cpd # | Structure | Name | Mtd | Int | MW | Mes |
|---|---|---|---|---|---|---|
| 234 | 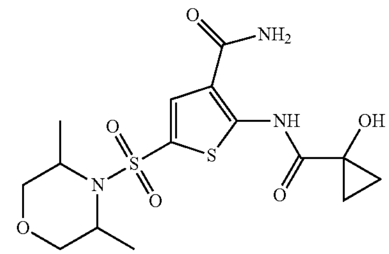 [SMILES: CC1COCC(C)N1S(=O)(=O)c1cc(C(N)=O)c(NC(=O)C2(O)CC2)s1] | 5-(3,5-dimethylmorpholinosulfonyl)-2-(1-hydroxycyclopropanecarboxamido) thiophene-3-carboxamide | I, H2, A, B1, E2, F2, J | 8 | 403 | 404 |
| 235 | 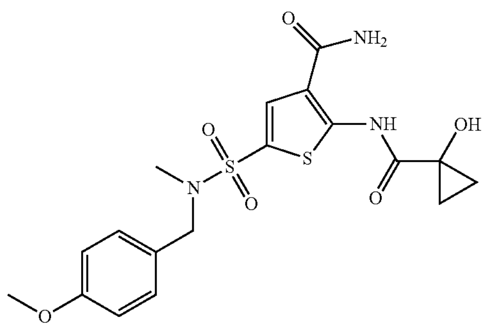 [SMILES: COc1ccc(CN(C)S(=O)(=O)c2cc(C(N)=O)c(NC(=O)C3(O)CC3)s2)cc1] | 2-(1-hydroxycyclopropanecarboxamido)-5-(N-(4-methoxybenzyl)-N-methylsulfamoyl) thiophene-3-carboxamide | I, H2, A, B1, E2, F2, J | 8 | 440 | 440 |
| 236 | 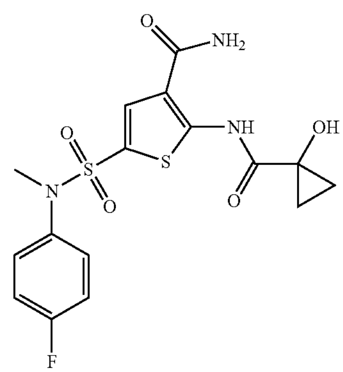 [SMILES: CN(c1ccc(F)cc1)S(=O)(=O)c1cc(C(N)=O)c(NC(=O)C2(O)CC2)s1] | 5-(N-(4-fluorophenyl)-N-methylsulfamoyl)-2-(1-hydroxycyclopropanecarboxamido) thiophene-3-carboxamide | I, H2, A, B1, E2, F2, J | 8 | 413 | 414 |
| 237 | 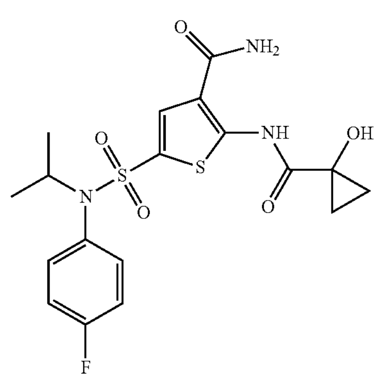 [SMILES: CC(C)N(c1ccc(F)cc1)S(=O)(=O)c1cc(C(N)=O)c(NC(=O)C2(O)CC2)s1] | 5-(N-(4-fluorophenyl)-N-isopropylsulfamoyl)-2-(1-hydroxycyclopropanecarboxamido) thiophene-3-carboxamide | I, H2, A, B1, E2, F2, J | 8 | 442 | 442 |

TABLE II-continued

List of final compounds

| Cpd # | Structure | Name | Mtd | Int | MW | Mes |
|---|---|---|---|---|---|---|
| 238 | 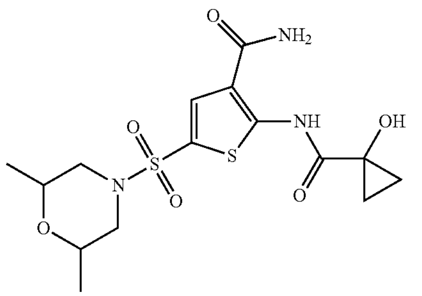 [SMILES: CC1CN(S(=O)(=O)c2cc(C(N)=O)c(NC(=O)C3(O)CC3)s2)CC(C)O1] | 5-(2,6-dimethylmorpholinosulfonyl)-2-(1-hydroxycyclopropanecarboxamido)thiophene-3-carboxamide | I, H2, A, B1, E2, F2, J | 8 | 403 | 404 |
| 239 | 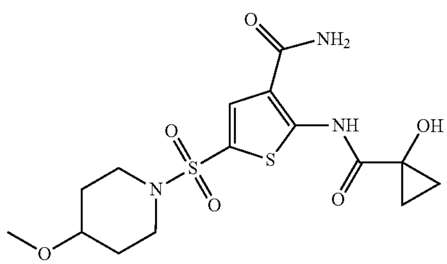 [SMILES: COC1CCN(S(=O)(=O)c2cc(C(N)=O)c(NC(=O)C3(O)CC3)s2)CC1] | 2-(1-hydroxycyclopropanecarboxamido)-5-(4-methoxypiperidin-1-ylsulfonyl)thiophene-3-carboxamide | I, H2, A, B1, E2, F2, J | 8 | 403 | 404 |
| 240 | 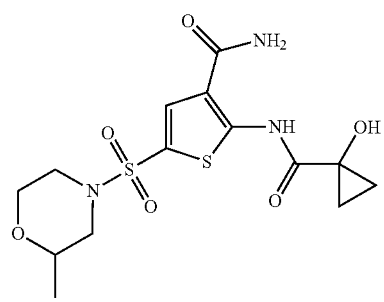 [SMILES: CC1CN(S(=O)(=O)c2cc(C(N)=O)c(NC(=O)C3(O)CC3)s2)CCO1] | 2-(1-hydroxycyclopropanecarboxamido)-5-(2-methylmorpholinosulfonyl)thiophene-3-carboxamide | I, K, H2, A, E2, F2 | 8 | 389 | 390 |
| 241 | 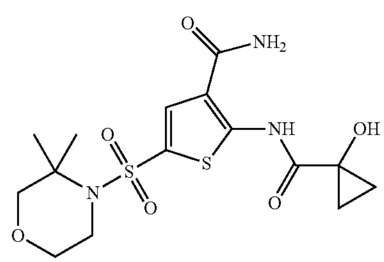 [SMILES: CC1(C)COCCN1S(=O)(=O)c1cc(C(N)=O)c(NC(=O)C2(O)CC2)s1] | 5-(3,3-dimethylmorpholinosulfonyl)-2-(1-hydroxycyclopropanecarboxamido)thiophene-3-carboxamide | I, K, H2, A, E2, F2 | 8 | 403 | 404 |
| 242 | 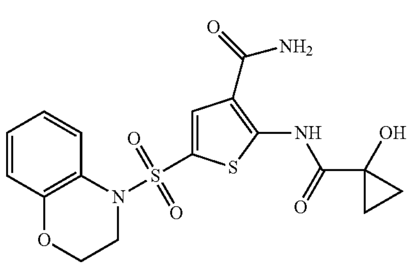 [SMILES: NC(=O)c1cc(S(=O)(=O)N2CCOc3ccccc32)sc1NC(=O)C1(O)CC1] | 5-(2H-benzo[b][1,4]oxazin-4(3H)-ylsulfonyl)-2-(1-hydroxycyclopropanecarboxamido)thiophene-3-carboxamide | I, K, H2, A, E2, F2 | 8 | 423 | 424 |

TABLE II-continued

List of final compounds

| Cpd # | Structure | Name | Mtd | Int | MW | Mes |
|---|---|---|---|---|---|---|
| 243 | 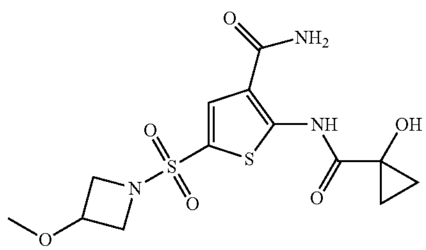 [SMILES: COC1CN(S(=O)(=O)c2cc(C(N)=O)c(NC(=O)C3(O)CC3)s2)C1] | 2-(1-hydroxycyclopropanecarboxamido)-5-(3-methoxyazetidin-1-ylsulfonyl)thiophene-3-carboxamide | I, K, H2, A, E2, F2 | 8 | 375 | 376 |
| 244 | 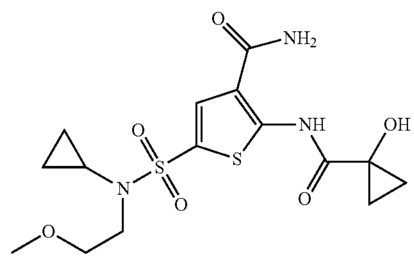 [SMILES: COCCN(C1CC1)S(=O)(=O)c1cc(C(N)=O)c(NC(=O)C2(O)CC2)s1] | 5-(N-cyclopropyl-N-(2-methoxyethyl)sulfamoyl)-2-(1-hydroxycyclopropanecarboxamido)thiophene-3-carboxamide | I, K, H2, A, E2, F2 | 8 | 403 | 404 |
| 245 | 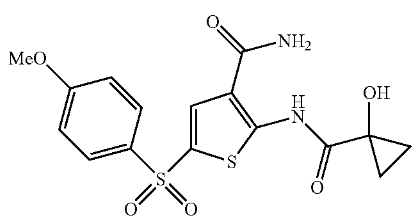 [SMILES: COc1ccc(S(=O)(=O)c2cc(C(N)=O)c(NC(=O)C3(O)CC3)s2)cc1] | 2-(1-hydroxycyclopropanecarboxamido)-5-(4-methoxyphenylsulfonyl)thiophene-3-carboxamide | A, C, D1, H3, I, J | 8 | 396 | 397 |
| 246 | 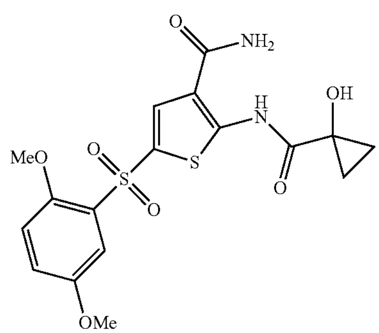 [SMILES: COc1ccc(OC)c(S(=O)(=O)c2cc(C(N)=O)c(NC(=O)C3(O)CC3)s2)c1] | 5-(2,5-dimethoxyphenylsulfonyl)-2-(1-hydroxycyclopropanecarboxamido)thiophene-3-carboxamide | A, C, D1, H3, I, J | 8 | 426 | 427 |
| 247 | 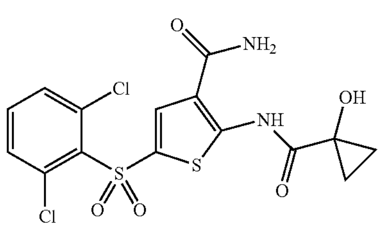 [SMILES: NC(=O)c1cc(S(=O)(=O)c2c(Cl)cccc2Cl)sc1NC(=O)C1(O)CC1] | 5-(2,6-dichlorophenylsulfonyl)-2-(1-hydroxycyclopropanecarboxamido)thiophene-3-carboxamide | A, B2, D1, H3, I, J | 8 | 435 | 435 |
| 248 | 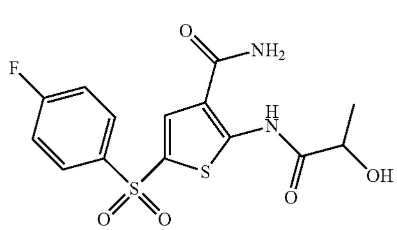 [SMILES: CC(O)C(=O)Nc1sc(S(=O)(=O)c2ccc(F)cc2)cc1C(N)=O] | 5-(4-fluorophenylsulfonyl)-2-(2-hydroxypropanamido)thiophene-3-carboxamide | A, C, D1, G, H1, J | 1 | 372 | 373 |

TABLE II-continued

List of final compounds

| Cpd # | Structure | Name | Mtd | Int | MW | Mes |
|---|---|---|---|---|---|---|
| 249 | 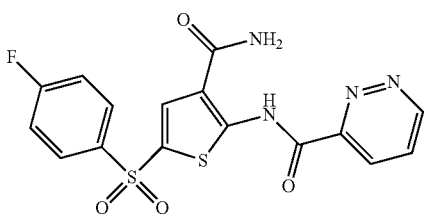 [SMILES: NC(=O)c1cc(S(=O)(=O)c2ccc(F)cc2)sc1NC(=O)c1cccnn1] | N-(3-carbamoyl-5-(4-fluorophenylsulfonyl)thiophen-2-yl)pyridazine-3-carboxamide | A, C, D1, G, H1 | 1 | 406 | 407 |
| 250 | 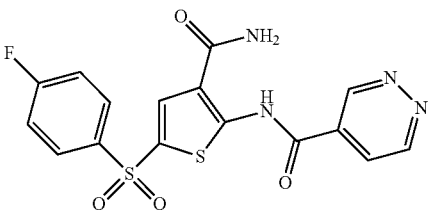 [SMILES: NC(=O)c1cc(S(=O)(=O)c2ccc(F)cc2)sc1NC(=O)c1ccnnc1] | N-(3-carbamoyl-5-(4-fluorophenylsulfonyl)thiophen-2-yl)pyridazine-4-carboxamide | A, C, D1, G, H1 | 1 | 406 | 407 |
| 251 | 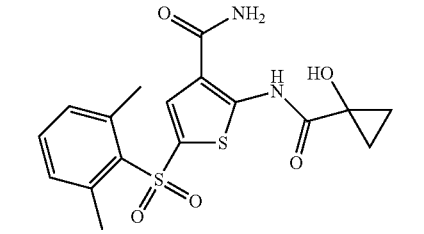 [SMILES: Cc1cccc(C)c1S(=O)(=O)c1cc(C(N)=O)c(NC(=O)C2(O)CC2)s1] | 5-(2,6-dimethylphenylsulfonyl)-2-(1-hydroxycyclopropanecarboxamido)thiophene-3-carboxamide | A, B2, D1, H3, I, J | 8 | 394 | 395 |
| 252 | 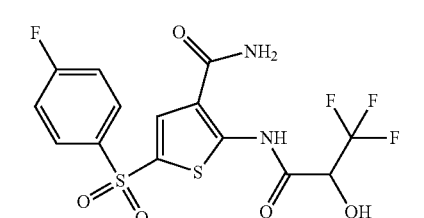 | 5-(4-fluorophenylsulfonyl)-2-(3,3,3-trifluoro-2-hydroxypropanamido)thiophene-3-carboxamide | A, C, D1, G, I, H1, J | 2 | 426 | 427 |
| 253 | 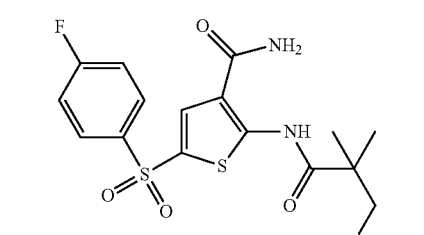 | 5-(4-fluorophenylsulfonyl)-2-(3-hydroxy-2,2-dimethylpropanamido)thiophene-3-carboxamide | A, C, D1, G, I, H1, J | 2 | 400 | 401 |
| 254 | 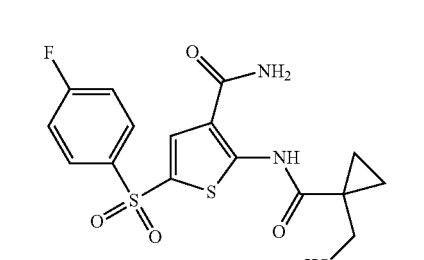 | 5-(4-fluorophenylsulfonyl)-2-(1-(hydroxymethyl)cyclopropanecarboxamido)thiophene-3-carboxamide | A, C, D1, G, I, H1, J | 2 | 398 | 399 |

TABLE II-continued

List of final compounds

| Cpd # | Structure | Name | Mtd | Int | MW | Mes |
|---|---|---|---|---|---|---|
| 255 | | N-(3-carbamoyl-5-(4-fluorophenylsulfonyl)thiophen-2-yl)-4-hydroxytetrahydro-2H-pyran-4-carboxamide | A, C, D1, G, I, H1, J1 | 8 | 428 | 429.0 |
| 255 | | 5-(2-chloro-4-fluorophenylsulfonyl)-2-(1-hydroxycyclopropanecarboxamido)thiophene-3-carboxamide | A, B2, D1, H, I, J1, K | 8 | 419 | 419.0 |
| 256 | 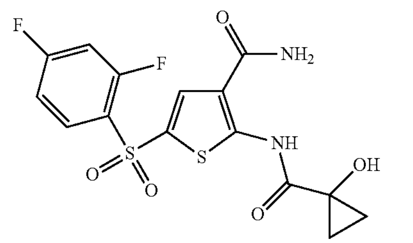 [SMILES: NC(=O)c1cc(S(=O)(=O)c2ccc(F)cc2F)sc1NC(=O)C1(O)CC1] | 5-(2,4-difluorophenylsulfonyl)-2-(1-hydroxycyclopropanecarboxamido)thiophene-3-carboxamide | A, B2, D1, H, I, J1, K | 8 | 402 | 403.0 |
| 257 | 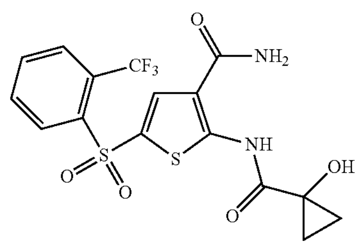 [SMILES: NC(=O)c1cc(S(=O)(=O)c2ccccc2C(F)(F)F)sc1NC(=O)C1(O)CC1] | 2-(1-hydroxycyclopropanecarboxamido)-5-(2-(trifluoromethyl)phenylsulfonyl)thiophene-3-carboxamide | A, B2, D1, H, I, J1, K | 8 | 434 | 435.0 |
| 258 | 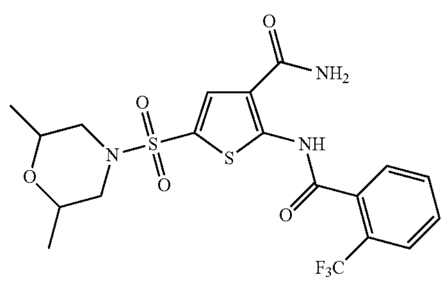 [SMILES: CC1CN(S(=O)(=O)c2cc(C(N)=O)c(NC(=O)c3ccccc3C(F)(F)F)s2)CC(C)O1] | 5-(2,6-dimethylmorpholinosulfonyl)-2-(2-(trifluoromethyl)benzamido)thiophene-3-carboxamide | E1, F1, H2, K | 8 | 492 | 491.8 |
| 259 | 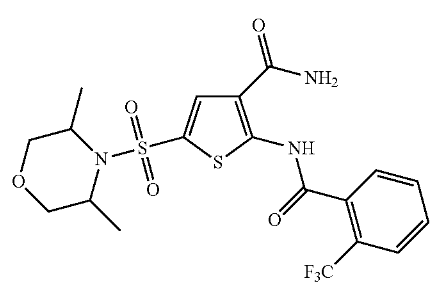 [SMILES: CC1COCC(C)N1S(=O)(=O)c1cc(C(N)=O)c(NC(=O)c2ccccc2C(F)(F)F)s1] | 5-(3,5-dimethylmorpholinosulfonyl)-2-(2-(trifluoromethyl)benzamido)thiophene-3-carboxamide | E1, F1, H2, K | 8 | 492 | 491.8 |

TABLE II-continued

List of final compounds

| Cpd # | Structure | Name | Mtd | Int | MW | Mes |
|---|---|---|---|---|---|---|
| 260 | 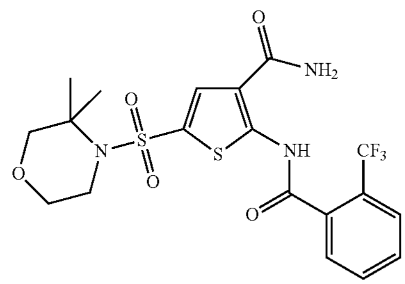 [SMILES: CC1(C)COCCN1S(=O)(=O)c1cc(C(N)=O)c(NC(=O)c2ccccc2C(F)(F)F)s1] | 5-(3,3-dimethylmorpholinosulfonyl)-2-(2-(trifluoromethyl)benzamido)thiophene-3-carboxamide | E1, F1, H2, K | 8 | 492 | 491.8 |
| 261 | 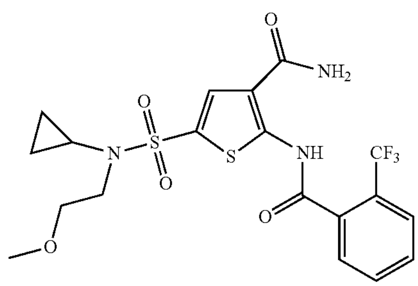 [SMILES: COCCN(C1CC1)S(=O)(=O)c1cc(C(N)=O)c(NC(=O)c2ccccc2C(F)(F)F)s1] | 5-(N-cyclopropyl-N-(2-methoxyethyl)sulfamoyl)-2-(2-(trifluoromethyl)benzamido)thiophene-3-carboxamide | E1, F1, H2, K | 8 | 492 | 491.8 |
| 262 | 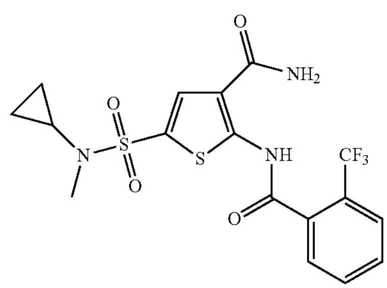 [SMILES: CN(C1CC1)S(=O)(=O)c1cc(C(N)=O)c(NC(=O)c2ccccc2C(F)(F)F)s1] | 5-(N-cyclopropyl-N-methylsulfamoyl)-2-(2-(trifluoromethyl)benzamido)thiophene-3-carboxamide | E1, F1, H2, K | 8 | 447 | 447.8 |
| 263 | 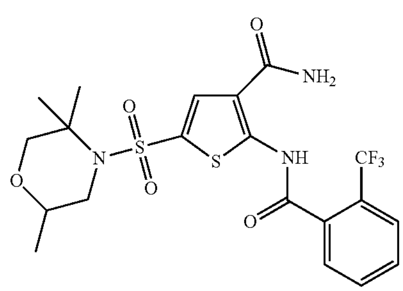 [SMILES: CC1CN(S(=O)(=O)c2cc(C(N)=O)c(NC(=O)c3ccccc3C(F)(F)F)s2)C(C)(C)CO1] | 2-(2-(trifluoromethyl)benzamido)-5-(2,5,5-trimethylmorpholinosulfonyl)thiophene-3-carboxamide | E1, F1, H2, K | 8 | 506 | 505.8 |
| 264 | 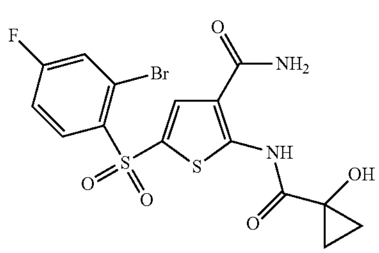 | 5-(2-bromo-4-fluorophenylsulfonyl)-2-(1-hydroxycyclopropanecarboxamido)thiophene-3-carboxamide | A, B2, D1, H, I, K | 8 | 463 | 465.0 |

TABLE II-continued

List of final compounds

| Cpd # | Structure | Name | Mtd | Int | MW | Mes |
|---|---|---|---|---|---|---|
| 265 | 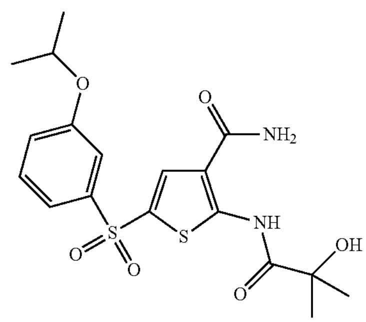 [SMILES: CC(C)Oc1cccc(S(=O)(=O)c2cc(C(N)=O)c(NC(=O)C(C)(C)O)s2)c1] | 2-(2-hydroxy-2-methylpropanamido)-5-(3-isopropoxyphenylsulfonyl)thiophene-3-carboxamide | A, B2, D1, H, I, J1, K | 8 | 427 | 426.8 |
| 266 | 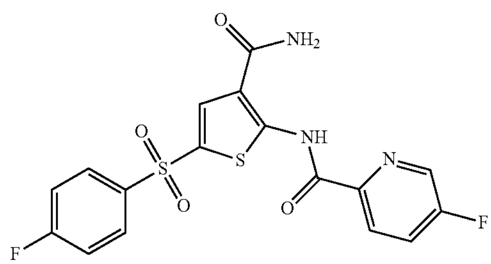 [SMILES: NC(=O)c1cc(S(=O)(=O)c2ccc(F)cc2)sc1NC(=O)c1ccc(F)cn1] | N-(3-carbamoyl-5-(4-fluorophenylsulfonyl)thiophen-2-yl)-5-fluoropicolinamide | C, D1, G, H1 | 1 | 423 | 424.0 |
| 267 | 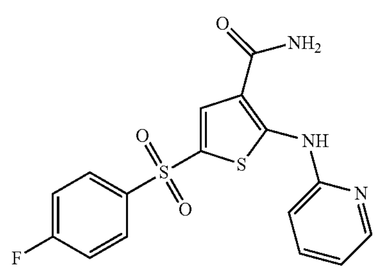 [SMILES: NC(=O)c1cc(S(=O)(=O)c2ccc(F)cc2)sc1Nc1ccccn1] | 5-(4-fluorophenylsulfonyl)-2-(pyridin-2-ylamino)thiophene-3-carboxamide | C, D1, G, B3 | 1 | 377 | 378.0 |
| 268 | 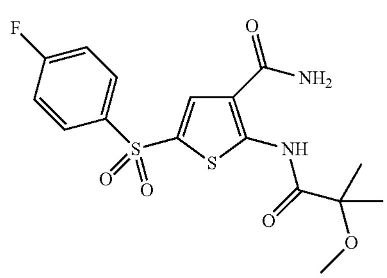 [SMILES: COC(C)(C)C(=O)Nc1sc(S(=O)(=O)c2ccc(F)cc2)cc1C(N)=O] | 5-(4-fluorophenylsulfonyl)-2-(2-methoxy-2-methylpropanamido)thiophene-3-carboxamide | A, C, D1, G, H1 | 8 | 400 | 401.0 |
| 269 | 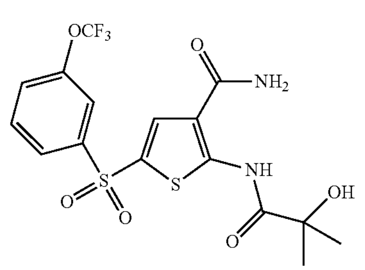 [SMILES: CC(C)(O)C(=O)Nc1sc(S(=O)(=O)c2cccc(OC(F)(F)F)c2)cc1C(N)=O] | 2-(2-hydroxy-2-methylpropanamido)-5-(3-(trifluoromethoxy)phenylsulfonyl)thiophene-3-carboxamide | A, B2, D1, H, I, J1, K | 8 | 452 | 453.1 |

TABLE II-continued

List of final compounds

| Cpd # | Structure | Name | Mtd | Int | MW | Mes |
|---|---|---|---|---|---|---|
| 270 | 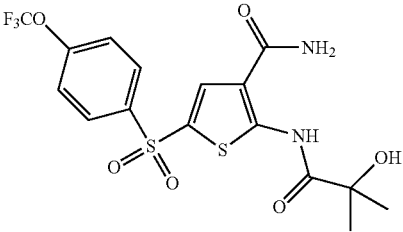 [SMILES: CC(C)(O)C(=O)Nc1sc(S(=O)(=O)c2ccc(OC(F)(F)F)cc2)cc1C(N)=O] | 2-(2-hydroxy-2-methylpropanamido)-5-(4-(trifluoromethoxy)phenylsulfonyl)thiophene-3-carboxamide | A, B2, D1, H, I, J1, K | 8 | 452 | 453.0 |
| 271 | 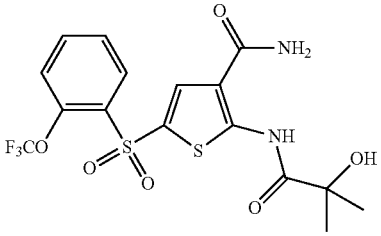 [SMILES: CC(C)(O)C(=O)Nc1sc(S(=O)(=O)c2ccccc2OC(F)(F)F)cc1C(N)=O] | 2-(2-hydroxy-2-methylpropanamido)-5-(2-(trifluoromethoxy)phenylsulfonyl)thiophene-3-carboxamide | A, B2, D1, H, I, J1, K | 8 | 452 | |
| 272 | 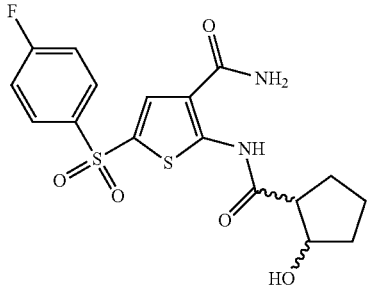 [SMILES: NC(=O)c1cc(S(=O)(=O)c2ccc(F)cc2)sc1NC(=O)C1CCCC1O] | 5-(4-fluorophenylsulfonyl)-2-(2-hydroxycyclopentanecarboxamido)thiophene-3-carboxamide | A, B2, D1, H, I, J1, K | 8 | 412 | 452.8 |
| 273 | 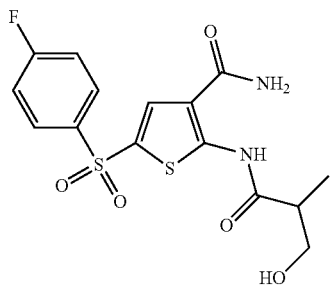 [SMILES: CC(CO)C(=O)Nc1sc(S(=O)(=O)c2ccc(F)cc2)cc1C(N)=O] | 5-(4-fluorophenylsulfonyl)-2-(3-hydroxy-2-methylpropanamido)thiophene-3-carboxamide | A, C, D1, G, I, H1, J | 8 | 386 | 453.0 |
| 274 | 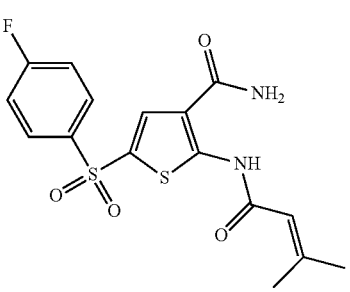 [SMILES: CC(C)=CC(=O)Nc1sc(S(=O)(=O)c2ccc(F)cc2)cc1C(N)=O] | 5-(4-fluorophenylsulfonyl)-2-(3-methylbut-2-enamido)thiophene-3-carboxamide | A, C, D1, G, I, H1, J | 8 | 382 | 413.0 |

TABLE II-continued

List of final compounds

| Cpd # | Structure | Name | Mtd | Int | MW | Mes |
|---|---|---|---|---|---|---|
| 275 | 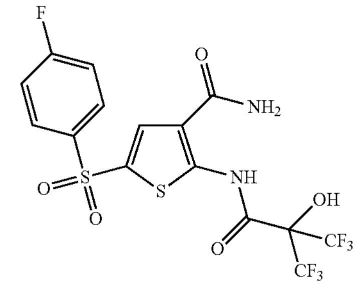 [SMILES: NC(=O)c1cc(S(=O)(=O)c2ccc(F)cc2)sc1NC(=O)C(O)(C(F)(F)F)C(F)(F)F] | 5-(4-fluorophenylsulfonyl)-2-(3,3,3-trifluoro-2-hydroxy-2-(trifluoromethyl)propanamido)thiophene-3-carboxamide | A, C, D1, G, I, H1, J | 8 | 494 | 387.0 |
| 276 | 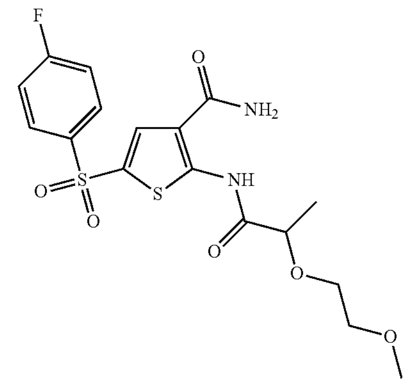 [SMILES: COCCOC(C)C(=O)Nc1sc(S(=O)(=O)c2ccc(F)cc2)cc1C(N)=O] | 5-(4-fluorophenylsulfonyl)-2-(2-(2-methoxyethoxy)propanamido)thiophene-3-carboxamide | A, C, D1, G, H4 | 8 | 430 | 383.0 |
| 277 | 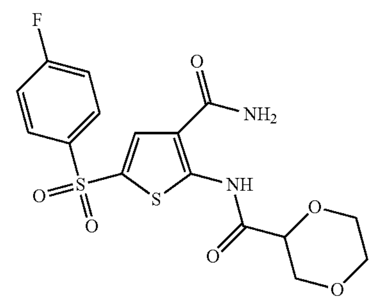 [SMILES: NC(=O)c1cc(S(=O)(=O)c2ccc(F)cc2)sc1NC(=O)C1COCCO1] | N-(3-carbamoyl-5-(4-fluorophenylsulfonyl)thiophen-2-yl)-1,4-dioxane-2-carboxamide | A, C, D1, G, H1 | 8 | 414 | 495.0 |
| 278 | 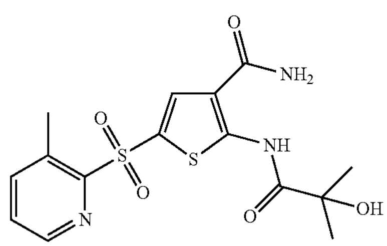 [SMILES: Cc1cccnc1S(=O)(=O)c1cc(C(N)=O)c(NC(=O)C(C)(C)O)s1] | 2-(2-hydroxy-2-methylpropanamido)-5-(3-methylpyridin-2-ylsulfonyl)thiophene-3-carboxamide | A, C, D1, G, H1 | 8 | 383 | 431.0 |
| 279 | 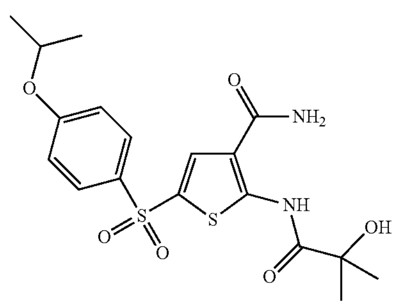 [SMILES: CC(C)Oc1ccc(S(=O)(=O)c2cc(C(N)=O)c(NC(=O)C(C)(C)O)s2)cc1] | 2-(2-hydroxy-2-methylpropanamido)-5-(4-isopropoxyphenylsulfonyl)thiophene-3-carboxamide | M3, A, C, D1, H, I, J1, K | 8 | 427 | 415.0 |

TABLE II-continued

List of final compounds

| Cpd # | Structure | Name | Mtd | Int | MW | Mes |
|---|---|---|---|---|---|---|
| 280 | 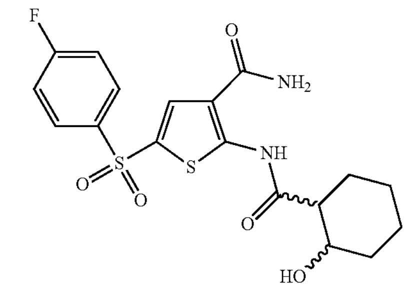 [SMILES: NC(=O)c1cc(S(=O)(=O)c2ccc(F)cc2)sc1NC(=O)C1CCCCC1O] | 5-(4-fluorophenylsulfonyl)-2-(2-hydroxycyclohexanecarboxamido)thiophene-3-carboxamide | A, C, D1, H, I, J1, K | 8 | 426 | 384.1 |
| 281 | 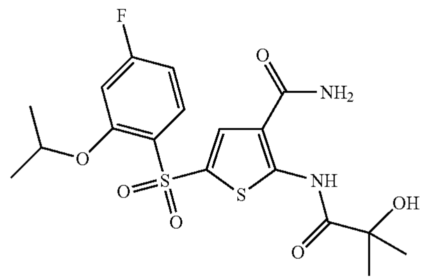 [SMILES: CC(C)Oc1cc(F)ccc1S(=O)(=O)c1cc(C(N)=O)c(NC(=O)C(C)(C)O)s1] | 5-(4-fluoro-2-isopropoxyphenylsulfonyl)-2-(2-hydroxy-2-methylpropanamido)thiophene-3-carboxamide | A, C, D1, G, I, H1, J1 | 8 | 445 | 427.1 |
| 282 | 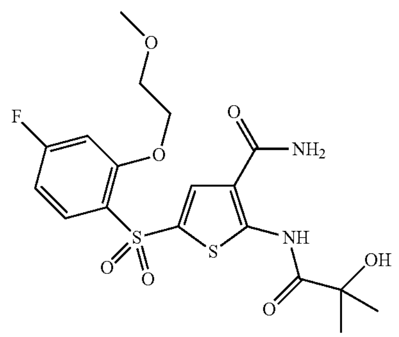 [SMILES: COCCOc1cc(F)ccc1S(=O)(=O)c1cc(C(N)=O)c(NC(=O)C(C)(C)O)s1] | 5-(4-fluoro-2-(2-methoxyethoxy)phenylsulfonyl)-2-(2-hydroxy-2-methylpropanamido)thiophene-3-carboxamide | M1, A, B2, D1, H, I, J2, K | 8 | 461 | 427.0 |
| 283 | 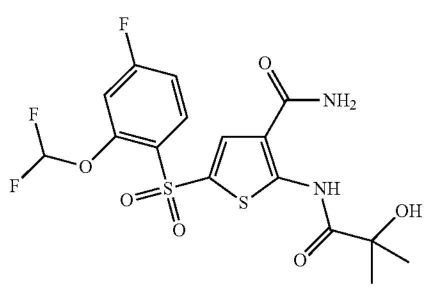 [SMILES: CC(C)(O)C(=O)Nc1sc(S(=O)(=O)c2ccc(F)cc2OC(F)F)cc1C(N)=O] | 5-(2-(difluoromethoxy)-4-fluorophenylsulfonyl)-2-(2-hydroxy-2-methylpropanamido)thiophene-3-carboxamide | M1, A, B2, D1, H, I, J2, K | 8 | 452 | 445.1 |
| 284 | 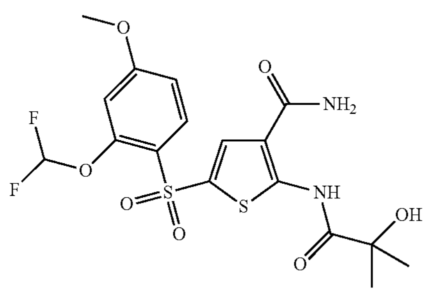 [SMILES: COc1ccc(S(=O)(=O)c2cc(C(N)=O)c(NC(=O)C(C)(C)O)s2)c(OC(F)F)c1] | 5-(2-(difluoromethoxy)-4-methoxyphenylsulfonyl)-2-(2-hydroxy-2-methylpropanamido)thiophene-3-carboxamide | M1, A, B2, D1, H, I, J2, K | 8 | 464 | 461.1 |

TABLE II-continued

List of final compounds

| Cpd # | Structure | Name | Mtd | Int | MW | Mes |
|---|---|---|---|---|---|---|
| 285 | 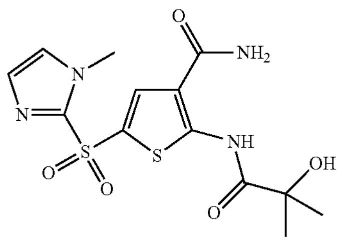 [SMILES: Cn1ccnc1S(=O)(=O)c1cc(C(N)=O)c(NC(=O)C(C)(C)O)s1] | 2-(2-hydroxy-2-methylpropanamido)-5-(1-methyl-1H-imidazol-2-ylsulfonyl) thiophene-3-carboxamide | M1, A, B2, D1, H, I, J2, K | 8 | 372 | 452.9 |
| 286 | 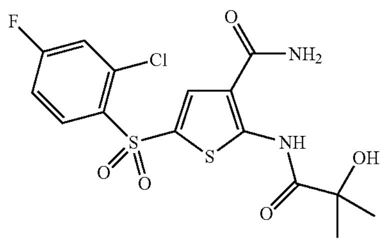 [SMILES: CC(C)(O)C(=O)Nc1sc(S(=O)(=O)c2ccc(F)cc2Cl)cc1C(N)=O] | 5-(2-chloro-4-fluorophenylsulfonyl)-2-(2-hydroxy-2-methylpropanamido) thiophene-3-carboxamide | A, B2, D1, H, I, J2, K | 8 | 421 | 465.0 |
| 287 | 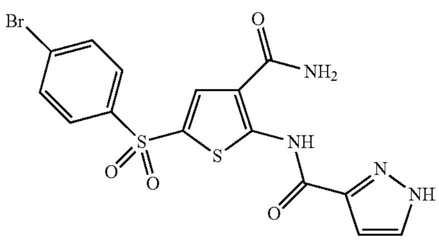 [SMILES: NC(=O)c1cc(S(=O)(=O)c2ccc(Br)cc2)sc1NC(=O)c1cc[nH]n1] | N-(5-(4-bromophenylsulfonyl)-3-carbamoylthiophen-2-yl)-1H-pyrazole-3-carboxamide | A, B2, D1, H, I, J2, K | 8 | 455 | 373.0 |
| 288 | 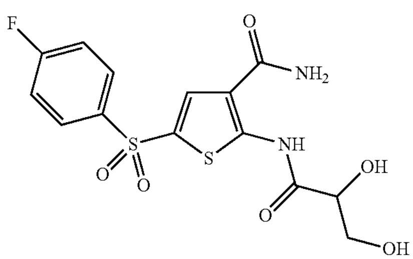 [SMILES: NC(=O)c1cc(S(=O)(=O)c2ccc(F)cc2)sc1NC(=O)C(O)CO] | 2-(2,3-dihydroxypropanamido)-5-(4-fluorophenylsulfonyl) thiophene-3-carboxamide | A, B2, D1, H, I, J2, K | 8 | 388 | 421.0 |
| 289 | 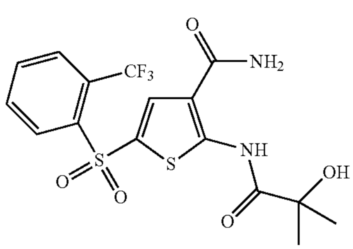 [SMILES: CC(C)(O)C(=O)Nc1sc(S(=O)(=O)c2ccccc2C(F)(F)F)cc1C(N)=O] | 2-(2-hydroxy-2-methylpropanamido)-5-(2-(trifluoromethyl)phenylsulfonyl) thiophene-3-carboxamide | K, H2, A, C, D1 | 8 | 436 | 420.9 |
| 290 | 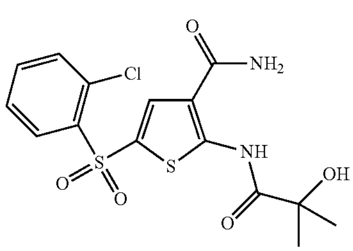 [SMILES: CC(C)(O)C(=O)Nc1sc(S(=O)(=O)c2ccccc2Cl)cc1C(N)=O] | 5-(2-chlorophenylsulfonyl)-2-(2-hydroxy-2-methylpropanamido) thiophene-3-carboxamide | A, C, D1, G, H1, J4 | CA (8) | 403 | 454.9/ 456.9 |

TABLE II-continued

List of final compounds

| Cpd # | Structure | Name | Mtd | Int | MW | Mes |
|---|---|---|---|---|---|---|
| 291 | 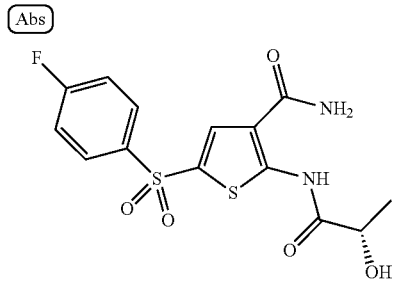 [SMILES: C[C@H](O)C(=O)Nc1sc(S(=O)(=O)c2ccc(F)cc2)cc1C(N)=O] | (S)-5-(4-fluorophenylsulfonyl)-2-(2-hydroxypropanamido)thiophene-3-carboxamide | A, B2, D1, H, I, J2, K | 8 | 372 | 388.9 |
| 292 | 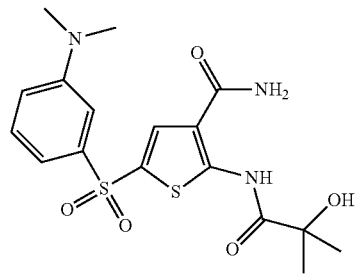 [SMILES: CN(C)c1cccc(S(=O)(=O)c2cc(C(N)=O)c(NC(=O)C(C)(C)O)s2)c1] | 5-(3-(dimethylamino)phenylsulfonyl)-2-(2-hydroxy-2-methylpropanamido)thiophene-3-carboxamide | A, B2, D1, H, I, J2, K | 8 | 412 | 437.0 |
| 293 | 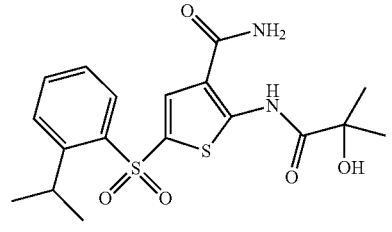 [SMILES: CC(C)c1ccccc1S(=O)(=O)c1cc(C(N)=O)c(NC(=O)C(C)(C)O)s1] | 2-(2-hydroxy-2-methylpropanamido)-5-(2-isopropylphenylsulfonyl)thiophene-3-carboxamide | A, C, D1, G, H2, J1 | 8 | 411 | 402.9 |
| 294 | 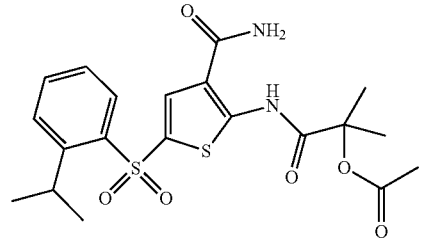 [SMILES: CC(=O)OC(C)(C)C(=O)Nc1sc(S(=O)(=O)c2ccccc2C(C)C)cc1C(N)=O] | 1-(3-carbamoyl-5-(2-isopropylphenylsulfonyl)thiophen-2-ylamino)-2-methyl-1-oxopropan-2-yl acetate | O2, A, C, D1, H, I, J2, K | 8 | 453 | 372.9 |
| 295 | 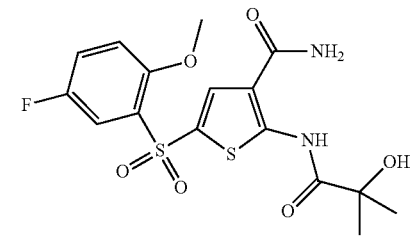 [SMILES: COc1ccc(F)cc1S(=O)(=O)c1cc(C(N)=O)c(NC(=O)C(C)(C)O)s1] | 5-(5-fluoro-2-methoxyphenylsulfonyl)-2-(2-hydroxy-2-methylpropanamido)thiophene-3-carboxamide | A, C, D1, H, I, J2, K | 8 | 416 | 411.8 |
| 296 | 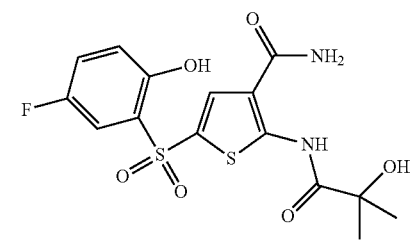 [SMILES: CC(C)(O)C(=O)Nc1sc(S(=O)(=O)c2cc(F)ccc2O)cc1C(N)=O] | 5-(5-fluoro-2-hydroxyphenylsulfonyl)-2-(2-hydroxy-2-methylpropanamido)thiophene-3-carboxamide | A, C, D1, H, I, J2, K | 8 | 402 | 411.1 |

TABLE II-continued

List of final compounds

| Cpd # | Structure | Name | Mtd | Int | MW | Mes |
|---|---|---|---|---|---|---|
| 297 | 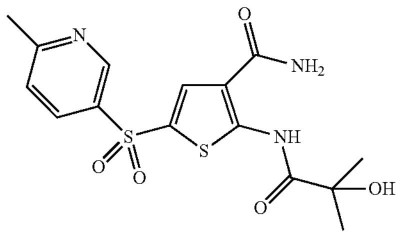 [SMILES: Cc1ccc(S(=O)(=O)c2cc(C(N)=O)c(NC(=O)C(C)(C)O)s2)cn1] | 2-(2-Hydroxy-2-methyl-propionylamino)-5-(6-methyl-pyridine-3-sulfonyl)-thiophene-3-carboxylic acid amide | A, C, D1, H, I, J2, K | 8 | 383 | 453.1 |
| 298 | 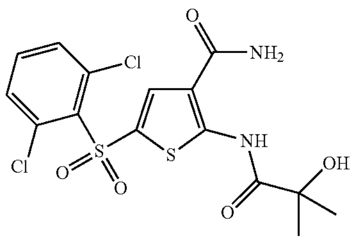 [SMILES: CC(C)(O)C(=O)Nc1sc(S(=O)(=O)c2c(Cl)cccc2Cl)cc1C(N)=O] | 5-(2,6-Dichloro-benzenesulfonyl)-2-(2-hydroxy-2-methyl-propionylamino)-thiophene-3-carboxylic acid amide | A, C, D1, H, I, J2, K | 8 | 437 | 416.8 |
| 299 | 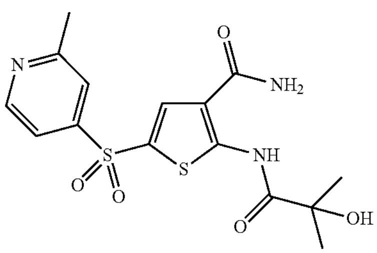 [SMILES: Cc1cc(S(=O)(=O)c2cc(C(N)=O)c(NC(=O)C(C)(C)O)s2)ccn1] | 2-(2-Hydroxy-2-methyl-propionylamino)-5-(2-methyl-pyridine-4-sulfonyl)-thiophene-3-carboxylic acid amide | M1, O2, A, C, D1, H, I, J2, K | 8 | 383 | 403.0 |
| 300 | 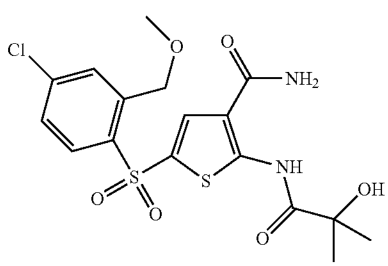 [SMILES: COCc1cc(Cl)ccc1S(=O)(=O)c1cc(C(N)=O)c(NC(=O)C(C)(C)O)s1] | 5-(4-fluoro-2-(methoxymethyl)phenylsulfonyl)-2-(2-hydroxy-2-methylpropanamido)thiophene-3-carboxamide | A, B2, D1, H, I, J2, K | 8 | 430 | 384.0 |
| 301 | 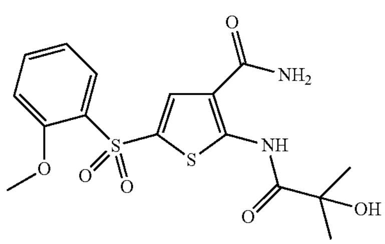 [SMILES: COc1ccccc1S(=O)(=O)c1cc(C(N)=O)c(NC(=O)C(C)(C)O)s1] | 2-(2-hydroxy-2-methylpropanamido)-5-(2-methoxyphenylsulfonyl)thiophene-3-carboxamide | M1, O2, A, C, D1, H, I, J2, K | 8 | 398 | 436.7 |
| 302 | 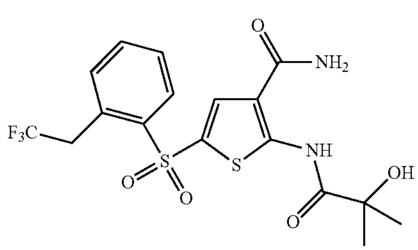 [SMILES: CC(C)(O)C(=O)Nc1sc(S(=O)(=O)c2ccccc2CC(F)(F)F)cc1C(N)=O] | 2-(2-hydroxy-2-methylpropanamido)-5-(2-(2,2,2-trifluoroethyl)phenylsulfonyl)thiophene-3-carboxamide | M1, A, C, D1, H, I, J2, K | 8 | 450 | 383.8 |

TABLE II-continued

List of final compounds

| Cpd # | Structure | Name | Mtd | Int | MW | Mes |
|---|---|---|---|---|---|---|
| 303 | 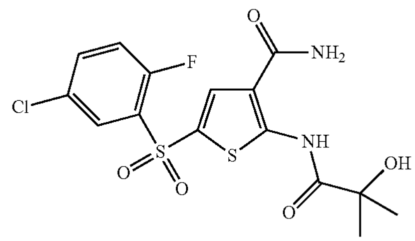 [SMILES: CC(C)(O)C(=O)Nc1sc(S(=O)(=O)c2cc(Cl)ccc2F)cc1C(N)=O] | 5-(5-chloro-2-fluorophenylsulfonyl)-2-(2-hydroxy-2-methylpropanamido)thiophene-3-carboxamide | M1, A, C, D1, H, I, J2, K | 8 | 421 | 430.8 |
| 304 | 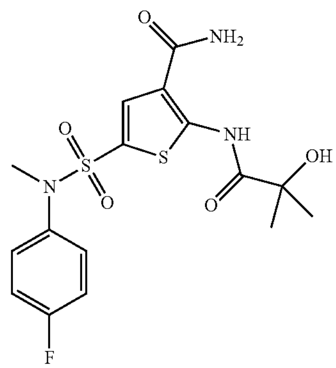 [SMILES: CN(c1ccc(F)cc1)S(=O)(=O)c1cc(C(N)=O)c(NC(=O)C(C)(C)O)s1] | 5-(N-(4-fluorophenyl)-N-methylsulfamoyl)-2-(2-hydroxy-2-methylpropanamido)thiophene-3-carboxamide | A, C, D1, H, I, J2, K | 8 | 415 | 430.8 |
| 305 | 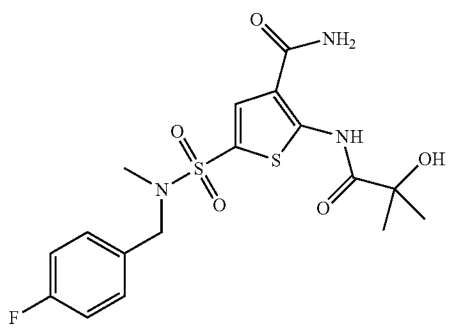 [SMILES: CN(Cc1ccc(F)cc1)S(=O)(=O)c1cc(C(N)=O)c(NC(=O)C(C)(C)O)s1] | 5-(N-(4-fluorobenzyl)-N-methylsulfamoyl)-2-(2-hydroxy-2-methylpropanamido)thiophene-3-carboxamide | A, C, D1, H, I, J2, K | 8 | 429 | 398.9 |
| 306 | 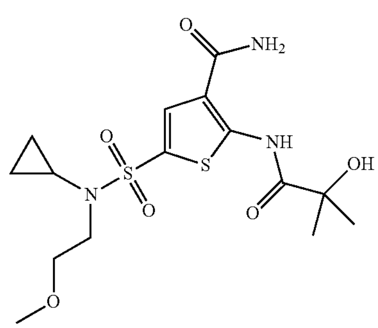 [SMILES: COCCN(C1CC1)S(=O)(=O)c1cc(C(N)=O)c(NC(=O)C(C)(C)O)s1] | 5-(N-cyclopropyl-N-(2-methoxyethyl)sulfamoyl)-2-(2-hydroxy-2-methylpropanamido)thiophene-3-carboxamide | A, C, D1, H, I, J2, K | 8 | 405 | 450.8 |
| 307 | 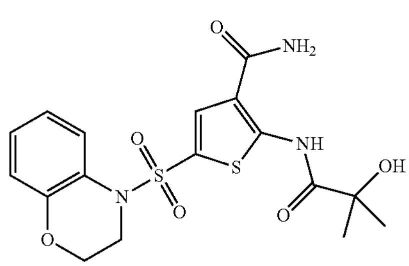 [SMILES: CC(C)(O)C(=O)Nc1sc(S(=O)(=O)N2CCOc3ccccc32)cc1C(N)=O] | 5-(2H-benzo[b][1,4]oxazin-4(3H)-ylsulfonyl)-2-(2-hydroxy-2-methylpropanamido)thiophene-3-carboxamide | O1, A, B2, D1, H, I, J2, K | 8 | 425 | 450.8 |

TABLE II-continued

List of final compounds

| Cpd # | Structure | Name | Mtd | Int | MW | Mes |
|---|---|---|---|---|---|---|
| 308 | 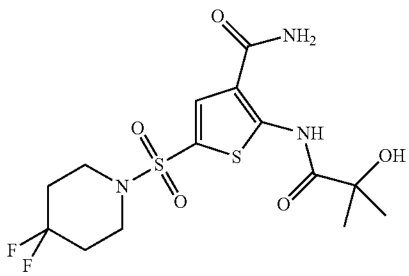 [SMILES: CC(C)(O)C(=O)Nc1sc(S(=O)(=O)N2CCC(F)(F)CC2)cc1C(N)=O] | 5-(4,4-difluoropiperidin-1-ylsulfonyl)-2-(2-hydroxy-2-methylpropanamido)thiophene-3-carboxamide | I, K, H2, A, E2, F2, J2 | 8 | 411 | 420.9 |
| 309 | 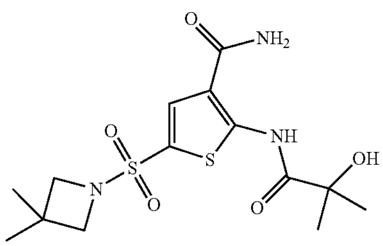 [SMILES: CC1(C)CN(S(=O)(=O)c2cc(C(N)=O)c(NC(=O)C(C)(C)O)s2)C1] | 5-(3,3-Dimethyl-azetidine-1-sulfonyl)-2-(2-hydroxy-2-methyl-propionylamino)-thiophene-3-carboxylic acid amide | I, K, H2, A, E2, F2, J2 | 8 | 375 | 416.0 |
| 310 | 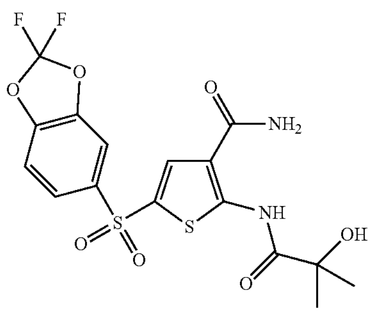 [SMILES: CC(C)(O)C(=O)Nc1sc(S(=O)(=O)c2ccc3c(c2)OC(F)(F)O3)cc1C(N)=O] | 5-(2,2-difluorobenzo[d][1,3]dioxol-5-ylsulfonyl)-2-(2-hydroxy-2-methylpropanamido)thiophene-3-carboxamide | I, K, H2, A, E2, F2, J2 | 8 | 448 | 430.1 |
| 311 | 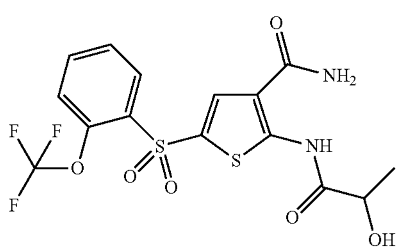 [SMILES: CC(O)C(=O)Nc1sc(S(=O)(=O)c2ccccc2OC(F)(F)F)cc1C(N)=O] | 2-(2-hydroxypropanamido)-5-(2-(trifluoromethoxy)phenylsulfonyl)thiophene-3-carboxamide | I, K, H2, A, E2, F2, J2 | 8 | 438 | 406.0 |
| 312 | 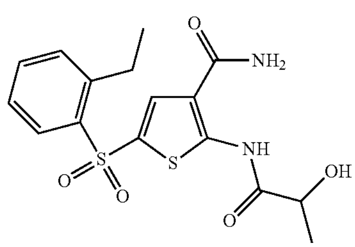 [SMILES: CCc1ccccc1S(=O)(=O)c1cc(C(N)=O)c(NC(=O)C(C)O)s1] | 5-(2-Ethyl-benzenesulfonyl)-2-(2-hydroxy-propionylamino)-thiophene-3-carboxylic acid amide | I, K, H2, A, E2, F2, J2 | 8 | 382 | 426.1 |
| 313 | 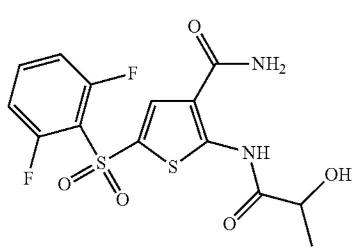 [SMILES: CC(O)C(=O)Nc1sc(S(=O)(=O)c2c(F)cccc2F)cc1C(N)=O] | 5-(2,6-Difluoro-benzenesulfonyl)-2-(2-hydroxy-propionylamino)-thiophene-3-carboxylic acid amide | I, K, H2, A, E2, F2, J2 | 8 | 390 | 412.0 |

TABLE II-continued

List of final compounds

| Cpd # | Structure | Name | Mtd | Int | MW | Mes |
|---|---|---|---|---|---|---|
| 314 | 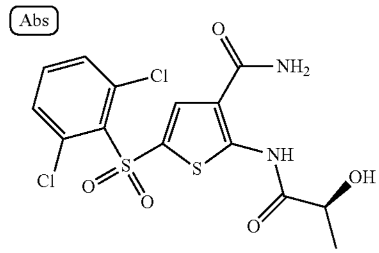 [SMILES: C[C@H](O)C(=O)Nc1sc(S(=O)(=O)c2c(Cl)cccc2Cl)cc1C(N)=O] | 5-(2,6-Dichloro-benzenesulfonyl)-2-((S)-2-hydroxy-propionylamino)-thiophene-3-carboxylic acid amide | M1, A, C, D1, H, I, J2, K | 8 | 423 | 376.1 |
| 315 | 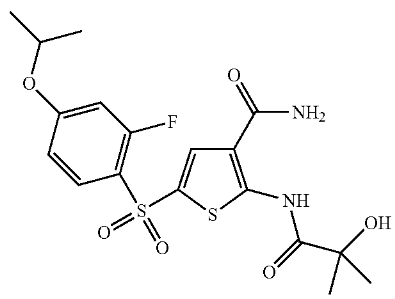 [SMILES: CC(C)Oc1ccc(S(=O)(=O)c2cc(C(N)=O)c(NC(=O)C(C)(C)O)s2)c(F)c1] | 5-(2-Fluoro-4-isopropoxy-benzenesulfonyl)-2-(2-hydroxy-2-methyl-propionylamino)-thiophene-3-carboxylic acid amide | H1, A, C, D1, J2 | 8 | 445 | 448.7 |
| 316 | 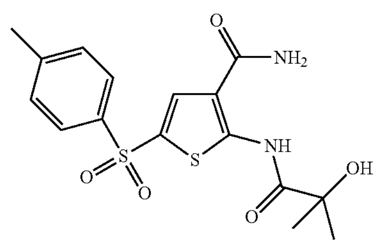 [SMILES: Cc1ccc(S(=O)(=O)c2cc(C(N)=O)c(NC(=O)C(C)(C)O)s2)cc1] | 2-(2-Hydroxy-2-methyl-propionylamino)-5-(toluene-4-sulfonyl)-thiophene-3-carboxylic acid amide | H1, A, C, D1 | 8 | 382 | 439.0 |
| 317 | 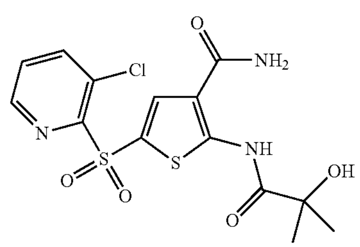 [SMILES: CC(C)(O)C(=O)Nc1sc(S(=O)(=O)c2ncccc2Cl)cc1C(N)=O] | 5-(3-Chloro-pyridine-2-sulfonyl)-2-(2-hydroxy-2-methyl-propionylamino)-thiophene-3-carboxylic acid amide | A, C, D1, H, I, J2, K | CA (8) | 404 | 439.0 |
| 318 | 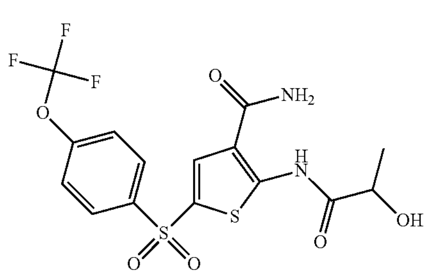 [SMILES: CC(O)C(=O)Nc1sc(S(=O)(=O)c2ccc(OC(F)(F)F)cc2)cc1C(N)=O] | 2-(2-Hydroxy-propionylamino)-5-(4-trifluoromethoxy-benzenesulfonyl)-thiophene-3-carboxylic acid amide | O1, A, B2, D1, H, I, J2, K | 8 | 438 | 383.0 |

TABLE II-continued

List of final compounds

| Cpd # | Structure | Name | Mtd | Int | MW | Mes |
|---|---|---|---|---|---|---|
| 319 | 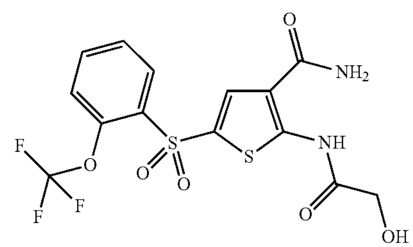 [SMILES: NC(=O)c1cc(S(=O)(=O)c2ccccc2OC(F)(F)F)sc1NC(=O)CO] | 2-(2-Hydroxy-acetylamino)-5-(2-trifluoromethoxy-benzensulfonyl)-thiophene-3-carboxylic acid amide | A, B2, D1, H, I, J2, K | 8 | 424 | 390.8 |
| 320 | 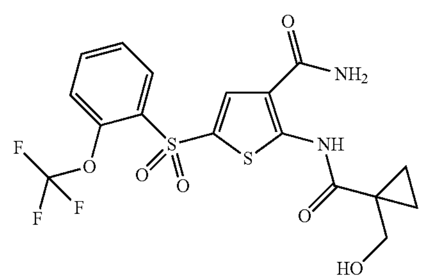 [SMILES: NC(=O)c1cc(S(=O)(=O)c2ccccc2OC(F)(F)F)sc1NC(=O)C1(CO)CC1] | 2-[(1-Hydroxymethyl-cyclopropanecarbonyl)-amino]-5-(2-trifluoromethoxy-benzenesulfonyl)-thiophene-3-carboxylic acid amide | M1, A, B2, D1, H, I, J2, K | 8 | 464 | 422.7 |
| 321 | 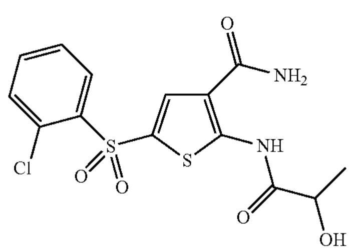 [SMILES: CC(O)C(=O)Nc1sc(S(=O)(=O)c2ccccc2Cl)cc1C(N)=O] | 5-(2-Chloro-benzenesulfonyl)-2-(2-hydroxy-propionylamino)-thiophene-3-carboxylic acid amide | P, A, H, I, J2, K | 8 | 389 | 444.8 |
| 322 | 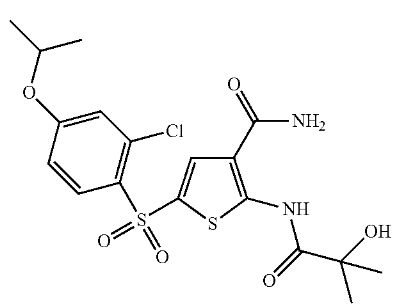 [SMILES: CC(C)Oc1ccc(S(=O)(=O)c2cc(C(N)=O)c(NC(=O)C(C)(C)O)s2)c(Cl)c1] | 5-(2-Chloro-4-isopropoxy-benzenesulfonyl)-2-(2-hydroxy-2-methyl-propionylamino)-thiophene-3-carboxylic acid amide | A, B2, D1, H, I, J2, K | 8 | 461 | 383.1 |
| 323 | 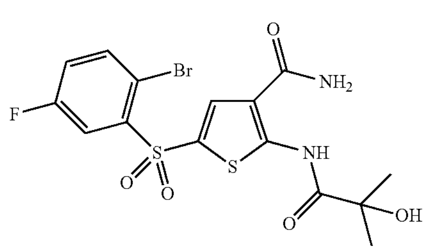 [SMILES: CC(C)(O)C(=O)Nc1sc(S(=O)(=O)c2cc(F)ccc2Br)cc1C(N)=O] | 5-(2-Bromo-5-fluoro-benzenesulfonyl)-2-(2-hydroxy-2-methyl-propionylamino)-thiophene-3-carboxylic acid amide | H1, A, B2, D1 | 8 | 465 | 404.1 |

TABLE II-continued

List of final compounds

| Cpd # | Structure | Name | Mtd | Int | MW | Mes |
|---|---|---|---|---|---|---|
| 324 | 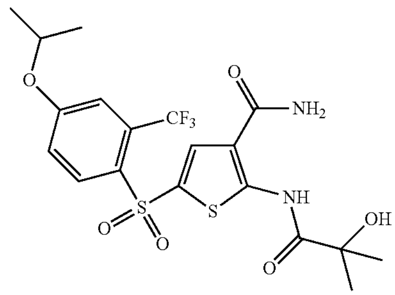 | 2-(2-Hydroxy-2-methyl-propionylamino)-5-(4-isopropoxy-2-trifluoromethyl-benzenesulfonyl)-thiophene-3-carboxylic acid amide | A, C, D1, G, H2, J2 | 8 | 495 | 439.0 |
| 325 | 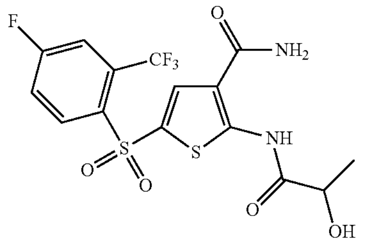 [SMILES: CC(O)C(=O)Nc1sc(S(=O)(=O)c2ccc(F)cc2C(F)(F)F)cc1C(N)=O] | 5-[4-fluoro-2-(trifluoromethyl)phenyl]sulfonyl-2-(2-hydroxypropanoylamino)thiophene-3-carboxamide | A, C, D1, G, I, H1, J2 | 8 | 440 | 425.0 |
| 326 | 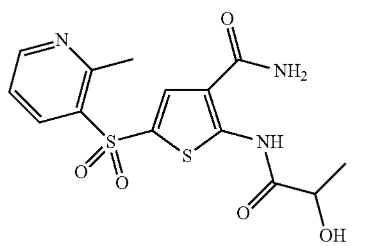 [SMILES: Cc1ncccc1S(=O)(=O)c1cc(C(N)=O)c(NC(=O)C(C)O)s1] | 2-(2-hydroxypropanoylamino)-5-[(2-methyl-3-pyridyl)sulfonyl]thiophene-3-carboxamide | H1, A, B2, D1/D2 | 8 | 369 | 465.0 |
| 327 | 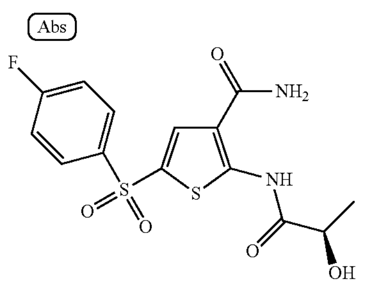 [SMILES: C[C@@H](O)C(=O)Nc1sc(S(=O)(=O)c2ccc(F)cc2)cc1C(N)=O] | 5-(4-fluorophenyl)sulfonyl-2-[[(2R)-2-hydroxypropanoyl]amino]thiophene-3-carboxamide | M2, A, D1, H, I, J2, K | 8 | 372 | 388.8/ 390.8 |
| 328 | 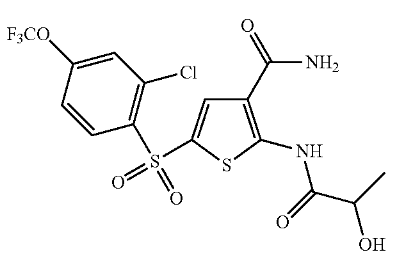 [SMILES: CC(O)C(=O)Nc1sc(S(=O)(=O)c2ccc(OC(F)(F)F)cc2Cl)cc1C(N)=O] | 5-[2-chloro-4-(trifluoromethoxy)phenyl]sulfonyl-2-(2-hydroxypropanoylamino)thiophene-3-carboxamide | A, B2, D1, H, I, J2, K | 8 | 473 | 460.8 |

TABLE II-continued

List of final compounds

| Cpd # | Structure | Name | Mtd | Int | MW | Mes |
|---|---|---|---|---|---|---|
| 329 | 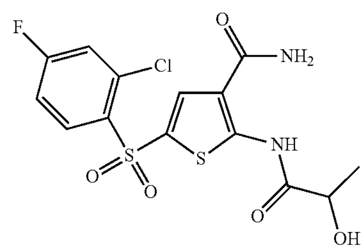 | 5-(2-chloro-4-fluoro-phenyl)sulfonyl-2-(2-hydroxypropanoylamino)thiophene-3-carboxamide | M2, A, D1, H, I, J2, K | 8 | 407 | 466.7 |
| 330 | 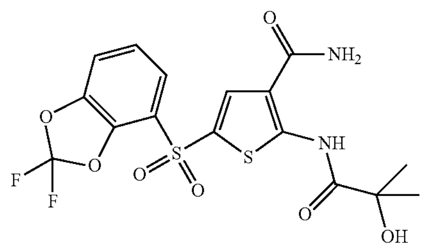 [SMILES: CC(C)(O)C(=O)Nc1sc(S(=O)(=O)c2cccc3c2OC(F)(F)O3)cc1C(N)=O] | 5-[(2,2-difluoro-1,3-benzodioxol-4-yl)sulfonyl]-2-[(2-hydroxy-2-methyl-propanoyl)amino]thiophene-3-carboxamide | M2, A, D1, H, I, J3, K | 8 | 448 | 494.8 |
| 331 | 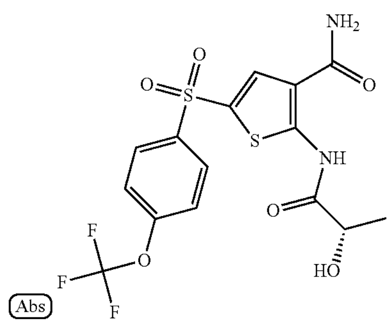 [SMILES: C[C@H](O)C(=O)Nc1sc(S(=O)(=O)c2ccc(OC(F)(F)F)cc2)cc1C(N)=O] | 2-[[(2S)-2-hydroxypropanoyl]amino]-5-[4-(trifluoromethoxy)phenyl]sulfonyl-thiophene-3-carboxamide | M1, O2, A, C, D2, H, I, J2, K | 8 | 438 | 440.9 |
| 332 | 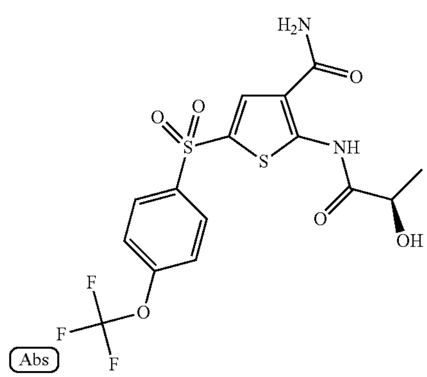 [SMILES: C[C@@H](O)C(=O)Nc1sc(S(=O)(=O)c2ccc(OC(F)(F)F)cc2)cc1C(N)=O] | 2-[[(2R)-2-hydroxypropanoyl]amino]-5-[4-(trifluoromethoxy)phenyl]sulfonyl-thiophene-3-carboxamide | A, C, D1, G, H1, J1 | 8 | 438 | 369.9 |
| 333 | 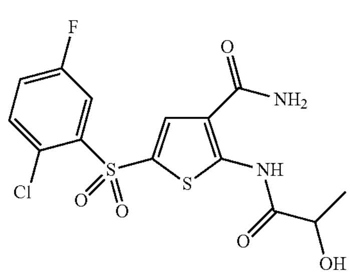 [SMILES: CC(O)C(=O)Nc1sc(S(=O)(=O)c2cc(F)ccc2Cl)cc1C(N)=O] | 5-(2-chloro-5-fluoro-phenyl)sulfonyl-2-(2-hydroxypropanoylamino)thiophene-3-carboxamide | O1, A, B2, D1, H, I, J3, K | 8 | 407 | 373.0 |

TABLE II-continued

List of final compounds

| Cpd # | Structure | Name | Mtd | Int | MW | Mes |
|---|---|---|---|---|---|---|
| 334 | 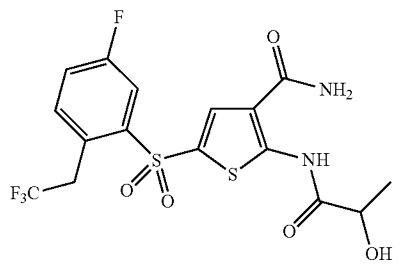 [SMILES: CC(O)C(=O)Nc1sc(S(=O)(=O)c2cc(F)ccc2CC(F)(F)F)cc1C(N)=O] | 5-[5-fluoro-2-(2,2,2-trifluoroethyl)phenyl]sulfonyl-2-(2-hydroxypropanoylamino)thiophene-3-carboxamide | A, B2, D1, H, I, K | 8 | 454 | 472.7 |
| 335 | 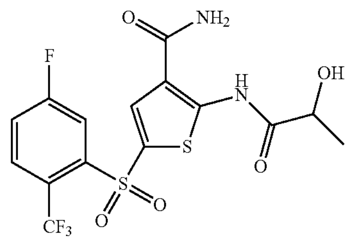 [SMILES: CC(O)C(=O)Nc1sc(S(=O)(=O)c2cc(F)ccc2C(F)(F)F)cc1C(N)=O] | 5-[5-fluoro-2-(trifluoromethyl)phenyl]sulfonyl-2-(2-hydroxypropanoylamino)thiophene-3-carboxamide | M2, A, D1, H, I, J3, K | 8 | 440 | 406.8 |
| 336 | 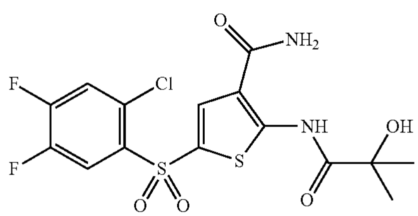 [SMILES: CC(C)(O)C(=O)Nc1sc(S(=O)(=O)c2cc(F)c(F)cc2Cl)cc1C(N)=O] | 5-(2-Chloro-4,5-difluoro-benzenesulfonyl)-2-(2-hydroxy-2-methyl-propionylamino)-thiophene-3-carboxylic acid amide | A, H1, B2, D1 | 8 | 439 | 449.0 |
| 337 | 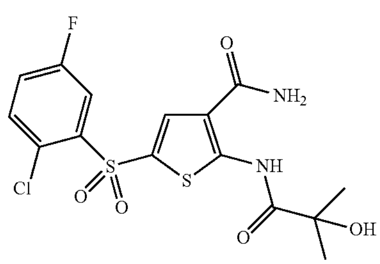 [SMILES: CC(C)(O)C(=O)Nc1sc(S(=O)(=O)c2cc(F)ccc2Cl)cc1C(N)=O] | 5-(2-chloro-5-fluoro-phenyl)sulfonyl-2-[(2-hydroxy-2-methyl-propanoyl)amino]thiophene-3-carboxamide | M2, A, D2, H, I, J3, K | 8 | 421 | 439.0 |
| 338 | 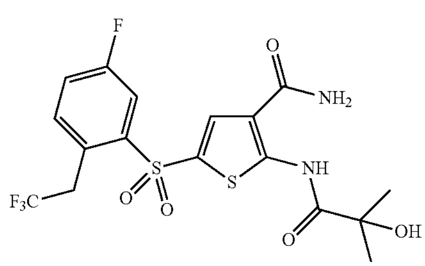 [SMILES: CC(C)(O)C(=O)Nc1sc(S(=O)(=O)c2cc(F)ccc2CC(F)(F)F)cc1C(N)=O] | 5-[5-fluoro-2-(2,2,2-trifluoroethyl)phenyl]sulfonyl-2-[(2-hydroxy-2-methyl-propanoyl)amino]thiophene-3-carboxamide | A, H1, B2, D1 | 8 | 468 | |
| 339 | 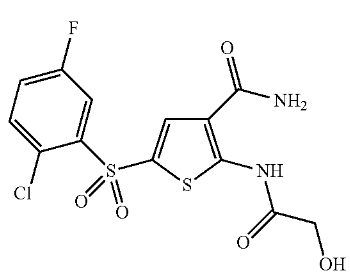 [SMILES: NC(=O)c1cc(S(=O)(=O)c2cc(F)ccc2Cl)sc1NC(=O)CO] | 5-(2-Chloro-5-fluoro-benzensulfonyl)-2-(2-hydroxy-acetylamino)-thiophene-3-carboxylic acid amide | M2, A, D2, H, I, J3, K | 8 | 393 | 439.0 |

TABLE II-continued

List of final compounds

| Cpd # | Structure | Name | Mtd | Int | MW | Mes |
|---|---|---|---|---|---|---|
| 340 | 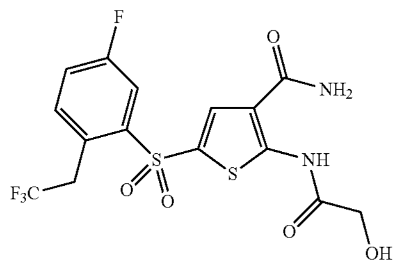 [SMILES: NC(=O)c1cc(S(=O)(=O)c2cc(F)ccc2CC(F)(F)F)sc1NC(=O)CO] | 5-[5-Fluoro-2-(2,2,2-trifluoro-ethyl)-benzenesulfonyl]-2-(2-hdyroxy-acetylamino)-thiophene-3-carboxylic acid amide | M2, A, D2, H, I, J3, K | 8 | 440 | 406.8 |
| 341 | 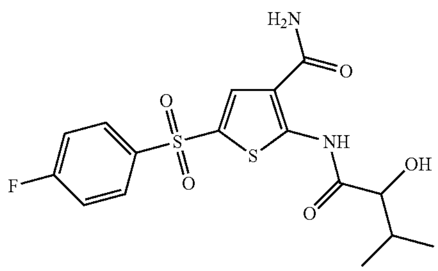 [SMILES: CC(C)C(O)C(=O)Nc1sc(S(=O)(=O)c2ccc(F)cc2)cc1C(N)=O] | 5-(4-fluorophenyl)sulfonyl-2-[(2-hydroxy-3-methyl-butanoyl)amino]thiophene-3-carboxamide | D2, G, H1, O4 | 8 | 400 | 454.8 |
| 342 | 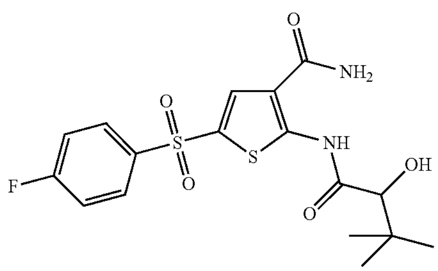 [SMILES: CC(C)(C)C(O)C(=O)Nc1sc(S(=O)(=O)c2ccc(F)cc2)cc1C(N)=O] | 5-(4-fluorophenyl)sulfonyl-2-[(2-hydroxy-3,3-dimethyl-butanoyl)amino]thiophene-3-carboxamide | D2, G, H1, O3 | 8 | 414 | 441.0 |
| 343 | 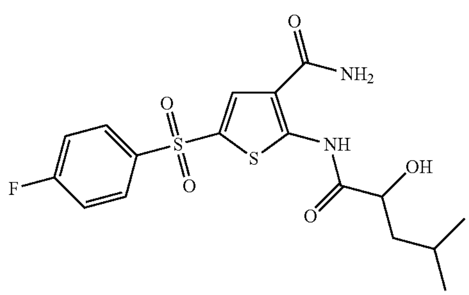 [SMILES: CC(C)CC(O)C(=O)Nc1sc(S(=O)(=O)c2ccc(F)cc2)cc1C(N)=O] | 5-(4-fluorophenyl)sulfonyl-2-[(2-hydroxy-4-methyl-pentanoyl)amino]thiophene-3-carboxamide | D2, G, H1, O3 | 8 | 414 | 438.9 |
| 344 | 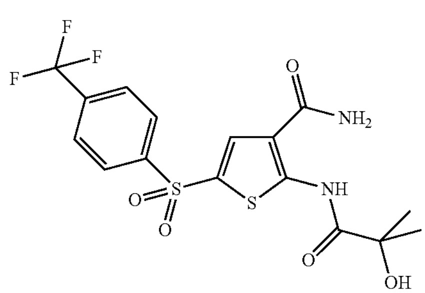 [SMILES: CC(C)(O)C(=O)Nc1sc(S(=O)(=O)c2ccc(C(F)(F)F)cc2)cc1C(N)=O] | 2-[(2-hydroxy-2-methyl-propanoyl)amino]-5-[4-(trifluoromethyl)phenyl]sulfonyl-thiophene-3-carboxamide | B2, D2, G | 8 | 436 | 420.8 |

TABLE II-continued

List of final compounds

| Cpd # | Structure | Name | Mtd | Int | MW | Mes |
|---|---|---|---|---|---|---|
| 345 | 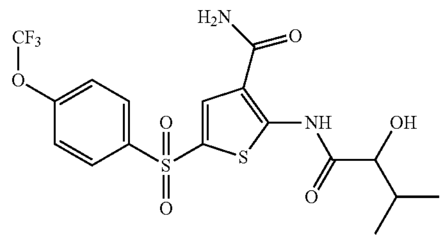 [SMILES: CC(C)C(O)C(=O)Nc1sc(S(=O)(=O)c2ccc(OC(F)(F)F)cc2)cc1C(N)=O] | 2-[(2-hydroxy-3-methyl-butanoyl)amino]-5-[4-(trifluoromethoxy)phenyl]sulfonyl-thiophene-3-carboxamide | A, B2, D2, G H1, O4 | 8 | 466.5 | 467.1 |
| 346 | 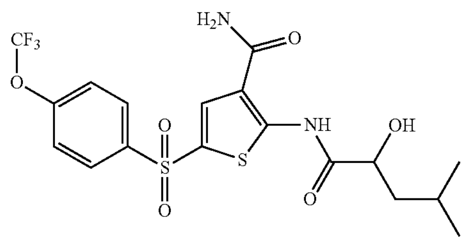 [SMILES: CC(C)CC(O)C(=O)Nc1sc(S(=O)(=O)c2ccc(OC(F)(F)F)cc2)cc1C(N)=O] | 2-[(2-hydroxy-4-methyl-pentanoyl)amino]-5-[4-(trifluoromethoxy)phenyl]sulfonyl-thiophene-3-carboxamide | A, B2, D2, G, H1, O4 | 8 | 480.5 | 481.2 |
| 347 | 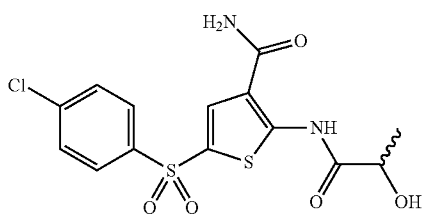 [SMILES: CC(O)C(=O)Nc1sc(S(=O)(=O)c2ccc(Cl)cc2)cc1C(N)=O] | 5-(4-chlorophenyl)sulfonyl-2-[[(2S)-2-hydroxypropanoyl]amino]thiophene-3-carboxamide, Enantiomer 1 | H1, A, B2, D2, G | 8 | 388.9 | 389.2 |
| 348 | 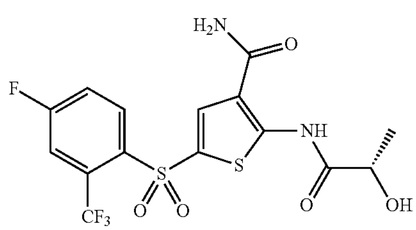 [SMILES: C[C@H](O)C(=O)Nc1sc(S(=O)(=O)c2ccc(F)cc2C(F)(F)F)cc1C(N)=O] | 5-[4-fluoro-2-(trifluoromethyl)phenyl]sulfonyl-2-[[(2S)-2-hydroxypropanoyl]amino]thiophene-3-carboxamide, Enantiomer 1 | H1, A, D2, G | 8 | 440.4 | 441.3 |
| 349 | 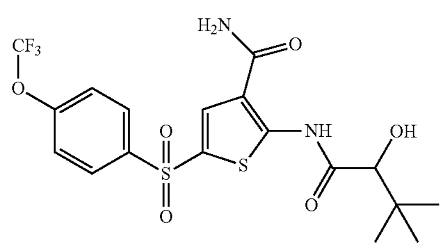 [SMILES: CC(C)(C)C(O)C(=O)Nc1sc(S(=O)(=O)c2ccc(OC(F)(F)F)cc2)cc1C(N)=O] | 2-[(2-hydroxy-3,3-dimethyl-butanoyl)amino]-5-[4-(trifluoromethoxy)phenyl]sulfonyl-thiophene-3-carboxamide | A, B2, (D2, G), H1, O4 | 8 | 480.5 | 481.1 |
| 350 | 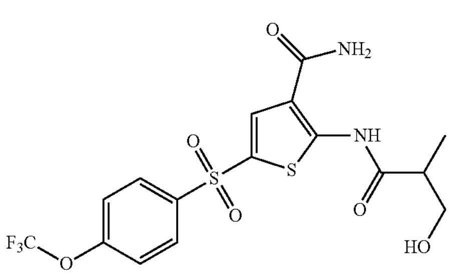 [SMILES: CC(CO)C(=O)Nc1sc(S(=O)(=O)c2ccc(OC(F)(F)F)cc2)cc1C(N)=O] | 2-[(3-hydroxy-2-methyl-propanoyl)amino]-5-[4-(trifluoromethoxy)phenyl]sulfonyl-thiophene-3-carboxamide | H1, A, M2, D2, O3 | 8 | 452.4 | 453.0 |

TABLE II-continued

List of final compounds

| Cpd # | Structure | Name | Mtd | Int | MW | Mes |
|---|---|---|---|---|---|---|
| 351 | 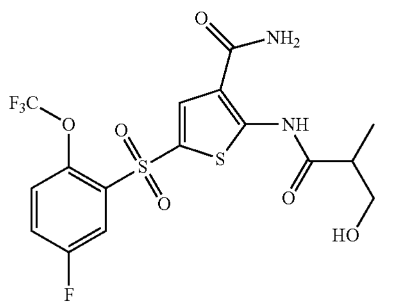 [SMILES: CC(CO)C(=O)Nc1sc(S(=O)(=O)c2cc(F)ccc2OC(F)(F)F)cc1C(N)=O] | 5-[5-fluoro-2-(trifluoromethoxy)phenyl]sulfonyl-2-[(3-hydroxy-2-methyl-propanoyl)amino]thiophene-3-carboxamide | H1, A, M2, D2, O3 | 8 | 470.4 | 471.0 |
| 352 | 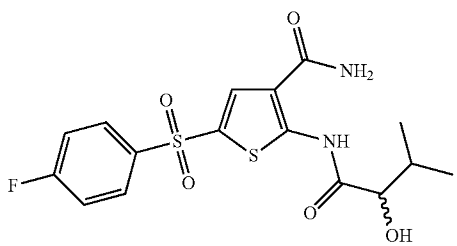 [SMILES: CC(C)C(O)C(=O)Nc1sc(S(=O)(=O)c2ccc(F)cc2)cc1C(N)=O] | 5-(4-fluorophenyl)sulfonyl-2-[[(2S)-2-hydroxy-3-methyl-butanoyl]amino]thiophene-3-carboxamide, Enantiomer 1 | D2, G, H1, G | 8 | 400.5 | 399.08 (MH−) |
| 353 | 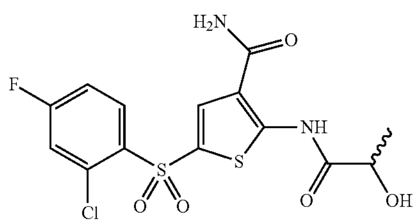 [SMILES: CC(O)C(=O)Nc1sc(S(=O)(=O)c2ccc(F)cc2Cl)cc1C(N)=O] | 5-(2-chloro-4-fluoro-phenyl)sulfonyl-2-[[(2S)-2-hydroxypropanoyl]amino]thiophene-3-carboxamide, Enantiomer 1 | H1, A, B2, D2, G | 8 | 406.8 | 407.3 |
| 354 | 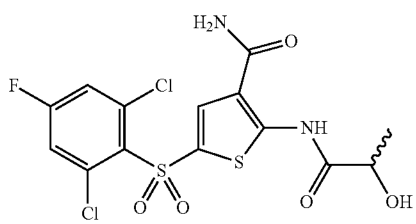 [SMILES: CC(O)C(=O)Nc1sc(S(=O)(=O)c2c(Cl)cc(F)cc2Cl)cc1C(N)=O] | 5-(2,6-dichloro-4-fluoro-phenyl)sulfonyl-2-[[(2S)-2-hydroxypropanoyl]amino]thiophene-3-carboxamide, Enantiomer 1 | H1, A, B2, D2, G | 8 | 441.3 | 441.2 |
| 355 | 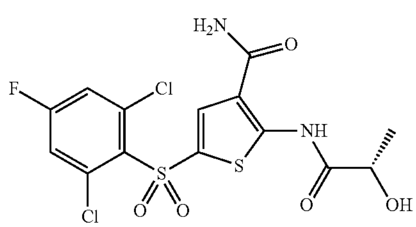 [SMILES: C[C@H](O)C(=O)Nc1sc(S(=O)(=O)c2c(Cl)cc(F)cc2Cl)cc1C(N)=O] | 5-(2,6-dichloro-4-fluoro-phenyl)sulfonyl-2-[[(2S)-2-hydroxypropanoyl]amino]thiophene-3-carboxamide | H1, A, B2, D2, J3 | Int 8 | 441.3 | 441.24 |
| 356 | 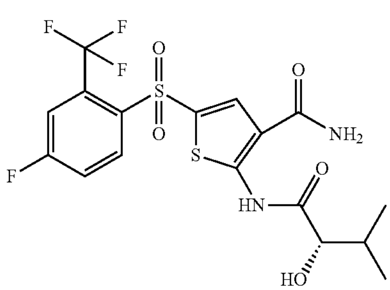 [SMILES: CC(C)[C@H](O)C(=O)Nc1sc(S(=O)(=O)c2ccc(F)cc2C(F)(F)F)cc1C(N)=O] | 5-[4-fluoro-2-(trifluoromethyl)phenyl]sulfonyl-2-[[(2S)-2-hydroxy-3-methyl-butanoyl]amino]thiophene-3-carboxamide | I, H1, A, M1, M2, D2, J3 | Int 8 | 468.4 | 469.25 |

TABLE II-continued

List of final compounds

| Cpd # | Structure | Name | Mtd | Int | MW | Mes |
|---|---|---|---|---|---|---|
| 357 | 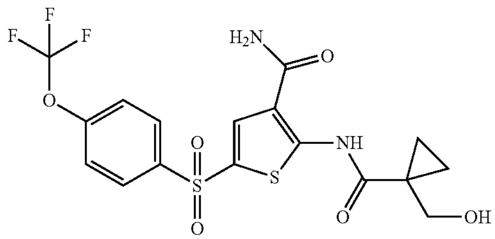 [SMILES: NC(=O)c1cc(S(=O)(=O)c2ccc(OC(F)(F)F)cc2)sc1NC(=O)C1(CO)CC1] | 2-[[1-(hydroxymethyl)cyclopropanecarbonyl]amino]-5-[4-(trifluoromethoxy)phenyl]sulfonyl-thiophene-3-carboxamide | B2, D2, G, H1, O3 | Int 3 | 464.4 | 465.11 |
| 358 | 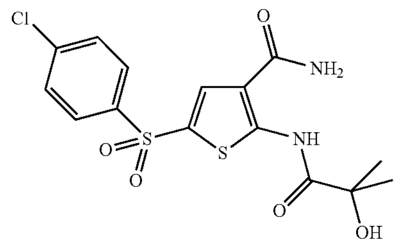 [SMILES: CC(C)(O)C(=O)Nc1sc(S(=O)(=O)c2ccc(Cl)cc2)cc1C(N)=O] | 5-(4-chlorophenyl)sulfonyl-2-[(2-hydroxy-2-methyl-propanoyl)amino]thiophene-3-carboxamide | B2, D2, J3 | Int 11 | 402.9 | 403.26 |
| 359 | 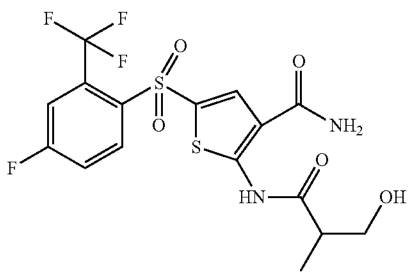 [SMILES: CC(CO)C(=O)Nc1sc(S(=O)(=O)c2ccc(F)cc2C(F)(F)F)cc1C(N)=O] | 5-[4-fluoro-2-(trifluoromethyl)phenyl]sulfonyl-2-[(3-hydroxy-2-methyl-propanoyl)amino]thiophene-3-carboxamide | H1, A, M1, M2, D2, O3 | Int 8 | 454.4 | 453.08 (MH−) |
| 360 | 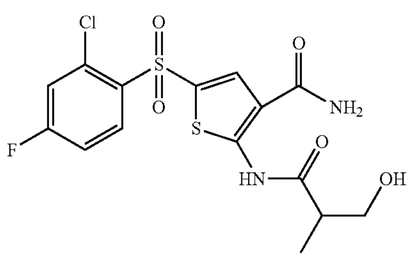 [SMILES: CC(CO)C(=O)Nc1sc(S(=O)(=O)c2ccc(F)cc2Cl)cc1C(N)=O] | 5-(2-chloro-4-fluoro-phenyl)sulfonyl-2-[(3-hydroxy-2-methyl-propanoyl)amino]thiophene-3-carboxamide | H1, A, M1, M2, D2, O3 | Int 8 | 420.9 | 420.99 (MH−) |
| 361 | 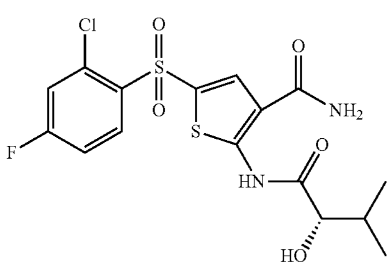 [SMILES: CC(C)[C@H](O)C(=O)Nc1sc(S(=O)(=O)c2ccc(F)cc2Cl)cc1C(N)=O] | 5-(2-chloro-4-fluoro-phenyl)sulfonyl-2-[[(2S)-2-hydroxy-3-methyl-butanoyl]amino]thiophene-3-carboxamide | I, H1, A, M1, M2, D2, J3 | Int 8 | 434.9 | 432.99 (MH−) |
| 362 | 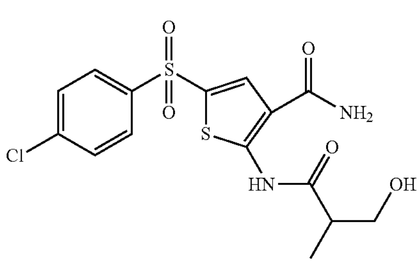 [SMILES: CC(CO)C(=O)Nc1sc(S(=O)(=O)c2ccc(Cl)cc2)cc1C(N)=O] | 5-(4-chlorophenyl)sulfonyl-2-[(3-hydroxy-2-methyl-propanoyl)amino]thiophene-3-carboxamide | H1, A, B2, D2, O3 | Int 8 | 402.9 | 403.26 |

TABLE II-continued

List of final compounds

| Cpd # | Structure | Name | Mtd | Int | MW | Mes |
|---|---|---|---|---|---|---|
| 363 | 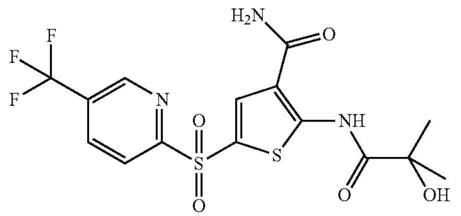 | 2-[(2-hydroxy-2-methyl-propanoyl)amino]-5-[[5-(trifluoromethyl)-2-pyridyl]sulfonyl]thiophene-3-carboxamide | M1, M2, D2, J3 | Int 12 | 437.4 | 438.05 |
| 364 | 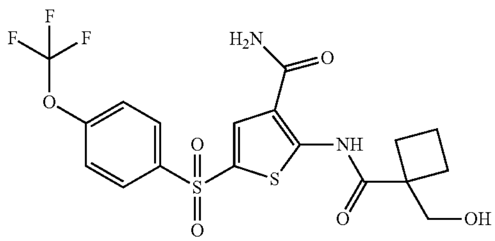 [SMILES: NC(=O)c1cc(S(=O)(=O)c2ccc(OC(F)(F)F)cc2)sc1NC(=O)C1(CO)CCC1] | 2-[[1-(hydroxymethyl)cyclobutanecarbonyl]amino]-5-[4-(trifluoromethoxy)phenyl]sulfonyl-thiophene-3-carboxamide | I, B2, D2, G, H1, J | Int 3 | 478.5 | 479.07 |
| 365 | 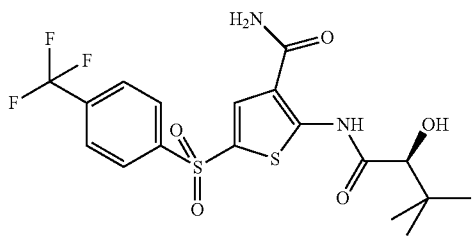 [SMILES: CC(C)(C)[C@H](O)C(=O)Nc1sc(S(=O)(=O)c2ccc(C(F)(F)F)cc2)cc1C(N)=O] | 2-[[(2S)-2-hydroxy-3,3-dimethyl-butanoyl]amino]-5-[4-(trifluoromethyl)phenyl]sulfonyl-thiophene-3-carboxamide | I, B2, D2, J3, H1, J | Int 8 | 464.5 | 465.34 |
| 366 | 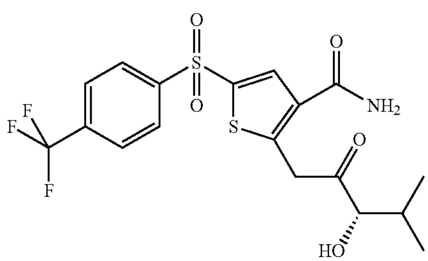 [SMILES: CC(C)[C@H](O)C(=O)Cc1sc(S(=O)(=O)c2ccc(C(F)(F)F)cc2)cc1C(N)=O] | 2-[[(2S)-2-hydroxy-3-methyl-butanoyl]amino]-5-[4-(trifluoromethyl)phenyl]sulfonyl-thiophene-3-carboxamide | I, H1, A, B2, D2, J3 | Int 8 | 450.5 | 449.06 (MH−) |
| 367 | 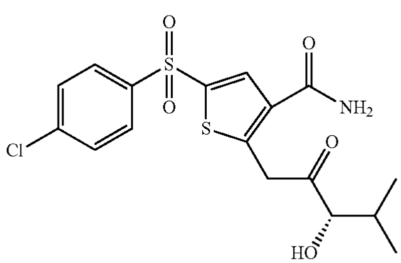 [SMILES: CC(C)[C@H](O)C(=O)Cc1sc(S(=O)(=O)c2ccc(Cl)cc2)cc1C(N)=O] | 5-(4-chlorophenyl)sulfonyl-2-[[(2S)-2-hydroxy-3-methyl-butanoyl]amino]thiophene-3-carboxamide | I, H1, A, B2, D2, J3 | Int 8 | 416.9 | 417.16 |
| 368 | 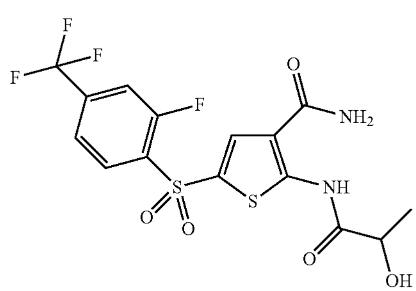 [SMILES: CC(O)C(=O)Nc1sc(S(=O)(=O)c2ccc(C(F)(F)F)cc2F)cc1C(N)=O] | 5-[2-fluoro-4-(trifluoromethyl)phenyl]sulfonyl-2-(2-hydroxypropanoylamino)thiophene-3-carboxamide | H1, A, M1, M2, D2, J1 | Int 8 | 440.4 | 441.07 |

TABLE II-continued

List of final compounds

| Cpd # | Structure | Name | Mtd | Int | MW | Mes |
|---|---|---|---|---|---|---|
| 369 | 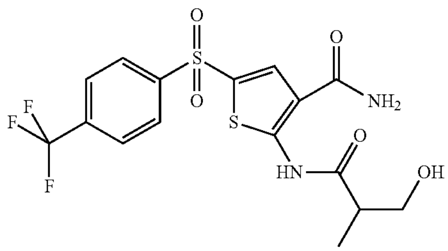 [SMILES: CC(CO)C(=O)Nc1sc(S(=O)(=O)c2ccc(C(F)(F)F)cc2)cc1C(N)=O] | 2-[(3-hydroxy-2-methyl-propanoyl)amino]-5-[4-(trifluoromethyl)phenyl]sulfonyl-thiophene-3-carboxamide | H1, A, B2, D2, O3 | Int 8 | 436.4 | 437.21 (MH−) |
| 370 | 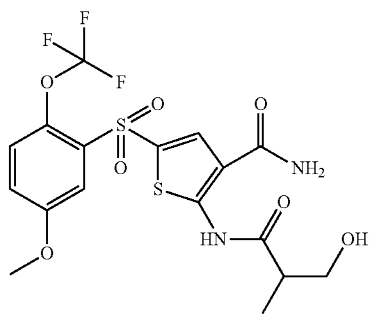 [SMILES: COc1ccc(OC(F)(F)F)c(S(=O)(=O)c2cc(C(N)=O)c(NC(=O)C(C)CO)s2)c1] | 2-[(3-hydroxy-2-methyl-propanoyl)amino]-5-[5-methoxy-2-(trifluoromethoxy)phenyl]sulfonyl-thiophene-3-carboxamide | H1, A, M1, M2, D2, O3 | Int 8 | 482.5 | 483.25 |
| 371 | 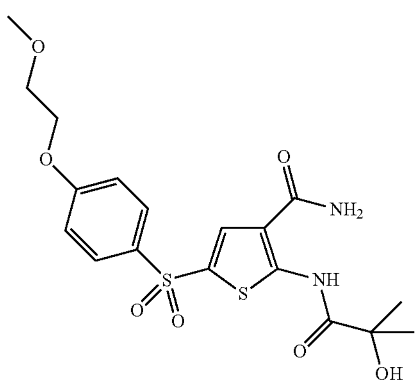 [SMILES: COCCOc1ccc(S(=O)(=O)c2cc(C(N)=O)c(NC(=O)C(C)(C)O)s2)cc1] | 2-[(2-hydroxy-2-methyl-propanoyl)amino]-5-[4-(2-methoxyethoxy)phenyl]sulfonyl-1-thiophene-3-carboxamide | B2, D2, J3 | Int 11 | 442.5 | 443.13 |
| 372 | 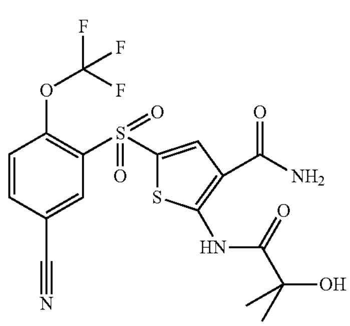 [SMILES: CC(C)(O)C(=O)Nc1sc(S(=O)(=O)c2cc(C#N)ccc2OC(F)(F)F)cc1C(N)=O] | 5-[5-cyano-2-(trifluoromethoxy)phenyl]sulfonyl-2-[(2-hydroxy-2-methyl-propanoyl)amino]thiophene-3-carboxamide | M1, M2, D2, J3 | Int 12 | 477.4 | 476.03 (MH−) |

TABLE II-continued

List of final compounds

| Cpd # | Structure | Name | Mtd | Int | MW | Mes |
|---|---|---|---|---|---|---|
| 373 | 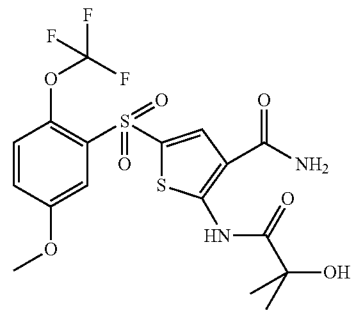 [SMILES: COc1ccc(OC(F)(F)F)c(S(=O)(=O)c2cc(C(N)=O)c(NC(=O)C(C)(C)O)s2)c1] | 2-[(2-hydroxy-2-methyl-propanoyl)amino]-5-[5-methoxy-2-(trifluoromethoxy)phenyl]sulfonyl-thiophene-3-carboxamide | M1, M2, D2, J3 | Int 12 | 482.5 | 483.31 |
| 374 | 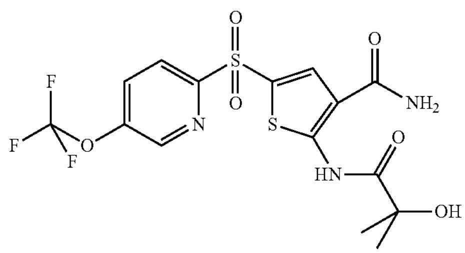 [SMILES: CC(C)(O)C(=O)Nc1sc(S(=O)(=O)c2ccc(OC(F)(F)F)cn2)cc1C(N)=O] | 2-[(2-hydroxy-2-methyl-propanoyl)amino]-5-[[5-(trifluoromethoxy)-2-pyridyl]sulfonyl]thiophene-3-carboxamide | M4, D2, J3 | Int 13 | 453.4 | 454.19 |
| 375 | 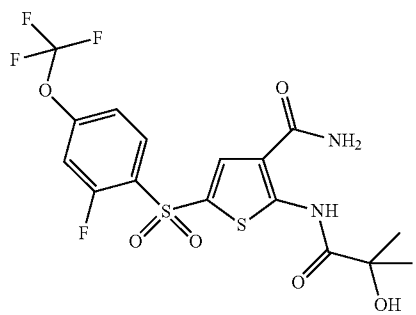 [SMILES: CC(C)(O)C(=O)Nc1sc(S(=O)(=O)c2ccc(OC(F)(F)F)cc2F)cc1C(N)=O] | 5-[2-fluoro-4-(trifluoromethoxy)phenyl]sulfonyl-2-[(2-hydroxy-2-methyl-propanoyl)amino]thiophene-3-carboxamide | M1, M2, D2, J3 | Int 12 | 470.4 | 471.01 |
| 376 | 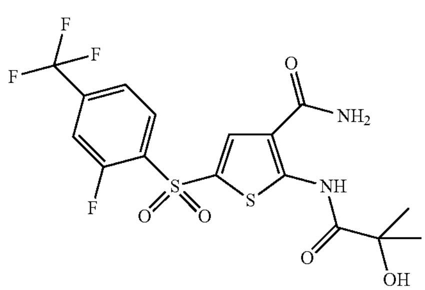 [SMILES: CC(C)(O)C(=O)Nc1sc(S(=O)(=O)c2ccc(C(F)(F)F)cc2F)cc1C(N)=O] | 5-[2-fluoro-4-(trifluoromethyl)phenyl]sulfonyl-2-[(2-hydroxy-2-methyl-propanoyl)amino]thiophene-3-carboxamide | M1, M2, D2, J3 | Int 12 | 454.4 | 455.02 |
| 377 | 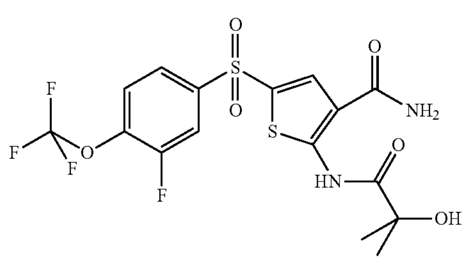 [SMILES: CC(C)(O)C(=O)Nc1sc(S(=O)(=O)c2ccc(OC(F)(F)F)c(F)c2)cc1C(N)=O] | 5-[3-fluoro-4-(trifluoromethoxy)phenyl]sulfonyl-2-[(2-hydroxy-2-methyl-propanoyl)amino]thiophene-3-carboxamide | M1, M2, D2, J3 | Int 12 | 470.4 | 471.27 |

TABLE II-continued

List of final compounds

| Cpd # | Structure | Name | Mtd | Int | MW | Mes |
|---|---|---|---|---|---|---|
| 378 | 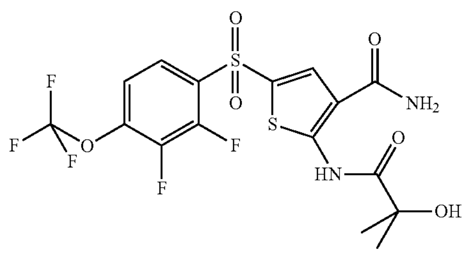 | 5-[2,3-difluoro-4-(trifluoromethoxy)phenyl]sulfonyl-2-[(2-hydroxy-2-methyl-propanoyl)amino]thiophene-3-carboxamide | M1, M2, D2, J3 | Int 12 | 488.4 | 487.07 (MH−) |
| 379 | 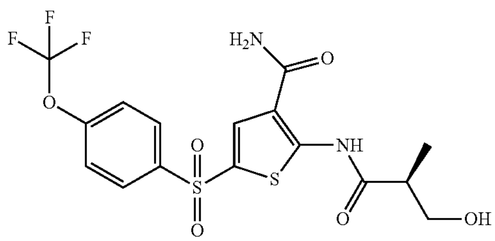 [SMILES: C[C@@H](CO)C(=O)Nc1sc(S(=O)(=O)c2ccc(OC(F)(F)F)cc2)cc1C(N)=O] | 2-[[(2S)-3-hydroxy-2-methyl-propanoyl]amino]-5-[4-(trifluoromethoxy)phenyl]sulfonyl-thiophene-3-carboxamide | I, B2, D2, G, H1, J | Int 3 | 452.4 | 452.99 |
| 380 | 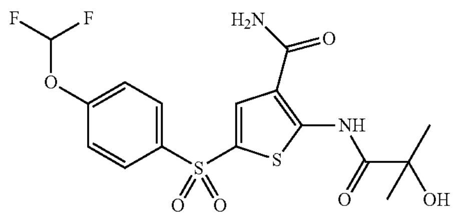 [SMILES: CC(C)(O)C(=O)Nc1sc(S(=O)(=O)c2ccc(OC(F)F)cc2)cc1C(N)=O] | 5-[4-(difluoromethoxy)phenyl]sulfonyl-2-[(2-hydroxy-2-methyl-propanoyl)amino]thiophene-3-carboxamide | B2, J3, D2 | Int 12 | 434.4 | 435.28 |
| 381 | 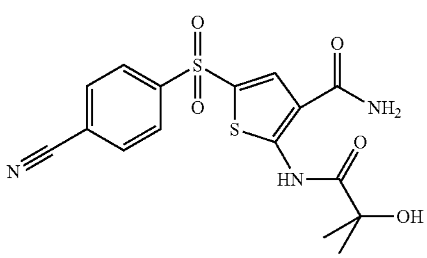 [SMILES: CC(C)(O)C(=O)Nc1sc(S(=O)(=O)c2ccc(C#N)cc2)cc1C(N)=O] | 5-(4-cyanophenyl)sulfonyl-2-[(2-hydroxy-2-methyl-propanoyl)amino]thiophene-3-carboxamide | B2, J3, D2 | Int 12 | 393.4 | 392.03 (MH−) |
| 382 | 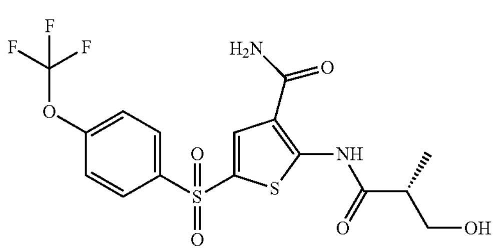 [SMILES: C[C@H](CO)C(=O)Nc1sc(S(=O)(=O)c2ccc(OC(F)(F)F)cc2)cc1C(N)=O] | 2-[[(2R)-3-hydroxy-2-methyl-propanoyl]amino]-5-[4-(trifluoromethoxy)phenyl]sulfonyl-thiophene-3-carboxamide | I, B2, D2, G, H1, J | Int 3 | 452.4 | 452.99 |
| 383 | 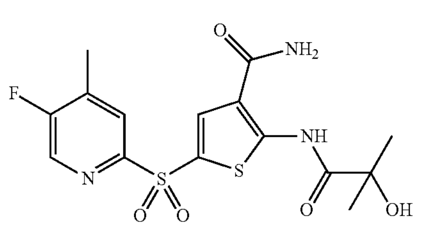 [SMILES: Cc1cc(S(=O)(=O)c2cc(C(N)=O)c(NC(=O)C(C)(C)O)s2)ncc1F] | 5-[(5-fluoro-4-methyl-2-pyridyl)sulfonyl]-2-[(2-hydroxy-2-methyl-propanoyl)amino]thiophene-3-carboxamide | M4, D2, J3 | Int 13 | 401.4 | 402.01 |

TABLE II-continued

List of final compounds

| Cpd # | Structure | Name | Mtd | Int | MW | Mes |
|---|---|---|---|---|---|---|
| 384 | 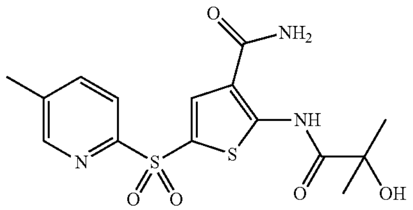 [SMILES: Cc1ccc(S(=O)(=O)c2cc(C(N)=O)c(NC(=O)C(C)(C)O)s2)nc1] | 2-[(2-hydroxy-2-methyl-propanoyl)amino]-5-[(5-methyl-2-pyridyl)sulfonyl]thiophene-3-carboxamide | M4, D2, J3 | Int 13 | 383.4 | 384.03 |
| 385 | 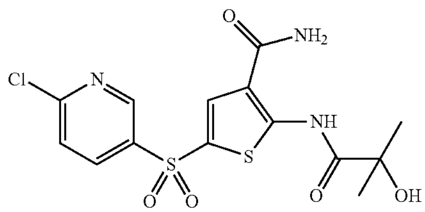 [SMILES: CC(C)(O)C(=O)Nc1sc(S(=O)(=O)c2ccc(Cl)nc2)cc1C(N)=O] | 5-[(6-chloro-3-pyridyl)sulfonyl]-2-[(2-hydroxy-2-methyl-propanoyl)amino]thiophene-3-carboxamide | M4, D2, J3 | Int 13 | 403.9 | 403.96, 405.88 |
| 386 | 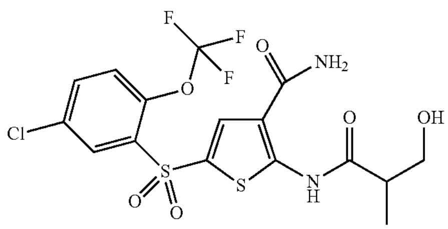 [SMILES: CC(CO)C(=O)Nc1sc(S(=O)(=O)c2cc(Cl)ccc2OC(F)(F)F)cc1C(N)=O] | 5-[5-chloro-2-(trifluoromethoxy)phenyl]sulfonyl-2-[(3-hydroxy-2-methyl-propanoyl)amino]thiophene-3-carboxamide | H1, A, B2, D2, O3 | Int 8 | 486.9 | 484.87 (MH−) |
| 387 | 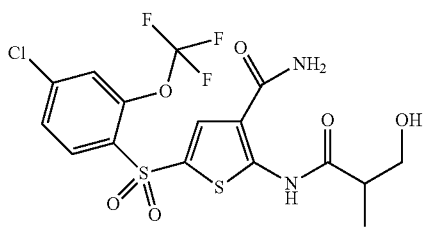 [SMILES: CC(CO)C(=O)Nc1sc(S(=O)(=O)c2ccc(Cl)cc2OC(F)(F)F)cc1C(N)=O] | 5-[4-chloro-2-(trifluoromethoxy)phenyl]sulfonyl-2-[(3-hydroxy-2-methyl-propanoyl)amino]thiophene-3-carboxamide | H1, A, B2, D2, O3 | Int 8 | 486.9 | 485.08 (MH−) |
| 388 | 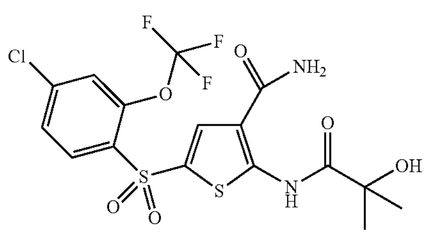 [SMILES: CC(C)(O)C(=O)Nc1sc(S(=O)(=O)c2ccc(Cl)cc2OC(F)(F)F)cc1C(N)=O] | 5-[4-chloro-2-(trifluoromethoxy)phenyl]sulfonyl-2-[(2-hyroxy-2-methyl-propanoyl)amino]thiophene-3-carboxamide | M1, M2, D2, J3 | Int 12 | 486.9 | 485.08 (MH−) |
| 389 | 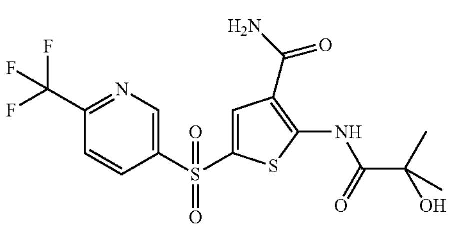 [SMILES: CC(C)(O)C(=O)Nc1sc(S(=O)(=O)c2ccc(C(F)(F)F)nc2)cc1C(N)=O] | 2-[(2-hydroxy-2-methyl-propanoyl)amino]-5-[[6-(trifluoromethyl)-3-pyridyl]sulfonyl]thiophene-3-carboxamide | M1, M2, D2, J3 | Int 12 | 437.4 | 437.97 |

TABLE II-continued

List of final compounds

| Cpd # | Structure | Name | Mtd | Int | MW | Mes |
|---|---|---|---|---|---|---|
| 390 | 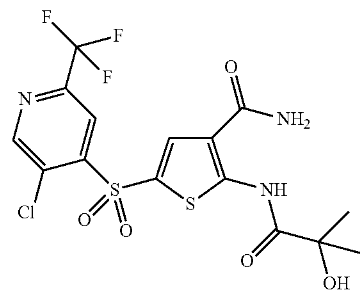 [SMILES: CC(C)(O)C(=O)Nc1sc(S(=O)(=O)c2cc(C(F)(F)F)ncc2Cl)cc1C(N)=O] | 5-[[5-chloro-2-(trifluoromethyl)-4-pyridyl]sulfonyl]-2-[(2-hydroxy-2-methyl-propanoyl)amino]thiophene-3-carboxamide | M4, D2, J3 | Int 13 | 471.9 | 469.99, 471.89 (MH−) |
| 391 | 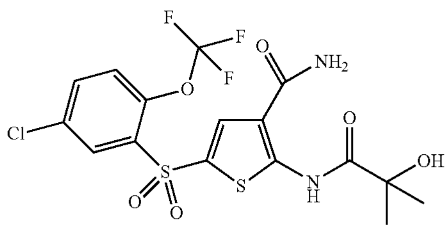 [SMILES: CC(C)(O)C(=O)Nc1sc(S(=O)(=O)c2cc(Cl)ccc2OC(F)(F)F)cc1C(N)=O] | 5-[5-chloro-2-(trifluoromethoxy)phenyl]sulfonyl-2-[(2-hydroxy-2-methyl-propanoyl)amino]thiophene-3-carboxamide | M1, M2, D2, J3 | Int 12 | 486.9 | 487.14 |
| 392 | 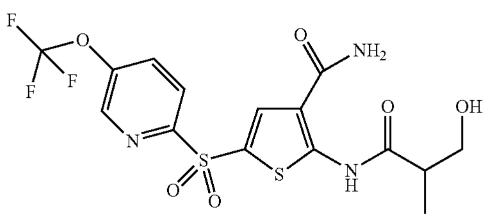 [SMILES: CC(CO)C(=O)Nc1sc(S(=O)(=O)c2ccc(OC(F)(F)F)cn2)cc1C(N)=O] | 2-[(3-hydroxy-2-methyl-propanoyl)amino]-5-[[5-(trifluoromethoxy)-2-pyridyl]sulfonyl]thiophene-3-carboxamide | H1, A, M1, M2, D2, O3 | Int 8 | 453.4 | 454.18 |
| 393 | 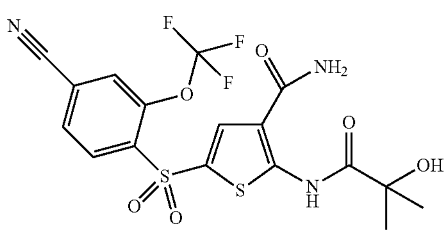 [SMILES: CC(C)(O)C(=O)Nc1sc(S(=O)(=O)c2ccc(C#N)cc2OC(F)(F)F)cc1C(N)=O] | 5-[4-cyano-2-(trifluoromethoxy)phenyl]sulfonyl-2-[(2-hydroxy-2-methyl-propanoyl)amino]thiophene-3-carboxamide | M4, D2, J3 | Int 13 | 477.4 | 476.08 (MH−) |
| 394 | 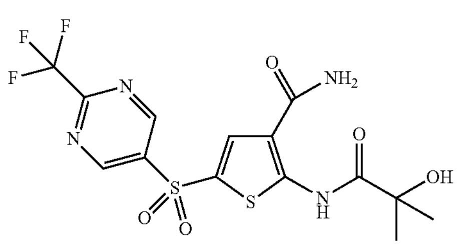 [SMILES: CC(C)(O)C(=O)Nc1sc(S(=O)(=O)c2cnc(C(F)(F)F)nc2)cc1C(N)=O] | 2-[(2-hydroxy-2-methyl-propanoyl)amino]-5-[2-(trifluoromethyl)pyrimidin-5-yl]sulfonyl-thiophene-3-carboxamide | M4, D2, J3 | Int 13 | 438.4 | 437.05 (MH−) |
| 395 | 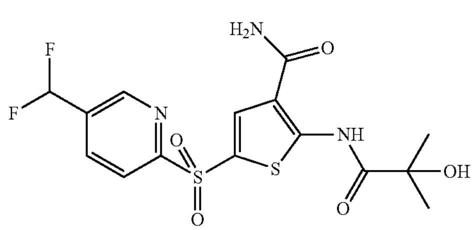 [SMILES: CC(C)(O)C(=O)Nc1sc(S(=O)(=O)c2ccc(C(F)F)cn2)cc1C(N)=O] | 5-[[5-(difluoromethyl)-2-pyridyl]sulfonyl]-2-[(2-hydroxy-2-methyl-propanoyl)amino]thiophene-3-carboxamide | M4, D2, J3 | Int 13 | 419.4 | 420.17 |

TABLE II-continued

List of final compounds

| Cpd # | Structure | Name | Mtd | Int | MW | Mes |
|---|---|---|---|---|---|---|
| 396 | 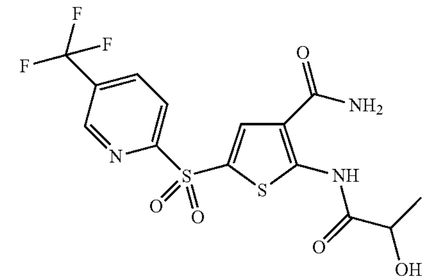 [SMILES: CC(O)C(=O)Nc1sc(S(=O)(=O)c2ccc(C(F)(F)F)cn2)cc1C(N)=O] | 2-(2-hydroxypropanoylamino)-5-[[5-(trifluoromethyl)-2-pyridyl]sulfonyl]thiophene-3-carboxamide | H1, A, M1, M4, D2, J3 | Int 8 | 423.4 | 423.94 |
| 397 | 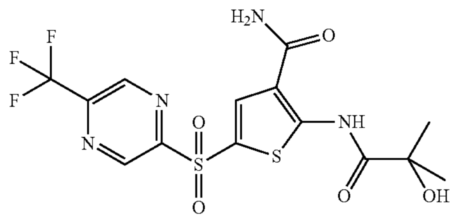 [SMILES: CC(C)(O)C(=O)Nc1sc(S(=O)(=O)c2cnc(C(F)(F)F)cn2)cc1C(N)=O] | 2-[(2-hydroxy-2-methyl-propanoyl)amino]-5-[5-(trifluoromethyl)pyrazin-2-yl]sulfonyl-thiophene-3-carboxamide | M4, D2, J3 | Int 13 | 438.4 | 439.01 |
| 398 | 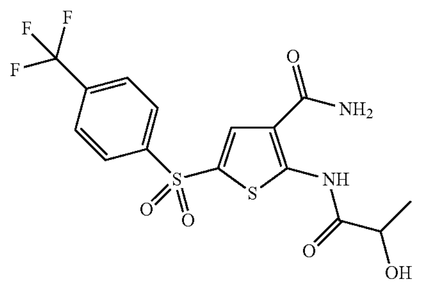 [SMILES: CC(O)C(=O)Nc1sc(S(=O)(=O)c2ccc(C(F)(F)F)cc2)cc1C(N)=O] | 2-(2-hydroxypropanoylamino)-5-[4-(trifluoromethyl)phenyl]sulfonyl-thiophene-3-carboxamide | H1, A, B2, D2, J3 | Int 8 | 422.4 | 422.98 |
| 399 | 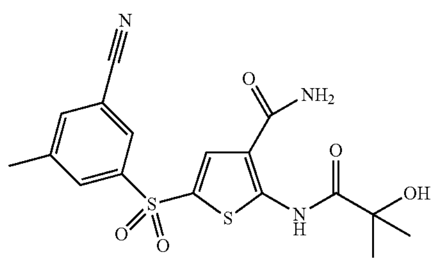 [SMILES: Cc1cc(C#N)cc(S(=O)(=O)c2cc(C(N)=O)c(NC(=O)C(C)(C)O)s2)c1] | 5-(3-cyano-5-methyl-phenyl)sulfonyl-2-[(2-hydroxy-2-methyl-propanoyl)amino]thiophene-3-carboxamide | M1, M2, J3, D2 | Int 12 | 407.5 | 408.02 |
| 400 | 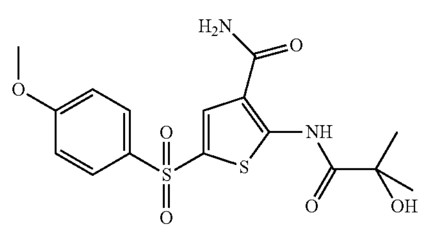 [SMILES: COc1ccc(S(=O)(=O)c2cc(C(N)=O)c(NC(=O)C(C)(C)O)s2)cc1] | 2-[(2-hydroxy-2-methyl-propanoyl)amino]-5-(4-methoxyphenyl)sulfonyl-thiophene-3-carboxamide | M1, M2, J3, D2 | Int 12 | 398.5 | 399 |
| 401 | 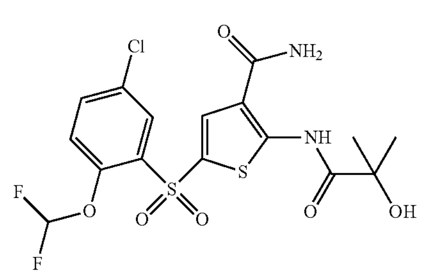 [SMILES: CC(C)(O)C(=O)Nc1sc(S(=O)(=O)c2cc(Cl)ccc2OC(F)F)cc1C(N)=O] | 5-[5-chloro-2-(difluoromethoxy)phenyl]sulfonyl-2-[(2-hydroxy-2-methyl-propanoyl)amino]thiophene-3-carboxamide | Q, M1, M2, D2, J3 | Int 12 | 468.9 | 468.7 |

TABLE II-continued

List of final compounds

| Cpd # | Structure | Name | Mtd | Int | MW | Mes |
|---|---|---|---|---|---|---|
| 402 | 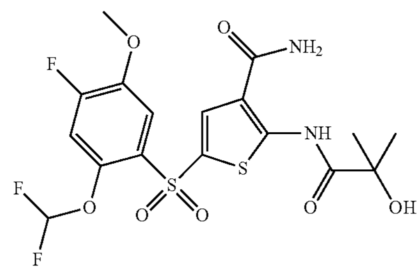 [SMILES: COc1cc(S(=O)(=O)c2cc(C(N)=O)c(NC(=O)C(C)(C)O)s2)c(OC(F)F)cc1F] | 5-[2-(difluoromethoxy)-4-fluoro-5-methoxy-phenyl]sulfonyl-2-[(2-hydroxy-2-methyl-propanoyl)amino]thiophene-3-carboxamide | Q, M1, M2, D2, J3 | Int 12 | 482.5 | 483.0 |
| 403 | 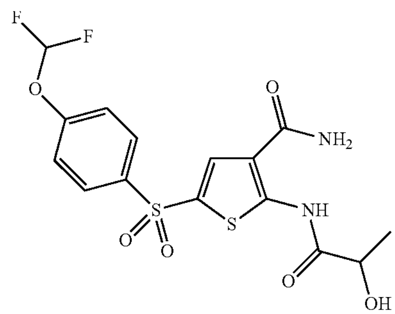 [SMILES: CC(O)C(=O)Nc1sc(S(=O)(=O)c2ccc(OC(F)F)cc2)cc1C(N)=O] | 5-[4-(difluoromethoxy)phenyl]sulfonyl-2-(2-hydroxypropanoylamino)thiophene-3-carboxamide | H1, A, B2, D2, J3 | Int 8 | 420.4 | 421.00 |
| 404 | 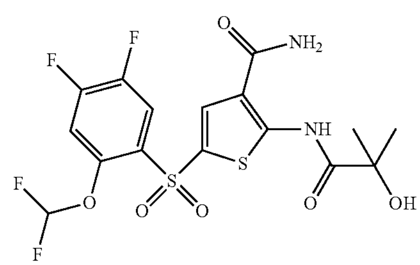 [SMILES: CC(C)(O)C(=O)Nc1sc(S(=O)(=O)c2cc(F)c(F)cc2OC(F)F)cc1C(N)=O] | 5-[2-(difluoromethoxy)-4,5-difluoro-phenyl]sulfonyl-2-[(2-hydroxy-2-methyl-propanoyl)amino]thiophene-3-carboxamide | Q, M1, M2, D2, J3 | Int 12 | 470.4 | 471.0 |
| 405 | 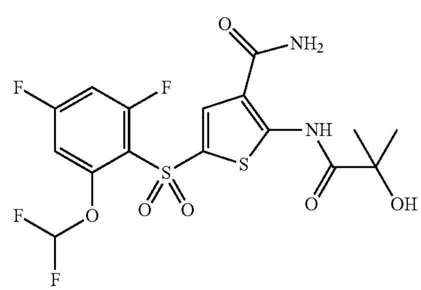 [SMILES: CC(C)(O)C(=O)Nc1sc(S(=O)(=O)c2c(F)cc(F)cc2OC(F)F)cc1C(N)=O] | 5-[2-(difluoromethoxy)-4,6-difluoro-phenyl]sulfonyl-2-[(2-hydroxy-2-methyl-propanoyl)amino]thiophene-3-carboxamide | Q, M1, M2, D2, J3 | Int 12 | 470.4 | 471.0 |
| 406 | 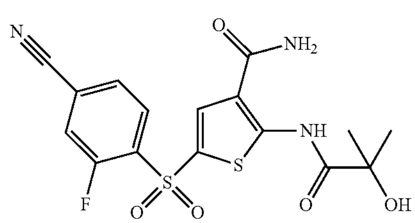 [SMILES: CC(C)(O)C(=O)Nc1sc(S(=O)(=O)c2ccc(C#N)cc2F)cc1C(N)=O] | 5-(4-cyano-2-fluoro-phenyl)sulfonyl-2-[(2-hydroxy-2-methyl-propanoyl)amino]thiophene-3-carboxamide | M1, M2, D2, J3 | Int 12 | 411.4 | 411.8 |

TABLE II-continued

List of final compounds

| Cpd # | Structure | Name | Mtd | Int | MW | Mes |
|---|---|---|---|---|---|---|
| 407 | 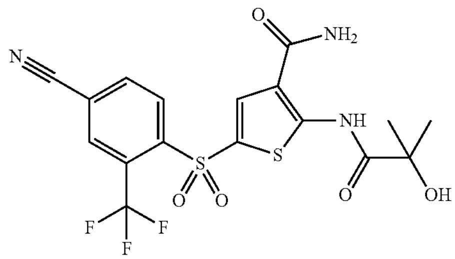 [SMILES: CC(C)(O)C(=O)Nc1sc(S(=O)(=O)c2ccc(C#N)cc2C(F)(F)F)cc1C(N)=O] | 5-[4-cyano-2-(trifluoromethyl)phenyl]sulfonyl-2-[(2-hydroxy-2-methyl-propanoyl)amino]thiophene-3-carboxamide | M1, M2, D2, J3 | Int 12 | 461.4 | 462.0 |
| 408 | 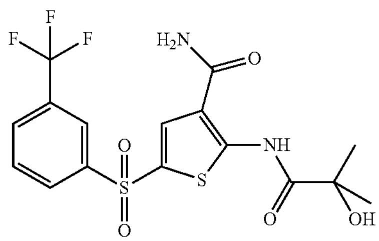 [SMILES: CC(C)(O)C(=O)Nc1sc(S(=O)(=O)c2cccc(C(F)(F)F)c2)cc1C(N)=O] | 2-[(2-hydroxy-2-methyl-propanoyl)amino]-5-[3-(trifluoromethyl)phenyl]sulfonyl-thiophene-3-carboxamide | M1, M2, D2, J3 | Int 12 | 436.4 | 437.06 |
| 409 | 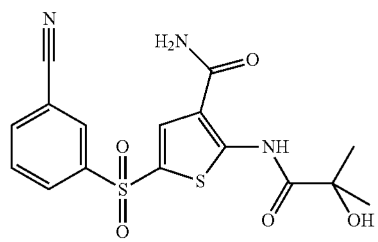 [SMILES: CC(C)(O)C(=O)Nc1sc(S(=O)(=O)c2cccc(C#N)c2)cc1C(N)=O] | 5-(3-cyanophenyl)sulfonyl-2-[(2-hydroxy-2-methyl-propanoyl)amino]thiophene-3-carboxamide | M1, M2, D2, J3 | Int 12 | 393.4 | 394.06 |
| 410 | 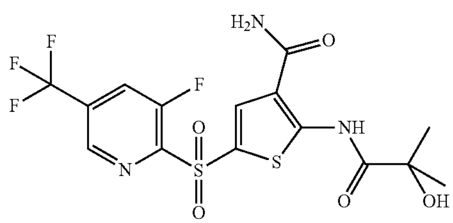 [SMILES: CC(C)(O)C(=O)Nc1sc(S(=O)(=O)c2ncc(C(F)(F)F)cc2F)cc1C(N)=O] | 5-[[3-fluoro-5-(trifluoromethyl)-2-pyridyl]sulfonyl]-2-[(2-hydroxy-2-methyl-propanoyl)amino]thiophene-3-carboxamide | M4, D2, J3 | Int 13 | 455.4 | 456.05 |
| 411 | 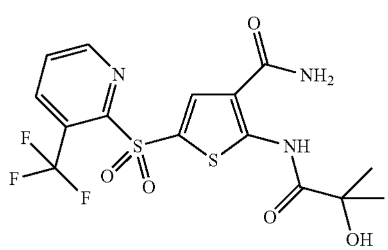 [SMILES: CC(C)(O)C(=O)Nc1sc(S(=O)(=O)c2ncccc2C(F)(F)F)cc1C(N)=O] | 2-[(2-hydroxy-2-methyl-propanoyl)amino]-5-[[3-(trifluoromethyl)-2-pyridyl]sulfonyl]thiophene-3-carboxamide | M4, D2, J3 | Int 13 | 437.4 | 438.05 |
| 412 | 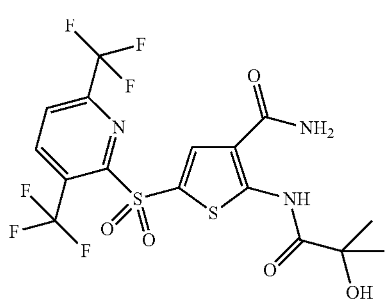 [SMILES: CC(C)(O)C(=O)Nc1sc(S(=O)(=O)c2nc(C(F)(F)F)ccc2C(F)(F)F)cc1C(N)=O] | 5-[[3,6-bis(trifluoromethyl)-2-pyridyl]sulfonyl]-2-[(2-hydroxy-2-methyl-propanoyl)amino]thiophene-3-carboxamide | M4, D2, J3 | Int 13 | 505.4 | 506.09 |

TABLE II-continued

List of final compounds

| Cpd # | Structure | Name | Mtd | Int | MW | Mes |
|---|---|---|---|---|---|---|
| 413 | 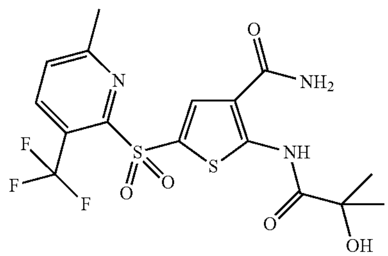 [SMILES: Cc1ccc(C(F)(F)F)c(S(=O)(=O)c2cc(C(N)=O)c(NC(=O)C(C)(C)O)s2)n1] | 2-[(2-hydroxy-2-methyl-propanoyl)amino]-5-[[6-methyl-3-(trifluoromethyl)-2-pyridyl]sulfonyl]thiophene-3-carboxamide | M4, D2, J3 | Int 13 | 451.4 | 452.03 |
| 414 | 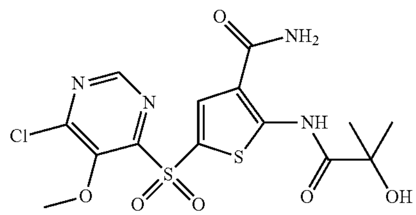 [SMILES: COc1c(Cl)ncnc1S(=O)(=O)c1cc(C(N)=O)c(NC(=O)C(C)(C)O)s1] | 5-(6-chloro-5-methoxy-pyrimidin-4-yl)sulfonyl-2-[(2-hydroxy-2-methyl-propanoyl)amino]thiophene-3-carboxamide | M4, D2, J3 | Int 13 | 434.9 | 434.8 |
| 415 | 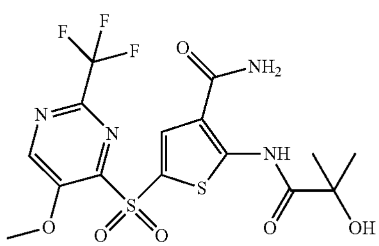 [SMILES: COc1cnc(C(F)(F)F)nc1S(=O)(=O)c1cc(C(N)=O)c(NC(=O)C(C)(C)O)s1] | 2-[(2-hydroxy-2-methyl-propanoyl)amino]-5-[5-methoxy-2-(trifluoromethyl)pyrimidin-4-yl]sulfonyl-thiophene-3-carboxamide | M4, D2, J3 | Int 13 | 468.4 | |
| 416 | 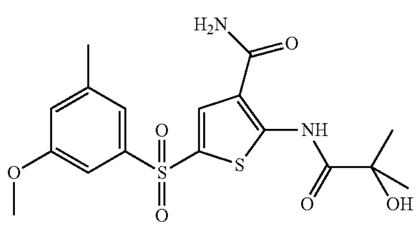 [SMILES: COc1cc(C)cc(S(=O)(=O)c2cc(C(N)=O)c(NC(=O)C(C)(C)O)s2)c1] | 2-[(2-hydroxy-2-methyl-propanoyl)amino]-5-(3-methoxy-5-methyl-phenyl)sulfonyl-thiophene-3-carboxamide | M1, M2, D2, J3 | Int 12 | 412.5 | 413.04 |
| 417 | 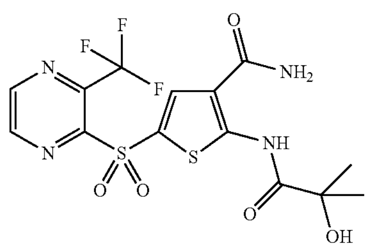 [SMILES: CC(C)(O)C(=O)Nc1sc(S(=O)(=O)c2nccnc2C(F)(F)F)cc1C(N)=O] | 2-[(2-hydroxy-2-methyl-propanoyl)amino]-5-[3-(trifluoromethyl)pyrazin-2-yl]sulfonyl-thiophene-3-carboxamide | M4, D2, J3 | Int 13 | 438.4 | 439.03 |
| 418 | 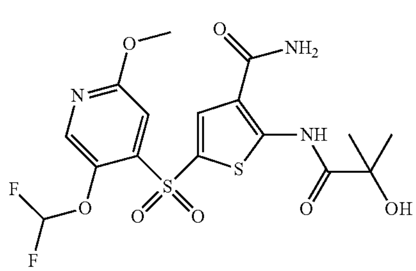 [SMILES: COc1cc(S(=O)(=O)c2cc(C(N)=O)c(NC(=O)C(C)(C)O)s2)c(OC(F)F)cn1] | 5-[[5-(difluoromethoxy)-2-methoxy-4-pyridyl]sulfonyl]-2-[(2-hydroxy-2-methyl-propanoyl)amino]thiophene-3-carboxamide | Q, M4, D2, J3 | Int 13 | 465.5 | 465.8 |

TABLE II-continued

List of final compounds

| Cpd # | Structure | Name | Mtd | Int | MW | Mes |
|---|---|---|---|---|---|---|
| 419 | 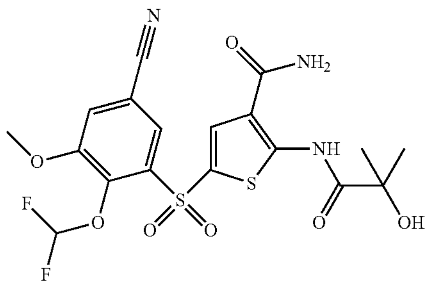 [SMILES: COc1cc(C#N)cc(S(=O)(=O)c2cc(C(N)=O)c(NC(=O)C(C)(C)O)s2)c1OC(F)F] | 5-[5-cyano-2-(difluoromethoxy)-3-methoxy-phenyl]sulfonyl-2-[(2-hydroxy-2-methyl-propanoyl)amino]thiophene-3-carboxamide | Q, M4, D2, J3 | Int 13 | 489.5 | 489.8 |
| 420 | 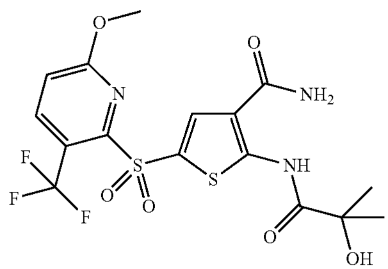 [SMILES: COc1ccc(C(F)(F)F)c(S(=O)(=O)c2cc(C(N)=O)c(NC(=O)C(C)(C)O)s2)n1] | 2-[(2-hydroxy-2-methyl-propanoyl)amino]-5-[[6-methoxy-3-(trifluoromethyl)-2-pyridyl]sulfonyl]thiophene-3-carboxamide | M4, D2, J3, C2 | Int 13 | 467.4 | 468.03 |
| 421 | 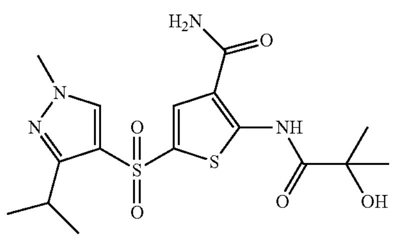 [SMILES: CC(C)c1nn(C)cc1S(=O)(=O)c1cc(C(N)=O)c(NC(=O)C(C)(C)O)s1] | 2-[(2-hydroxy-2-methyl-propanoyl)amino]-5-(3-isopropyl-1-methyl-pyrazol-4-yl)sulfonyl-thiophene-3-carboxamide | M1, M2, D2, J3 | Int 12 | 414.5 | 415.15 |
| 422 | 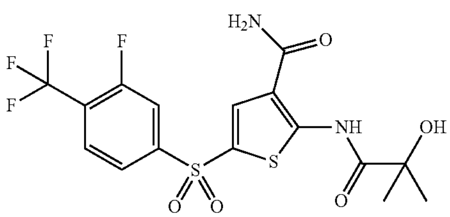 [SMILES: CC(C)(O)C(=O)Nc1sc(S(=O)(=O)c2ccc(C(F)(F)F)c(F)c2)cc1C(N)=O] | 5-[3-fluoro-4-(trifluoromethyl)phenyl]sulfonyl-2-[(2-hydroxy-2-methyl-propanoyl)amino]thiophene-3-carboxamide | M1, M2, D2, J3 | Int 12 | 454.4 | 455.0 |
| 423 | 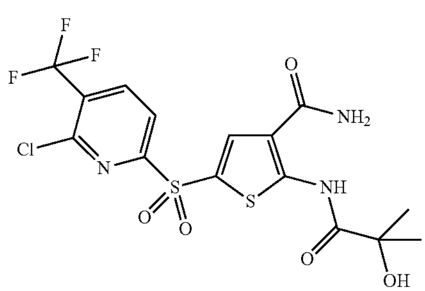 [SMILES: CC(C)(O)C(=O)Nc1sc(S(=O)(=O)c2ccc(C(F)(F)F)c(Cl)n2)cc1C(N)=O] | 5-[[6-chloro-5-(trifluoromethyl)-2-pyridyl]sulfonyl]-2-[(2-hydroxy-2-methyl-propanoyl)amino]thiophene-3-carboxamide | M4, D2, J3 | Int 13 | 471.9 | 472.00, 474 |
| 424 | 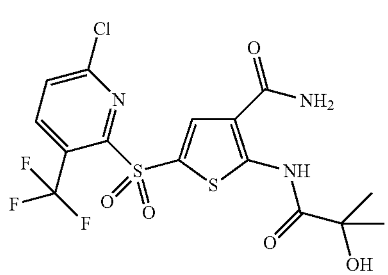 [SMILES: CC(C)(O)C(=O)Nc1sc(S(=O)(=O)c2nc(Cl)ccc2C(F)(F)F)cc1C(N)=O] | 5-[[6-chloro-3-(trifluoromethyl)-2-pyridyl]sulfonyl]-2-[(2-hydroxy-2-methyl-propanoyl)amino]thiophene-3-carboxamide | M4, D2, J3 | Int 13 | 471.9 | 472.03, 473.98 |

TABLE II-continued

List of final compounds

| Cpd # | Structure | Name | Mtd | Int | MW | Mes |
|---|---|---|---|---|---|---|
| 425 | 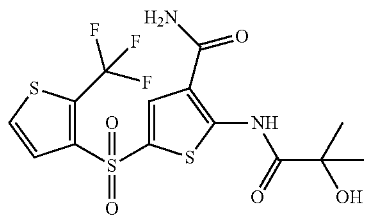 [SMILES: CC(C)(O)C(=O)Nc1sc(S(=O)(=O)c2ccsc2C(F)(F)F)cc1C(N)=O] | 2-[(2-hydroxy-2-methyl-propanoyl)amino]-5-[[2-(trifluoromethyl)-3-thienyl]sulfonyl]thiophene-3-carboxamide | M1, M2, D2, J3 | Int 12 | 442.5 | 443.01 |
| 426 | 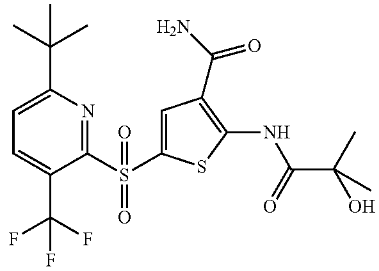 [SMILES: CC(C)(O)C(=O)Nc1sc(S(=O)(=O)c2nc(C(C)(C)C)ccc2C(F)(F)F)cc1C(N)=O] | 5-[[6-tert-butyl-3-(trifluoromethyl)-2-pyridyl]sulfonyl]-2-[(2-hydroxy-2-methyl-propanoyl)amino]thiophene-3-carboxamide | M4, D2, J3 | Int 13 | 493.5 | 494.14 |
| 427 | 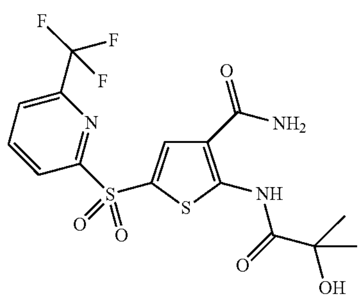 [SMILES: CC(C)(O)C(=O)Nc1sc(S(=O)(=O)c2cccc(C(F)(F)F)n2)cc1C(N)=O] | 2-[(2-hydroxy-2-methyl-propanoyl)amino]-5-[[6-(trifluoromethyl)-2-pyridyl]sulfonyl]thiophene-3-carboxamide | M4, D2, J3 | Int 13 | 437.4 | 438.08 |
| 428 | 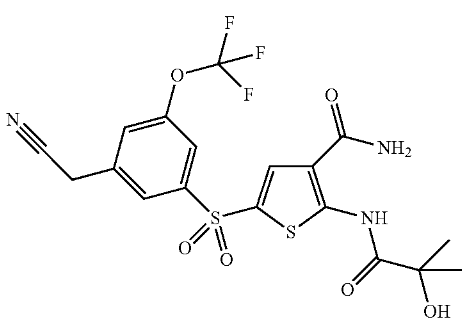 [SMILES: CC(C)(O)C(=O)Nc1sc(S(=O)(=O)c2cc(CC#N)cc(OC(F)(F)F)c2)cc1C(N)=O] | 5-[3-(cyanomethyl)-5-(trifluoromethoxy)phenyl]sulfonyl-2-[(2-hydroxy-2-methyl-propanoyl)amino]thiophene-3-carboxamide | M1, M2, D2, J3 | Int 12 | 491.5 | 492.08 |
| 429 | 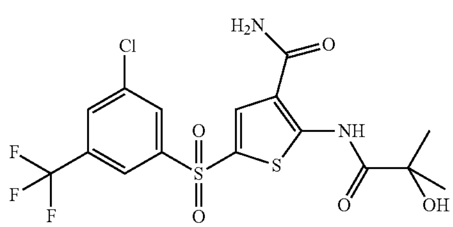 [SMILES: CC(C)(O)C(=O)Nc1sc(S(=O)(=O)c2cc(Cl)cc(C(F)(F)F)c2)cc1C(N)=O] | 5-[3-chloro-5-(trifluoromethyl)phenyl]sulfonyl-2-[(2-hydroxy-2-methyl-propanoyl)amino]thiophene-3-carboxamide | M1, M2, D2, J3 | Int 12 | 470.9 | 471.8 |

TABLE II-continued

List of final compounds

| Cpd # | Structure | Name | Mtd | Int | MW | Mes |
|---|---|---|---|---|---|---|
| 430 | 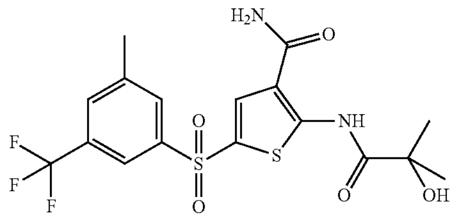 [SMILES: Cc1cc(C(F)(F)F)cc(S(=O)(=O)c2cc(C(N)=O)c(NC(=O)C(C)(C)O)s2)c1] | 2-[(2-hydroxy-2-methyl-propanoyl)amino]-5-[3-methyl-5-(trifluoromethyl)phenyl]sulfonyl-thiophene-3-carboxamide | M1, M2, D2, J3 | Int 12 | 450.5 | 451.07 |
| 431 | 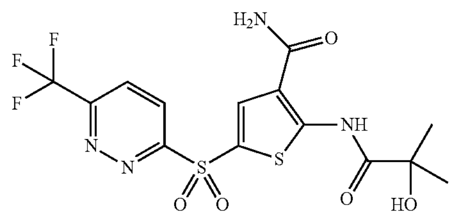 [SMILES: CC(C)(O)C(=O)Nc1sc(S(=O)(=O)c2ccc(C(F)(F)F)nn2)cc1C(N)=O] | 2-[(2-hydroxy-2-methyl-propanoyl)amino]-5-[6-(trifluoromethyl)pyridazin-3-yl]sulfonyl-thiophene-3-carboxamide | M4, D2, J3 | Int 13 | 438.4 | 439 |
| 432 | 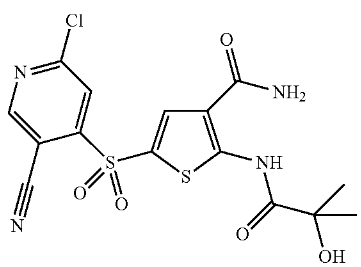 [SMILES: CC(C)(O)C(=O)Nc1sc(S(=O)(=O)c2cc(Cl)ncc2C#N)cc1C(N)=O] | 5-[(2-chloro-5-cyano-4-pyridyl)sulfonyl]-2-[(2-hydroxy-2-methyl-propanoyl)amino]thiophene-3-carboxamide | M4, D2, J3 | Int 13 | 428.9 | 428.8-430.8 |
| 433 | 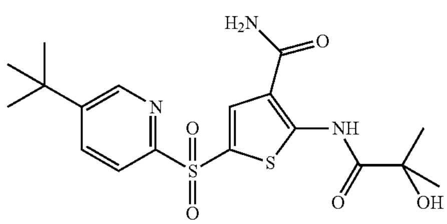 [SMILES: CC(C)(O)C(=O)Nc1sc(S(=O)(=O)c2ccc(C(C)(C)C)cn2)cc1C(N)=O] | 5-[(5-tert-butyl-2-pyridyl)sulfonyl]-2-[(2-hdyroxy-2-methyl-propanoyl)amino]thiophene-3-carboxamide | B3, D2, J3 | Int 13 | 425.53 | 426.13 |
| 434 | 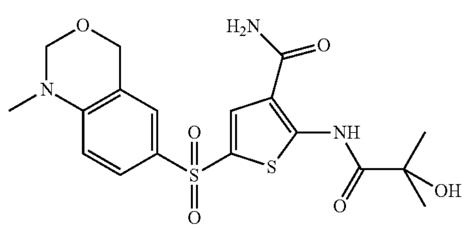 [SMILES: CN1COCc2cc(S(=O)(=O)c3cc(C(N)=O)c(NC(=O)C(C)(C)O)s3)ccc21] | 2-[(2-hdyroxy-2-methyl-propanoyl)amino]-5-[(1-methyl-2,4-dihydro-3,1-benzoxazin-6-yl)sulfonyl]thiophene-3-carboxamide | M1, M2, D2, O2, J3 | Int 12 | 439.51 | 440.16 |
| 435 | 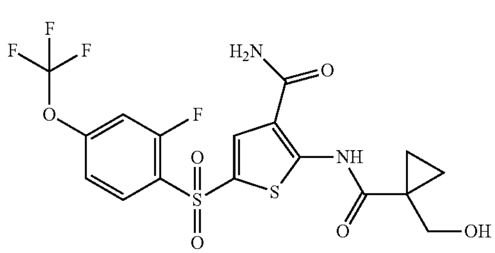 [SMILES: NC(=O)c1cc(S(=O)(=O)c2ccc(OC(F)(F)F)cc2F)sc1NC(=O)C1(CO)CC1] | 5-[2-fluoro-4-(trifluoromethoxy)phenyl]sulfonyl-2-[[1-(hydroxymethyl)cyclopropanecarbonyl]amino]thiophene-3-carboxamide | M1, M2, D2, G, H1, O3 | Int 2 | 482.43 | 483.01 |

TABLE II-continued

List of final compounds

| Cpd # | Structure | Name | Mtd | Int | MW | Mes |
|---|---|---|---|---|---|---|
| 436 | 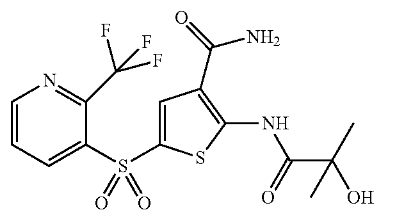 [SMILES: CC(C)(O)C(=O)Nc1sc(S(=O)(=O)c2cccnc2C(F)(F)F)cc1C(N)=O] | 2-[(2-hydroxy-2-methyl-propanoyl)amino]-5-[[2-(trifluoromethyl)-3-pyridyl]sulfonyl]thiophene-3-carboxamide | M4, D2, J3 | Int 13 | 437.42 | 438.01 |
| 437 | 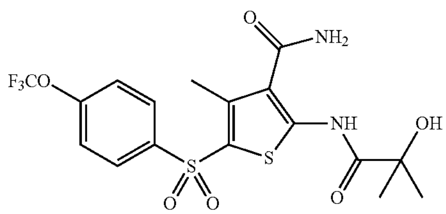 [SMILES: Cc1c(S(=O)(=O)c2ccc(OC(F)(F)F)cc2)sc(NC(=O)C(C)(C)O)c1C(N)=O] | 2-[(2-hydroxy-2-methyl-propanoyl)amino]-4-methyl-5-[4-(trifluoromethoxy)phenyl]sulfonyl-thiophene-3-carboxamide | A, B2, D2, H2, J3 | Int 9 | 466.45 | 466.8 |
| 438 | 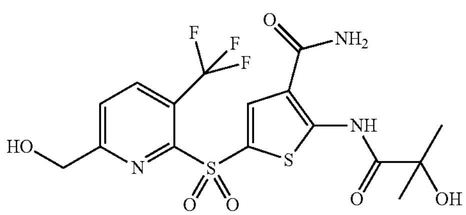 [SMILES: CC(C)(O)C(=O)Nc1sc(S(=O)(=O)c2nc(CO)ccc2C(F)(F)F)cc1C(N)=O] | 2-[(2-hydroxy-2-methyl-propanoyl)amino]-5-[[6-(hydroxymethyl)-3-(trifluoromethyl)-2-pyridyl]sulfonyl]thiophene-3-carboxamide | M4, D2, O3, J3 | Int 13 | 467.45 | 468 |
| 439 | 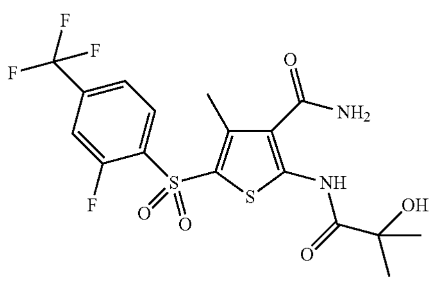 [SMILES: Cc1c(S(=O)(=O)c2ccc(C(F)(F)F)cc2F)sc(NC(=O)C(C)(C)O)c1C(N)=O] | 5-[2-fluoro-4-(trifluoromethyl)phenyl]sulfonyl-2-[(2-hydroxy-2-methyl-propanoyl)amino]-4-methyl-thiophene-3-carboxamide | A, D2, M1, M2, H2, J3 | Int 9 | 468.44 | 468.8 |
| 440 | 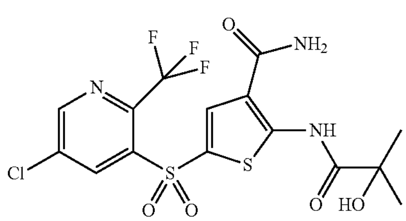 [SMILES: CC(C)(O)C(=O)Nc1sc(S(=O)(=O)c2cc(Cl)cnc2C(F)(F)F)cc1C(N)=O] | 5-[[5-chloro-2-(trifluoromethyl)-3-pyridyl]sulfonyl]-2-[(2-hydroxy-2-methyl-propanoyl)amino]thiophene-3-carboxamide | B3, D2, J3 | Int 13 | 471.86 | 471.96, 474.0 |
| 441 | 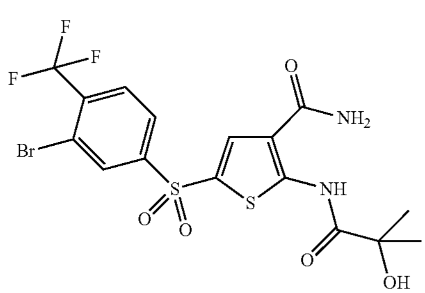 | 5-[[5-bromo-6-(trifluoromethyl)-3-pyridyl]sulfonyl]-2-[(2-hydroxy-2-methyl-propanoyl)amino]thiophene-3-carboxamide | B3, D2, J3 | Int 13 | 516.62 | 516.0, 517.90 |

TABLE II-continued

List of final compounds

| Cpd # | Structure | Name | Mtd | Int | MW | Mes |
|---|---|---|---|---|---|---|
| 442 | 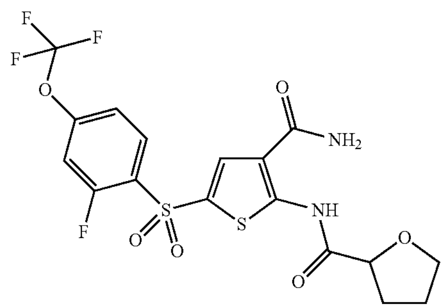 [SMILES: NC(=O)c1cc(S(=O)(=O)c2ccc(OC(F)(F)F)cc2F)sc1NC(=O)C1CCCO1] | N-[3-carbamoyl-5-[4-(trifluoromethoxy)phenyl]sulfonyl-2-thienyl]tetrahydrofuran-2-carboxamide | B2, D2, G, H1 | Int 3 | 464.4 | 464.8 |
| 443 | 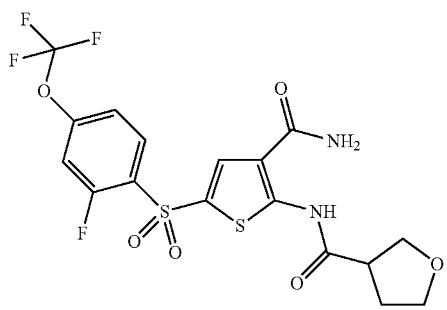 [SMILES: NC(=O)c1cc(S(=O)(=O)c2ccc(OC(F)(F)F)cc2F)sc1NC(=O)C1CCOC1] | N-[3-carbamoyl-5-[4-(trifluoromethoxy)phenyl]sulfonyl-2-thienyl]tetrahydrofuran-3-carboxamide | B2, D2, G, H1 | Int 3 | 464.4 | 464.8 |
| 444 | 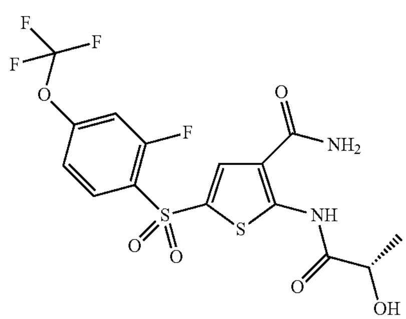 [SMILES: C[C@H](O)C(=O)Nc1sc(S(=O)(=O)c2ccc(OC(F)(F)F)cc2F)cc1C(N)=O] | 5-[2-fluoro-4-(trifluoromethoxy)phenyl]sulfonyl-2-[[(2S)-2-hydroxypropanoyl]amino]thiophene-3-carboxamide | M1, M2, D2, G, H5 | Int 2 | 456.4 | 457.03 |
| 445 | 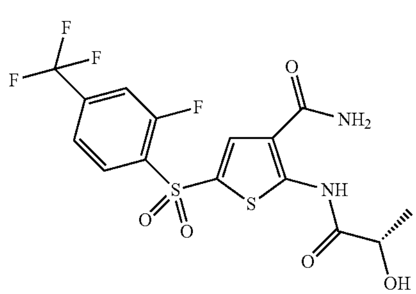 [SMILES: C[C@H](O)C(=O)Nc1sc(S(=O)(=O)c2ccc(C(F)(F)F)cc2F)cc1C(N)=O] | 5-[2-fluoro-4-(trifluoromethyl)phenyl]sulfonyl-2-[[(2S)-2-hydroxypropanoyl]amino]thiophene-3-carboxamide | M1, M2, D2, G, H5 | Int 2 | 440.4 | 441.08 |
| 446 | 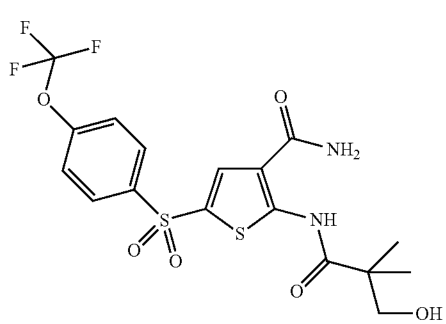 [SMILES: CC(C)(CO)C(=O)Nc1sc(S(=O)(=O)c2ccc(OC(F)(F)F)cc2)cc1C(N)=O] | 2-[(3-hydroxy-2,2-dimethyl-propanoyl)amino]-5-[4-(trifluoromethoxy)phenyl]sulfonyl-thiophene-3-carboxamide | I, B2, D2, G, H1, J | Int 3 | 466.5 | 467.07 |

TABLE II-continued

List of final compounds

| Cpd # | Structure | Name | Mtd | Int | MW | Mes |
|---|---|---|---|---|---|---|
| 447 | 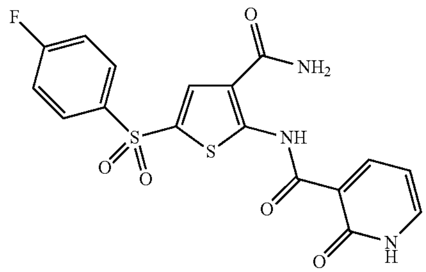 [SMILES: NC(=O)c1cc(S(=O)(=O)c2ccc(F)cc2)sc1NC(=O)c1ccc[nH]c1=O] | N-(3-carbamoyl-5-(4-fluorophenylsulfonyl)thiophen-2-yl)-2-oxo-1,2-dihydropyridine-3-carboxamide | A, C, D1, H1, R | 8 | 421 | 422 |

TABLE III

NMR Data of Representative Compounds of the Invention

| Cpd # | (δ) NMR data |
|---|---|
| 1 | $^1$H NMR δ (ppm)(DMSO-$d_6$): 13.39 (1 H, s), 8.27 (1 H, s br), 8.12 (1 H, s), 7.86 (1 H, s br), 7.59 (1 H, d), 7.03 (1 H, d), 2.96 (4 H, t), 2.55 (3 H, s), 1.58 (4 H, m), 1.41 (2 H, m). |
| 66 | $^1$H NMR δ (ppm)(DMSO-$d_6$): 13.60 (1 H, d), 8.34 (2 H, m), 8.81 (1 H, m), 7.92 (2 H, m), 7.76 (2 H, m), 3.21 (4 H, m), 2.19 (4 H, m). |
| 101 | $^1$H NMR δ (ppm)(DMSO-$d_6$): 13.72 (1 H, s), 12.23 (1 H, s), 8.01 (4 H, m), 7.73 (4 H, m), 6.93 (1 H, s), 3.32 (3 H, s). |
| 143 | $^1$H NMR δ (ppm)(DMSO-$d_6$): 13.92 (1 H, s), 11.86 (1 H, s), 8.09 (2 H, m), 7.99 (1 H, d), 7.55 (1 H, m), 7.45 (1 H, m), 7.02 (2 H, m), 3.72 (4 H, m), 2.98 (4 H, m). |
| 145 | $^1$H NMR δ (ppm)(DMSO-$d_6$): 13.78 (1 H, s), 13.37 (1 H, s), 8.25 (2 H, m), 8.05 (1 H, m), 7.82 (1 H, m), 7.43 (3 H, m), 7.24 (2 H, m), 6.91 (1 H, m), 4.20 (2 H, s), 2.65 (2 H, s). |
| 173 | $^1$H NMR δ (ppm)(DMSO-$d_6$): 13.72 (1 H, s), 13.37 (1 H, s), 8.18 (1 H, s), 8.00 (2 H m), 7.73 (1 H, s), 7.12 (4 H, m), 6.83 (1 H, s), 3.18 (3 H, s) |
| 206 | $^1$H NMR δ (ppm)(DMSO-$d_6$): 13.72 (1 H, s), 13.35 (1 H, s), 8.26 (1 H, s), 8.22 (1 H, s), 8.01 (1 H, m), 7.78 (1 H, s), 6.90 (1 H, m), 3.50 (4 H, s), 1.03 (6 H, s) |
| 222 | $^1$H NMR δ (ppm)(DMSO-$d_6$): 13.19 (1 H, s br), 8.34 (1 H, s br), 8.21 (1 H, s br), 8.07 (1 H, dd), 7.74 (1 H, s br), 7.35 (2 H, m), 6.99 (1 H, s br), 2.55 (3 H, s), 1.19 (2 H, m), 1.10 (2 H, m). |
| 224 | $^1$H NMR δ (ppm)(DMSO-$d_6$): 13.15 (1 H, s), 8.34 (1 H, s br), 8.14 (1 H, s), 7.99 (2 H, dd), 7.75 (1 H, s), 7.49 (2 H, t), 7.00 (1 H, s), 1.21 (2 H, m), 1.11 (2 H, m) |
| 225 | $^1$H NMR δ (ppm)(DMSO-$d_6$): 13.16 (1 H, s br), 8.35 (1 H, s), 8.15 (1 H, s br), 7.92 (2 H, d), 7.76 (1 H, s br), 7.73 (2 H, d), 7.00 (1 H, s), 1.21 (2 H, m), 1.11 (2 H, m). |
| 227 | $^1$H NMR δ (ppm)(DMSO-$d_6$): 13.16 (1 H, s br), 8.38 (1 H, s), 8.15 (1 H, s br), 7.78 (2 H, m), 7.73 (2 H, m), 7.60 (1 H, m), 7.02 (1 H, s), 1.21 (2 H, m), 1.12 (2 H, m). |
| 228 | $^1$H NMR δ (ppm)(DMSO-$d_6$): 13.19 (1 H, s br), 8.37 (1 H, s), 8.21 (1 H, s br), 7.98 (1 H, dd), 7.77 (1 H, s br), 7.69 (1 H, m), 7.63 (1 H, dd), 7.47 (1 H, m), 6.99 (1 H, m), 1.20 (2 H, m), 1.10-1.05 (9 H, m). |
| 331 | $^1$H NMR δ (ppm)(DMSO-$d_6$): 12.89 (1 H, s), 8.36 (1 H, s), 8.12 (1 H, s br), 8.08-8.04 (2 H, m), 7.71 (1H, s br), 7.64 (2 H, d), 6.27 (1H, d), 4.34-4.28 (1 H, m), 1.31 (3H, d). |
| 344 | $^1$H NMR δ (ppm)(DMSO-$d_6$): 12.96 (s, 1 H), 8.40 (s, 1H)), 8.09-8.19 (m, 3H), 8.03 (d, J = 8.5 Hz, 2 H), 7.73(s, 1 H), 6.14 (s, 1 H), 1.34 (s, 6 H) |
| 345 | $^1$H NMR δ (ppm)(DMSO-$d_6$): 12.89 (s, 1 H), 8.36 (s, 1 H), 8.12 (br. s., 1 H), 8.07 (d, 2 H), 7.71 (s, 1 H), 7.64 (d, 2 H), 6.26 (d, 1 H), 4.07 (dd, 1 H), 2.07 (dtt, 1 H), 0.94 (d, 3 H), 0.75 (d, 3 H) |
| 346 | H NMR δ (ppm)(DMSO-$d_6$): 12.93 (s, 1 H), 8.36 (s, 1 H), 8.12 (br. s., 1 H), 8.06 (d, 2 H), 7.73 (s, 1 H), 7.64 (d, 2 H), 6.28 (d, 1 H), 4.20 (dt, 1 H), 1.80 (dquin, 1 H), 1.36-1.58 (m, 2 H), 0.88 (t, 6 H) |
| 349 | H NMR δ (ppm)(DMSO-$d_6$): 12.87 (s, 1 H), 8.36 (s, 1 H), 8.11 (br. s., 1 H), 8.07 (d, 2 H), 7.69 (br. s., 1 H), 7.64 (d, 2 H), 6.36 (d, 1 H), 3.82 (d, 1 H), 0.91 (s, 9 H) |
| 357 | $^1$H NMR δ (ppm)(DMSO-$d_6$): 13.09 (s, 1 H), 8.32 (s, 1 H), 8.06 (br. s., 1 H), 8.03 (d, 2 H), 7.62 (dd, 2 H), 7.58-7.61 (m, 1 H), 5.36 (t, 1 H), 3.59 (d, 2 H), 1.04-1.16 (m, 2 H), 0.85-0.93 (m, 2 H) |
| 363 | $^1$H NMR δ (ppm)(DMSO-$d_6$): 13.03 (s, 1 H), 9.20 (s, 1 H), 8.58 (d, 1 H), 8.44 (s, 1 H), 8.35 (d, 1 H), 8.18 (br. s., 1 H), 7.71 (br. s., 1 H), 6.14 (s, 1 H), 1.35 (s, 6 H) |
| 364 | $^1$H NMR δ (ppm)(DMSO-$d_6$): 12.63 (s, 1 H), 8.34 (s, 1 H), 8.12 (br. s., 1 H), 8.05 (d, 2 H), 7.67 (br. s., 1 H), 7.64 (d, 2 H), 5.38 (t, 1 H), 3.68 (d, 2 H), 2.19-2.34 (m, 2 H), 1.90-1.98 (m, 3 H), 1.72-1.85 (m, 1 H) |
| 375 | $^1$H NMR δ (ppm)(DMSO-$d_6$): 13.02 (s, 1H), 8.42 (s, 1H), 8.19 (br. s., 1H), 8.11 (t, 1H), 7.63-7.75 (m, 2H), 7.43-7.55 (m, 1H), 6.13 (s, 1H), 1.33 (s, 6H) |
| 376 | $^1$H NMR δ (ppm)(DMSO-$d_6$): 13.04 (1 H, s), 8.47 (1 H, s), 8.22-8.18 (2 H,m), 8.03 (1 H, d), 7.88 (1 H, d), 7.72 (1H, s), 6.14 (1H, s) 1.34 (6H, s). |
| 418 | $^1$H NMR δ (ppm)(DMSO-$d_6$): 13.03 (1 H, s), 8.39 (1 H, s), 8.28 (1 H, s), 8.16 (1 H, s br), 7.73 (1 H, s br), 7.31 (1 H, s), 7.17 (1H, t), 6.16 (1 H, s), 3.91 (3 H, s), 1.34 (6H, s). |

TABLE III-continued

NMR Data of Representative Compounds of the Invention

| Cpd # | (δ) NMR data |
|---|---|
| 422 | $^1$H NMR δ (ppm)(DMSO-$d_6$): 12.97 (1 H, s), 8.43 (1 H, s), 8.09 (3 H, m), 7.94 (1 H, d), 7.76 (1H, s br), 6.16 (1H, s), 1.34 (6H, s). |
| 437 | $^1$H NMR δ (ppm)(DMSO-$d_6$): 11.85 (1 H, s), 8.06 (2 H, d), 7.88 (1 H, s br), 7.62 (2 H, d), 7.52 (1 H, s br), 6.19 (1 H, s), 2.48 (3 H, s), 1.34 (6 H, s). |
| 444 | $^1$H NMR (DMSO-$d_6$) δ: 12.96 (s, 1H), 8.42 (s, 1H), 8.19 (s, 1H), 8.12 (m, 1H), 7.63-7.79 (m, 2H), 7.50 (d, 1H), 6.28 (d, 1H), 4.23-4.43 (m, 1H), 1.30 (d, 3H) |
| 445 | $^1$H NMR (DMSO-$d_6$) δ: 12.98 (s, 1H), 8.46 (d, 1H), 8.15-8.26 (m, 2H), 8.02 (d, 1H), 7.87 (d, 1H), 7.72 (s, 1H), 6.28 (d, 1H), 4.25-4.39 (m, 1H), 1.30 (d, 3H) |
| 446 | $^1$H NMR (DMSO-$d_6$) δ: 12.85 (s, 1H), 8.34 (s, 1H), 8.13 (br. s., 1H), 7.98-8.07 (m, 2H), 7.70 (br. s., 1H), 7.62 (m, 2H), 5.74 (s, 1H), 5.20-5.30 (m, 1H), 3.41 (d, 2H), 1.14 (s, 6H) |

Biological Examples

Example 5

In Vitro Assays

5.1. YFP-halide Influx Assay for the CFTR-ΔF508 Mutation-Gluconate Buffer

The YFP halide influx assay measures the functionality of the cystic fibrosis Transmembrane Conductance regulator (CFTR) channels in the cystic fibrosis bronchial epithelium cell line CFBE41o-. The assay is used to evaluate the capacity of compounds to increase the open probability of existing CFTR channels in the membrane. It makes use of the observation that the yellow fluorescent protein (YFP) variant YFP H148Q, I152L has its fluorescence substantially quenched by halide ions like Cl$^-$ and I$^-$. (Galietta, Haggie, & Verkman, 2001) (Nagai, et al., 2002)

For this purpose, CFBE41o-cells are seeded in 96 well plates (6000 CFBE cells/well). One day after seeding, the CFBE cells are transduced with adenoviral vectors that direct the expression of the CFTR ΔF508 mutant and of the YFP reporter. Cells are incubated at 27° C., 5% $CO_2$ for 24 hours so as to allow for the proper folding and migration to the membrane of the CFTR channel or treated with a CFTR modulator during 24 hours at 37° C.

The next day the CFTR channels are activated by treatment with the cAMP inducer forskolin (10.67 μM) and test compound in gluconate buffer (137 mM disodiumgluconate, 2.7 mM KCl, 1.76 mM $KH_2PO_4$, 10.1 mM $Na_2HPO_4$, 5 mM glucose) for 10 minutes prior to addition of an I$^-$ solution (137 mM NaI, 2.7 mM KI, 1.76 mM $KH_2PO_4$, 10.1 mM $Na_2HPO_4$, 5 mM glucose). The I$^-$-induced quenching of fluorescence is recorded immediately after injection of I$^-$ for 7 seconds. The capacity of a compound to increase the channel opening is directly correlated with the decrease in fluorescence, and is expressed as (1-(fluorescence after 7 seconds (F)/fluorescence before injection (F0))) and an $EC_{50}$ can be derived from a (1-F/F0) vs compound concentration plot.

TABLE IV

Illustrative $EC_{50}$ measured by YFP-halide influx assay for the CFTR- ΔF508 of the compounds of the invention.

| Cpd# | $EC_{50}$ | $EC_{50}$ (nM) |
|---|---|---|
| 1 | *** | 135.0 |
| 2 | *** | 483.0 |
| 3 | *** | 107.0 |
| 4 | **** | 94.0 |
| 5 | ** | 943.8 |
| 6 | *** | 321.1 |
| 7 | * | 1083.0 |
| 8 | ** | 646.5 |
| 9 | ** | 603.4 |
| 10 | ** | 628.3 |
| 11 | ** | 567.9 |
| 12 | ** | 887.1 |
| 13 | *** | 400.6 |
| 14 | *** | 356.9 |
| 15 | *** | 168.9 |
| 16 | **** | 99.7 |
| 17 | *** | 264.9 |
| 18 | *** | 471.8 |
| 19 | *** | 117.8 |
| 20 | *** | 391.7 |
| 21 | *** | 483.9 |
| 22 | *** | 317.0 |
| 23 | ** | 641.7 |
| 24 | ** | 772.4 |
| 25 | ** | 944.7 |
| 26 | *** | 289.3 |
| 27 | *** | 289.7 |
| 28 | ** | 624.2 |
| 29 | *** | 272.2 |
| 30 | ** | 909.9 |
| 31 | *** | 184.0 |
| 32 | * | 1502.0 |
| 33 | * | 9840.0 |
| 34 | *** | 290.4 |
| 35 | * | 3280.0 |
| 36 | **** | 92.3 |
| 37 | *** | 292.8 |
| 38 | ** | 899.8 |
| 39 | *** | 292.6 |
| 40 | ** | 574.2 |
| 41 | * | 9840.0 |
| 42 | ** | 739.5 |
| 43 | ** | 670.1 |
| 44 | ** | 695.6 |
| 45 | * | 1280.0 |
| 46 | *** | 283.8 |
| 47 | * | 2663.0 |
| 48 | *** | 252.7 |
| 49 | ** | 841.7 |
| 50 | *** | 390.8 |
| 51 | ** | 598.8 |
| 52 | *** | 204.5 |
| 53 | * | 1257.0 |
| 54 | * | 3160.0 |
| 55 | * | 3330.0 |
| 56 | *** | 206.3 |
| 57 | * | 2492.0 |
| 58 | * | 3330.0 |
| 59 | *** | 182.4 |

TABLE IV-continued

Illustrative $EC_{50}$ measured by YFP-halide influx assay for the CFTR-ΔF508 of the compounds of the invention.

| Cpd# | $EC_{50}$ | $EC_{50}$ (nM) |
|---|---|---|
| 60 | * | 1898.0 |
| 61 | * | 10000.0 |
| 62 | * | 2178.0 |
| 63 | *** | 250.7 |
| 64 | * | 2159.0 |
| 65 | * | 1570.0 |
| 66 | *** | 152.6 |
| 67 | *** | 249.9 |
| 68 | *** | 128.8 |
| 69 | *** | 147.2 |
| 70 | ** | 920.7 |
| 71 | ** | 797.5 |
| 72 | *** | 325.5 |
| 73 | **** | 25.1 |
| 74 | *** | 135.2 |
| 75 | *** | 418.4 |
| 76 | ** | 621.1 |
| 77 | * | 3330.0 |
| 78 | *** | 400.7 |
| 79 | * | 10000.0 |
| 80 | * | 10000.0 |
| 81 | * | 10000.0 |
| 82 | *** | 468.2 |
| 83 | **** | 42.8 |
| 84 | * | 3190.0 |
| 85 | *** | 114.4 |
| 86 | *** | 138.1 |
| 87 | **** | 44.1 |
| 88 | *** | 162.2 |
| 89 | *** | 378.5 |
| 90 | *** | 260.7 |
| 91 | * | 1525.0 |
| 92 | ** | 952.6 |
| 93 | * | 3330.0 |
| 94 | * | 3330.0 |
| 95 | **** | 99.4 |
| 96 | *** | 253.0 |
| 97 | * | 10000.0 |
| 98 | * | 10000.0 |
| 99 | * | 1938.0 |
| 100 | *** | 120.8 |
| 101 | **** | 20.5 |
| 102 | *** | 214.7 |
| 103 | **** | 38.4 |
| 104 | *** | 370.3 |
| 105 | *** | 395.6 |
| 106 | *** | 213.4 |
| 107 | *** | 129.8 |
| 108 | *** | 197.9 |
| 109 | **** | 28.6 |
| 110 | *** | 143.9 |
| 111 | **** | 84.3 |
| 112 | *** | 351.7 |
| 113 | **** | 29.2 |
| 114 | **** | 90.7 |
| 115 | *** | 235.3 |
| 116 | **** | 59.7 |
| 117 | *** | 137.5 |
| 118 | **** | 36.0 |
| 119 | **** | 78.3 |
| 120 | *** | 487.7 |
| 121 | **** | 74.9 |
| 122 | *** | 293.5 |
| 123 | **** | 76.9 |
| 124 | ** | 502.9 |
| 125 | ** | 579.6 |
| 126 | *** | 191.2 |
| 127 | ** | 659.4 |
| 128 | *** | 399.7 |
| 129 | *** | 274.7 |
| 130 | *** | 383.2 |
| 131 | ** | 921.0 |
| 132 | * | 3330.0 |
| 133 | *** | 270.5 |
| 134 | ** | 945.5 |
| 135 | * | 10000.0 |
| 136 | *** | 291.1 |
| 137 | *** | 263.4 |
| 138 | *** | 312.8 |
| 139 | *** | 113.6 |
| 140 | **** | 29.3 |
| 141 | **** | 29.7 |
| 142 | **** | 70.7 |
| 143 | **** | 29.2 |
| 144 | *** | 365.1 |
| 145 | **** | 19.5 |
| 146 | *** | 241.2 |
| 147 | *** | 242.0 |
| 148 | *** | 344.3 |
| 149 | ** | 517.3 |
| 150 | ** | 638.3 |
| 151 | *** | 357.3 |
| 152 | **** | 82.1 |
| 153 | **** | 46.0 |
| 154 | *** | 104.5 |
| 155 | * | 10000.0 |
| 156 | *** | 361.1 |
| 157 | **** | 86.5 |
| 158 | **** | 50.5 |
| 159 | *** | 406.8 |
| 160 | **** | 48.4 |
| 161 | *** | 221.4 |
| 162 | *** | 330.7 |
| 163 | *** | 271.9 |
| 164 | * | 10000.0 |
| 165 | * | 10000.0 |
| 166 | ** | 815.4 |
| 167 | * | 3050.0 |
| 168 | * | 1664.0 |
| 169 | *** | 210.0 |
| 170 | **** | 38.0 |
| 171 | *** | 103.8 |
| 172 | **** | 15.4 |
| 173 | **** | 21.0 |
| 174 | * | 2374.0 |
| 175 | *** | 105.8 |
| 176 | * | 1458.0 |
| 177 | *** | 178.5 |
| 178 | ** | 524.3 |
| 179 | **** | 22.2 |
| 180 | *** | 122.6 |
| 181 | *** | 143.6 |
| 182 | **** | 97.9 |
| 183 | *** | 152.9 |
| 184 | ** | 679.1 |
| 185 | *** | 334.9 |
| 186 | *** | 270.2 |
| 187 | * | 1597.0 |
| 188 | * | 2104.0 |
| 189 | *** | 122.1 |
| 190 | **** | 73.9 |
| 191 | **** | 90.0 |
| 192 | **** | 60.6 |
| 193 | *** | 113.6 |
| 194 | *** | 153.9 |
| 195 | *** | 258.5 |
| 196 | * | 2098.0 |
| 197 | **** | 91.0 |
| 198 | **** | 97.2 |
| 199 | * | 1974.0 |
| 200 | * | 3330.0 |
| 201 | * | 3330.0 |
| 202 | ** | 705.9 |
| 203 | * | 3330.0 |
| 204 | *** | 218.4 |
| 205 | * | 1151.0 |
| 206 | **** | 72.6 |
| 207 | *** | 316.6 |
| 208 | ** | 573.2 |
| 209 | **** | 73.9 |

TABLE IV-continued

Illustrative EC$_{50}$ measured by YFP-halide influx assay for the CFTR- ΔF508 of the compounds of the invention.

| Cpd# | EC$_{50}$ | EC$_{50}$ (nM) |
|---|---|---|
| 210 | **** | 73.5 |
| 211 | *** | 319.6 |
| 212 | *** | 183.6 |
| 213 | **** | 87.3 |
| 214 | *** | 116.7 |
| 215 | *** | 292.2 |
| 216 | ** | 708.7 |
| 217 | *** | 195.0 |
| 218 | *** | 196.4 |
| 219 | * | 10000.0 |
| 220 | * | 10000.0 |
| 221 | *** | 110.0 |
| 222 | **** | 22.9 |
| 223 | **** | 37.9 |
| 224 | *** | 103.0 |
| 226 | **** | 42.2 |

0.1-100 nM ****
>100-500 nM ***
>500-1000 nM **
>1000 nM *

5.2. YFP-halide Influx Assay for the CFTR-ΔF508 Mutation-PBS Buffer

The YFP halide influx assay measures the functionality of the cystic fibrosis Transmembrane Conductance regulator (CFTR) channels in the cystic fibrosis bronchial epithelium cell line CFBE41o-. The assay is used to evaluate the capacity of compounds to increase the open probability of existing CFTR channels in the membrane. It makes use of the observation that the yellow fluorescent protein (YFP) variant YFP H148Q, I152L has its fluorescence substantially quenched by halide ions like Cl$^-$ and I$^-$. (Galietta, Haggie, & Verkman, 2001) (Nagai, et al., 2002)

For this purpose, CFBE41o-cells are seeded in 96 well plates (6000 CFBE cells/well). One day after seeding, the CFBE cells are transduced with adenoviral vectors that direct the expression of the CFTR ΔF508 mutant and of the YFP reporter. Cells are incubated at 27° C., 5% CO$_2$ for 24 hours so as to allow for the proper folding and migration to the membrane of the CFTR channel or treated with a CFTR modulator during 24 hours at 37° C.

The next day the CFTR channels are activated by treatment with the cAMP inducer forskolin (10.67 μM) and test compound in 1×D-PBS (from Gibco, Cat n#14090-041) for 10 minutes prior to addition of an I$^-$ solution (137 mM NaI, 2.7 mM KI, 1.76 mM KH$_2$PO$_4$, 10.1 mM Na$_2$HPO$_4$, 5 mM glucose). The I$^-$ induced quenching of fluorescence is recorded immediately after injection of I$^-$ for 7 seconds. The capacity of a compound to increase the channel opening is directly correlated with the decrease in fluorescence, and is expressed as (1-(fluorescence after 7 seconds (F)/fluorescence before injection (F0))) and an EC$_{50}$ can be derived from a (1-F/F0) vs compound concentration plot.

TABLE V

Illustrative EC$_{50}$ measured by YFP-halide influx assay (PBS Buffer) for the CFTR-ΔF508 of the compounds of the invention.

| Cpd # | EC$_{50}$ | EC$_{50}$ (nM) |
|---|---|---|
| 73 | **** | 16.5 |
| 78 | *** | 220.4 |
| 83 | **** | 30.8 |
| 122 | *** | 114.1 |
| 158 | **** | 35.5 |
| 160 | **** | 38.7 |
| 171 | **** | 37.5 |
| 175 | **** | 61.7 |
| 179 | **** | 31.2 |
| 183 | **** | 25.7 |
| 192 | **** | 33.4 |
| 194 | **** | 38.3 |
| 206 | **** | 31.4 |
| 207 | *** | 124.9 |
| 209 | **** | 34.5 |
| 212 | **** | 70.3 |
| 213 | *** | 117.8 |
| 214 | **** | 37.2 |
| 215 | ** | 861.7 |
| 216 | *** | 216.3 |
| 217 | *** | 164.3 |
| 218 | **** | 72.7 |
| 219 | * | 10000.0 |
| 220 | * | 2308.0 |
| 221 | **** | 49.4 |
| 222 | **** | 26.1 |
| 223 | **** | 31.8 |
| 224 | **** | 54.1 |
| 225 | **** | 36.2 |
| 226 | **** | 36.9 |
| 227 | **** | 41.5 |
| 228 | **** | 20.5 |
| 229 | * | 3102.0 |
| 230 | ** | 987.8 |
| 231 | **** | 26.0 |
| 232 | *** | 127.8 |
| 233 | *** | 129.6 |
| 234 | *** | 283.1 |
| 235 | **** | 46.8 |
| 236 | **** | 46.4 |
| 237 | **** | 66.3 |
| 238 | *** | 224.2 |
| 239 | *** | 292.3 |
| 240 | ** | 610.6 |
| 241 | *** | 246.5 |
| 242 | **** | 17.3 |
| 243 | * | 1618.5 |
| 244 | *** | 152.9 |
| 245 | **** | 60.3 |
| 246 | **** | 78.5 |
| 247 | **** | 10.8 |
| 248 | **** | 85.8 |
| 249 | * | 2895.0 |
| 250 | * | 10000.0 |
| 251 | **** | 20.8 |
| 252 | **** | 49.1 |
| 253 | **** | 73.0 |
| 254 | **** | 30.3 |
| 254 | *** | 136.9 |
| 255 | **** | 11.0 |
| 256 | **** | 26.2 |
| 257 | **** | 16.3 |
| 258 | *** | 101.8 |
| 259 | *** | 144.2 |
| 260 | **** | 94.4 |
| 261 | **** | 31.9 |
| 262 | **** | 69.1 |
| 263 | **** | 81.1 |
| 264 | **** | 30.1 |
| 265 | **** | 42.2 |
| 266 | *** | 197.0 |
| 267 | ** | 652.7 |
| 268 | *** | 194.8 |
| 269 | **** | 33.0 |
| 270 | **** | 19.7 |
| 271 | **** | 8.1 |
| 272 | **** | 48.9 |
| 273 | *** | 110.8 |
| 274 | *** | 231.3 |

TABLE V-continued

Illustrative EC$_{50}$ measured by YFP-halide influx assay (PBS Buffer) for the CFTR-ΔF508 of the compounds of the invention.

| Cpd # | EC$_{50}$ | EC$_{50}$ (nM) |
|---|---|---|
| 275 | *** | 220.4 |
| 276 | ** | 777.0 |
| 277 | *** | 388.7 |
| 278 | * | 1396.0 |
| 279 | **** | 55.5 |
| 280 | **** | 28.0 |
| 281 | **** | 41.1 |
| 282 | *** | 156.7 |
| 283 | **** | 47.7 |
| 284 | **** | 51.0 |
| 285 | * | 10000.0 |
| 286 | **** | 46.2 |
| 288 | * | 2361.0 |
| 289 | **** | 31.1 |
| 290 | **** | 34.3 |
| 291 | **** | 81.2 |
| 292 | **** | 70.0 |
| 293 | **** | 15.1 |
| 294 | *** | 228.4 |
| 295 | **** | 95.2 |
| 296 | ** | 726.8 |
| 297 | *** | 367.1 |
| 298 | **** | 6.2 |
| 299 | ** | 914.9 |
| 300 | **** | 26.2 |
| 301 | *** | 173.6 |
| 302 | **** | 11.3 |
| 303 | **** | 37.5 |
| 304 | **** | 78.5 |
| 305 | **** | 31.5 |
| 306 | *** | 254.4 |
| 307 | **** | 32.8 |
| 308 | *** | 234.3 |
| 309 | *** | 115.2 |
| 310 | **** | 42.6 |
| 311 | **** | 15.2 |

0.1-100 nM ****
>100-500 nM ***
>500-1000 nM **
>1000 nM *

5.3. YFP-halide Influx Assay for the CFTR-ΔF508 Mutation

The YFP halide influx assay measures the functionality of the cystic fibrosis Transmembrane Conductance regulator (CFTR) channels in the cystic fibrosis bronchial epithelium cell line CFBE41o-. The assay is used to evaluate the capacity of compounds to increase the open probability of existing CFTR channels in the membrane. It makes use of the observation that the yellow fluorescent protein (YFP) variant YFP H148Q, I152L has its fluorescence substantially quenched by halide ions like Cl— and I—. (Galietta, Haggie, & Verkman, 2001) (Nagai, et al., 2002)

For this purpose, CFBE41o-cells are seeded in 384 well plates (3000 CFBE cells/well). One day after seeding, the CFBE cells are transduced with adenoviral vectors that direct the expression of the CFTR ΔF508 mutant and of the YFP reporter. Cells are incubated at 27° C., 5% CO2 for 24 hours so as to allow for the proper folding and migration to the membrane of the CFTR channel or treated with a CFTR modulator during 24 h at 37° C.

The next day the CFTR channels are activated by treatment with the cAMP inducer forskolin (10.67 μM) and test compound in 1×D-PBS in a total volume of 30 μL (from Gibco, Cat n#14090-041) for 10 min prior to addition of 30 μl of following I— solution (375 mM Nat, 7.5 mM KI, 1.76 mM KH$_2$PO$_4$, 10.1 mM Na$_2$HPO$_4$, 13.75 mM glucose). The I— induced quenching of fluorescence is recorded on an immediately after injection of I— for 2 min on an FDSS/μCell (Hamamatsu). The capacity of a compound to increase the channel opening is directly correlated with the decrease in fluorescence, and is expressed as (1-(fluorescence after 36 seconds (F)/fluorescence before injection (F0))) and an EC50 can be derived from a (1-F/F0) vs compound concentration plot.

TABLE VI

Illustrative EC$_{50}$ measured by YFP-halide influx assay for the CFTR-ΔF508 of the compounds of the invention.

| Cpd # | EC$_{50}$ | EC$_{50}$ (nM) |
|---|---|---|
| 3 | *** | 108.7 |
| 4 | *** | 134.9 |
| 16 | *** | 186.7 |
| 36 | **** | 13.1 |
| 73 | **** | 15.7 |
| 78 | *** | 146.3 |
| 83 | **** | 12.1 |
| 87 | **** | 84.3 |
| 95 | *** | 100.6 |
| 101 | **** | 26.8 |
| 103 | **** | 54.6 |
| 109 | **** | 28.9 |
| 111 | *** | 199.1 |
| 113 | **** | 5.8 |
| 114 | *** | 101.8 |
| 116 | **** | 63.5 |
| 118 | **** | 9.6 |
| 119 | *** | 187.1 |
| 121 | *** | 292.1 |
| 122 | **** | 68.4 |
| 123 | **** | 76.4 |
| 139 | **** | 55.5 |
| 140 | **** | 10.3 |
| 141 | **** | 98.2 |
| 142 | *** | 293.9 |
| 143 | **** | 27.2 |
| 145 | **** | 71.0 |
| 152 | *** | 135.2 |
| 153 | **** | 46.0 |
| 154 | *** | 427.2 |
| 157 | **** | 60.9 |
| 158 | **** | 79.5 |
| 160 | *** | 209.8 |
| 170 | *** | 184.1 |
| 171 | **** | 81.4 |
| 172 | **** | 42.0 |
| 173 | **** | 15.8 |
| 175 | **** | 96.8 |
| 179 | **** | 84.9 |
| 182 | *** | 433.2 |
| 183 | **** | 12.7 |
| 190 | **** | 83.3 |
| 191 | *** | 197.4 |
| 192 | **** | 20.7 |
| 193 | **** | 49.5 |
| 194 | **** | 20.7 |
| 197 | **** | 24.8 |
| 198 | **** | 20.2 |
| 206 | **** | 6.9 |
| 207 | **** | 48.1 |
| 209 | **** | 6.0 |
| 210 | **** | 13.4 |
| 213 | **** | 52.8 |
| 214 | **** | 25.8 |
| 221 | **** | 26.1 |
| 222 | **** | 33.2 |
| 223 | **** | 62.1 |
| 224 | **** | 35.0 |
| 225 | **** | 26.5 |
| 226 | **** | 33.8 |
| 227 | **** | 39.3 |
| 228 | **** | 29.0 |
| 231 | **** | 31.8 |
| 235 | **** | 76.6 |
| 236 | **** | 25.2 |
| 237 | *** | 108.2 |

TABLE VI-continued

Illustrative $EC_{50}$ measured by YFP-halide influx assay for the CFTR-ΔF508 of the compounds of the invention.

| Cpd # | $EC_{50}$ | $EC_{50}$ (nM) |
|---|---|---|
| 242 | **** | 9.6 |
| 245 | *** | 113.3 |
| 246 | **** | 75.1 |
| 247 | **** | 18.5 |
| 248 | **** | 70.1 |
| 251 | **** | 47.2 |
| 253 | **** | 50.8 |
| 254 | **** | 27.8 |
| 255 | **** | 33.0 |
| 256 | **** | 23.1 |
| 257 | **** | 26.1 |
| 258 | *** | 156.8 |
| 260 | **** | 87.5 |
| 261 | **** | 92.4 |
| 262 | *** | 114.7 |
| 263 | *** | 147.7 |
| 264 | **** | 19.4 |
| 265 | **** | 91.7 |
| 269 | **** | 10.1 |
| 270 | **** | 18.3 |
| 271 | **** | 7.5 |
| 272 | *** | 101.7 |
| 273 | *** | 148.3 |
| 279 | *** | 115.5 |
| 280 | *** | 116.9 |
| 281 | *** | 136.0 |
| 283 | **** | 69.6 |
| 284 | **** | 85.2 |
| 286 | **** | 26.5 |
| 289 | **** | 28.4 |
| 290 | **** | 27.6 |
| 291 | **** | 17.3 |
| 292 | *** | 182.2 |
| 293 | **** | 7.6 |
| 295 | **** | 35.6 |
| 298 | **** | 5.5 |
| 300 | **** | 30.0 |
| 302 | **** | 8.1 |
| 303 | **** | 8.5 |
| 304 | *** | 109.1 |
| 305 | **** | 23.9 |
| 307 | **** | 28.5 |
| 310 | **** | 66.1 |
| 311 | **** | 3.5 |
| 312 | **** | 10.5 |
| 313 | **** | 38.3 |
| 314 | **** | 7.5 |
| 315 | **** | 42.4 |
| 316 | **** | 31.1 |
| 317 | *** | 240.5 |
| 318 | **** | 20.2 |
| 319 | **** | 8.2 |
| 320 | **** | 12.9 |
| 321 | **** | 12.3 |
| 322 | **** | 41.1 |
| 323 | **** | 9.4 |
| 324 | **** | 84.2 |
| 325 | **** | 11.1 |
| 326 | * | 1058.0 |
| 327 | *** | 134.5 |
| 328 | **** | 25.8 |
| 329 | **** | 23.2 |
| 330 | **** | 5.3 |
| 331 | **** | 8.0 |
| 332 | **** | 22.8 |
| 333 | **** | 12.6 |
| 334 | **** | 3.7 |
| 335 | **** | 5.7 |
| 336 | **** | 12.2 |
| 337 | **** | 5.5 |
| 338 | **** | 5.4 |
| 339 | **** | 8.1 |
| 340 | **** | 8.0 |
| 341 | **** | 20.2 |
| 342 | *** | 105.4 |
| 343 | **** | 92.4 |
| 344 | **** | 36.0 |
| 345 | *** | 111.5 |
| 346 | *** | 469.8 |
| 347 | **** | 19.1 |
| 348 | **** | 16.4 |
| 349 | *** | 342.6 |
| 350 | **** | 39.0 |
| 351 | **** | 3.0 |
| 352 | **** | 12.24 |
| 353 | **** | 10.8 |
| 355 | **** | 5.404 |
| 356 | **** | 17.185 |
| 357 | **** | 29.685 |
| 358 | *** | 110.2 |
| 359 | **** | 9.6325 |
| 360 | **** | 9.553 |
| 361 | **** | 7.0125 |
| 362 | **** | 22.34 |
| 363 | **** | 28.545 |
| 364 | **** | 30.415 |
| 365 | **** | 29.89 |
| 366 | **** | 22.635 |
| 367 | **** | 23.34 |
| 368 | **** | 17.273 |
| 369 | **** | 11.618 |
| 370 | **** | 2.4955 |
| 371 | *** | 107.09 |
| 372 | **** | 4.8005 |
| 373 | **** | 13.247 |
| 374 | **** | 58.335 |
| 375 | **** | 7.527 |
| 376 | **** | 8.0713 |
| 377 | **** | 40.45 |
| 378 | **** | 26.132 |
| 379 | **** | 16.725 |
| 380 | **** | 17.579 |
| 381 | **** | 55.92 |
| 382 | **** | 66.09 |
| 383 | *** | 135.3 |
| 384 | *** | 158.5 |
| 385 | **** | 62.65 |
| 386 | **** | 1.9965 |
| 387 | **** | 22.29 |
| 388 | **** | 43.28 |
| 389 | **** | 46.267 |
| 390 | **** | 44.09 |
| 391 | **** | 14.902 |
| 392 | **** | 84.59 |
| 393 | **** | 14.763 |
| 394 | *** | 353.6 |
| 395 | *** | 293.9 |
| 396 | *** | 109.8 |
| 397 | **** | 30.733 |
| 398 | **** | 22.778 |
| 399 | **** | 56.635 |
| 400 | **** | 56.66 |
| 401 | **** | 6.5255 |
| 402 | **** | 25.64 |
| 403 | **** | 27.47 |
| 404 | **** | 14.26 |
| 405 | **** | 19.57 |
| 406 | **** | 56.11 |
| 407 | **** | 50.63 |
| 408 | **** | 10.95 |
| 409 | **** | 47.74 |
| 410 | **** | 14.14 |
| 411 | **** | 61.05 |
| 412 | **** | 3.57 |
| 413 | **** | 12.79 |
| 414 | *** | 111.5 |
| 415 | *** | 304.9 |
| 416 | **** | 17.671 |
| 417 | *** | 147.2 |
| 418 | **** | 8.181 |

TABLE VI-continued

Illustrative EC$_{50}$ measured by YFP-halide influx assay for the CFTR-ΔF508 of the compounds of the invention.

| Cpd # | EC$_{50}$ | EC$_{50}$ (nM) |
|---|---|---|
| 419 | **** | 26.57 |
| 420 | **** | 8.053 |
| 421 | **** | 69.04 |
| 422 | **** | 15.321 |
| 423 | **** | 10.892 |
| 424 | **** | 3.1885 |
| 425 | **** | 6.9045 |
| 426 | **** | 2.58 |
| 427 | **** | 42.045 |
| 428 | **** | 76.075 |
| 429 | **** | 17.485 |
| 430 | **** | 10.691 |
| 431 | *** | 149.56 |
| 432 | **** | 47.86 |
| 433 | **** | 48.775 |
| 434 | *** | 227 |
| 435 | **** | 16.462 |
| 436 | **** | 32.105 |
| 437 | **** | 6.241 |
| 438 | *** | 216.1 |
| 439 | **** | 7.1587 |
| 440 | **** | 12.993 |
| 441 | **** | 30.305 |
| 442 | **** | 90.94 |
| 443 | *** | 107.48 |
| 444 | **** | 19.57 |
| 445 | **** | 19.61 |
| 446 | **** | 41.27 |

0.1-100 nM ****
>100-500 nM ***
>500-1000 nM **
>1000 nM *

5.4. YFP-halide Influx Assay for the CFTR-G551D Mutation

The YFP halide influx assay measures the functionality of the cystic fibrosis Transmembrane Conductance regulator (CFTR) channels. The assay is used to evaluate the capacity of compounds to increase the channel opening of existing mutant CFTR channels in the membrane. It makes use of the observation that the yellow fluorescent protein (YFP) variant YFP H148Q, I152L, F47L has its fluorescence substantially quenched by halide ions like Cl$^-$ and I$^-$. (Galietta, Haggie, & Verkman, 2001)

For this purpose, HEK293-cells are seeded in 96 well plates. During seeding, the cells are reverse-transfected with plasmid vectors that direct the expression of the CFTR G551D mutant and of the YFP reporter. Cells are incubated at 37° C., 5% CO$_2$ for 24 hours so as to allow for sufficient expression of the CFTR protein.

The next day the CFTR channels are activated by treatment with the cAMP inducer forskolin (10.67 µM) and test compound in D-PBS (Gibco) for 10 minutes prior to addition of an I$^-$ solution (137 mM NaI, 2.7 mM KI, 1.76 mM KH$_2$PO$_4$, 10.1 mM Na$_2$HPO$_4$, 5 mM glucose). The I$^-$-induced quenching of fluorescence is recorded immediately after injection of I$^-$ for 7 seconds. The capacity of a compound to increase the channel opening is directly correlated with the decrease in fluorescence, and is expressed as (1-(fluorescence after 7 seconds (F)/fluorescence before injection (F0))) and an EC$_{50}$ can be derived from a (1-F/F0) vs compound concentration plot.

Similar YHA assays were developed for other channel gating defective or channel conductance defective CFTR mutants to determine effect of compound on channel activity. Examples of mutants are G178R, G1349D, S549N, R117H, R334W. This assay is also used for additional class I CFTR mutants, including G542X, W1282X; class II mutants including N1303K, and for class III mutants including S1251N.

TABLE VII

Illustrative EC$_{50}$ measured by YFP-halide influx assay for the CFTR-G551D of the compounds of the invention.

| Cpd # | EC$_{50}$ | EC$_{50}$ (nM) |
|---|---|---|
| 73 | *** | 231.5 |
| 78 | * | 3071.5 |
| 83 | *** | 338.8 |
| 122 | * | 5685.0 |
| 140 | **** | 67.4 |
| 141 | *** | 257.9 |
| 142 | ** | 536.4 |
| 143 | *** | 231.7 |
| 145 | *** | 215.0 |
| 157 | *** | 241.3 |
| 158 | * | 1869.8 |
| 160 | *** | 271.8 |
| 171 | ** | 755.9 |
| 172 | *** | 136.5 |
| 175 | ** | 527.0 |
| 179 | *** | 332.3 |
| 183 | ** | 526.5 |
| 189 | *** | 225.8 |
| 190 | *** | 278.4 |
| 191 | *** | 245.2 |
| 192 | *** | 297.6 |
| 193 | *** | 206.2 |
| 194 | *** | 184.7 |
| 197 | *** | 157.7 |
| 198 | *** | 136.1 |
| 206 | *** | 134.1 |
| 207 | *** | 441.9 |
| 209 | *** | 313.7 |
| 210 | *** | 470.5 |
| 213 | ** | 541.1 |
| 218 | *** | 409.9 |
| 221 | * | 1156.3 |
| 222 | ** | 582.6 |
| 223 | *** | 327.3 |
| 224 | ** | 511.0 |
| 225 | *** | 294.7 |
| 226 | ** | 540.2 |
| 227 | *** | 472.0 |
| 228 | **** | 93.0 |
| 231 | ** | 676.4 |
| 232 | * | 1045.0 |
| 233 | * | 10000.0 |
| 236 | * | 6665.0 |
| 242 | *** | 163.4 |
| 245 | ** | 621.0 |
| 246 | ** | 626.9 |
| 247 | *** | 113.4 |
| 248 | * | 1386.0 |
| 251 | * | 1253.5 |
| 252 | *** | 213.5 |
| 253 | * | 3330.0 |
| 254 | ** | 878.2 |
| 254 | * | 1412.0 |
| 255 | *** | 483.4 |
| 256 | * | 1773.1 |
| 257 | *** | 332.9 |
| 263 | * | 3330.0 |
| 264 | * | 1018.0 |
| 265 | * | 1995.0 |
| 269 | ** | 934.5 |
| 270 | *** | 478.3 |
| 271 | *** | 177.9 |
| 272 | ** | 770.7 |
| 273 | * | 3078.3 |
| 275 | * | 1717.0 |
| 276 | * | 3330.0 |
| 277 | * | 3330.0 |
| 278 | * | 10000.0 |
| 279 | ** | 613.7 |
| 280 | * | 1664.5 |
| 281 | * | 1540.8 |
| 282 | * | 3330.0 |
| 283 | ** | 564.4 |
| 284 | ** | 793.3 |
| 285 | * | 10000.0 |

TABLE VII-continued

Illustrative EC$_{50}$ measured by YFP-halide influx assay for the CFTR-G551D of the compounds of the invention.

| Cpd # | EC$_{50}$ | EC$_{50}$ (nM) |
| --- | --- | --- |
| 286 | ** | 857.3 |
| 288 | * | 10000.0 |
| 289 | *** | 190.5 |
| 290 | ** | 880.1 |
| 291 | * | 1507.0 |
| 292 | * | 2284.5 |
| 293 | *** | 109.7 |
| 294 | * | 1326.0 |
| 295 | * | 1009.0 |
| 296 | * | 10000.0 |
| 297 | * | 3330.0 |
| 298 | *** | 206.8 |
| 299 | * | 3330.0 |
| 300 | * | 1757.5 |
| 301 | * | 10000.0 |
| 302 | *** | 307.1 |
| 303 | * | 1672.2 |
| 304 | * | 3330.0 |
| 305 | ** | 802.5 |
| 306 | * | 10000.0 |
| 307 | ** | 793.4 |
| 308 | * | 1026.2 |
| 309 | * | 2855.5 |
| 310 | * | 1761.0 |
| 311 | ** | 607.4 |
| 312 | * | 1823.5 |
| 313 | * | 2930.0 |
| 314 | *** | 457.9 |
| 315 | ** | 827.9 |
| 316 | * | 1159.6 |
| 317 | * | 3330.0 |
| 318 | ** | 716.4 |
| 319 | *** | 376.7 |
| 320 | **** | 97.3 |
| 321 | * | 1928.0 |
| 322 | ** | 919.0 |
| 323 | *** | 227.0 |
| 324 | * | 3160.0 |
| 325 | * | 2790.5 |
| 326 | * | 10000.0 |
| 327 | * | 3330.0 |
| 328 | *** | 427.2 |
| 329 | * | 1404.2 |
| 330 | **** | 62.2 |
| 331 | ** | 561.5 |
| 332 | ** | 525.1 |
| 333 | ** | 754.0 |
| 334 | *** | 150.4 |
| 335 | *** | 106.7 |
| 336 | ** | 872.1 |
| 337 | ** | 879.4 |
| 338 | ** | 859.2 |
| 339 | * | 1750.0 |
| 340 | *** | 478.3 |
| 341 | * | 1510.2 |
| 342 | ** | 770.9 |
| 343 | * | 1418.5 |
| 344 | *** | 236.7 |
| 345 | ** | 528.0 |
| 346 | ** | 681.6 |
| 347 | * | 1386.8 |
| 348 | * | 2552.5 |
| 349 | ** | 931.1 |
| 350 | ** | 667.5 |
| 351 | **** | 37.3 |
| 352 | * | >1342.4 |
| 353 | * | 1716.03 |
| 354 | * | 1257.0 |
| 355 | ** | 942 |
| 356 | ** | 501.75 |
| 357 | *** | 300.9 |
| 358 | * | 2685 |
| 359 | * | 2058 |
| 360 | ** | 634.75 |
| 361 | *** | 280.15 |
| 362 | * | 1227 |
| 363 | *** | 490.55 |
| 364 | *** | 365.9 |
| 365 | *** | 306.45 |
| 366 | *** | 457.8 |
| 367 | ** | 793.7 |
| 368 | *** | 320.67 |
| 369 | ** | 691.4 |
| 370 | **** | 57.4 |
| 371 | * | 3330 |
| 372 | **** | 72.585 |
| 373 | *** | 100.42 |
| 374 | * | 1330.3 |
| 375 | ** | 681.1 |
| 376 | ** | 522.06 |
| 377 | ** | 711.42 |
| 378 | * | 1851.5 |
| 379 | ** | 654.53 |
| 380 | *** | 449.9 |
| 381 | * | 1308 |
| 382 | ** | 873.3 |
| 383 | * | 2612.5 |
| 384 | * | 2735 |
| 385 | * | 1178.8 |
| 386 | **** | 25.905 |
| 387 | * | 1410 |
| 388 | ** | 695.05 |
| 389 | ** | 813.33 |
| 390 | ** | 668.27 |
| 391 | **** | 53.22 |
| 392 | * | 1603.5 |
| 393 | ** | 661.67 |
| 394 | * | 10000 |
| 395 | * | 1857 |
| 396 | * | 1352 |
| 397 | * | 1786 |
| 398 | ** | 514.9 |
| 399 | * | 1904 |
| 400 | * | 1954.5 |
| 401 | *** | 125.56 |
| 402 | * | 1398.3 |
| 403 | * | 1609.5 |
| 404 | ** | 553.07 |
| 405 | * | 4523.4 |
| 406 | * | 1310 |
| 407 | * | 3330 |
| 408 | * | 1771.3 |
| 409 | * | 2371 |
| 410 | ** | 707.97 |
| 411 | * | 4918.3 |
| 412 | **** | 96.39 |
| 413 | * | 1477.3 |
| 414 | * | 10000 |
| 415 | * | 10000 |
| 416 | ** | 772.72 |
| 417 | * | 6665 |
| 418 | *** | 390 |
| 419 | ** | 677.6 |
| 420 | *** | 196.55 |
| 421 | * | 5531.2 |
| 422 | ** | 872.45 |
| 423 | ** | 842.17 |
| 424 | *** | 402.9 |
| 425 | ** | 761.67 |
| 426 | **** | 61.27 |
| 427 | * | 2231 |
| 428 | * | 3330 |
| 429 | ** | 935.53 |
| 430 | * | 1498.6 |
| 431 | * | 2218 |
| 432 | * | 5553 |
| 433 | * | 1303.5 |
| 434 | * | 1932 |
| 435 | * | 1919.7 |
| 436 | * | 1732.2 |

TABLE VII-continued

Illustrative EC$_{50}$ measured by YFP-halide influx assay for the CFTR-G551D of the compounds of the invention.

| Cpd # | EC$_{50}$ | EC$_{50}$ (nM) |
|---|---|---|
| 437 | * | 10000 |
| 438 | * | 10000 |
| 439 | * | 6665 |
| 440 | * | 2191 |
| 441 | * | 10000 |
| 442 | * | 3330 |
| 443 | * | 3330 |

0.1-100 nM ****
>100-500 nM ***
>500-1000 nM **
>1000 nM *
NA: Not active

TABLE VIII

Illustrative EC$_{50}$ measured by YFP-halide influx assay for the CFTR-G178R of the compounds of the invention.

| Cpd # | EC$_{50}$ | EC$_{50}$ (nM) |
|---|---|---|
| 73 | **** | 44.7 |
| 83 | **** | 71.3 |
| 254 | **** | 58.0 |
| 270 | *** | 291.2 |
| 271 | **** | 23.9 |
| 286 | *** | 165.1 |
| 290 | *** | 206.6 |
| 298 | *** | 103.5 |
| 320 | **** | 56.2 |
| 323 | *** | 188.7 |
| 325 | * | 1882.0 |
| 329 | * | 1685.0 |
| 331 | **** | 67.7 |
| 333 | ** | 620.1 |
| 334 | **** | 44.5 |
| 337 | **** | 27.2 |
| 360 | *** | 122.7 |
| 363 | **** | 69 |
| 368 | **** | 32.67 |
| 369 | **** | 74.64 |
| 373 | **** | 19.68 |
| 374 | ** | 609.55 |
| 375 | **** | 93.413 |
| 376 | **** | 86.91 |
| 377 | *** | 241 |
| 379 | **** | 75.8 |
| 380 | *** | 107 |
| 387 | **** | 87.59 |
| 389 | **** | 91.5 |
| 390 | *** | 102.61 |
| 391 | **** | 12.925 |
| 393 | **** | 56.7 |
| 394 | * | 3330 |
| 397 | *** | 417.2 |
| 401 | *** | 104.7 |
| 402 | *** | 247.8 |
| 404 | *** | 126 |
| 405 | * | 10000 |
| 407 | * | 1526 |
| 408 | **** | 42.75 |
| 410 | **** | 80.14 |
| 411 | *** | 136.2 |
| 412 | **** | 11.1 |
| 413 | **** | 44.68 |
| 416 | *** | 268.5 |
| 418 | **** | 14.41 |
| 419 | *** | 249.6 |
| 420 | *** | 109.8 |
| 421 | * | 1594.5 |
| 422 | **** | 64.4 |
| 423 | *** | 161.8 |
| 424 | *** | 178.1 |

TABLE VIII-continued

Illustrative EC$_{50}$ measured by YFP-halide influx assay for the CFTR-G178R of the compounds of the invention.

| Cpd # | EC$_{50}$ | EC$_{50}$ (nM) |
|---|---|---|
| 425 | * | 1272 |
| 426 | **** | 9.849 |
| 427 | ** | 669.9 |
| 429 | *** | 142 |
| 430 | *** | 282.6 |
| 432 | * | 1110 |
| 433 | *** | 217 |
| 435 | **** | 33.76 |

0.1-100 nM ****
>100-500 nM ***
>500-1000 nM **
>1000 nM *
NA: Not active

TABLE IX

Illustrative EC$_{50}$ measured by YFP-halide influx assay for the CFTR-G1349D of the compounds of the invention.

| Cpd # | EC$_{50}$ | EC$_{50}$ (nM) |
|---|---|---|
| 73 | **** | 41.6 |
| 83 | *** | 151.9 |
| 254 | *** | 141.1 |
| 270 | *** | 211.5 |
| 271 | **** | 37.5 |
| 286 | *** | 303.6 |
| 290 | *** | 257.8 |
| 298 | **** | 69.5 |
| 320 | **** | 31.6 |
| 323 | *** | 459.2 |
| 325 | * | 2574.0 |
| 329 | * | 2051.0 |
| 331 | *** | 117.4 |
| 333 | ** | 847.3 |
| 334 | **** | 47.7 |
| 337 | **** | 48.7 |
| 360 | *** | 223.4 |
| 363 | *** | 320.4 |
| 368 | *** | 100.4 |
| 369 | *** | 195.1 |
| 373 | **** | 31.89 |
| 374 | ** | 806.6 |
| 375 | *** | 145.71 |
| 376 | *** | 173.34 |
| 377 | *** | 134.96 |
| 379 | **** | 58.64 |
| 380 | *** | 275.6 |
| 387 | **** | 83.55 |
| 389 | *** | 204.4 |
| 390 | *** | 292.95 |
| 391 | **** | 25.917 |
| 393 | *** | 159.1 |
| 394 | * | 3330 |
| 397 | *** | 413.2 |
| 401 | **** | 49.28 |
| 402 | * | 3330 |
| 404 | * | 1487 |
| 405 | * | 3330 |
| 407 | * | 3330 |
| 408 | *** | 149.5 |
| 410 | *** | 119.8 |
| 411 | * | 1044 |
| 412 | **** | 7.471 |
| 413 | *** | 133.9 |
| 416 | *** | 352.8 |
| 418 | **** | 18.4 |
| 419 | ** | 617.3 |
| 420 | **** | 94.95 |
| 421 | * | 1542.3 |
| 422 | *** | 211.8 |
| 423 | * | 1110 |

TABLE IX-continued

Illustrative EC$_{50}$ measured by YFP-halide influx assay for the CFTR-G1349D of the compounds of the invention.

| Cpd # | EC$_{50}$ | EC$_{50}$ (nM) |
|---|---|---|
| 424 | * | 2428 |
| 425 | *** | 364.2 |
| 426 | **** | 6.064 |
| 427 | *** | 437.9 |
| 429 | *** | 229.3 |
| 430 | * | 3330 |
| 432 | * | 3330 |
| 433 | * | 3330 |
| 435 | *** | 117.3 |
| 437 | * | 10000 |

0.1-100 nM ****
\>100-500 nM ***
\>500-1000 nM **
\>1000 nM *
NA: Not active

TABLE X

Illustrative EC$_{50}$ measured by YFP-halide influx assay for the CFTR-S549N of the compounds of the invention.

| Cpd # | EC$_{50}$ | EC$_{50}$ (nM) |
|---|---|---|
| 73 | *** | 161.6 |
| 83 | *** | 353.2 |
| 254 | *** | 242.9 |
| 270 | *** | 414.9 |
| 271 | **** | 60.9 |
| 286 | * | 1150.5 |
| 290 | ** | 871.1 |
| 298 | *** | 164.0 |
| 320 | *** | 130.8 |
| 323 | * | 1514.0 |
| 325 | * | 2136.0 |
| 329 | * | 2686.0 |
| 331 | ** | 521.7 |
| 333 | ** | 547.3 |
| 334 | *** | 335.9 |
| 337 | *** | 107.0 |
| 360 | *** | 187.8 |
| 363 | *** | 221.1 |
| 368 | **** | 55.48 |
| 369 | *** | 445.3 |
| 373 | **** | 70.52 |
| 374 | * | 1829 |
| 375 | *** | 199.17 |
| 376 | *** | 250.93 |
| 377 | ** | 935.1 |
| 379 | *** | 154.9 |
| 380 | *** | 387.3 |
| 387 | *** | 210.4 |
| 389 | ** | 531 |
| 390 | *** | 322.4 |
| 391 | **** | 42.085 |
| 393 | *** | 255.6 |
| 394 | * | 10000 |
| 397 | ** | 678 |
| 401 | **** | 91.45 |
| 402 | * | 1016 |
| 404 | * | 1806 |
| 405 | * | 1369 |
| 407 | * | 2855 |
| 408 | ** | 525.2 |
| 410 | *** | 104.1 |
| 411 | ** | 861.3 |
| 412 | **** | 11.32 |
| 413 | **** | 64.7 |
| 416 | * | 1780 |
| 418 | *** | 183.6 |
| 419 | ** | 621.4 |
| 420 | *** | 145.9 |
| 421 | * | 1110 |

TABLE X-continued

Illustrative EC$_{50}$ measured by YFP-halide influx assay for the CFTR-S549N of the compounds of the invention.

| Cpd # | EC$_{50}$ | EC$_{50}$ (nM) |
|---|---|---|
| 422 | ** | 542.5 |
| 423 | * | 1912 |
| 424 | *** | 332 |
| 425 | ** | 714.9 |
| 426 | **** | 26.21 |
| 427 | * | 1017 |
| 429 | ** | 506.7 |
| 430 | ** | 702.5 |
| 432 | * | 1478 |
| 433 | *** | 404.7 |
| 435 | *** | 241.6 |
| 437 | *** | 120.9 |

0.1-100 nM ****
\>101-500 nM ***
\>500-1000 nM **
\>1000 nM *
NA: Not active

TABLE XI

Illustrative EC$_{50}$ measured by YFP-halide influx assay for the CFTR-R117H of the compounds of the invention.

| Cpd # | EC$_{50}$ | EC$_{50}$ (nM) |
|---|---|---|
| 73 | *** | 168.3 |
| 83 | *** | 221.8 |
| 254 | *** | 127.4 |
| 270 | *** | 180.7 |
| 271 | **** | 40.0 |
| 286 | *** | 160.4 |
| 290 | *** | 166.5 |
| 298 | **** | 97.2 |
| 320 | **** | 87.7 |
| 323 | *** | 341.6 |
| 325 | ** | 793.4 |
| 329 | ** | 851.3 |
| 331 | **** | 95.0 |
| 333 | *** | 466.9 |
| 334 | *** | 118.0 |
| 337 | **** | 56.3 |
| 360 | **** | 49.34 |
| 363 | **** | 90.58 |
| 368 | **** | 33.67 |
| 369 | *** | 141.9 |
| 373 | **** | 46.13 |
| 374 | *** | 364.65 |
| 375 | *** | 253 |
| 376 | *** | 138.41 |
| 377 | ** | 779.15 |
| 379 | **** | 96.66 |
| 380 | *** | 144.5 |
| 387 | **** | 49.47 |
| 389 | *** | 246.6 |
| 390 | *** | 220.92 |
| 391 | **** | 33.785 |
| 393 | **** | 47.59 |
| 394 | * | 3315 |
| 397 | *** | 259 |
| 401 | **** | 86.5 |
| 402 | *** | 272.8 |
| 404 | *** | 282.8 |
| 405 | *** | 154.8 |
| 407 | *** | 262.4 |
| 408 | ** | 534.8 |
| 410 | *** | 138.5 |
| 411 | *** | 488.1 |
| 412 | **** | 35.43 |
| 413 | **** | 71.06 |
| 416 | *** | 351.2 |
| 418 | *** | 191.8 |
| 419 | *** | 465.3 |

TABLE XI-continued

Illustrative $EC_{50}$ measured by YFP-halide influx assay for the CFTR-R117H of the compounds of the invention.

| Cpd # | $EC_{50}$ | $EC_{50}$ (nM) |
|---|---|---|
| 420 | **** | 97.22 |
| 421 | * | 1926.2 |
| 422 | *** | 448.2 |
| 423 | *** | 248.8 |
| 424 | **** | 97.31 |
| 425 | *** | 144.3 |
| 426 | **** | 83.08 |
| 427 | * | 1353 |
| 429 | *** | 208.2 |
| 430 | *** | 321.5 |
| 432 | *** | 359.1 |
| 433 | ** | 676.5 |
| 435 | *** | 172.9 |
| 437 | *** | 263.8 |

0.1-100 nM ****
>100-500 nM ***
>500-1000 nM **
>1000 nM *
NA: Not active

Example 6

Cellular Assays 6.1. Ussing Chambers Assay

The ussing chambers assay measures the functionality of the cystic fibrosis Transmembrane Conductance regulator (CFTR) by measuring the short circuit current ($I_{sc}$) generated over the basolateral and apical membrane of lung epithelial cells. In order to measure the $I_{sc}$, the epithelium is short circuited by injecting a current that is adjusted by a feed-back amplifier to keep the transepithelial potential ($V_t$) at 0 mV. The amount of current required is adjusted by a feedback circuit and continuously measured. Intermittently the voltage is clamped to values different from 0 mV thus enabling an estimate of the transepithelial resistance ($R_t$).

For this purpose, bronchial epithelial cells isolated from CF patients homozygous for the CFTR ΔF508 mutation (hAEC-CF, Epithelix) or heterozygous for CFTR G551D and ΔF508 mutations (University of Chapel Hill, North Carolina) are plated on type IV collagen-coated Snapwell supports (Corning-Costar). Human airway epithelia are generated by provision of an air-liquid interface for 21 days to form well-differentiated polarized cultures that resemble in vivo pseudo-stratified ciliated epithelium (Fulcher, Gabriel, Burns, Yankaskas, & Randell, 205). In the case of the homozygous ΔF508 CFTR samples, the differentiated cells are treated with 3 μM VX809 to allow sufficient expression of properly folded CFTR protein on the membrane (48 hours basolateral treatment and 24 hours apical treatment), prior to electrophysiological recordings. For heterozygous G551D/ ΔF508, differentiated cells are used as such for the recordings.

For electrophysiological recording, the human airway epithelia are mounted in Ussing chambers for measurement of short-circuit current ($I_{sc}$). The epithelia are bathed in a NaCl-Ringer solution (120 mM NaCl, 25 mM $NaHCO_3$, 1.2 mM $CaCl_2$, 1.2 mM $MgCl_2$, 0.8 mM $KH_2PO_4$, 0.8 mM $K_2HPO_4$, pH 7.4, 5 mM glucose) on the basolateral side and a glutamate-ringer solution (120 mM sodium glutamate, 25 mM $NaHCO_3$, 1.2 mM $CaCl_2$, 1.2 mM $MgCl_2$, 0.8 mM $KH_2PO_4$, 0.8 mM $K_2HPO_4$, pH 7.4, 5 mM glucose) on the apical side to generate a gradient. Both chambers are gassed with 95% $O_2$, 5% $CO_2$, and maintained at 27° C. Apical amiloride is used to inhibit the endogenous ENaC currents while forkolin is applied on both apical and basolateral side to stimulate CFTR. After forskolin triggering, compounds are added on both side to test their potential for increasing CFTR gating. The increase in $I_{sc}$ is used as a measure for the increased CFTR activity, $EC_{50}$ values can be generated by measuring impact of different concentrations of compound on Short circuit current on primary cells. Inh-172, an inhibitor specific for CFTR, is used to test the specificity of the tested compounds.

6.2. Patch-Clamp Assays

Patch clamp is a very versatile and powerful technique which can be used to study individual ion channel activity in an isolated patch of cell membrane. Patch-clamp experiments can be performed to quantify the effects of compounds on CFTR channel activity in inside-out patches excised from cells overexpressing Wild type CFTR, ΔF508 CFTR or G551D CFTR channels. Specifically, the open probability of ΔF508, wild-type or G551D CFTR can be calculated from different patches for statistical analysis. The impact of the compound on the open probability of the CFTR channel will be compared with the open probability in absence of compound as measured or as described in literature. Modulators of CFTR will increase the open probability of the mutant CFTR.

6.3. TECC Assay 6.3.1. Protocol

The TECC (Tranepithelial Clamp Circuit, EP-design) assay measures the functionality of the cystic fibrosis Transmembrane Conductance regulator (CFTR) by measuring the short circuit current ($I_{sc}$) generated over the basolateral and apical membrane of lung epithelial cells. In TECC the transepithelial potential PD and transepithelial resistance ($R_t$) are measured in an open circuit and transformed to $I_{sc}$ using Ohm's law. 24 wells can be measured simultaneously allowing a higher throughput compared to Ussing chambers.

For this purpose, bronchial epithelial cells isolated from CF patients homozygous for the CFTR ΔF508 mutation (hAEC-CF, Epithelix) are plated on type IV collagen-coated Transwell supports (Costar). Human airway epithelia are generated by provision of an air-liquid interface for 21 days to form well-differentiated polarized cultures that resemble in vivo pseudo-stratified ciliated epithelium (Fulcher, Gabriel, Burns, Yankaskas, & Randell, 205). In the case of the homozygous ΔF508 CFTR samples, the differentiated cells are treated with 3 μM VX809 (2626 South Loop West, Suite 225, Houston, Tex. 77054 USA, Cat n#51565) to allow sufficient expression of properly folded CFTR protein on the membrane (48 hours basolateral treatment and 24 hours apical treatment), prior to electrophysiological recordings.

For electrophysiological recording, the human airway epithelia are mounted in the TECC heating plate for electrophysiological measurement and kept at 37° C. The epithelia are bathed in a NaCl-Ringer solution (120 mM NaCl, 25 mM $NaHCO_3$, 1.2 mM $CaCl_2$, 1.2 mM $MgCl_2$, 0.8 mM $KH_2PO_4$, 0.8 mM $K_2HPO_4$, pH 7.4, 5 mM glucose) on both the basolateral and apical sides. Apical amiloride is used to inhibit the endogenous ENaC currents while forkolin is applied on both apical and basolateral side to stimulate CFTR. After forskolin triggering, compounds are added on both sides to test their potential for increasing CFTR gating. Measurements are done during a 20 minute timeframe with recordings every 2 minutes. The increase in $I_{sc}$ is used as a measure for the increased CFTR activity, $EC_{50}$ values can be generated by measuring impact of different concentrations of compound on $I_{sc}$ on primary cells, for this purpose each transwell is treated with a different compound concentration. Inh-172, an inhibitor specific for CFTR, is used to test the specificity of the tested compounds.

6.3.2. Results

When subjected to this protocol, the following values were obtained. The difference between ΔIsc measured as DMSO (baseline), and the ΔIsc measured with the compound tested.

Example 7

Pharmacokinetic, DMPK and Toxicity Assays 7.1. Thermodynamic Solubility

A solution of 1 mg/mL of the test compound is prepared in a 0.2M phosphate buffer pH 7.4 or a 0.1M citrate buffer pH 3.0 at room temperature in a glass vial.

The samples are rotated in a Rotator drive STR 4 (Stuart Scientific, Bibby) at speed 3.0 at room temperature for 24 h.

After 24 h, 800 µL of the sample is transferred to an eppendorf tube and centrifuged 5 min at 14000 rpm. 200 µL of the supernatant of the sample is then transferred to a MultiscreenR Solubility Plate (Millipore, MSSLBPC50) and the supernatant is filtered (10-12" Hg) with the aid of a vacuum manifold into a clean Greiner polypropylene V-bottom 96 well plate (Cat no. 651201). 5 µL of the filtrate is diluted into 95 µL (F20) of the same buffer used to incubate in the plate containing the standard curve (Greiner, Cat no. 651201).

The standard curve for the compound is prepared freshly in DMSO starting from a 10 mM DMSO stock solution diluted factor 2 in DMSO (5000 µM) and then further diluted in DMSO up to 19.5 µM. 3 µL of the dilution series as from 5000 µM is then transferred to a 97 µL acetonitrile-buffer mixture (50/50). The final concentration range is 2.5 to 150 µM.

The plate is sealed with sealing mats (MA96RD-045, www.kinesis.co.uk) and samples are measured at room temperature on LCMS (ZQ 1525 from Waters) under optimized conditions using Quanoptimize to determine the appropriate mass of the molecule.

The samples are analyzed on LCMS with a flow rate of 1 mL/min. Solvent A is 15 mM ammonia and solvent B is acetonitrile. The sample is run under positive ion spray on an XBridge C18 3.5 µM (2.1×30 mm) column, from Waters. The solvent gradient has a total run time of 2 min and ranges from 5% B to 95% B.

Peak areas are analyzed with the aid of Masslynx software package and peak areas of the samples are plotted against the standard curve to obtain the solubility of the compound.

Solubility values are reported in µM or µg/mL.

7.2. Aqueous Solubility

Starting from a 10 mM stock in DMSO, a serial dilution of the compound is prepared in DMSO. The dilution series is transferred to a 96 NUNC Maxisorb plate F-bottom (Cat no. 442404) and 0.1M phosphate buffer pH7.4 or 0.1M citrate buffer pH3.0 at room temperature is added.

The final concentration ranges from 300 µM to 18.75 µM in 5 equal dilution steps. The final DMSO concentration does not exceed 3%. 200 µM Pyrene is added to the corner points of each 96 well plate and serves as a reference point for calibration of Z-axis on the microscope.

The assay plates are sealed and incubated for 1 h at 37° C. while shaking at 230 rpm. The plates are then scanned under a white light microscope, yielding individual pictures of the precipitate per concentration. The precipitate is analyzed and converted into a number with a software tool which can be plotted onto a graph. The first concentration at which the compound appears completely dissolved is the concentration reported; however the true concentration lies somewhere between this concentration and one dilution step higher.

Solubility values measured according to this protocol are reported in µg/mL.

7.3. Plasma Protein Binding (Equilibrium Dialysis)

A 10 mM stock solution of the compound in DMSO is diluted with a factor 5 in DMSO. This solution is further diluted in freshly thawed human, rat, mouse or dog plasma (BioReclamation INC) with a final concentration of 10 µM and final DMSO concentration of 0.5% (5.5 µL in 1094.5 µL plasma in a PP-Masterblock 96well (Greiner, Cat no. 780285))

A Pierce Red Device plate with inserts (ThermoScientific, Cat no. 89809) is prepared and filled with 750 µL PBS in the buffer chamber and 500 µL of the spiked plasma in the plasma chamber. The plate is incubated for 4 h at 37° C. while shaking at 230 rpm. After incubation, 120 µL of both chambers is transferred to 360 µL acetonitrile in a 96-well round bottom, PP deep-well plates (Nunc, Cat no. 278743) and sealed with an aluminum foil lid. The samples are mixed and placed on ice for 30 min. This plate is then centrifuged 30 min at 1200 rcf at 4° C. and the supernatant is transferred to a 96 v-bottom PP plate (Greiner, 651201) for analysis on LCMS.

The plate is sealed with sealing mats (MA96RD-04S) of www.kinesis.co.uk and samples are measured at room temperature on LCMS (ZQ 1525 from Waters) under optimized conditions using Quanoptimize to determine the appropriate mass of the molecule.

The samples are analyzed on LCMS with a flow rate of 1 mL/min. Solvent A is 15 mM ammonia and solvent B is acetonitrile. The sample is run under positive ion spray on an XBridge C18 3.5 µM (2.1×30 mm) column, from Waters. The solvent gradient has a total run time of 2 min and ranges from 5% B to 95% B.

Peak area from the compound in the buffer chamber and the plasma chamber are considered to be 100% compound. The percentage bound to plasma is derived from these results and is reported as percentage bound to plasma.

The solubility of the compound in the final test concentration in PBS is inspected by microscope to indicate whether precipitation is observed or not.

7.4. Caco2 Permeability

Bi-directional Caco-2 assays are performed as described below. Caco-2 cells are obtained from European Collection of Cell Cultures (ECACC, cat 86010202) and used after a 21 day cell culture in 24-well Transwell plates (Fisher TKT-545-020B).

$2 \times 10^5$ cells/well are seeded in plating medium consisting of DMEM+GlutaMAXI+1% NEAA+10% FBS (FetalClone II)+1% Pen/Strep. The medium is changed every 2-3 days.

Test and reference compounds (propranolol and rhodamine-123 or vinblastine, all purchased from Sigma) are prepared in Hanks' Balanced Salt Solution containing 25 mM HEPES (pH7.4) and added to either the apical (125 µL) or basolateral (600 µL) chambers of the Transwell plate assembly at a concentration of 10 µM with a final DMSO concentration of 0.25%.

50 µM Lucifer Yellow (Sigma) is added to the donor buffer in all wells to assess integrity of the cell layers by monitoring Lucifer Yellow permeation. As Lucifer Yellow (LY) cannot freely permeate lipophilic barriers, a high degree of LY transport indicates poor integrity of the cell layer.

After a 1 h incubation at 37° C. while shaking at an orbital shaker at 150 rpm, 70 µL aliquots are taken from both apical (A) and basal (B) chambers and added to 100 µl 50:50 acetonitrile:water solution containing analytical internal standard (0.5 µM carbamazepine) in a 96 well plate.

Lucifer yellow is measured with a Spectramax Gemini XS (Ex 426 nm and Em 538 nm) in a clean 96 well plate containing 150 μL of liquid from basolateral and apical side.

Concentrations of compound in the samples are measured by high performance liquid-chromatography/mass spectroscopy (LC-MS/MS).

Apparent permeability ($P_{app}$) values are calculated from the relationship:

$$P_{app} = [\text{compound}]_{acceptor\ final} \times V_{acceptor} / ([\text{compound}]_{donor\ initial} \times V_{donor}) / T_{inc} \times V_{donor} / \text{surface area} \times 60 \times 10^{-6}\ \text{cm/s}$$

V=chamber volume
$T_{inc}$=incubation time.
Surface area=0.33 cm²

The Efflux ratios, as an indication of active efflux from the apical cell surface, are calculated using the ratio of $P_{app}$ B>A/$P_{app}$ A>B.

The following assay acceptance criteria are used:
Propranolol: $P_{app}$ (A>B) value≥20(×10⁻⁶ cm/s)
Rhodamine 123 or Vinblastine: $P_{app}$ (A>B) value<5 (×10⁻⁶ cm/s) with Efflux ratio≥5.
Lucifer yellow permeability: ≤100 nm/s 7.5. MDCKII-MDR1 Permeability MDCKII-MDR1 cells are Madin-Darby canine kidney epithelial cells, over-expressing human multi-drug resistance (MDR1) gene, coding for P-glycoprotein (P-gp). Cells are obtained from Netherlands Cancer Institute and used after a 3-4 day cell culture in 24-well Millicell cell culture insert plates (Millipore, PSRP010R5). Bi-directional MDCKII-MDR1 permeability assay is performed as described below.

3×10⁵ cells/mL (1.2×10⁵ cells/well) are seeded in plating medium consisting of DMEM+1% Glutamax-100+1% Antibiotic/Antimycotic+10% FBS (Biowest, S1810). Cells are left in $CO_2$ incubator for 3-4 days. The medium is changed 24 h after seeding and on the day of experiment.

Test and reference compounds (amprenavir and propranolol) are prepared in Dulbecco's phosphate buffer saline (D-PBS, pH7.4) and added to either the apical (400 μL) or basolateral (800 μL) chambers of the Millicell cell culture insert plates assembly at a final concentration of 10 μM (0.5 μM in case of amprenavir) with a final DMSO concentration of 1%.

100 μM Lucifer Yellow (Sigma) is added to the all donor buffer solutions, in order to assess integrity of the cell monolayers by monitoring Lucifer Yellow permeation. Lucifer yellow is a fluorescent marker for the paracellular pathway and it is used as an internal control in every monolayer to verify tight junction integrity during the assay.

After a 1 h incubation at 37° C. while shaking at an orbital shaker at 150 rpm, 75 μL aliquots are taken from both apical (A) and basal (B) chambers and added to 225 μL acetonitrile: water solution (2:1) containing analytical internal standard (10 ng/mL warfarin) in a 96 well plate. Aliquoting is also performed at the beginning of the experiment from donor solutions to obtain initial (Co) concentration.

Concentration of compound in the samples is measured by high performance liquid-chromatography/mass spectroscopy (LC-MS/MS).

Lucifer yellow is measured with a Fluoroscan Ascent FL Thermo Scientific (Ex 485 nm and Em 530 nm) in a 96 well plate containing 150 μL of liquid from all receiver wells (basolateral or apical side).

7.6. Microsomal Stability

A 10 mM stock solution of compound in DMSO is diluted to 6 μM in a 105 mM phosphate buffer, pH7.4 in a 96 deep well plate (Greiner, Cat no. 780285) and pre-warmed at 37° C.

A Glucose-6-phosphate-dehydrogenase (G6PDH, Roche, 10127671001) working stock solution of 700 U/mL is diluted with a factor 1:700 in a 105 mM phosphate buffer, pH7.4. A co-factor mix containing 0.528M $MgCl_2.6H_2O$ (Sigma, M2670), 0.528M glucose-6-phosphate (Sigma, G-7879) and 0.208M NADP+(Sigma, N-0505) is diluted with a factor 1:8 in a 105 mM phosphate buffer, pH7.4.

A working solution is made containing 1 mg/mL liver microsomes (Provider, Xenotech) of the species of interest (human, mouse, rat, dog . . . ), 0.8 U/mL G6PDH and co-factor mix (6.6 mM $MgCl_2$, 6.6 mM glucose-6-phosphate, 2.6 mM NADP+). This mix is pre-incubated for 15 min, but never more than 20 min, at rt.

After pre-incubation, compound dilution and the mix containing the microsomes, are added together in equal amount and incubated for 30 min at 300 rpm. For the time point of 0 min, two volumes of MeOH are added to the compound dilution before the microsome mix is added. The final concentration during incubation are: 3 μM test compound or control compound, 0.5 mg/mL microsomes, 0.4 U/mL G6PDH, 3.3 mM $MgCl_2$, 3.3 mM glucose-6-phosphate and 1.3 mM NaDP+.

After 30 min of incubation, the reaction is stopped with 2 volumes of MeOH.

Of both time points, samples are mixed, centrifuged and the supernatant is harvested for analysis on LC-MS/MS. The instrument responses (i.e. peak heights) are referenced to the zero time-point samples (as 100%) in order to determine the percentage of compound remaining. Standard compounds Propanolol and Verapamil are included in the assay design.

The data on microsomal stability are expressed as a percentage of the total amount of compound remaining after 30 min.

7.7. Pharmacokinetic Study in Rodents 7.7.1. Animals

Sprague-Dawley rats (male, 5-6 weeks old) are obtained from Janvier (France). Rats are acclimatized for at least 5 days before treatment and are kept on a 12 h light/dark cycle. Temperature is maintained at approximately 22° C., and food and water are provided ad libitum. Two days before administration of the test compounds, rats may undergo surgery to place a catheter in the jugular vein under isoflurane anesthesia. After the surgery, rats are housed individually. Rats are deprived of food for at least 16 h before oral dosing and 6 h after. Water is provided ad libitum.

7.7.2. Plasma Pharmacokinetic Studies

Compounds are formulated in PEG200/physiological saline (25/75) for the intravenous route and in 0.5% methylcellulose and EtOH/PEG 200/Methylcellulose 0.5% (Oct. 25, 1965 v/v/v) for the oral route. Test compounds are orally dosed as a single esophageal gavage at 5 mg/kg under a dosing volume of 5 mL/kg and intravenously dosed as a bolus via the caudal vein at 1 mg/kg under a dosing volume of 5 mL/kg. Each group consist of 3 rats. Blood samples are collected via the jugular vein with lithium heparin as anti-coagulant at the following time points: 0.05 (intravenous route), 0.25 (oral route), 0.5, 1, 3, 5, 8 and 24 h. Alternatively, blood samples are collected at the retro-orbital sinus with lithium heparin as anti-coagulant at the following time points 0.25, 1, 3 and 6 h (oral route). Whole blood samples are centrifuged at 1500 g for 10 min and the resulting plasma samples are stored at −20° C. pending analysis.

7.7.3. Lung Distribution Studies

Compounds are formulated in 0.5% methylcellulose and EtOH/PEG 200/Methylcellulose 0.5% (Oct. 25, 1965 v/v/v) by the oral route. Test compounds are orally dosed as a single esophageal gavage at 10 mg/kg under a dosing volume of 5 mL/kg. Each group consists of 12 rats. At each time point, typically 1, 3, 6 and 24 h, animals are euthanized and blood and lung samples are collected. Whole blood samples are centrifuged at 1500 g for 10 min and the resulting plasma samples, along with the lung samples, are stored at −20° C. pending analysis.

7.7.4. Quantification of Compound Levels in Plasma and Lung Samples

Lung samples are milled in the presence of ceramic beads and proteins present in plasma and lung samples are precipitated with an organic solvent. Concentrations of each test compound are determined by an LC-MS/MS method in which the mass spectrometer is operated in positive or negative electrospray mode.

7.7.5. Determination of Pharmacokinetic Parameters

Pharmacokinetic parameters are calculated using Winnonlin® or Phoenix® (Pharsight®, United States).

7.7.6. Data Analysis

For each animal, the lung-to-plasma ratio is determined as the ratio between compound concentration in lung and in plasma. At each sampling time point, mean, standard error of the mean (sem) and coefficient of variation (CV %) are calculated using data from three animals.

7.7.7. PXR Cellular Activation Assay

The assay allows determining the CIP induction activity of a compound, using Human Pregnane X Receptor (PXR), which primary function is to up regulate the synthesis of the cytochrome P450 in the presence of toxic agents.

This Activation Assay is outsourced to Cyprotex. (15 Beech Lane, Macclesfield, Cheshire. SK10 2DR United Kingdom. Tel: +44 (0)1625 505100).

Transcriptional activation is monitored by luminescence. Data are expressed as fold activation relative to the vehicle control. The use of 5 or more doses of test compound and positive control allows for the derivation of $EC_{50}$ and Emax values from nonlinear regression analysis of the log dose-response curves.

Test compound values are compared to those obtained for the positive control (10 μM rifampicin).

The significant response threshold for set at 35% of the maximal response obtained with the positive control.

7.7.8. Direct CYP450 Inhibition in Human Liver Microsomes

The assay measures the inhibition potency of a compound of the major CYP450 isoenzymes.

A 5 mM stock solution of test compound is prepared in methanol. This stock is serially diluted 1:3 in 50 mM potassium phosphate buffer pH 7.4, resulting in seven concentrations of test compound (0.14-100 μM, 2% methanol).

The obtained compound dilution is added to human hepatic microsomes at 20 mg protein/mL (BD Biosciences, either Cat. No. 452161, or alternatively Cat. No. 452117) and probe substrate (see table below).

After pre-warming the solution for 5 min at 37° C., the reaction is started by adding cofactor mix (7.65 mg/mL glucose-6-phosphate, 1.7 mg/mL NADP, 6 U/mL of glucose-6-phosphate dehydrogenase).

After incubation at 37° C. (Table below), the reaction (50 μL) is terminated by adding 150 μL of an acetonitrile:methanol (2:1) solution with internal standard (warfarin). Samples are centrifuged (535 g, 25 min, +4° C.) and the supernatant fractions analyzed by LC-MS/MS.

The percentage of metabolism reduction is measured as follows:

$$\text{Metabolism reduction} = \frac{[Subst]T0 - [Met]Tinc}{[Subst]T0} * 100$$

[Met] Tinc=concentration of probe substrate

[Subst]T0=Initial concentration of probe metabolite

Percent of control activity vs concentration plots are generated and fitted using GraphPad Prism software to generate $IC_{50}$.

TABLE XII

Isoforms and test conditions

| P450 Isoform | Microsomes (mg/mL) | Probe Substrate | Probe metabolite | Incubation (min) | Positive Control | Negative Control |
|---|---|---|---|---|---|---|
| 1A2 | 0.1 | Phenacetin (35 μM) | Acetaminophen | 10 | Furafylline | Sulphaphenazole |
| 2C9 | 0.1 | Diclofenac (10 μM) | 4'-OH-diclofenac | 5 | Sulphaphenazole | Furafylline |
| 2C19 | 0.25 | S-(+)-Mephenytoin (30 μM) | 4'-OH-mephenytoin | 15 | Tranylcypromine | Phenacetin |
| 2D6 | 0.1 | Bufuralol (10 μM) | OH-bufuralol | 10 | Quinidine | Sulphaphenazole |
| 3A4 | 0.1 | Midazolam (3 μM) | 1'-OH-midazolam | 5 | Ketoconazole | Sulphaphenazole |
| 3A4 | 0.25 | Testosterone (100 μM) | 6β-OH-testosterone | 15 | Ketoconazole | Sulphaphenazole |
| 3A4 | 0.1 | Nifedipine (5 μM) | Oxidized nifedipine | 5 | Ketoconazole | Sulphaphenazole |
| 3A4 | 0.1 | Atorvastatin (10 μM) | 2-OH Atorvastatin | 10 | Ketoconazole | Sulphaphenazole |

7.7.9. CYP450 Reaction Phenotyping

7.7.9.1. Protocol

The aim of this assay is to evaluate which of the major CYP450 isoenzyme(s) is/are involved in the metabolism of a test compound.

A 1 mM stock solution of test compound is prepared in DMSO. This stock is diluted in 50 mM potassium phosphate buffer pH 7.4, resulting in a final assay concentration of test compound of 1 μM, 01% DMSO. This compound dilution is added to cDNA-expressed human cytochrome P450 isoenzymes (BD Biosciences, Cat N° CYP1A2: 456203; CYP2C19: 456259; CYP2C9: 456258; CYP3A4: 456202; CYP2D6: 456217), specific conditions depended on the isoform studies: see Table XIII.

After pre-warming 10 min at 37° C., the reaction is started by adding cofactor mix (final reaction concentrations in the assay were: 0.6 U/ml Glucose-6-phophate-dehydrogenase (G6PDH), 3.3 mM $MgCl_2$, 3.3 mM glucose-6-phosphate and 1.3 mM NADP+ for CYP3A4, CYP2C9, CYP2C19 and CYP1A2. And 0.6 U/mL G6PDH, 0.41 mM $MgCl_2$, 0.41 mM glucose-6-phosphate and 8.2 µM NADP+ for CYP2D6).

In parallel, a stability control is performed by incubating the test compound with denaturated (by heat) enzymes and cofactor mix to evaluate the stability of thereof during the incubation time. For each time points, after incubation at 37° C. (see Table VIII), samples (50 µL) are terminated with 100 µL acetonitrile solution with internal standard (warfarin). Samples are centrifuged (805 g, 20 minutes, +4° C.) and the supernatant fractions are filtered (Varian Captiva Cat N°: A5960002), diluted in water/acetonitrile (85/15) and analyzed by LC-MS/MS (see Table 3). The instrument responses (ratio of test compound and internal standard peak areas) are referenced to the zero time-point samples (100%) in order to determine the percentage of compound remaining. Plots of the % of test compound remaining are used to determine the profile of metabolism of the test compound using Graph Pad Prism software.

TABLE XIII

Assay conditions for CYP reaction phenotyping

| Cytochrome P450 Isoform | Enzyme (mg/mL) | Incubation (min) | Positive Control |
|---|---|---|---|
| 1A2 | 0.1 | 0-30-60 | Phenacetin (1 µM) |
| 2C9 | 0.1 | 0-30-60 | Diclofenac (1 µM) |
| 2C19 | 0.1 | 0-30-60 | Omeprazol (1 µM) |
| 2D6 | 0.1 | 0-30-60 | Dextromethorphan (1 µM) |
| 3A4 | 0.1 | 0-30-60 | Testosterone (1 µM) |

FINAL REMARKS

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

REFERENCES

Bobadilla, J. L., Macek, M. J., Fine, J. P., & Farrell, P. M. (2002). Cystic fibrosis: a worldwide analysis of CFTR mutations—correlation with incidence data and application to screening. *Hum Mutat*, 19(6), 575-606.

Bundgard, H. (1985). In *Design of Prodrugs* (pp. 7-9, 21-24). Amsterdam: Elsevier.

Fulcher, M. L., Gabriel, S., Burns, K. A., Yankaskas, J. R., & Randell, S. H. (205). Well-Differentiated Human Airway Epithelial Cell Cultures. In *Methods in Molecular Medicine, vol. 107: Human Cell Culture Protocols, Second Edition* (pp. 183-206). Totowa, N.J.: Humana Press.

Galietta, L. J., Haggie, P. M., & Verkman, A. S. (2001). Green fluorescent protein-based halide indicators with improved chloride and iodide affinities. *FEBS letters*, 499(3), 220-4.

Greene, T W; Wuts, P G M; (1991). *Protecting Groups in Organic Synthesis, Second Edition*. New York: Wiley.

Kerem, B., Rommens, J. M., Buchanan, J. A., Markiewicz, D., Cox, T. K., Chakravati, A., . . . Tsui, L. (1989). Identification of the Cystic Fibrosis Gene: Genetic Analysis. *Science New Series*, 245(4922), 1073-1080.

Morello J P, J., Petäjä-Repo, U. E., Bichet, D. G., & Bouvier, M. (2000). Pharmacological chaperones: a new twist on receptor folding. *Trends Pharmacol Sci*, 21(12), 466-9.

Nagai, T., Ibata, K., Park, E. S., Kubota, M., Mikoshiba, K., & Miyawaki, A. (2002). A variant of yellow fluorescent protein with fast and efficient maturation for cell-biological applications. *Nature Biotechnology*, 20, 87-90.

Pasyl, E. A., & Foskett, J. K. (1995). Mutant (delta F508) cystic fibrosis transmembrane conductance regulator Cl— channel is functional when retained in endoplasmic reticulum of mammalian cells. *J Biol Chem*, 270(21), 12347-50.

Quinton, P. M. (1990). Cystic fibrosis: a disease in electrolyte transport. *FASEB J*, 4(10), 2709-17.

Rowe, S. M., & Verkman, A. S. (2013). Cystic Fibrosis Transmembrane Regulator Correctors and Potentiators. *Cold Spring Harb Perspect Med*(3), a009761.

Shastry, B. S. (2003). Neurodegenerative disorders of protein aggregation. *Neurochem Int*, 43(1), 1-7.

Zhang, W., Fujii, N., & Naren, A. P. (2012). Recent advances and new perspectives in targeting CFTR for therapy of cystic fibrosis and enterotoxin-induced secretory diarrheas. *Future Med Chem*, 4(3), 329-345.

The invention claimed is:
1. A compound according to Formula I

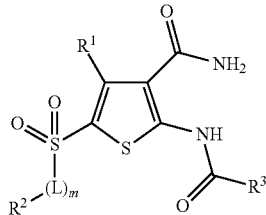

wherein
R¹ is H, —CH₃, —CF₃, or cyclopropyl;
L is —NR⁴—;
the subscript m is 0, or 1;
R² is
- C$_{1-4}$ alkyl or C$_{1-4}$ alkyl substituted with one or more independently selected R⁵ groups,
- C$_{3-7}$ cycloalkyl,
- 4-10 membered monocyclic, bridged-, spiro-, or fused bicyclic heterocycloalkyl comprising one or more heteroatoms independently selected from N, O, and S, and optionally substituted with one or more independently selected R$^a$ groups,
- 5-6 membered monocyclic heterocycloalkenyl comprising one or more heteroatoms independently selected from N, O, and S, and optionally substituted with one or more independently selected R$^a$ groups,
- C$_{6-10}$ mono or bicyclic aryl optionally substituted with one or more independently selected R$^b$, or
- 5-10 membered monocyclic or fused bicyclic heteroaryl, comprising one or more heteroatoms independently selected from N, O, and S, and optionally substituted with one or more independently selected R$^b$;

R³ is
- C$_{3-7}$ cycloalkyl optionally substituted with one or more independently selected R$^c$ groups,
- 4-7 membered monocyclic heterocycloalkyl comprising one or more heteroatoms independently selected from O, and S, and optionally substituted with R$^c$,
- C$_{6-10}$ mono or bicyclic aryl optionally substituted with one or more independently selected R$^d$ groups,
- phenyl fused to a 5-6 membered heterocycloalkyl comprising one or more heteroatoms independently selected from N, O, and S, and optionally substituted with one or more independently selected R$^d$ groups,
- phenyl fused to a C$_{5-6}$ cycloalkyl, optionally substituted with one or more independently selected R$^d$ groups,
- 5-10 membered mono or fused bicyclic heteroaryl comprising one or more heteroatoms independently selected from N, O, and S, and optionally substituted with one or more independently selected R$^d$ groups,
- 5-6 membered monocyclic heteroaryl comprising one or more heteroatoms independently selected from N, O, and S, fused to a 5-6 membered heterocycloalkyl comprising one or more heteroatoms independently selected from N, O, and S, and optionally substituted with one or more independently selected R$^d$ groups,
- 5-6 membered monocyclic heteroaryl comprising one or more heteroatoms independently selected from N, O, and S, fused to a C$_{5-6}$ cycloalkyl comprising one or more heteroatoms independently selected from N, O, and S, and optionally substituted with one or more independently selected R$^d$ groups,
- C$_{2-6}$ alkenyl,
- C$_{3-6}$ alkyl, or
- C$_{1-6}$ alkyl substituted with one or more independently selected R$^e$ groups;

R⁴ is
- C$_{1-6}$ alkyl or C$_{1-6}$ alkyl substituted with one or more independently selected R⁶ groups, or
- C$_{3-7}$ cycloalkyl;

each R⁵ is independently selected from
- halo,
- OH,
- —CN,
- C$_{1-4}$ alkoxy,
- —NR$^{8e}$R$^{8f}$,
- C$_{3-7}$ cycloalkyl,
- 6 membered mono or fused bicyclic heteroaryl comprising one or more heteroatoms independently selected from N, O, and S, and
- phenyl optionally substituted with one or more independently selected
  - halo,
  - C$_{1-4}$ alkyl optionally substituted with one or more independently selected halo, or
  - C$_{1-4}$ alkoxy;

each R⁶, is independently selected from
- halo,
- OH,
- —CN,
- —NR$^{8g}$R$^{8h}$, and
- C$_{1-4}$ alkoxy;

each R$^a$ is selected from
- halo,
- CN,
- oxo,
- C$_{1-4}$ alkyl or C$_{1-4}$ alkyl substituted with one or more independently selected R$^{7a}$,
- C$_{1-4}$ alkoxy or C$_{14}$ alkoxy substituted with one or more independently selected R$^{7a}$,
- —C(=O)O—C$_{1-4}$ alkyl,
- phenyl,
- 5-10 membered mono, or fused bicyclic heteroaryl comprising one or more heteroatoms independently selected from N, O, or S, and optionally substituted with one or more independently selected C$_{1-4}$ alkyl, and
- —NR$^{8a}$R$^{8b}$;

each R$^b$ is selected from
- halo,
- —CN,
- C$_{1-4}$ alkyl or C$_{1-4}$ alkyl substituted with one or more independently selected R$^{7b}$,
- C$_{1-4}$ alkoxy or C$_{1-4}$ alkoxy substituted with one or more independently selected R$^{7b}$,
- —OC(=O)C$_{1-4}$ alkyl, and
- —NR$^{8c}$R$^{8d}$;

each R$^c$ is selected from
- halo,
- OH,
- —CN,
- oxo,
- C$_{1-4}$ alkyl or C$_{1-4}$ alkyl substituted with one or more independently selected R$^{7c}$),
- C$_{1-4}$ alkoxy or C$_{1-4}$ alkoxy substituted with one or more independently selected R$^{7c}$), phenyl or phenyl substituted with one or more independently selected halo, $C_{1-4}$ alkyl, $C_{1-4}$ alkoxy, —CN, or —NR$^{9a}$R$^{9b}$), and 5-6 membered monocyclic heteroaryl comprising one or more heteroatoms independently selected from N, O, or S or N, O, or S substituted with one or more independently selected halo, $C_{1-4}$ alkyl, $C_{1-4}$ alkoxy, CN, —NR$^{9c}$R$^{9d}$;

each R$^d$ is selected from
halo,
—CN,
—OH,
$C_{1-4}$ alkyl or $C_{1-4}$ alkyl substituted with one or more independently selected R$^{7d}$,
$C_{1-4}$ alkoxy or $C_{1-4}$ alkoxy substituted with one or more independently selected R$^{7d}$,
$C_{3-7}$ cycloalkyl,
5-10 membered mono or fused bicyclic heteroaryl comprising one or more heteroatoms independently selected from N, O, or S, and
—NH-Phenyl;

each R$^e$ is selected from
halo,
OH,
—CN,
$C_{1-4}$ alkoxy or $C_{1-4}$ alkoxy substituted with one or more independently selected R$^{7e}$,
$C_{3-7}$ cycloalkyl,
phenyl or phenyl with one or more independently selected halo, $C_{1-4}$ alkyl, $C_{1-4}$ alkoxy, CN, and —NR$^{9e}$R$^{9f}$, and
5-6 membered monocyclic heteroaryl comprising one or more heteroatoms independently selected from N, O, and S or N, O, and S substituted with one or more independently selected halo, $C_{1-4}$ alkyl, $C_{1-4}$ alkoxy, CN, and —NR$^{9g}$R$^{9h}$;

each R$^{7a}$, R$^{7b}$, R$^{7c}$, R$^{7d}$, and R$^{7e}$ is independently selected from
halo,
OH,
—CN,
—NR$^{8i}$R$^{8j}$, and
$C_{1-4}$ alkoxy;

each R$^{8a}$, R$^{8b}$, R$^{8c}$, R$^{8d}$, R$^{8e}$, R$^{8f}$, R$^{8g}$, R$^{8h}$, R$^{8i}$, or R$^{8j}$ is independently selected from H, and $C_{1-4}$ alkyl;

each R$^{9a}$, R$^{9b}$, R$^{9c}$, R$^{9d}$, R$^{9e}$, R$^{9f}$, R$^{9g}$, or R$^{9h}$ is independently selected from H, and $C_{1-4}$ alkyl;

or a pharmaceutically acceptable salt, or a solvate, or a pharmaceutically acceptable salt of a solvate thereof.

2. A compound or pharmaceutically acceptable salt thereof, according to claim 1, wherein the compound is according to Formula II:

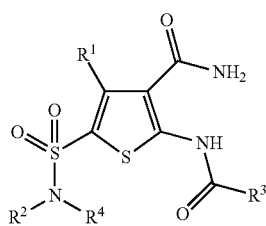

wherein R$^1$, R$^2$, R$^3$, and R$^4$ are as described in claim 1.

3. A compound or pharmaceutically acceptable salt thereof, according to claim 2, wherein R$^4$ is $C_{1-6}$ alkyl.

4. A compound or pharmaceutically acceptable salt thereof, according to claim 1, wherein the compound is according to Formula III:

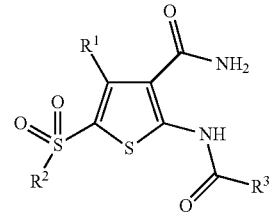

wherein R$^1$, R$^2$, and R$^3$ are as described in claim 1.

5. A compound or pharmaceutically acceptable salt thereof, according to claim 4, wherein R$^2$ is phenyl substituted with one or more independently selected R$^b$.

6. A compound or pharmaceutically acceptable salt thereof, according to claim 5, wherein R$^b$ is F, Cl, or CN.

7. A compound or pharmaceutically acceptable salt thereof, according to claim 1, wherein the compound is according to Formula IV:

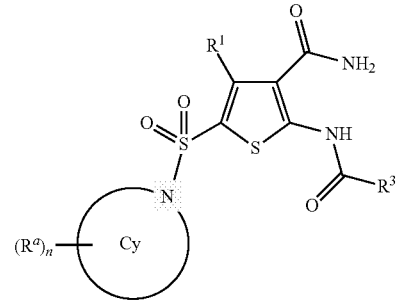

wherein Cy is 4-10 membered monocyclic or fused bicyclical heterocycloalkyl comprising one or more heteroatoms independently selected from N, O, and S, R$^a$ is as described in claim 1, and the subscript n is 0, 1 or 2.

8. A compound or pharmaceutically acceptable salt thereof, according to claim 7, wherein Cy is azetidinyl, pyrrolidinyl, tetrahydropyranyl, piperidinyl, morpholinyl 2-oxa-5-aza-bicyclo[2.2.1]heptanyl, [1,4]oxazepanyl, 2,3-dihydro-1H-isoindolyl, or 1,2,3,4-tetrahydro-isoquinolinyl.

9. A compound or pharmaceutically acceptable salt thereof, according to claim 1, wherein R$^3$ is phenyl, substituted with one or more independently selected R$^d$ groups.

10. A compound or pharmaceutically acceptable salt thereof, according to claim 1, wherein R$^3$ is furanyl, thiophenyl, pyrazolyl, imidazolyl, thiazolyl, oxazolyl, pyridinyl, pyridazinyl, pyrimidyl, or pyrazinyl, each of which is substituted with one or more independently selected R$^d$ groups.

11. A compound or pharmaceutically acceptable salt thereof, according to claim 10, wherein R$^d$ is F, Cl, OH, or CN.

12. A compound or pharmaceutically acceptable salt thereof, according to claim 10, wherein R$^d$ is —CH$_3$, —CH$_2$—CH$_3$, —CH(CH$_3$)$_2$, —OCH$_3$, or —OCH$_2$—CH$_3$, each of which is optionally substituted with one or more independently selected R$^{7d}$.

13. A compound or pharmaceutically acceptable salt thereof, according to claim 12, wherein $R^{7d}$ is F, Cl, OH, CN, or —OCH$_3$.

14. A compound or pharmaceutically acceptable salt thereof, according to claims 1, wherein $R^3$ is —CH(CH$_3$)$_2$, —C(CH$_3$)$_3$, —C(CH$_3$)$_2$—CH$_3$, or —C(CH$_3$)H—CH$_2$(CH$_3$), each of which is substituted with one or more independently selected $R^e$ groups.

15. A compound or pharmaceutically acceptable salt thereof, according to claim 14, wherein $R^e$ is F, Cl, OH, or CN.

16. A compound or pharmaceutically acceptable salt thereof, according to claim 1, wherein $R^1$ is H.

17. A compound or pharmaceutically acceptable salt thereof, according to claim 1, wherein $R^1$ is —CH$_3$.

18. A pharmaceutical composition comprising a pharmaceutically acceptable carrier and a pharmaceutically effective amount of a compound according to claim 1.

19. A method for the treatment of cystic fibrosis, comprising administering to a mammal afflicted with cystic fibrosis the compound or salt according to claim 1 in an amount of sufficient to effect the treatment.

20. The method of claim 19, wherein the cystic fibrosis is caused by a Class I, II, III, IV and/or VI mutation.

21. A compound selected from the group consisting of:
N-(3-carbamoyl-5-(piperidin-1-ylsulfonyl)thiophen-2-yl)-5-methylthiophene-2-carboxamide,
N-(3-carbamoyl-5-(piperidin-1-ylsulfonyl)thiophen-2-yl)-4-fluorobenzo[b]thiophene-2-carboxamide,
N-(3-carbamoyl-5-(N-ethyl-N-methylsulfamoyl)thiophen-2-yl)-5-methylthiophene-2-carboxamide,
N-(3-carbamoyl-5-(N,N-diethylsulfamoyl)thiophen-2-yl)-5-methylthiophene-2-carboxamide,
N-(3-carbamoyl-5-(4-methylpiperazin-1-ylsulfonyl)thiophen-2-yl)-5-methylthiophene-2-carboxamide,
N-(5-(N-benzyl-N-methylsulfamoyl)-3-carbamoylthiophen-2-yl)-5-methylthiophene-2-carboxamide,
N-(3-carbamoyl-5-(N-methyl-N-phenylsulfamoyl)thiophen-2-yl)-5-methylthiophene-2-carboxamide,
N-(3-carbamoyl-5-(isoindolin-2-ylsulfonyl)thiophen-2-yl)-5-methylthiophene-2-carboxamide,
N-(3-carbamoyl-5-(piperidin-1-ylsulfonyl)thiophen-2-yl)-4,5,6,7-tetrahydrobenzo[b]thiophene-2-carboxamide,
N-(3-carbamoyl-5-(piperidin-1-ylsulfonyl)thiophen-2-yl)benzo[b]thiophene-2-carboxamide,
2-(3-cyanobenzamido)-5-(piperidin-1-ylsulfonyl)thiophene-3-carboxamide,
N-(3-carbamoyl-5-(piperidin-1-ylsulfonyl)thiophen-2-yl)benzo[d]thiazole-6-carboxamide,
2-(cyclopentanecarboxamido)-5-(piperidin-1-ylsulfonyl)thiophene-3-carboxamide,
2-(3-fluorobenzamido)-5-(piperidin-1-ylsulfonyl)thiophene-3-carboxamide,
N-(3-carbamoyl-5-(N,N-dimethylsulfamoyl)thiophen-2-yl)-5-methylthiophene-2-carboxamide,
N-(3-carbamoyl-5-(phenylsulfonyl)thiophen-2-yl)-5-methylthiophene-2-carboxamide,
2-(2-chlorobenzamido)-5-(piperidin-1-ylsulfonyl)thiophene-3-carboxamide,
2-(3-methoxybenzamido)-5-(piperidin-1-ylsulfonyl)thiophene-3-carboxamide,
2-(2-fluorobenzamido)-5-(piperidin-1-ylsulfonyl)thiophene-3-carboxamide,
2-(4-chlorobenzamido)-5-(piperidin-1-ylsulfonyl)thiophene-3-carboxamide,
2-(4-methoxybenzamido)-5-(piperidin-1-ylsulfonyl)thiophene-3-carboxamide,
2-(4-cyanobenzamido)-5-(piperidin-1-ylsulfonyl)thiophene-3-carboxamide,
5-tert-butyl-N-(3-carbamoyl-5-(piperidin-1-ylsulfonyl)thiophen-2-yl)thiophene-2-carboxamide,
2-(2-methoxybenzamido)-5-(piperidin-1-ylsulfonyl)thiophene-3-carboxamide,
2-(2-cyanobenzamido)-5-(piperidin-1-ylsulfonyl)thiophene-3-carboxamide,
2-(4-fluorobenzamido)-5-(piperidin-1-ylsulfonyl)thiophene-3-carboxamide,
2-(4-tert-butylbenzamido)-5-(piperidin-1-ylsulfonyl)thiophene-3-carboxamide,
2-butyramido-5-(piperidin-1-ylsulfonyl)thiophene-3-carboxamide,
5-(piperidin-1-ylsulfonyl)-2-pivalamidothiophene-3-carboxamide,
N-(3-carbamoyl-5-(piperidin-1-ylsulfonyl)thiophen-2-yl)-1-methyl-1H-pyrazole-3-carboxamide,
2-(1-methylcyclopropanecarboxamido)-5-(piperidin-1-ylsulfonyl)thiophene-3-carboxamide,
2-(2-(4-fluorophenyl)acetamido)-5-(piperidin-1-ylsulfonyl)thiophene-3-carboxamide,
N-(3-carbamoyl-5-(piperidin-1-ylsulfonyl)thiophen-2-yl)-5-methyl-1,3,4-oxadiazole-2-carboxamide,
N-(3-carbamoyl-5-(piperidin-1-ylsulfonyl)thiophen-2-yl)pyrazine-2-carboxamide,
N-(3-carbamoyl-5-(piperidin-1-ylsulfonyl)thiophen-2-yl)-1H-imidazole-4-carboxamide,
N-(3-carbamoyl-5-(piperidin-1-ylsulfonyl)thiophen-2-yl)-1H-pyrazole-3-carboxamide,
2-(4,4-difluorocyclohexanecarboxamido)-5-(piperidin-1-ylsulfonyl)thiophene-3-carboxamide,
5-(piperidin-1-ylsulfonyl)-2-(1-(trifluoromethyl)cyclopropanecarboxamido)thiophene-3carboxamide,
N-(3-carbamoyl-5-(piperidin-1-ylsulfonyl)thiophen-2-yl)-5-fluorothiophene-2-carboxamide,
2-(3-phenylpropanamido)-5-(piperidin-1-ylsulfonyl)thiophene-3-carboxamide,
N-(3-carbamoyl-5-(piperidin-1-ylsulfonyl)thiophen-2-yl)pyrazolo[1,5-a]pyrimidine-3-carboxamide,
2-(cyclopropanecarboxamido)-5-(piperidin-1-ylsulfonyl)thiophene-3-carboxamide,
1-tert-butyl-N-(3-carbamoyl-5-(piperidin-1-ylsulfonyl)thiophen-2-yl)-1H-pyrazole-4-carboxamide,
2-(3,3-difluorocyclobutanecarboxamido)-5-(piperidin-1-ylsulfonyl)thiophene-3-carboxamide,
2-(1-methylcyclopropanecarboxamido)-5-(morpholinosulfonyl)thiophene-3-carboxamide,
2-(2-fluorobenzamido)-5-(morpholinosulfonyl)thiophene-3-carboxamide,
5-(morpholinosulfonyl)-2-pivalamidothiophene-3-carboxamide,
2-(2-methoxybenzamido)-5-(morpholinosulfonyl)thiophene-3-carboxamide,
2-(4-tert-butylbenzamido)-5-(morpholinosulfonyl)thiophene-3-carboxamide,
N-(3-carbamoyl-5-(morpholinosulfonyl)thiophen-2-yl)benzo[b]thiophene-2-carboxamide,
5-tert-butyl-N-(3-carbamoyl-5-(morpholinosulfonyl)thiophen-2-yl)thiophene-2-carboxamide,
2-(2-cyclopropylbenzamido)-5-(piperidin-1-ylsulfonyl)thiophene-3-carboxamide,
2-(3-(1H-pyrazol-1-yl)benzamido)-5-(piperidin-1-ylsulfonyl)thiophene-3-carboxamide, 2-(3-(1H-pyrazol-3-yl)benzamido)-5-(piperidin-1-ylsulfonyl)thiophene-3-carboxamide,
N-(3-carbamoyl-5-(pyrrolidin-1-ylsulfonyl)thiophen-2-yl)benzo[b]thiophene-2-carboxamide,
N-(3-carbamoyl-5-(pyrrolidin-1-ylsulfonyl)thiophen-2-yl)-1H-pyrazole-3-carboxamide,
2-(1-phenylcyclopropanecarboxamido)-5-(piperidin-1-ylsulfonyl)thiophene-3-carboxamide,
2-(1-cyanocyclopropanecarboxamido)-5-(piperidin-1-ylsulfonyl)thiophene-3-carboxamide,
N-(3-carbamoyl-5-(piperidin-1-ylsulfonyl)thiophen-2-yl)thiazole-4-carboxamide,
N-(3-carbamoyl-5-(piperidin-1-ylsulfonyl)thiophen-2-yl)pyrazolo[1,5-a]pyridine-3-carboxamide,
2-(1-(4-chlorophenyl)cyclopropanecarboxamido)-5-(piperidin-1-ylsulfonyl)thiophene-3-carboxamide,
N-(3-carbamoyl-5-(piperidin-1-ylsulfonyl)thiophen-2-yl)thiazole-5-carboxamide,
N-(3-carbamoyl-5-(morpholinosulfonyl)thiophen-2-yl)-1H-pyrazole-3-carboxamide,
N-(3-carbamoyl-5-(piperidin-1-ylsulfonyl)thiophen-2-yl)-5-(pyridin-3-yl)thiophene-2-carboxamide,
2-(4-tert-butylb enzamido)-5-(4,4-difluoropiperidin-1-ylsulfonyl)thiophene-3-carboxamide,
5-(4,4-difluoropiperidin-1-ylsulfonyl)-2-(2-fluorobenzamido)thiophene-3-carboxamide,
5-(4,4-difluoropiperidin-1-ylsulfonyl)-2-pivalamidothiophene-3-carboxamide,
5-tert-butyl-N-(3-carbamoyl-5-(morpholinosulfonyl)thiophen-2-yl)-1H-pyrazole-3-carboxamide,
N-(3-carbamoyl-5-(morpholinosulfonyl)thiophen-2-yl)-5-ethyl-1H-pyrazole-3-carboxamide,
2-(2-methoxy-4-(phenylamino)benzamido)-5-(morpholinosulfonyl)thiophene-3-carboxamide,
5-(N-benzyl-N-methylsulfamoyl)-2-(1-(2,2-difluorobenzo[d][1,3]dioxo1-5-yl)cyclopropanecarboxamido)thiophene-3-carboxamide,
5-(N-benzyl-N-methylsulfamoyl)-2-(2-fluorobenzamido)thiophene-3-carboxamide,
N-(5-(N-benzyl-N-methylsulfamoyl)-3-carbamoylthiophen-2-yl)-1H-pyrazole-3-carboxamide,
5-(N,N-dimethylsulfamoyl)-2-(2-fluorobenzamido)thiophene-3-carboxamide,
N-(3-carbamoyl-5-(N,N-dimethylsulfamoyl)thiophen-2-yl)-1H-pyrazole-3-carboxamide,
N-(3-carbamoyl-5-(morpholinosulfonyl)thiophen-2-yl)thiazole-4-carboxamide,
N-(3-carbamoyl-5-(morpholinosulfonyl)thiophen-2-yl)-3-fluoropicolinamide,
5-(morpholinosulfonyl)-2-(2-(trifluoromethyl)benzamido)thiophene-3-carboxamide,
N-(3-carbamoyl-5-(morpholinosulfonyl)thiophen-2-yl)pyridazine-3-carboxamide,
N-(3-carbamoyl-5-(morpholinosulfonyl)thiophen-2-yl)pyridazine-4-carboxamide,
N-(3-carbamoyl-5-(morpholinosulfonyl)thiophen-2-yl)pyrimidine-2-carboxamide
N-(5-(benzylsulfonyl)-3-carbamoylthiophen-2-yl)-5-methylthiophene-2-carboxamide,
N-(3-carbamoyl-5-(phenylsulfonyl)thiophen-2-yl)-1H-pyrazole-3-carboxamide,
N-(3-carbamoyl-5-(tetrahydro-2H-pyran-4-ylsulfonyl)thiophen-2-yl)-5-methylthiophene-2-carboxamide,
2-(2-fluorobenzamido)-4-methyl-5-(morpholinosulfonyl)thiophene-3-carboxamide,
N-(3-carbamoyl-4-methyl-5-(phenylsulfonyl)thiophen-2-yl)-5-methylthiophene-2-carboxamide,
2-(2-fluorobenzamido)-4-methyl-5-(phenylsulfonyl)thiophene-3-carboxamide,
5-(N-benzyl-N-methylsulfamoyl)-2-pivalamidothiophene-3-carboxamide,
N-(3-carbamoyl-5-(pyridin-2-ylsulfonyl)thiophen-2-yl)-5-methylthiophene-2-carboxamide,
N-(3-carbamoyl-4-methyl-5-(morpholinosulfonyl)thiophen-2-yl)-1H-pyrazole-3-carboxamide,
N-(3-carbamoyl-5-(morpholinosulfonyl)thiophen-2-yl)picolinamide,
4-methyl-5-(morpholinosulfonyl)-2-pivalamidothiophene-3-carboxamide,
N-(3-carbamoyl-5-(morpholinosulfonyl)thiophen-2-yl)thiazole-2-carboxamide,
N-(3-carbamoyl-5-(morpholinosulfonyl)thiophen-2-yl)oxazole-4-carboxamide,
N-(3-carbamoyl-5-(phenylsulfonyl)thiophen-2-yl)-5-ethyl-1H-pyrazole-3-carboxamide
5-tert-butyl-N-(3-carbamoyl-5-(phenylsulfonyl)thiophen-2-yl)-1H-pyrazole-3-carboxamide,
N-(3-carbamoyl-5-(morpholinosulfonyl)thiophen-2-yl)-1H-pyrrole-2-carboxamide,
N-(3-carbamoyl-5-(morpholinosulfonyl)thiophen-2-yl)oxazole-2-carboxamide,
N-(3-carbamoyl-5-(morpholinosulfonyl)thiophen-2-yl)furan-2-carboxamide,
2-(2-fluorobenzamido)-5-(phenylsulfonyl)thiophene-3-carboxamide
N-(3-carbamoyl-4-methyl-5-(phenylsulfonyl)thiophen-2-yl)-1H-pyrazole-3-carboxamide,
N-(3-carbamoyl-5-(morpholinosulfonyl)thiophen-2-yl)-5-(trifluoromethyl)-1H-pyrazole-3-carboxamide,
N-(3-carbamoyl-4-methyl-5-(phenylsulfonyl)thiophen-2-yl)-5-ethyl-1H-pyrazole-3-carboxamide,
4-methyl-5-(phenylsulfonyl)-2-(2-(trifluoromethyl)benzamido)thiophene-3-carboxamide,
4-methyl-5-(morpholinosulfonyl)-2-(2-(trifluoromethyl)benzamido)thiophene-3-carboxamide,
2-(2-fluorobenzamido)-5-(N-(4-fluorobenzyl)-N-methylsulfamoyl)thiophene-3-carboxamide,
5-(N-tert-butyl-N-methylsulfamoyl)-2-(2-fluorobenzamido)thiophene-3-carboxamide,
5-(N-(2,2-difluoroethyl)-N-methylsulfamoyl)-2-(2-fluorobenzamido)thiophene-3-carboxamide,
N-(3-carbamoyl-5-(4-fluorophenylsulfonyl)thiophen-2-yl)-1H-pyrazole-3-carboxamide,
N-(3-carbamoyl-5-(4-fluorophenylsulfonyl)thiophen-2-yl)-5-ethyl-1H-pyrazole-3-carboxamide,
2-(2-fluorobenzamido)-5-(4-fluorophenylsulfonyl)thiophene-3-carboxamide,
5-(4-fluorophenylsulfonyl)-2-pivalamidothiophene-3-carboxamide,
N-(3-carbamoyl-5-(3-fluorophenylsulfonyl)thiophen-2-yl)-1H-pyrazole-3-carboxamide,
N-(3-carbamoyl-5-(3-fluorophenylsulfonyl)thiophen-2-yl)-5-ethyl-1H-pyrazole-3-carboxamide,
2-(2-fluorobenzamido)-5-(3-fluorophenylsulfonyl)thiophene-3-carboxamide,
N-(3-carbamoyl-5-(2-fluorophenylsulfonyl)thiophen-2-yl)-5-ethyl-1H-pyrazole-3-carboxamide,
2-(2-fluorobenzamido)-5-(2-fluorophenylsulfonyl)thiophene-3-carboxamide,
N-(3-carbamoyl-5-(3,4-difluorophenylsulfonyl)thiophen-2-yl)-1H-pyrazole-3-carboxamide,
N-(3-carbamoyl-5-(3,4-difluorophenylsulfonyl)thiophen-2-yl)-5-ethyl-1H-pyrazole-3-carboxamide, 5-(3,4-difluorophenylsulfonyl)-2-pivalamidothiophene-3-carboxamide,
5-(2-ethylphenylsulfonyl)-2-(2-fluorobenzamido)thiophene-3-carboxamide,
5-(3-fluorophenylsulfonyl)-2-pivalamidothiophene-3-carboxamide,
2-(2-fluorobenzamido)-5-(4-methoxypiperidin-1-ylsulfonyl)thiophene-3-carboxamide,
2-(2-fluorobenzamido)-5-(N-methyl-N-(4-methylbenzyl)sulfamoyl)thiophene-3-carboxamide,
5-(N-(cyanomethyl)-N-methylsulfamoyl)-2-(2-fluorobenzamido)thiophene-3-carboxamide,
5-(3,3-difluoroazetidin-1-ylsulfonyl)-2-(2-fluorobenzamido)thiophene-3-carboxamide,
2-(2-fluorobenzamido)-5-(methylsulfonyl)thiophene-3-carboxamide,
5-(ethylsulfonyl)-2-(2-fluorobenzamido)thiophene-3-carboxamide,
5-(cyclohexylsulfonyl)-2-(2-fluorobenzamido)thiophene-3-carboxamide,
2-(2-fluorobenzamido)-5-(4-methoxybenzylsulfonyl)thiophene-3-carboxamide,
2-(1-hydroxycyclopropanecarboxamido)-5-(morpholinosulfonyl)thiophene-3-carboxamide,
N-(3-carbamoyl-5-(morpholinosulfonyl)thiophen-2-yl)-2-methylthiazole-4-carboxamide,
2-(4-chloro-2-fluorobenzamido)-5-(morpholinosulfonyl)thiophene-3-carboxamide,
2-(3-cyclopropylbenzamido)-5-(morpholinosulfonyl)thiophene-3-carboxamide,
2-(2-methoxy-4-methylbenzamido)-5-(morpholinosulfonyl)thiophene-3-carboxamide,
2-(2-methylbenzamido)-5-(morpholinosulfonyl)thiophene-3-carboxamide,
2-(3-hydroxybenzamido)-5-(morpholinosulfonyl)thiophene-3-carboxamide,
2-(2,4-difluorobenzamido)-5-(morpholinosulfonyl)thiophene-3-carboxamide,
5-(4,4-difluoropiperidin-1-ylsulfonyl)-2-(1-hydroxycyclopropanecarboxamido)thiophene-3-carboxamide,
N-(3-carbamoyl-5-(4,4-difluoropiperidin-1-ylsulfonyl)thiophen-2-yl)-1H-pyrazole-3-carboxamide,
N-(3-carbamoyl-5-(4,4-difluoropiperidin-1-ylsulfonyl)thiophen-2-yl)-5-ethyl-1H-pyrazole-3-carboxamide,
5-tert-butyl-N-(3-carbamoyl-5-(4,4-difluoropiperidin-1-ylsulfonyl)thiophen-2-yl)-1H-pyrazole-3-carboxamide,
2-(2-Hydroxy-benzoylamino)-5-(morpholine-4-sulfonyl)-thiophene-3-carboxylic acid amide,
5-(((1S,4S)-2-oxa-5-azabicyclo[2.2.1]heptan-5-ylsulfonyl)-2-(2-fluorobenzamido)thiophene-3-carboxamide,
N-(3-carbamoyl-5-(N-(4-fluorobenzyl)-N-methylsulfamoyl)thiophen-2-yl)-1H-pyrazole-3-carboxamide,
N-(5-(1,4-oxazepan-4-ylsulfonyl)-3-carbamoylthiophen-2-yl)-1H-pyrazole-3-carboxamide,
2-(2-fluorobenzamido)-5-(N-(4-methoxybenzyl)-N-methylsulfamoyl)thiophene-3-carboxamide,
tert-butyl 2-(4-carbamoyl-5-(2-fluorobenzamido)thiophen-2-ylsulfonyl)-2,8-diazaspiro[4.5]decane-8-carboxylate,
2-(2-fluorobenzamido)-5-(4-(2-hydroxypropan-2-yl)piperidin-1-ylsulfonyl)thiophene-3-carboxamide,
5-(3,4-dihydroisoquinolin-2(1H)-ylsulfonyl)-2-(2-fluorobenzamido)thiophene-3-carboxamide,
2-(2-fluorobenzamido)-5-(isoindolin-2-ylsulfonyl)thiophene-3-carboxamide,
5-(N-cyclopropyl-N-methylsulfamoyl)-2-(2-fluorobenzamido)thiophene-3-carboxamide,
2-(2-fluorobenzamido)-5-(N-isopropyl-N-methylsulfamoyl)thiophene-3-carboxamide,
5-(N,N-diisopropylsulfamoyl)-2-(2-fluorobenzamido)thiophene-3-carboxamide,
2-(2-fluorobenzamido)-5-(N-methyl-N-(1-methylpiperidin-4-yl)sulfamoyl)thiophene-3-carboxamide,
5-(N-cyclopropyl-N-(3-fluorobenzyl)sulfamoyl)-2-(2-fluorobenzamido)thiophene-3-carboxamide,
2-(2-fluorobenzamido)-5-(N-(2-methoxyethyl)-N-(2,2,2-trifluoroethyl)sulfamoyl)thiophene-3-carboxamide,
2-(2-fluorobenzamido)-5-(4-(trifluoromethyl)-5,6-dihydropyridin-1(2H)-ylsulfonyl)thiophene-3-carboxamide,
2-(2-fluorobenzamido)-5-(4-phenylpiperidin-1-ylsulfonyl)thiophene-3-carboxamide,
N-(3-carbamoyl-5-(N-(3-fluoro-4-methoxybenzyl)-N-methylsulfamoyl)thiophen-2-yl)-1H-pyrazole-3-carboxamide,
2-(2-fluorobenzamido)-5-(N-methyl-N-(tetrahydro-2H-pyran-4-yl)sulfamoyl)thiophene-3-carboxamide,
5-(4-cyanopiperidin-1-ylsulfonyl)-2-(2-fluorobenzamido)thiophene-3-carboxamide,
2-(2-fluorobenzamido)-5-(isopropylsulfonyl)thiophene-3-carboxamide,
5-(tert-butylsulfonyl)-2-(2-fluorobenzamido)thiophene-3-carboxamide,
2-(2-fluorobenzamido)-5-(tetrahydro-2H-pyran-4-ylsulfonyl)thiophene-3-carboxamide,
N-(3-carbamoyl-5-(morpholinosulfonyl)thiophen-2-yl)-5-methyl-1H-pyrazole-3-carboxamide,
3-tert-butyl-N-(3-carbamoyl-5-(morpholinosulfonyl)thiophen-2-yl)-1-methyl-1H-pyrazole-5-carboxamide,
2-(4-fluoro-2-methoxybenzamido)-5-(morpholinosulfonyl)thiophene-3-carboxamide,
2-(4-fluoro-2-methylbenzamido)-5-(morpholinosulfonyl)thiophene-3-carboxamide,
N-(3-carbamoyl-5-(N-methyl-N-(4-methylbenzyl)sulfamoyl)thiophen-2-yl)-1H-pyrazole-3-carboxamide,
N-(3-carbamoyl-5-(N-(4-methoxybenzyl)-N-methylsulfamoyl)thiophen-2-yl)-1H-pyrazole-3-carboxamide,
N-(3-carbamoyl-5-(N-(2,4-difluorobenzyl)-N-methylsulfamoyl)thiophen-2-yl)-1H-pyrazole-3-carboxamide,
N-(3-carbamoyl-5-(N-(4-fluorophenyl)-N-methylsulfamoyl)thiophen-2-yl)-1H-pyrazole-3-carboxamide,
5-(4-(dimethylamino)piperidin-1-ylsulfonyl)-2-(2-fluorobenzamido)thiophene-3-carboxamide,
N-(3-carbamoyl-5-(N-methyl-N-(4-(trifluoromethyl)benzyl)sulfamoyl)thiophen-2-yl)-1H-pyrazole-3-carboxamide,
5-(3-cyanoazetidin-1-ylsulfonyl)-2-(2-fluorobenzamido)thiophene-3-carboxamide,
5-(3-fluoroazetidin-1-ylsulfonyl)-2-(2-fluorobenzamido)thiophene-3-carboxamide,
2-(2-fluorobenzamido)-5-(pyridin-2-ylsulfonyl)thiophene-3-carboxamide,
2-(2-fluorobenzamido)-5-(2-isopropylphenylsulfonyl)thiophene-3-carboxamide,
2-(2-fluorobenzamido)-5-(o-tolylsulfonyl)thiophene-3-carboxamide,
2-(2-fluorobenzamido)-5-(2-methoxyphenylsulfonyl)thiophene-3-carboxamide,
5-(2,5-dimethoxyphenylsulfonyl)-2-(2-fluorobenzamido)thiophene-3-carboxamide,
5-(3,3-dimethylazetidin-1-ylsulfonyl)-2-(2-fluorobenzamido)thiophene-3-carboxamide, 2-(2-fluorobenzamido)-5-(N-methyl-N-neopentylsulfamoyl)thiophene-3-carboxamide,
2-(2-fluorobenzamido)-5-(N-methyl-N-(3,3,3-trifluoropropyl)sulfamoyl)thiophene-3-carboxamide,
2-(2-fluorobenzamido)-5-(N-(3-methoxypropyl)-N-methylsulfamoyl)thiophene-3-carboxamide,
5-(3-(dimethylamino)azetidin-1-ylsulfonyl)-2-(2-fluorobenzamido)thiophene-3-carboxamide,
5-(2-oxa-6-azaspiro[3.3]heptan-6-ylsulfonyl)-2-(2-fluorobenzamido)thiophene-3-carboxamide,
N-(3-carbamoyl-5-(4,4-difluoropiperidin-1-ylsulfonyl)thiophen-2-yl)-5-(trifluoromethyl)-1H-pyrazole-3-carboxamide,
5-(4,4-difluoropiperidin-1-ylsulfonyl)-2-(2-hydroxybenzamido)thiophene-3-carboxamide,
N-(3-carbamoyl-5-(N-cyclopropyl-N-(4-fluorobenzyl)sulfamoyl)thiophen-2-yl)-1H-pyrazole-3-carboxamide,
N-(3-carbamoyl-5-(N-methyl-N-neopentylsulfamoyl)thiophen-2-yl)-1H-pyrazole-3-carboxamide,
N-(3-carbamoyl-5-(N-(cyclopropylmethyl)-N-methylsulfamoyl)thiophen-2-yl)-1H-pyrazole-3-carboxamide,
N-(3-carbamoyl-5-(N-methyl-N-(3,3,3-trifluoropropyl)sulfamoyl)thiophen-2-yl)-1H-pyrazole-3-carboxamide,
N-(3-carbamoyl-5-(N-methyl-N-(2,2,2-trifluoro-1-phenylethyl)sulfamoyl)thiophen-2-yl)-1H-pyrazole-3-carboxamide,
5-(4-fluoro-2-(hydroxymethyl)phenylsulfonyl)-2-(2-fluorobenzamido)thiophene-3-carboxamide,
2-(2-hydroxybenzamido)-5-(isopropylsulfonyl)thiophene-3-carboxamide,
2-(4-fluoro-2-hydroxybenzamido)-5-(morpholinosulfonyl)thiophene-3-carboxamide,
2-(1-hydroxycyclobutanecarboxamido)-5-(morpholinosulfonyl)thiophene-3-carboxamide,
N-(3-carbamoyl-5-(morpholinosulfonyl)thiophen-2-yl)-4-hydroxytetrahydro-2H-pyran-4-carboxamide,
2-(2-hydroxy-3,5-diisopropylbenzamido)-5-(morpholinosulfonyl)thiophene-3-carboxamide,
N-(3-carbamoyl-5-(4,4-difluoropiperidin-1-ylsulfonyl)thiophen-2-yl)-4-hydroxytetrahydro-2H-pyran-4-carboxamide,
2-(2-hydroxy-2-methylpropanamido)-5-(morpholinosulfonyl)thiophene-3-carboxamide,
N-(3-carbamoyl-5-(N-(3-methoxypropyl)-N-methylsulfamoyl)thiophen-2-yl)-1H-pyrazole-3-carboxamide,
N-(3-carbamoyl-5-(3-fluoroazetidin-1-ylsulfonyl)thiophen-2-yl)-1H-pyrazole-3-carboxamide,
N-(3-carbamoyl-5-(3,3-dimethylazetidin-1-ylsulfonyl)thiophen-2-yl)-1H-pyrazole-3-carboxamide,
N-(3-carbamoyl-5-(N-methyl-N-(pyridin-4-ylmethyl)sulfamoyl)thiophen-2-yl)-1H-pyrazole-3-carboxamide,
N-(5-(azetidin-1-ylsulfonyl)-3-carbamoylthiophen-2-yl)-1H-pyrazole-3-carboxamide,
N-(3-carbamoyl-5-(N-cyclopropyl-N-methylsulfamoyl)thiophen-2-yl)-1H-pyrazole-3-carboxamide,
N-(3-carbamoyl-5-(N-isopropyl-N-methylsulfamoyl)thiophen-2-yl)-1H-pyrazole-3-carboxamide,
2-(2-hydroxybenzamido)-5-(methylsulfonyl)thiophene-3-carboxamide,
2-(2,4-difluoro-6-hydroxybenzamido)-5-(morpholinosulfonyl)thiophene-3-carboxamide,
5-(4,4-difluoropiperidin-1-ylsulfonyl)-2-(1-hydroxycyclobutanecarboxamido)thiophene-3-carboxamide,
2-(2,4-difluoro-6-hydroxybenzamido)-5-(4,4-difluoropiperidin-1-ylsulfonyl)thiophene-3-carboxamide,
5-(4,4-difluoropiperidin-1-ylsulfonyl)-2-(2-hydroxy-3,5-diisopropylbenzamido)thiophene-3-carboxamide,
2-(2-hydroxy-3-methylbenzamido)-5-(morpholinosulfonyl)thiophene-3-carboxamide,
5-(4,4-difluoropiperidin-1-ylsulfonyl)-2-(3-hydroxy-2,2-dimethylpropanamido)thiophene-3-carboxamide,
5-(N-(cyclopropylmethyl)-N-methylsulfamoyl)-2-(2-fluorobenzamido)thiophene-3-carboxamide,
2-(2-hydroxy-2-methylpropanamido)-5-(methylsulfonyl)thiophene-3-carboxamide,
2-(2-hydroxy-2-methylpropanamido)-5-(isopropylsulfonyl)thiophene-3-carboxamide,
5-(4-fluorophenylsulfonyl)-2-(2-hydroxy-2-methylpropanamido)thiophene-3-carboxamide,
5-(4-fluoro-2-methylphenylsulfonyl)-2-(1-hydroxycyclopropanecarboxamido)thiophene-3-carboxamide
5-(4-fluorophenylsulfonyl)-2-(2-hydroxybenzamido)thiophene-3-carboxamide,
5-(4-fluorophenylsulfonyl)-2-(1-hydroxycyclopropanecarboxamido)thiophene-3-carboxamide,
5-(4-chlorophenylsulfonyl)-2-(1-hydroxycyclopropanecarboxamido)thiophene-3-carboxamide,
5-(4-fluorophenylsulfonyl)-2-(1-hydroxycyclobutanecarboxamido)thiophene-3-carboxamide,
5-(3-fluorophenylsulfonyl)-2-(1-hydroxycyclopropanecarboxamido)thiophene-3-carboxamide,
2-(1-hydroxycyclopropanecarboxamido)-5-(2-isopropylphenylsulfonyl)thiophene-3-carboxamide
5-(4-fluorophenylsulfonyl)-2-(3-methoxypropanamido)thiophene-3-carboxamide,
N-(3-carbamoyl-5-(4-fluorophenylsulfonyl)thiophen-2-yl)-2-fluoronicotinamide,
5-(N-(4-fluorobenzyl)-N-methylsulfamoyl)-2-(1-hydroxycyclopropanecarboxamido)thiophene-3-carboxamide,
5-(N-cyclopropyl-N-methylsulfamoyl)-2-(1-hydroxycyclopropanecarboxamido)thiophene-3-carboxamide,
5-(N,N-diisopropylsulfamoyl)-2-(1-hydroxycyclopropanecarboxamido)thiophene-3-carboxamide,
5-(3,5-dimethylmorpholinosulfonyl)-2-(1-hydroxycyclopropanecarboxamido)thiophene-3-carboxamide,
2-(1-hydroxycyclopropanecarboxamido)-5-(N-(4-methoxybenzyl)-N-methylsulfamoyl)thiophene-3-carboxamide,
5-(N-(4-fluorophenyl)-N-methylsulfamoyl)-2-(1-hydroxycyclopropanecarboxamido)thiophene-3-carboxamide,
5-(N-(4-fluorophenyl)-N-isopropyl sulfamoyl)-2-(1-hydroxycyclopropanecarboxamido)thiophene-3-carboxamide,
5-(2,6-dimethylmorpholinosulfonyl)-2-(1-hydroxycyclopropanecarboxamido)thiophene-3-carboxamide,
2-(1-hydroxycyclopropanecarboxamido)-5-(4-methoxypiperidin-1-ylsulfonyl)thiophene-3-carboxamide,
2-(1-hydroxycyclopropanecarboxamido)-5-(2-methylmorpholinosulfonyl)thiophene-3-carboxamide,
5-(3,3-dimethylmorpholinosulfonyl)-2-(1-hydroxycyclopropanecarboxamido)thiophene-3-carboxamide,
5-(2H-benzo[b][1,4]oxazin-4(3H)-ylsulfonyl)-2-(1-hydroxycyclopropanecarboxamido)thiophene-3-carboxamide,
2-(1-hydroxycyclopropanecarboxamido)-5-(3-methoxyazetidin-1-ylsulfonyl)thiophene-3-carboxamide,
5-(N-cyclopropyl-N-(2-methoxyethyl)sulfamoyl)-2-(1-hydroxycyclopropanecarboxamido)thiophene-3-carboxamide,
2-(1-hydroxycyclopropanecarboxamido)-5-(4-methoxyphenylsulfonyl)thiophene-3-carboxamide, 5-(2,5-dimethoxyphenylsulfonyl)-2-(1-hydroxycyclopropanecarboxamido)thiophene-3-carboxamide,
5-(2,6-dichlorophenylsulfonyl)-2-(1-hydroxycyclopropanecarboxamido)thiophene-3-carboxamide,
5-(4-fluorophenylsulfonyl)-2-(2-hydroxypropanamido)thiophene-3-carboxamide,
N-(3-carbamoyl-5-(4-fluorophenylsulfonyl)thiophen-2-yl)pyridazine-3-carboxamide,
N-(3-carbamoyl-5-(4-fluorophenylsulfonyl)thiophen-2-yl)pyridazine-4-carboxamide,
5-(2,6-dimethylphenylsulfonyl)-2-(1-hydroxycyclopropanecarboxamido)thiophene-3-carboxamide,
5-(4-fluorophenylsulfonyl)-2-(3,3,3-trifluoro-2-hydroxypropanamido)thiophene-3-carboxamide,
5-(4-fluorophenylsulfonyl)-2-(3-hydroxy-2,2-dimethylpropanamido)thiophene-3-carboxamide
5-(4-fluorophenylsulfonyl)-2-(1-(hydroxymethyl)cyclopropanecarboxamido)thiophene-3-carboxamide,
N-(3-carbamoyl-5-(4-fluorophenylsulfonyl)thiophen-2-yl)-4-hydroxytetrahydro-2H-pyran-4-carboxamide,
5-(2-chloro-4-fluorophenylsulfonyl)-2-(1-hydroxycyclopropanecarboxamido)thiophene-3-carboxamide,
5-(2,4-difluorophenylsulfonyl)-2-(1-hydroxycyclopropanecarboxamido)thiophene-3-carboxamide,
2-(1-hydroxycyclopropanecarboxamido)-5-(2-(trifluoromethyl)phenylsulfonyl)thiophene-3-carboxamide,
5-(2,6-dimethylmorpholinosulfonyl)-2-(2-(trifluoromethyl)benzamido)thiophene-3-carboxamide,
5-(3,5-dimethylmorpholinosulfonyl)-2-(2-(trifluoromethyl)benzamido)thiophene-3-carboxamide,
5-(3,3-dimethylmorpholinosulfonyl)-2-(2-(trifluoromethyl)benzamido)thiophene-3-carboxamide,
5-(N-cyclopropyl-N-(2-methoxyethyl)sulfamoyl)-2-(2-(trifluoromethyl)benzamido)thiophene-3-carboxamide,
5-(N-cyclopropyl-N-methylsulfamoyl)-2-(2-(trifluoromethyl)benzamido)thiophene-3-carboxamide,
2-(2-(trifluoromethyl)benzamido)-5-(2,5,5-trimethylmorpholinosulfonyl)thiophene-3-carboxamide,
5-(2-bromo-4-fluorophenylsulfonyl)-2-(1-hydroxycyclopropanecarboxamido)thiophene-3-carboxamide,
2-(2-hydroxy-2-methylpropanamido)-5-(3-isopropoxyphenylsulfonyl)thiophene-3-carboxamide,
N-(3-carbamoyl-5-(4-fluorophenylsulfonyl)thiophen-2-yl)-5-fluoropicolinamide,
5-(4-fluorophenylsulfonyl)-2-(pyridin-2-ylamino)thiophene-3-carboxamide,
5-(4-fluorophenylsulfonyl)-2-(2-methoxy-2-methylpropanamido)thiophene-3-carboxamide,
2-(2-hydroxy-2-methylpropanamido)-5-(3-(trifluoromethoxy)phenylsulfonyl)thiophene-3-carboxamide,
2-(2-hydroxy-2-methylpropanamido)-5-(4-(trifluoromethoxy)phenylsulfonyl)thiophene-3-carboxamide,
2-(2-hydroxy-2-methylpropanamido)-5-(2-(trifluoromethoxy)phenylsulfonyl)thiophene-3-carboxamide,
5-(4-fluorophenylsulfonyl)-2-(2-hydroxycyclopentanecarboxamido)thiophene-3-carboxamide,
5-(4-fluorophenylsulfonyl)-2-(3-hydroxy-2-methylpropanamido)thiophene-3-carboxamide,
5-(4-fluorophenylsulfonyl)-2-(3-methylbut-2-enamido)thiophene-3-carboxamide,
5-(4-fluorophenylsulfonyl)-2-(3,3,3-trifluoro-2-hydroxy-2-(trifluoromethyl)propanamido)thiophene-3-carboxamide,
5-(4-fluorophenylsulfonyl)-2-(2-(2-methoxyethoxy)propanamido)thiophene-3-carboxamide,
N-(3-carbamoyl-5-(4-fluorophenylsulfonyl)thiophen-2-yl)-1,4-dioxane-2-carboxamide,
2-(2-hydroxy-2-methylpropanamido)-5-(3-methylpyridin-2-ylsulfonyl)thiophene-3-carboxamide,
2-(2-hydroxy-2-methylpropanamido)-5-(4-isopropoxyphenylsulfonyl)thiophene-3-carboxamide,
5-(4-fluorophenylsulfonyl)-2-(2-hydroxycyclohexanecarboxamido)thiophene-3-carboxamide,
5-(4-fluoro-2-isopropoxyphenylsulfonyl)-2-(2-hydroxy-2-methylpropanamido)thiophene-3-carboxamide,
5-(4-fluoro-2-(2-methoxyethoxy)phenylsulfonyl)-2-(2-hydroxy-2-methylpropanamido)thiophene-3-carboxamide,
5-(2-(difluoromethoxy)-4-fluorophenylsulfonyl)-2-(2-hydroxy-2-methylpropanamido)thiophene-3-carboxamide,
5-(2-(difluoromethoxy)-4-methoxyphenylsulfonyl)-2-(2-hydroxy-2-methylpropanamido)thiophene-3-carboxamide,
2-(2-hydroxy-2-methylpropanamido)-5-(1-methyl-1H-imidazol-2-ylsulfonyl)thiophene-3-carboxamide,
5-(2-chloro-4-fluorophenylsulfonyl)-2-(2-hydroxy-2-methylpropanamido)thiophene-3-carboxamide,
N-(5-(4-bromophenylsulfonyl)-3-carbamoylthiophen-2-yl)-1H-pyrazole-3-carboxamide,
2-(2,3-dihydroxypropanamido)-5-(4-fluorophenylsulfonyl)thiophene-3-carboxamide,
2-(2-hydroxy-2-methylpropanamido)-5-(2-(trifluoromethyl)phenylsulfonyl)thiophene-3-carboxamide,
5-(2-chlorophenylsulfonyl)-2-(2-hydroxy-2-methylpropanamido)thiophene-3-carboxamide,
(S)-5-(4-fluorophenylsulfonyl)-2-(2-hydroxypropanamido)thiophene-3-carboxamide,
5-(3-(dimethylamino)phenylsulfonyl)-2-(2-hydroxy-2-methylpropanamido)thiophene-3-carboxamide,
2-(2-hydroxy-2-methylpropanamido)-5-(2-isopropylphenylsulfonyl)thiophene-3-carboxamide,
1-(3-carbamoyl-5-(2-isopropylphenylsulfonyl)thiophen-2-ylamino)-2-methyl-1-oxopropan-2-yl acetate,
5-(5-fluoro-2-methoxyphenylsulfonyl)-2-(2-hydroxy-2-methylpropanamido)thiophene-3-carboxamide,
5-(5-fluoro-2-hydroxyphenylsulfonyl)-2-(2-hydroxy-2-methylpropanamido)thiophene-3-carboxamide,
2-(2-Hydroxy-2-methyl-propionylamino)-5-(6-methyl-pyridine-3-sulfonyl)-thiophene-3-carboxylic acid amide
5-(2,6-Dichloro-benzenesulfonyl)-2-(2-hydroxy-2-methyl-propionylamino)-thiophene-3-carboxylic acid amide,
2-(2-Hydroxy-2-methyl-propionylamino)-5-(2-methyl-pyridine-4-sulfonyl)-thiophene-3-carboxylic acid amide,
5-(4-fluoro-2-(methoxymethyl)phenylsulfonyl)-2-(2-hydroxy-2-methylpropanamido)thiophene-3-carboxamide,
2-(2-hydroxy-2-methylpropanamido)-5-(2-methoxyphenylsulfonyl)thiophene-3-carboxamide,
2-(2-hydroxy-2-methylpropanamido)-5-(2-(2,2,2-trifluoroethyl)phenylsulfonyl)thiophene-3-carboxamide,
5-(5-chloro-2-fluorophenylsulfonyl)-2-(2-hydroxy-2-methylpropanamido)thiophene-3-carboxamide,
5-(N-(4-fluorophenyl)-N-methylsulfamoyl)-2-(2-hydroxy-2-methylpropanamido)thiophene-3-carboxamide,
5-(N-(4-fluorobenzyl)-N-methylsulfamoyl)-2-(2-hydroxy-2-methylpropanamido)thiophene-3-carboxamide, 5-(N-cyclopropyl-N-(2-methoxyethyl)sulfamoyl)-2-(2-hydroxy-2-methylpropanamido)thiophene-3-carboxamide,
5-(2H-benzo[b][1,4]oxazin-4(3H)-ylsulfonyl)-2-(2-hydroxy-2-methylpropanamido)thiophene-3-carboxamide
5-(4,4-difluoropiperidin-1-ylsulfonyl)-2-(2-hydroxy-2-methylpropanamido)thiophene-3-carboxamide,
5-(3,3-Dimethyl-azetidine-1-sulfonyl)-2-(2-hydroxy-2-methyl-propionylamino)-thiophene-3-carboxylic acid amide,
5-(2,2-difluorobenzo[d][1,3]dioxol-5-ylsulfonyl)-2-(2-hydroxy-2-methylpropanamido)thiophene-3-carboxamide,
2-(2-hydroxypropanamido)-5-(2-(trifluoromethoxy)phenylsulfonyl)thiophene-3-carboxamide,
5-(2-Ethyl-benzenesulfonyl)-2-(2-hydroxy-propionylamino)-thiophene-3-carboxylic acid amide,
5-(2,6-Difluoro-benzenesulfonyl)-2-(2-hydroxy-propionylamino)-thiophene-3-carboxylic acid amide,
5-(2,6-Dichloro-benzenesulfonyl)-2-((S)-2-hydroxy-propionylamino)-thiophene-3-carboxylic acid amide,
5-(2-Fluoro-4-isopropoxy-benzenesulfonyl)-2-(2-hydroxy-2-methyl-propionylamino)-thiophene-3-carboxylic acid amide,
2-(2-Hydroxy-2-methyl-propionylamino)-5-(toluene-4-sulfonyl)-thiophene-3-carboxylic acid amide,
5-(3-Chloro-pyridine-2-sulfonyl)-2-(2-hydroxy-2-methyl-propionylamino)-thiophene-3-carboxylic acid amide,
2-(2-Hydroxy-propionylamino)-5-(4-trifluoromethoxy-benzenesulfonyl)-thiophene-3-carboxylic acid amide,
2-(2-Hydroxy-acetylamino)-5-(2-trifluoromethoxy-benzenesulfonyl)-thiophene-3-carboxylic acid amide,
2-[(1-Hydroxymethyl-cyclopropanecarbonyl)-amino]-5-(2-trifluoromethoxy-benzenesulfonyl)-thiophene-3-carboxylic acid amide,
5-(2-Chloro-benzenesulfonyl)-2-(2-hydroxy-propionylamino)-thiophene-3-carboxylic acid amide,
5-(2-Chloro-4-isopropoxy-benzenesulfonyl)-2-(2-hydroxy-2-methyl-propionylamino)-thiophene-3-carboxylic acid amide,
5-(2-Bromo-5-fluoro-benzenesulfonyl)-2-(2-hydroxy-2-methyl-propionylamino)-thiophene-3-carboxylic acid amide,
2-(2-Hydroxy-2-methyl-propionylamino)-5-(4-isopropoxy-2-trifluoromethyl-benzenesulfonyl)-thiophene-3-carboxylic acid amide,
5-[4-fluoro-2-(trifluoromethyl)phenyl]sulfonyl-2-(2-hydroxypropanoylamino)thiophene-3-carboxamide,
2-(2-hydroxypropanoylamino)-5-[(2-methyl-3-pyridyl)sulfonyl]thiophene-3-carboxamide,
5-(4-fluorophenyl)sulfonyl-2-[[(2R)-2-hydroxypropanoyl]amino]thiophene-3-carboxamide,
5-[2-chloro-4-(trifluoromethoxy)phenyl]sulfonyl-2-(2-hydroxypropanoylamino)thiophene-3-carboxamide,
5-(2-chloro-4-fluoro-phenyl)sulfonyl-2-(2-hydroxypropanoylamino)thiophene-3-carboxamide,
5-[(2,2-difluoro-1,3-benzodioxol-4-yl)sulfonyl]-2-[(2-hydroxy-2-methyl-propanoyl)amino]thiophene-3-carboxamide,
2-[[(2S)-2-hydroxypropanoyl]amino]-5-[4-(trifluoromethoxy)phenyl]sulfonyl-thiophene-3-carboxamide,
2-[[(2R)-2-hydroxypropanoyl]amino]-5-[4-(trifluoromethoxy)phenyl]sulfonyl-thiophene-3-carboxamide,
5-(2-chloro-5-fluoro-phenyl)sulfonyl-2-(2-hydroxypropanoylamino)thiophene-3-carboxamide,
5-[5-fluoro-2-(2,2,2-trifluoroethyl)phenyl]sulfonyl-2-(2-hydroxypropanoylamino)thiophene-3-carboxamide,
5-[5-fluoro-2-(trifluoromethyl)phenyl]sulfonyl-2-(2-hydroxypropanoylamino)thiophene-3-carboxamide,
5-(2-Chloro-4,5-difluoro-benzenesulfonyl)-2-(2-hydroxy-2-methyl-propionylamino)-thiophene-3-carboxylic acid amide,
5-(2-chloro-5-fluoro-phenyl)sulfonyl-2-[(2-hydroxy-2-methyl-propanoyl)amino]thiophene-3-carboxamide,
5-[5-fluoro-2-(2,2,2-trifluoroethyl)phenyl]sulfonyl-2-[(2-hydroxy-2-methyl-propanoyl)amino]thiophene-3-carboxamide,
5-(2-Chloro-5-fluoro-benzenesulfonyl)-2-(2-hydroxy-acetylamino)-thiophene-3-carboxylic acid amide,
5-[5-Fluoro-2-(2,2,2-trifluoro-ethyl)-benzenesulfonyl]-2-(2-hydroxy-acetylamino)-thiophene-3-carboxylic acid amide,
5-(4-fluorophenyl)sulfonyl-2-[(2-hydroxy-3-methyl-butanoyl)amino]thiophene-3-carboxamide,
5-(4-fluorophenyl)sulfonyl-2-[(2-hydroxy-3,3-dimethyl-butanoyl)amino]thiophene-3-carboxamide,
5-(4-fluorophenyl)sulfonyl-2-[(2-hydroxy-4-methyl-pentanoyl)amino]thiophene-3-carboxamide,
2-[(2-hydroxy-2-methyl-propanoyl)amino]-5-[4-(trifluoromethoxy)phenyl]sulfonyl-thiophene-3-carboxamide,
2-[(2-hydroxy-3-methyl-butanoyl)amino]-5-[4-(trifluoromethoxy)phenyl]sulfonyl-thiophene-3-carboxamide,
2-[(2-hydroxy-4-methyl-pentanoyl)amino]-5-[4-(trifluoromethoxy)phenyl]sulfonyl-thiophene-3-carboxamide,
5-(4-chlorophenyl)sulfonyl-2-[[(2S)-2-hydroxypropanoyl]amino]thiophene-3-carboxamide,
5-[4-fluoro-2-(trifluoromethyl)phenyl]sulfonyl-2-[[(2S)-2-hydroxypropanoyl]amino]thiophene-3-carboxamide,
2-[(2-hydroxy-3,3-dimethyl-butanoyl)amino]-5-[4-(trifluoromethoxy)phenyl]sulfonyl-thiophene-3-carboxamide,
2-[(3-hydroxy-2-methyl-propanoyl)amino]-5-[4-(trifluoromethoxy)phenyl]sulfonyl-thiophene-3-carboxamide,
5-[5-fluoro-2-(trifluoromethoxy)phenyl]sulfonyl-2-[(3-hydroxy-2-methyl-propanoyl)amino]thiophene-3-carboxamide,
5-(4-fluorophenyl)sulfonyl-2-[[(2S)-2-hydroxy-3-methyl-butanoyl]amino]thiophene-3-carboxamide,
5-(2-chloro-4-fluoro-phenyl)sulfonyl-2-[[(2S)-2-hydroxypropanoyl]amino]thiophene-3-carboxamide,
5-(2,6-dichloro-4-fluoro-phenyl)sulfonyl-2-[[(2S)-2-hydroxypropanoyl]amino]thiophene-3-carboxamide,
5-(2,6-dichloro-4-fluoro-phenyl)sulfonyl-2-[[(2S)-2-hydroxypropanoyl]amino]thiophene-3-carboxamide,
5-[4-fluoro-2-(trifluoromethyl)phenyl]sulfonyl-2-[[(2S)-2-hydroxy-3-methyl-butanoyl]amino]thiophene-3-carboxamide,
2[[1-(hydroxymethyl)cyclopropanecarbonyl]amino]-5-[4-(trifluoromethoxy)phenyl]sulfonyl-thiophene-3-carboxamide,
5-(4-chlorophenyl)sulfonyl-2-[(2-hydroxy-2-methyl-propanoyl)amino]thiophene-3-carboxamide,
5-[4-fluoro-2-(trifluoromethyl)phenyl]sulfonyl-2-[(3-hydroxy-2-methyl-propanoyl)amino]thiophene-3-carboxamide,
5-(2-chloro-4-fluoro-phenyl)sulfonyl-2-[(3-hydroxy-2-methyl-propanoyl)amino]thiophene-3-carboxamide,
5-(2-chloro-4-fluoro-phenyl)sulfonyl-2-[[(2S)-2-hydroxy-3-methyl-butanoyl]amino]thiophene-3-carboxamide,
5-(4-chlorophenyl)sulfonyl-2-[(3-hydroxy-2-methyl-propanoyl)amino]thiophene-3-carboxamide, 2-[(2-hydroxy-2-methyl-propanoyl)amino]-5-[[5-(trifluoromethyl)-2-pyridyl]sulfonyl]thiophene-3-carboxamide,
2[[1-(hydroxymethyl)cyclobutanecarbonyl]amino]-5-[4-(trifluoromethoxy)phenyl]sulfonyl-thiophene-3-carboxamide,
2-[[(2S)-2-hydroxy-3,3-dimethyl-butanoyl]amino]-5-[4-(trifluoromethyl)phenyl]sulfonyl-thiophene-3-carboxamide,
2-[[(2S)-2-hydroxy-3-methyl-butanoyl]amino]-5-[4-(trifluoromethyl)phenyl]sulfonyl-thiophene-3-carboxamide,
5-(4-chlorophenyl)sulfonyl-2-[[(2S)-2-hydroxy-3-methyl-butanoyl]amino]thiophene-3-carboxamide,
5-[2-fluoro-4-(trifluoromethyl)phenyl]sulfonyl-2-(2-hydroxypropanoylamino)thiophene-3-carboxamide,
2-[(3-hydroxy-2-methyl-propanoyl)amino]-5-[4-(trifluoromethyl)phenyl]sulfonyl-thiophene-3-carboxamide,
2-[(3-hydroxy-2-methyl-propanoyl)amino]-5-[5-methoxy-2-(trifluoromethoxy)phenyl]sulfonyl-thiophene-3-carboxamide,
2-[(2-hydroxy-2-methyl-propanoyl)amino]-5-[4-(2-methoxyethoxy)phenyl]sulfonyl-thiophene-3-carboxamide,
5-[5-cyano-2-(trifluoromethoxy)phenyl]sulfonyl-2-[(2-hydroxy-2-methyl-propanoyl)amino]thiophene-3-carboxamide,
2-[(2-hydroxy-2-methyl-propanoyl)amino]-5-[5-methoxy-2-(trifluoromethoxy)phenyl]sulfonyl-thiophene-3-carboxamide,
2-[(2-hydroxy-2-methyl-propanoyl)amino]-5-[[5-(trifluoromethoxy)-2-pyridyl]sulfonyl]thiophene-3-carboxamide,
5-[2-fluoro-4-(trifluoromethoxy)phenyl]sulfonyl-2-[(2-hydroxy-2-methyl-propanoyl)amino]thiophene-3-carboxamide,
5-[2-fluoro-4-(trifluoromethyl)phenyl]sulfonyl-2-[(2-hydroxy-2-methyl-propanoyl)amino]thiophene-3-carboxamide,
5-[3-fluoro-4-(trifluoromethoxy)phenyl]sulfonyl-2-[(2-hydroxy-2-methyl-propanoyl)amino]thiophene-3-carboxamide,
5-[2,3-difluoro-4-(trifluoromethoxy)phenyl]sulfonyl-2-[(2-hydroxy-2-methyl-propanoyl)amino]thiophene-3-carboxamide,
2-[[(2S)-3-hydroxy-2-methyl-propanoyl]amino]-5-[4-(trifluoromethoxy)phenyl]sulfonyl-thiophene-3-carboxamide,
5-[4-(difluoromethoxy)phenyl]sulfonyl-2-[(2-hydroxy-2-methyl-propanoyl)amino]thiophene-3-carboxamide,
5-(4-cyanophenyl)sulfonyl-2-[(2-hydroxy-2-methyl-propanoyl)amino]thiophene-3-carboxamide,
2-[[(2R)-3-hydroxy-2-methyl-propanoyl]amino]-5-[4-(trifluoromethoxy)phenyl]sulfonyl-thiophene-3-carboxamide,
5-[(5-fluoro-4-methyl-2-pyridyl)sulfonyl]-2-[(2-hydroxy-2-methyl-propanoyl)amino]thiophene-3-carboxamide,
2-[(2-hydroxy-2-methyl-propanoyl)amino]-5-[(5-methyl-2-pyridyl)sulfonyl]thiophene-3-carboxamide,
5-[(6-chloro-3-pyridyl)sulfonyl]-2-[(2-hydroxy-2-methyl-propanoyl)amino]thiophene-3-carboxamide,
5-[5-chloro-2-(trifluoromethoxy)phenyl]sulfonyl-2-[(3-hydroxy-2-methyl-propanoyl)amino]thiophene-3-carboxamide,
5-[4-chloro-2-(trifluoromethoxy)phenyl]sulfonyl-2-[(3-hydroxy-2-methyl-propanoyl)amino]thiophene-3-carboxamide,
5-[4-chloro-2-(trifluoromethoxy)phenyl]sulfonyl-2-[(2-hydroxy-2-methyl-propanoyl)amino]thiophene-3-carboxamide,
2-[(2-hydroxy-2-methyl-propanoyl)amino]-5-[[6-(trifluoromethyl)-3-pyridyl]sulfonyl]thiophene-3-carboxamide,
5-[[5-chloro-2-(trifluoromethyl)-4-pyridyl]sulfonyl]-2-[(2-hydroxy-2-methyl-propanoyl)amino]thiophene-3-carboxamide,
5-[5-chloro-2-(trifluoromethoxy)phenyl]sulfonyl-2-[(2-hydroxy-2-methyl-propanoyl)amino]thiophene-3-carboxamide,
2-[(3-hydroxy-2-methyl-propanoyl)amino]-5-[[5-(trifluoromethoxy)-2-pyridyl]sulfonyl]thiophene-3-carboxamide,
5-[4-cyano-2-(trifluoromethoxy)phenyl]sulfonyl-2-[(2-hydroxy-2-methyl-propanoyl)amino]thiophene-3-carboxamide,
2-[(2-hydroxy-2-methyl-propanoyl)amino]-5-(2-(trifluoromethyl)pyrimidin-5-yl]sulfonyl-thiophene-3-carboxamide,
5-[[5-(difluoromethyl)-2-pyridyl]sulfonyl]-2-[(2-hydroxy-2-methyl-propanoyl)amino]thiophene-3-carboxamide,
2-(2-hydroxypropanoylamino)-5-[[5-(trifluoromethyl)-2-pyridyl]sulfonyl]thiophene-3-carboxamide,
2-[(2-hydroxy-2-methyl-propanoyl)amino]-5-5-(trifluoromethyl)pyrazin-2-yl]sulfonyl-thiophene-3-carboxamide,
2-(2-hydroxypropanoylamino)-5-[4-(trifluoromethyl)phenyl]sulfonyl-thiophene-3-carboxamide,
5-(3-cyano-5-methyl-phenyl)sulfonyl-2-[(2-hydroxy-2-methyl-propanoyl)amino]thiophene-3-carboxamide,
2-[(2-hydroxy-2-methyl-propanoyl)amino]-5-(4-methoxyphenyl)sulfonyl-thiophene-3-carboxamide,
5-[5-chloro-2-(difluoromethoxy)phenyl]sulfonyl-2-[(2-hydroxy-2-methyl-propanoyl)amino]thiophene-3-carboxamide,
5-[2-(difluoromethoxy)-4-fluoro-5-methoxy-phenyl]sulfonyl-2-[(2-hydroxy-2-methyl-propanoyl)amino]thiophene-3-carboxamide,
5-[4-(difluoromethoxy)phenyl]sulfonyl-2-(2-hydroxypropanoylamino)thiophene-3-carboxamide,
5-[2-(difluoromethoxy)-4,5-difluoro-phenyl]sulfonyl-2-[(2-hydroxy-2-methyl-propanoyl)amino]thiophene-3-carboxamide,
5-[2-(difluoromethoxy)-4,6-difluoro-phenyl]sulfonyl-2-[(2-hydroxy-2-methyl-propanoyl)amino]thiophene-3-carboxamide,
5-(4-cyano-2-fluoro-phenyl)sulfonyl-2-[(2-hydroxy-2-methyl-propanoyl)amino]thiophene-3-carboxamide,
5-[4-cyano-2-(trifluoromethyl)phenyl]sulfonyl-2-[(2-hydroxy-2-methyl-propanoyl)amino]thiophene-3-carboxamide,
2-[(2-hydroxy-2-methyl-propanoyl)amino]-5-[3-(trifluoromethyl)phenyl]sulfonyl-thiophene-3-carboxamide,
5-(3-cyanophenyl)sulfonyl-2-[(2-hydroxy-2-methyl-propanoyl)amino]thiophene-3-carboxamide,
5-[[3-fluoro-5-(trifluoromethyl)-2-pyridyl]sulfonyl]-2-[(2-hydroxy-2-methyl-propanoyl)amino]thiophene-3-carboxamide,
2-[(2-hydroxy-2-methyl-propanoyl)amino]-5-[[3-(trifluoromethyl)-2-pyridyl]sulfonyl]thiophene-3-carboxamide,
5-[[3,6-bis(trifluoromethyl)-2-pyridyl]sulfonyl]-2-[(2-hydroxy-2-methyl-propanoyl)amino]thiophene-3-carboxamide, 2-[(2-hydroxy-2-methyl-propanoyl)amino]-5-[[6-methyl-3-(trifluoromethyl)-2-pyridyl]sulfonyl]thiophene-3-carboxamide,
5-(6-chloro-5-methoxy-pyrimidin-4-yl)sulfonyl-2-[(2-hydroxy-2-methyl-propanoyl)amino]thiophene-3-carboxamide,
2-[(2-hydroxy-2-methyl-propanoyl)amino]-5-[5-methoxy-2-(trifluoromethyl)pyrimidin-4-yl]sulfonyl-thiophene-3-carboxamide,
2-[(2-hydroxy-2-methyl-propanoyl)amino]-5-(3-methoxy-5-methyl-phenyl)sulfonyl-thiophene-3-carboxamide,
2-[(2-hydroxy-2-methyl-propanoyl)amino]-5-[3-(trifluoromethyl)pyrazin-2-yl]sulfonyl-thiophene-3-carboxamide,
5-[[5-(difluoromethoxy)-2-methoxy-4-pyridyl]sulfonyl]-2-[(2-hydroxy-2-methyl-propanoyl)amino]thiophene-3-carboxamide,
5-[5-cyano-2-(difluoromethoxy)-3-methoxy-phenyl]sulfonyl-2-[(2-hydroxy-2-methyl-propanoyl)amino]thiophene-3-carboxamide,
2-[(2-hydroxy-2-methyl-propanoyl)amino]-5-[[6-methoxy-3-(trifluoromethyl)-2-pyridyl]sulfonyl]thiophene-3-carboxamide,
2-[(2-hydroxy-2-methyl-propanoyl)amino]-5-(3-isopropyl-1-methyl-pyrazol-4-yl)sulfonyl-thiophene-3-carboxamide,
5-[3-fluoro-4-(trifluoromethyl)phenyl]sulfonyl-2-[(2-hydroxy-2-methyl-propanoyl)amino]thiophene-3-carboxamide,
5-[[6-chloro-5-(trifluoromethyl)-2-pyridyl]sulfonyl]-2-[(2-hydroxy-2-methyl-propanoyl)amino]thiophene-3-carboxamide,
5-[[6-chloro-3-(trifluoromethyl)-2-pyridyl]sulfonyl]-2-[(2-hydroxy-2-methyl-propanoyl)amino]thiophene-3-carboxamide,
2-[(2-hydroxy-2-methyl-propanoyl)amino]-5-[[2-(trifluoromethyl)-3-thienyl]sulfonyl]thiophene-3-carboxamide,
5-[[6-tert-butyl-3-(trifluoromethyl)-2-pyridyl]sulfonyl]-2-[(2-hydroxy-2-methyl-propanoyl)amino]thiophene-3-carboxamide,
2-[(2-hydroxy-2-methyl-propanoyl)amino]-5-[[6-(trifluoromethyl)-2-pyridyl]sulfonyl]thiophene-3-carboxamide,
5-[3-(cyanomethyl)-5-(trifluoromethoxy)phenyl]sulfonyl-2-[(2-hydroxy-2-methyl-propanoyl)amino]thiophene-3-carboxamide,
5-[3-chloro-5-(trifluoromethyl)phenyl]sulfonyl-2-[(2-hydroxy-2-methyl-propanoyl)amino]thiophene-3-carboxamide,
2-[(2-hydroxy-2-methyl-propanoyl)amino]-5-[3-methyl-5-(trifluoromethyl)phenyl]sulfonyl-thiophene-3-carboxamide,
2-[(2-hydroxy-2-methyl-propanoyl)amino]-5-[6-(trifluoromethyl)pyridazin-3-yl]sulfonyl-thiophene-3-carboxamide,
5-[(2-chloro-5-cyano-4-pyridyl)sulfonyl]-2-[(2-hydroxy-2-methyl-propanoyl)amino]thiophene-3-carboxamide,
5-[(5-tert-butyl-2-pyridyl)sulfonyl]-2-[(2-hydroxy-2-methyl-propanoyl)amino]thiophene-3-carboxamide,
2-[(2-hydroxy-2-methyl-propanoyl)amino]-5-[(1-methyl-2,4-dihydro-3,1-benzoxazin-6-yl)sulfonyl]thiophene-3-carboxamide,
5-[2-fluoro-4-(trifluoromethoxy)phenyl]sulfonyl-2-[[1-(hydroxymethyl)cyclopropanecarbonyl]amino]thiophene-3-carboxamide,
2-[(2-hydroxy-2-methyl-propanoyl)amino]-5-[[2-(trifluoromethyl)-3-pyridyl]sulfonyl]thiophene-3-carboxamide,
2-[(2-hydroxy-2-methyl-propanoyl)amino]-4-methyl-5-[4-(trifluoromethoxy)phenyl]sulfonyl-thiophene-3-carboxamide,
2-[(2-hydroxy-2-methyl-propanoyl)amino]-5-[[6-(hydroxymethyl)-3-(trifluoromethyl)-2-pyridyl]sulfonylthiophene-3-carboxamide,
5-[2-fluoro-4-(trifluoromethyl)phenyl]sulfonyl-2-[(2-hydroxy-2-methyl-propanoyl)amino]-4-methyl-thiophene-3-carboxamide,
5-[[5-chloro-2-(trifluoromethyl)-3-pyridyl]sulfonyl]-2-[(2-hydroxy-2-methyl-propanoyl)amino]thiophene-3-carboxamide,
5-[[5-bromo-6-(trifluoromethyl)-3-pyridyl]sulfonyl]-2-[(2-hydroxy-2-methyl-propanoyl)amino]thiophene-3-carboxamide,
N-[3-carbamoyl-5-[4-(trifluoromethoxy)phenyl]sulfonyl-2-thienyl]tetrahydrofuran-2-carboxamide,
N-[3-carbamoyl-5-[4-(trifluoromethoxy)phenyl]sulfonyl-2-thienyl]tetrahydrofuran-3-carboxamide,
5-[2-fluoro-4-(trifluoromethoxy)phenyl]sulfonyl-2-[[(2S)-2-hydroxypropanoyl]amino]thiophene-3-carboxamide,
5-[2-fluoro-4-(trifluoromethyl)phenyl]sulfonyl-2-[[(2S)-2-hydroxypropanoyl]amino]thiophene-3-carboxamide,
2-[(3-hydroxy-2,2-dimethyl-propanoyl)amino]-5-[4-(trifluoromethoxy)phenyl]sulfonyl -thiophene-3-carboxamide, and
N-(3-carbamoyl-5-(4-fluorophenylsulfonyl)thiophen-2-yl)-2-oxo-1,2-dihydropyridine-3-carboxamide.

* * * * *